(12) United States Patent
Markosyan et al.

(10) Patent No.: US 12,378,590 B2
(45) Date of Patent: *Aug. 5, 2025

(54) HIGH-PURITY STEVIOL GLYCOSIDES

(71) Applicant: PURECIRCLE USA INC., Westchester, IL (US)

(72) Inventors: Avetik Markosyan, Kuala Lumpur (MY); Siew Yin Chow, Selangor (MY); Khairul Nizam Bin Nawi, Negeri Sembilan (MY); Kristina Chkhan, Kuala Lumpur (MY); Mohamad Afzaal Bin Hasim, Kuala Lumpur (MY); Saravanan A/L Ramandach, Negeri Sembilan (MY)

(73) Assignee: PURECIRCLE USA INC., Westchester, IL (US)

( * ) Notice: Subject to any disclaimer, the term of this patent is extended or adjusted under 35 U.S.C. 154(b) by 931 days.

This patent is subject to a terminal disclaimer.

(21) Appl. No.: 17/430,762

(22) PCT Filed: Feb. 15, 2020

(86) PCT No.: PCT/US2020/018460
§ 371 (c)(1),
(2) Date: Aug. 13, 2021

(87) PCT Pub. No.: WO2020/168312
PCT Pub. Date: Aug. 20, 2020

(65) Prior Publication Data
US 2022/0380824 A1 Dec. 1, 2022

Related U.S. Application Data

(60) Provisional application No. 62/823,381, filed on Mar. 25, 2019, provisional application No. 62/806,646, filed on Feb. 15, 2019.

(51) Int. Cl.
C12P 19/56 (2006.01)
A23L 27/30 (2016.01)
C07H 15/256 (2006.01)

(52) U.S. Cl.
CPC ............... C12P 19/56 (2013.01); A23L 27/36 (2016.08); C07H 15/256 (2013.01); C12Y 204/01242 (2013.01)

(58) Field of Classification Search
CPC .......... A23L 27/36; C07H 15/256; C07H 1/06
See application file for complete search history.

(56) References Cited

U.S. PATENT DOCUMENTS 9,907,326 B2 3/2018 Urai et al.
10,570,164 B2 2/2020 Prakash et al.
(Continued)

FOREIGN PATENT DOCUMENTS

CN 105283464 1/2016
CN 105838759 A 8/2016
(Continued)

OTHER PUBLICATIONS

Kim Olsson et al., "Microbial production of next generation stevia sweeteners", Microbial Cell Factories, vol. 11, Dec. 1, 2016, p. 1939.

Primary Examiner — Changqing Li

(57) ABSTRACT

Methods of preparing highly purified steviol glycosides. The methods include utilizing enzyme preparations and recombinant microorganisms for converting various starting compositions to target steviol glycosides. The highly purified steviol glycosides are useful as non-caloric sweetener, flavor enhancer, sweetness enhancer, and foaming suppressor in edible and chewable compositions such as any beverages, (Continued)

Rebaudioside 1a

Rebaudioside 1b confectioneries, bakery products, cookies, and chewing gums.

17 Claims, 176 Drawing Sheets

Specification includes a Sequence Listing.

(56) References Cited

U.S. PATENT DOCUMENTS

| | | | |
|---|---|---|---|
| 2014/0017378 A1* | 1/2014 | Purkayastha | A23L 27/36 |
| | | | 426/442 |
| 2014/0357588 A1* | 12/2014 | Markosyan | A24B 15/10 |
| | | | 536/18.1 |
| 2017/0303566 A1 | 10/2017 | Urai et al. | |
| 2021/0381019 A1* | 12/2021 | Mao | C07H 15/256 |

FOREIGN PATENT DOCUMENTS

| | | |
|---|---|---|
| CN | 113474464 | 10/2021 |
| EP | 3894577 A1 | 10/2021 |
| EP | 3764815 A4 | 1/2022 |
| WO | 2016120486 A1 | 8/2016 |
| WO | WO2016156616 | 10/2016 |
| WO | 2017218036 A1 | 12/2017 |
| WO | 2018213290 A1 | 11/2018 |
| WO | 2019178471 A1 | 9/2019 |
| WO | 2020/123877 A1 | 6/2020 |

* cited by examiner

Rebaudioside 1c

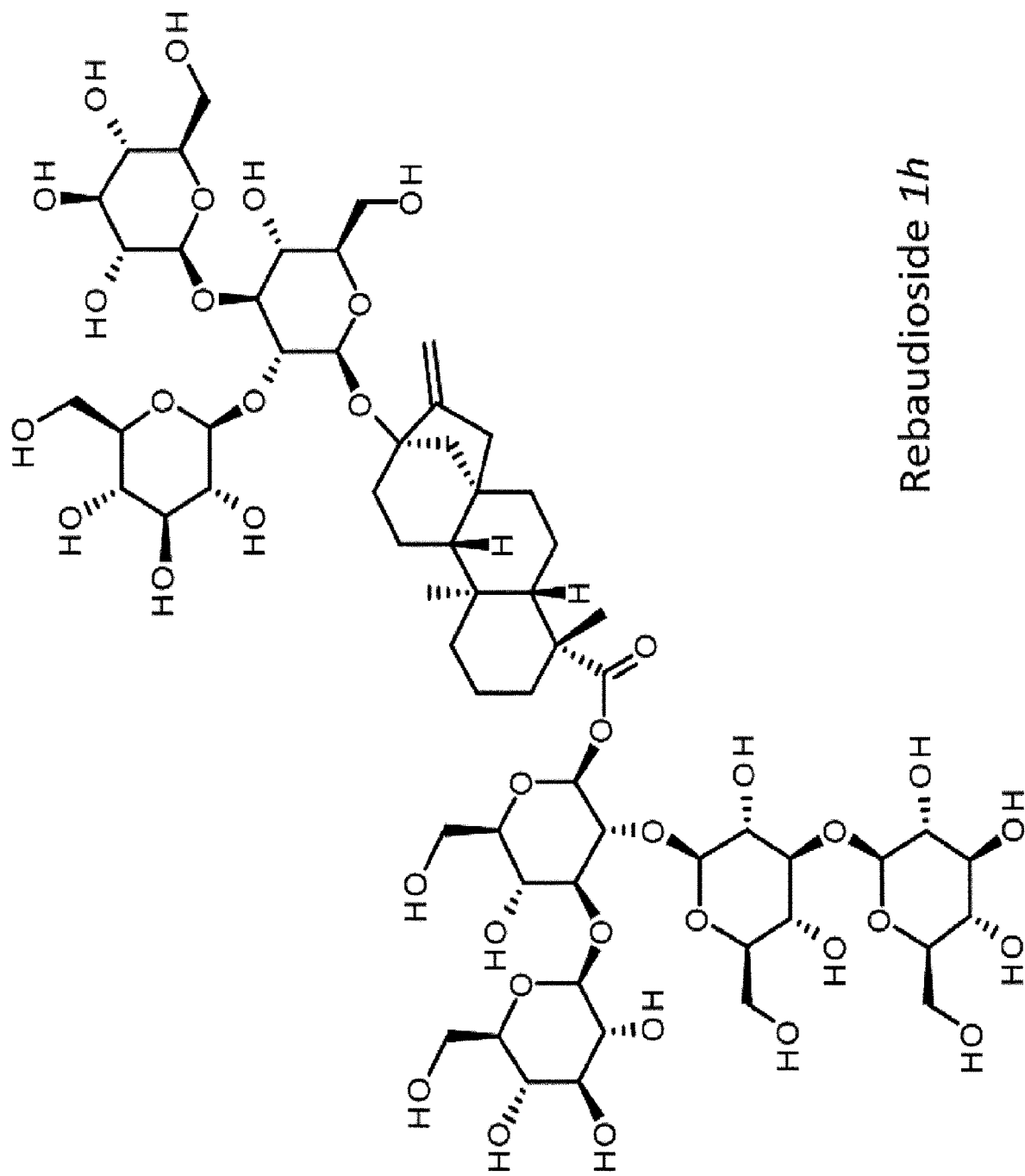
FIG. 1h Rebaudioside 1h

Rebaudioside 1i

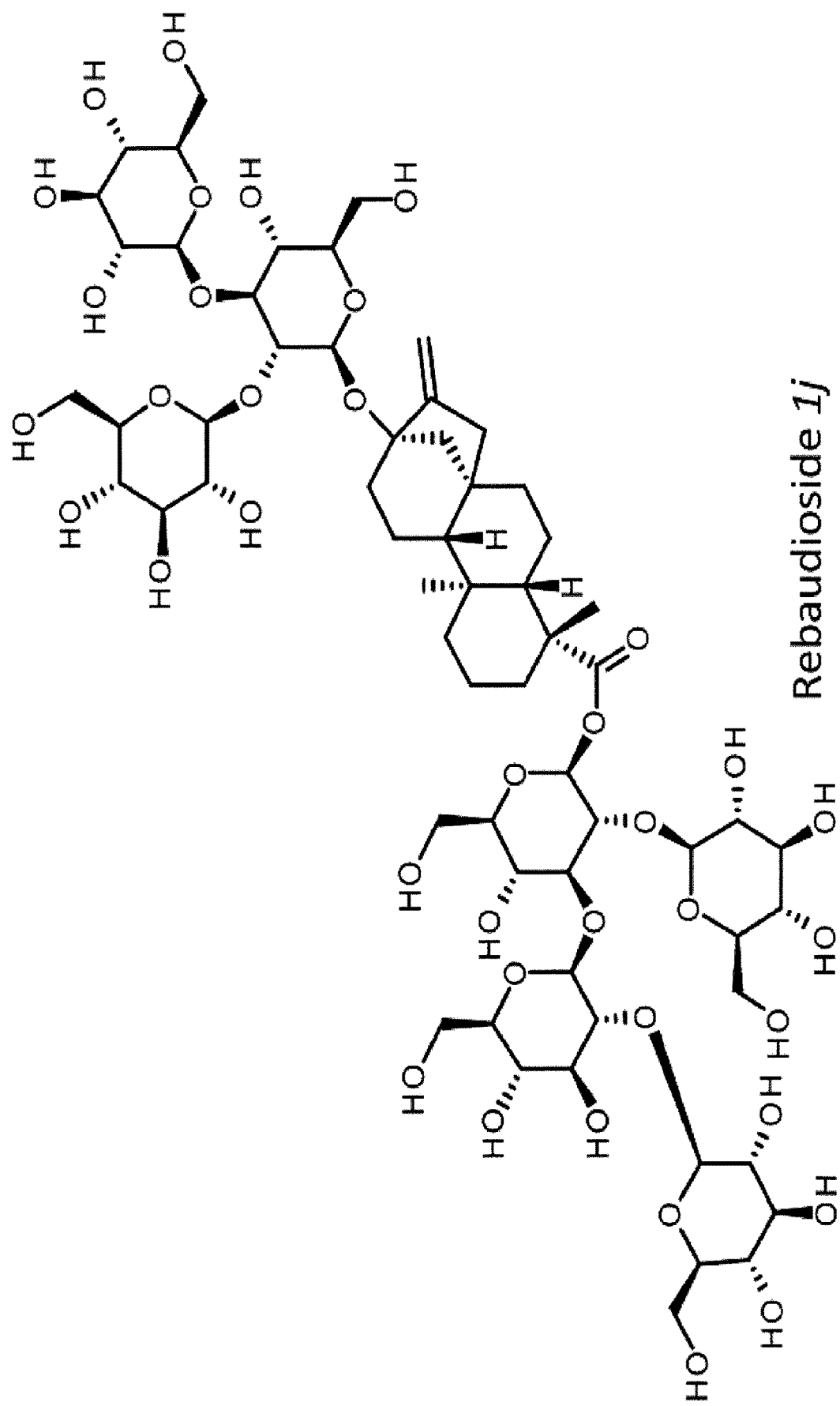
FIG. 1j Rebaudioside 1j

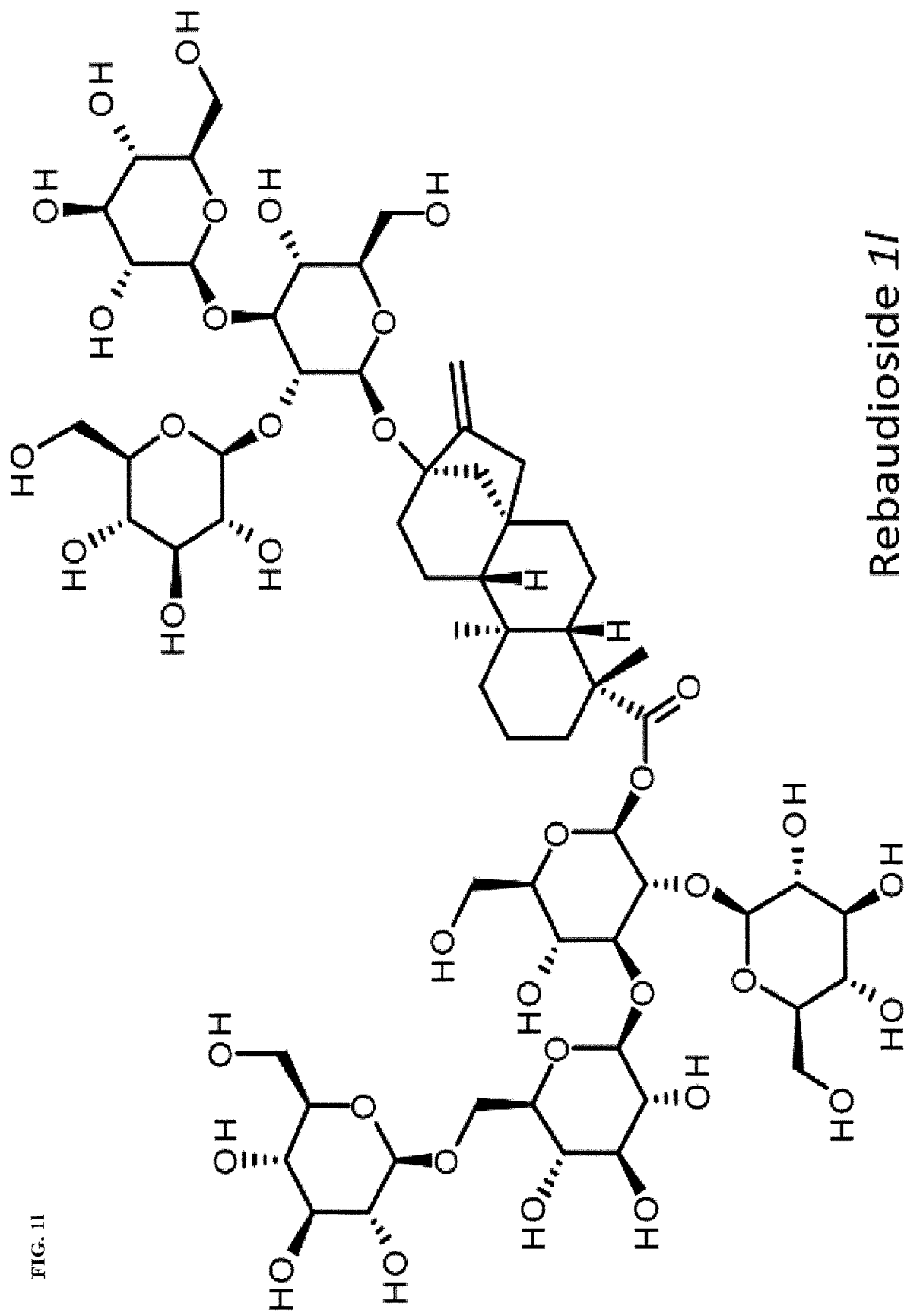
FIG. 1*l* Rebaudioside 1*l*

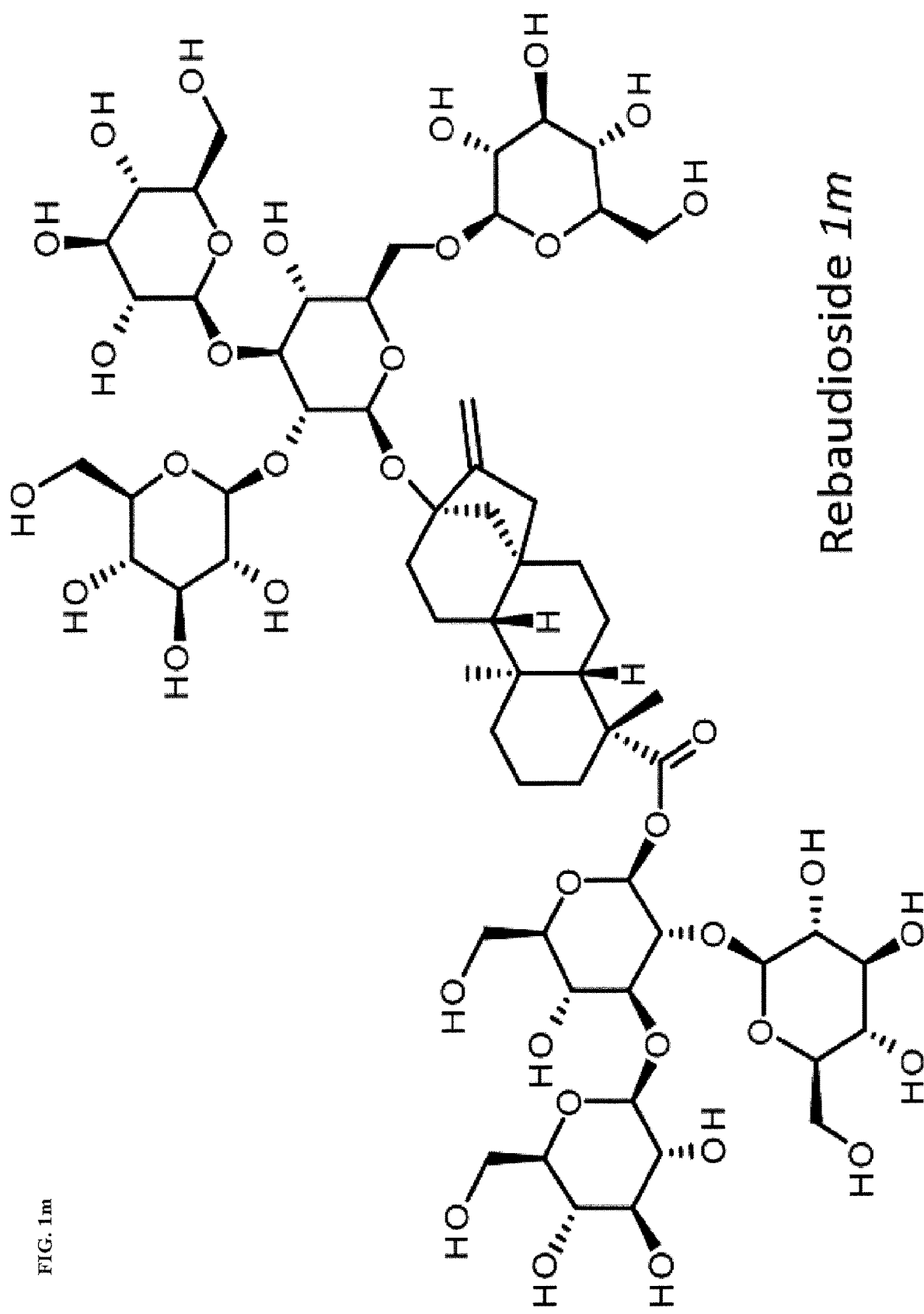
FIG. 1m  Rebaudioside 1m

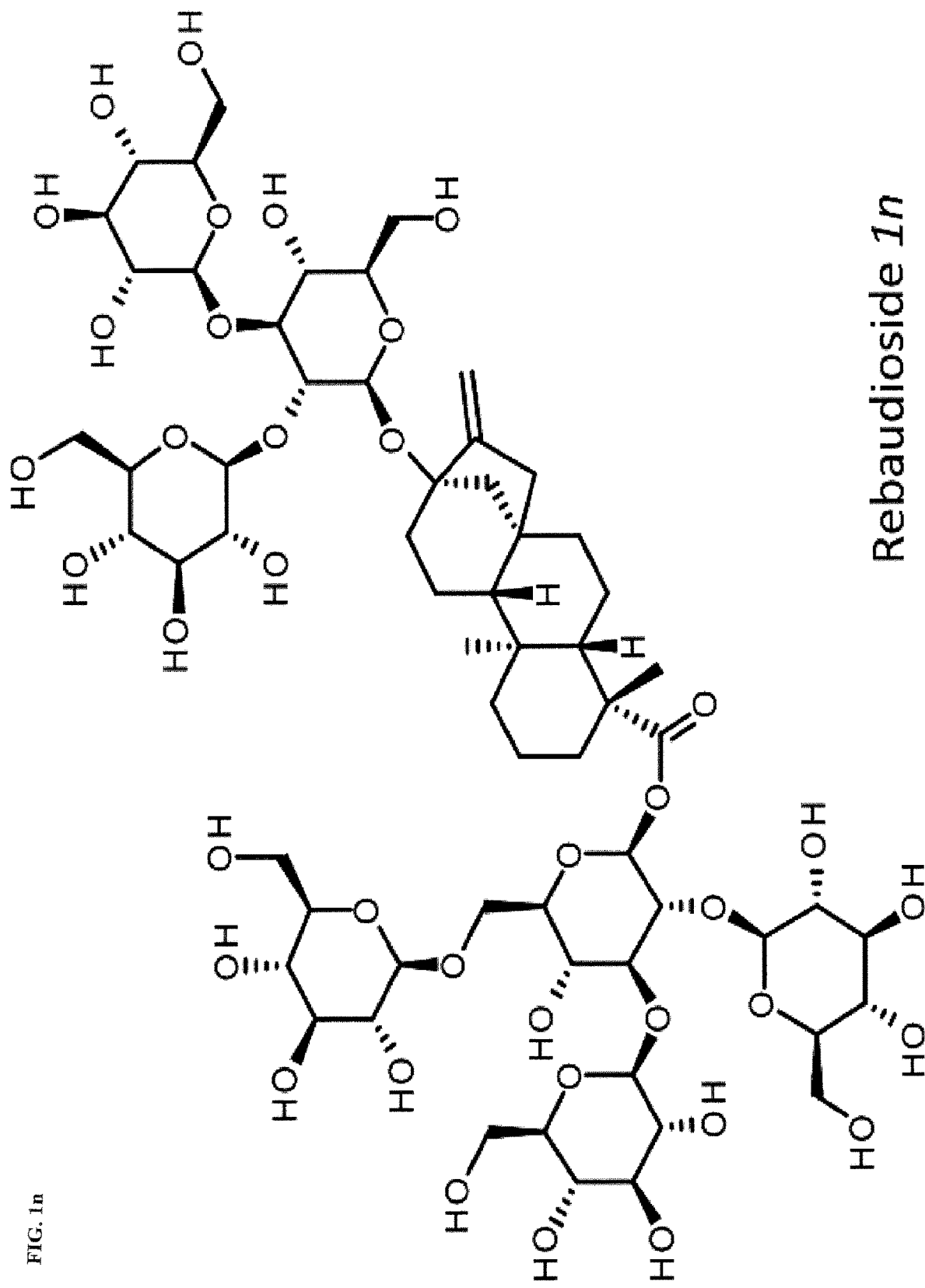
FIG. 1n  Rebaudioside 1n

Rebaudioside 1p

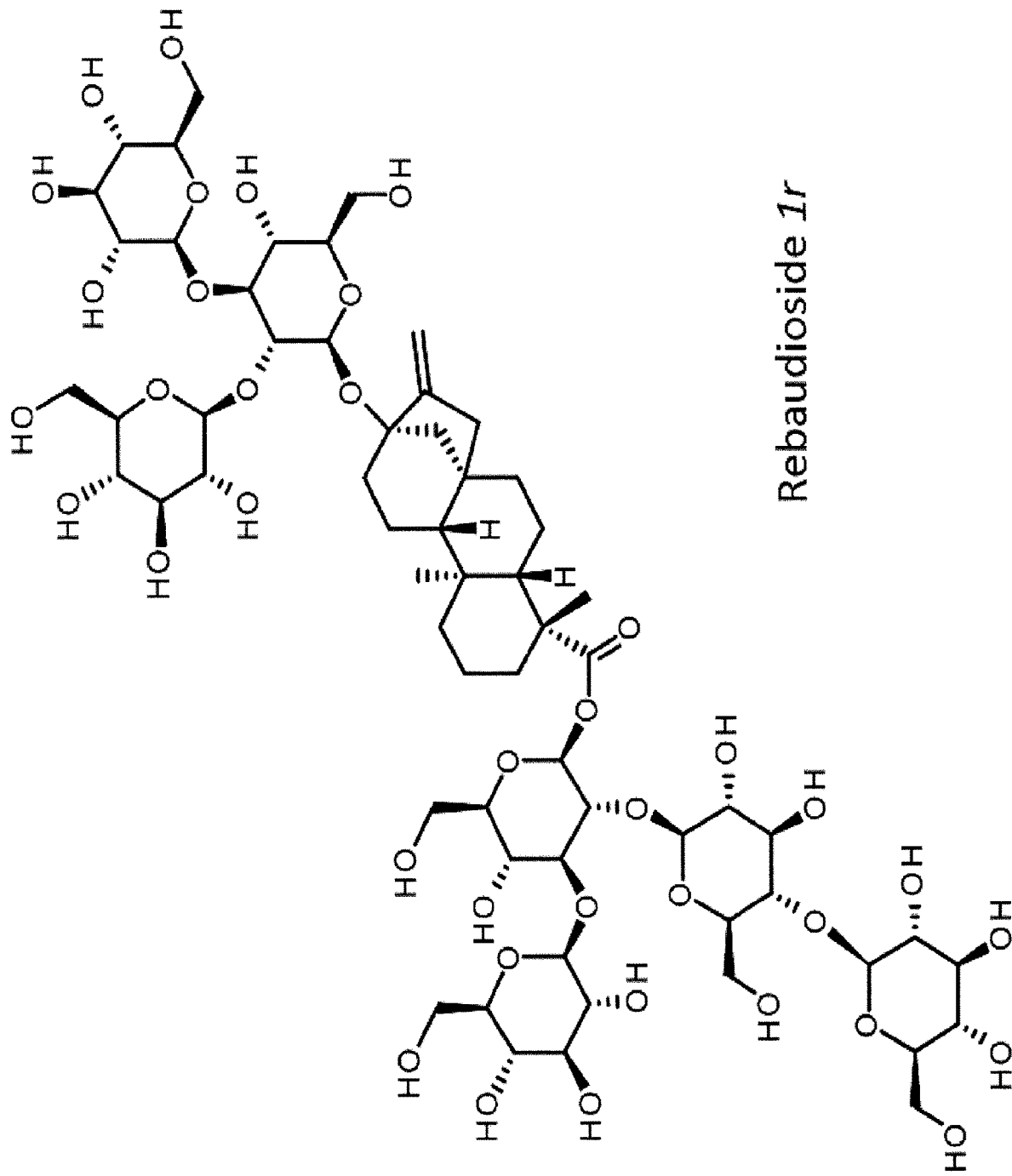
FIG. 1r  Rebaudioside 1r

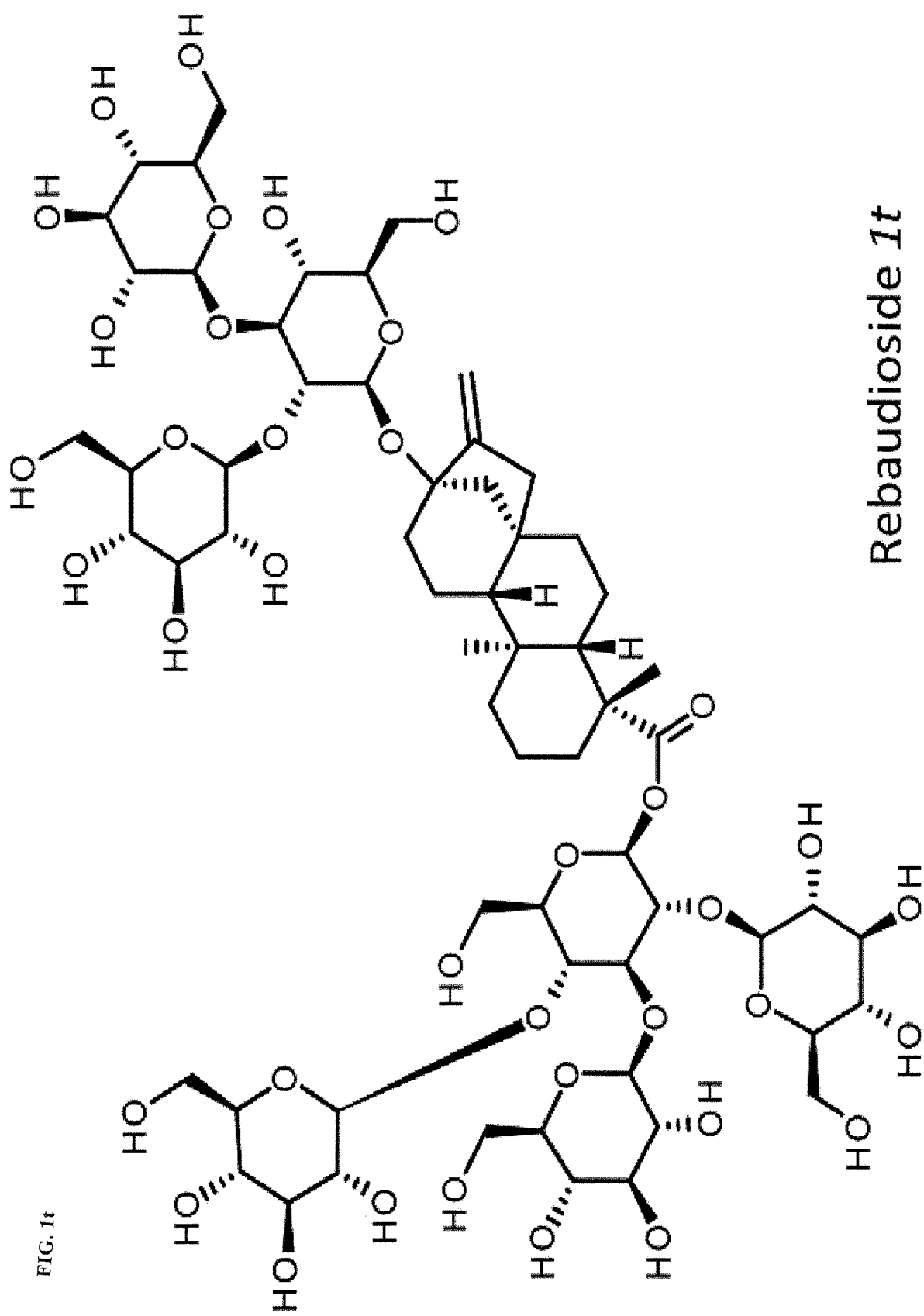
FIG. 1t  Rebaudioside 1t

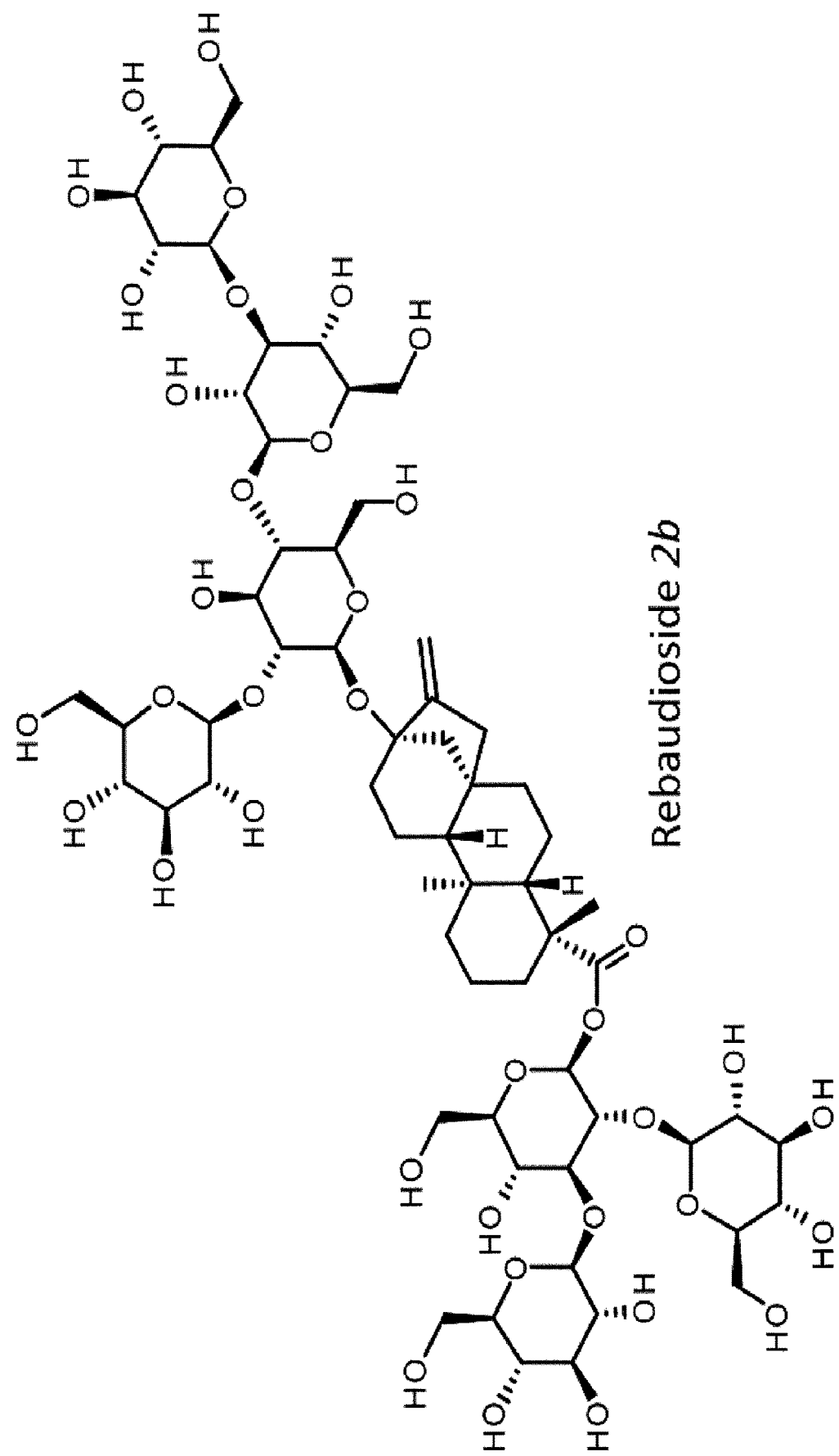
FIG. 2b Rebaudioside 2b

Rebaudioside 2n

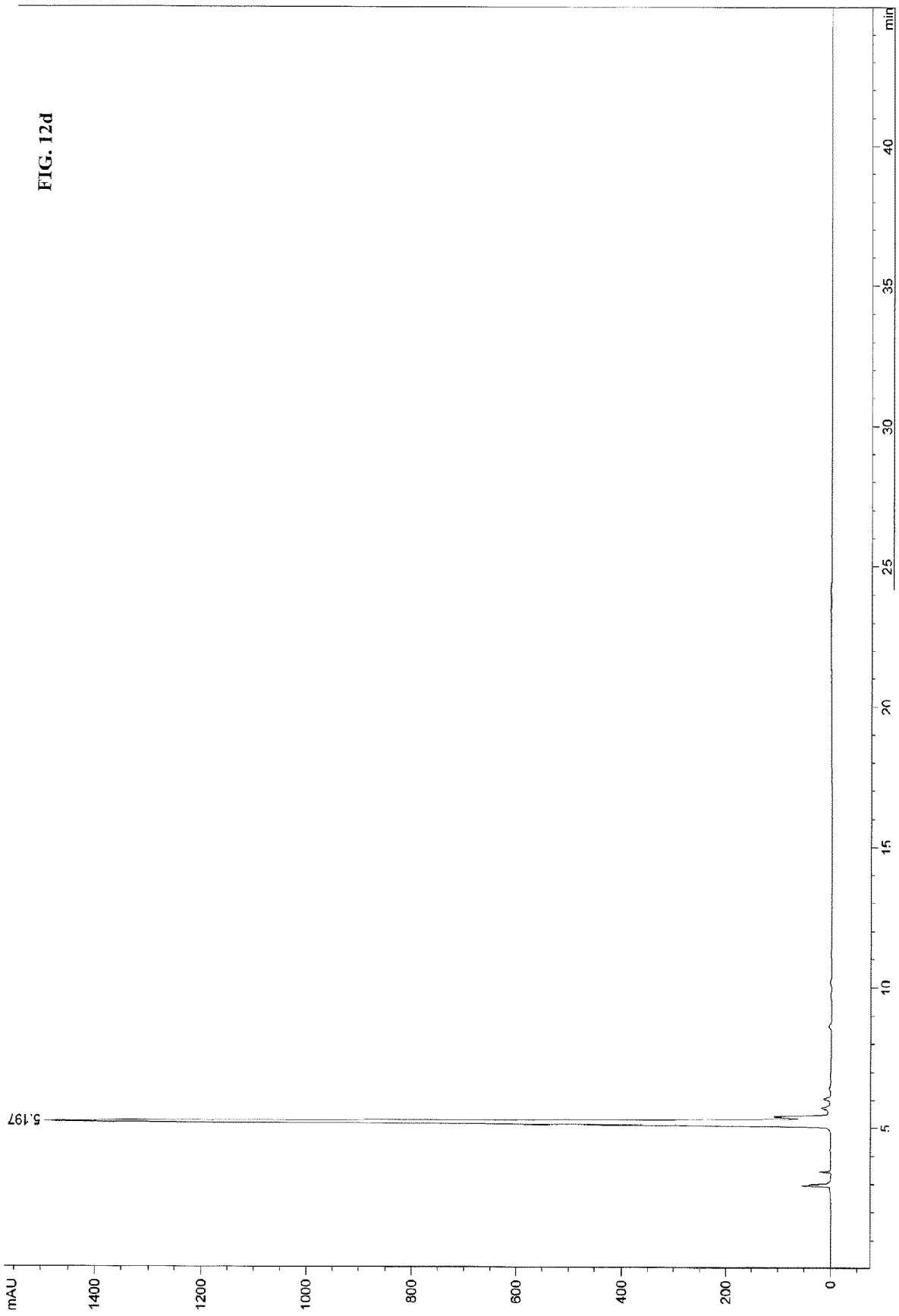

HIGH-PURITY STEVIOL GLYCOSIDES

CROSS-REFERENCE TO RELATED APPLICATIONS

This application is a U.S. national stage entry under 35 U.S.C. § 371 of International Patent Application No. PCT/US2020/018460, filed on Feb. 15, 2020, which claims the benefit of priority under 35 U.S.C. § 119 (e) of U.S. Provisional Application Ser. No. 62/806,646, filed on Feb. 15, 2019, and 62/823,381, filed on Mar. 25, 2019, the entire disclosures of which are incorporated herein by reference.

SEQUENCE LISTING

The text file entitled "PC_77WO_Final_ST25.txt," created on Apr. 10, 2018, having 15 kilobytes of data, and filed concurrently herewith, is hereby incorporated by reference in its entirety in this application.

TECHNICAL FIELD

The present invention relates to a process for preparing compositions comprising steviol glycosides, including highly purified steviol glycoside compositions.

BACKGROUND OF THE INVENTION

High intensity sweeteners possess a sweetness level that is many times greater than the sweetness level of sucrose. They are essentially non-caloric and are commonly used in diet and reduced-calorie products, including foods and beverages. High intensity sweeteners do not elicit a glycemic response, making them suitable for use in products targeted to diabetics and others interested in controlling for their intake of carbohydrates.

Steviol glycosides are a class of compounds found in the leaves of *Stevia rebaudiana* Bertoni, a perennial shrub of the Asteraceae (Compositae) family native to certain regions of South America. They are characterized structurally by a single base, steviol, differing by the presence of carbohydrate residues at positions C13 and C19. They accumulate in *Stevia* leaves, composing approximately 10%-20% of the total dry weight. On a dry weight basis, the four major glycosides found in the leaves of *Stevia* typically include stevioside (9.1%), rebaudioside A (3.8%), rebaudioside C (0.6-1.0%) and dulcoside A (0.3%). Other known steviol glycosides include rebaudioside B, C, D, E, F and M, steviolbioside and rubusoside.

Although methods are known for preparing steviol glycosides from *Stevia rebaudiana*, many of these methods are unsuitable for use commercially.

Accordingly, there remains a need for simple, efficient, and economical methods for preparing compositions comprising steviol glycosides, including highly purified steviol glycoside compositions.

SUMMARY OF THE INVENTION

As used herein, the abbreviation term "reb" refers to "rebaudioside". Both terms have the same meaning and may be used interchangeably.

As used herein, "biocatalysis" or "biocatalytic" refers to the use of natural or genetically engineered biocatalysts, such as enzymes, or cells comprising one or more enzyme, capable of single or multiple step chemical transformations on organic compounds. Biocatalysis processes include fermentation, biosynthesis, bioconversion and biotransformation processes. Both isolated enzymes, and whole-cell biocatalysis methods are known in the art. Biocatalyst protein enzymes can be naturally occurring or recombinant proteins.

As used herein, the term "steviol glycoside(s)" refers to a glycoside of steviol, including, but not limited to, naturally occurring steviol glycosides, e.g. steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s, synthetic steviol glycosides, e.g. enzymatically glucosylated steviol glycosides and combinations thereof.

As used herein, the term "SvG7" refers to any naturally occurring steviol glycosides or any synthetic steviol glycosides, including enzymatically glucosylated steviol glycosides and combinations thereof, specifically a molecule comprising steviol having seven glucose residues attached covalently including, but not limited to reb 1a, reb 1b, reb 1c, reb 1d, reb 1e, reb 1f reb 1g, reb 1h, reb 1i, reb 1j, reb 1k, reb 1l, reb 1m, reb 1n, reb 1o, reb 1p, reb 1q, reb 1r, reb 1s, reb 1t, reb 2a, reb 2b, reb 2c, reb 2d, reb 2e, reb 2f reb 2g, reb 2h, reb 2i, reb 2j, reb 2k, reb 2l, reb 2m, reb 2n, reb 2o, reb 2p, reb 2q, reb 2r, and/or reb 2s. SvG7 can refer to a single steviol glycoside having seven glucose residues attached covalently or a mixture of steviol glycosides having seven glucose residues attached covalently.

The present invention provides a process for preparing a composition comprising a target steviol glycoside by contacting a starting composition comprising an organic substrate with a microbial cell and/or enzyme preparation, thereby producing a composition comprising a target steviol glycoside.

The starting composition can be any organic compound comprising at least one carbon atom. In one embodiment, the starting composition is selected from the group consisting of steviol glycosides, polyols or sugar alcohols, various carbohydrates. The target steviol glycoside can be any steviol glycoside. In one embodiment, the target steviol glycoside is steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s, SvG7 or a synthetic steviol glycoside.

In one embodiment, the target steviol glycoside is rebaudioside 1a.

In one embodiment, the target steviol glycoside is rebaudioside 1b.

In one embodiment, the target steviol glycoside is rebaudioside 1c.

In one embodiment, the target steviol glycoside is rebaudioside 1d.

In one embodiment, the target steviol glycoside is rebaudioside 1e.

In one embodiment, the target steviol glycoside is rebaudioside 1f.

In one embodiment, the target steviol glycoside is rebaudioside 1g.

In one embodiment, the target steviol glycoside is rebaudioside 1h.

In one embodiment, the target steviol glycoside is rebaudioside 1i.

In one embodiment, the target steviol glycoside is rebaudioside 1j.

In one embodiment, the target steviol glycoside is rebaudioside 1k.

In one embodiment, the target steviol glycoside is rebaudioside 1l.

In one embodiment, the target steviol glycoside is rebaudioside 1m.

In one embodiment, the target steviol glycoside is rebaudioside 1n.

In one embodiment, the target steviol glycoside is rebaudioside 1o.

In one embodiment, the target steviol glycoside is rebaudioside 1p.

In one embodiment, the target steviol glycoside is rebaudioside 1q.

In one embodiment, the target steviol glycoside is rebaudioside 1r.

In one embodiment, the target steviol glycoside is rebaudioside 1s.

In one embodiment, the target steviol glycoside is rebaudioside 1t.

In one embodiment, the target steviol glycoside is rebaudioside 2a.

In one embodiment, the target steviol glycoside is rebaudioside 2b.

In one embodiment, the target steviol glycoside is rebaudioside 2c.

In one embodiment, the target steviol glycoside is rebaudioside 2d.

In one embodiment, the target steviol glycoside is rebaudioside 2e.

In one embodiment, the target steviol glycoside is rebaudioside 2f.

In one embodiment, the target steviol glycoside is rebaudioside 2g.

In one embodiment, the target steviol glycoside is rebaudioside 2h.

In one embodiment, the target steviol glycoside is rebaudioside 2i.

In one embodiment, the target steviol glycoside is rebaudioside 2j.

In one embodiment, the target steviol glycoside is rebaudioside 2k.

In one embodiment, the target steviol glycoside is rebaudioside 2l.

In one embodiment, the target steviol glycoside is rebaudioside 2m.

In one embodiment, the target steviol glycoside is rebaudioside 2n.

In one embodiment, the target steviol glycoside is rebaudioside 2o.

In one embodiment, the target steviol glycoside is rebaudioside 2p.

In one embodiment, the target steviol glycoside is rebaudioside 2q.

In one embodiment, the target steviol glycoside is rebaudioside 2r.

In one embodiment, the target steviol glycoside is rebaudioside 2s.

In one embodiment, the target steviol glycoside is rebaudioside M4.

In one embodiment, the target steviol glycoside is rebaudioside M5.

In one embodiment, the target steviol glycoside is SvG7.

In some preferred embodiments enzyme preparation comprising one or more enzymes, or a microbial cell comprising one or more enzymes, capable of converting the starting composition to target steviol glycosides are used. The enzyme can be located on the surface and/or inside the cell. The enzyme preparation can be provided in the form of a whole cell suspension, a crude lysate or as purified enzyme(s). The enzyme preparation can be in free form or immobilized to a solid support made from inorganic or organic materials.

In some embodiments, a microbial cell comprises the necessary enzymes and genes encoding thereof for converting the starting composition to target steviol glycosides. Accordingly, the present invention also provides a process for preparing a composition comprising a target steviol glycoside by contacting a starting composition comprising an organic substrate with a microbial cell comprising at least one enzyme capable of converting the starting composition to target steviol glycosides, thereby producing a medium comprising at least one target steviol glycoside.

The enzymes necessary for converting the starting composition to target steviol glycosides include the steviol biosynthesis enzymes, NDP-glucosyltransferases (NGTs), ADP-glucosyltransferases (AGTs), CDP-glucosyltransferases (CGTs), GDP-glucosyltransferases (GGTs), TDP-glucosyltransferases (TDPs), UDP-glucosyltransferases (UGTs) and/or NDP-recycling enzyme, ADP-recycling enzyme, CDP-recycling enzyme, GDP-recycling enzyme, TDP-recycling enzyme, and/or UDP-recycling enzyme.

In one embodiment, the steviol biosynthesis enzymes include mevalonate (MVA) pathway enzymes.

In another embodiment, the steviol biosynthesis enzymes include non-mevalonate 2-C-methyl-D-erythritol-4-phosphate pathway (MEP/DOXP) enzymes.

In one embodiment the steviol biosynthesis enzymes are selected from the group including geranylgeranyl diphosphate synthase, copalyl diphosphate synthase, kaurene synthase, kaurene oxidase, kaurenoic acid 13-hydroxylase (KAH), steviol synthetase, deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS), 1-hydroxy-2-methyl-2(E)-butenyl 4-diphosphate reductase (HDR), acetoacetyl-CoA thiolase, truncated HMG-CoA reductase, mevalonate kinase, phosphomevalonate kinase, mevalonate pyrophosphate decarboxylase, cytochrome P450 reductase etc.

The UDP-glucosyltransferase can be any UDP-glucosyltransferase capable of adding at least one glucose unit to steviol and/or a steviol glycoside substrate to provide the target steviol glycoside.

As used hereinafter, the term "SuSy_AT", unless specified otherwise, refers to sucrose synthase having amino-acid sequence "SEQ ID 1" as described in Example 1, or a polypeptide having substantial (>85%, >86%, >87%, >88%, >89%, >90%, >91%, >92%, >93%, >94%, >95%, >96%, >97%, >98%, >99%) amino-acid sequence identity to the SEQ ID 1 polypeptide as well as isolated nucleic acid molecules that code for those polypeptides.

As used hereinafter, the term "UGTSl2", unless specified otherwise, refers to UDP-glucosyltransferase having amino-acid sequence "SEQ ID 2" as described in Example 1 or a polypeptide having substantial (>85%, >86%, >87%, >88%, >89%, >90%, >91%, >92%, >93%, >94%, >95%, >96%, >97%, >98%, >99%) amino-acid sequence identity to the SEQ ID 2 polypeptide as well as isolated nucleic acid molecules that code for those polypeptides.

As used hereinafter, the term "UGT76G1", unless specified otherwise, refers to UDP-glucosyltransferase having amino-acid sequence "SEQ ID 3" as described in Example 1 or a polypeptide having substantial (>85%, >86%, >87%, >88%, >89%, >90%, >91%, >92%, >93%, >94%, >95%, >96%, >97%, >98%, >99%) amino-acid sequence identity to the SEQ ID 3 polypeptide as well as isolated nucleic acid molecules that code for those polypeptides.

In one embodiment, steviol biosynthesis enzymes and UDP-glucosyltransferases are produced in a microbial cell. The microbial cell may be, for example, E. coli, Saccharomyces sp., Aspergillus sp., Pichia sp., Bacillus sp., Yarrowia sp. etc. In another embodiment, the UDP-glucosyltransferases are synthesized.

In one embodiment, the UDP-glucosyltransferase is selected from group including UGT74G1, UGT85C2, UGT76G1, UGT91D2, UGTSl2, EUGT11 and UGTs having substantial (>85%, >86%, >87%, >88%, >89%, >90%, >91%, >92%, >93%, >94%, >95%, >96%, >97%, >98%, >99%) amino-acid sequence identity to these polypeptides as well as isolated nucleic acid molecules that code for these UGTs.

In one embodiment, steviol biosynthesis enzymes, UGTs, and UDP-glucose recycling system are present in one microorganism (microbial cell). The microorganism may be for example, E. coli, Saccharomyces sp., Aspergillus sp., Pichia sp., Bacillus sp., Yarrowia sp.

In one embodiment, the UDP-glucosyltransferase is any UDP-glucosyltransferase capable of adding at least one glucose unit to steviol or any starting steviol glycoside bearing an —OH functional group at C13 to give a target steviol glycoside having an —O-glucose beta glucopyranoside glycosidic linkage at C13. In a particular embodiment, the UDP-glucosyltransferase is UGT85C2, or a UGT having >85% amino-acid sequence identity with UGT85C2.

In another embodiment, the UDP-glucosyltransferase is any UDP-glucosyltransferase capable of adding at least one glucose unit to steviol or any starting steviol glycoside bearing a —COOH functional group at C19 to give a target steviol glycoside having a —COO-glucose beta-glucopyranoside glycosidic linkage at C19. In a particular embodiment, the UDP-glucosyltransferase is UGT74G1, or a UGT having >85% amino-acid sequence identity with UGT74G1.

In another embodiment, the UDP-glucosyltransferase is any UDP-glucosyltransferase capable of adding at least one glucose unit to any existing glucose on the C19 side of any starting steviol glycoside to give a target steviol glycoside with at least one additional glucose bearing at least one beta 1→2 glucopyranoside glycosidic linkage(s) at the newly formed glycosidic bond(s). In a particular embodiment, the UDP-glucosyltransferase is UGTSl2, or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to any existing glucose on the C19 side of any starting steviol glycoside to give a target steviol glycoside with at least one additional glucose bearing at least one beta 1→3 glucopyranoside glycosidic linkage(s) at the newly formed bond glycosidic bond(s). In a particular embodiment, the UDP-glucosyltransferase is UGT76G1, or a UGT having >85% amino-acid sequence identity with UGT76G1.

In another embodiment, the UDP-glucosyltransferase is any UDP-glucosyltransferase capable of adding at least one glucose unit to any existing glucose on the C19 side of any starting steviol glycoside to give a target steviol glycoside with at least one additional glucose bearing at least one beta 1→4 glucopyranoside glycosidic linkage(s) at the newly formed glycosidic bond(s). In a particular embodiment, the UDP-glucosyltransferase is UGTSl2, or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In another particular embodiment, the UDP-glucosyltransferase is UGT76G1, or a UGT having >85% amino-acid sequence identity with UGT76G1.

In another embodiment, the UDP-glucosyltransferase is any UDP-glucosyltransferase capable of adding at least one glucose unit to any existing glucose on the C19 side of any starting steviol glycoside to give a target steviol glycoside with at least one additional glucose bearing at least one beta 1→6 glucopyranoside glycosidic linkage(s) at the newly formed glycosidic bond(s). In a particular embodiment, the UDP-glucosyltransferase is UGTSl2, or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to any existing glucose on the C13 side of any starting steviol glycoside to give a target steviol glycoside with at least one additional glucose bearing at least one beta 1→2 glucopyranoside glycosidic linkage(s) at the newly formed glycosidic bond(s). In a particular embodiment, the UDP-glucosyltransferase is UGTSl2, or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to any existing glucose on the C13 side of any starting steviol glycoside to give a target steviol glycoside with at least one additional glucose bearing at least one beta 1→3 glucopyranoside glycosidic linkage(s) at the newly formed bond glycosidic bond(s). In a particular embodiment, the UDP-glucosyltransferase is UGT76G1, or a UGT having >85% amino-acid sequence identity with UGT76G1.

In another embodiment, the UDP-glucosyltransferase is any UDP-glucosyltransferase capable of adding at least one glucose unit to any existing glucose on the C13 side of any starting steviol glycoside to give a target steviol glycoside with at least one additional glucose bearing at least one beta 1→4 glucopyranoside glycosidic linkage(s) at the newly formed glycosidic bond(s). In a particular embodiment, the UDP-glucosyltransferase is UGTSl2, or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In another particular embodiment, the UDP-glucosyltransferase is UGT76G1, or a UGT having >85% amino-acid sequence identity with UGT76G1.

In another embodiment, the UDP-glucosyltransferase is any UDP-glucosyltransferase capable of adding at least one glucose unit to any existing glucose on the C13 side of any starting steviol glycoside to give a target steviol glycoside with at least one additional glucose bearing at least one beta 1→6 glucopyranoside glycosidic linkage(s) at the newly formed glycosidic bond(s). In a particular embodiment, the UDP-glucosyltransferase is UGTSl2, or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In one embodiment, the UDP-glucosyltransferase is any UDP-glucosyltransferase capable of adding at least one glucose unit to steviol to form steviolmonoside. In a particular embodiment, the UDP-glucosyltransferase is UGT85C2 or a UGT having >85% amino-acid sequence identity with UGT85C2 or a UGT having >85% amino-acid sequence identity with UGT85C2.

In another embodiment, the UDP-glucosyltransferase is any UDP-glucosyltransferase capable of adding at least one glucose unit to steviol to form steviolmonoside A. In a particular embodiment, the UDP-glucosyltransferase is UGT74G1 or a UGT having >85% amino-acid sequence identity with UGT74G1.

In another embodiment, the UDP-glucosyltransferase is any UDP-glucosyltransferase capable of adding at least one glucose unit to steviolmonoside to form steviolbioside. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to steviolmonoside to form steviolbioside D. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to steviolmonoside to form rubusoside. In a particular embodiment, the UDP-glucosyltransferase is UGT74G1 or a UGT having >85% amino-acid sequence identity with UGT74G1.

In one embodiment, the UDP-glucosyltransferase is any UDP-glucosyltransferase capable of adding at least one glucose unit to steviolmonoside A to form rubusoside. In a particular embodiment, the UDP-glucosyltransferase is UGT85C2 or a UGT having >85% amino-acid sequence identity with UGT85C2 or a UGT having >85% amino-acid sequence identity with UGT85C2.

In another embodiment, the UDP-glucosyltransferase is any UDP-glucosyltransferase capable of adding at least one glucose unit to steviolmonoside A to form steviolbioside A. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to steviolmonoside A to form steviolbioside B. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to steviolbioside to form rebaudioside B. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to steviolbioside to form stevioside. In a particular embodiment, the UDP-glucosyltransferase is UGT74G1 or a UGT having >85% amino-acid sequence identity with UGT74G1.

In another embodiment, the UDP-glucosyltransferase is any UDP-glucosyltransferase capable of adding at least one glucose unit to steviolbioside D to form rebaudioside B. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to steviolbioside D to form rebaudioside G. In a particular embodiment, the UDP-glucosyltransferase is UGT74G1 or a UGT having >85% amino-acid sequence identity with UGT74G1.

In another embodiment, the UDP-glucosyltransferase is any UDP-glucosyltransferase capable of adding at least one glucose unit to rubusoside to form stevioside. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rubusoside to form rebaudioside G. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rubusoside to form stevioside A. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rubusoside to form stevioside B. In a particular embodiment, the UDP-glucosyltransferase is UGT76G1 or a UGT having >85% amino-acid sequence identity with UGT76G1.

In one embodiment, the UDP-glucosyltransferase is any UDP-glucosyltransferase capable of adding at least one glucose unit to steviolbioside A to form stevioside A. In a particular embodiment, the UDP-glucosyltransferase is UGT85C2 or a UGT having >85% amino-acid sequence identity with UGT85C2 or a UGT having >85% amino-acid sequence identity with UGT85C2.

In another embodiment, the UDP-glucosyltransferase is any UDP-glucosyltransferase capable of adding at least one glucose unit to steviolbioside A to form stevioside C. In a particular embodiment, the UDP-glucosyltransferase is UGT76G1 or a UGT having >85% amino-acid sequence identity with UGT76G1.

In one embodiment, the UDP-glucosyltransferase is any UDP-glucosyltransferase capable of adding at least one glucose unit to steviolbioside B to form stevioside B. In a particular embodiment, the UDP-glucosyltransferase is UGT85C2 or a UGT having >85% amino-acid sequence identity with UGT85C2 or a UGT having >85% amino-acid sequence identity with UGT85C2.

In another embodiment, the UDP-glucosyltransferase is any UDP-glucosyltransferase capable of adding at least one glucose unit to steviolbioside B to form stevioside C. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside B to form rebaudioside A. In a particular embodiment, the UDP-glucosyltransferase is UGT74G1 or a UGT having >85% amino-acid sequence identity with UGT74G1.

In another embodiment, the UDP-glucosyltransferase is any UDP-glucosyltransferase capable of adding at least one glucose unit to stevioside to form rebaudioside A. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to stevioside to form rebaudioside E. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to stevioside to form rebaudioside E2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside G to form rebaudioside A. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside G to form rebaudioside E4. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside G to form rebaudioside E6. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to stevioside A to form rebaudioside E. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to stevioside A to form rebaudioside E4. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to stevioside A to form rebaudioside E3. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to stevioside B to form rebaudioside E2. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to stevioside B to form rebaudioside E6. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to stevioside B to form rebaudioside E3. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In one embodiment, the UDP-glucosyltransferase is any UDP-glucosyltransferase capable of adding at least one glucose unit to steviolbioside C to form rebaudioside E3. In a particular embodiment, the UDP-glucosyltransferase is UGT85C2 or a UGT having >85% amino-acid sequence identity with UGT85C2 or a UGT having >85% amino-acid sequence identity with UGT85C2.

In another embodiment, the UDP-glucosyltransferase is any UDP-glucosyltransferase capable of adding at least one glucose unit to rebaudioside A to form rebaudioside D. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside A to form rebaudioside 1. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside E to form rebaudioside D. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside E to form rebaudioside AM. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside E2 to form rebaudioside 1. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside E2 to form rebaudioside AM. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside E4 to form rebaudioside D. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside E4 to form rebaudioside D7. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside E6 to form rebaudioside 1. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside E6 to form rebaudioside D7. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside E3 to form rebaudioside AM In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside E3 to form rebaudioside D7. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside D to form rebaudioside M. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside 1 to form rebaudioside M. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside AM to form rebaudioside M. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside AM to form rebaudioside M4. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside AM to form rebaudioside M5. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside D7 to form rebaudioside M. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1a. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1b. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1c. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1d. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1e. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1f. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1g. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1h. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1i. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1j. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1k. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1l. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1m. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransfer-ase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1n. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1o. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1p. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1q. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1r. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1s. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1t. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2a. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2b. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2c. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2d. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2e. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2f. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2g. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2h. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2i. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2j. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2k. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2l. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2m. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2n. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2o. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2p. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2q. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2r. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2s. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 1q. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M5 to form rebaudioside 1m. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M5 to form rebaudioside 2m. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

Optionally, the method of the present invention further comprises recycling UDP to provide UDP-glucose. In one embodiment, the method comprises recycling UDP by providing a recycling catalyst and a recycling substrate, such that the biotransformation of steviol and/or the steviol glycoside substrate to the target steviol glycoside is carried out using catalytic amounts of UDP-glucosyltransferase and UDP-glucose.

In one embodiment, the recycling catalyst is sucrose synthase SuSy_At or a sucrose synthase having >85% amino-acid sequence identity with SuSy_At.

In one embodiment, the recycling substrate for UDP-glucose recycling catalyst is sucrose.

Optionally, the method of the present invention further comprises the use of transglycosidases that use oligo- or poly-saccharides as the sugar donor to modify recipient target steviol glycoside molecules. Non-limiting examples include cyclodextrin glycosyltransferase (CGTase), fructofuranosidase, amylase, saccharase, glucosucrase, beta-h-fructosidase, beta-fructosidase, sucrase, fructosylinvertase, alkaline invertase, acid invertase, fructofuranosidase. In some embodiments, glucose and sugar(s) other than glucose, including but not limited to fructose, xylose, rhamnose, arabinose, deoxyglucose, galactose are transferred to the recipient target steviol glycosides. In one embodiment, the recipient steviol glycoside is rebaudioside 1a, rebaudioside 1b, rebaudioside 1c, rebaudioside 1d rebaudioside 1e, rebaudioside 1f; rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f; rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, and/or rebaudioside 2s. In another embodiment, the recipient steviol glycoside is rebaudioside 4. In another embodiment, the recipient steviol glycoside is rebaudioside M5. In another embodiment, the recipient steviol glycoside is SvG7.

Optionally, the method of the present invention further comprises separating the target steviol glycoside from the medium to provide a highly purified target steviol glycoside composition. The target steviol glycoside can be separated by at least one suitable method, such as, for example, crystallization, separation by membranes, centrifugation, extraction, chromatographic separation or a combination of such methods.

In one embodiment, the target steviol glycoside can be produced within the microorganism. In another embodiment, the target steviol glycoside can be secreted out in the medium. In one another embodiment, the released steviol glycoside can be continuously removed from the medium. In yet another embodiment, the target steviol glycoside is separated after the completion of the conversion reaction.

In one embodiment, separation produces a composition comprising greater than about 80% by weight of the target steviol glycoside on an anhydrous basis, i.e., a highly purified steviol glycoside composition. In another embodiment, separation produces a composition comprising greater than about 90% by weight of the target steviol glycoside. In particular embodiments, the composition comprises greater than about 95% by weight of the target steviol glycoside. In other embodiments, the composition comprises greater than about 99% by weight of the target steviol glycoside.

The target steviol glycoside can be in any polymorphic or amorphous form, including hydrates, solvates, anhydrous or combinations thereof.

Purified target steviol glycosides can be used in consumable products as a sweetener, flavor modifier, flavor with modifying properties and/or foaming suppressor. Suitable consumer products include, but are not limited to, food, beverages, pharmaceutical compositions, tobacco products, nutraceutical compositions, oral hygiene compositions, and cosmetic compositions.

BRIEF DESCRIPTION OF THE DRAWINGS

FIG. 12c shows the HPLC chromatogram of rebaudioside 2a after purification by HPLC. The peak with retention time of 6.261 minutes correspond to rebaudioside 2a.

FIG. 12d shows the HPLC chromatogram of rebaudioside 2m after purification by HPLC. The peak with retention time of 5.197 minutes correspond to rebaudioside 2m.

FIG. 13g shows the LC chromatogram of rebaudioside 2a.

FIG. 13h shows the mass spectrum of rebaudioside 2a.

DETAILED DESCRIPTION

Figure 1A:
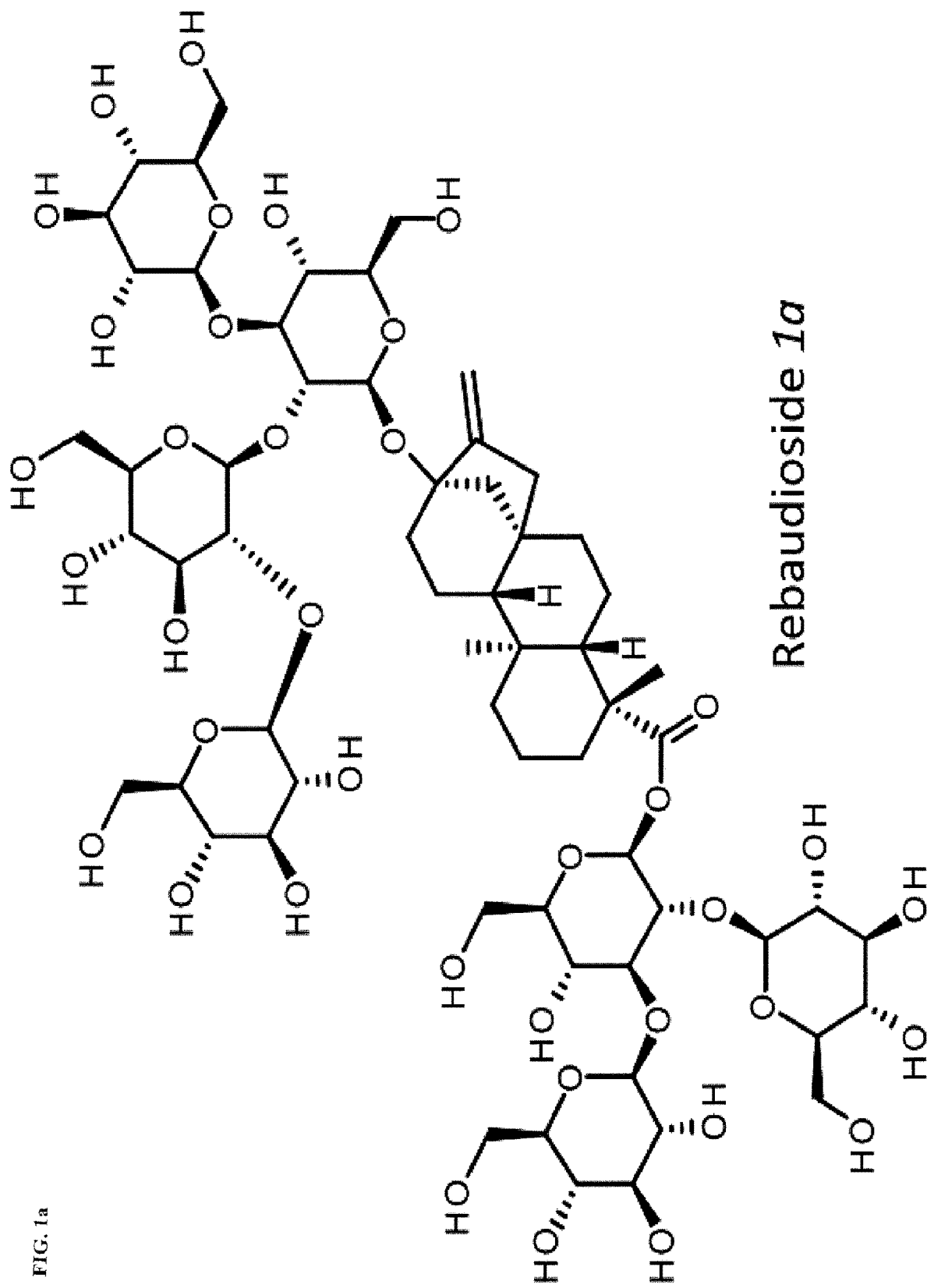
FIG. 1a through FIG. 1t show the chemical structure of some SvG7 steviol glycosides rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s and rebaudioside 1t respectively.
Figure 1B:
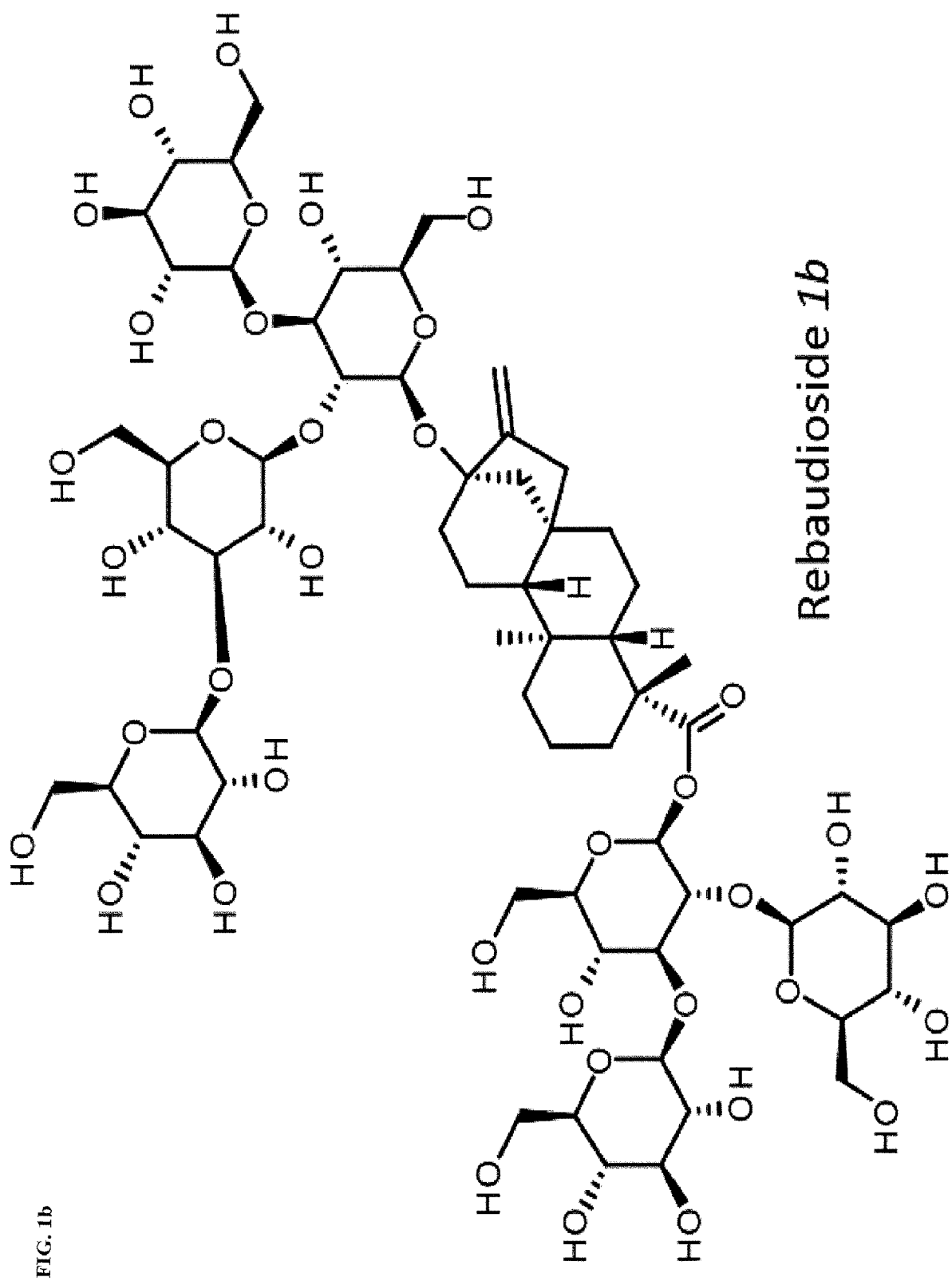
Figure 1C:
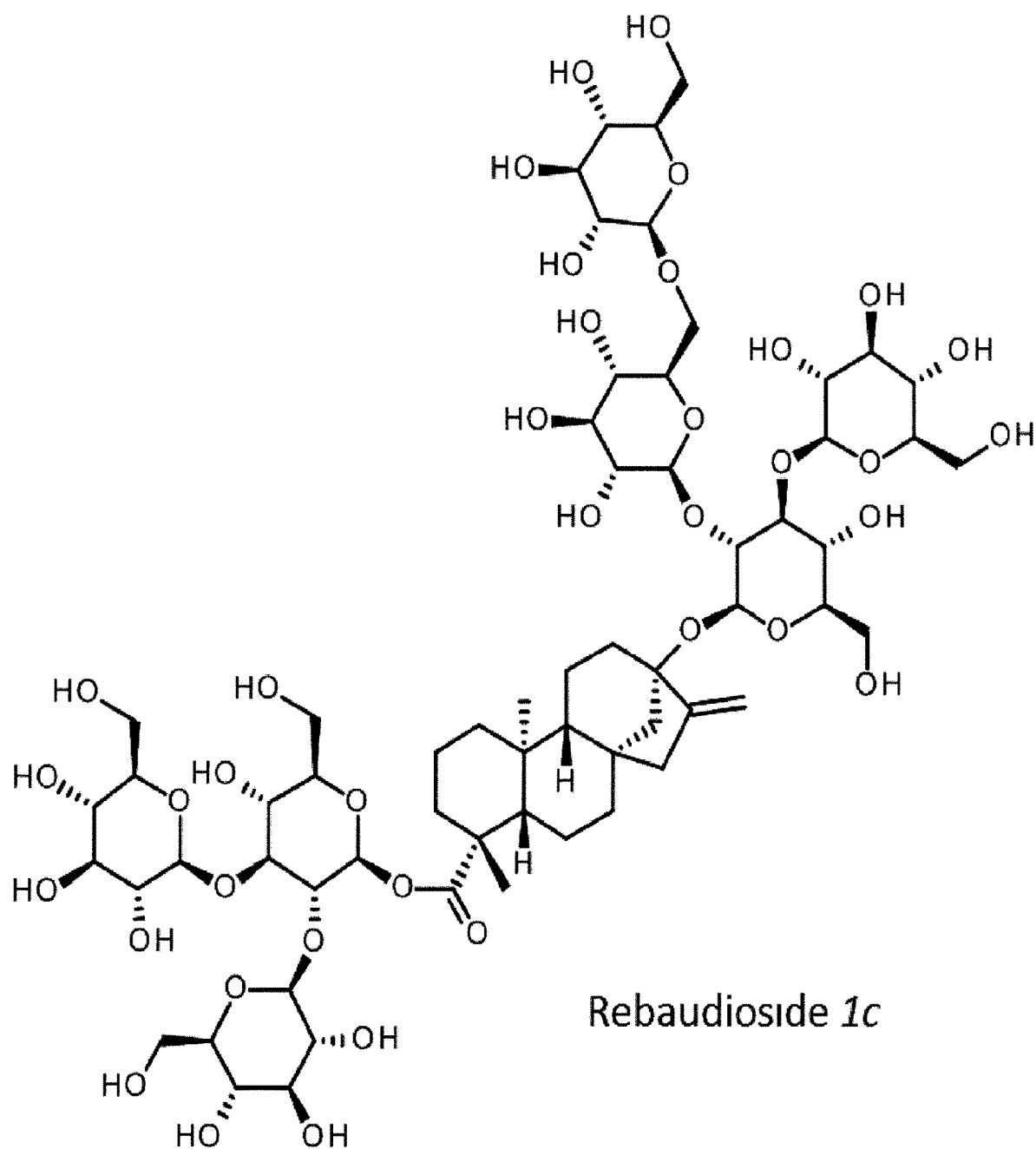
Figure 1D:
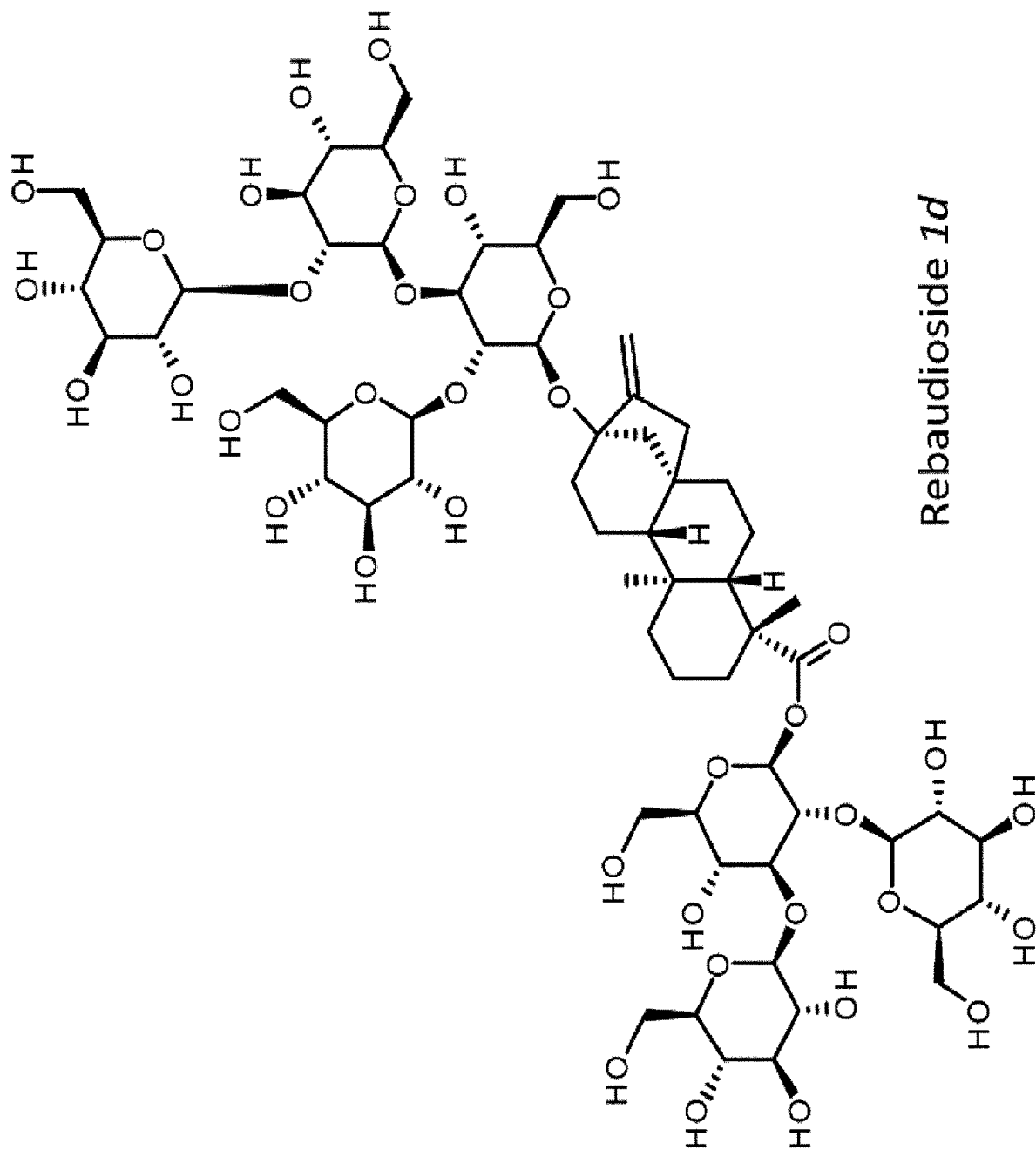
Figure 1E:
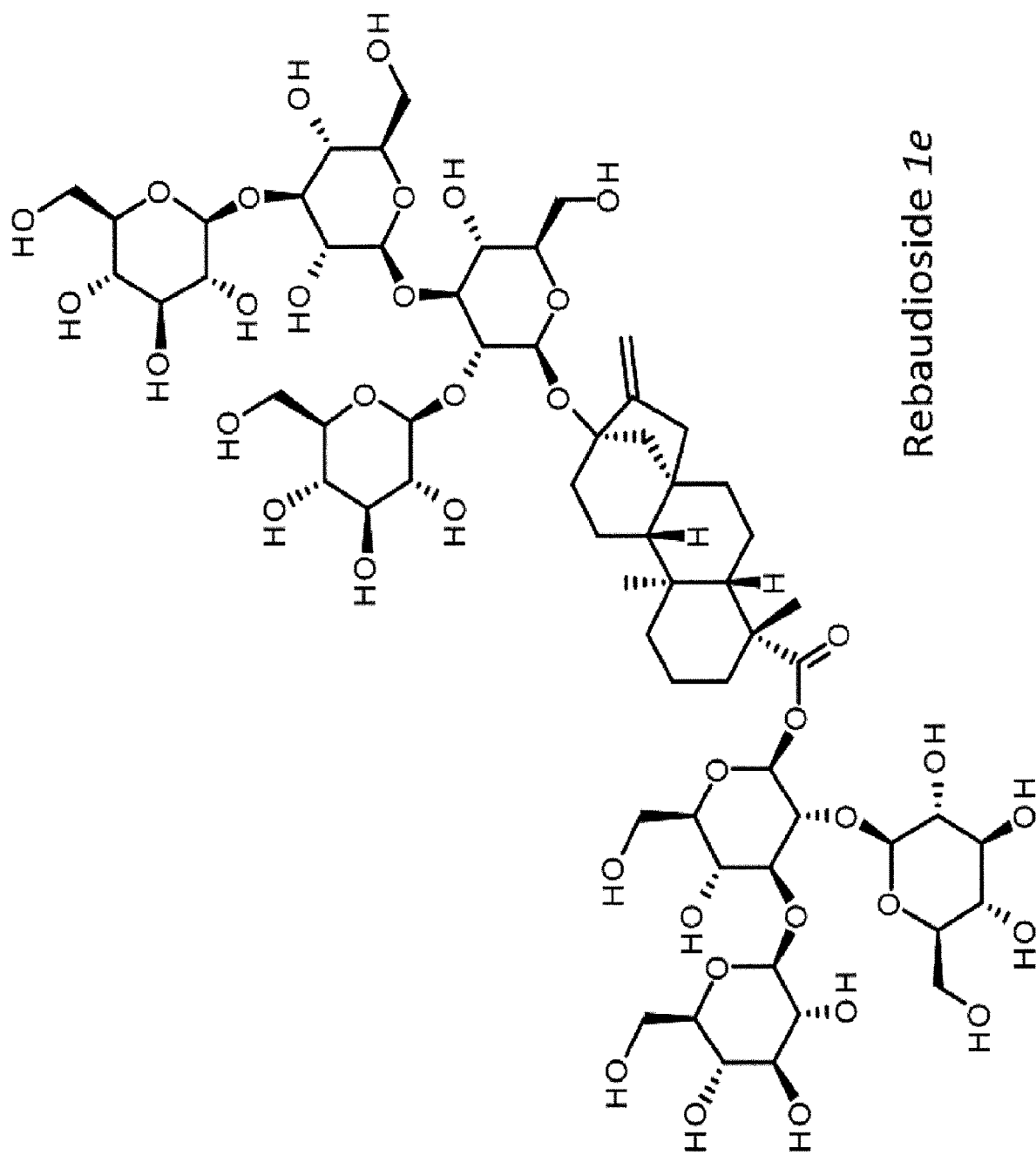
Figure 1F:
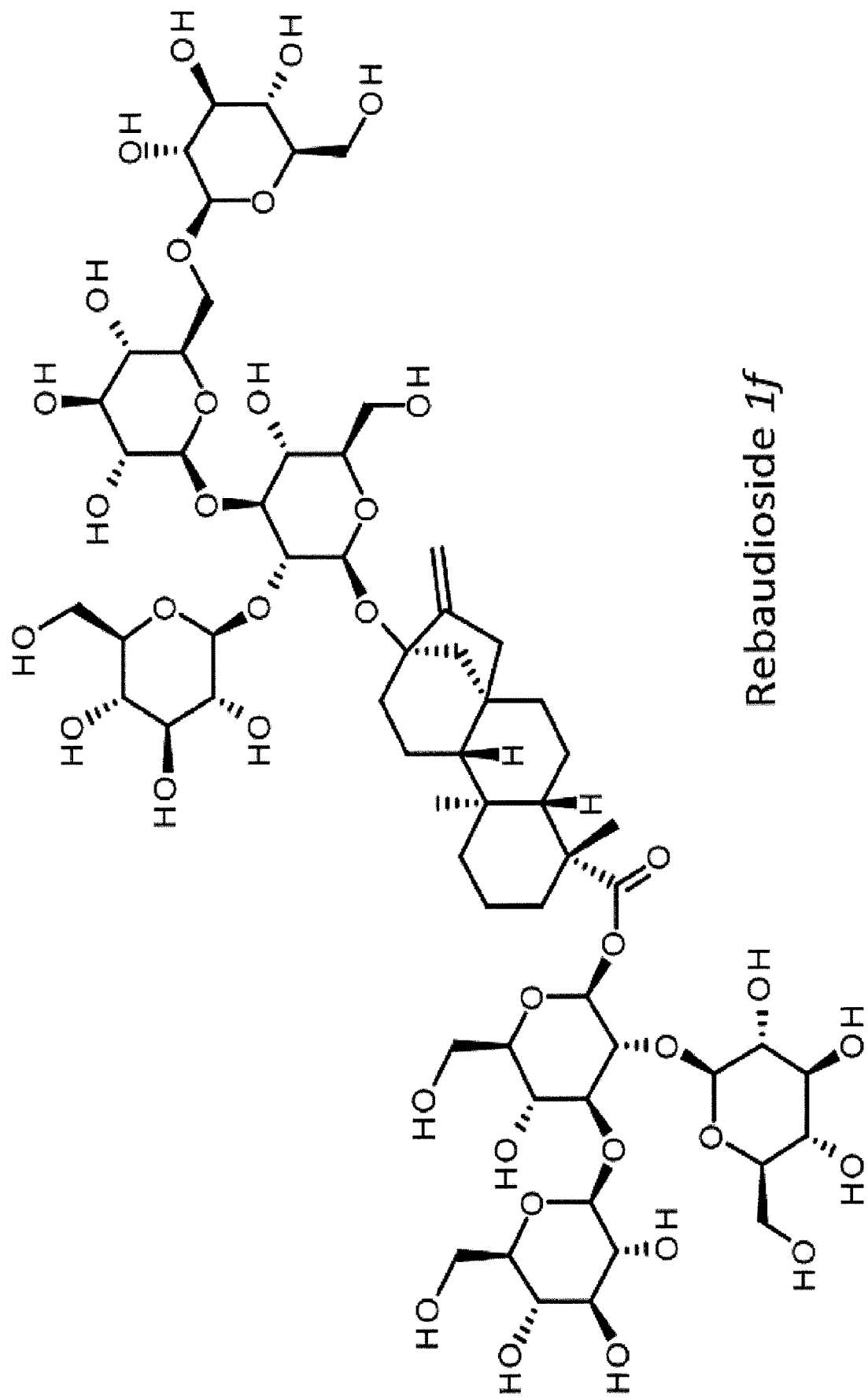
Figure 1G:
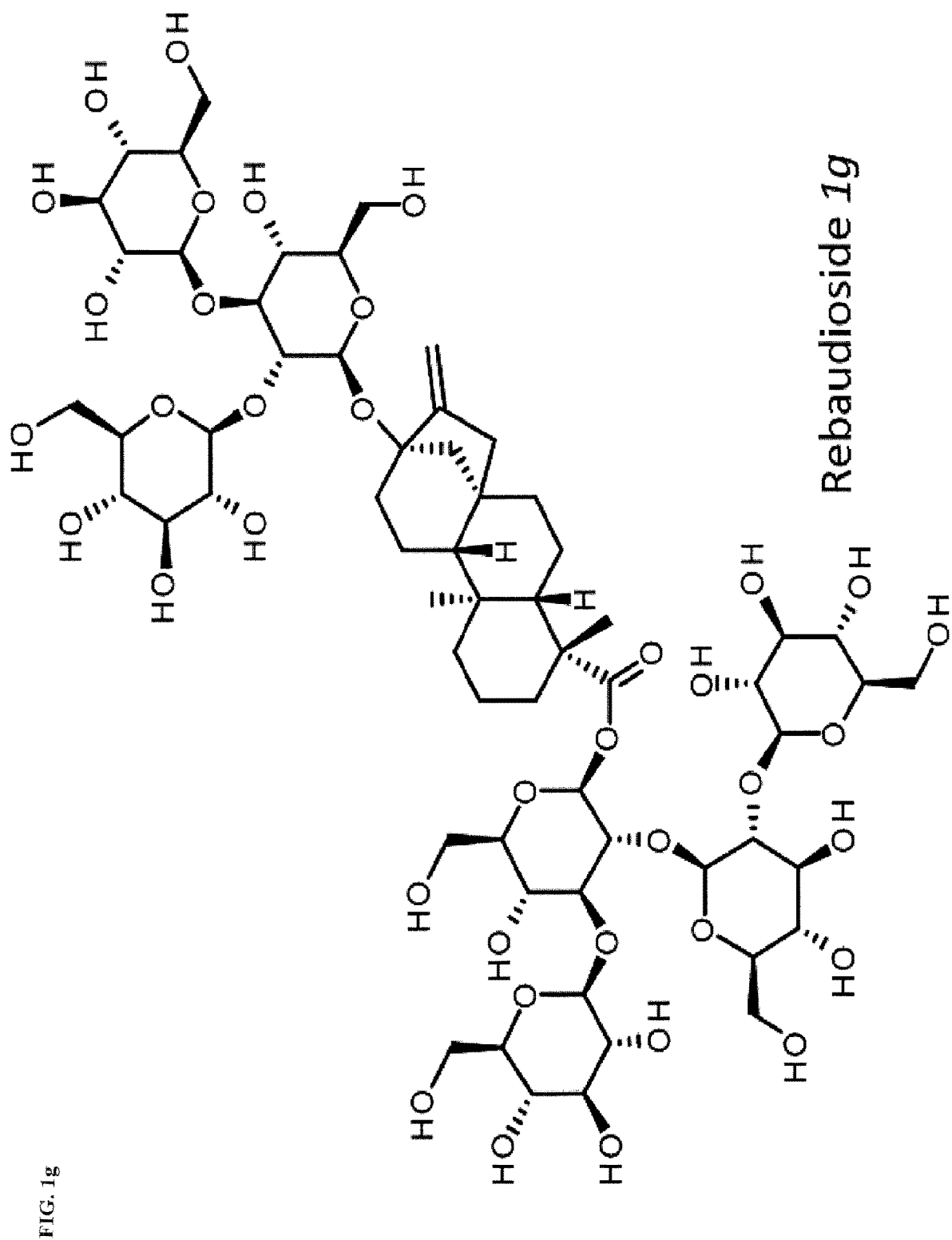
Figure 1I:
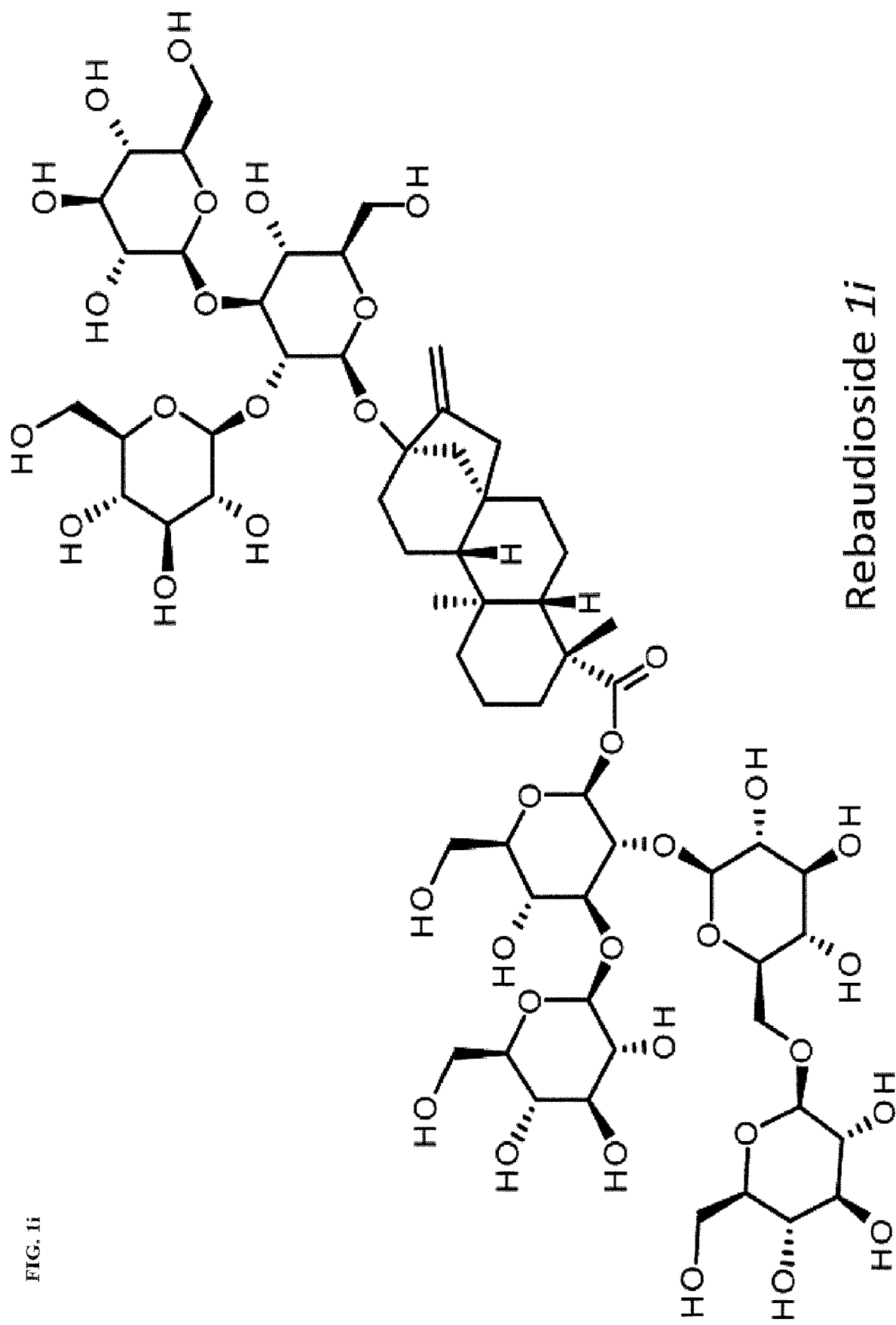
Figure 1K:
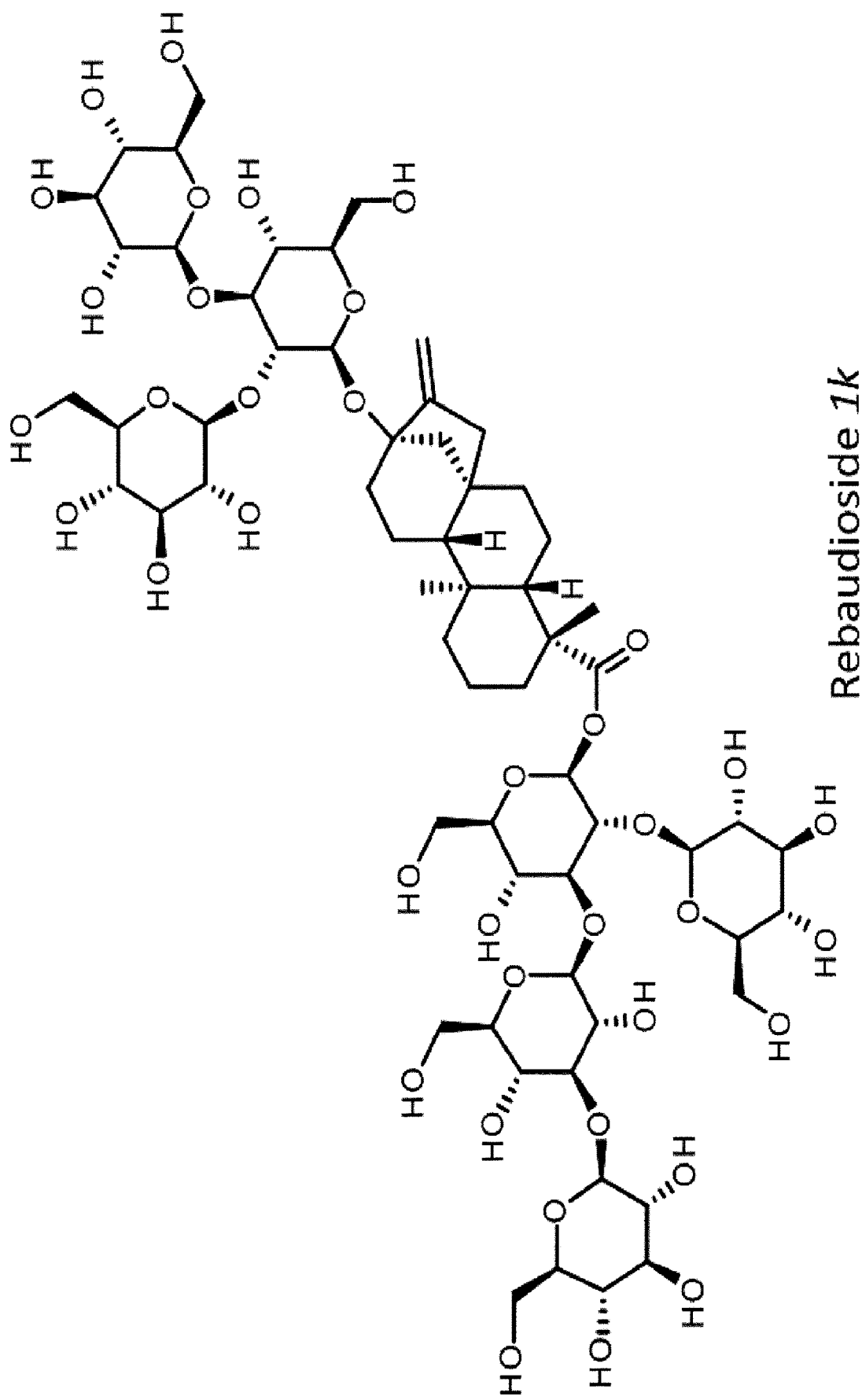
Figure 1O:
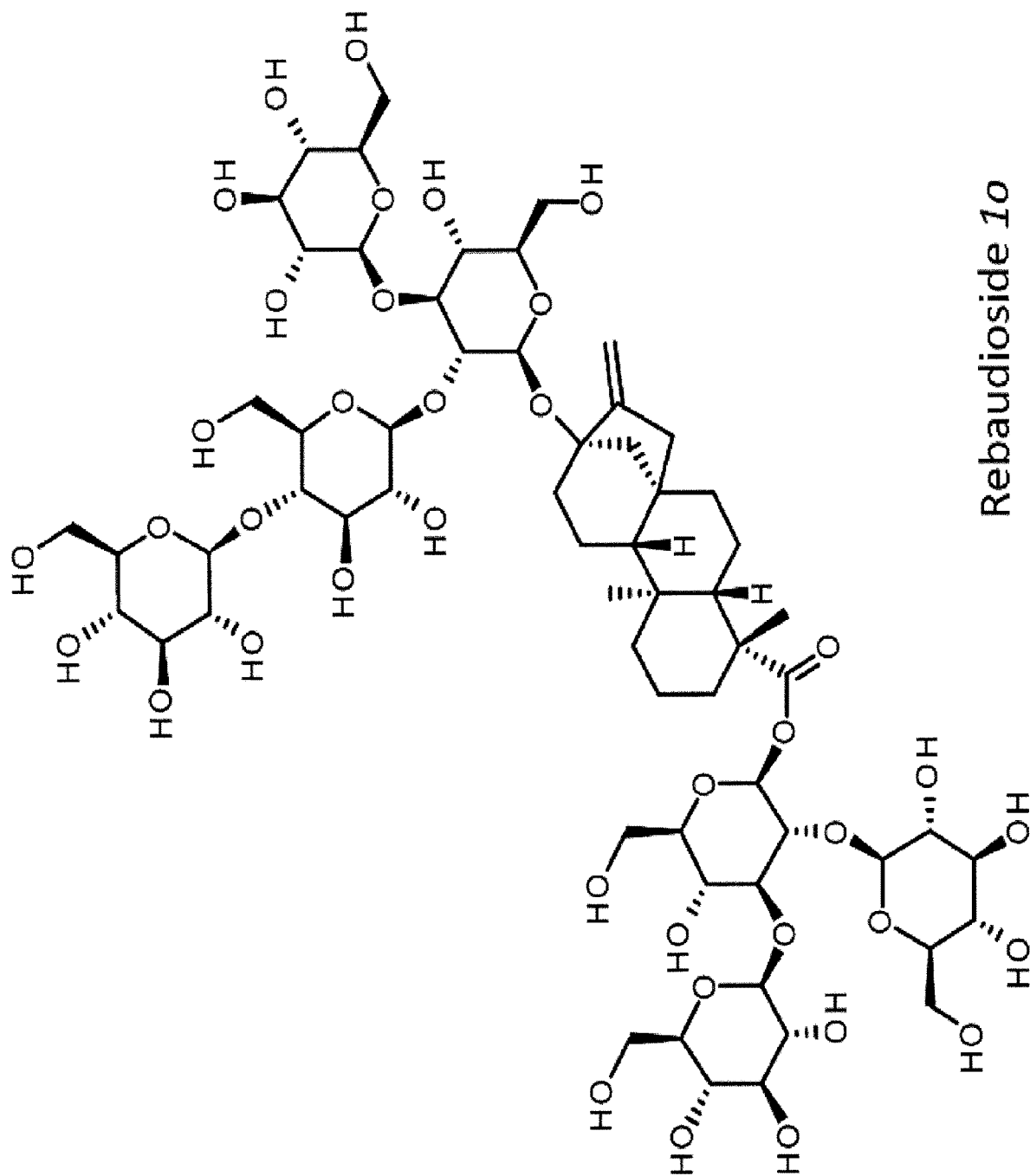
Figure 1P:
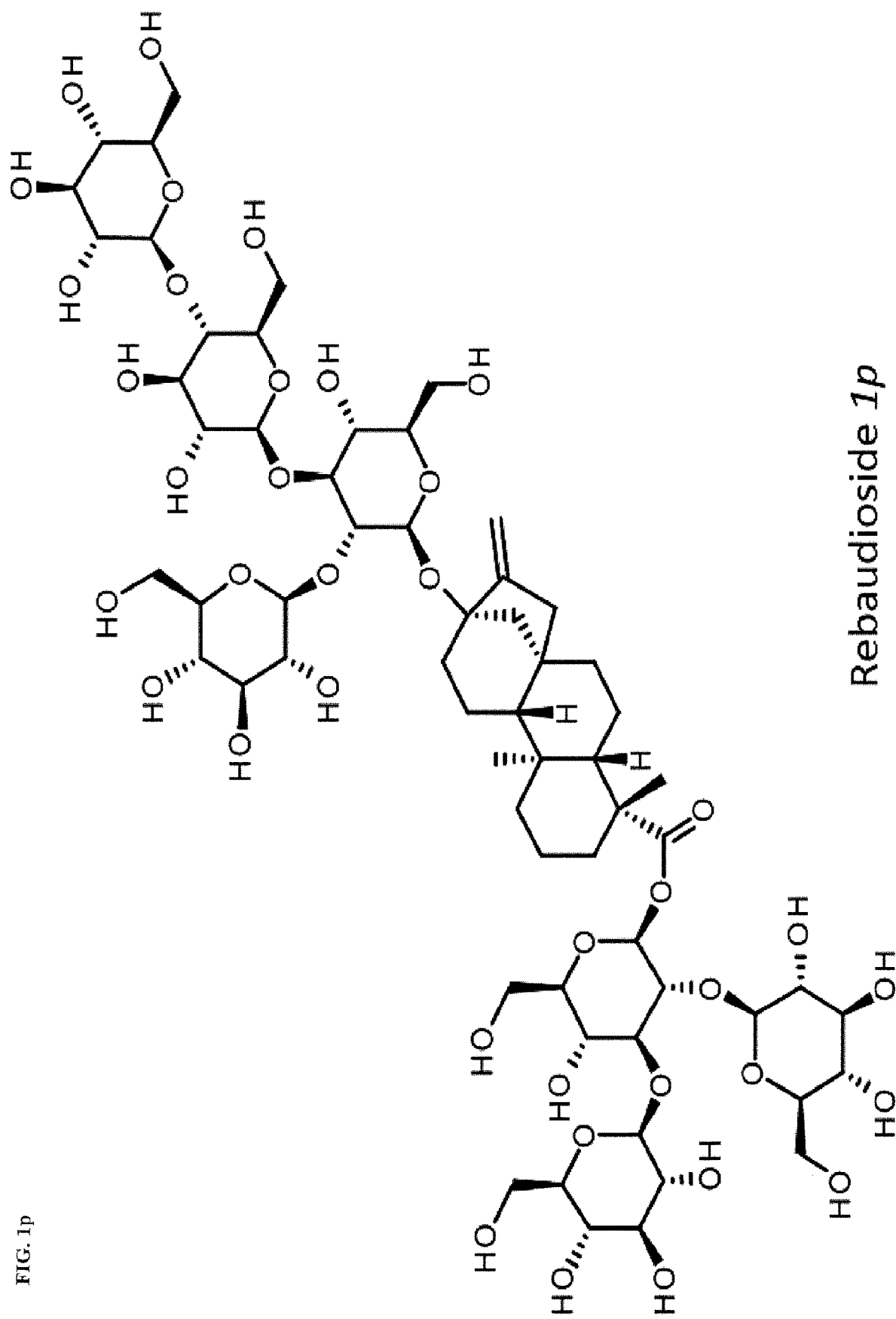
Figure 1Q:
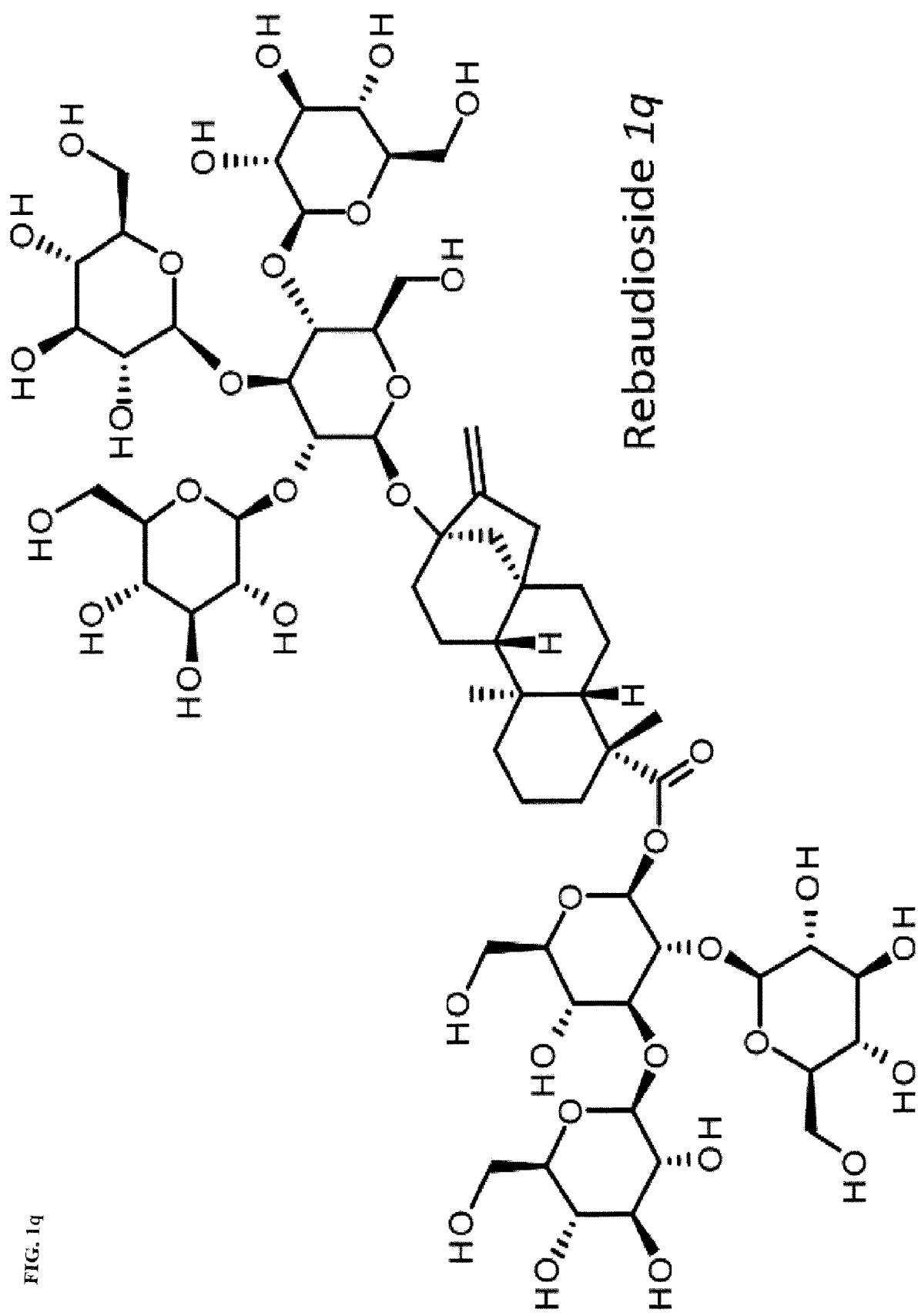
Figure 1S:
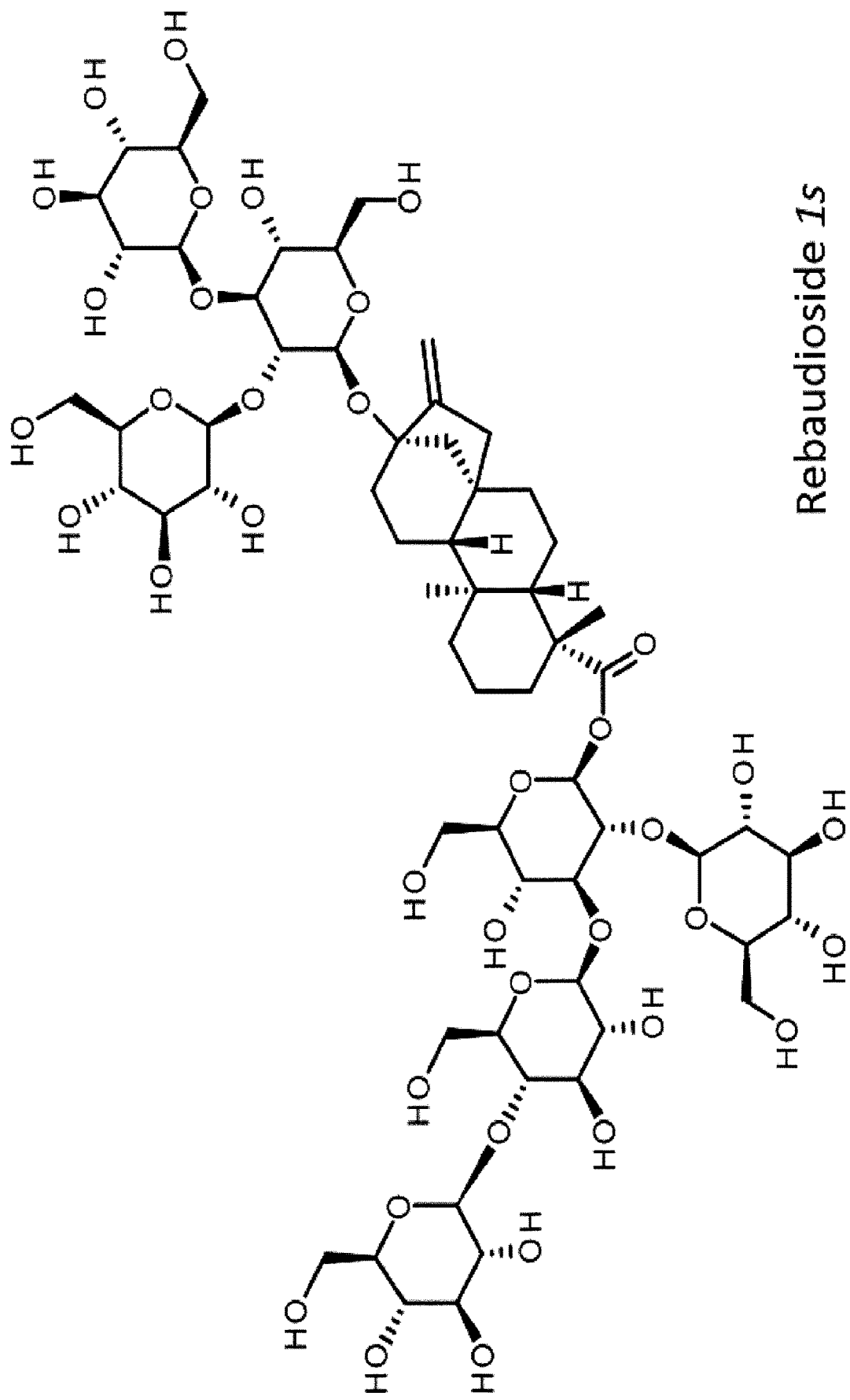
Figure 2A:
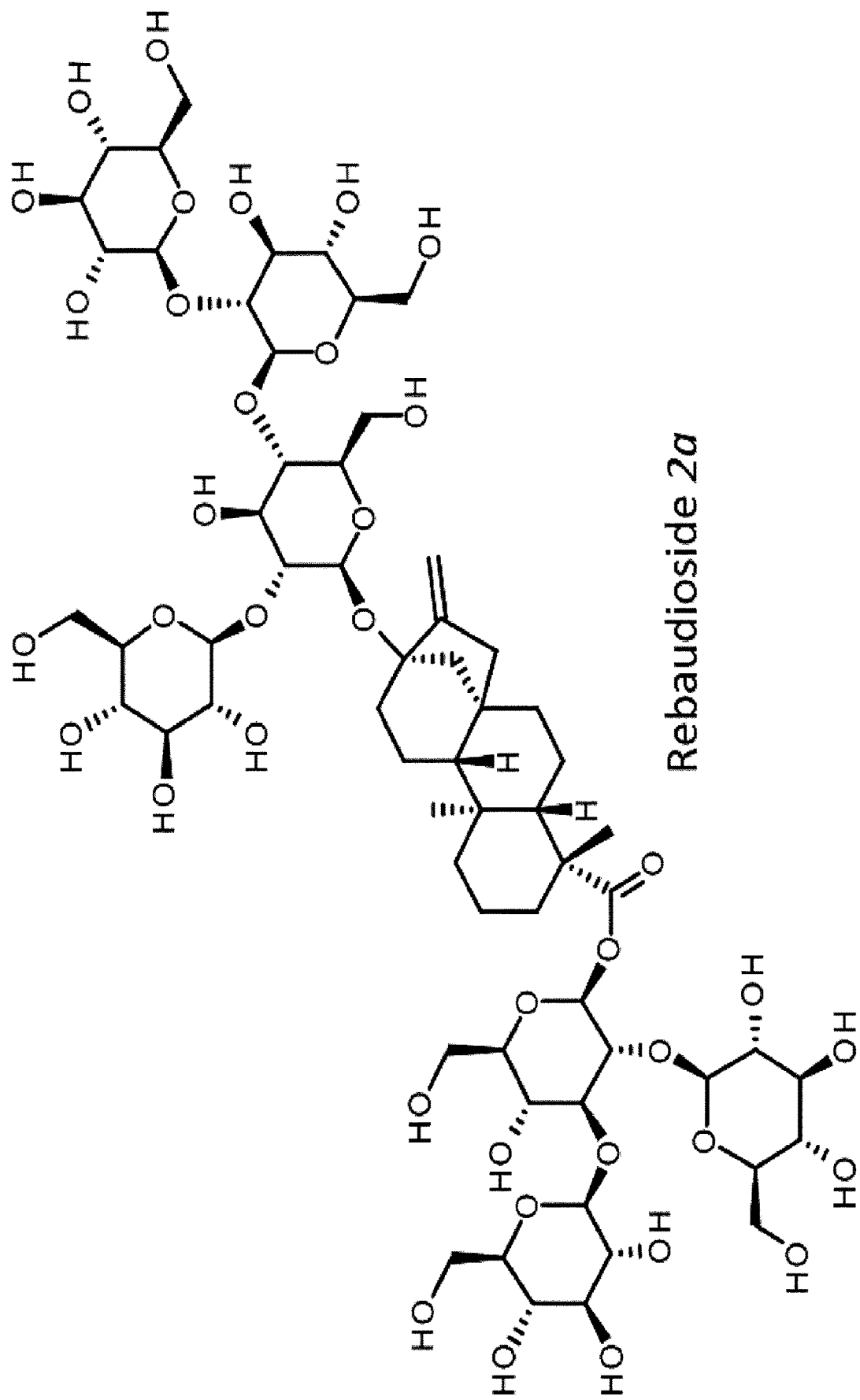
FIG. 2a through FIG. 2s show the chemical structure of some SvG7 steviol glycosides rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r and rebaudioside 2s respectively.
Figure 2C:
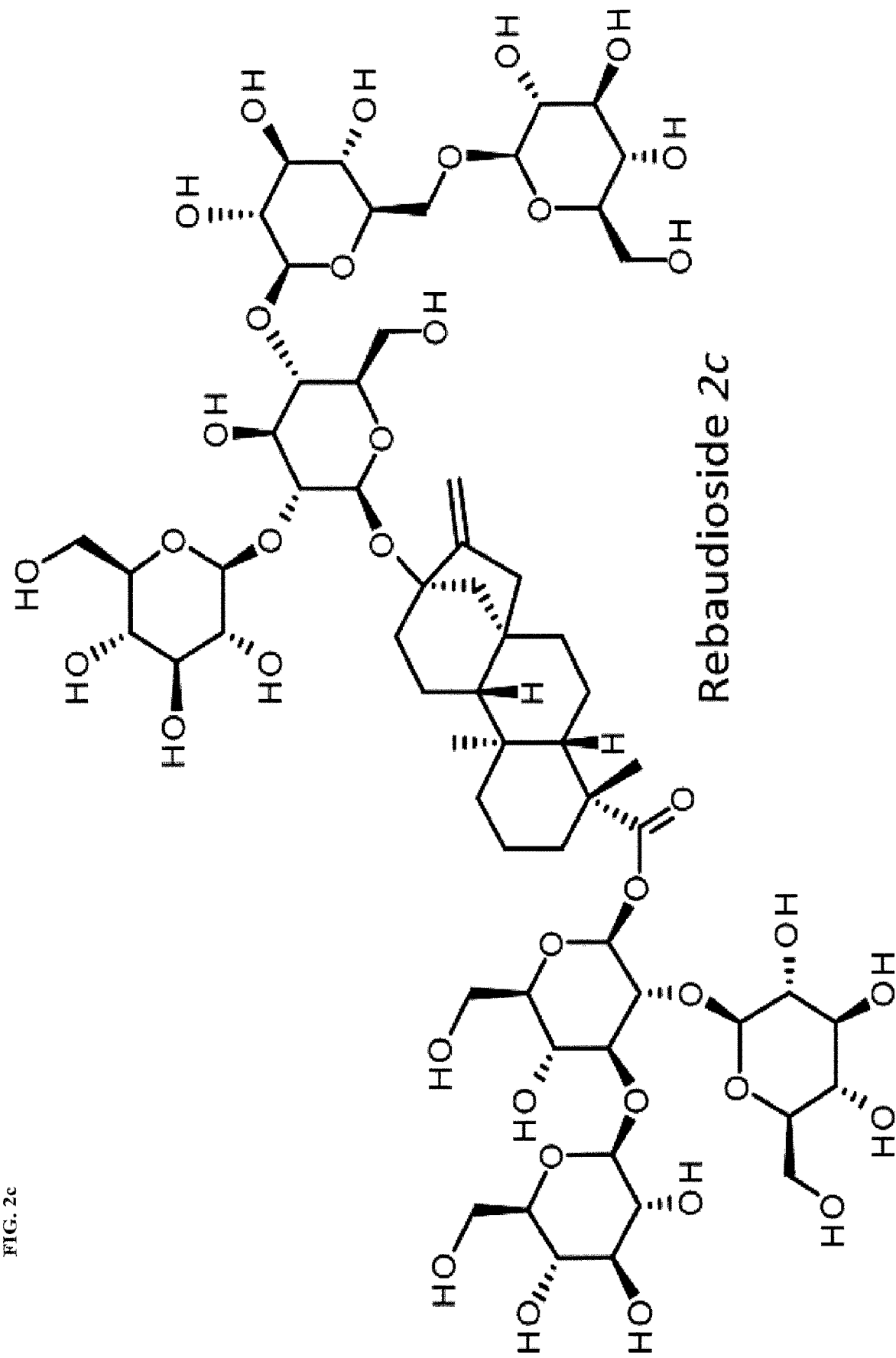
Figure 2D:
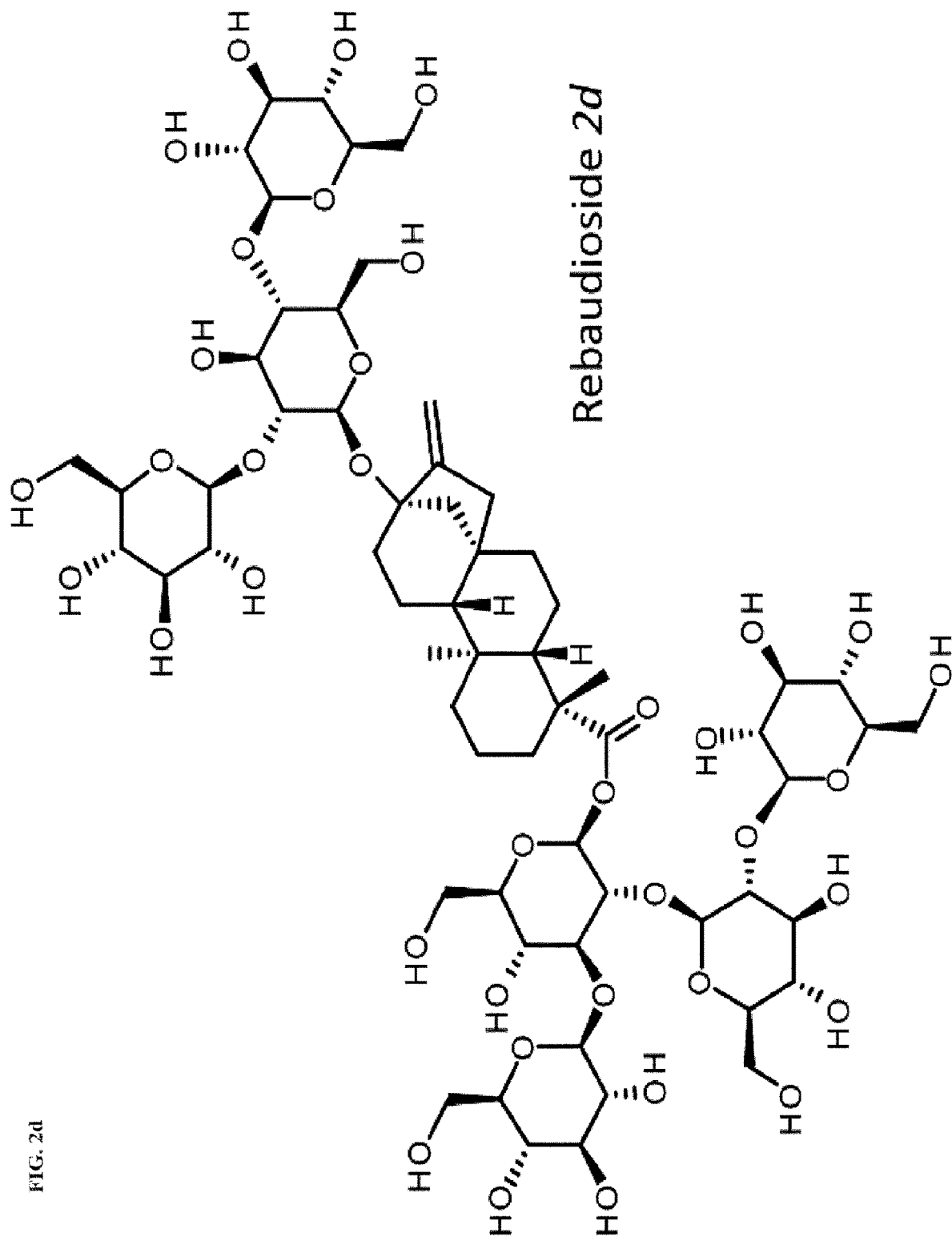
Figure 2E:
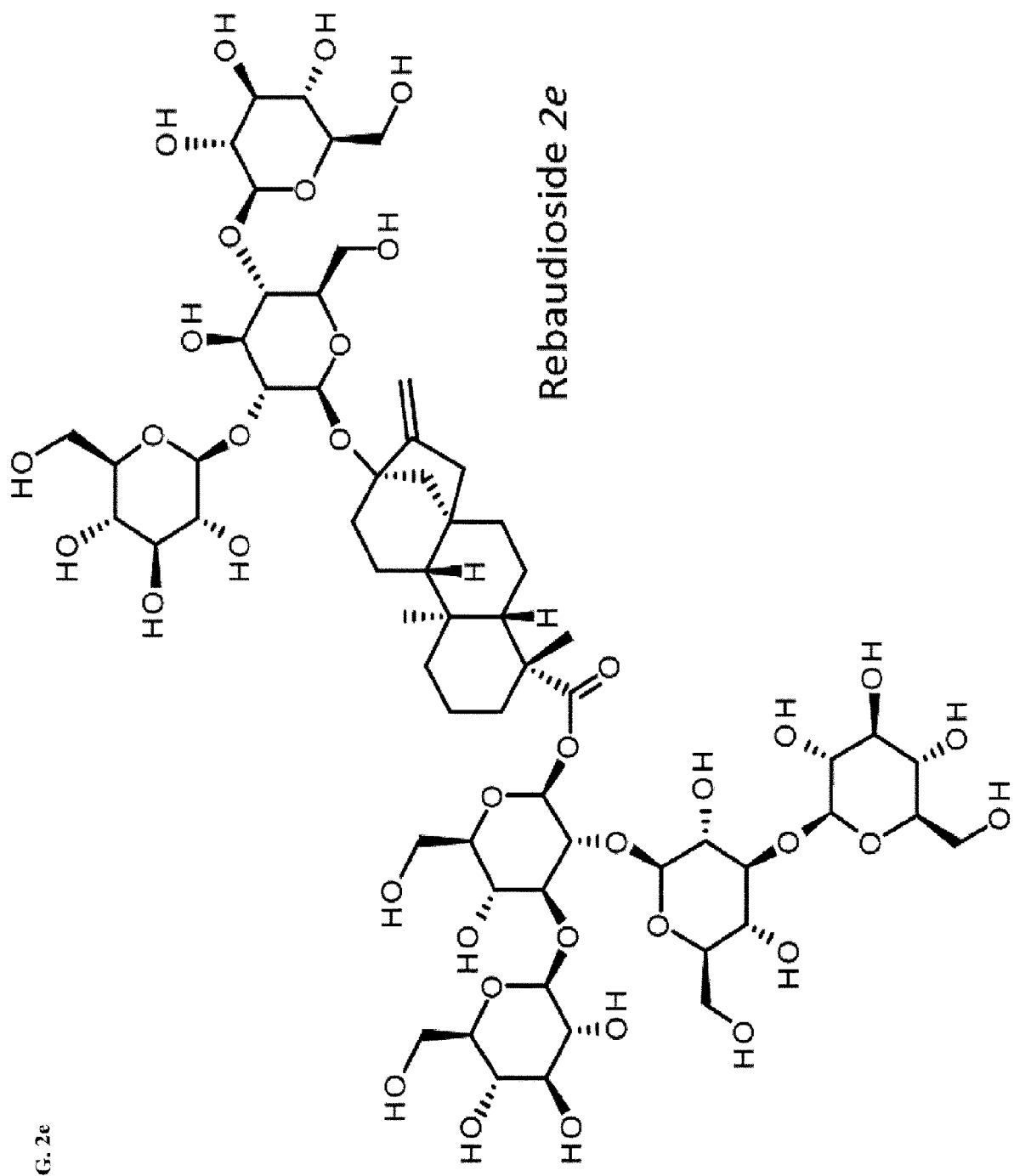
Figure 2F:
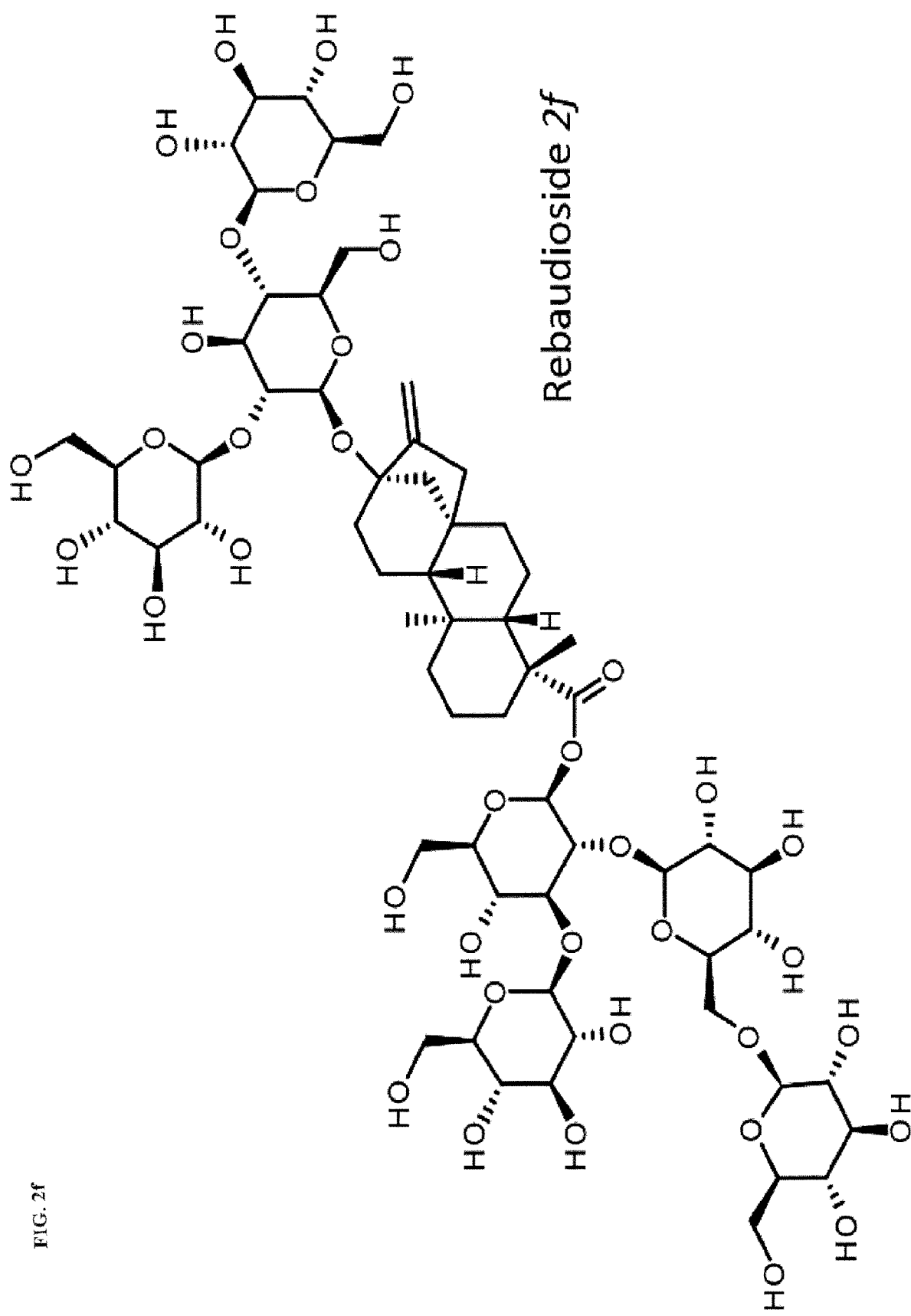
Figure 2G:
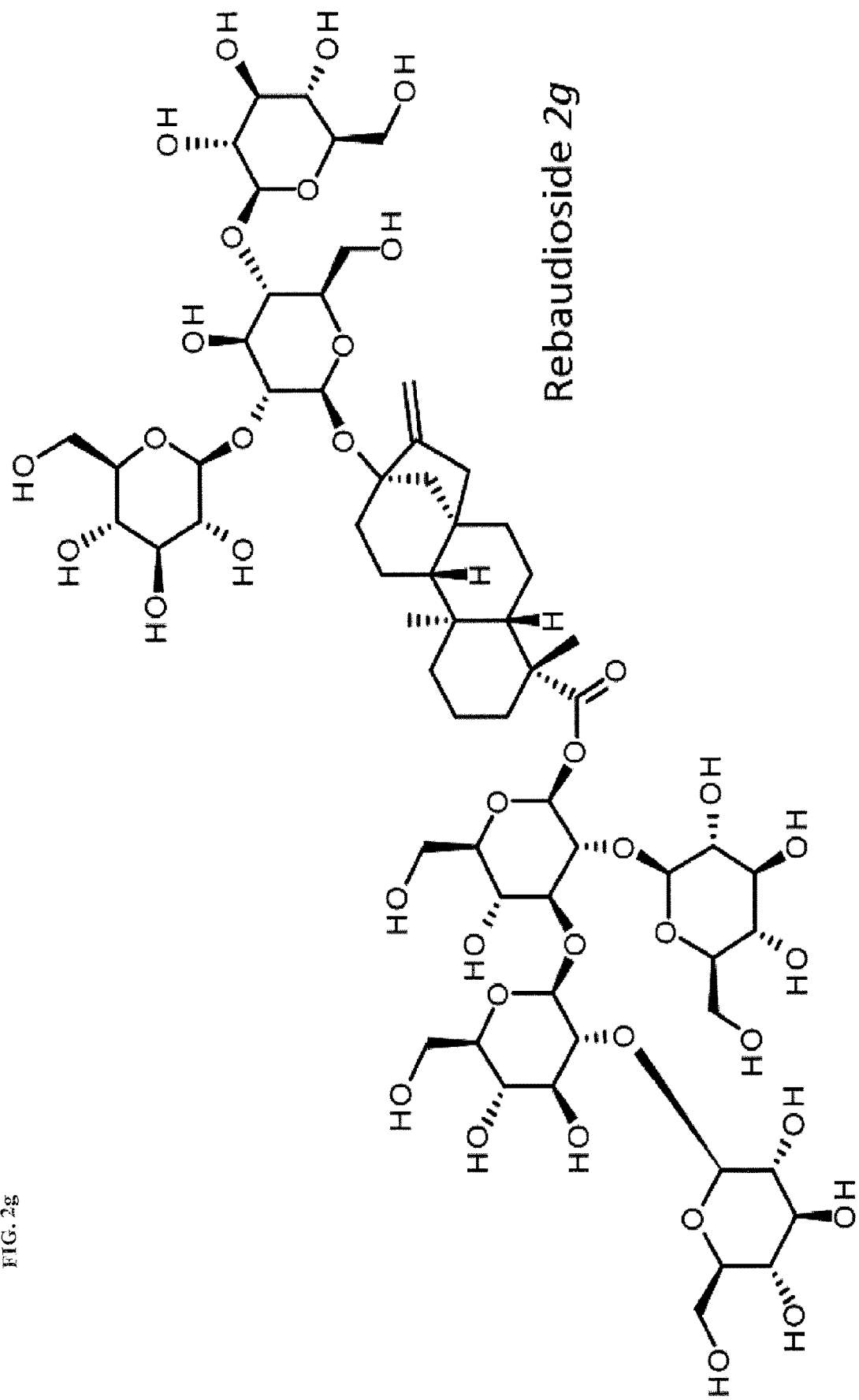
Figure 2H:
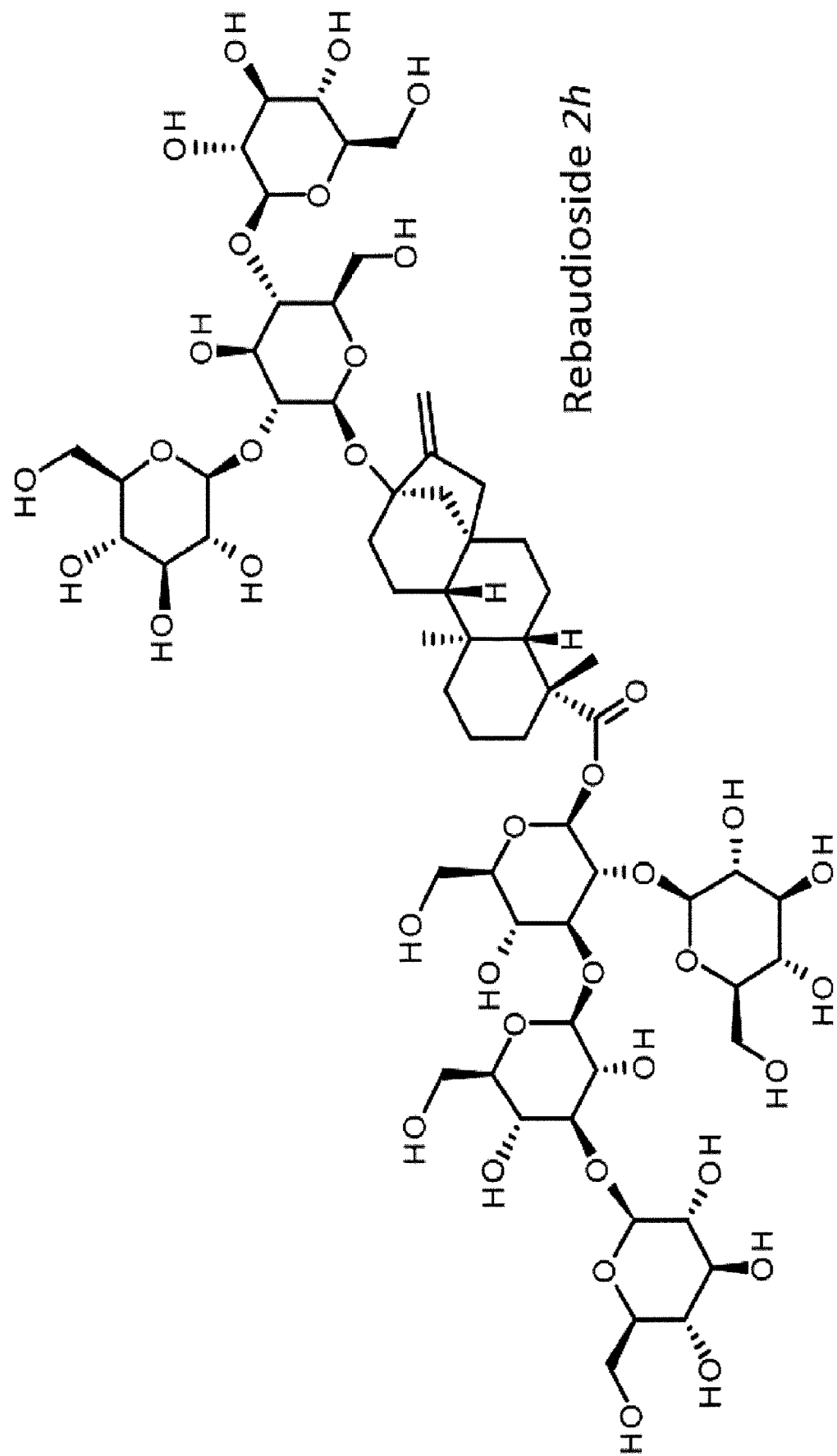
Figure 2I:
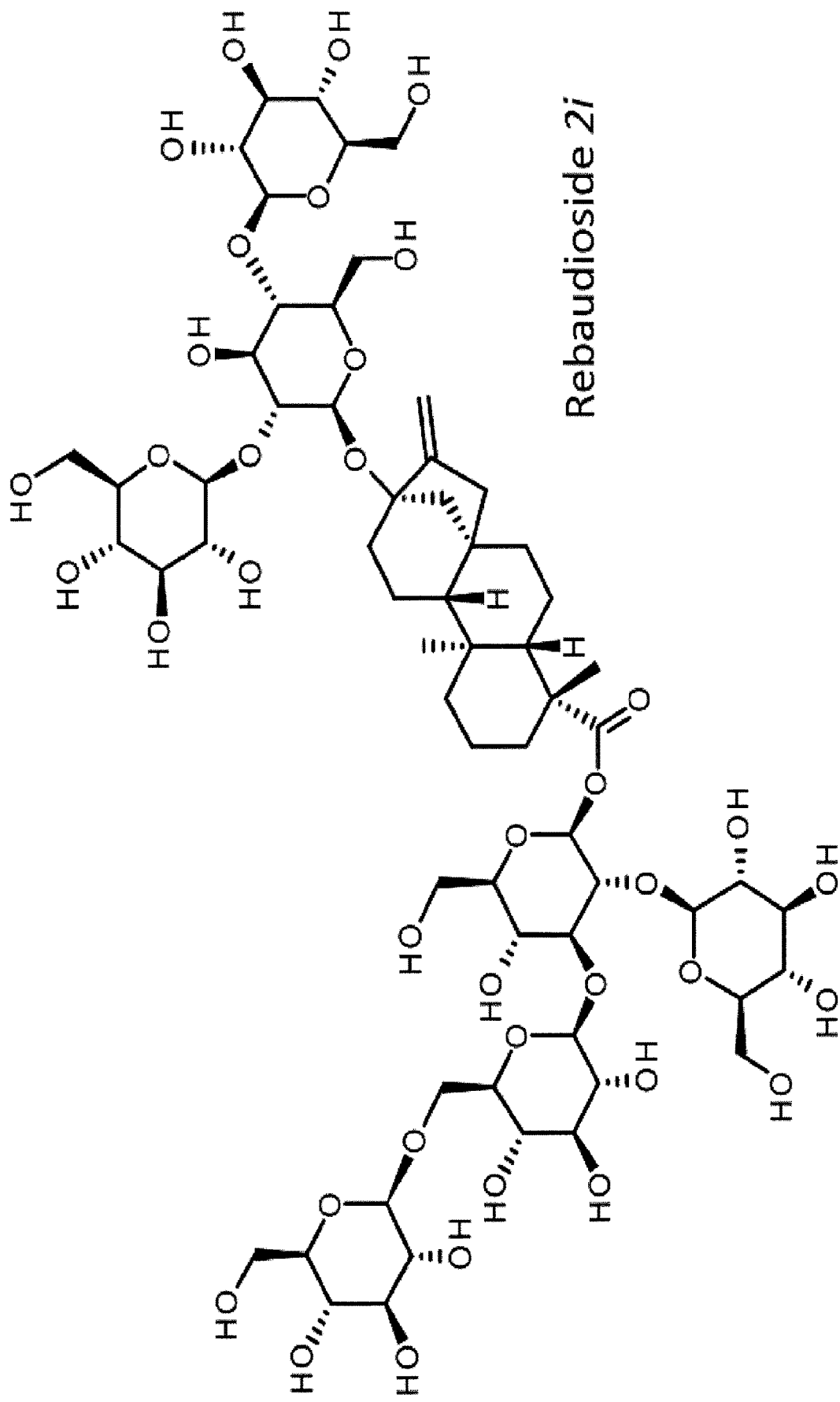
Figure 2J:
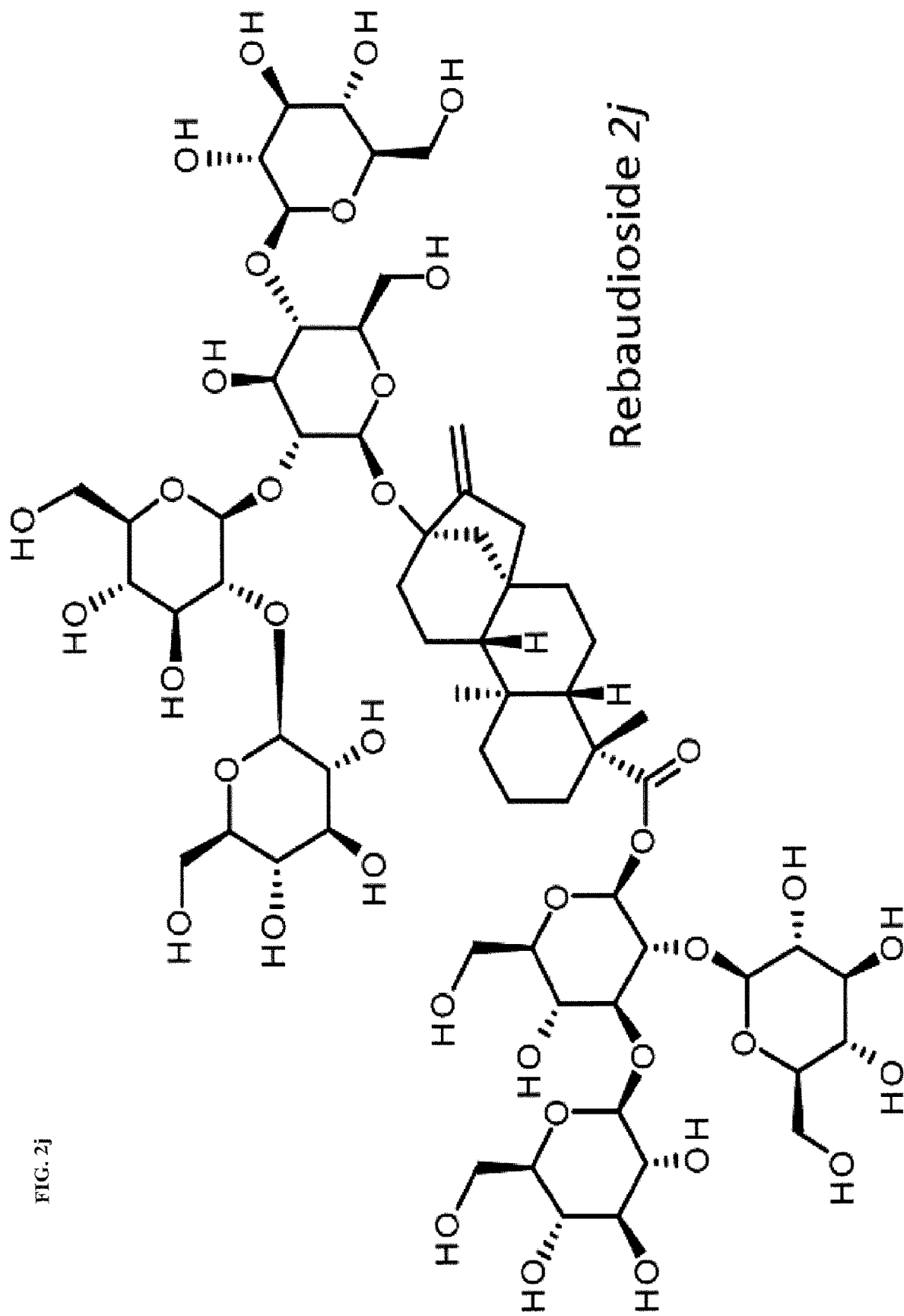
Figure 2K:
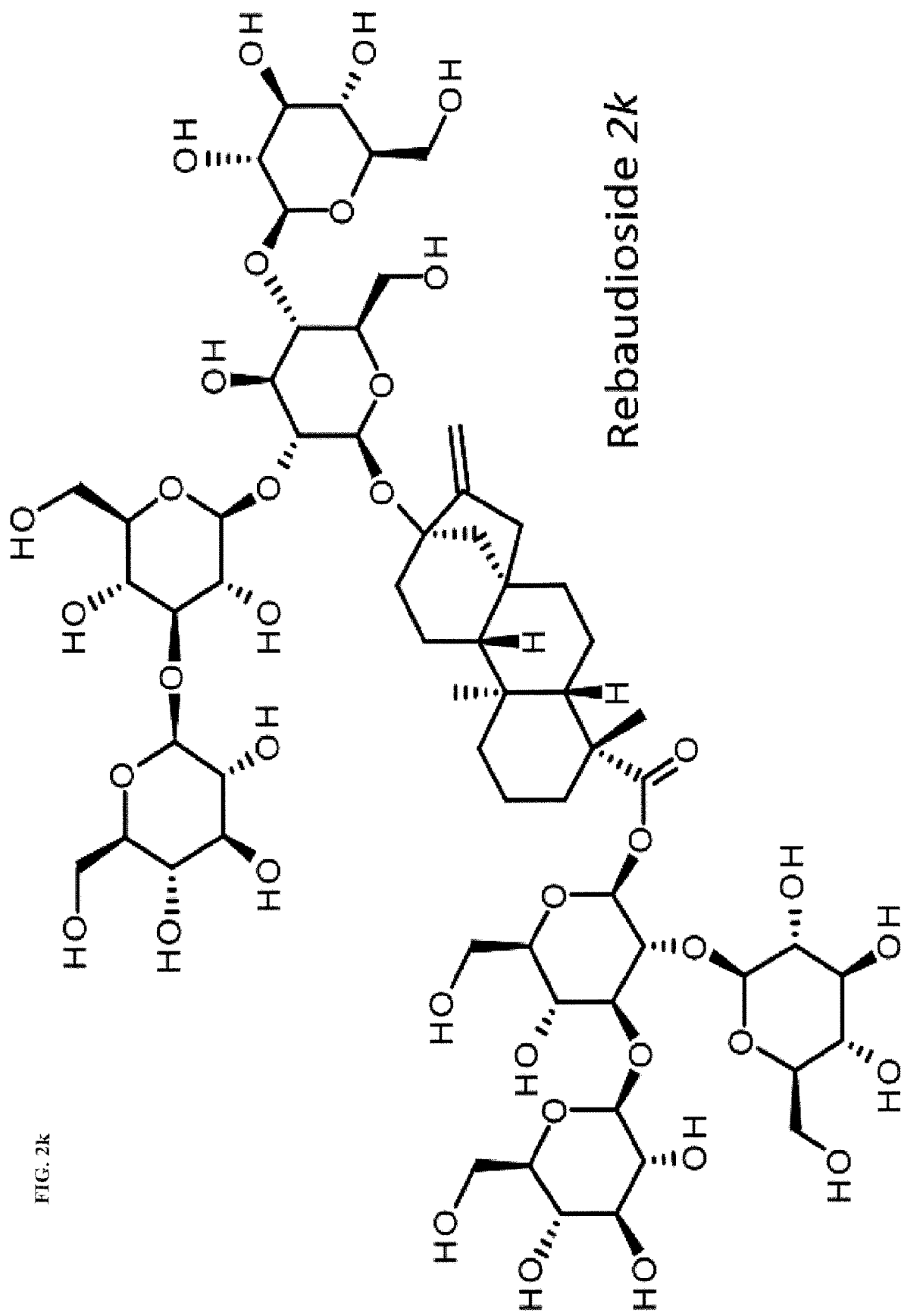
Figure 2I:
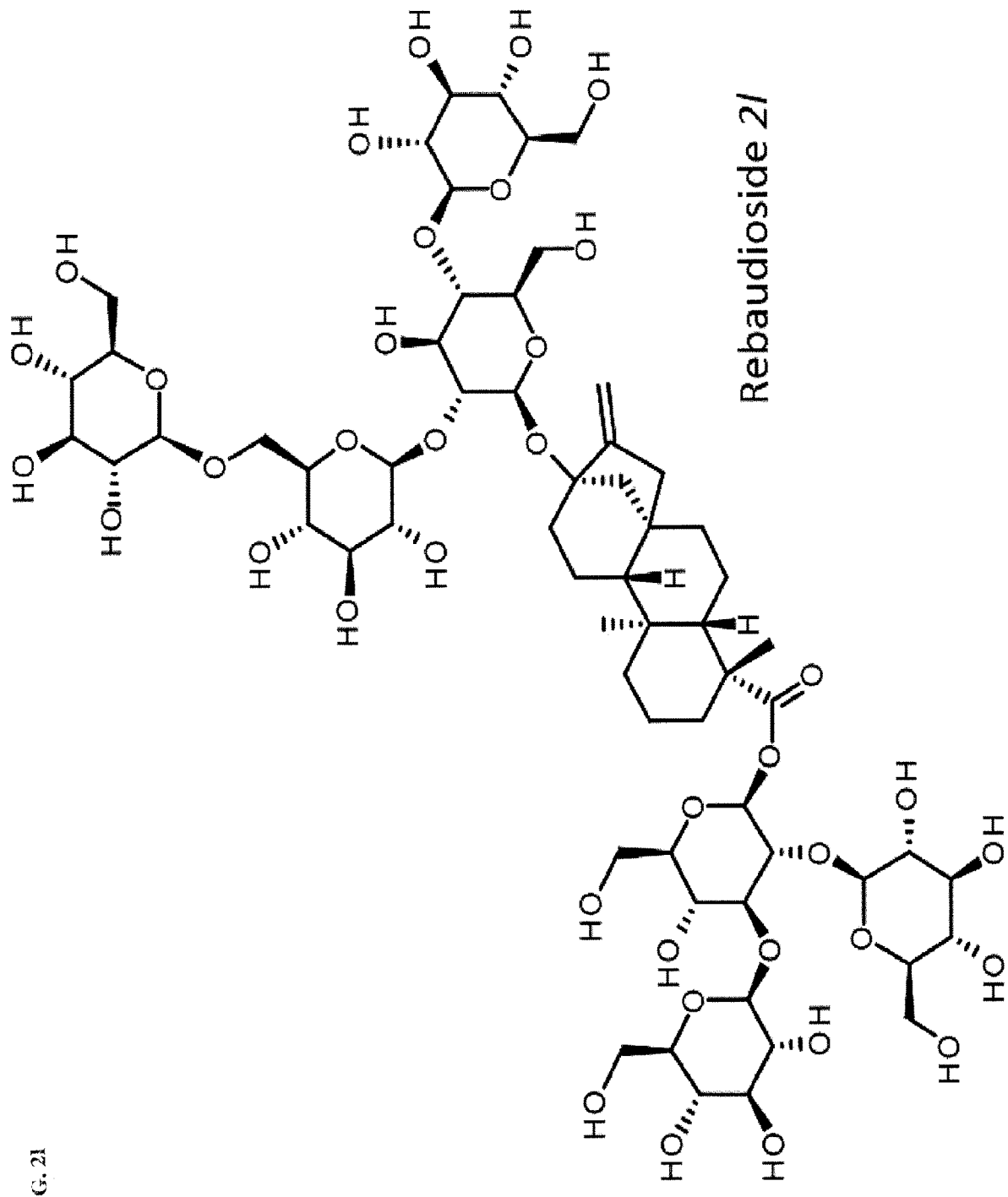
Figure 2M:
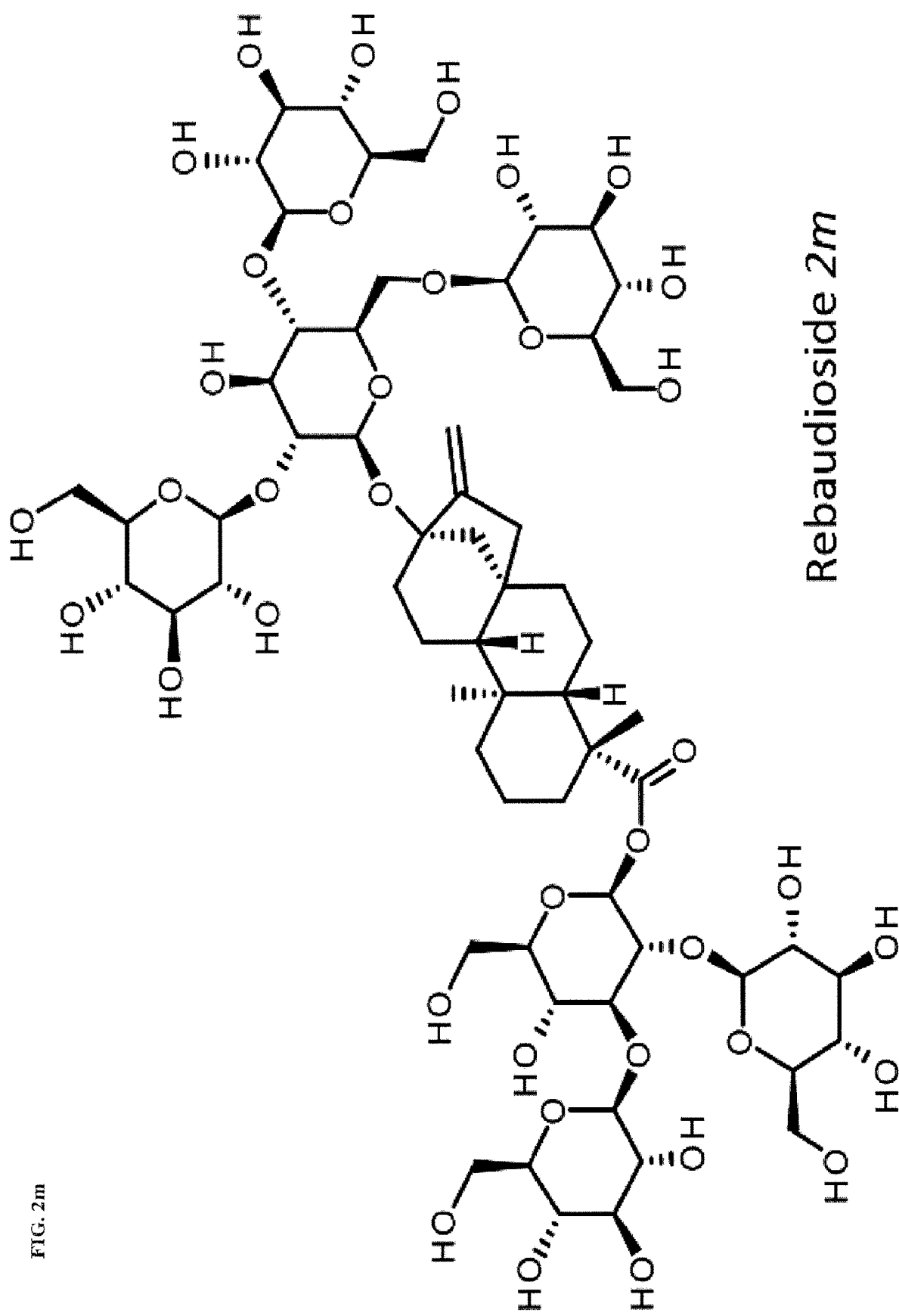
Figure 2N:
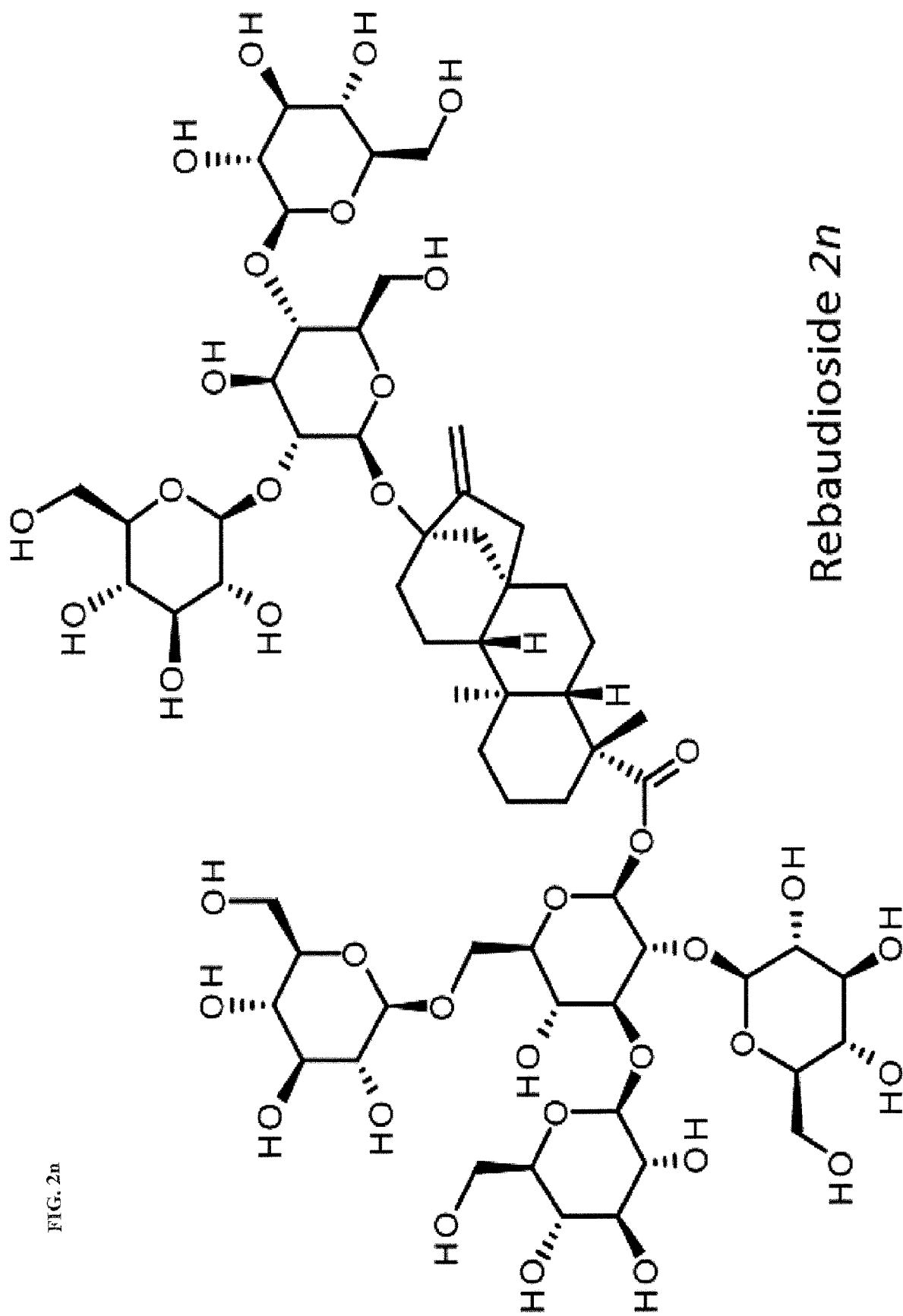
Figure 2O:
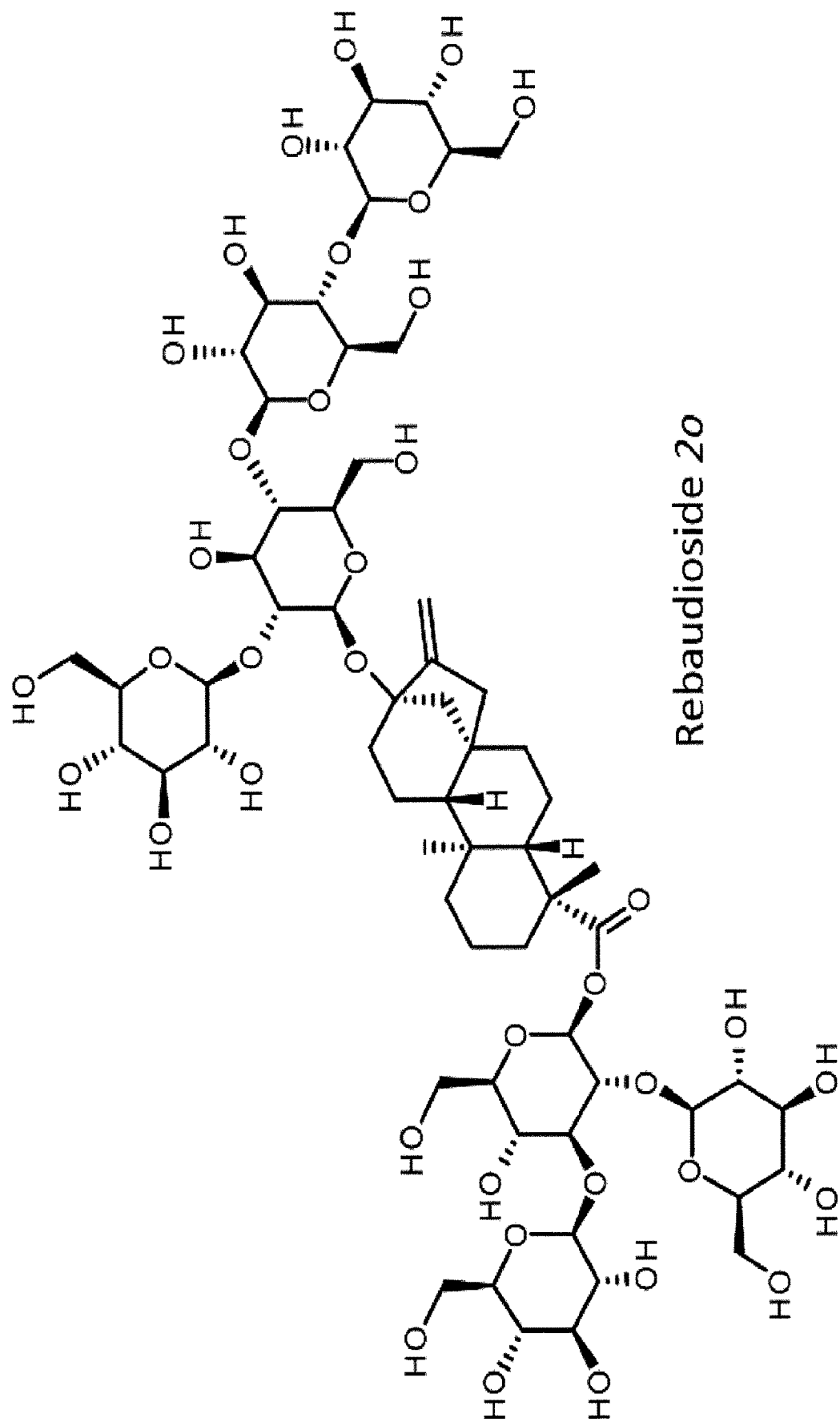
Figure 2P:
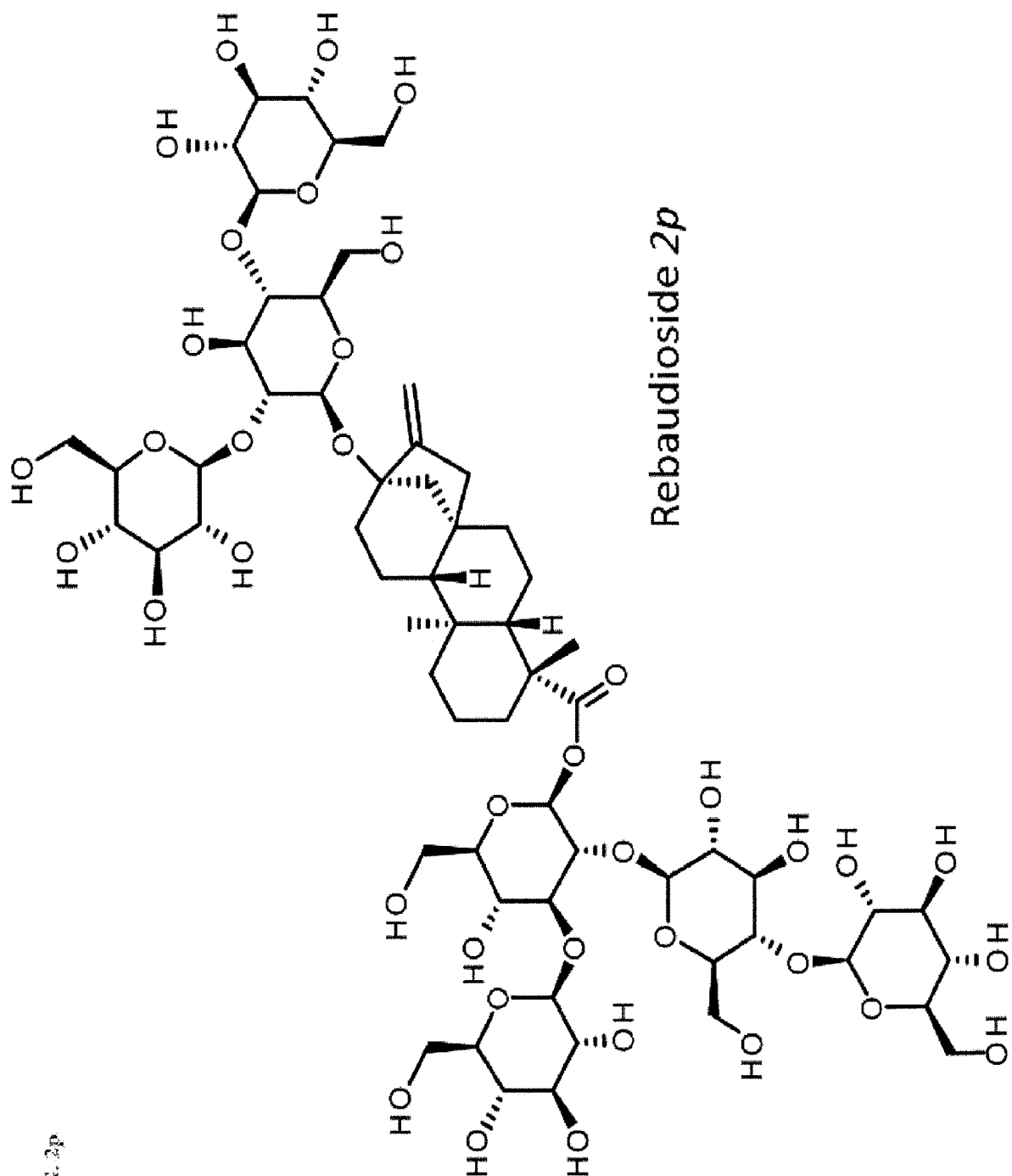
Figure 2Q:
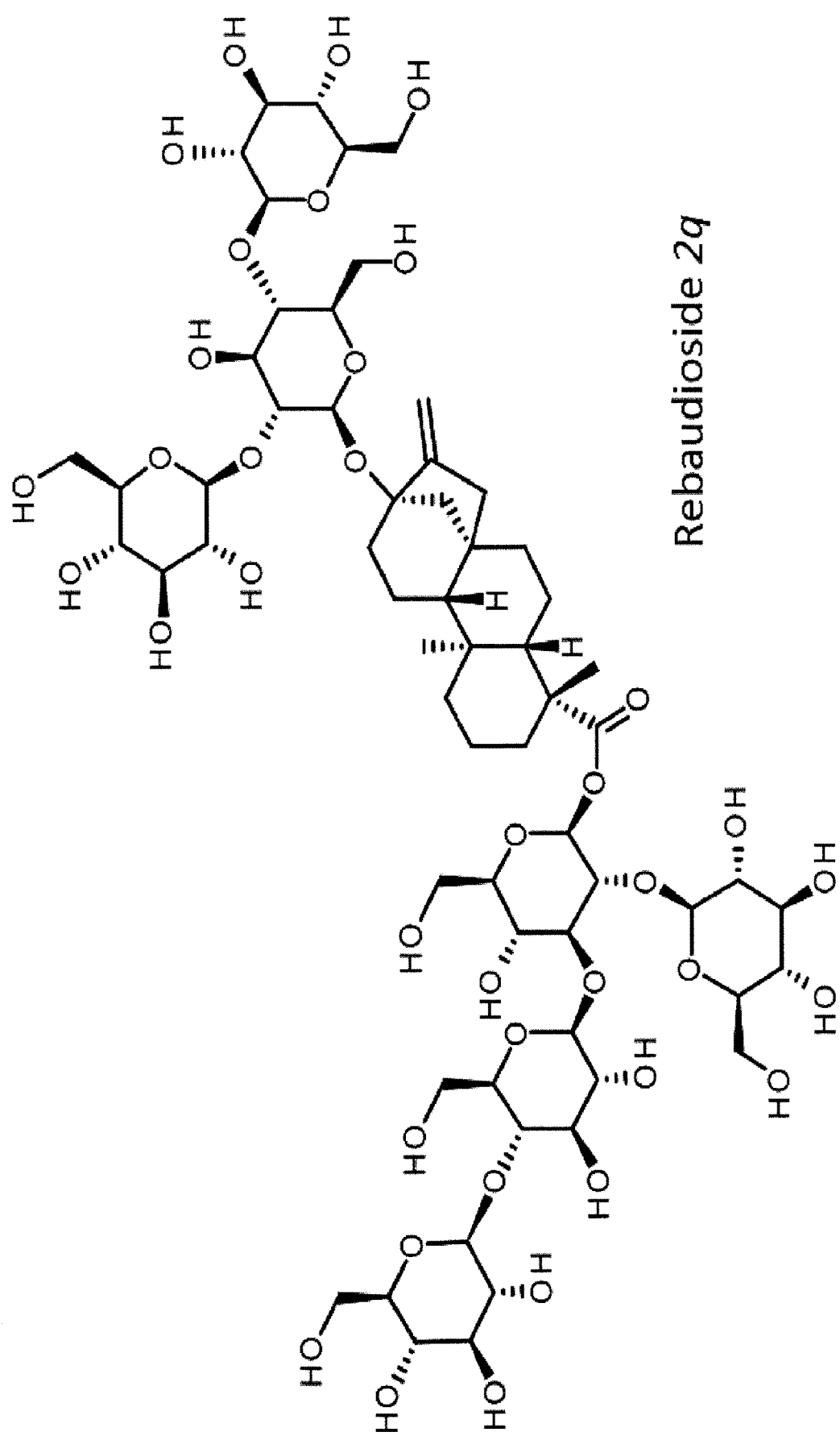
Figure 2R:
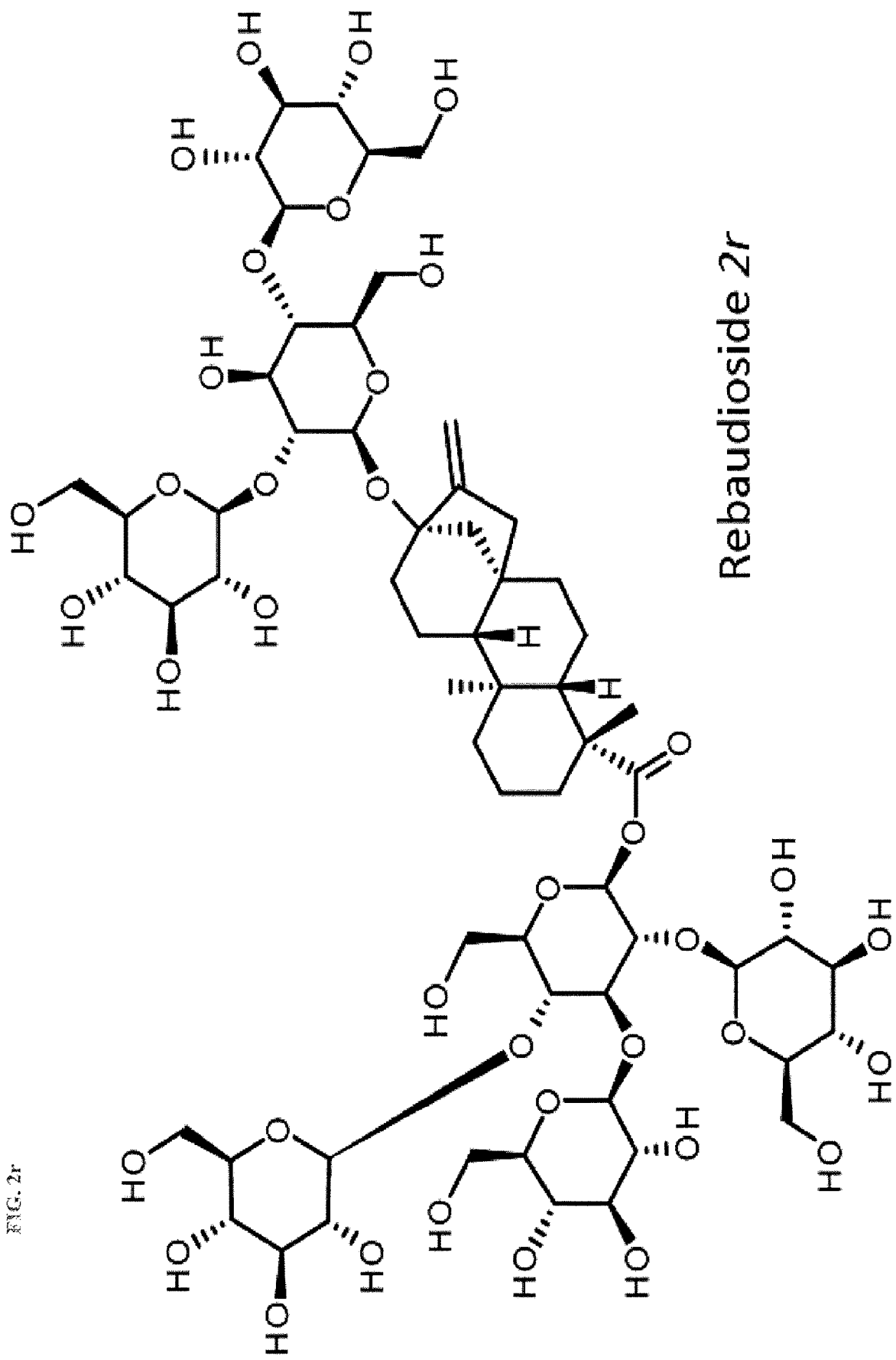
Figure 2S:
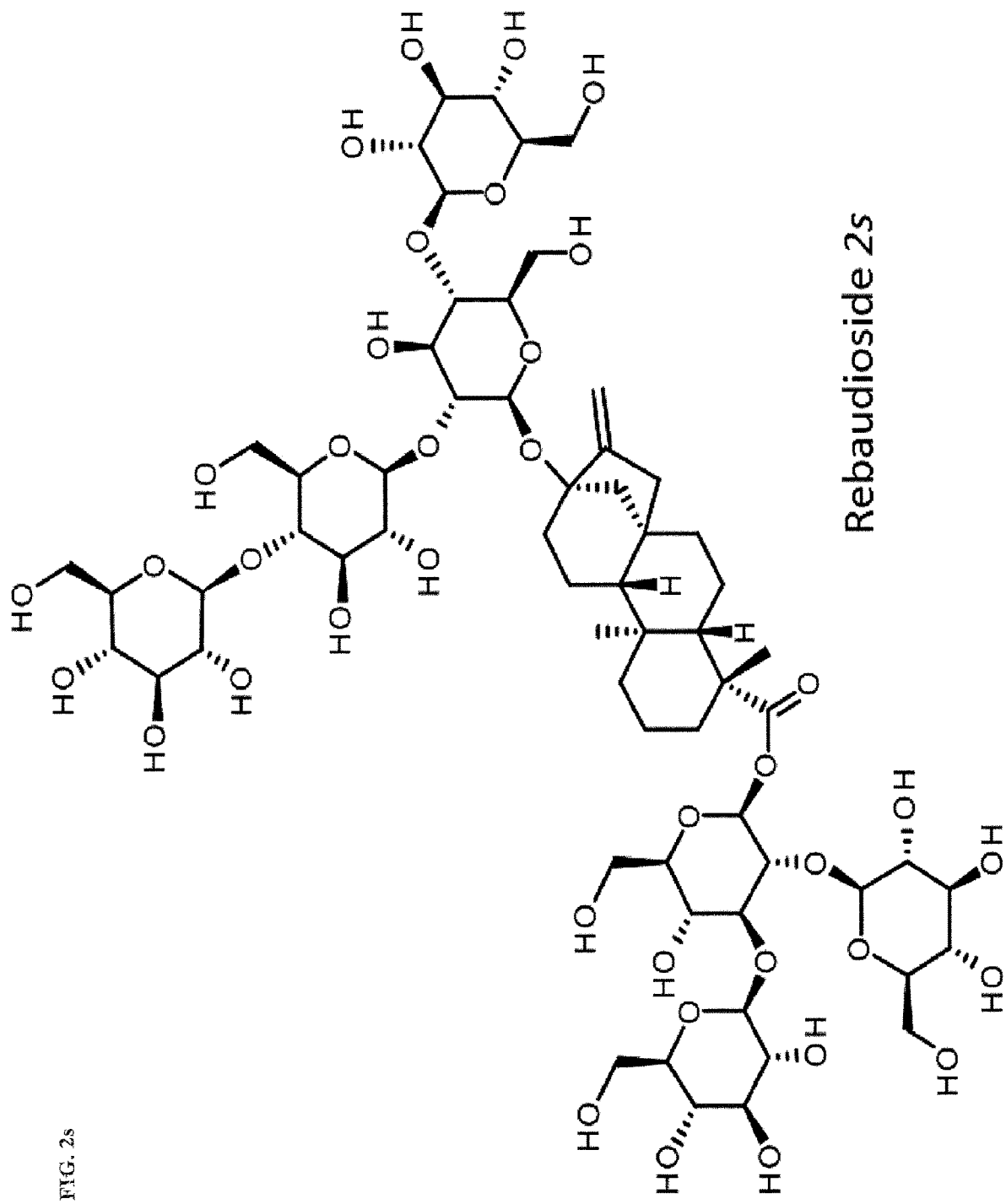
Figure 3A:
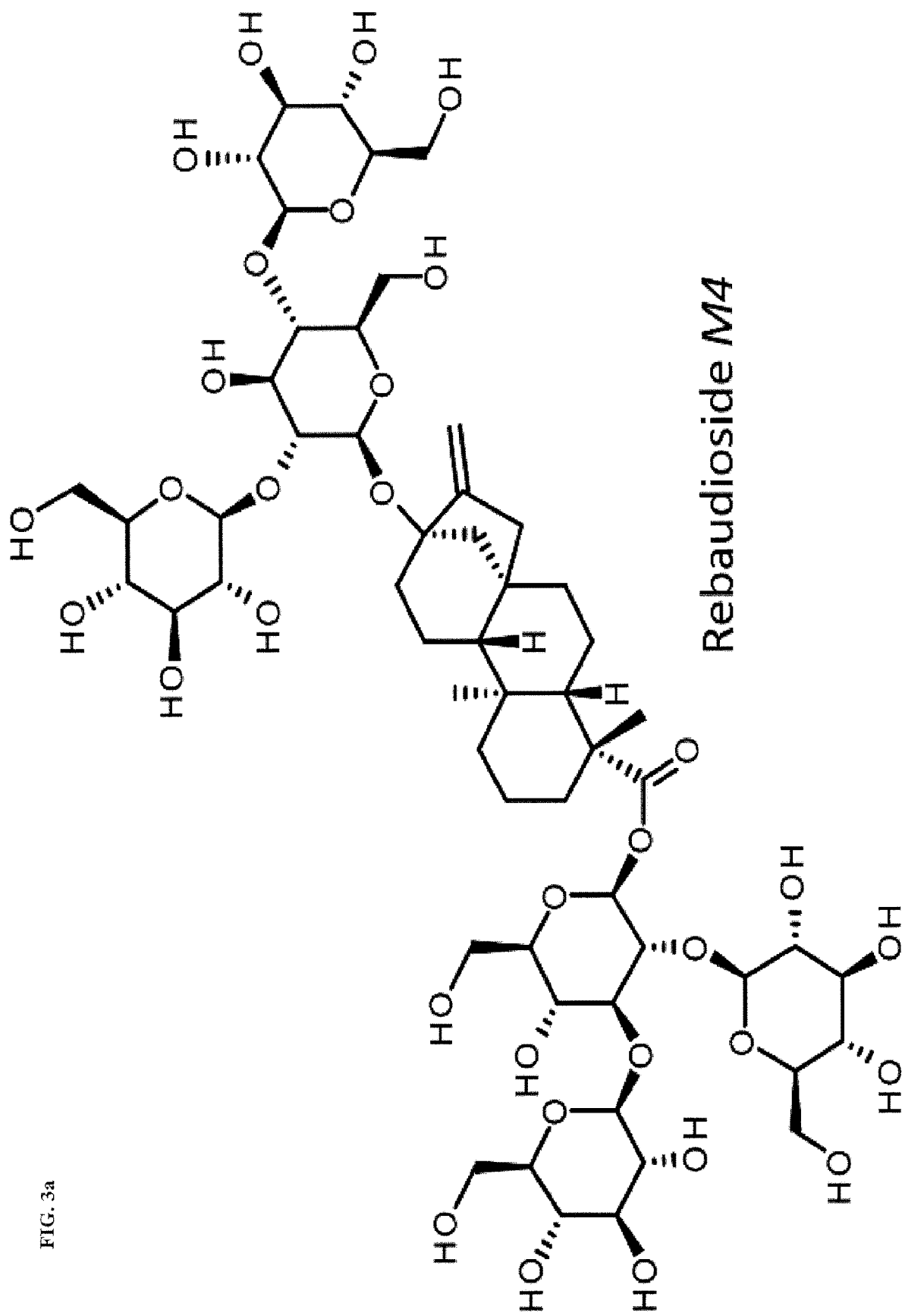
FIG. 3a through FIG. 3b show the chemical structure of rebaudioside M4 and rebaudioside M5 respectively.
Figure 3B:
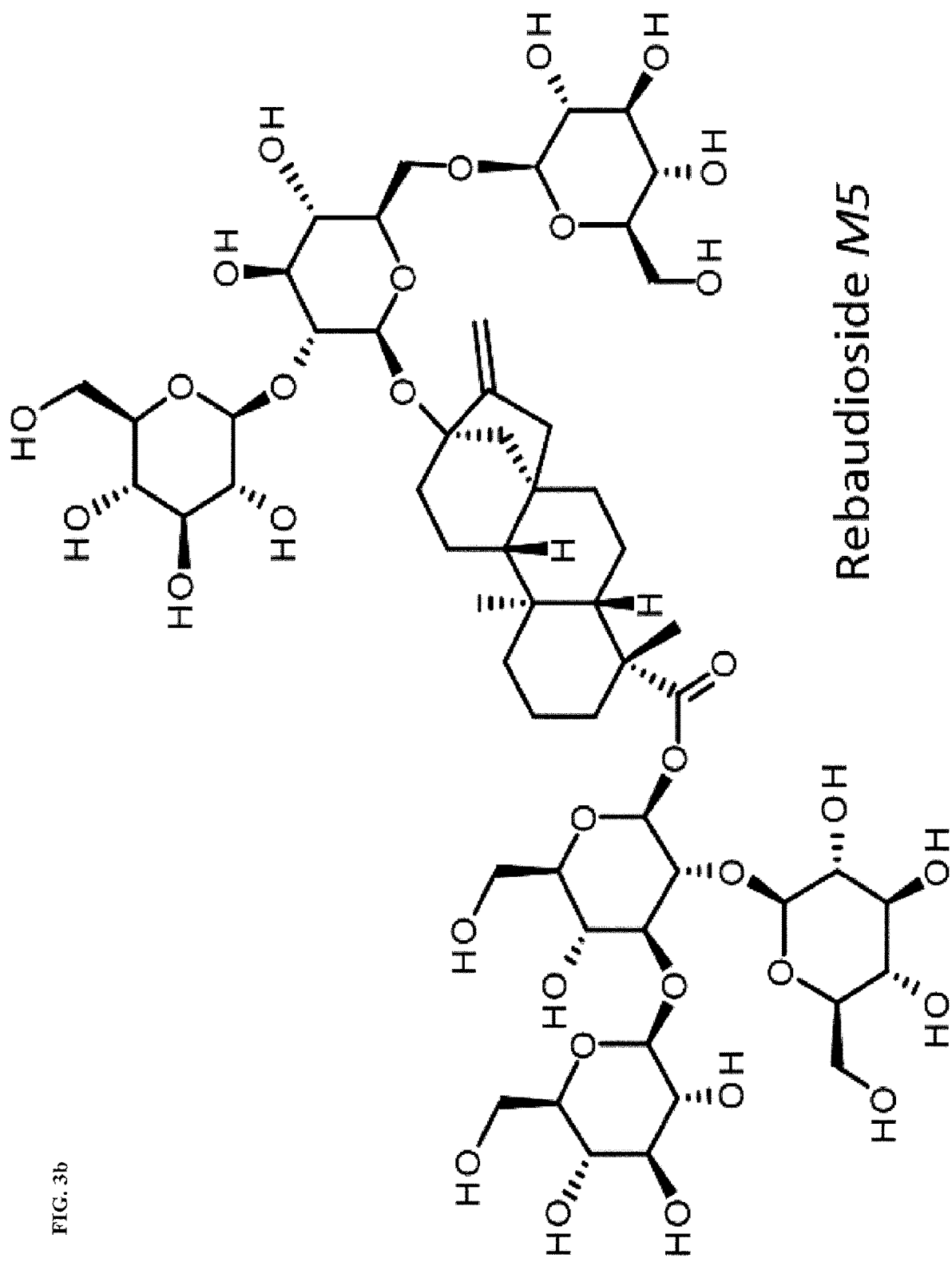
Figure 4A:
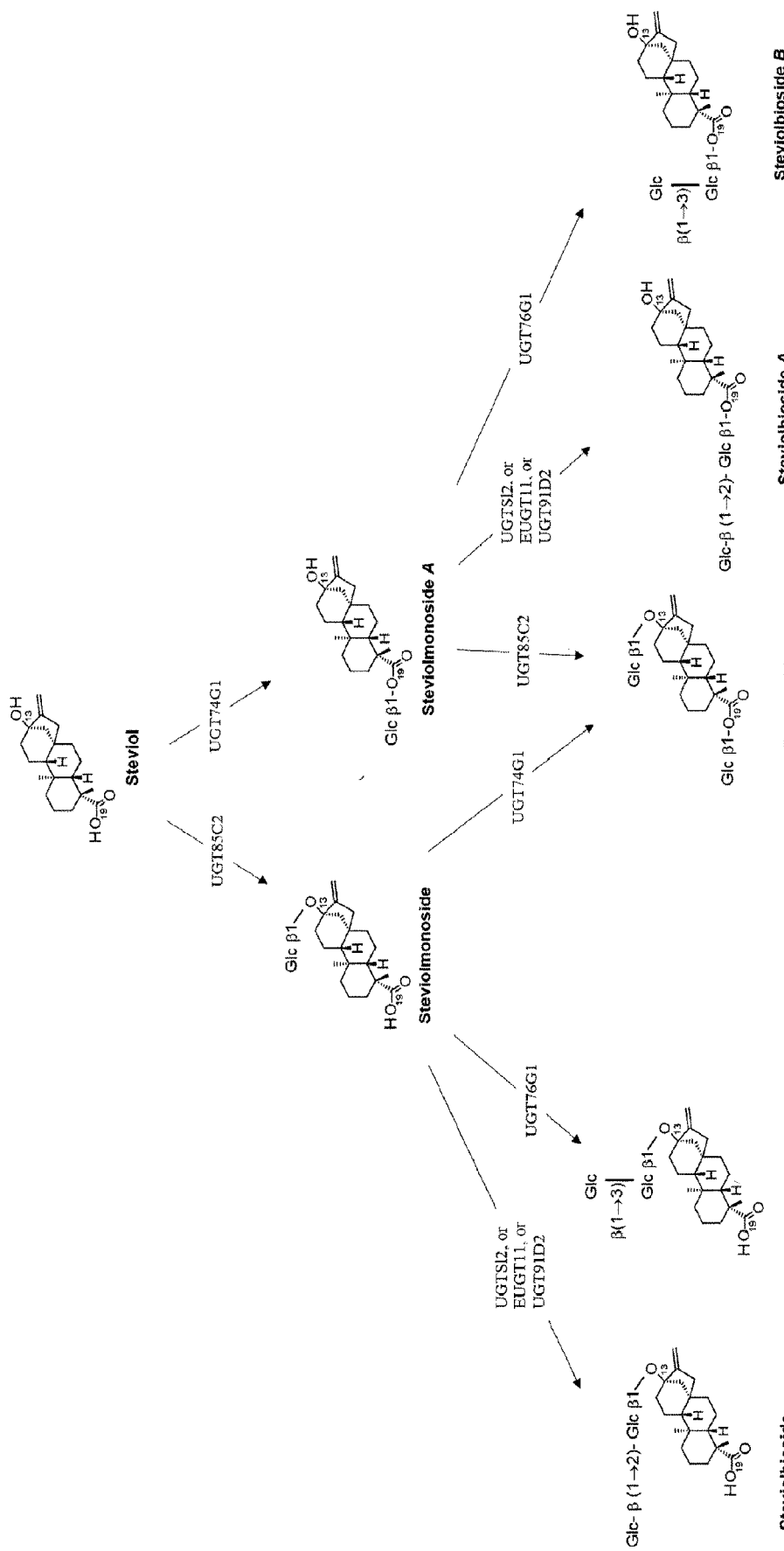
FIG. 4a through FIG. 4t show the pathways of producing rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s and rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, and rebaudioside 2s, rebaudioside M4, rebaudioside M5 and various steviol glycosides from steviol and the various intermediary steviol glycosides.
Figure 4B:
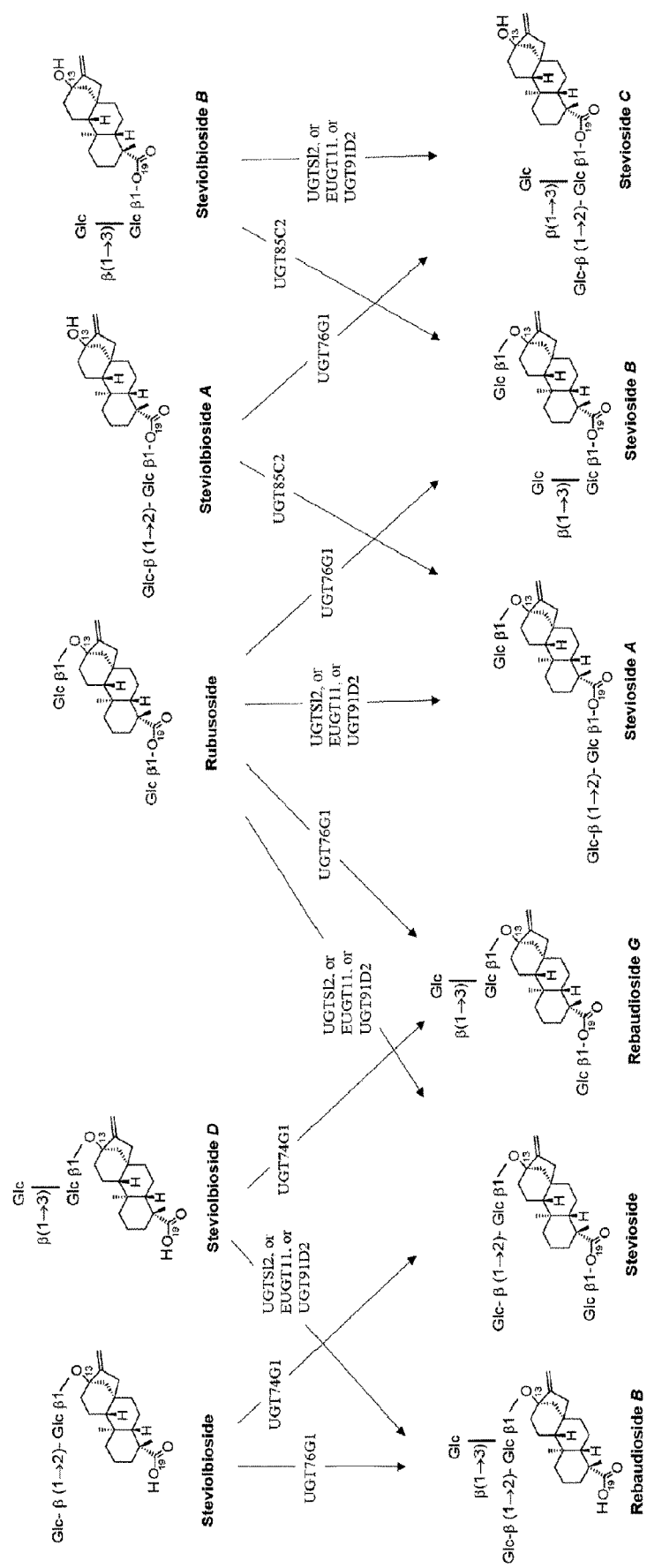
Figure 4C:
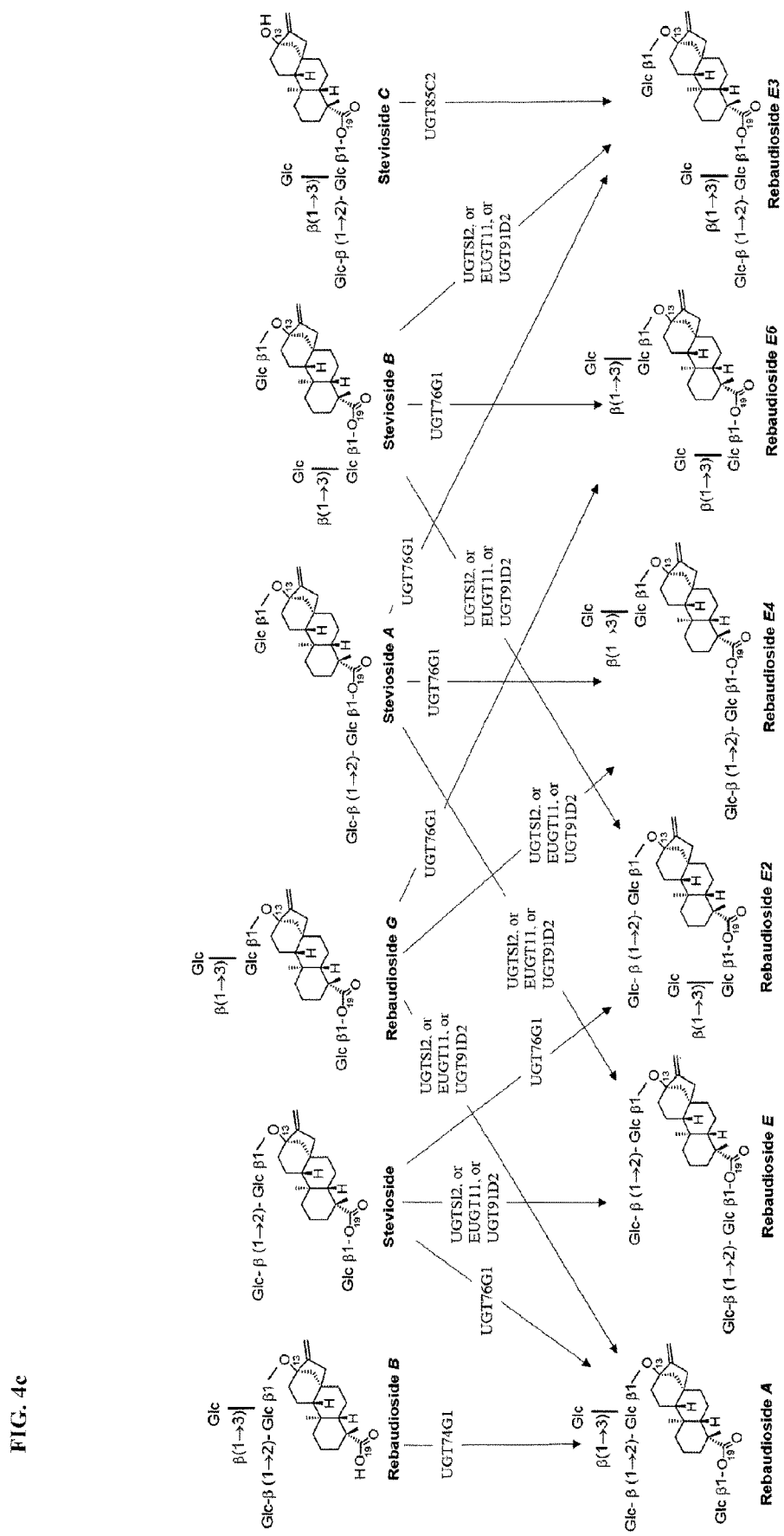
Figure 4D:
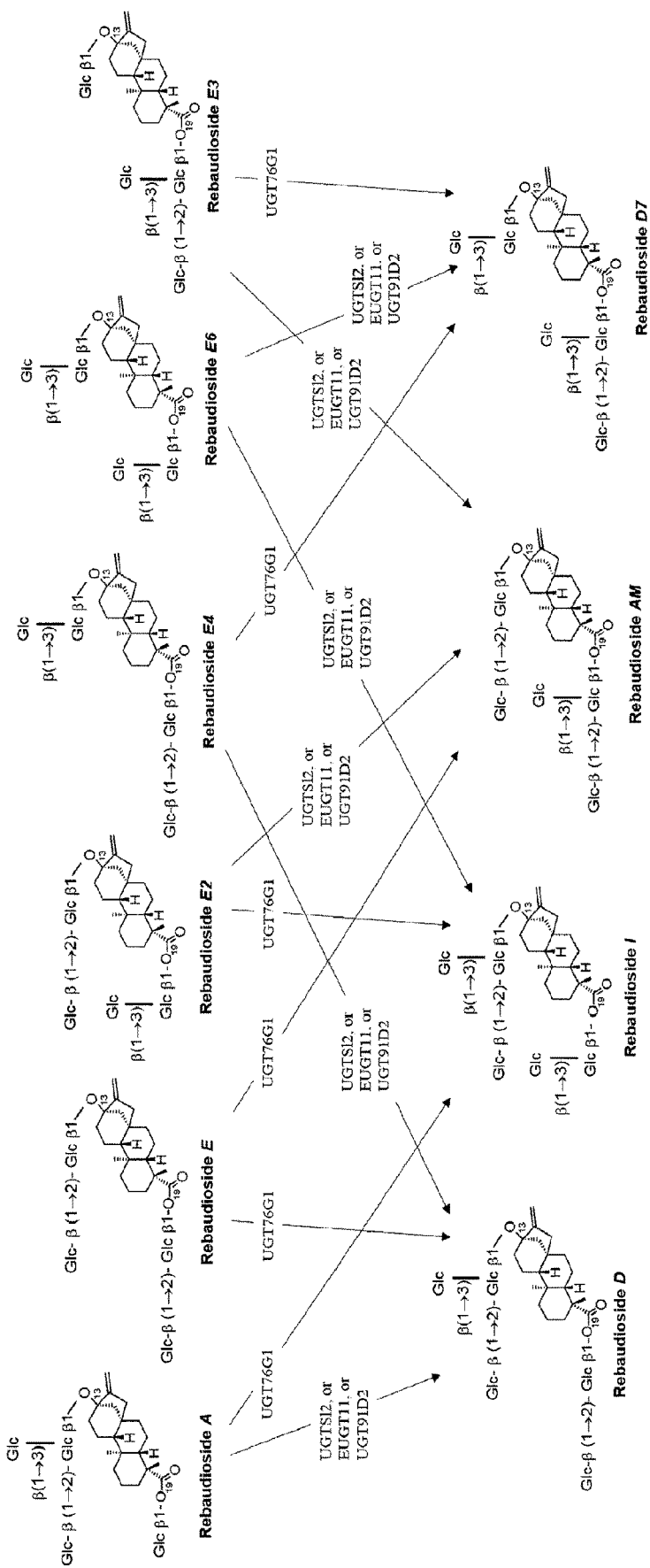
Figure 4E:
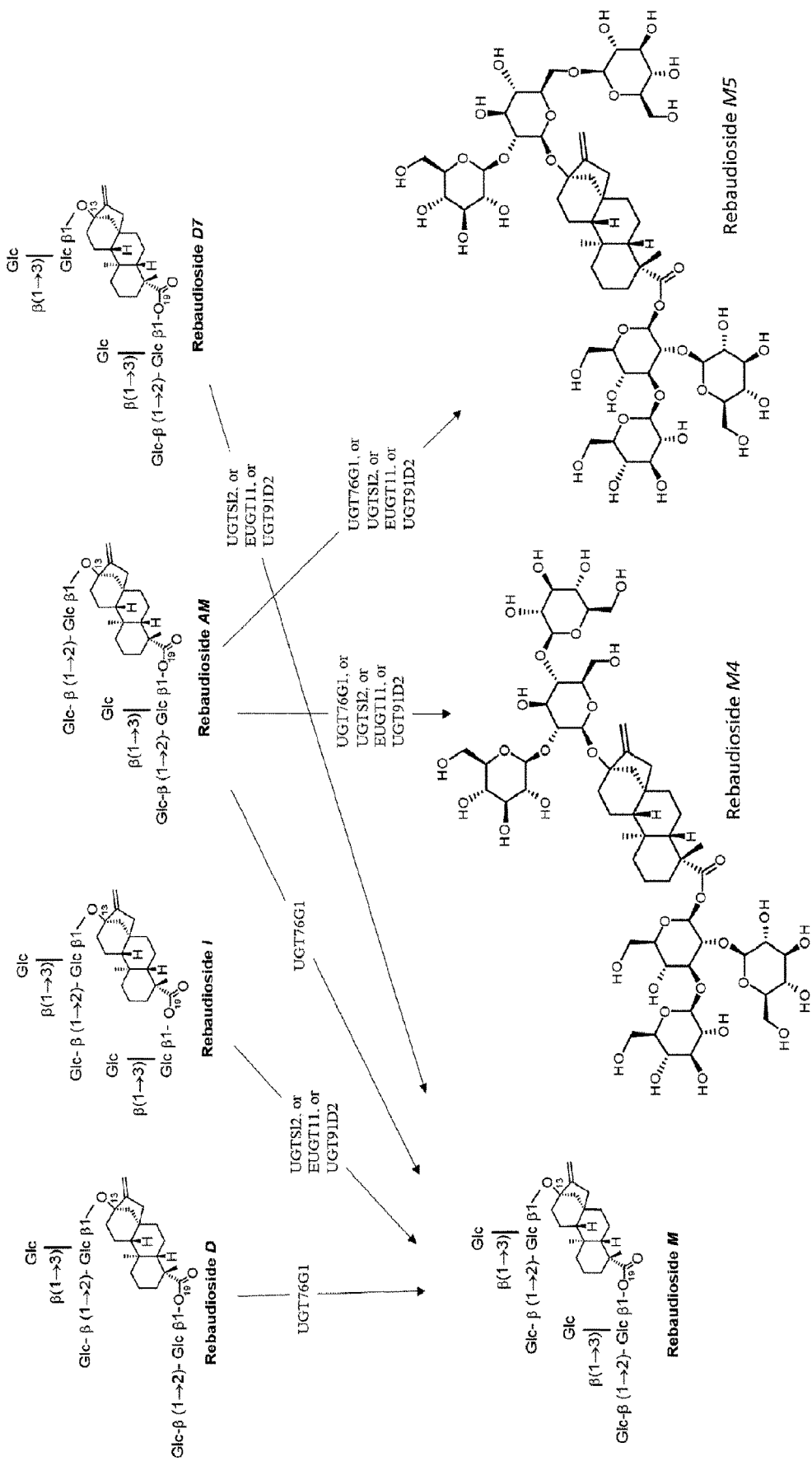
Figure 4F:
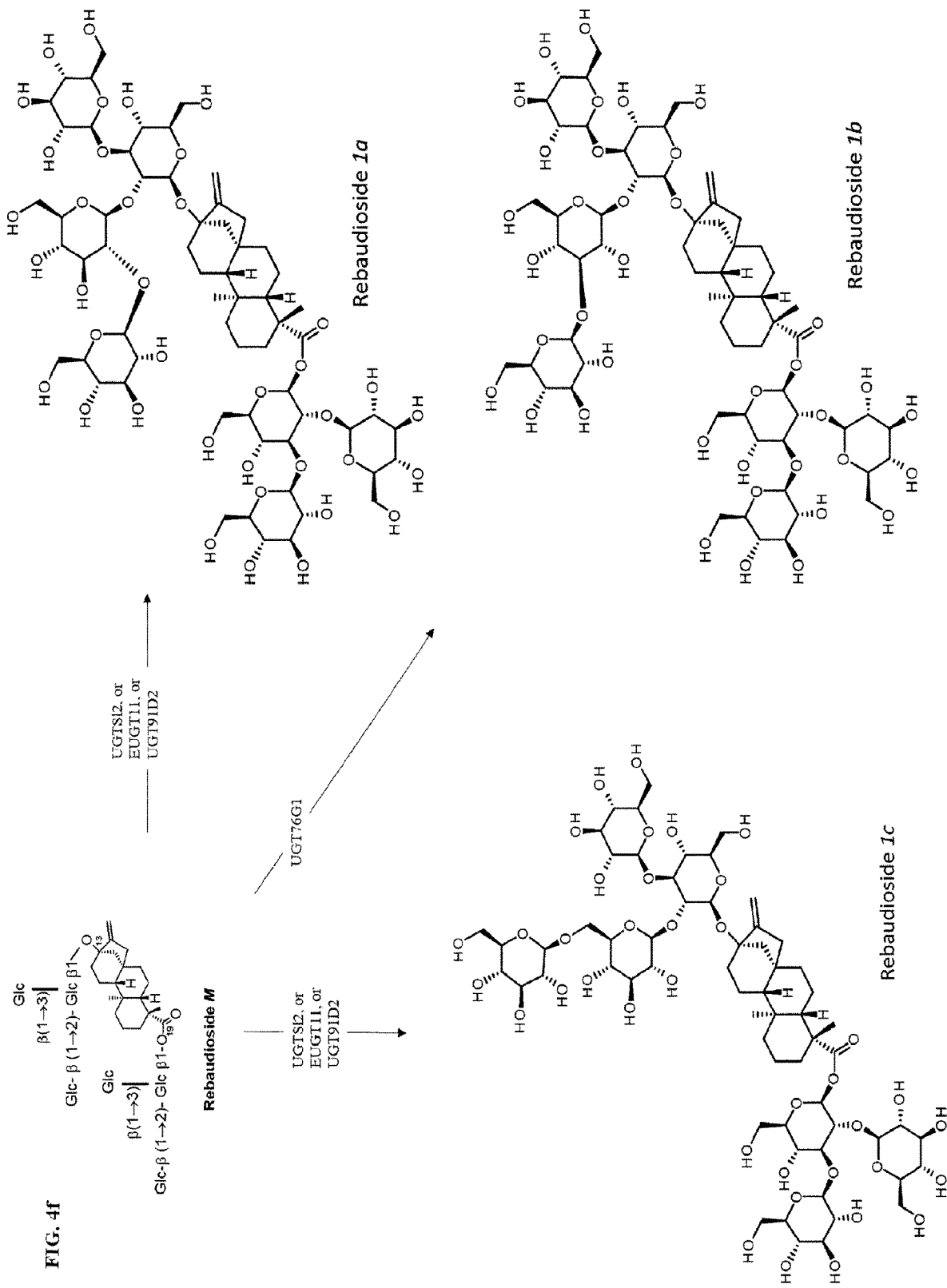
Figure 4G:
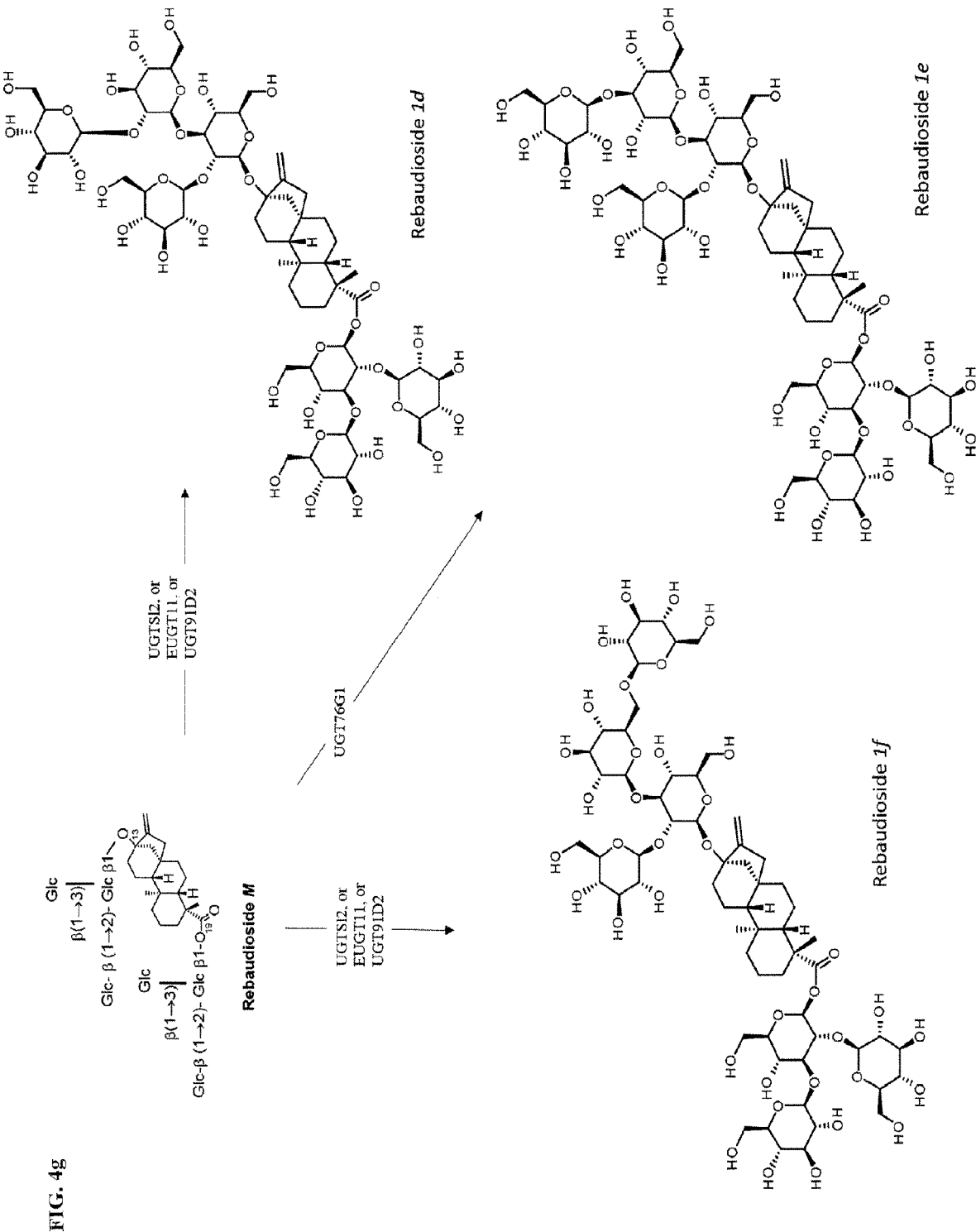
Figure 4H:
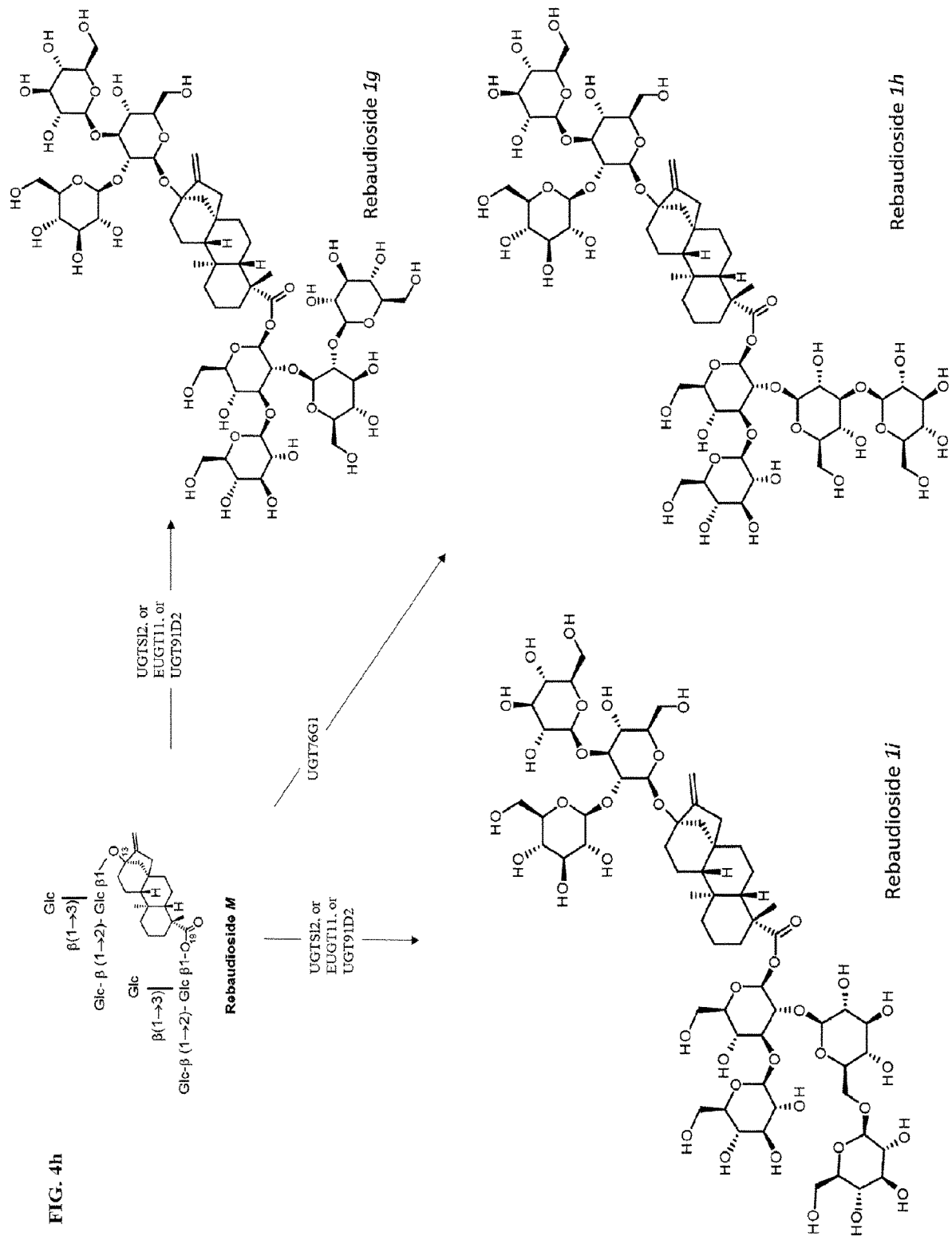
Figure 4I:
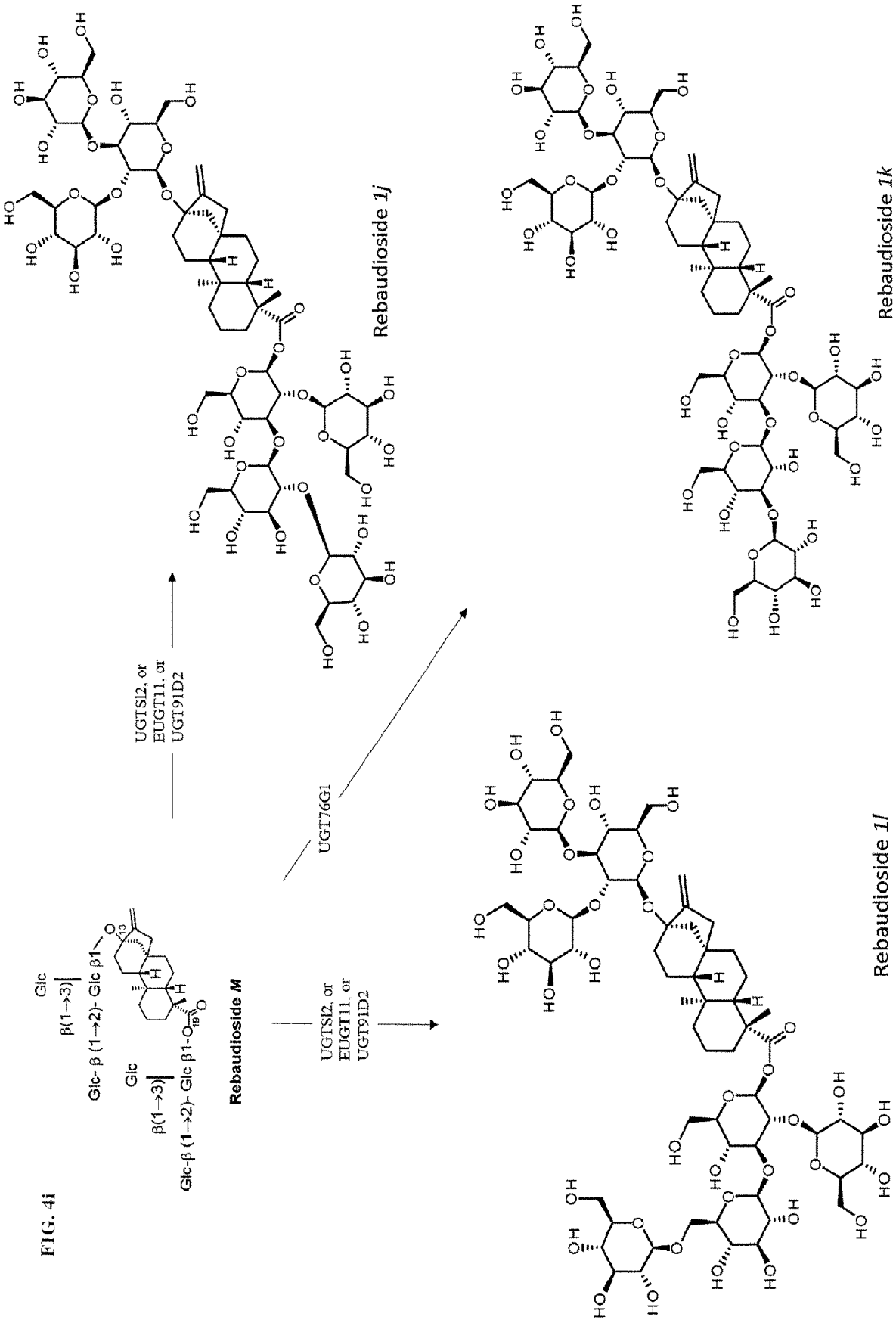
Figure 4J:
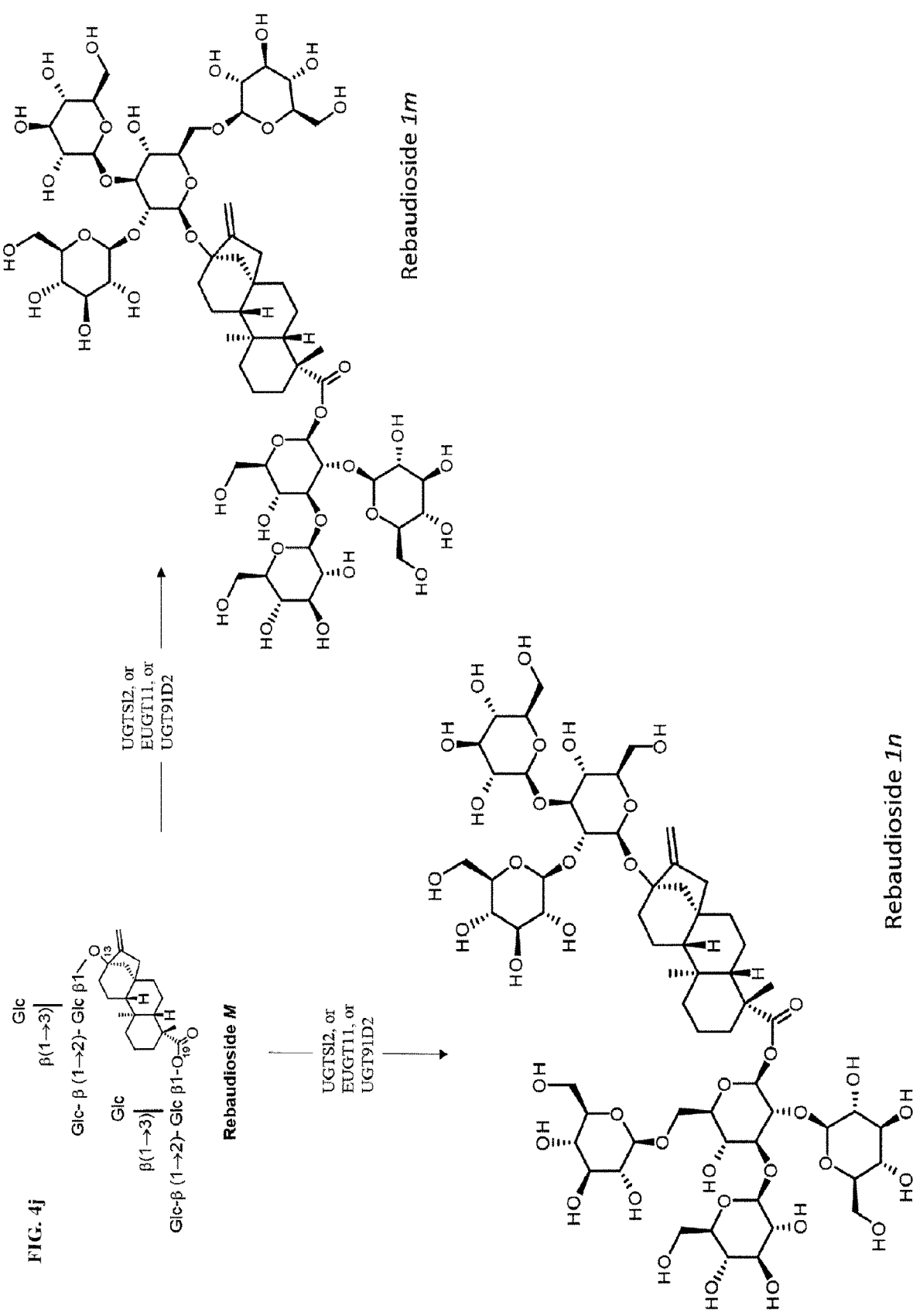
Figure 4K:
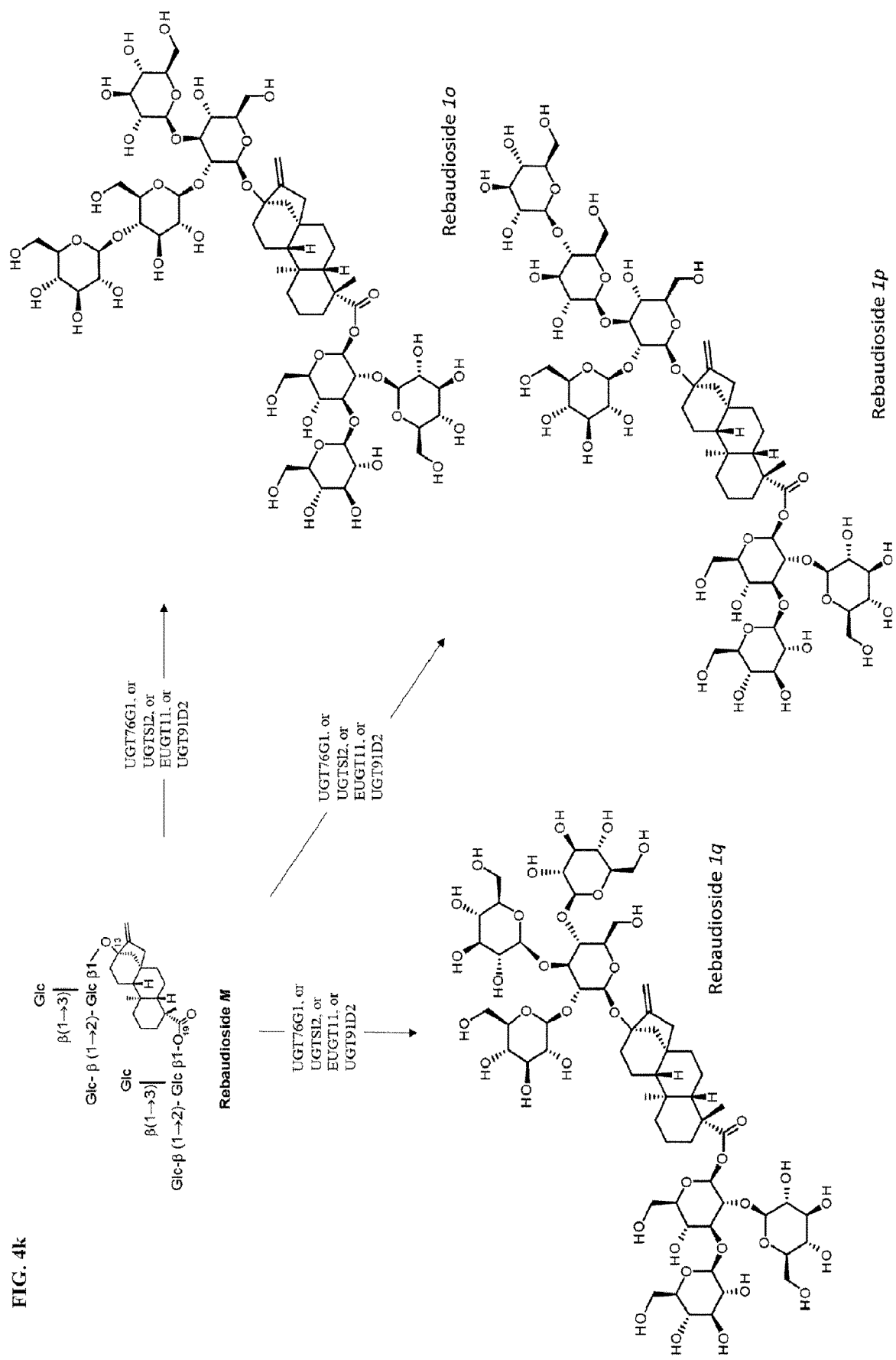
Figure 4L:
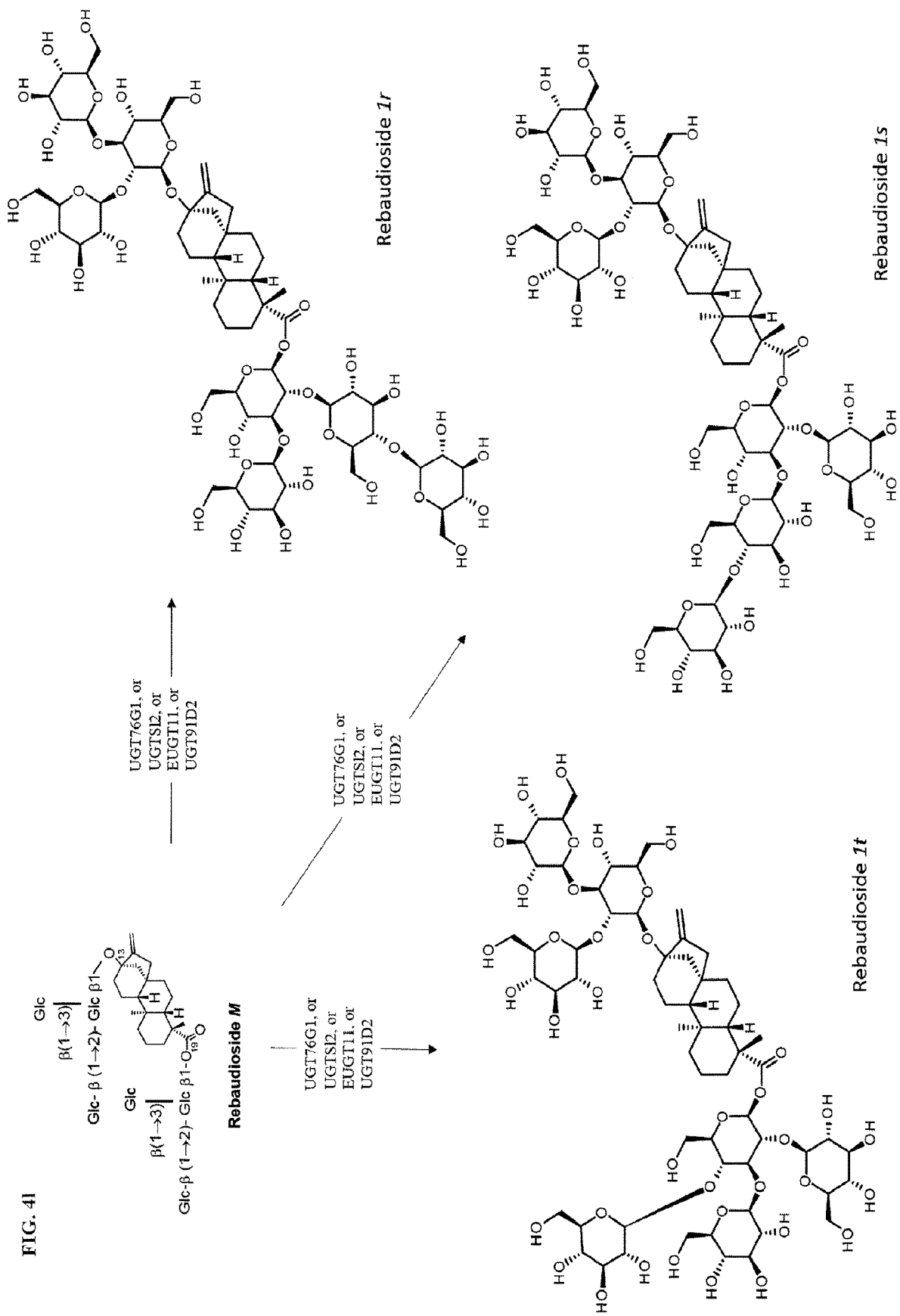
Figure 4M:
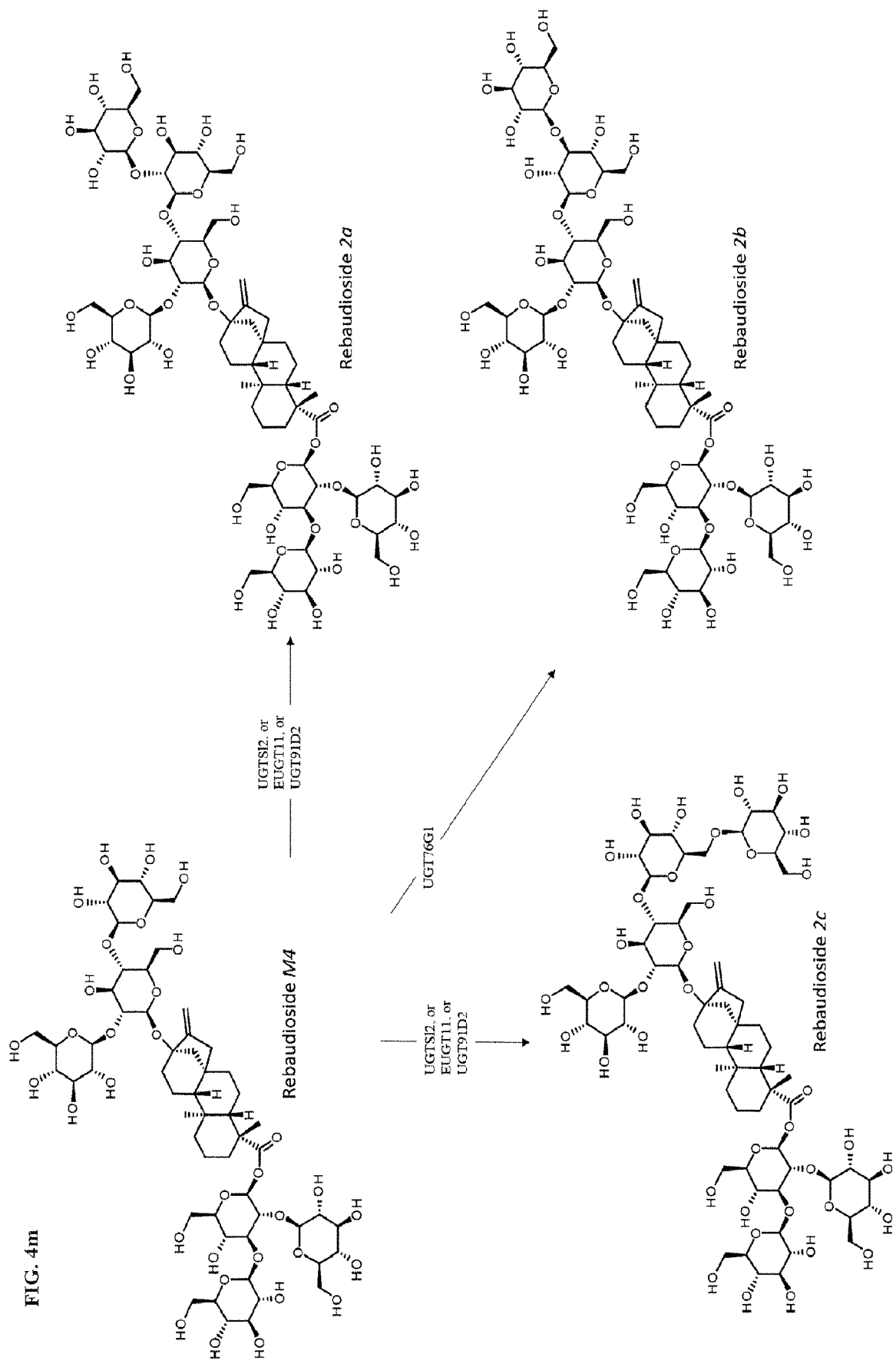
Figure 4N:
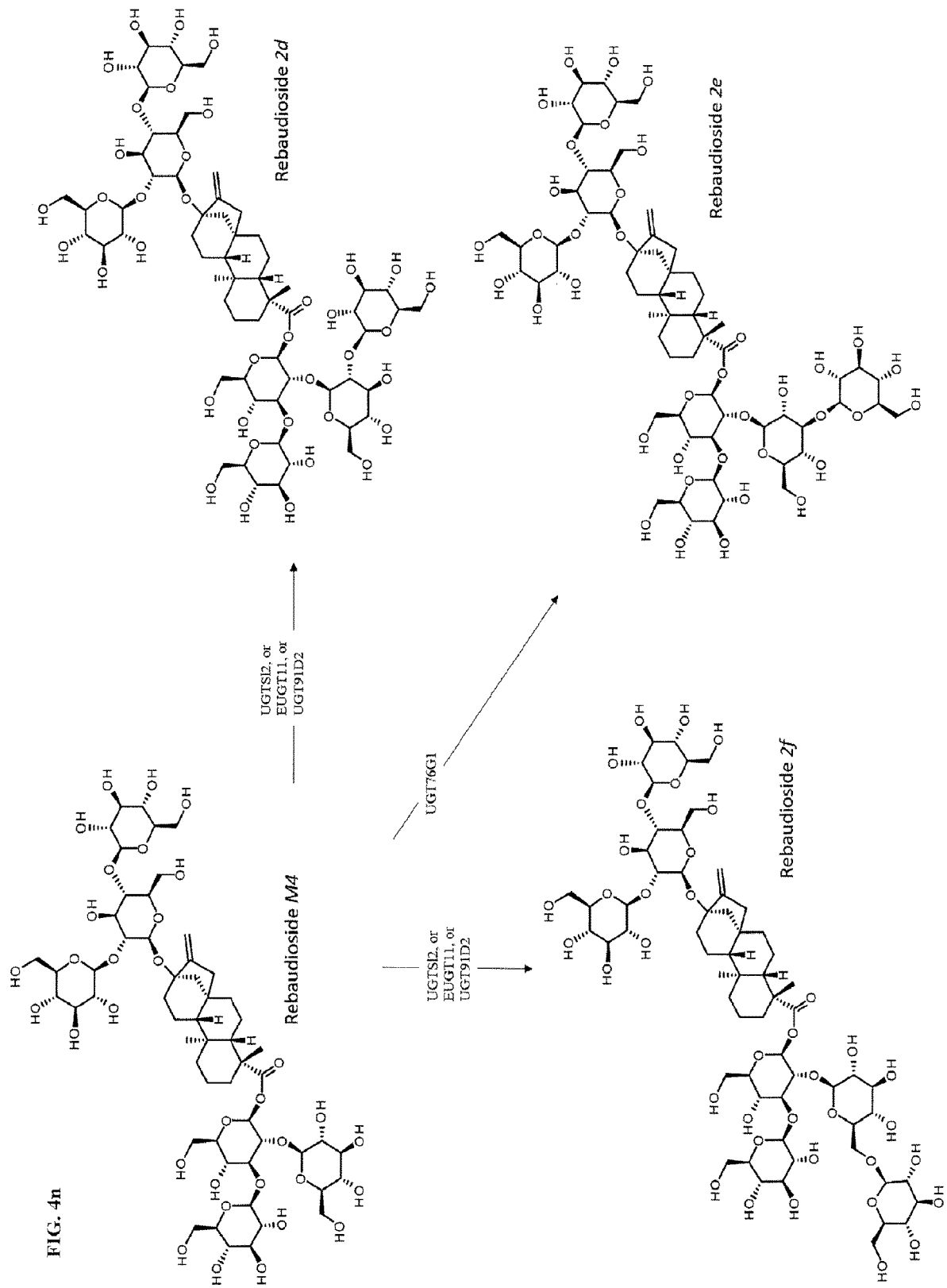
Figure 4O:
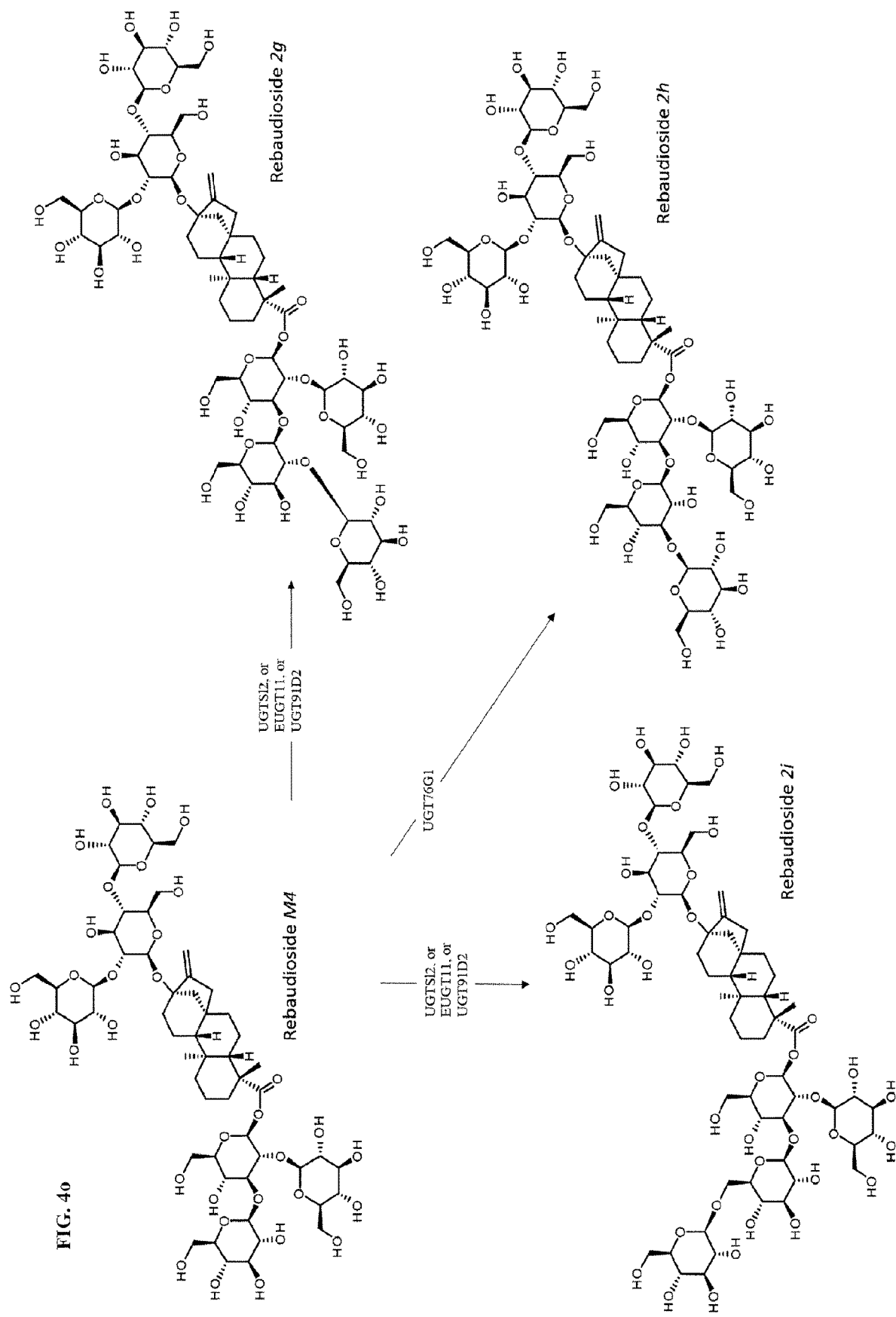
Figure 4P:
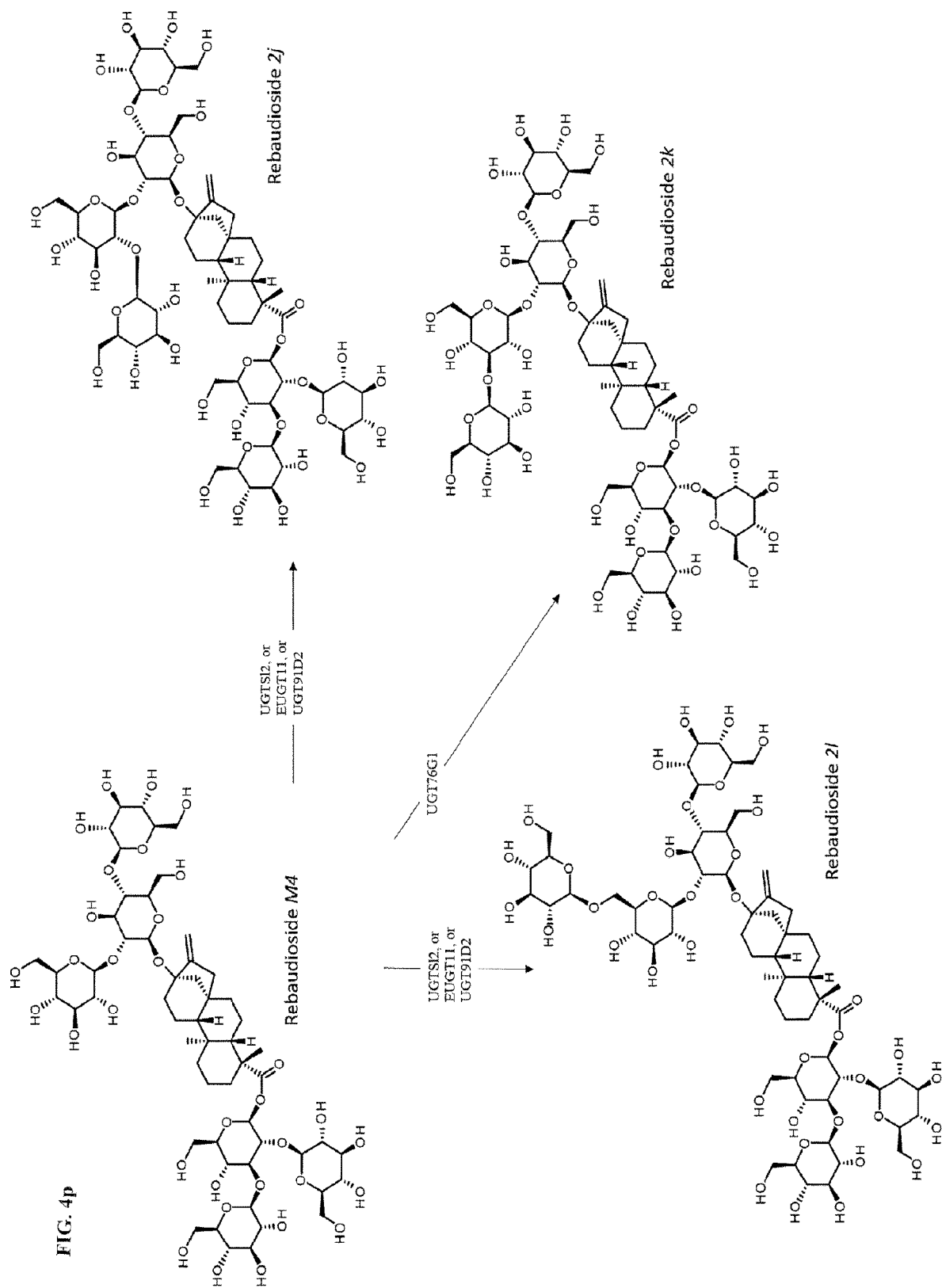
Figure 4Q:
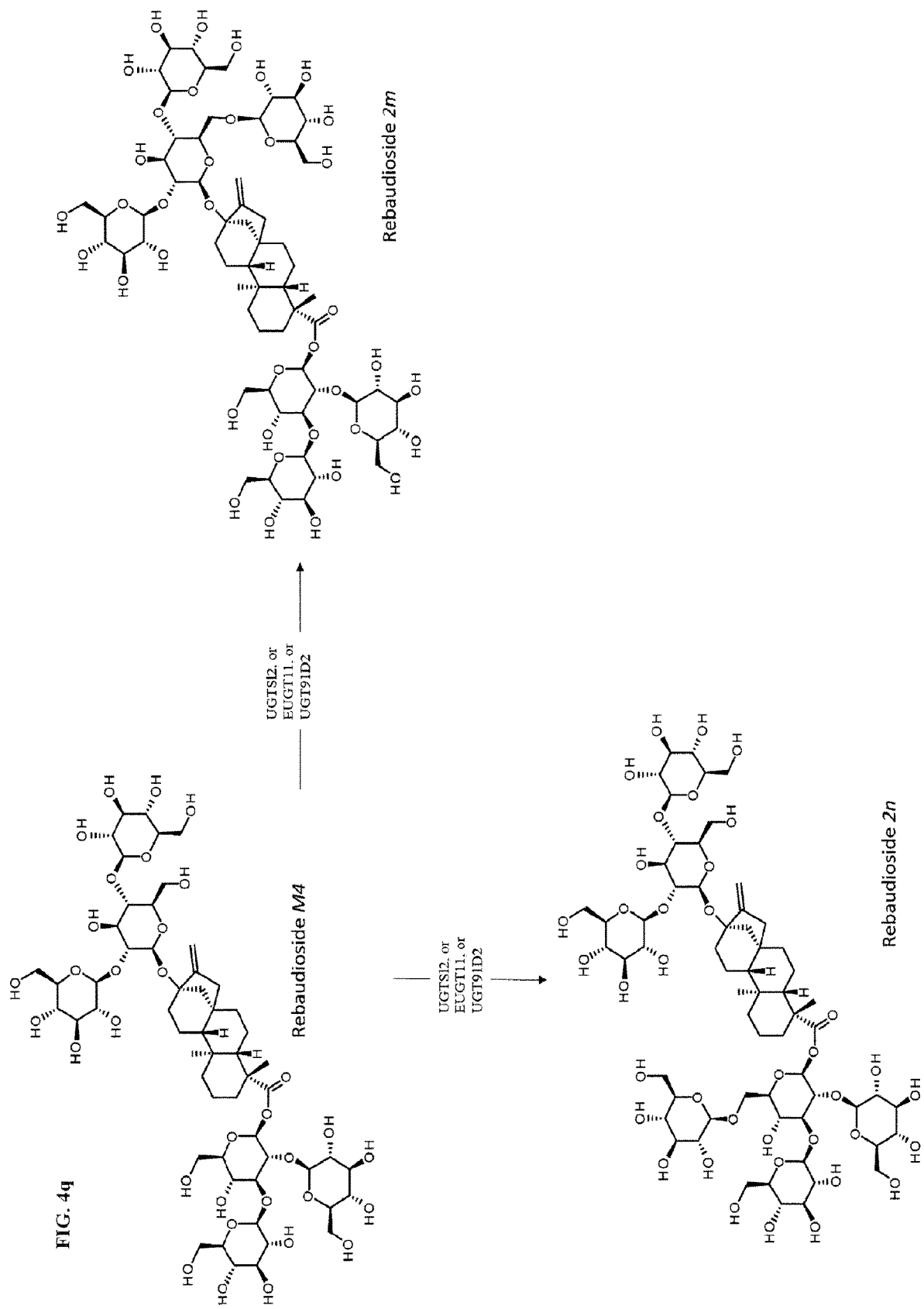
Figure 4R:
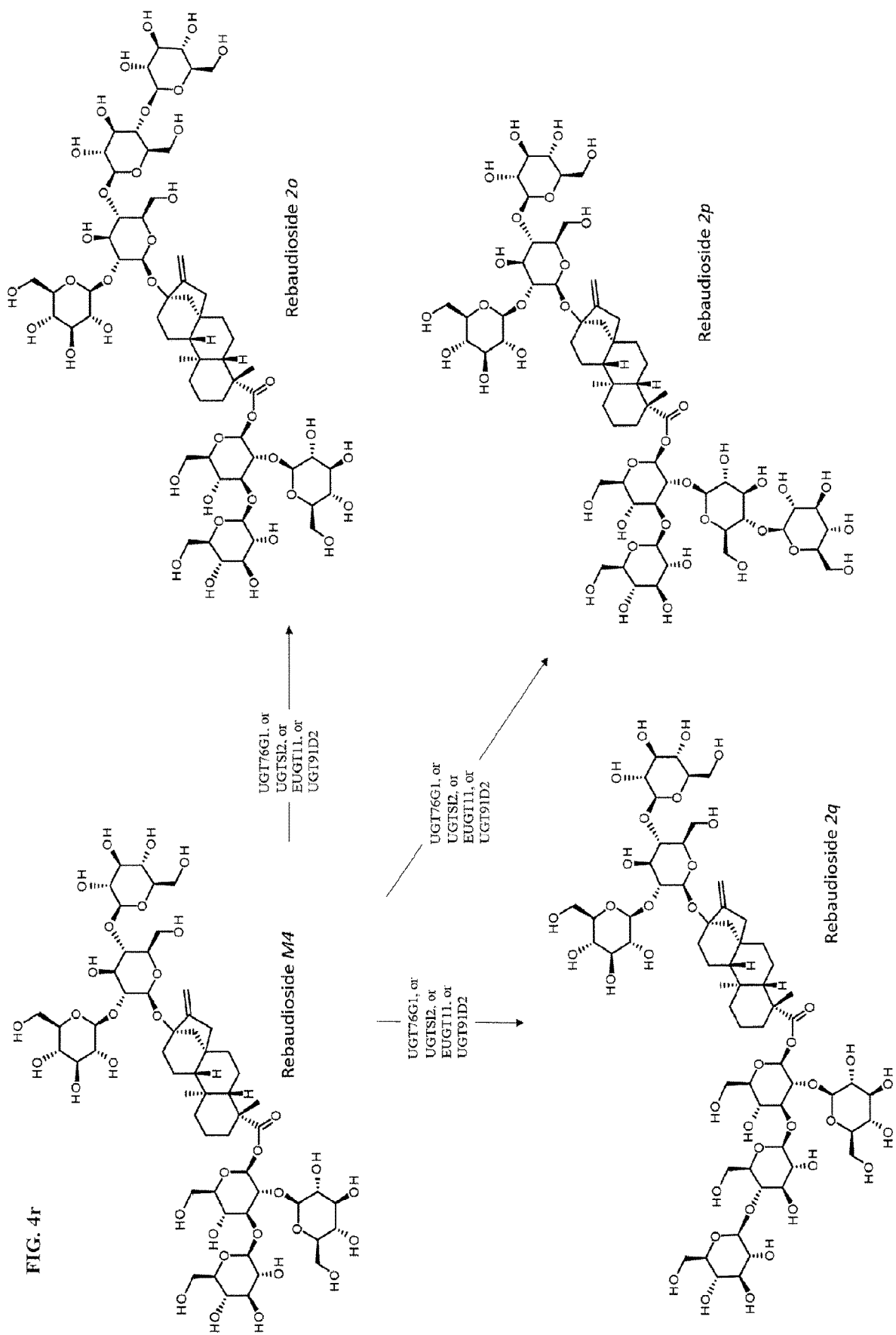
Figure 4S:
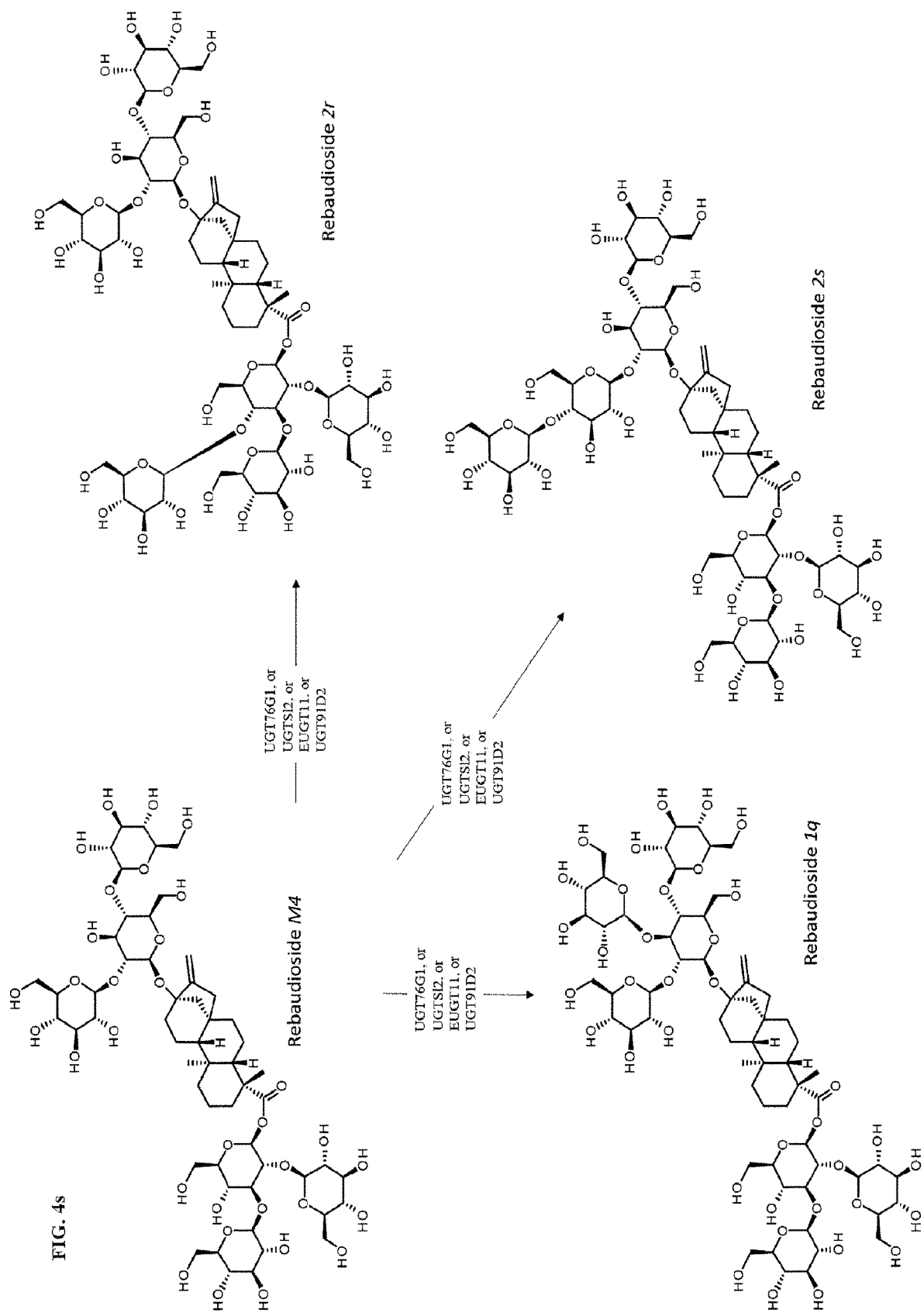
Figure 4T:
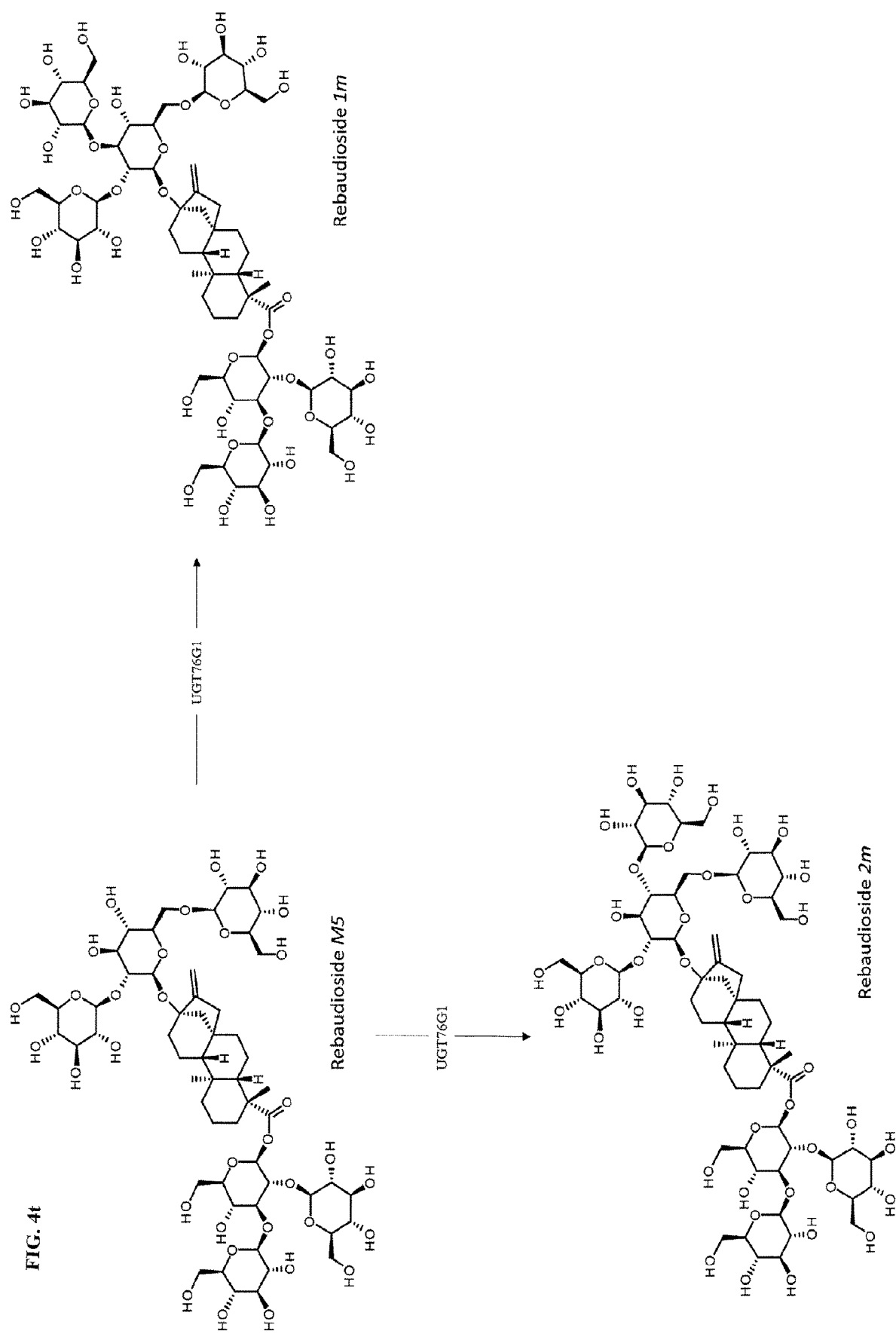
Figure 5A:
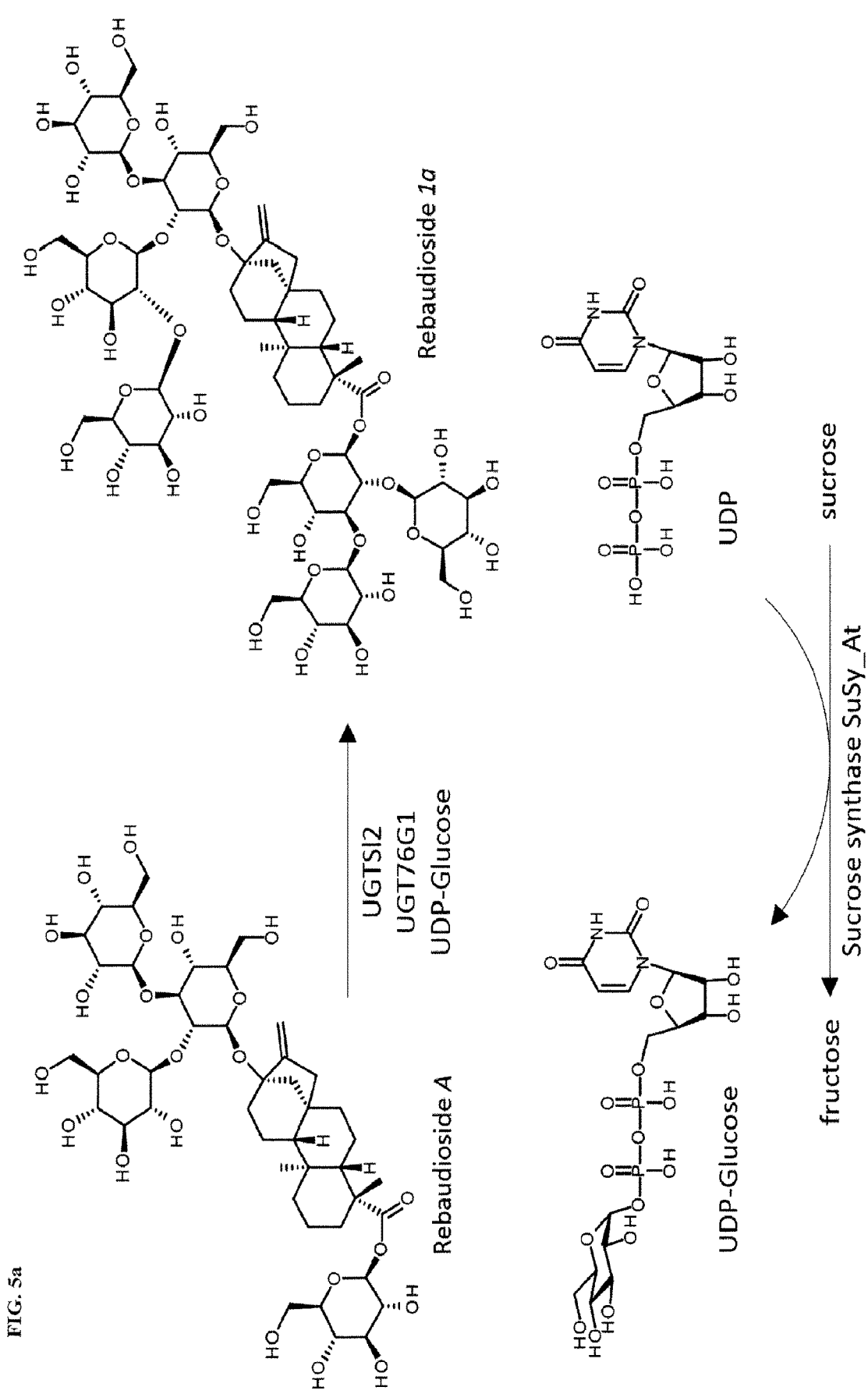
FIG. 5a through FIG. 5t show the biocatalytic production of rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m and rebaudioside 1n, rebaudioside 1o, rebaudioside 1p, rebaudioside 1q, rebaudioside 1r, rebaudioside 1s and rebaudioside 1t respectively, from rebaudioside A using the enzymes UGTSl2 and UGT76G1 and concomitant recycling of UDP to UDP-glucose via sucrose synthase SuSy_At.
Figure 5B:
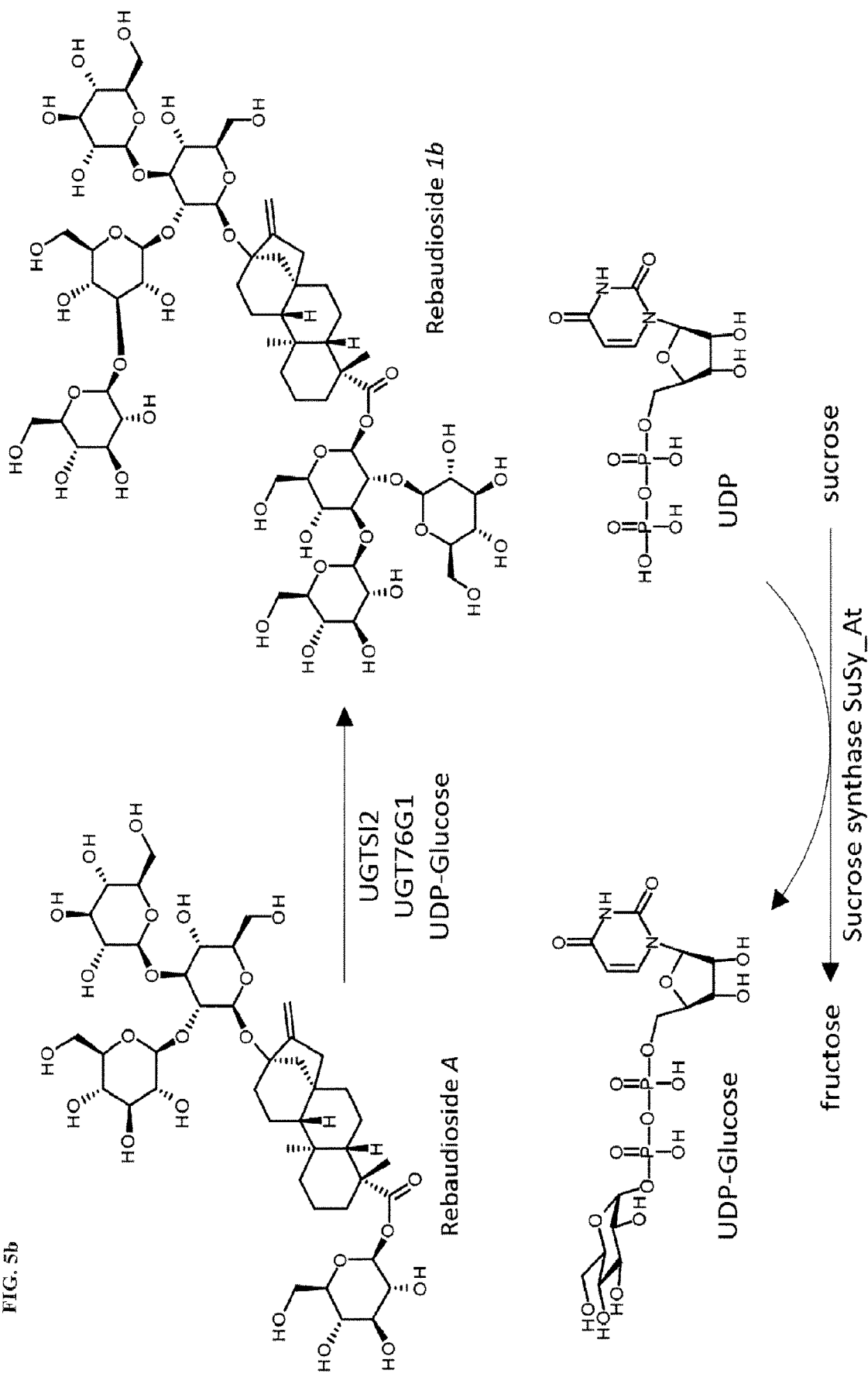
Figure 5C:
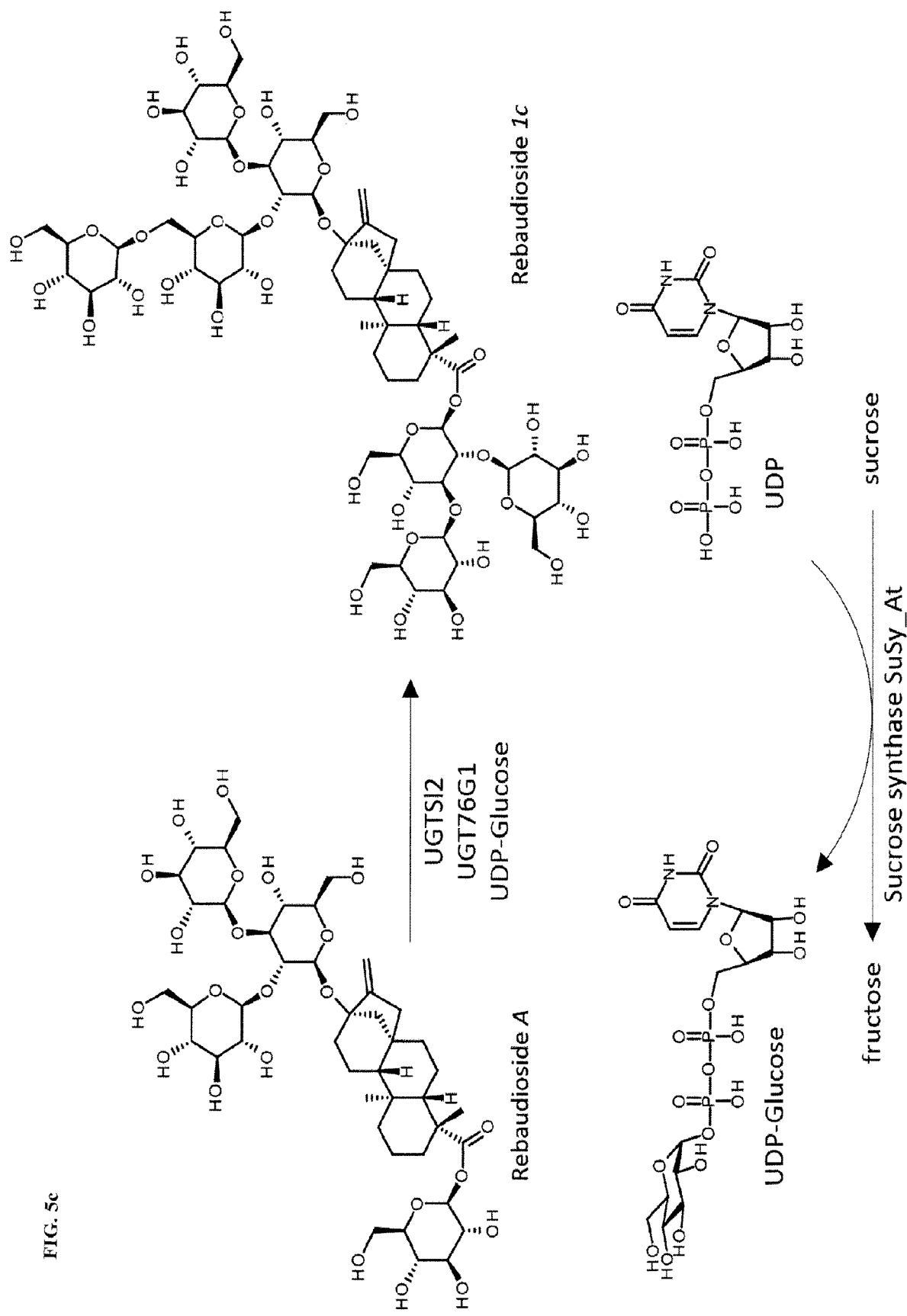
Figure 5D:
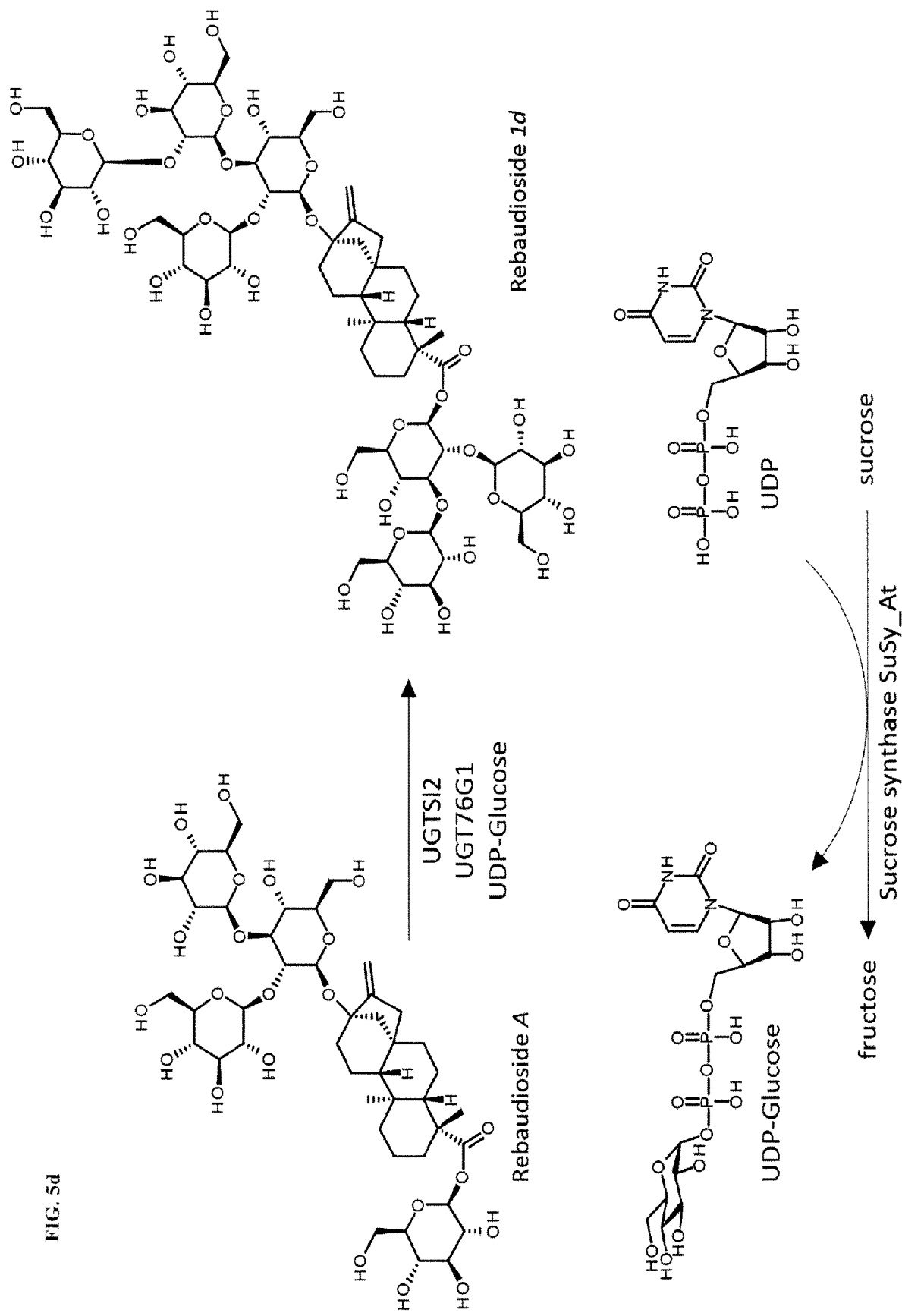
Figure 5E:
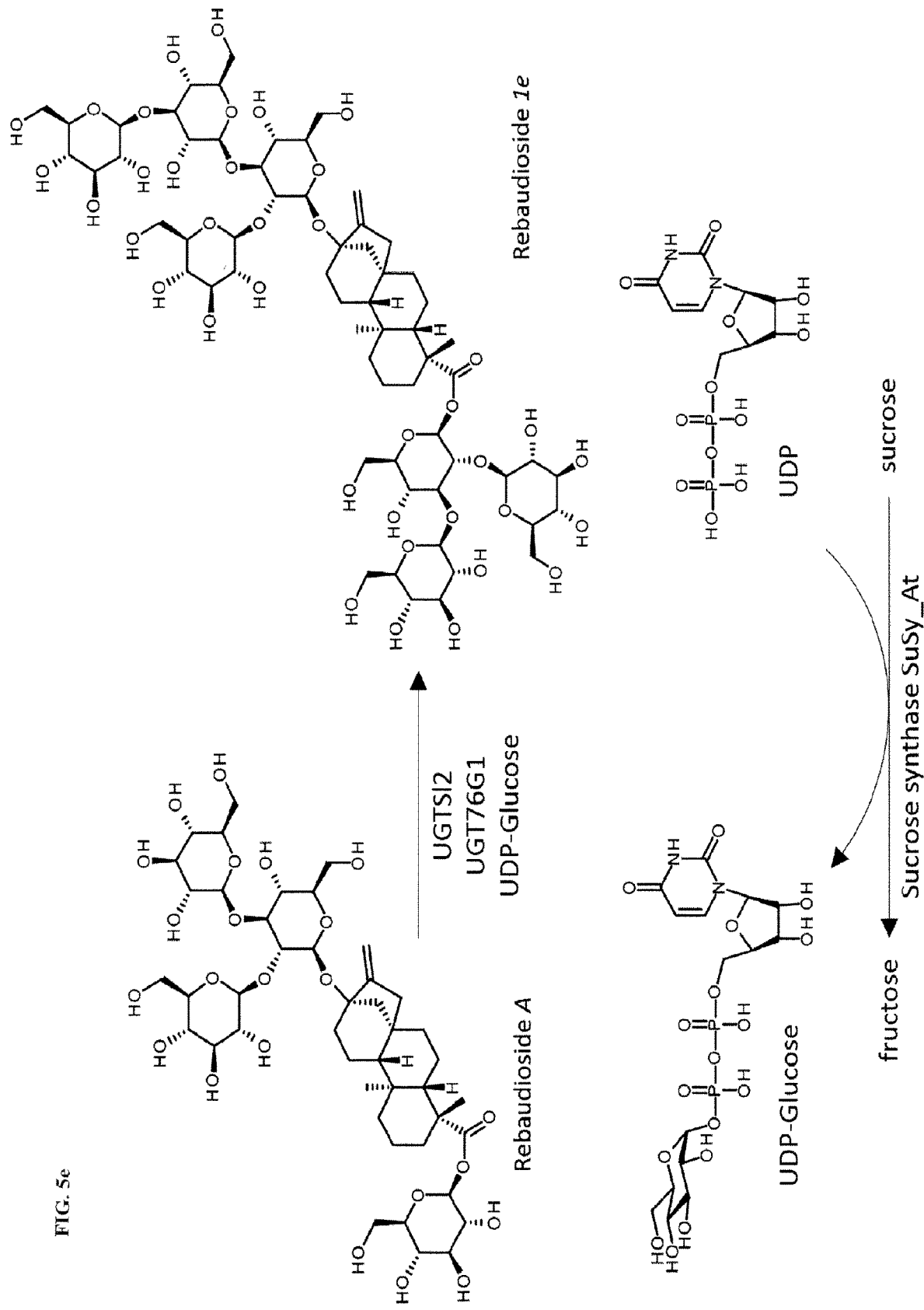
Figure 5F:
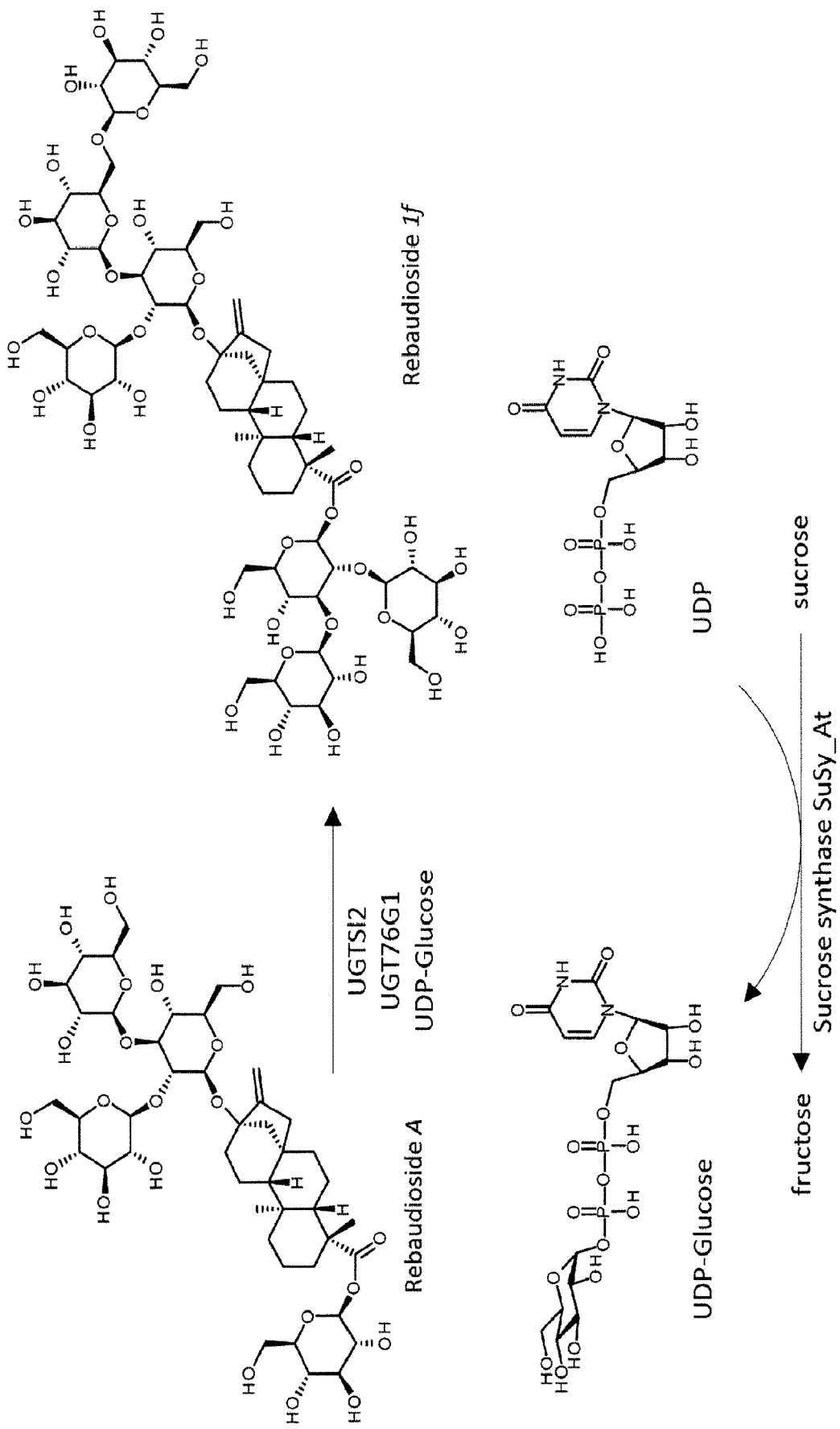
Figure 5G:
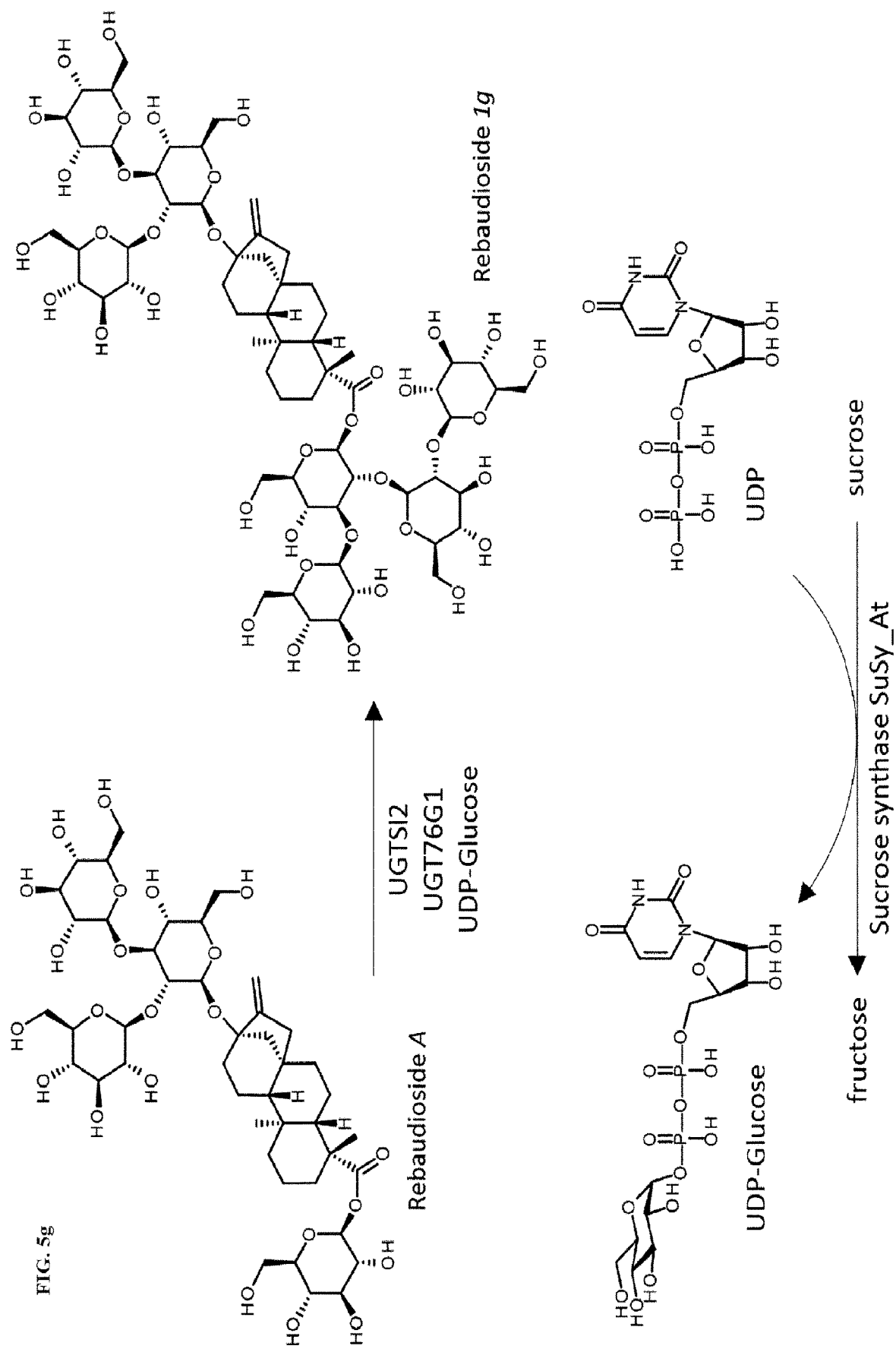
Figure 5H:
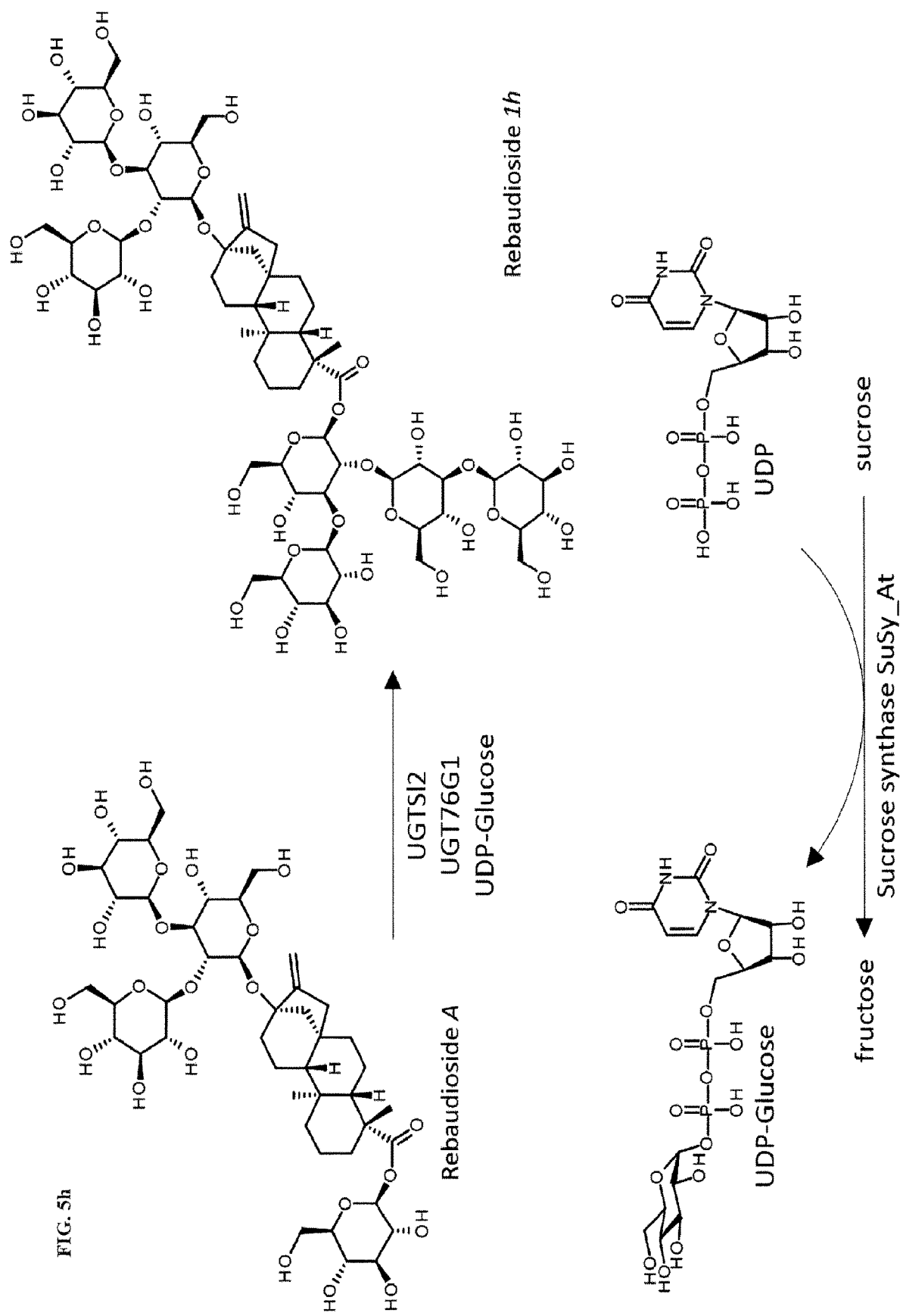
Figure 5I:
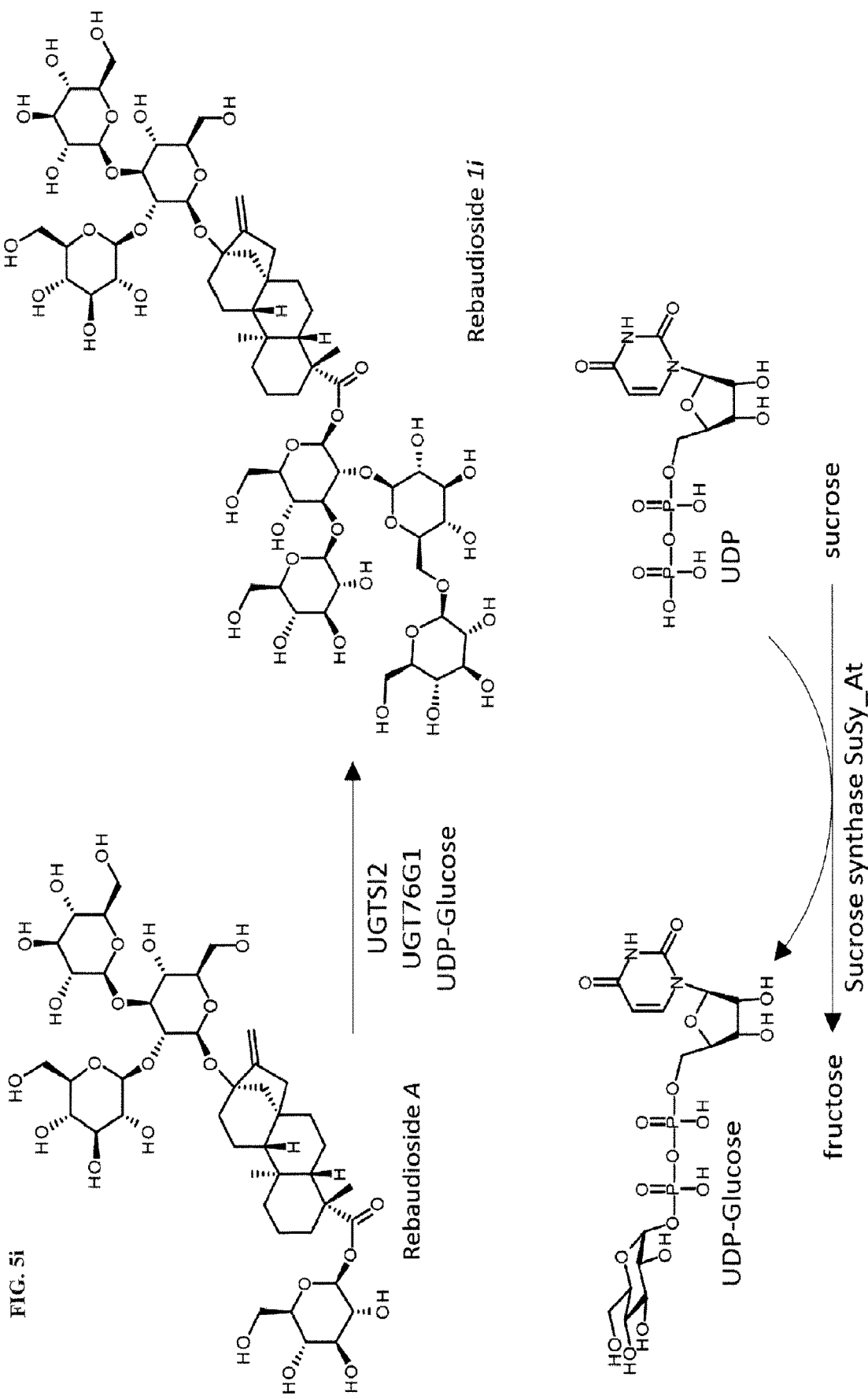
Figure 5J:
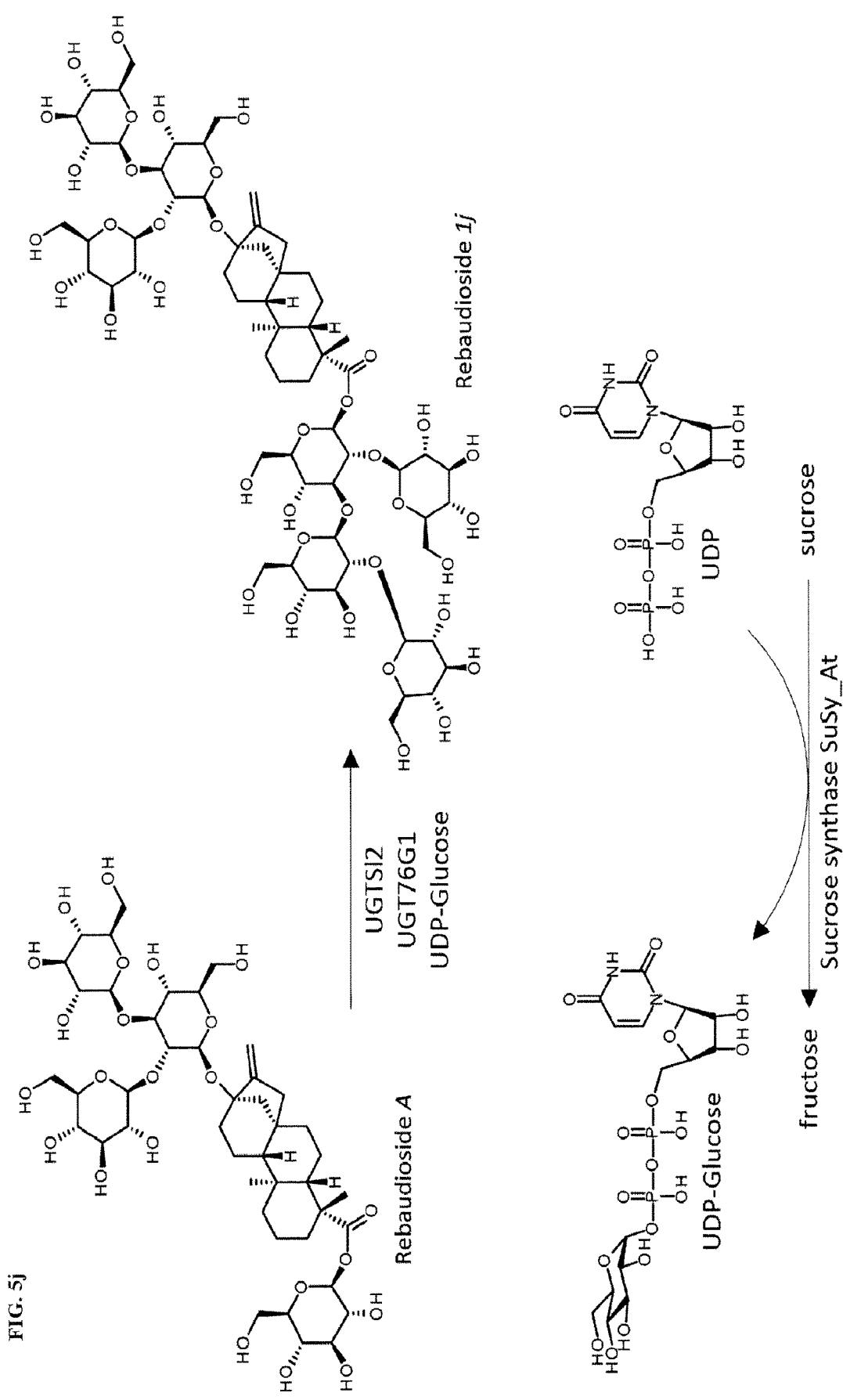
Figure 5K:
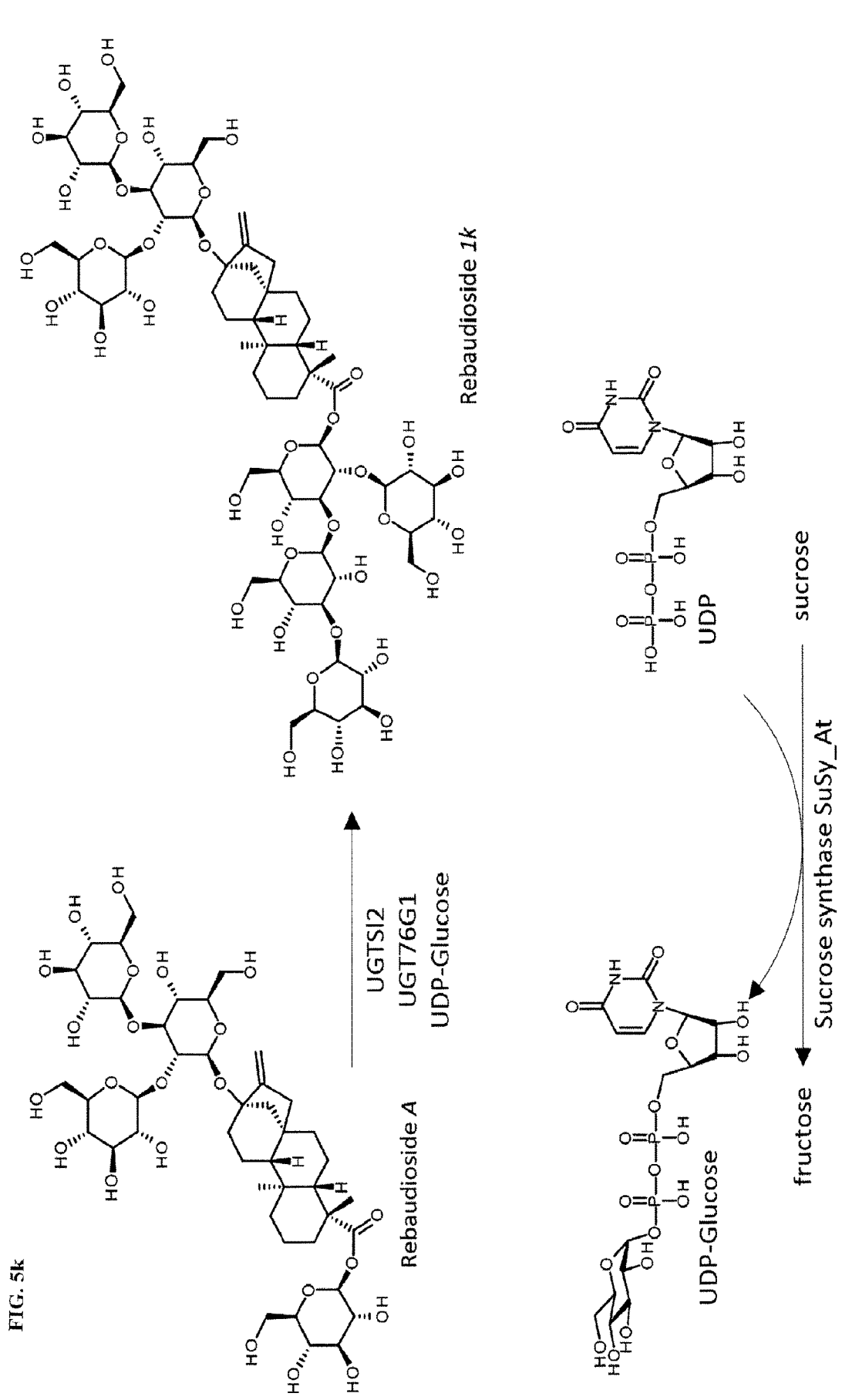
Figure 51:
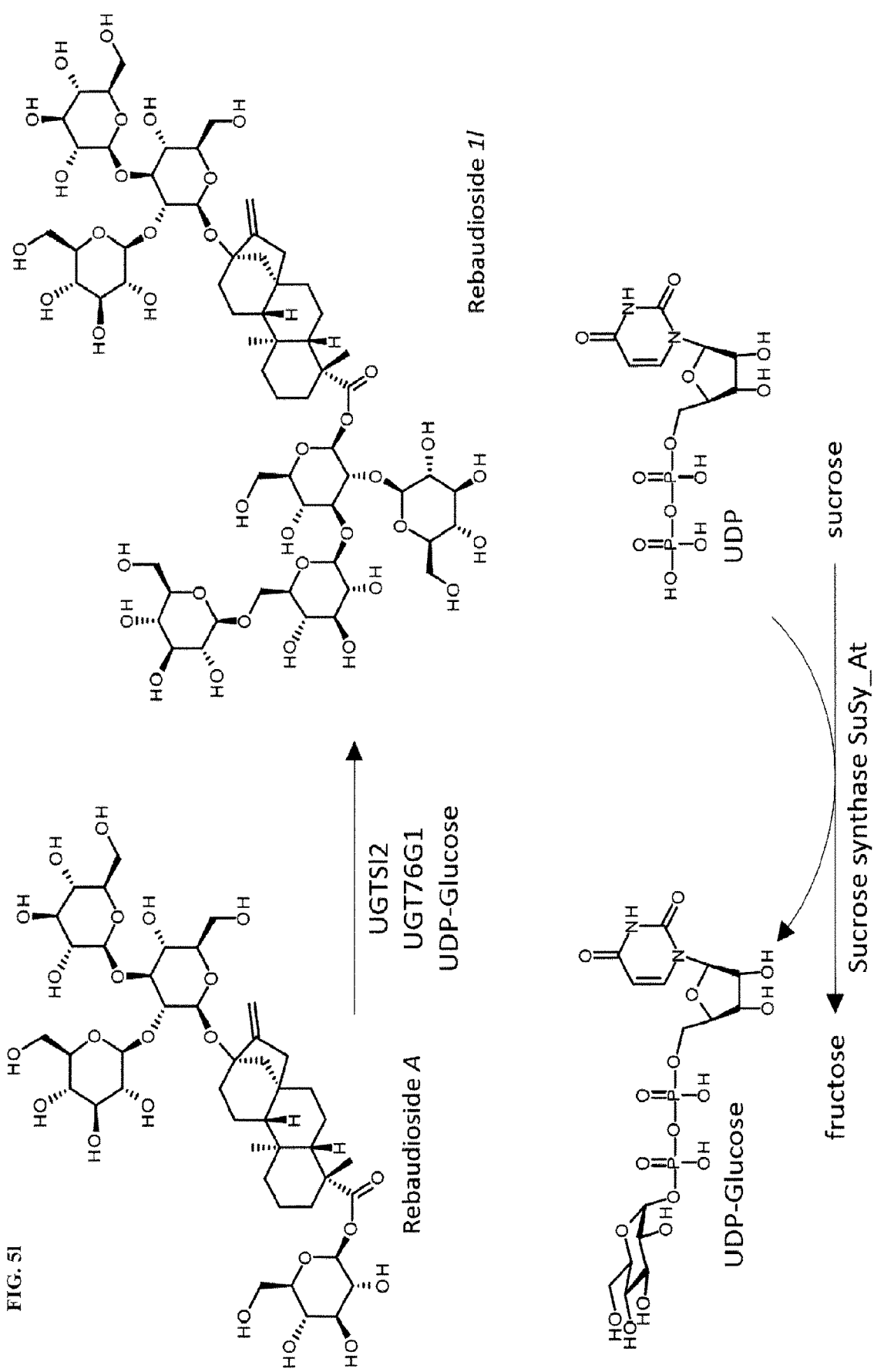
Figure 5M:
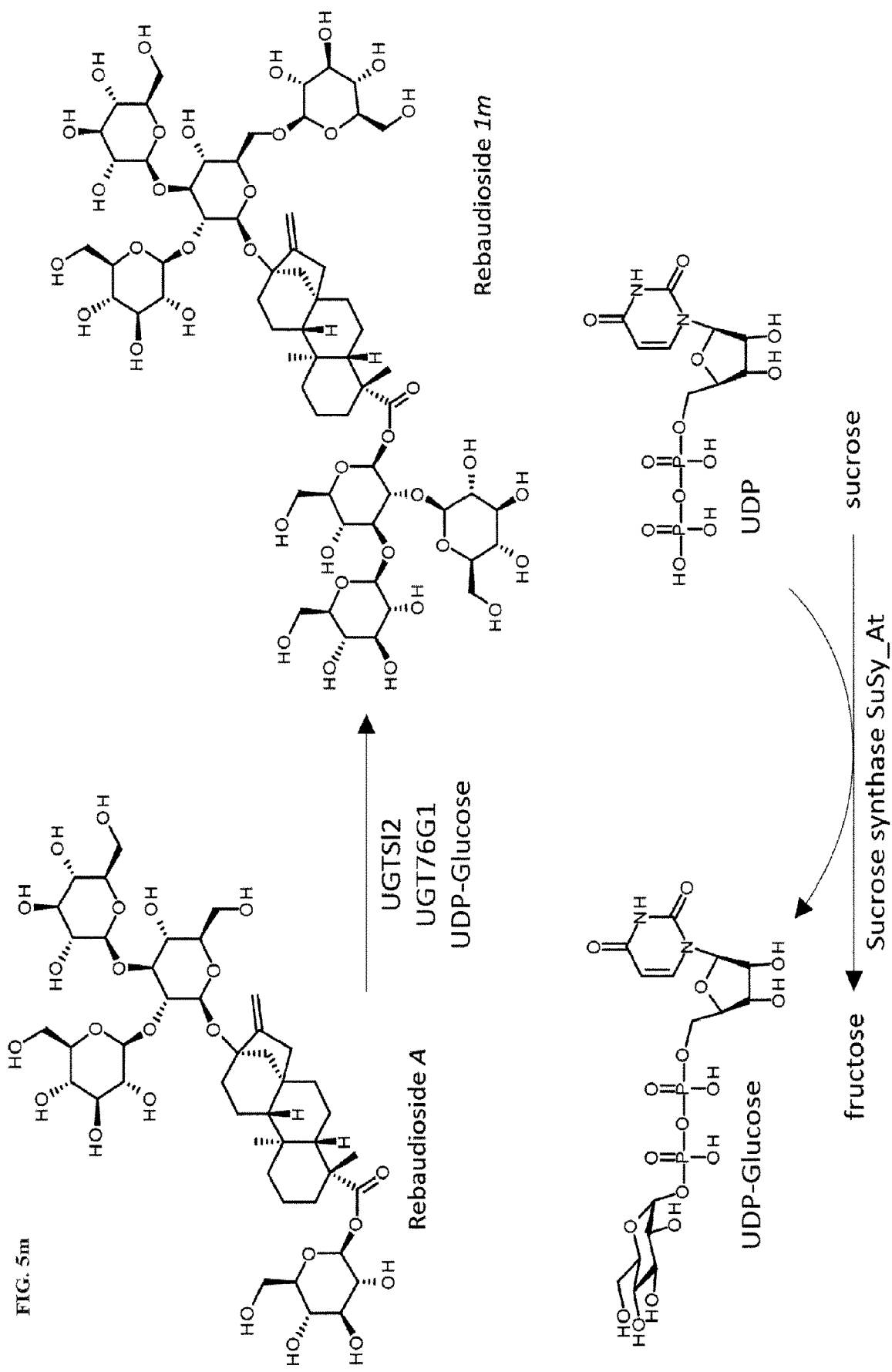
Figure 5N:
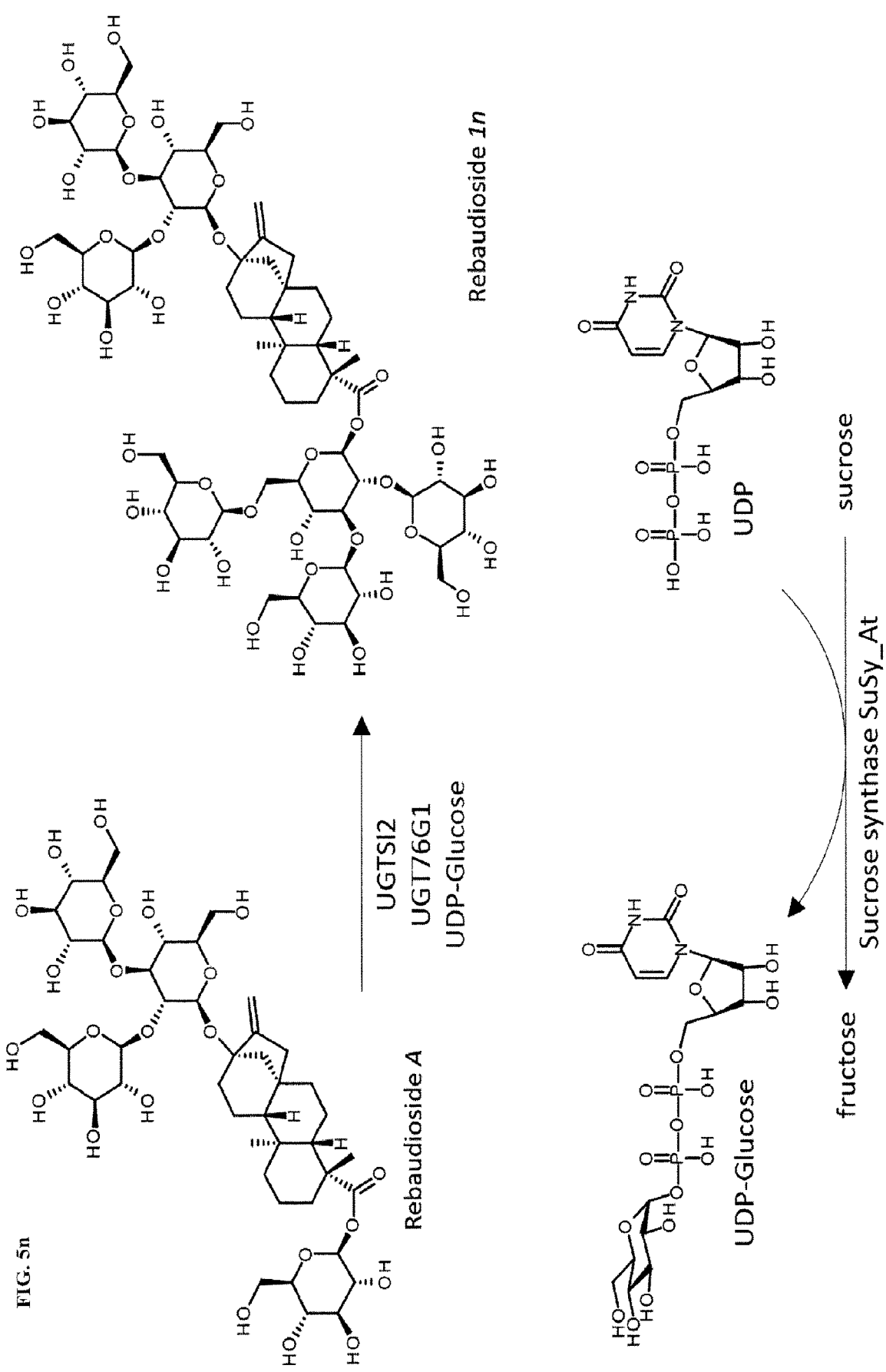
Figure 5O:
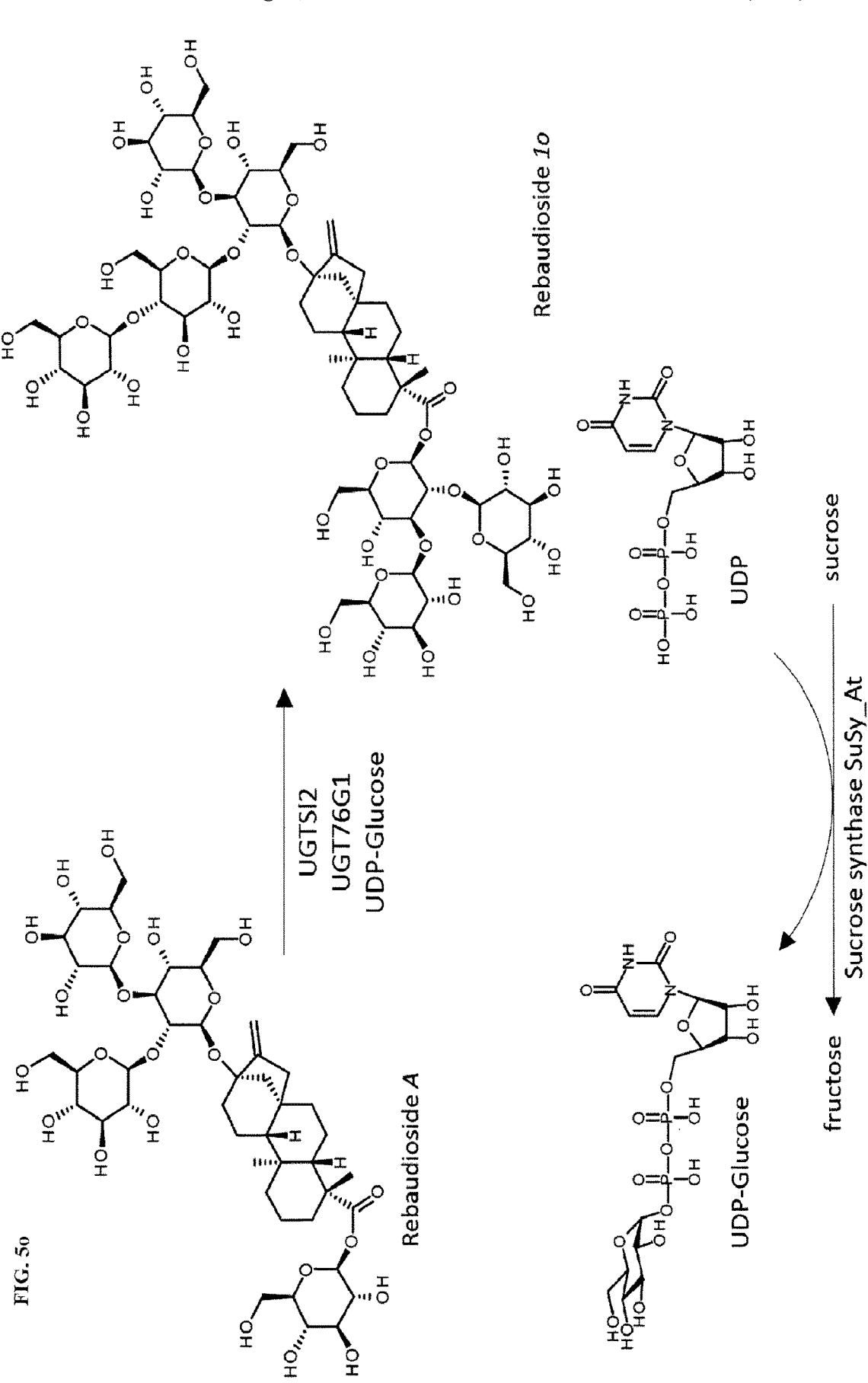
Figure 5P:
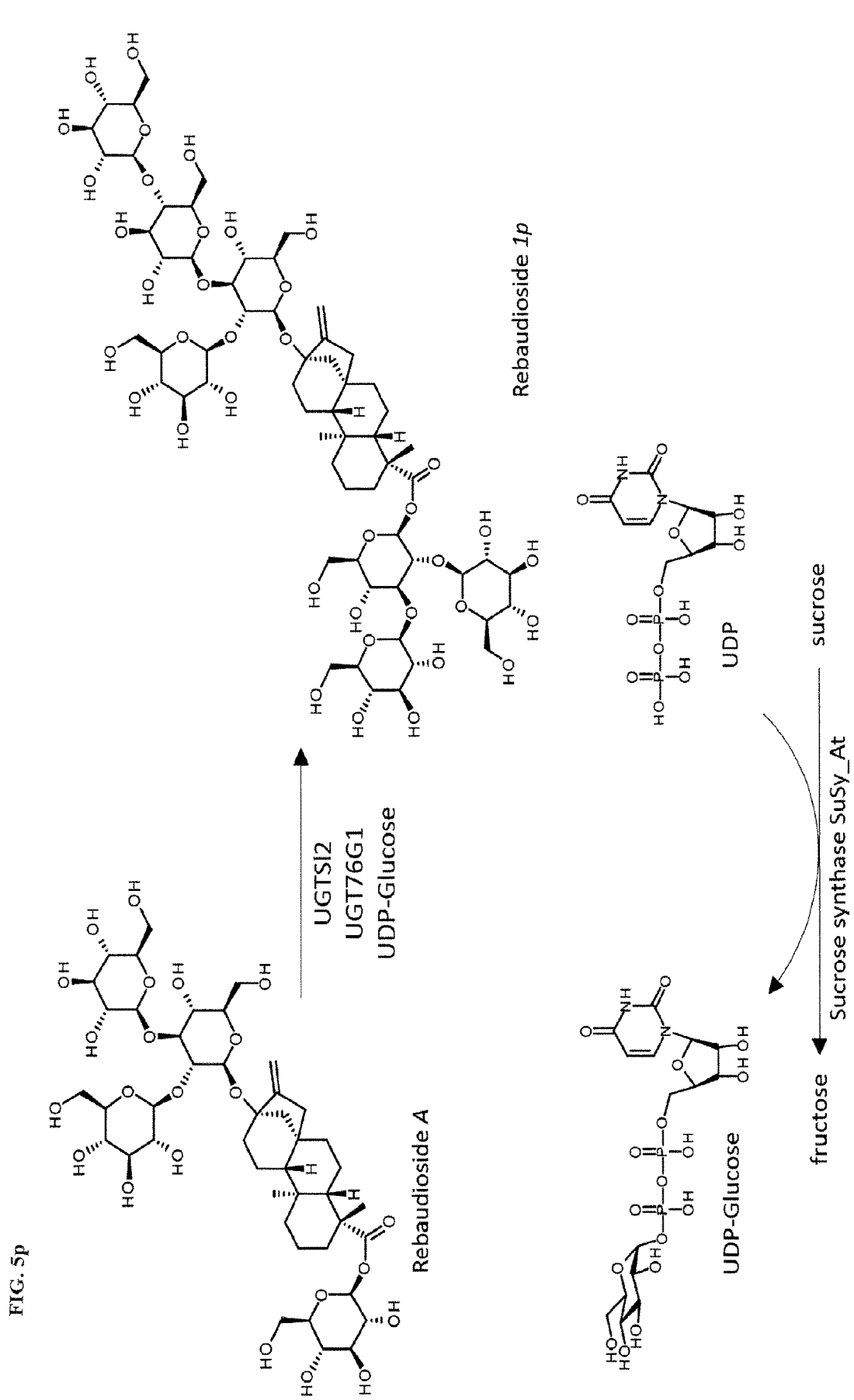
Figure 5Q:
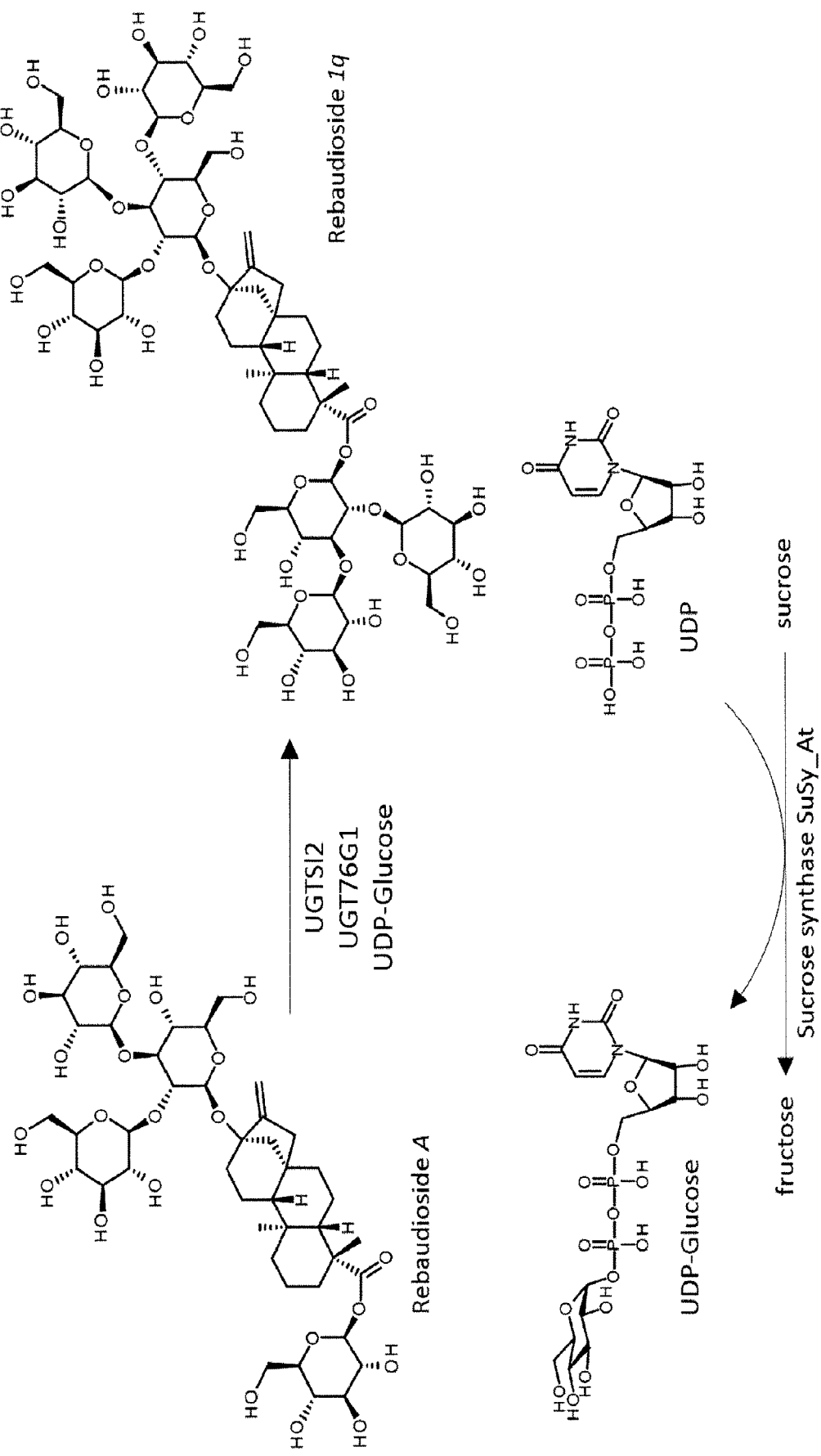
Figure 5R:
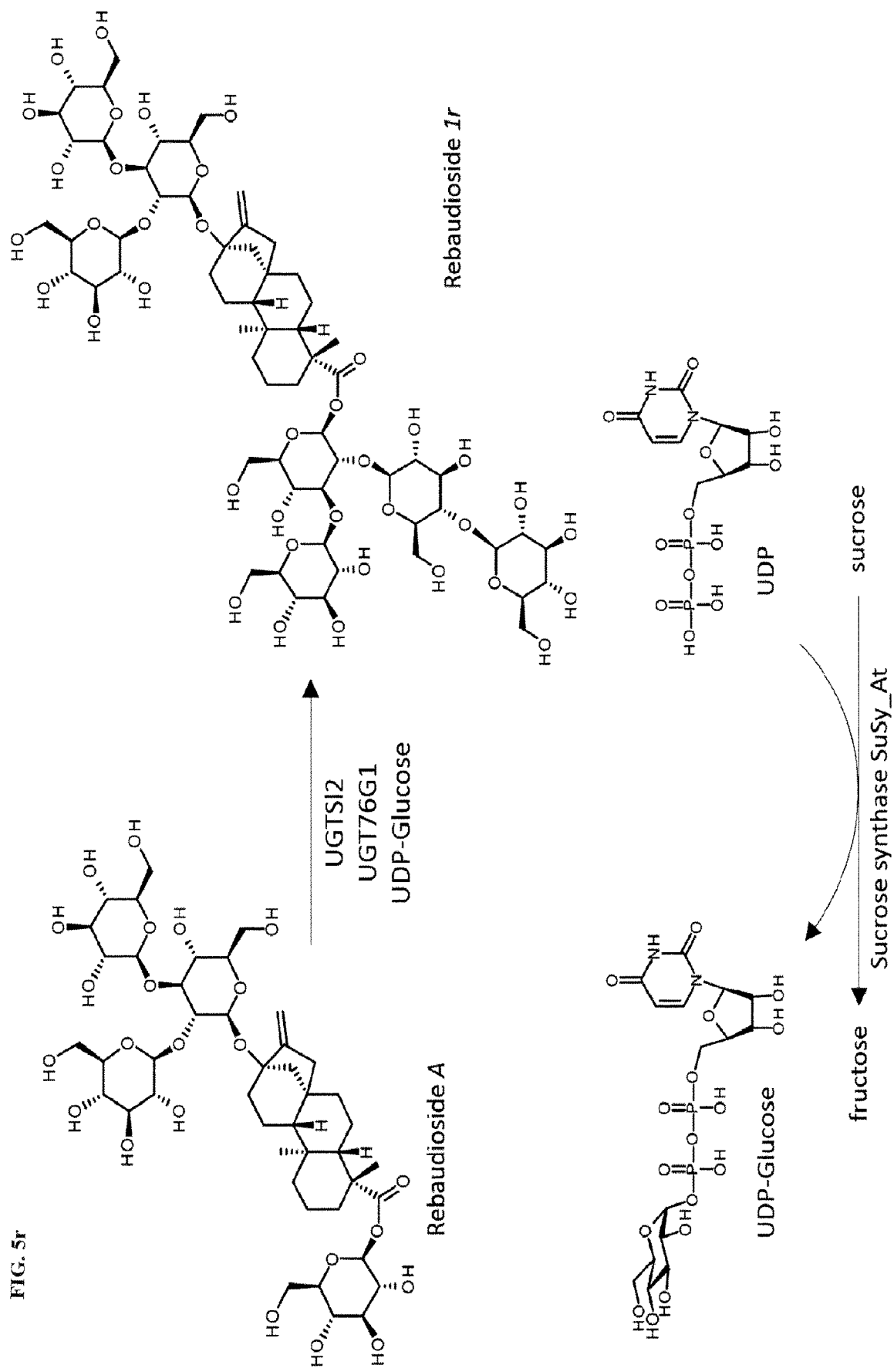
Figure 5S:
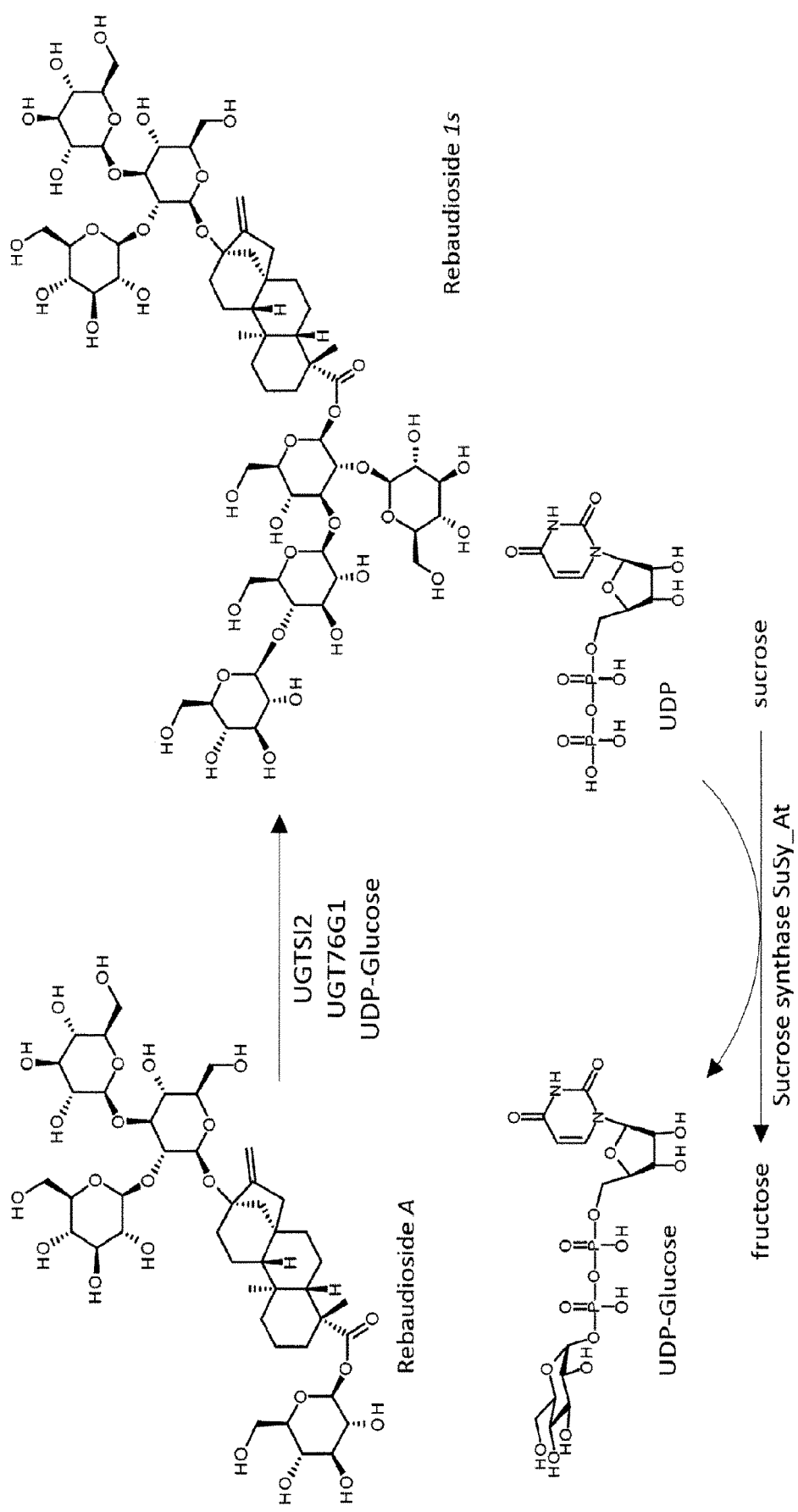
Figure 5T:
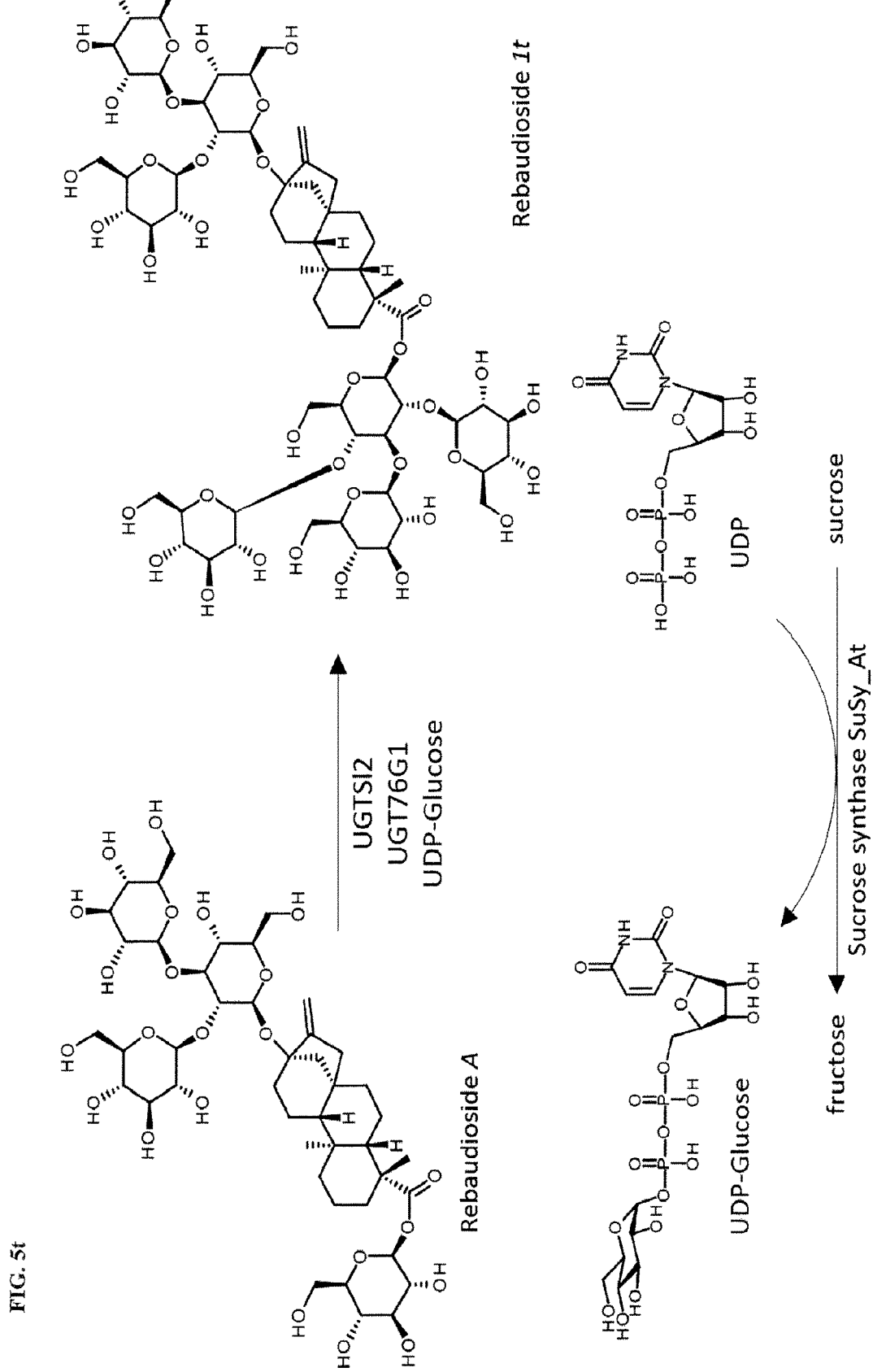
Figure 6A:
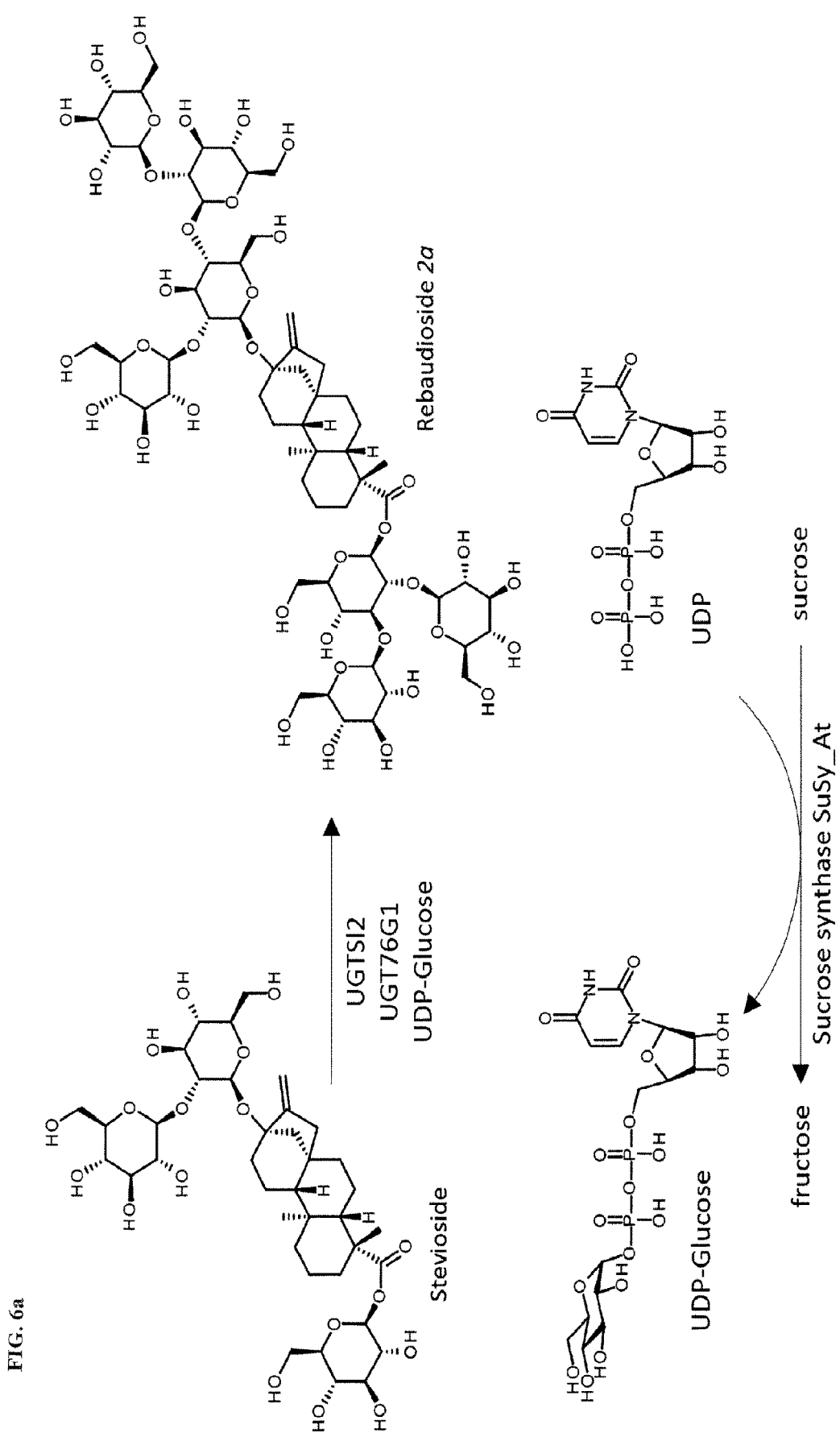
FIG. 6a through FIG. 6t show the biocatalytic production of rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and rebaudioside 1q, respectively, from stevioside using the enzymes UGTSl2 and UGT76G1 and concomitant recycling of UDP to UDP-glucose via sucrose synthase SuSy_At.
Figure 6B:
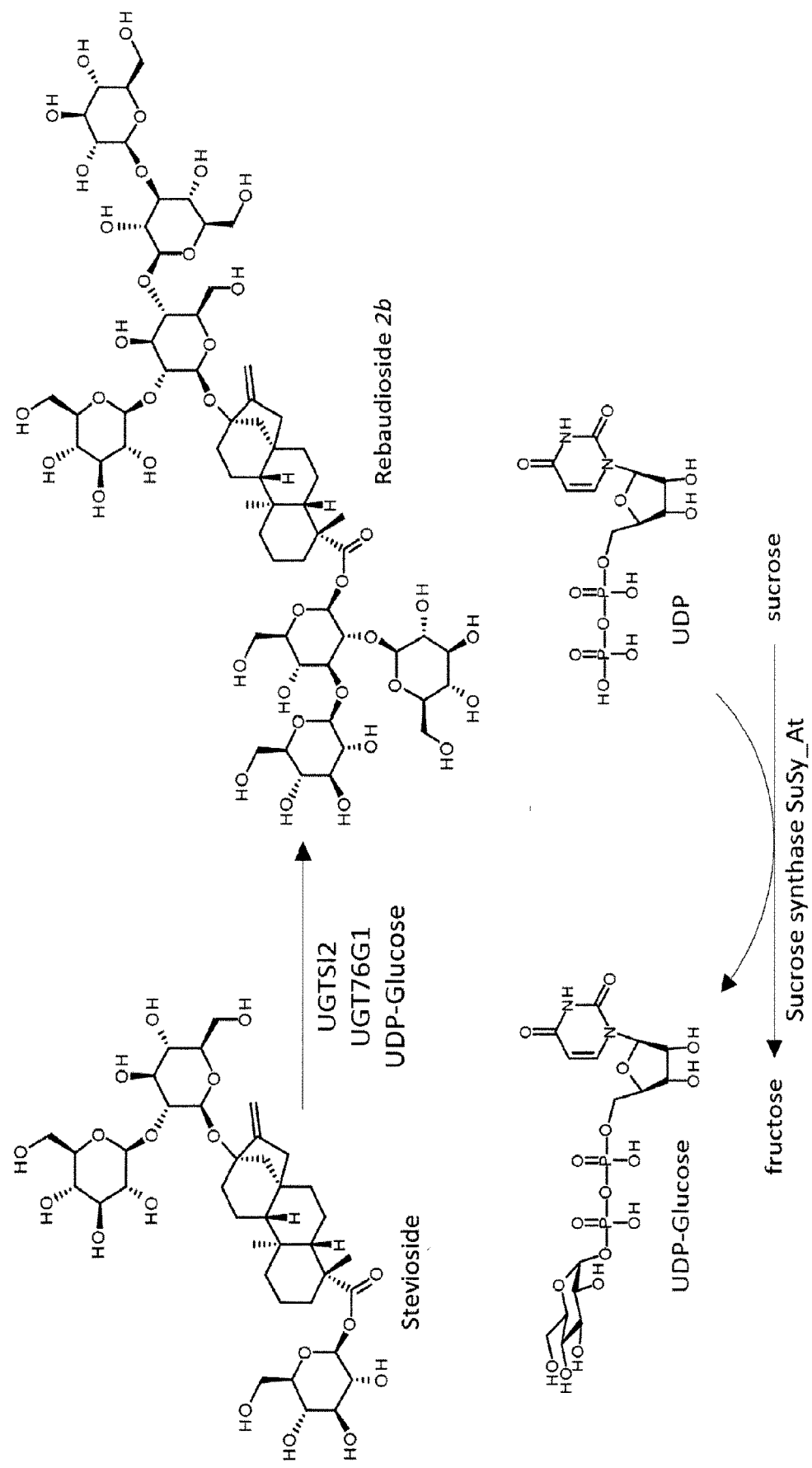
Figure 6C:
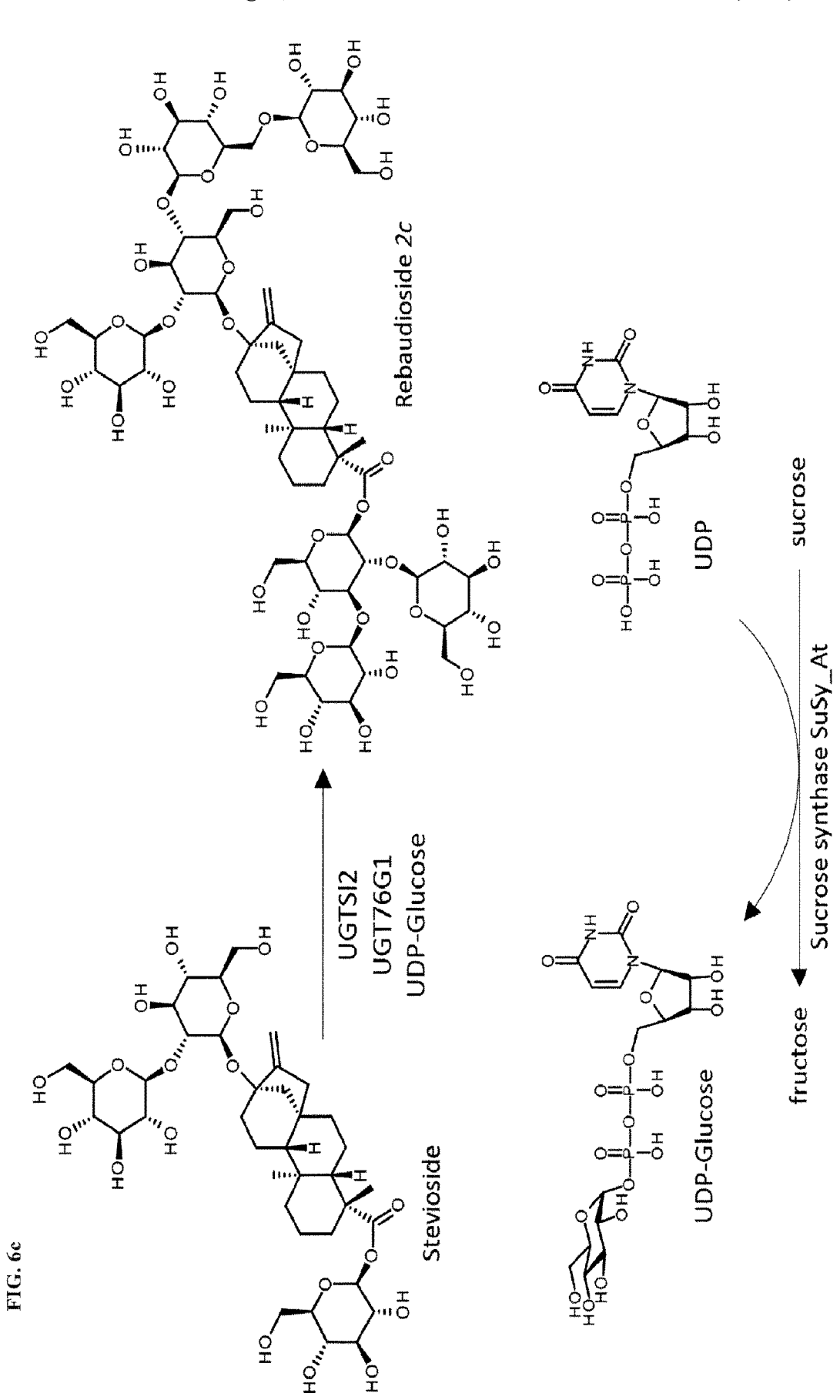
Figure 6D:
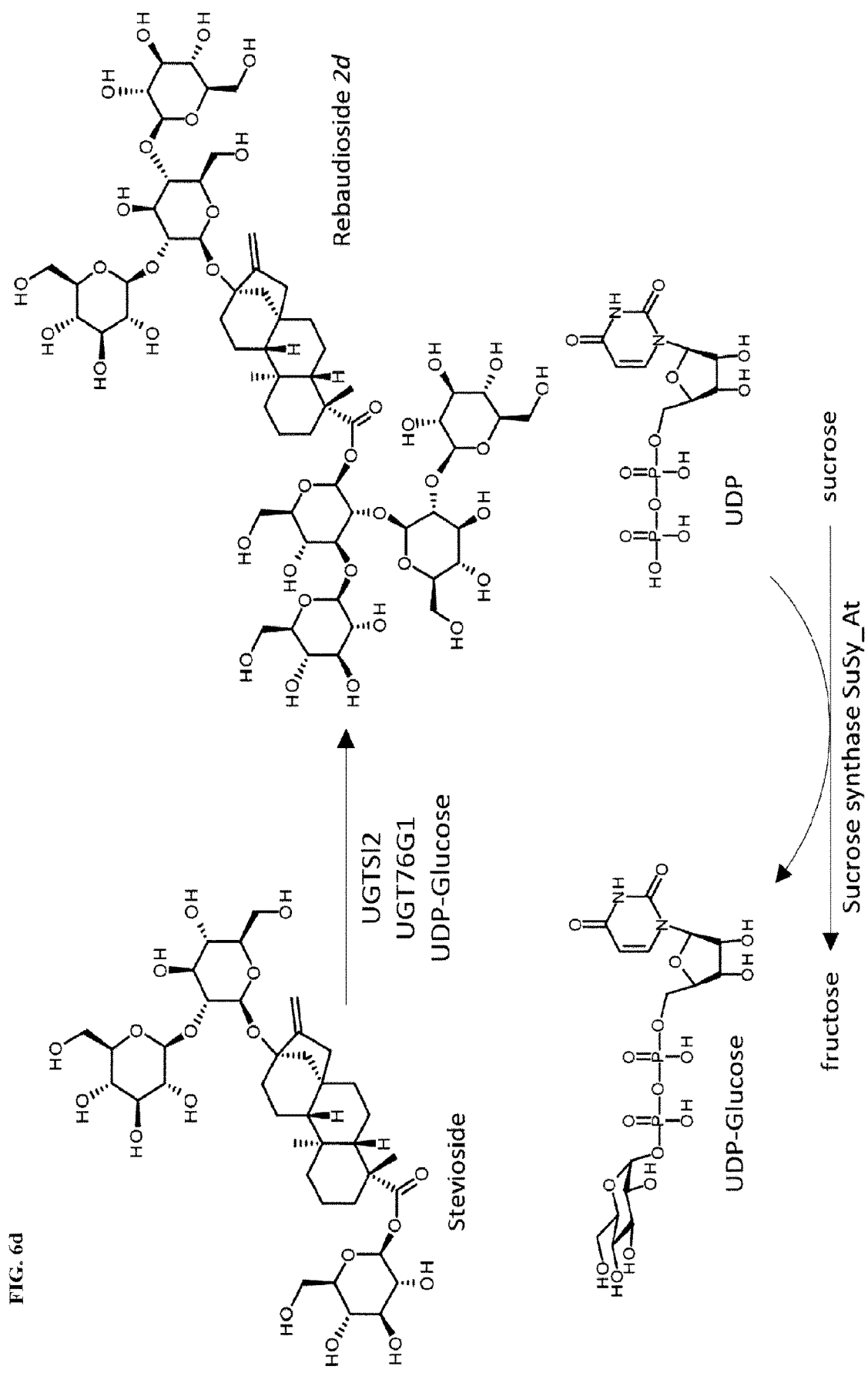
Figure 6E:
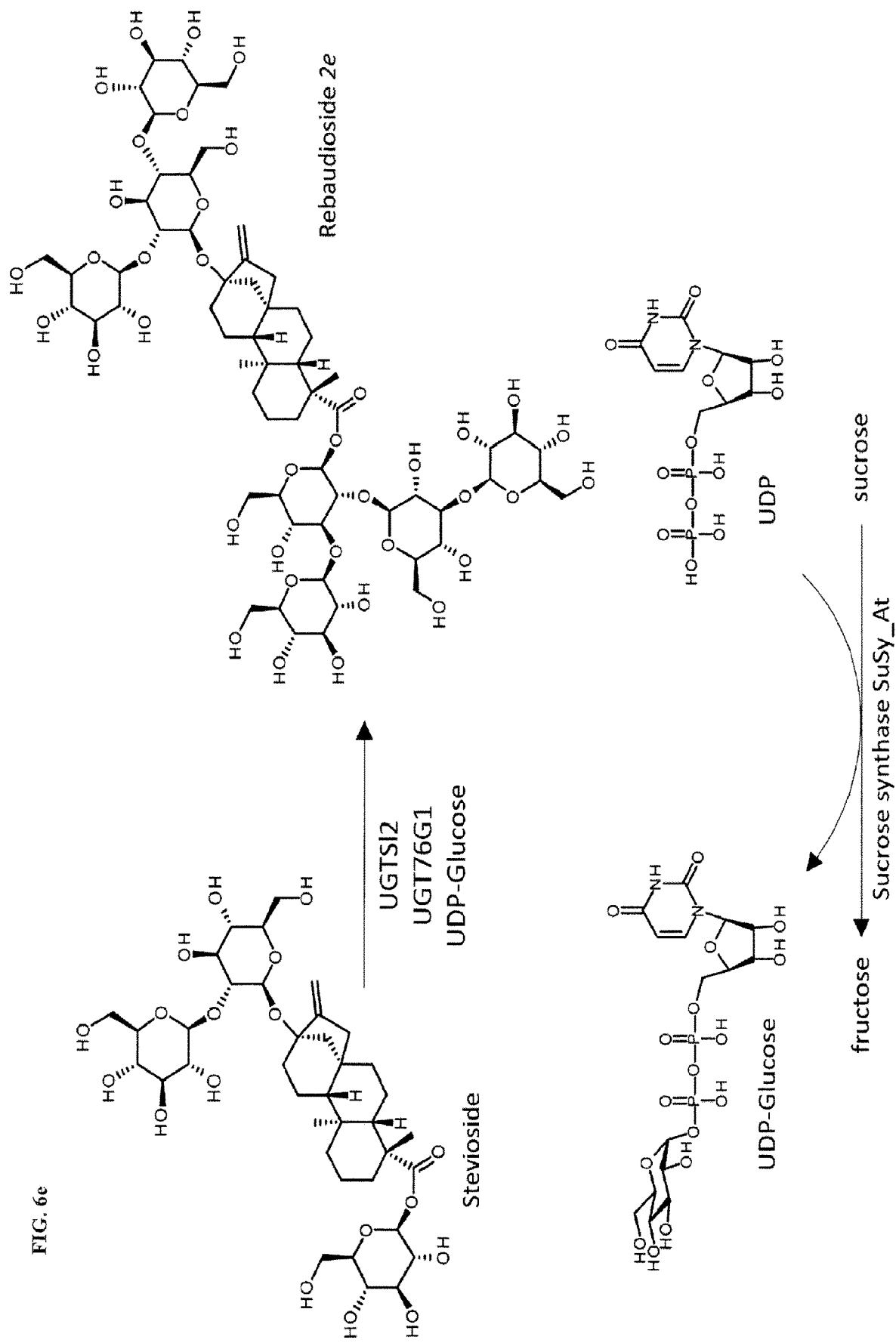
Figure 6F:
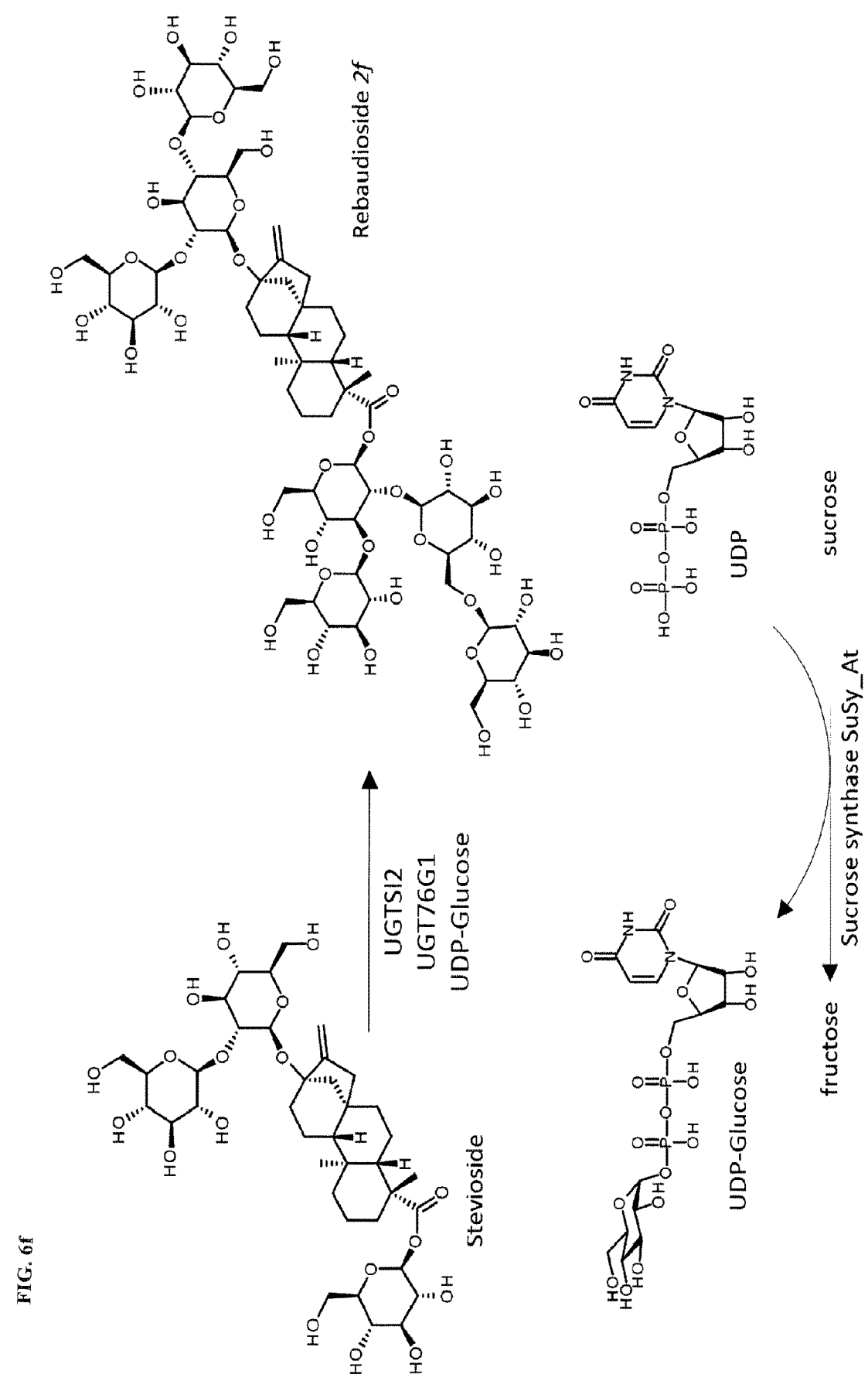
Figure 6G:
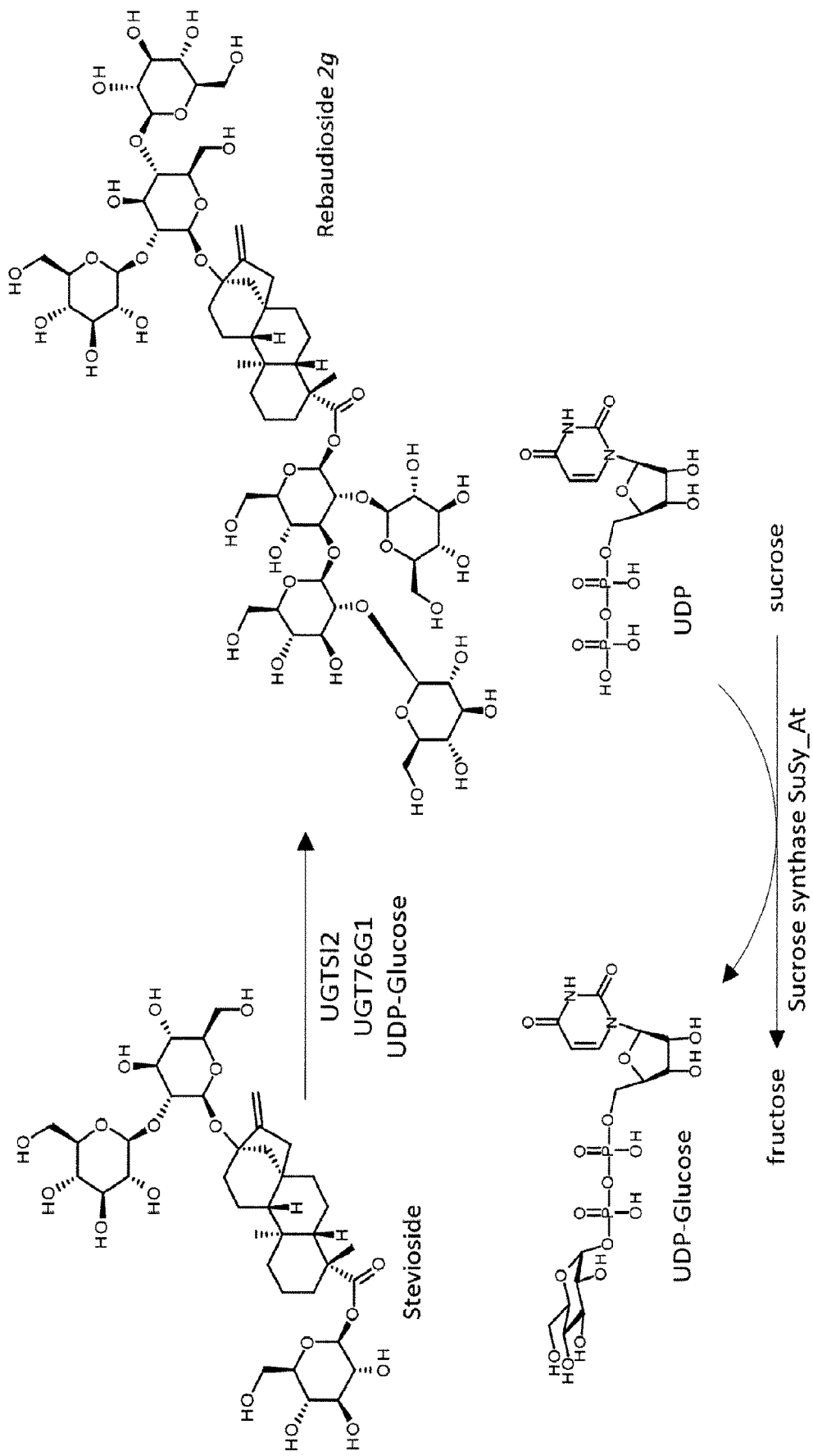
Figure 6H:
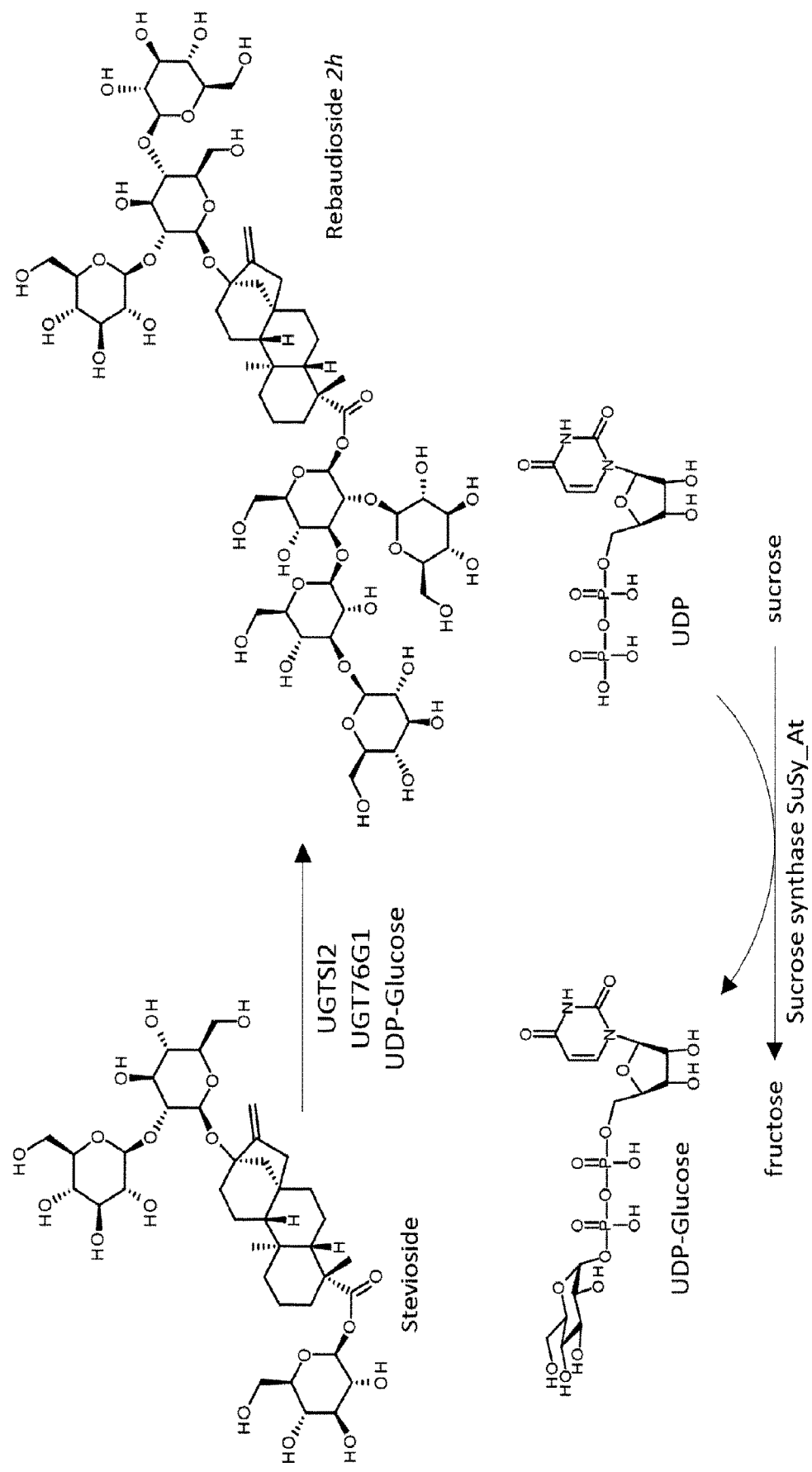
Figure 6I:
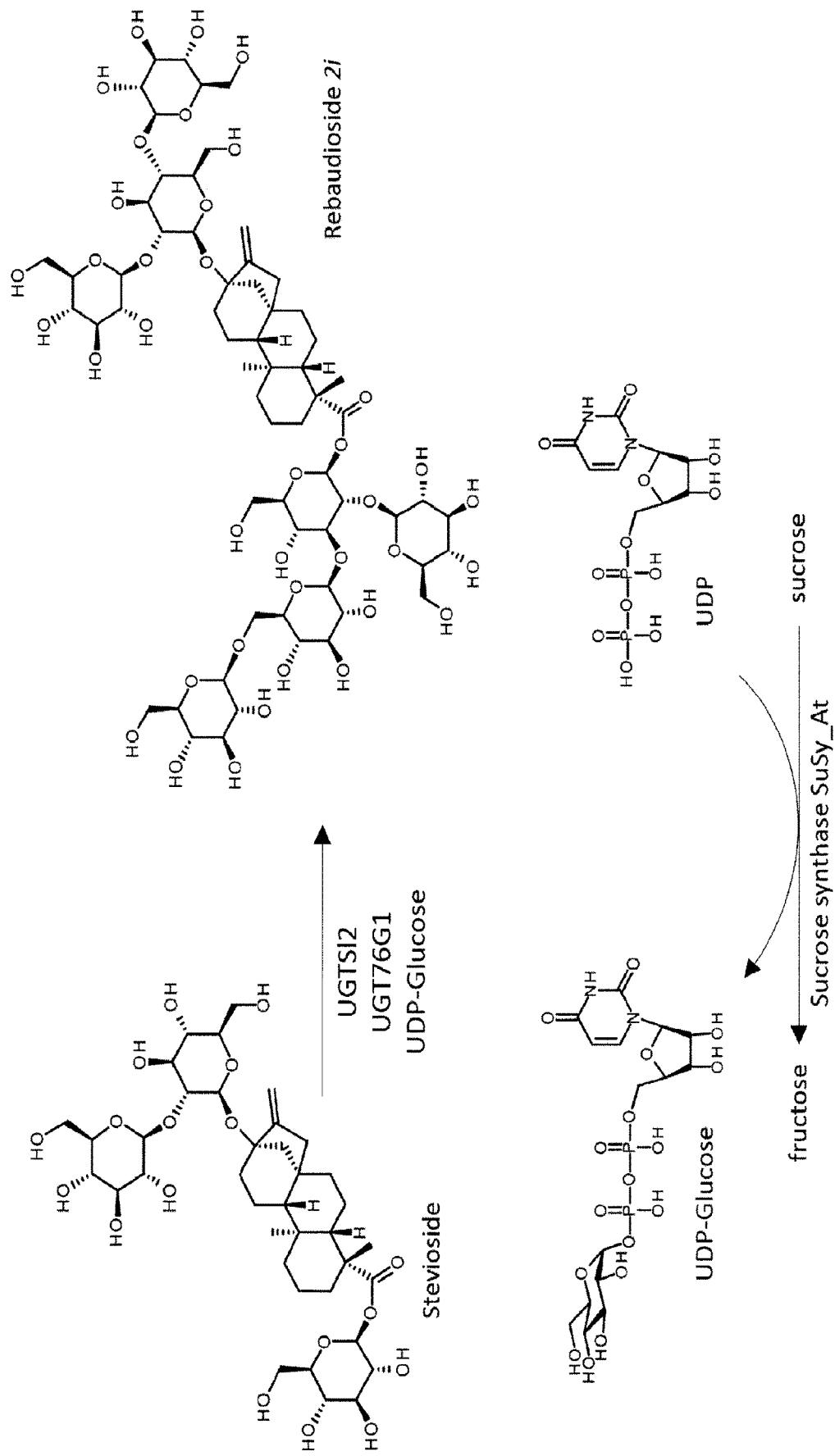
Figure 6J:
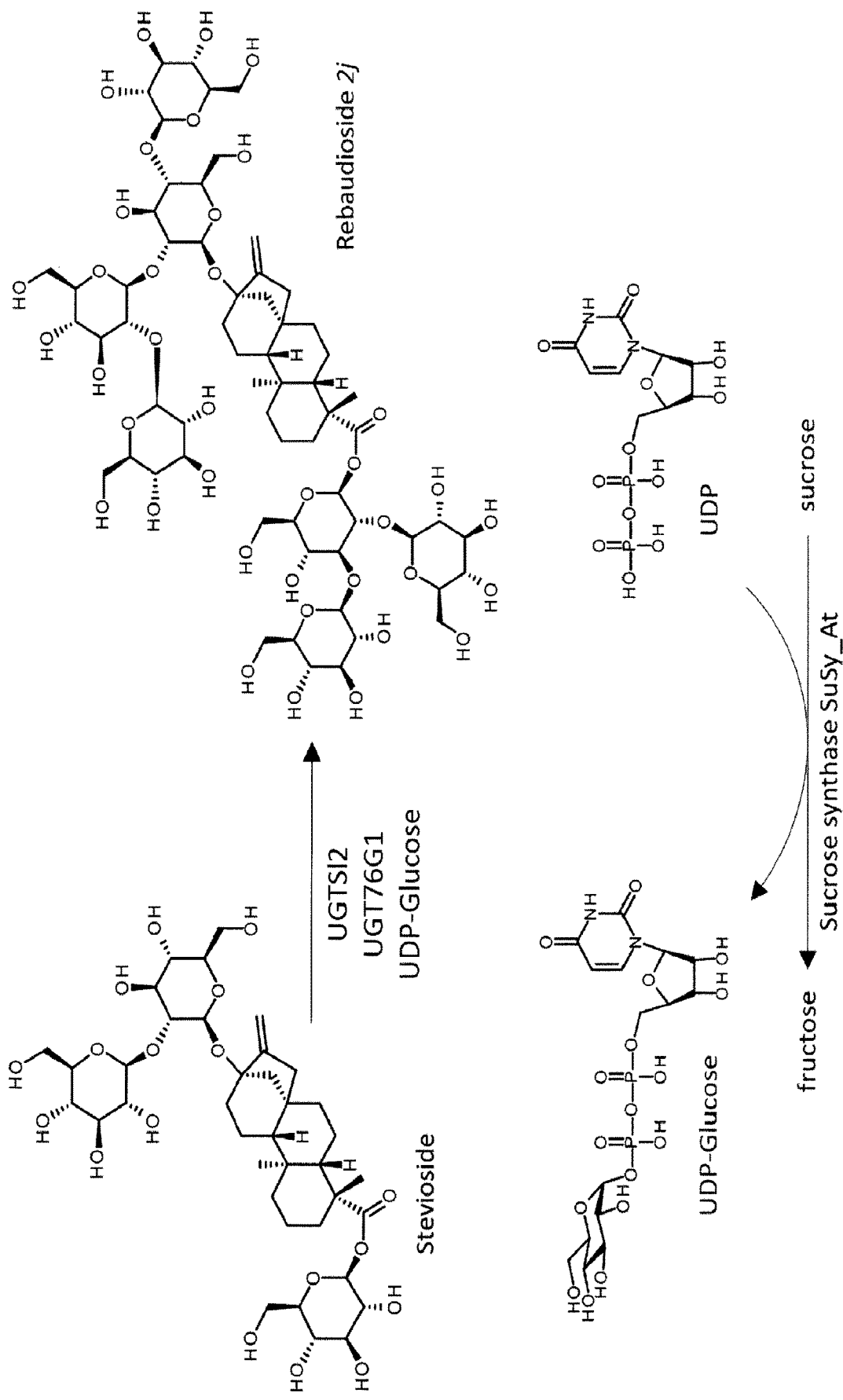
Figure 6K:
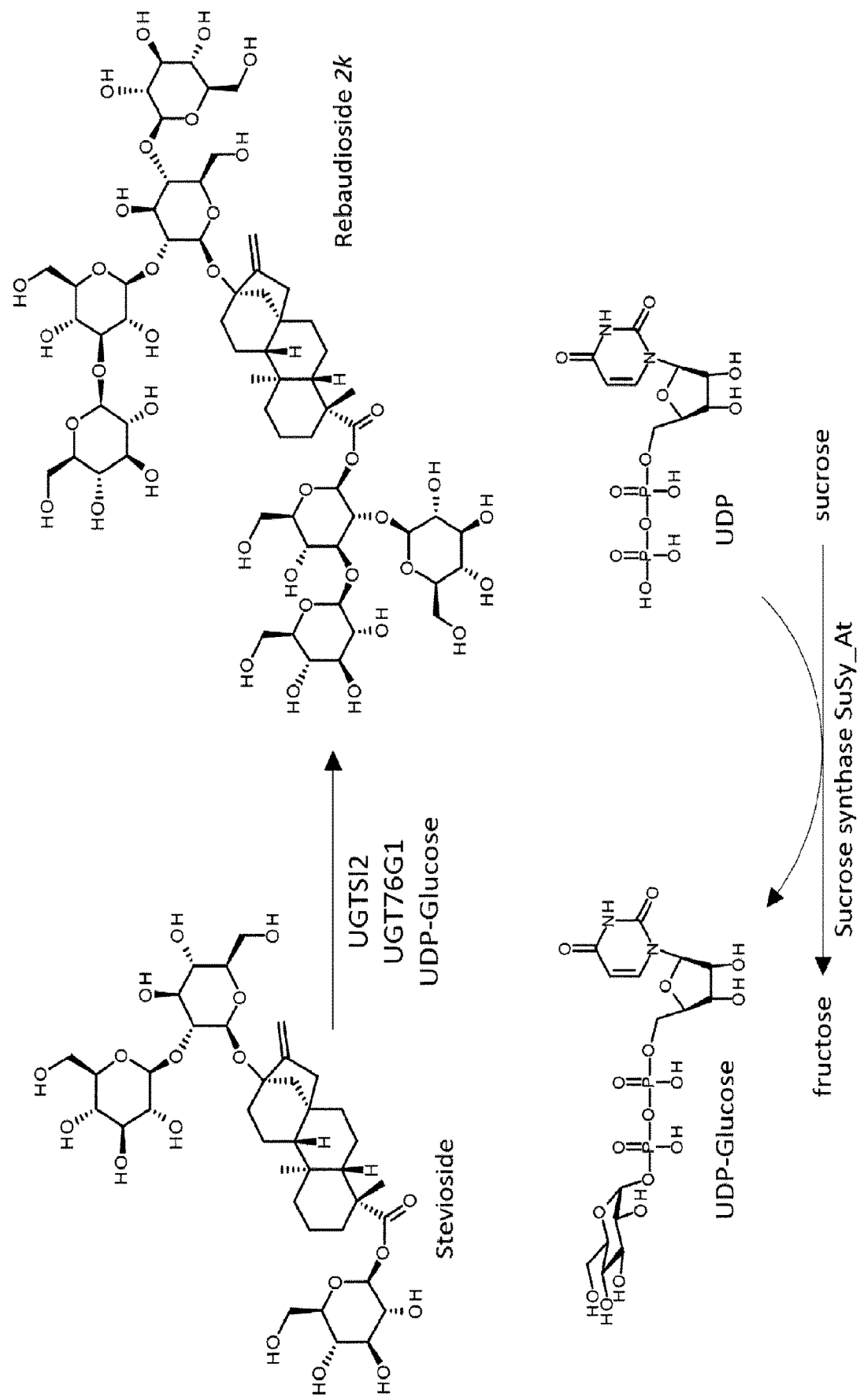
Figure 6I:
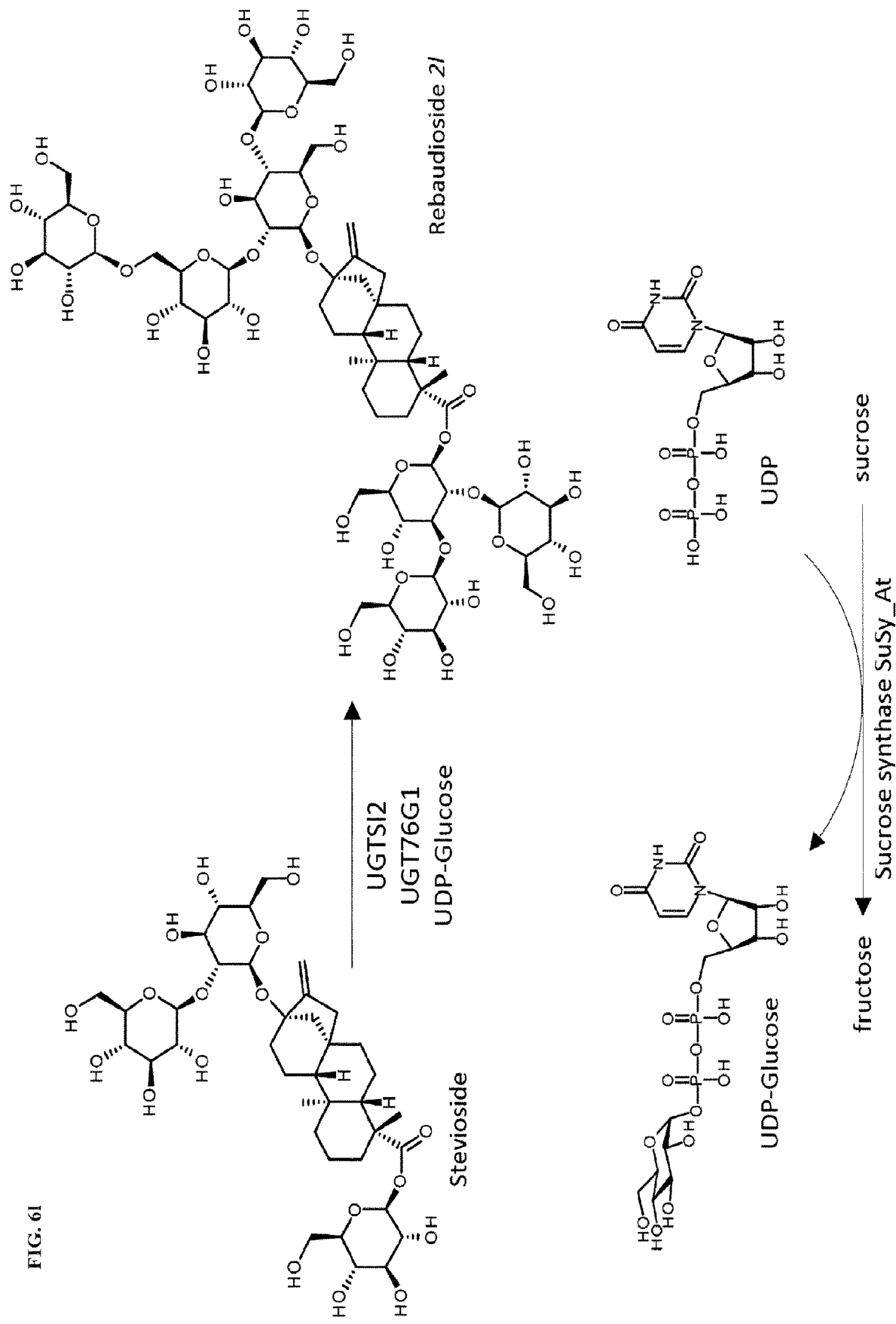
Figure 6M:
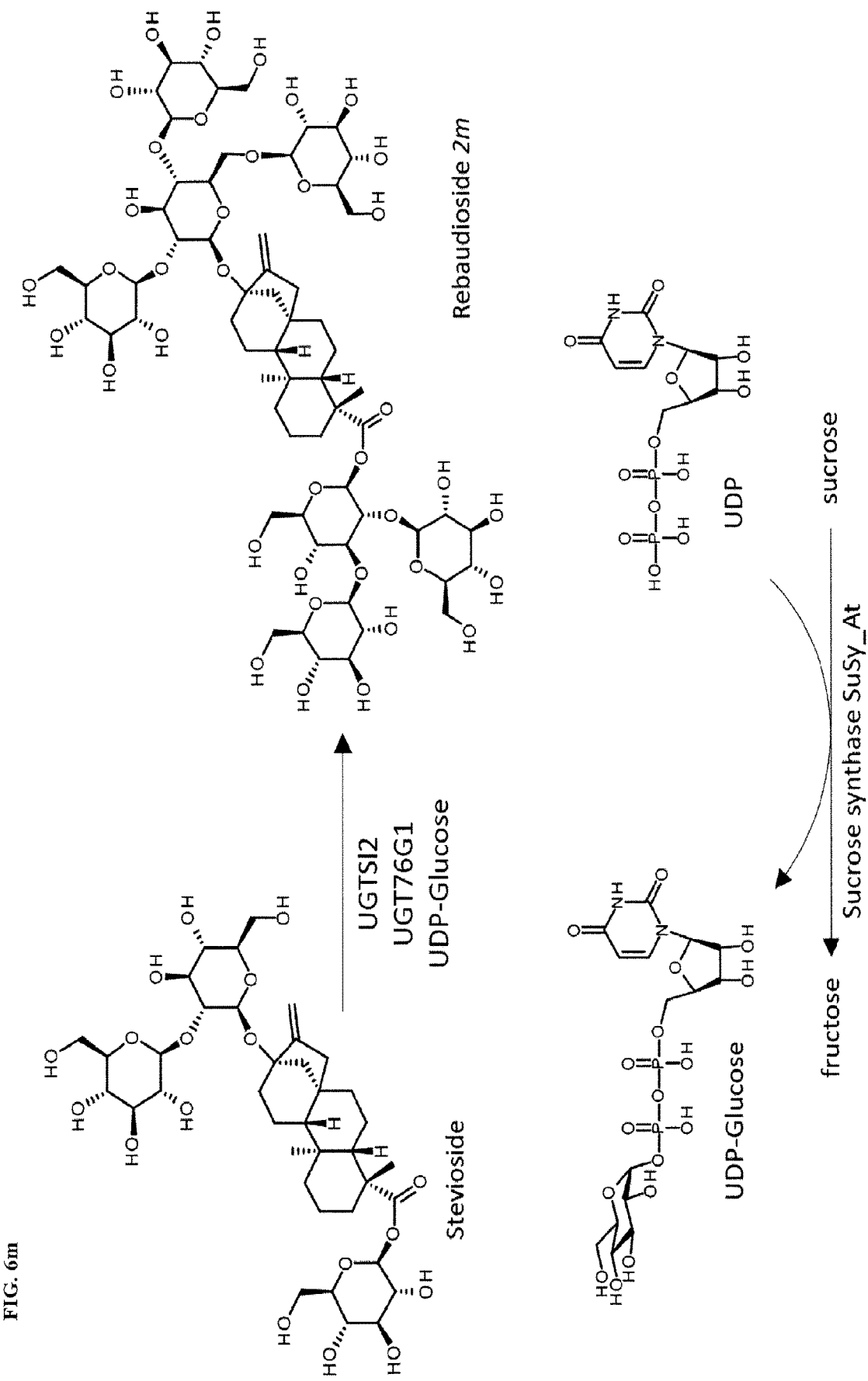
Figure 6N:
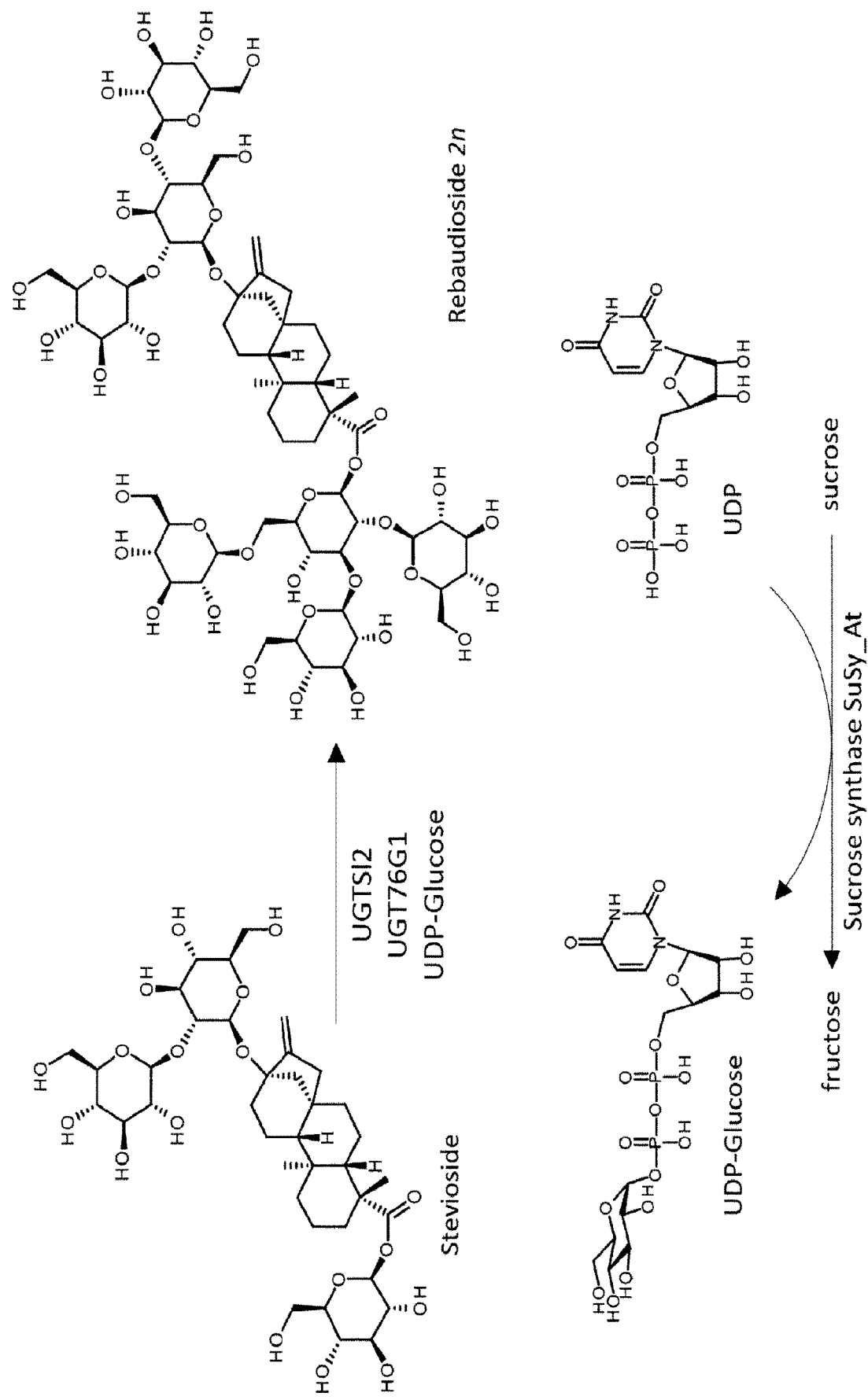
Figure 6O:
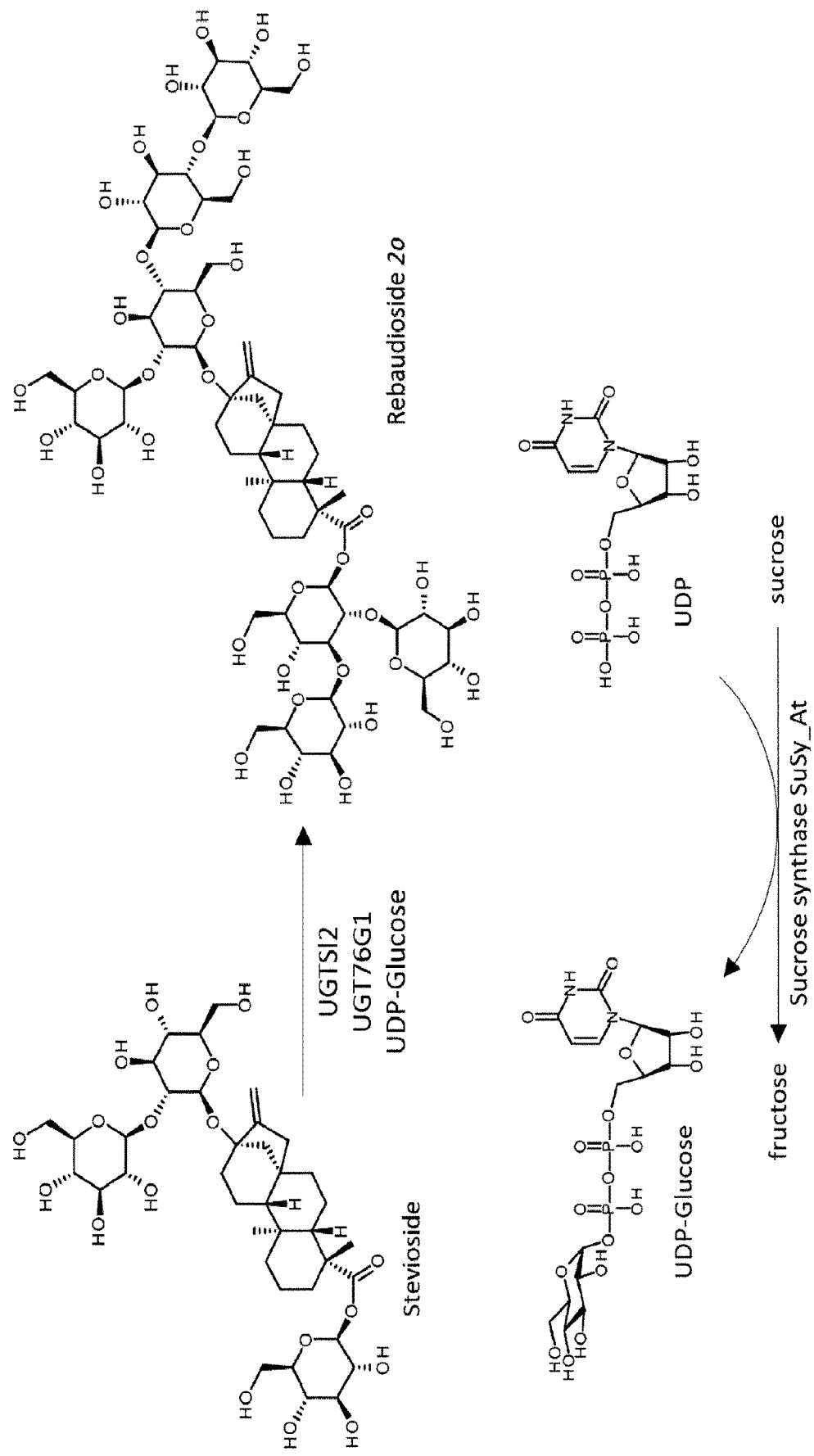
Figure 6P:
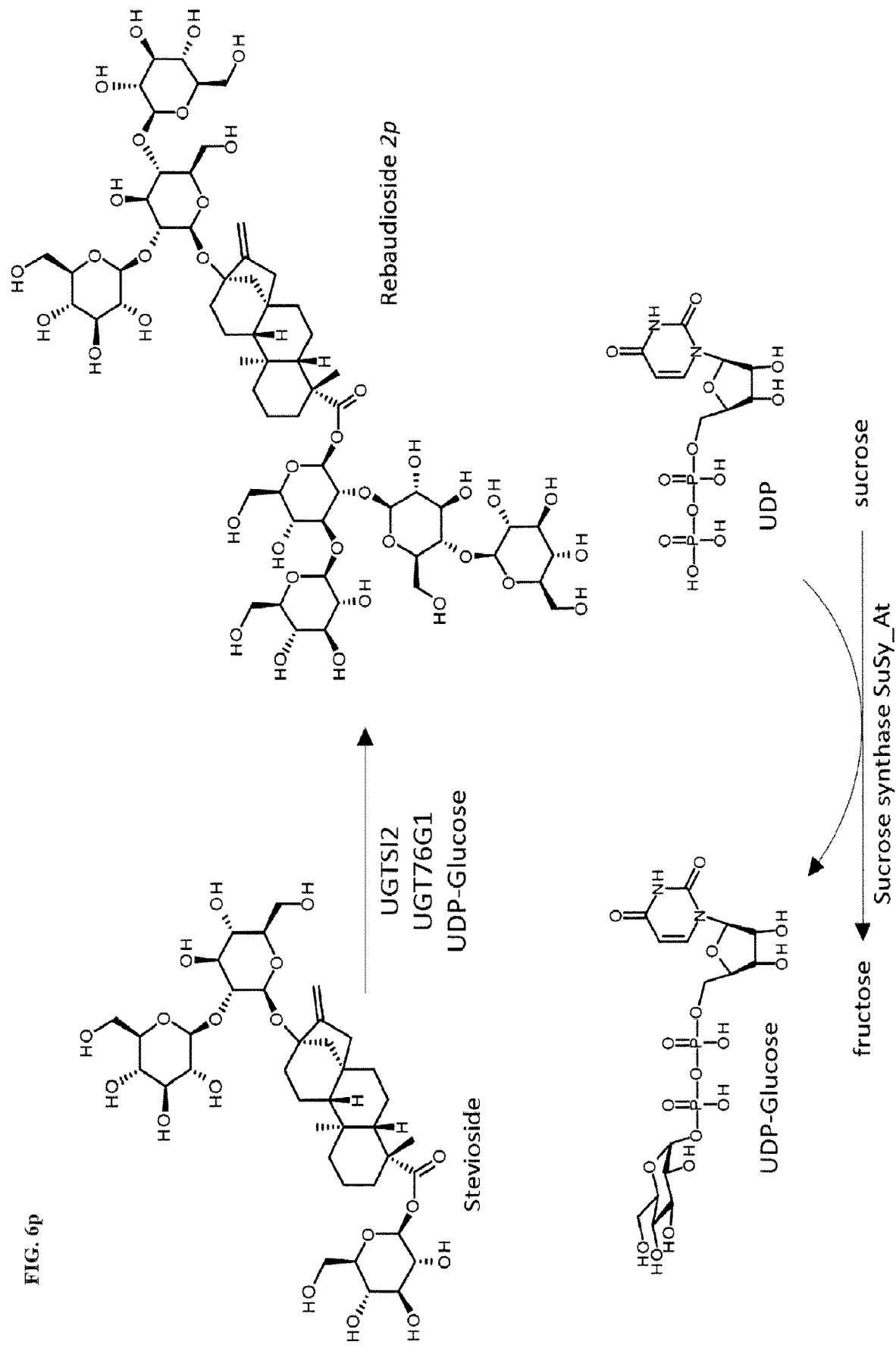
Figure 6Q:
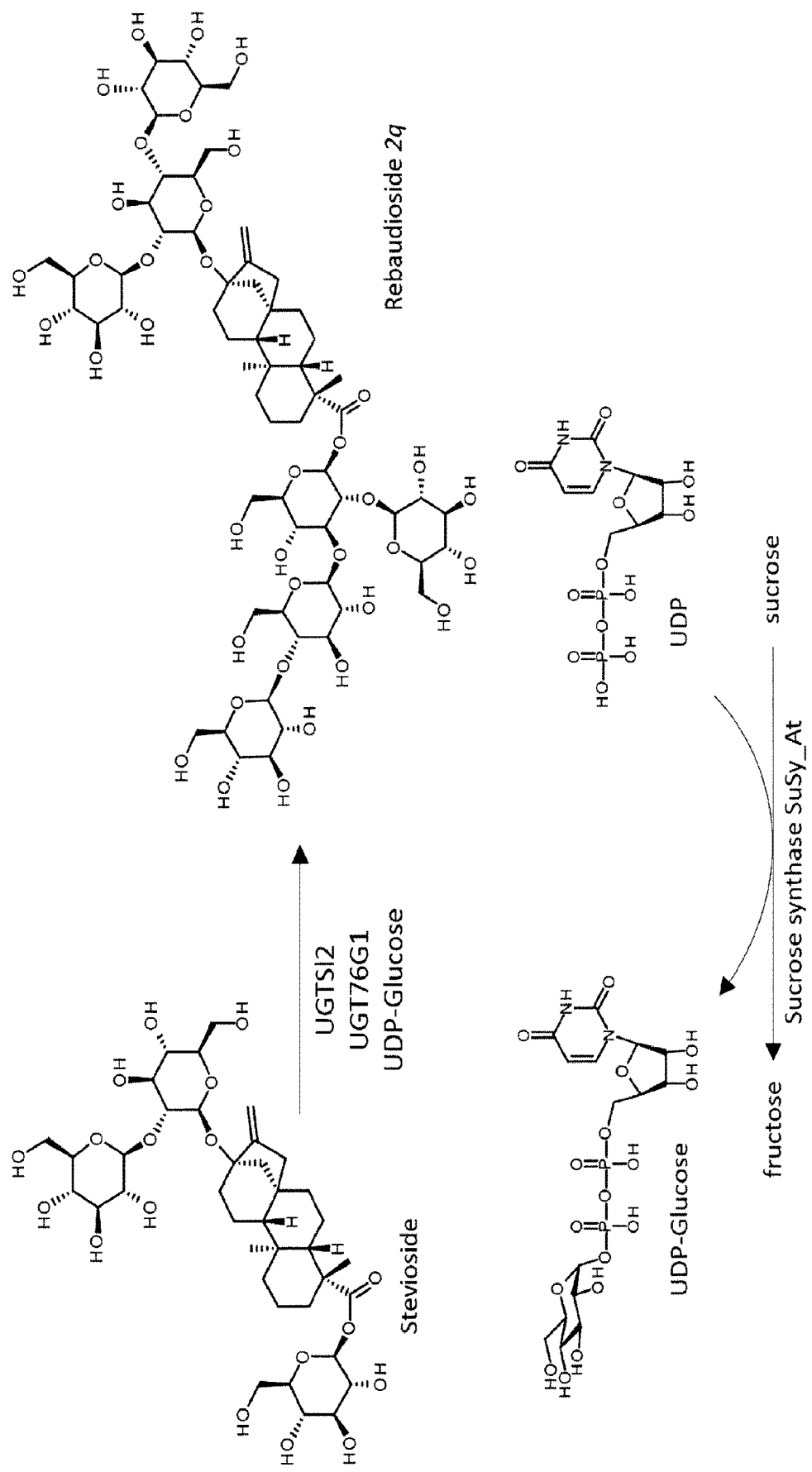
Figure 6R:
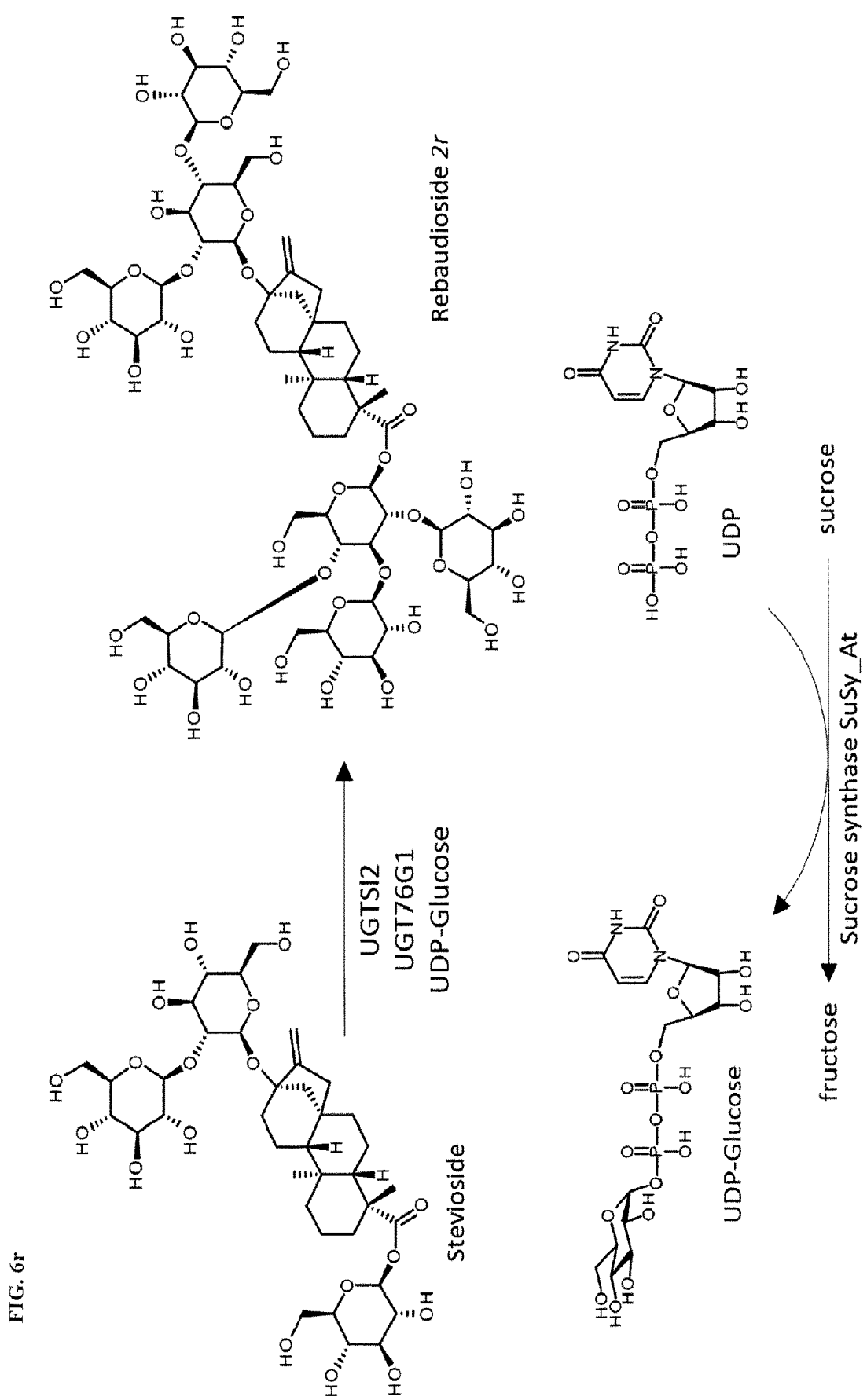
Figure 6S:
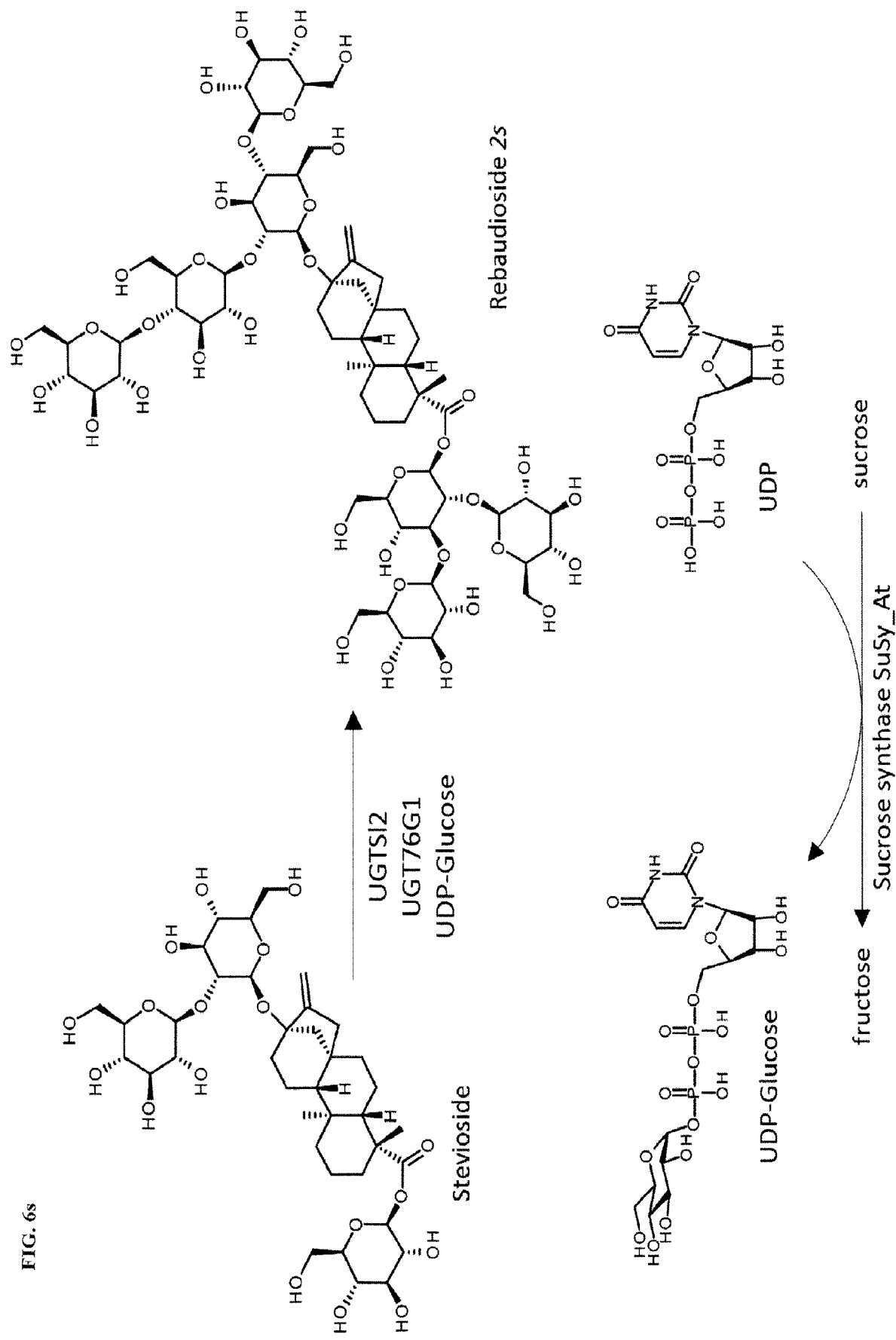
Figure 6T:
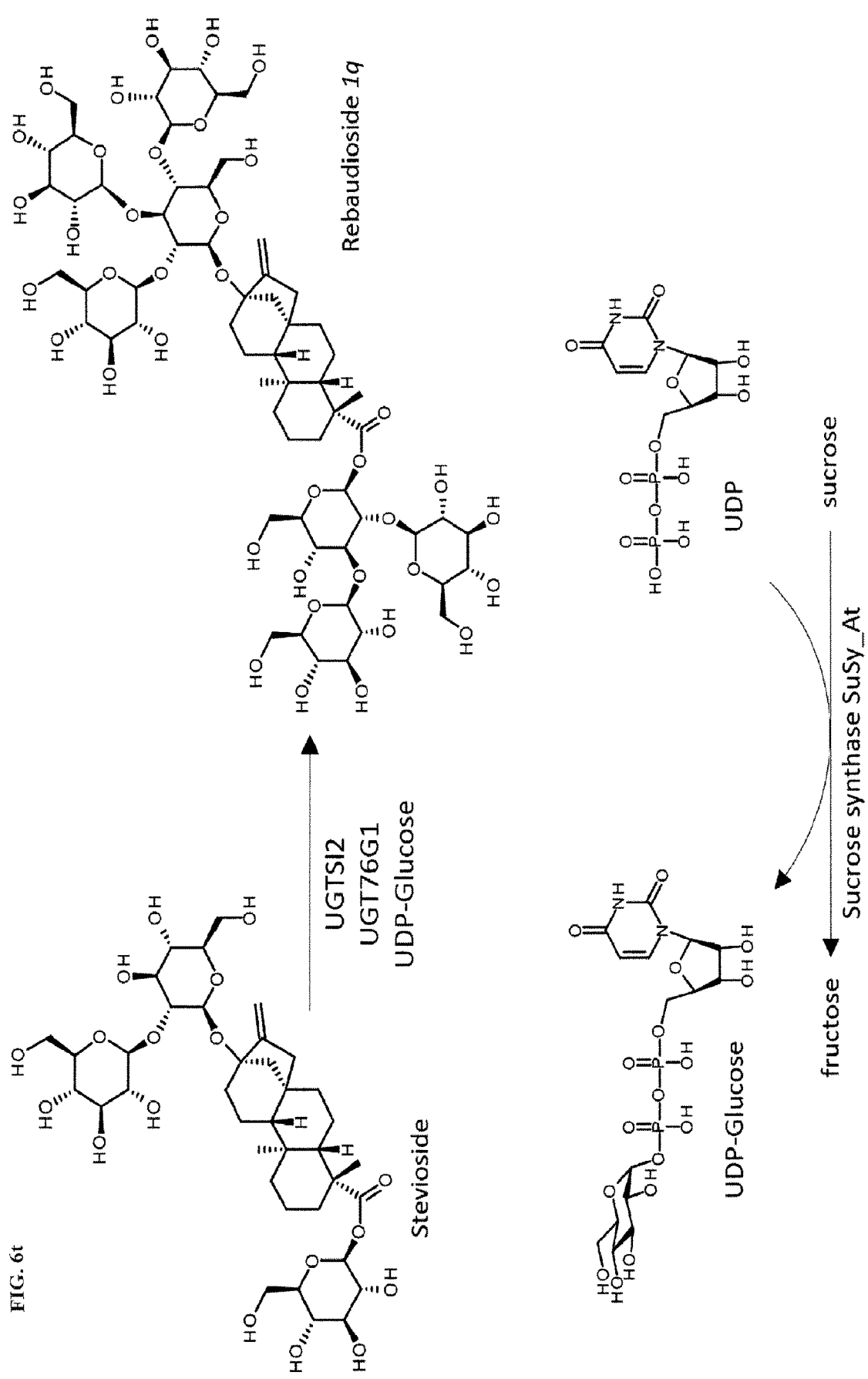
Figure 7A:
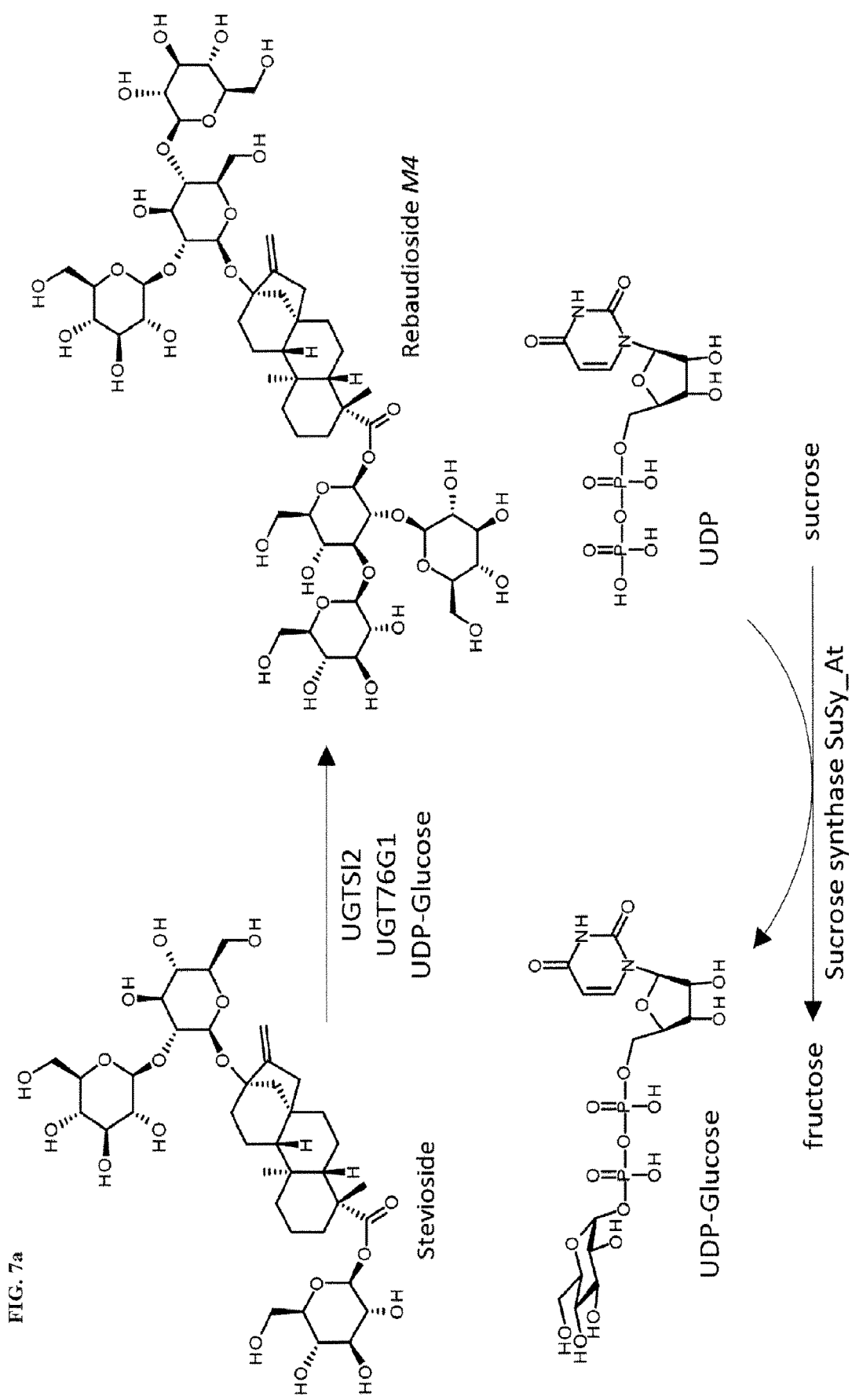
FIG. 7a through FIG. 7b show the biocatalytic production of rebaudioside M4 and rebaudioside M5, respectively from stevioside using the enzymes UGTSl2 and UGT76G1 and concomitant recycling of UDP to UDP-glucose via sucrose synthase SuSy_At.
Figure 7B:
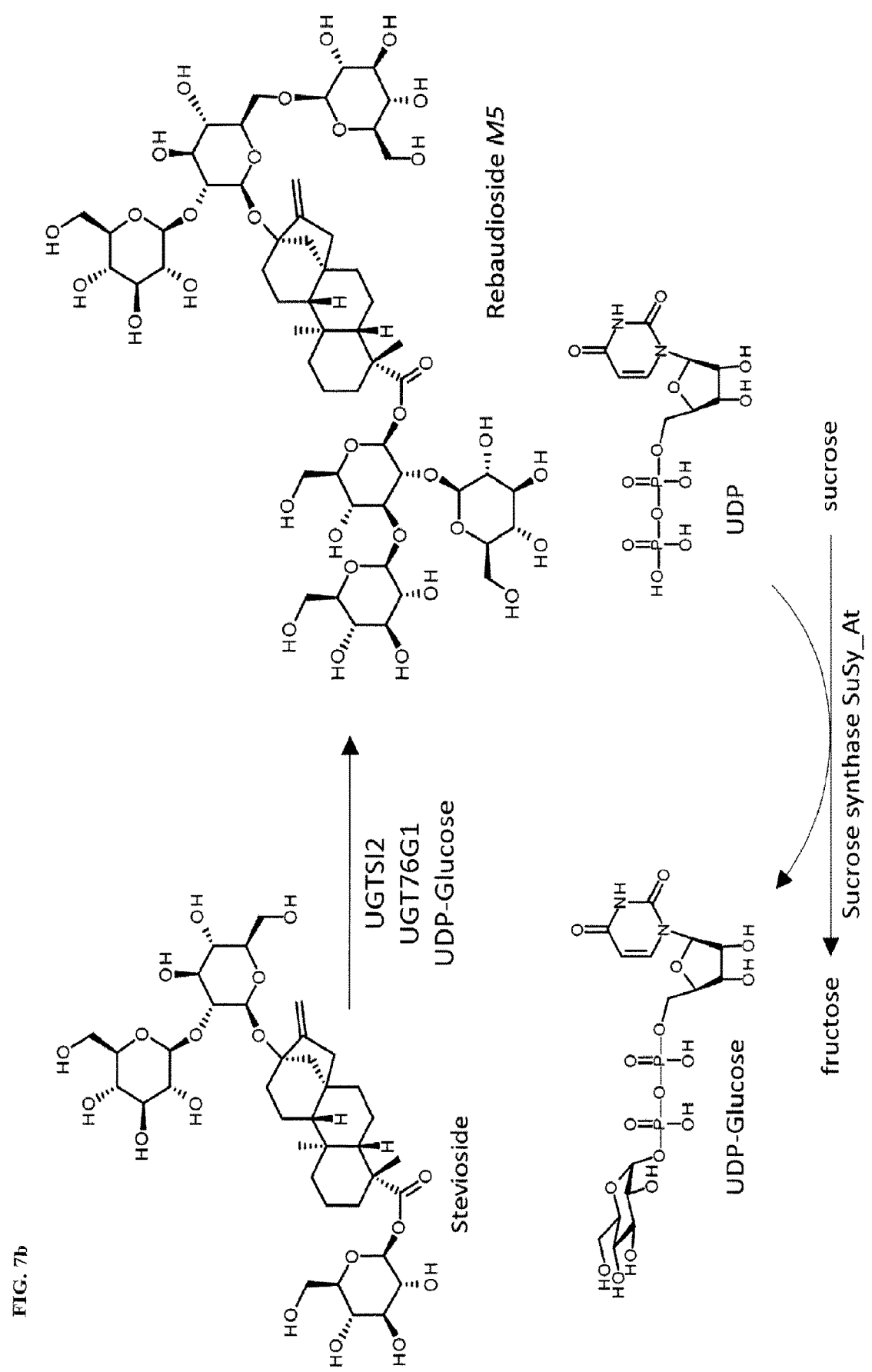
Figure 8A:
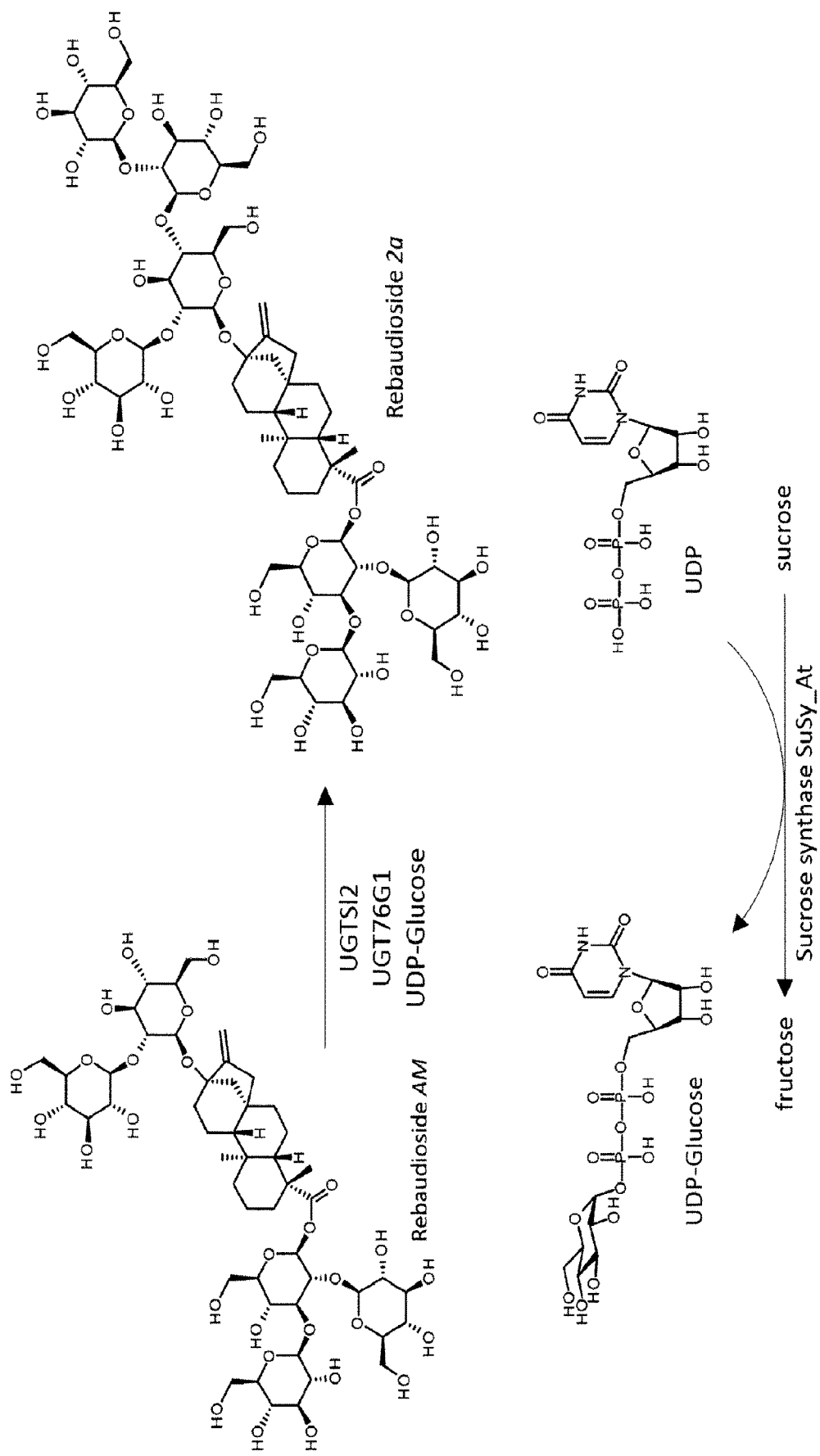
FIG. 8a through FIG. 8t show the biocatalytic production of rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and rebaudioside 1q, respectively, from rebaudioside AM using the enzymes UGTSl2 and UGT76G1 and concomitant recycling of UDP to UDP-glucose via sucrose synthase SuSy_At.
Figure 8B:
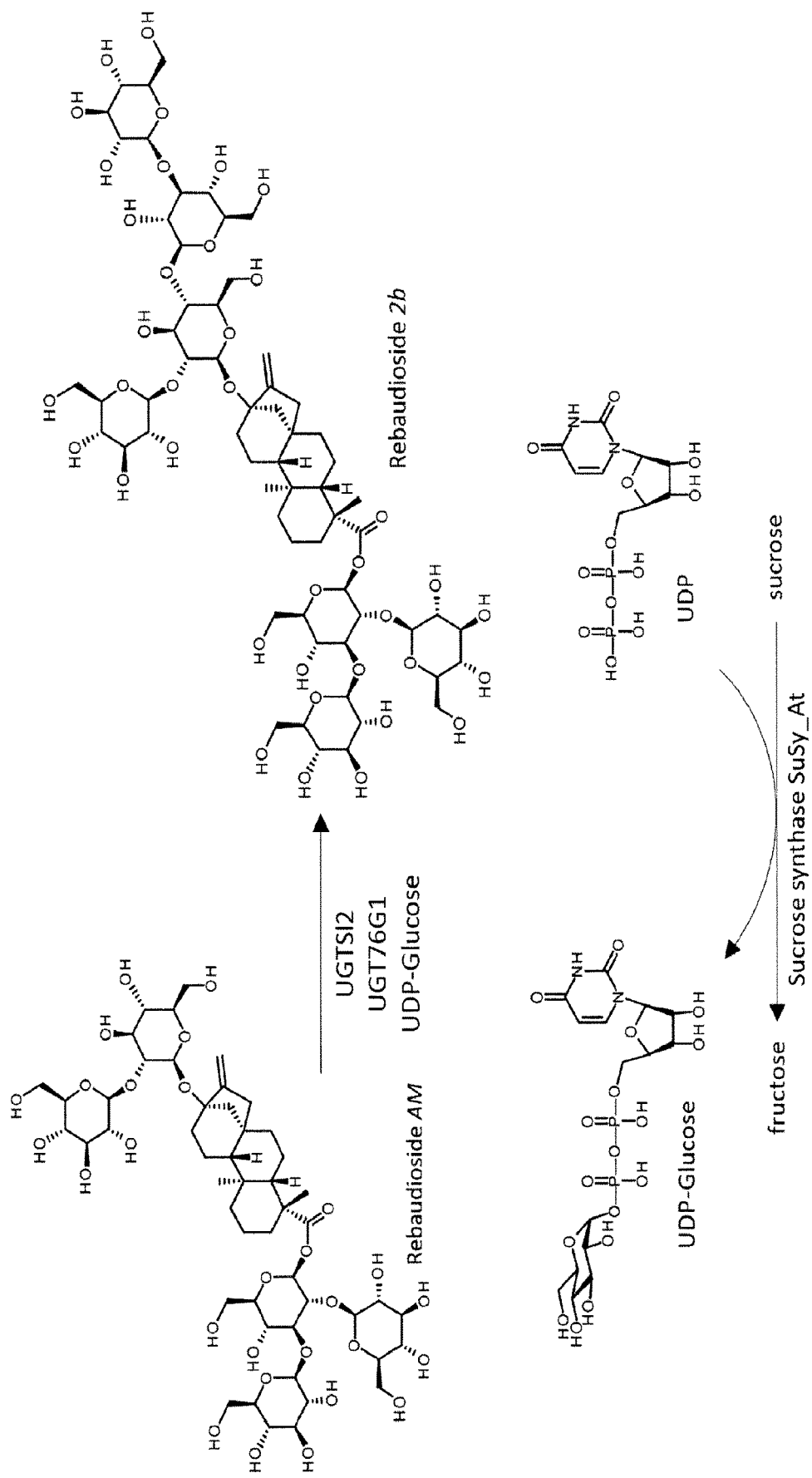
Figure 8C:
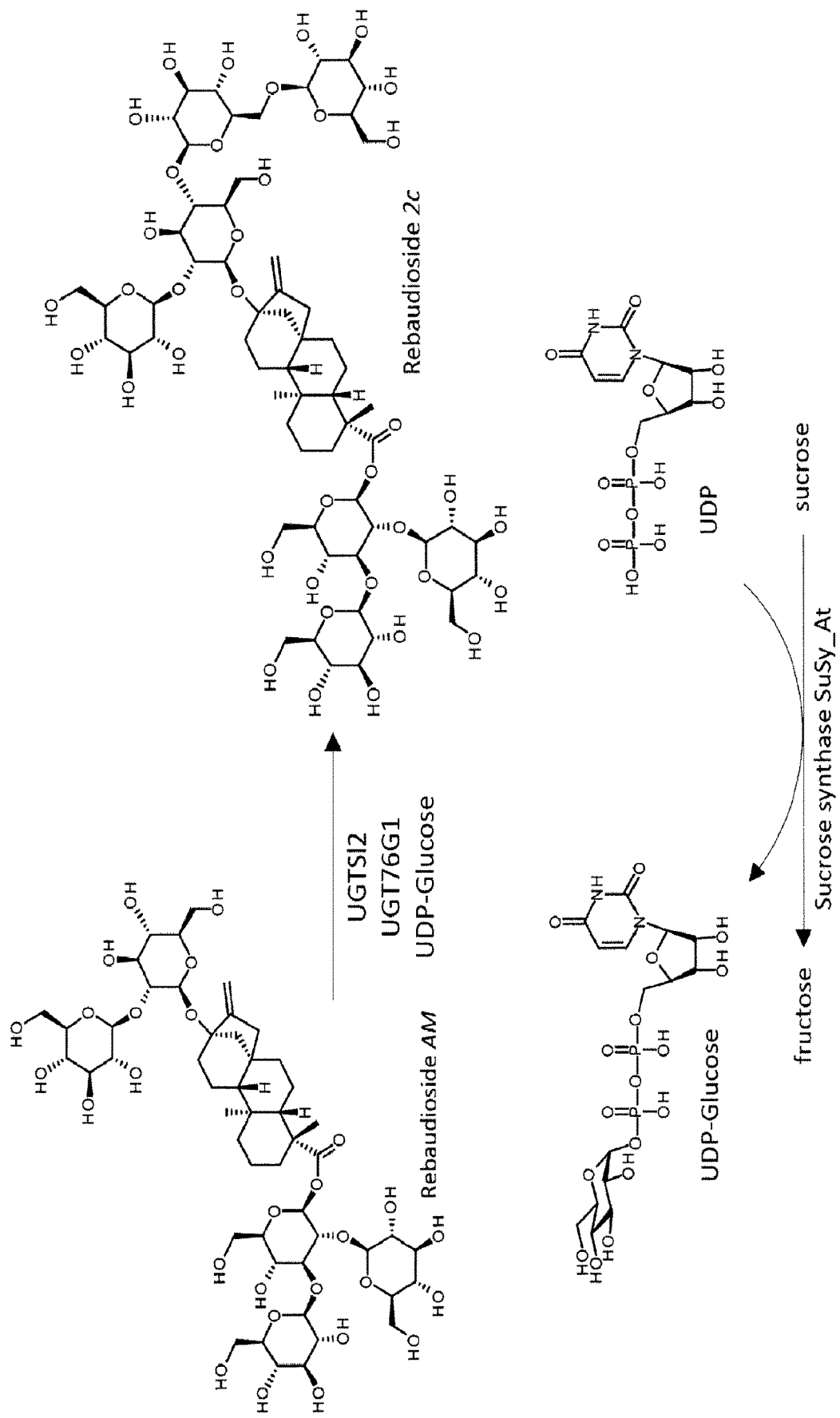
Figure 8D:
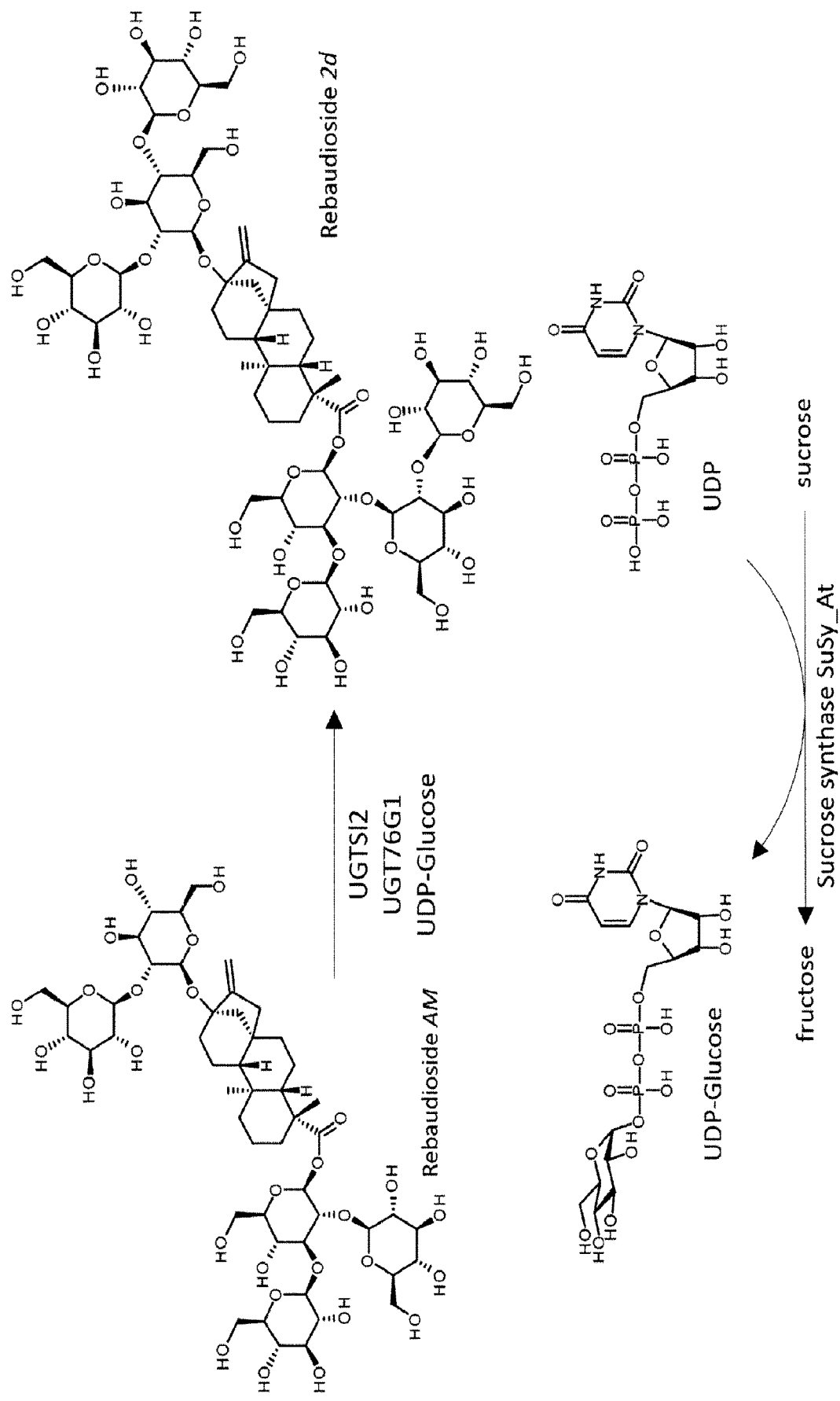
Figure 8E:
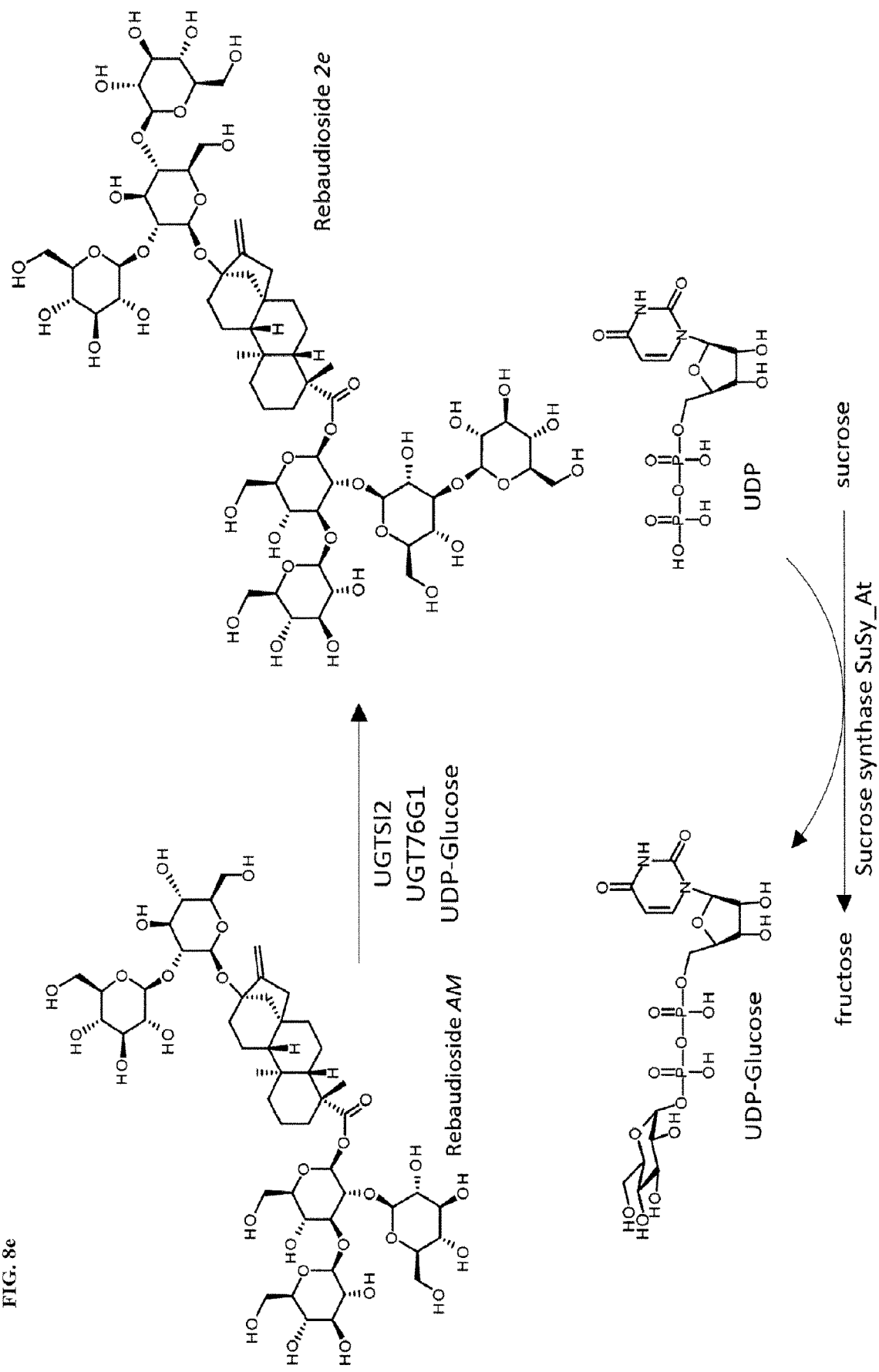
Figure 8F:
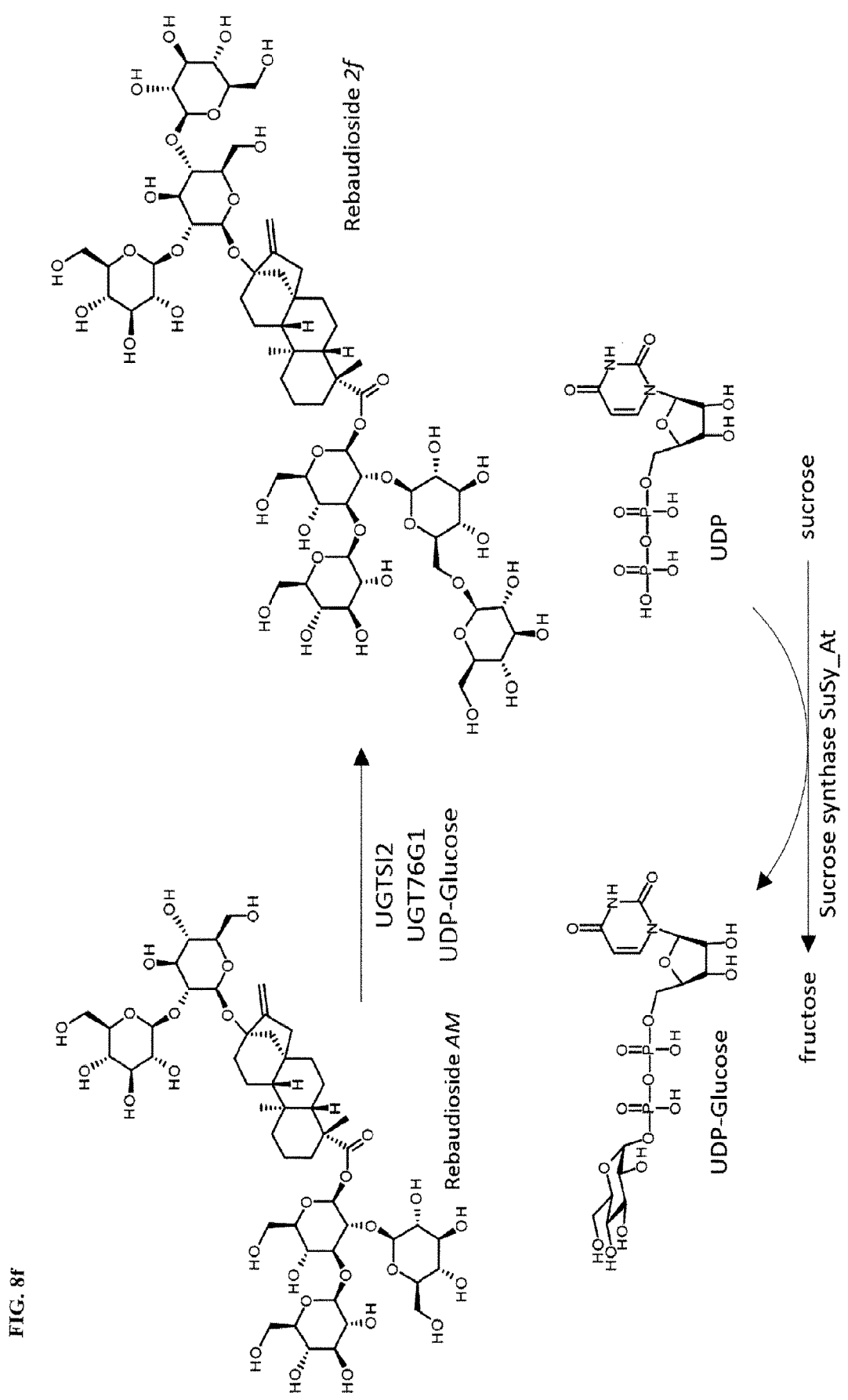
Figure 8G:
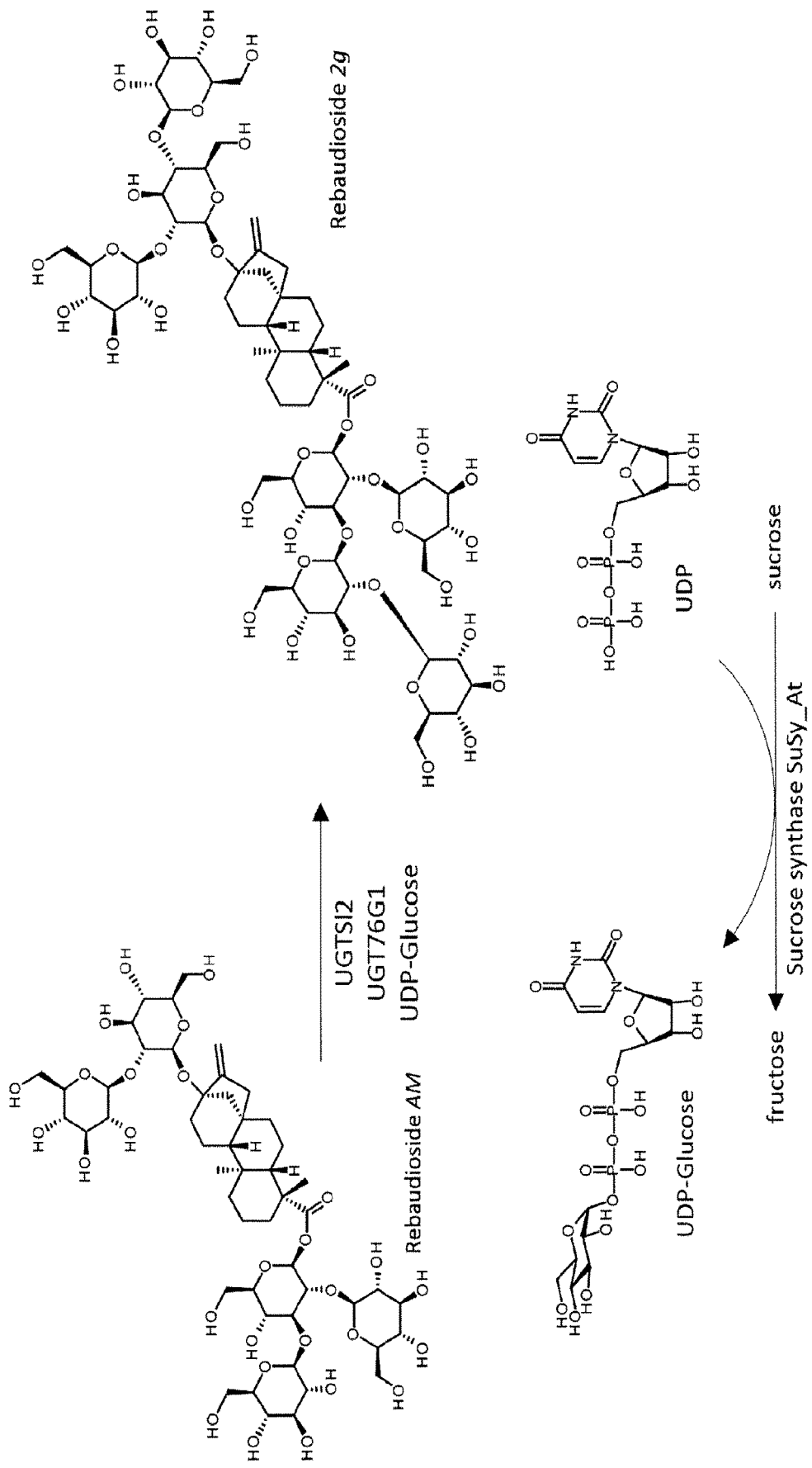
Figure 8H:
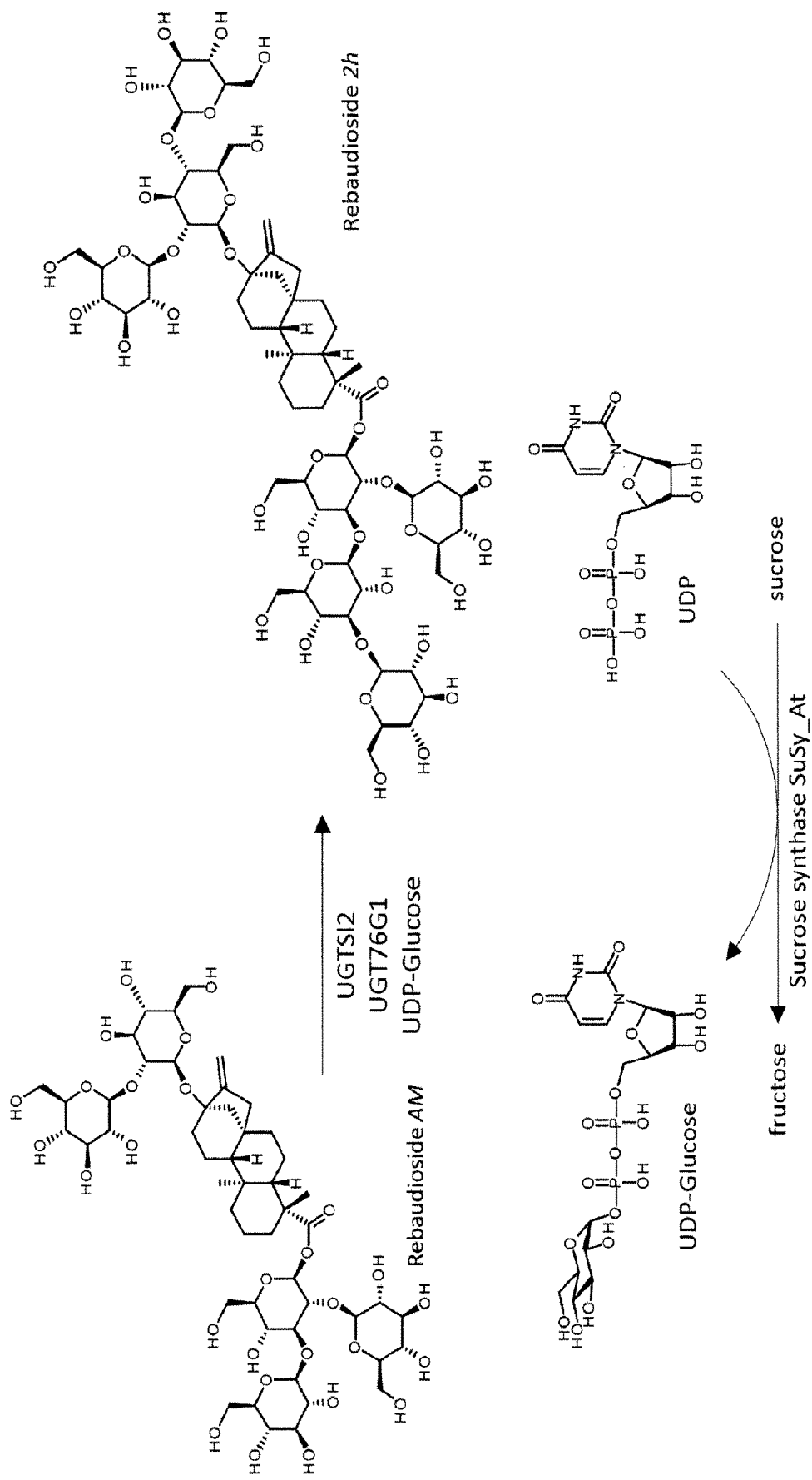
Figure 8I:
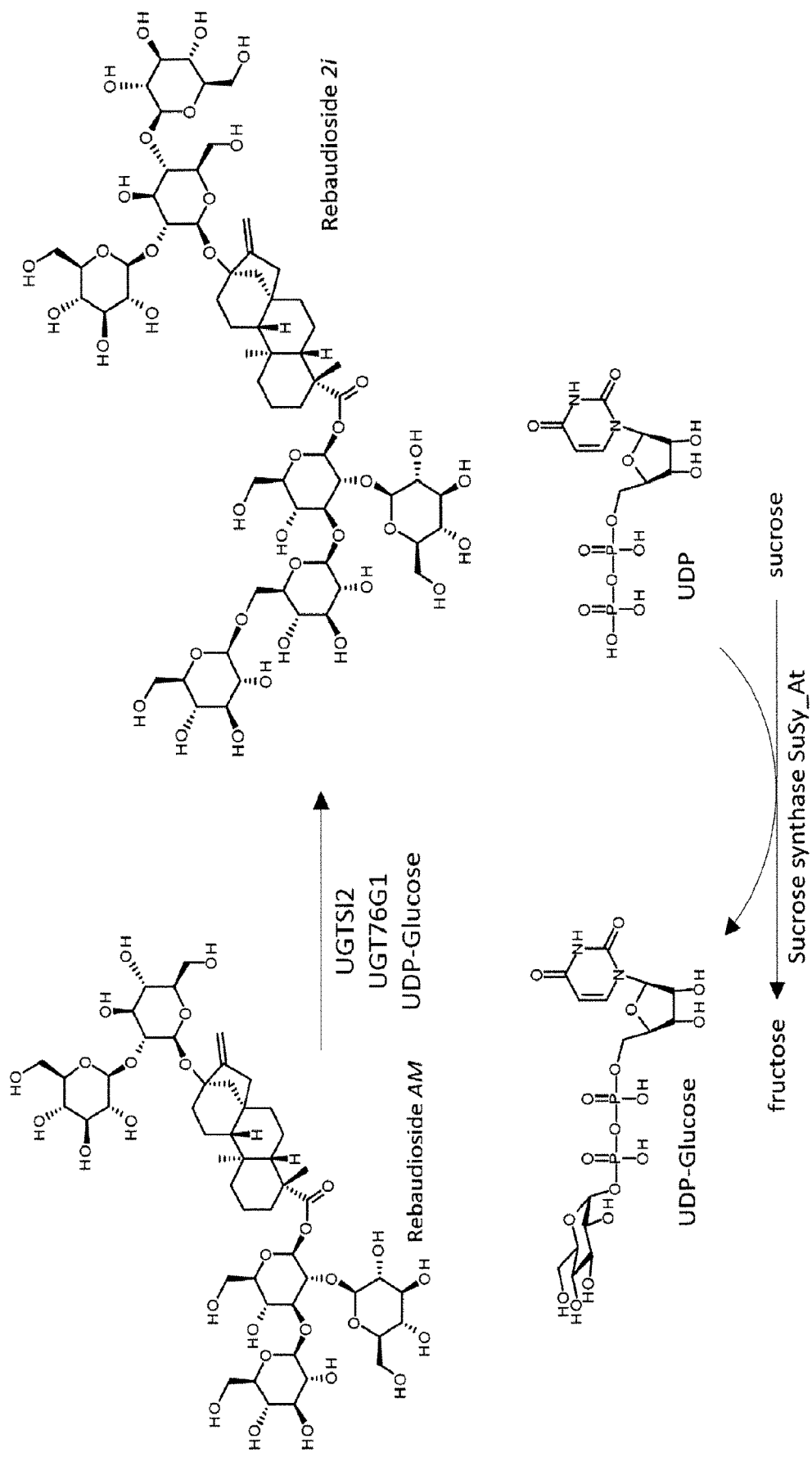
Figure 8J:
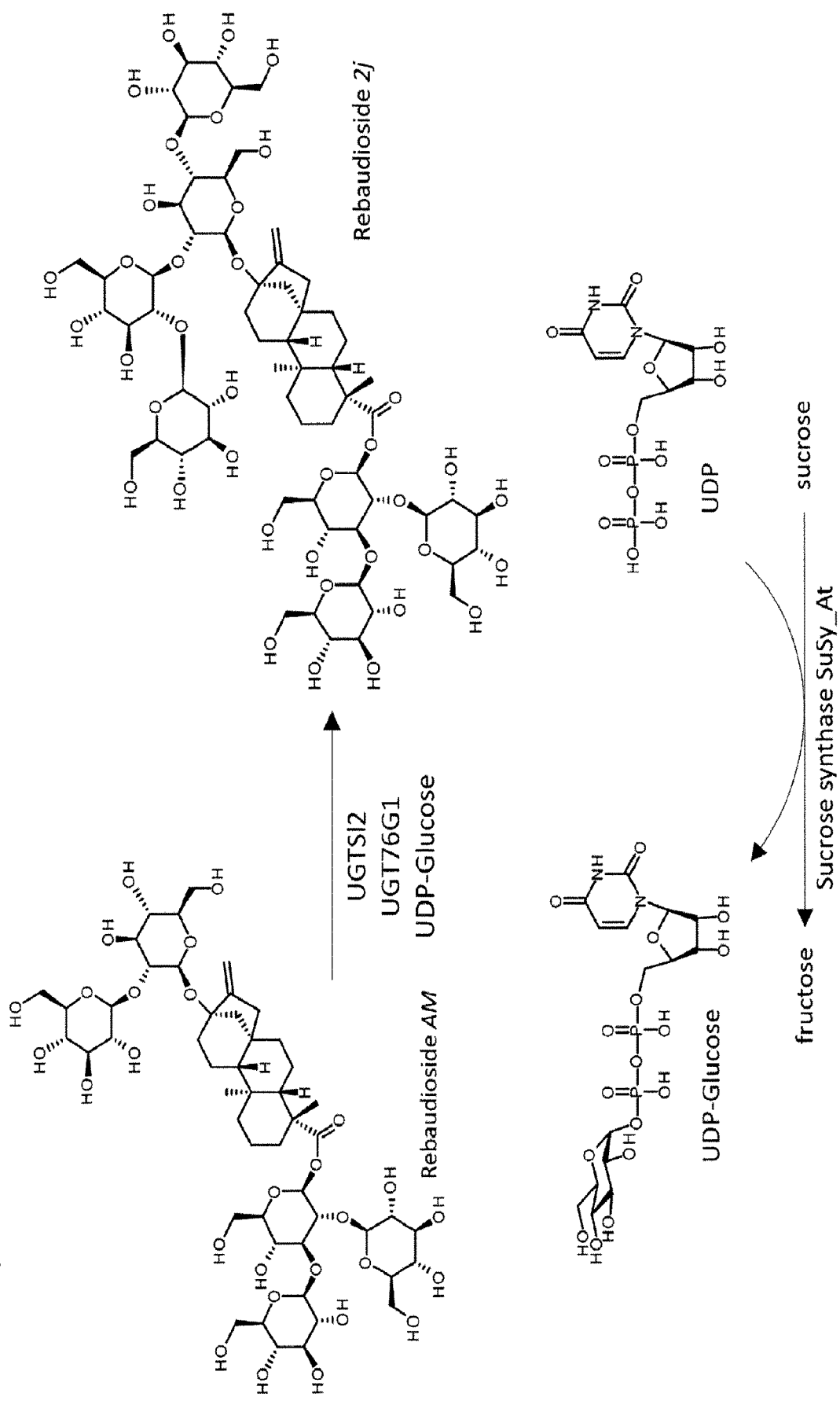
Figure 8K:
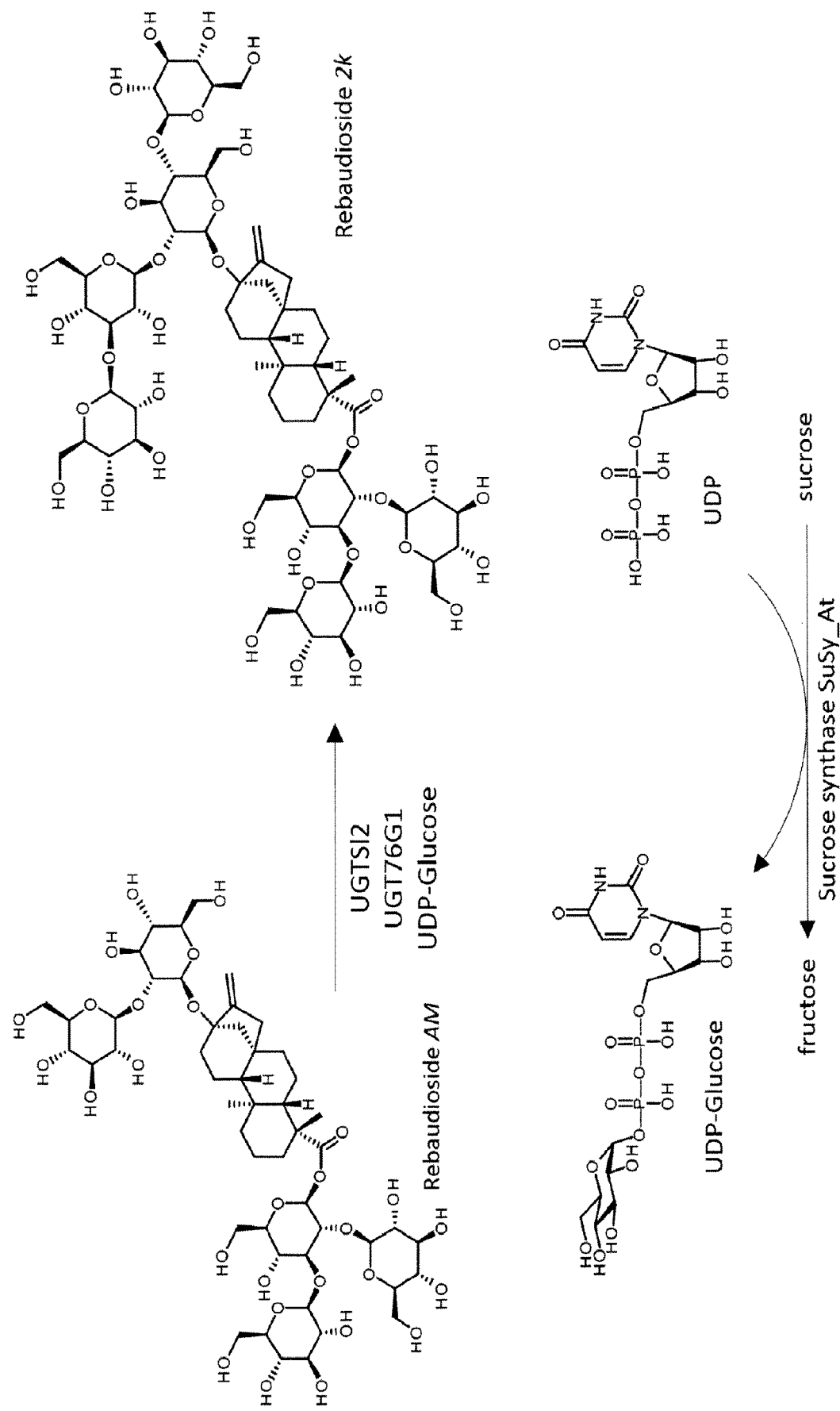
Figure 8L:
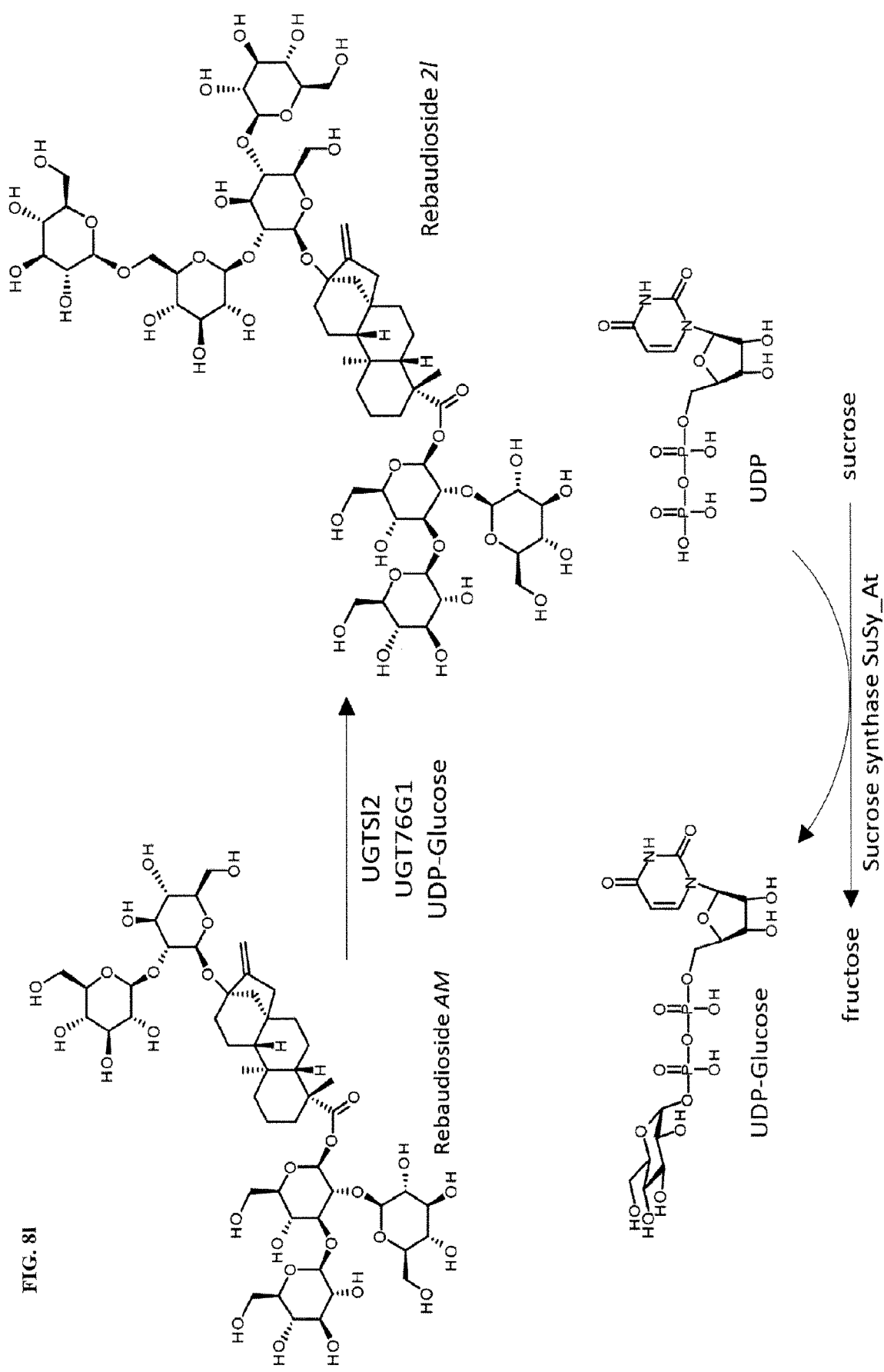
Figure 8M:
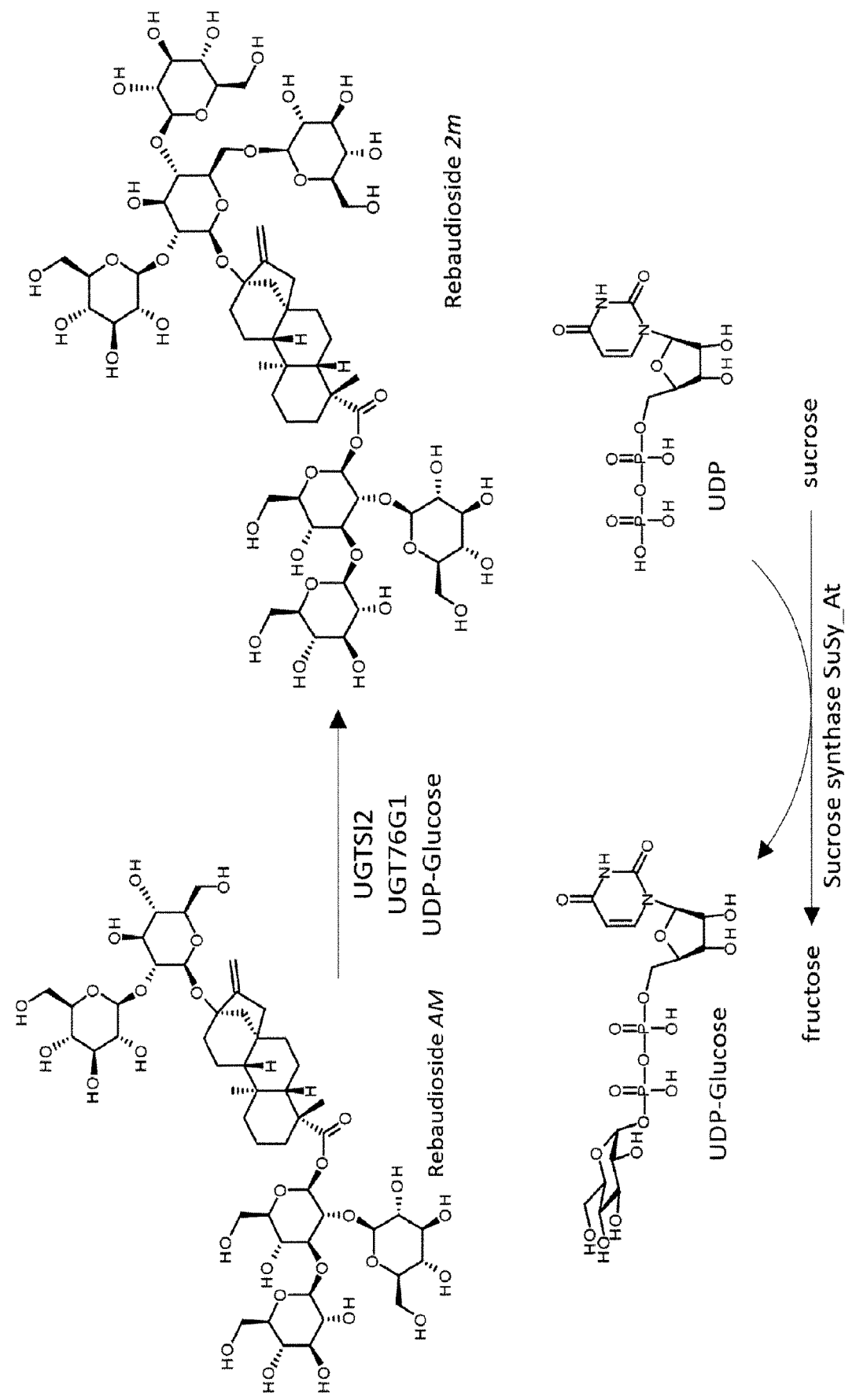
Figure 8N:
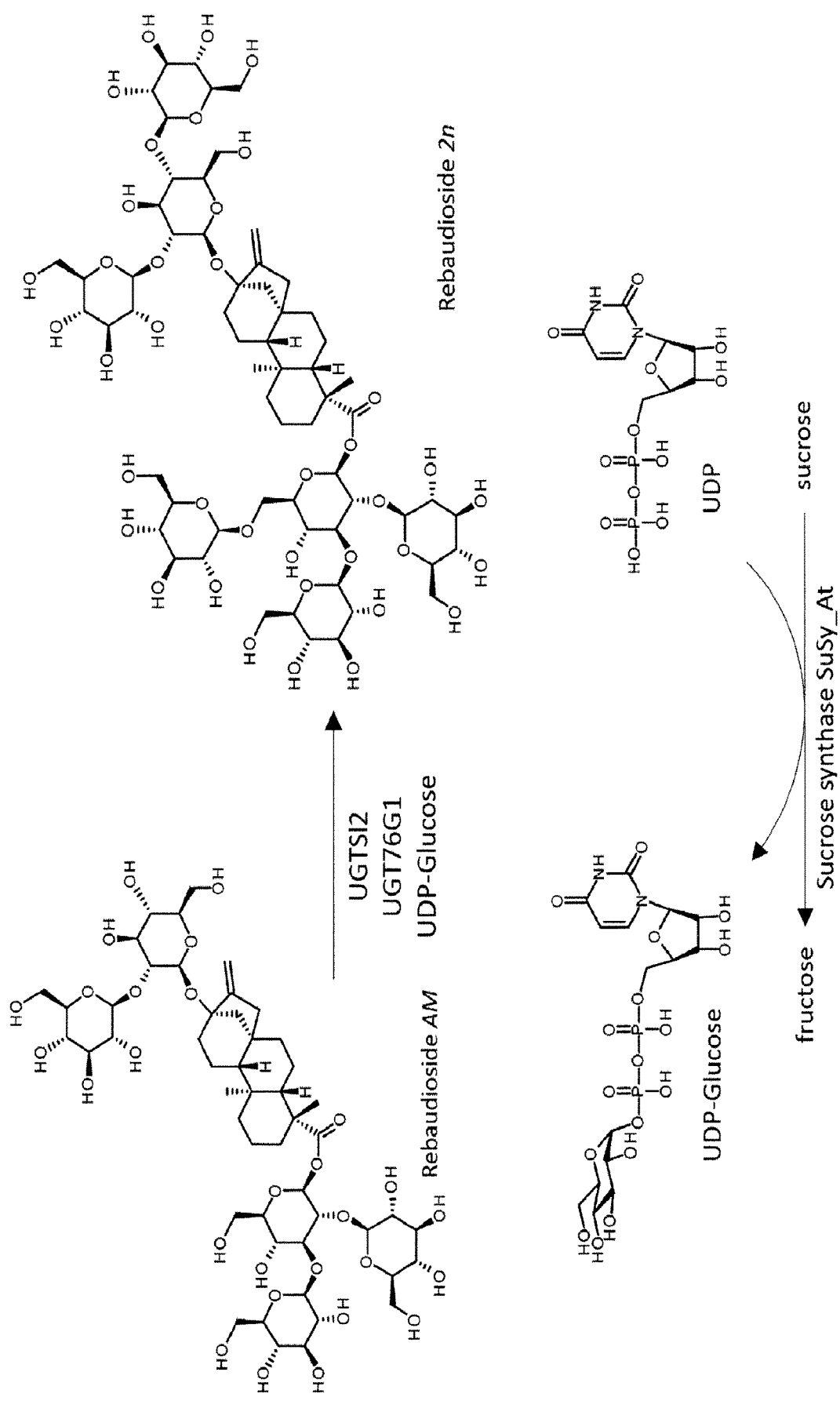
Figure 8O:
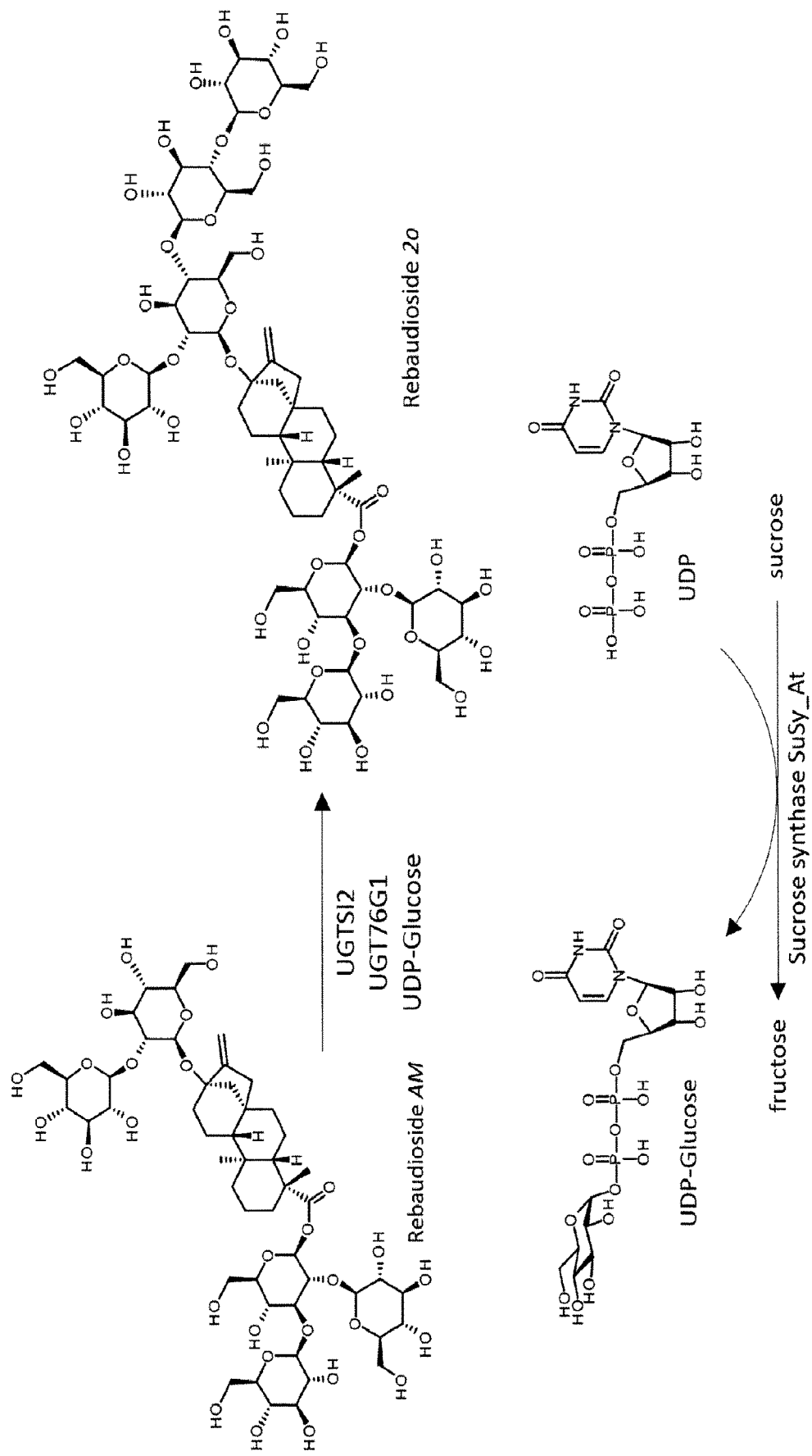
Figure 8P:
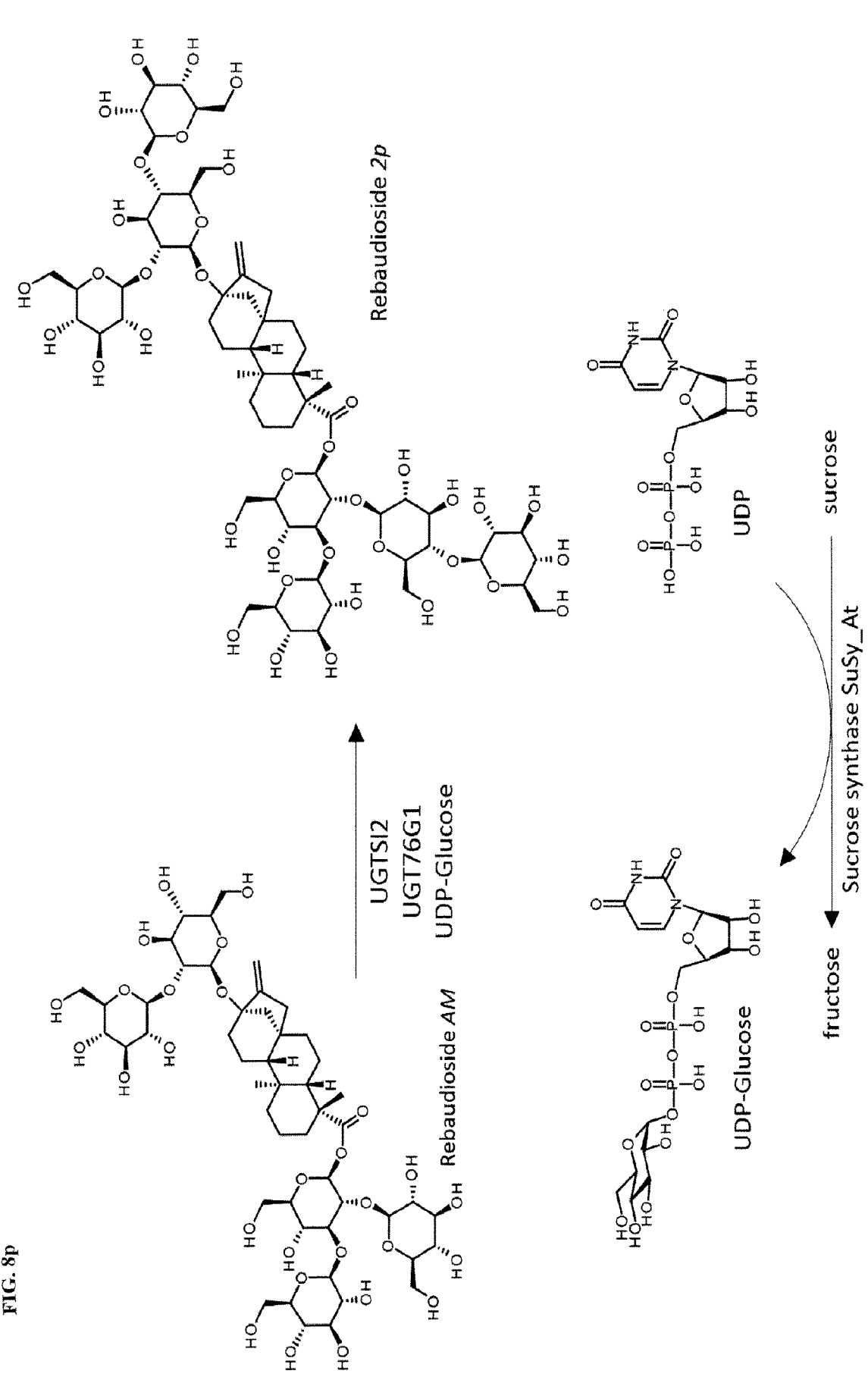
Figure 8Q:
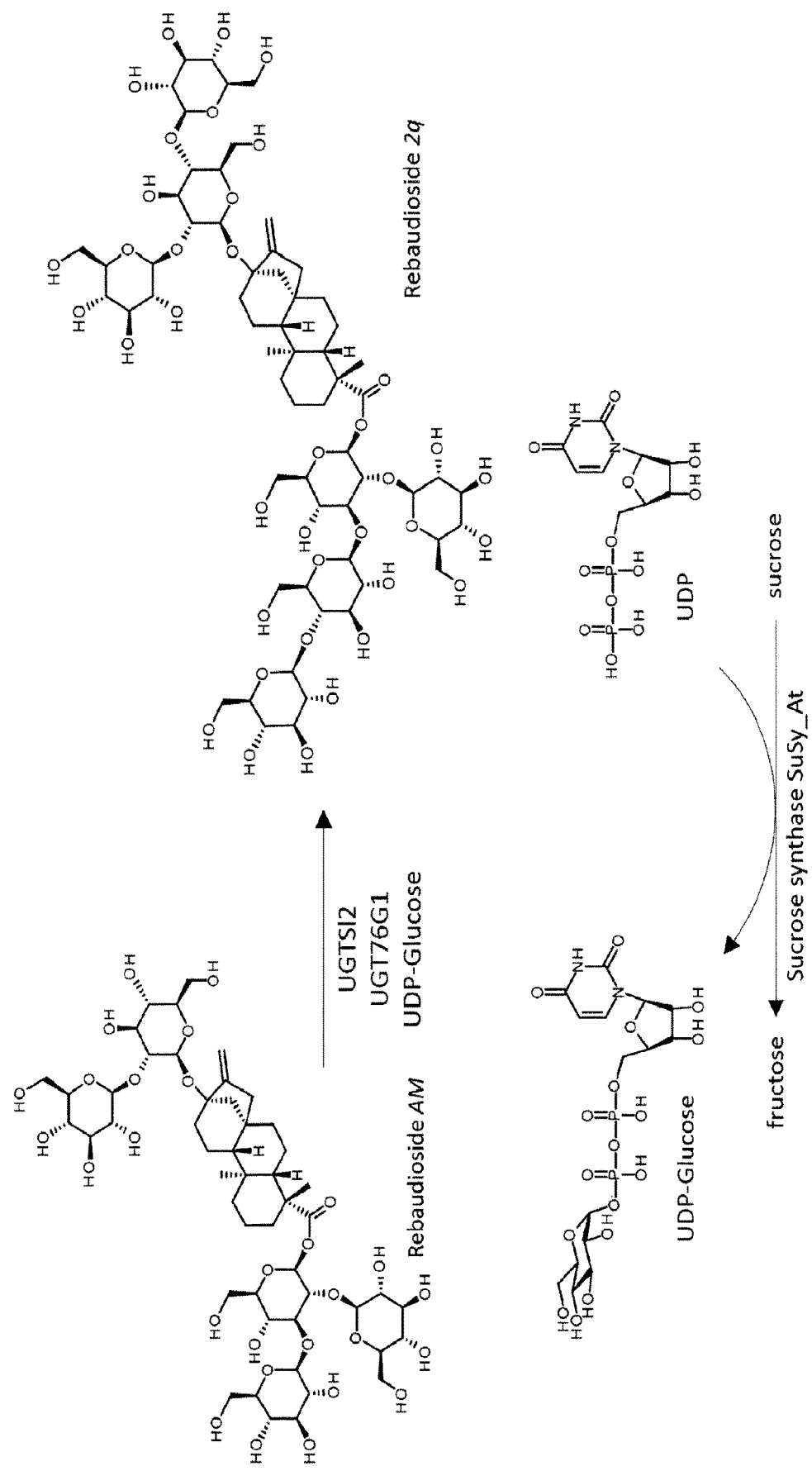
Figure 8R:
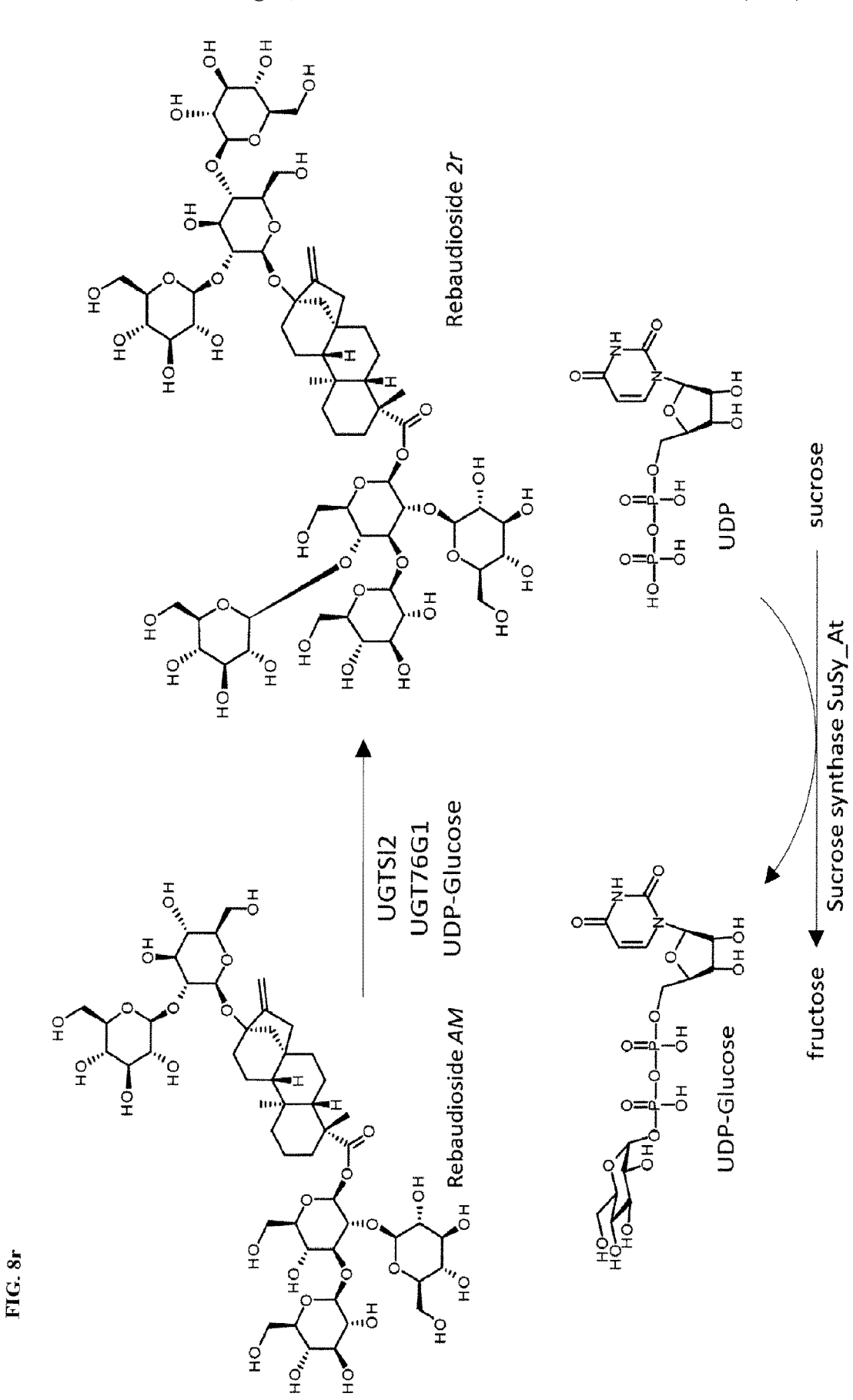
Figure 8S:
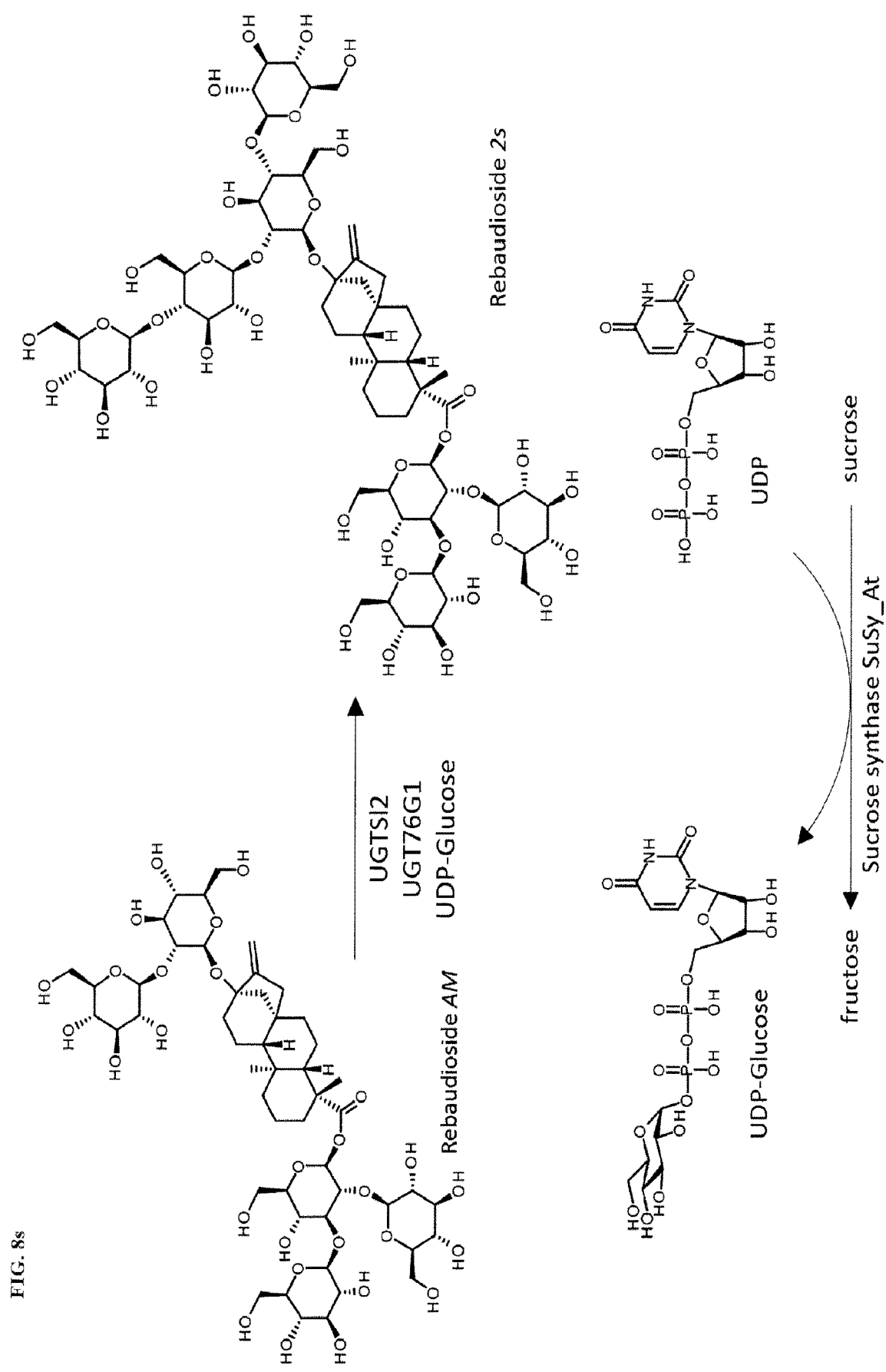
Figure 8T:
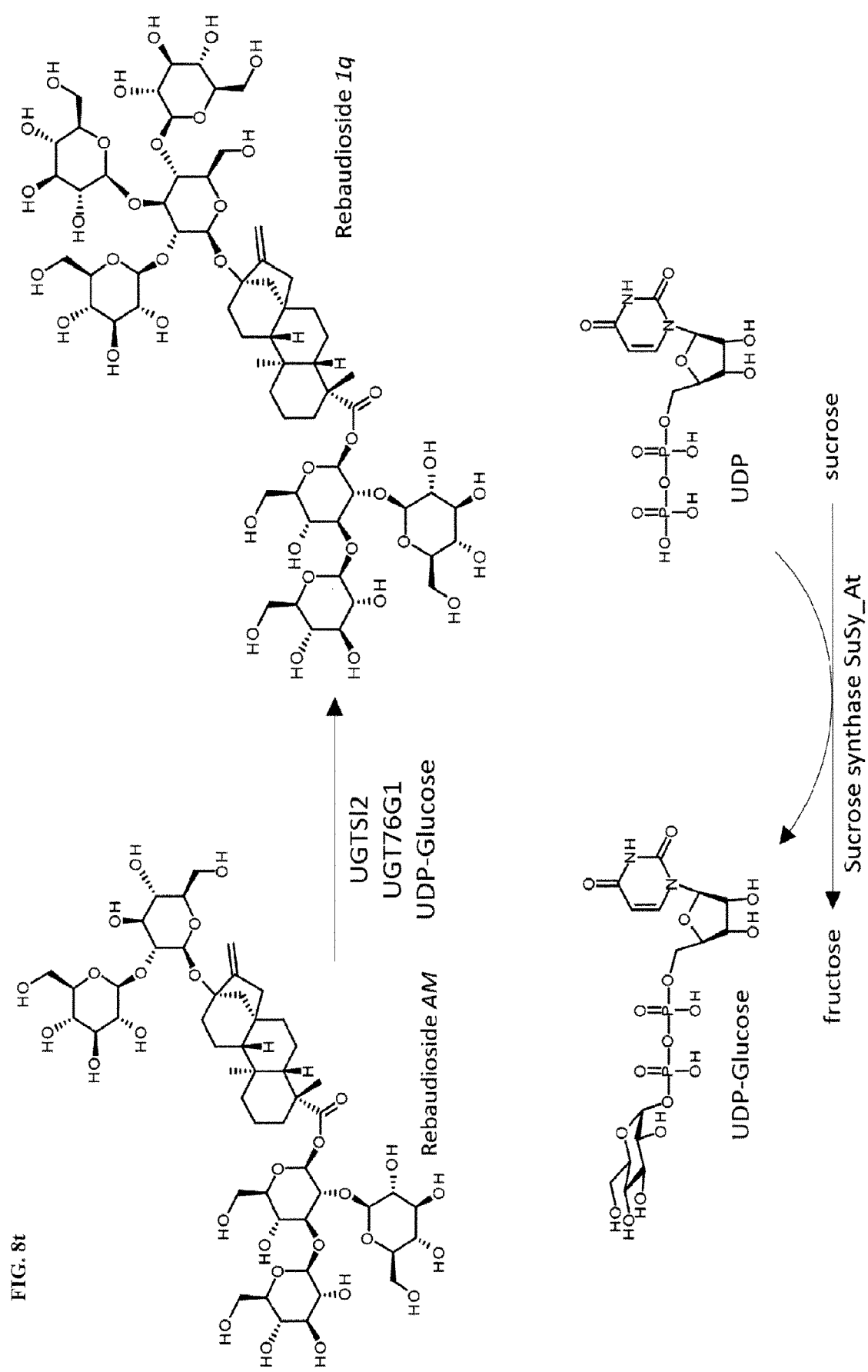
Figure 9A:
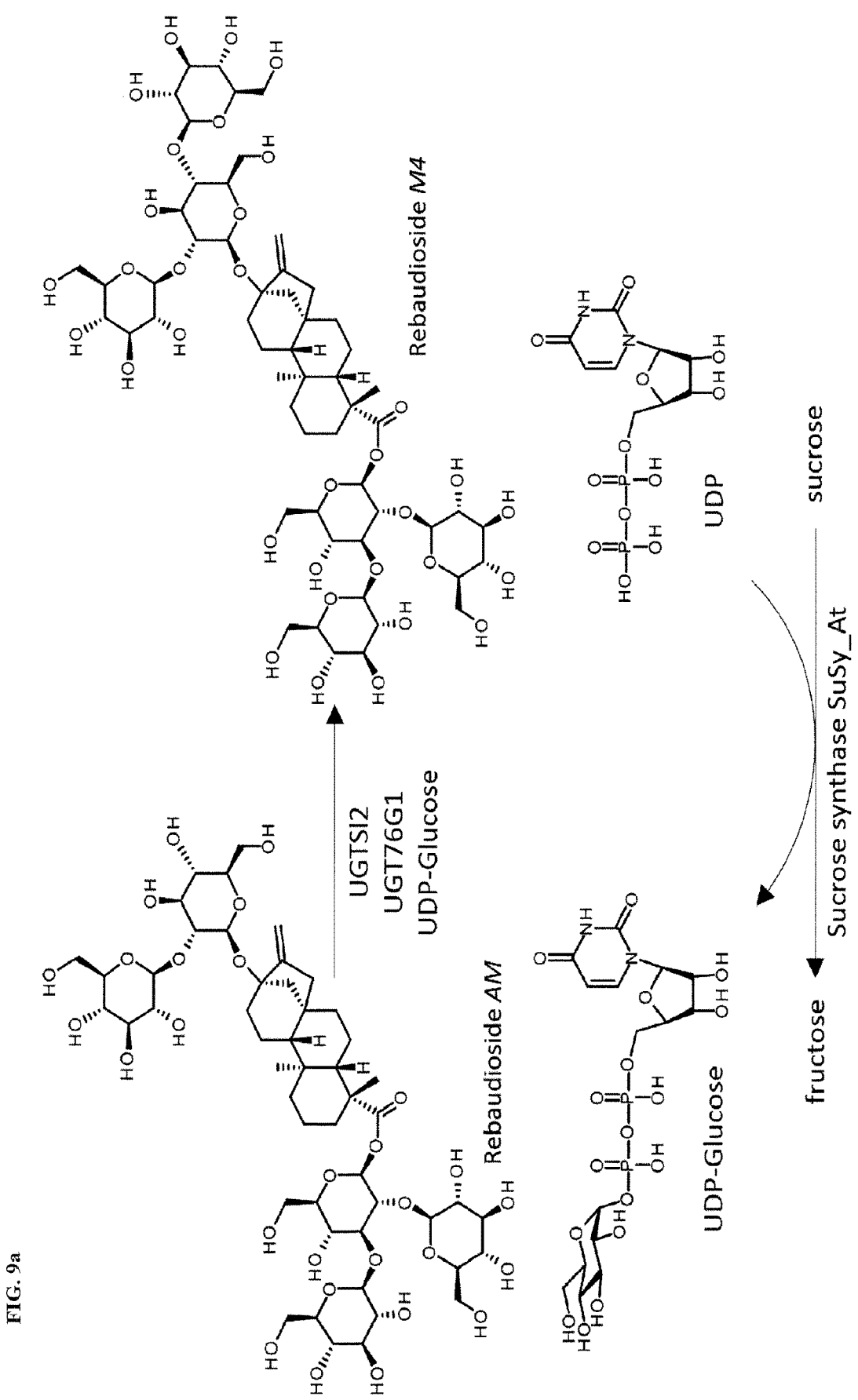
FIG. 9a through 9b show the biocatalytic production of rebaudioside M4 and rebaudioside M5, respectively from rebaudioside AM using the enzymes UGTSl2 and UGT76G1 and concomitant recycling of UDP to UDP-glucose via sucrose synthase SuSy_At.
Figure 9B:
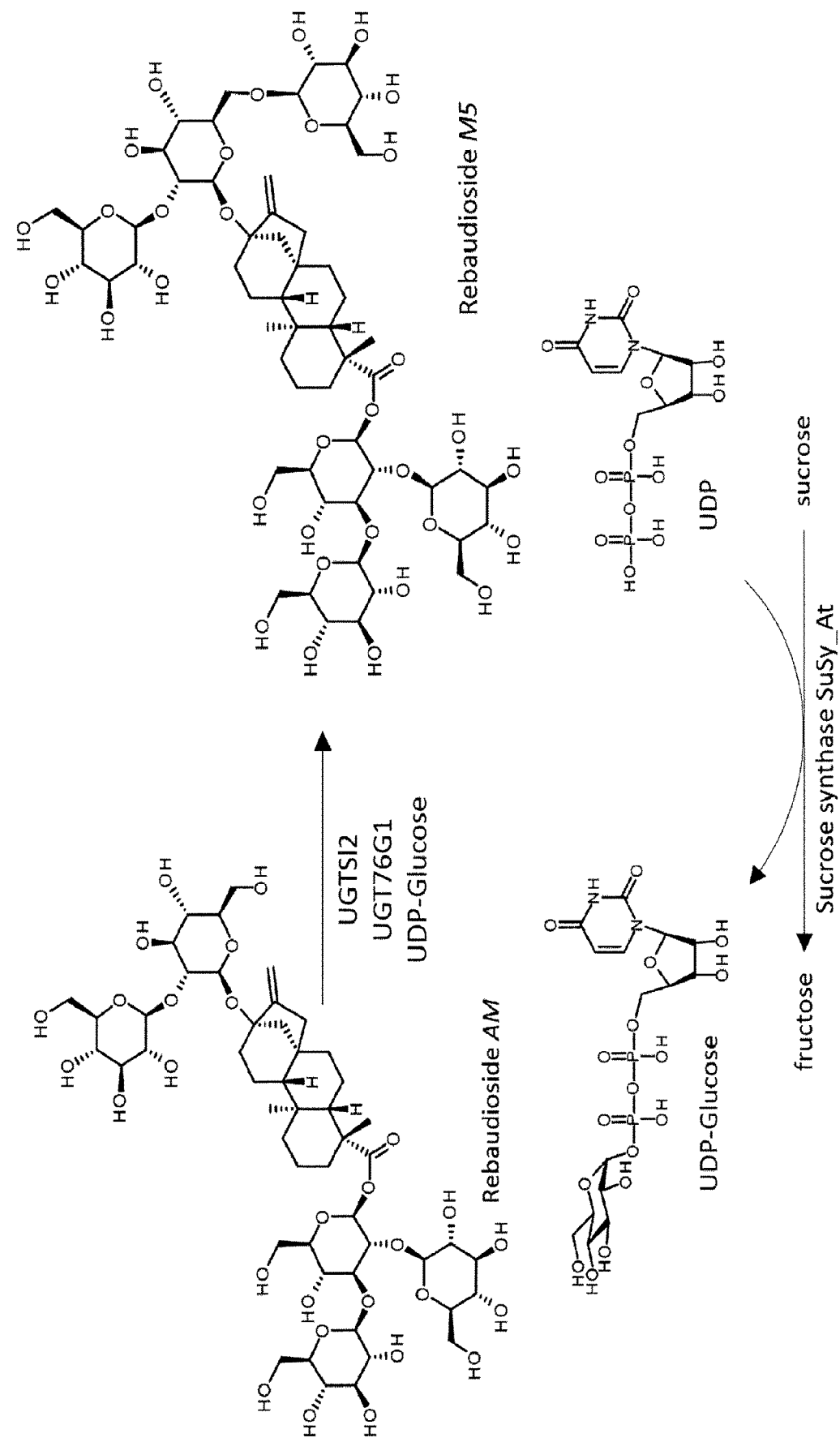
Figure 10A:
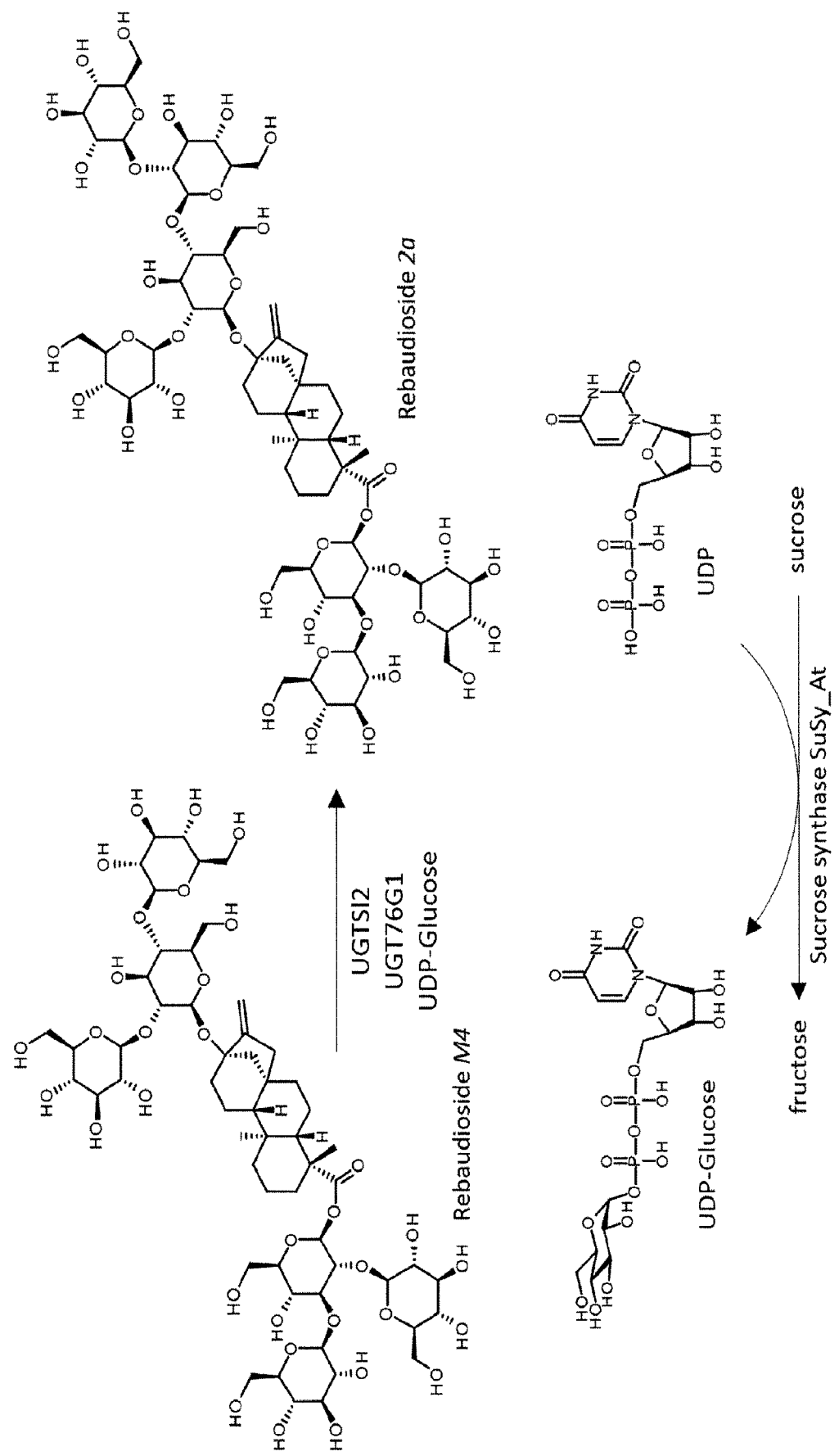
FIG. 10a through FIG. 10t show the biocatalytic production of rebaudioside 2a rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and rebaudioside 1q, respectively, from rebaudioside M4 using the enzymes UGTSl2 and UGT76G1 and concomitant recycling of UDP to UDP-glucose via sucrose synthase SuSy_At.
Figure 10B:
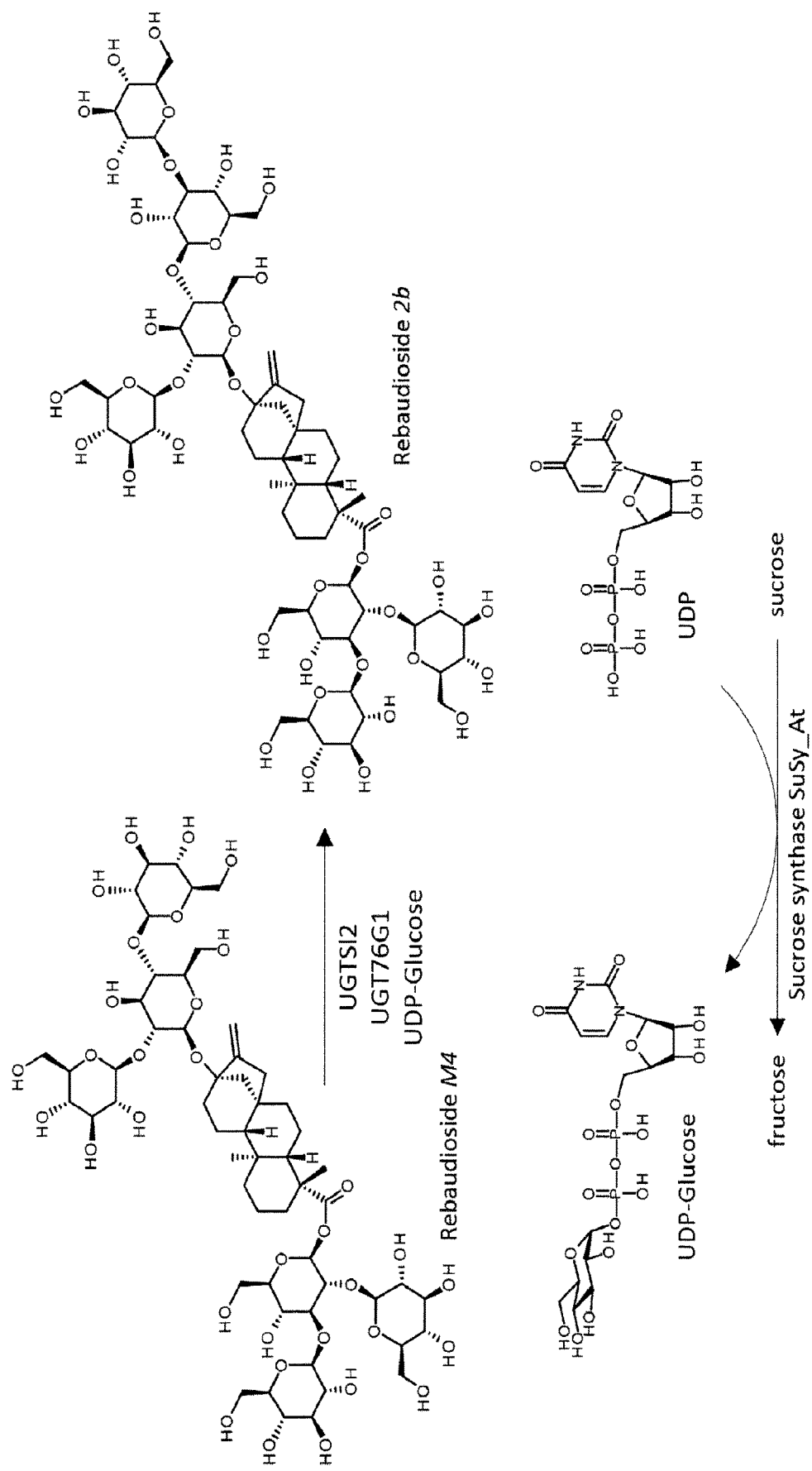
Figure 10C:
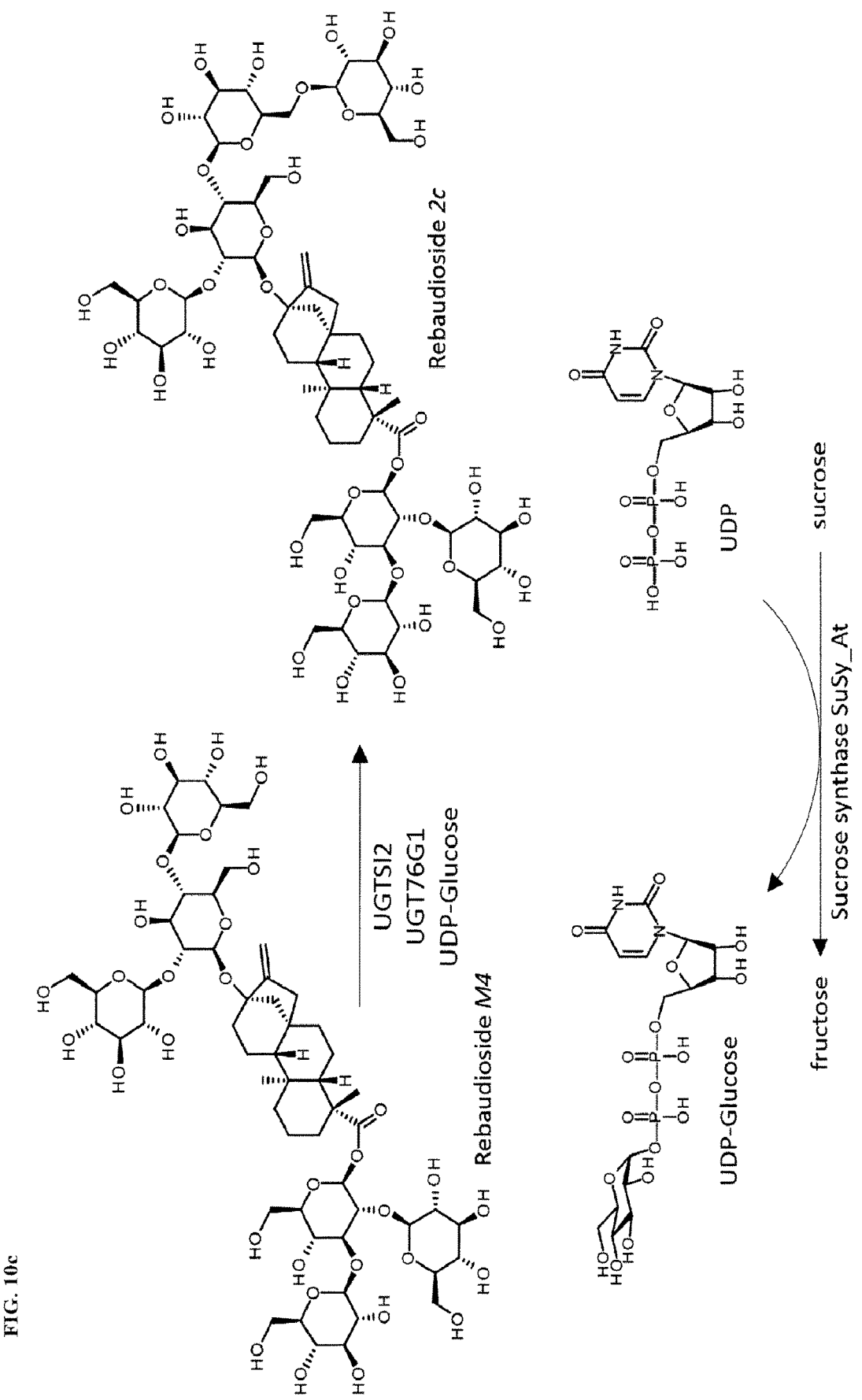
Figure 10D:
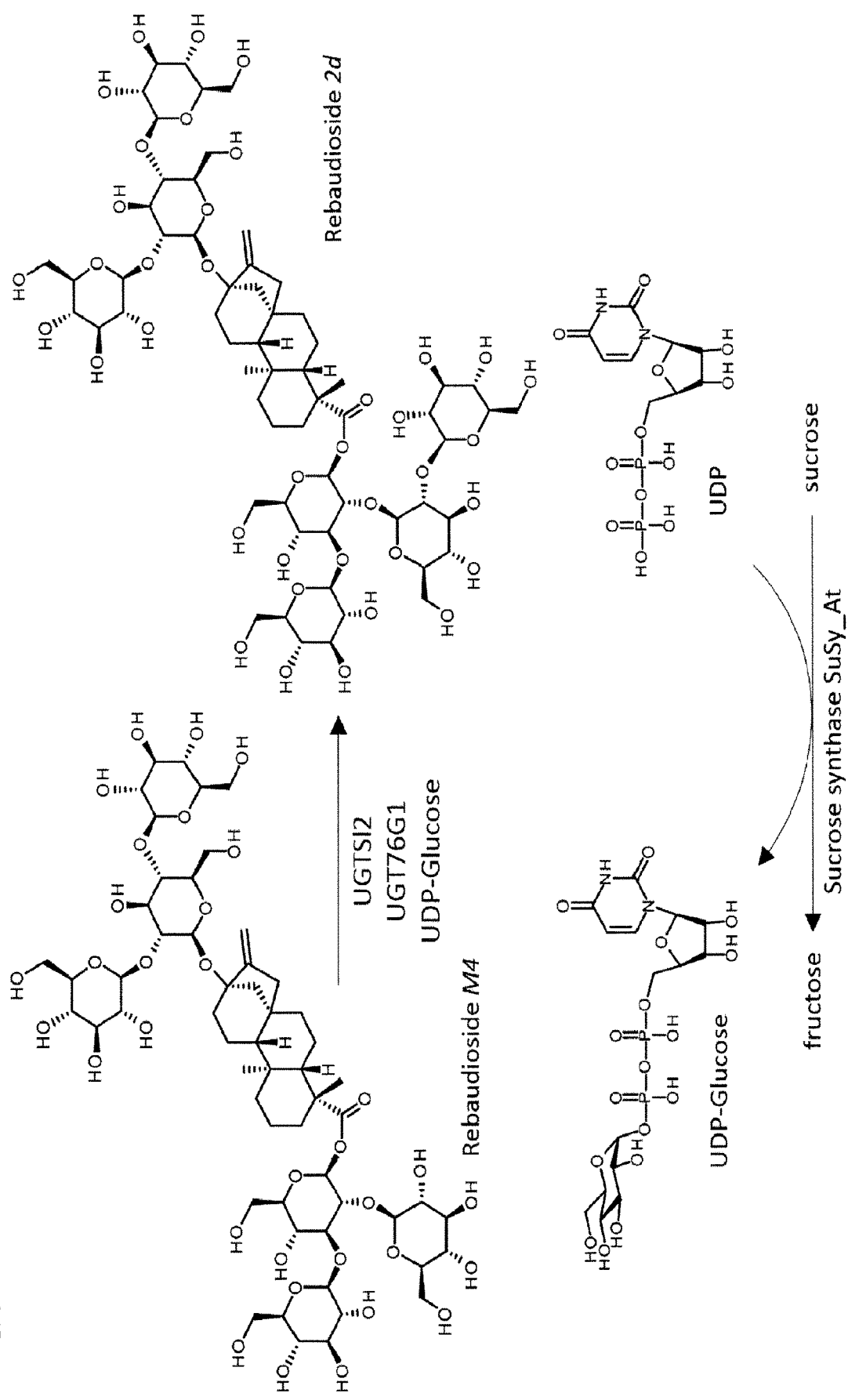
Figure 10E:
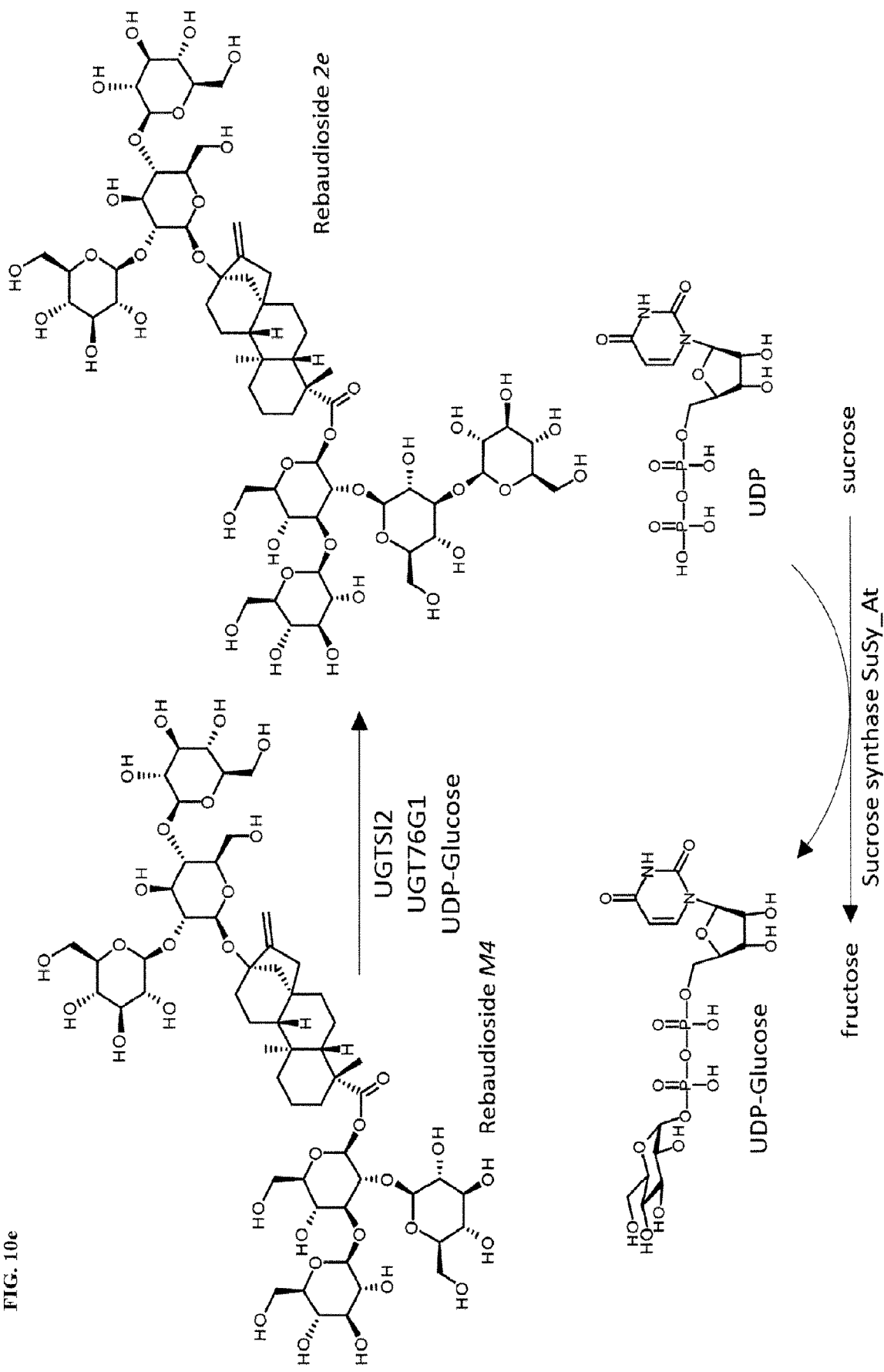
Figure 10F:
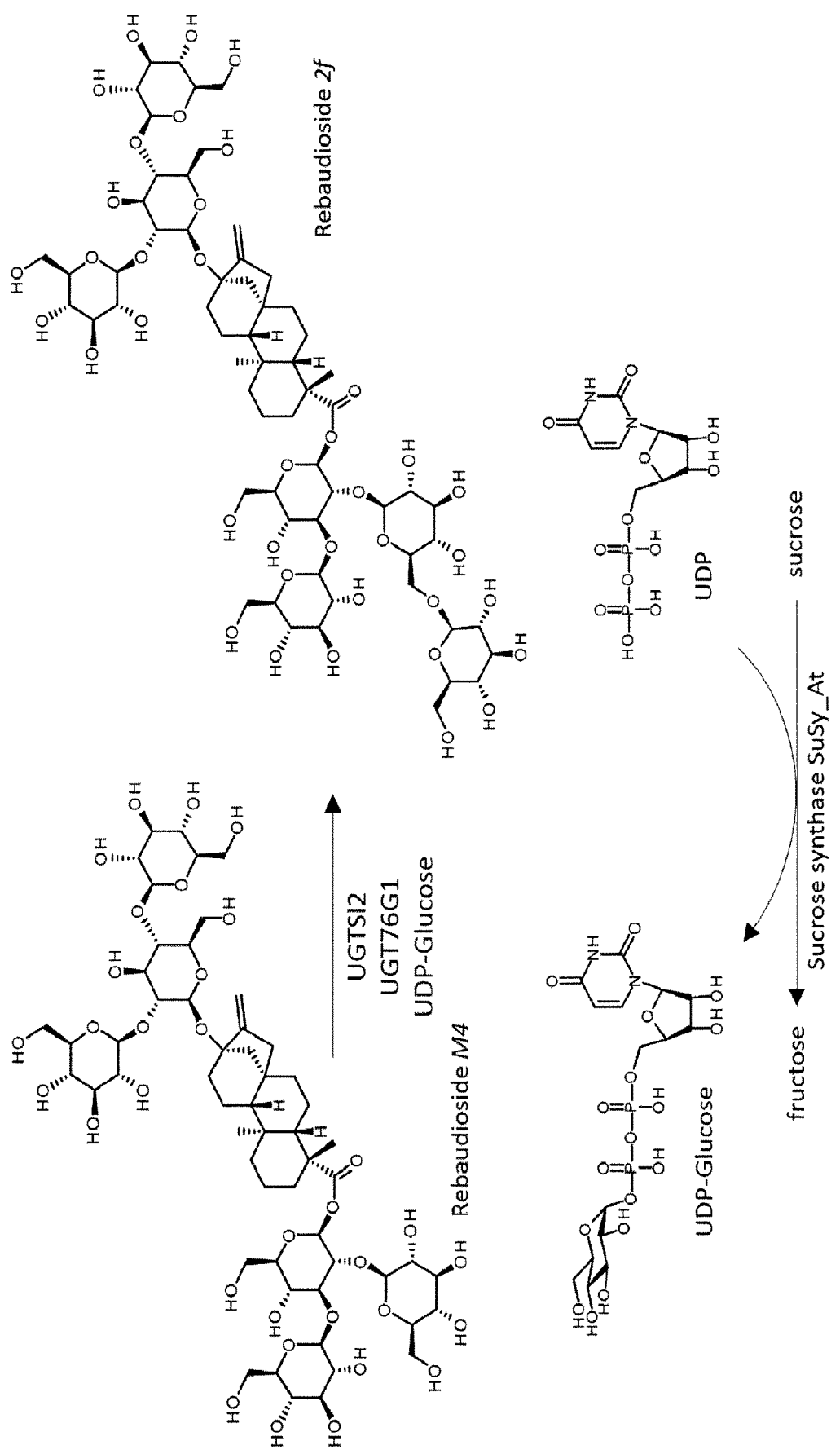
Figure 10G:
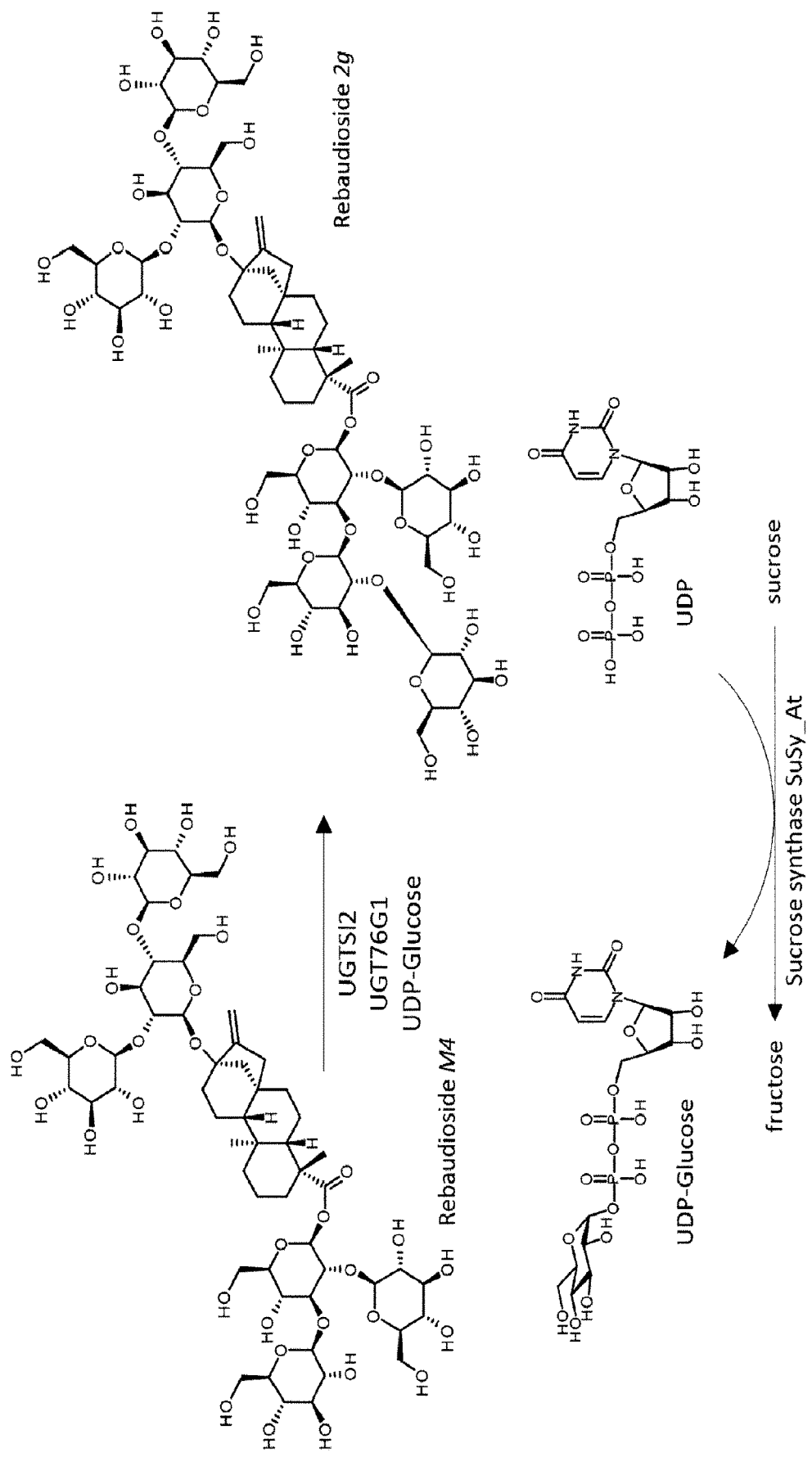
Figure 10H:
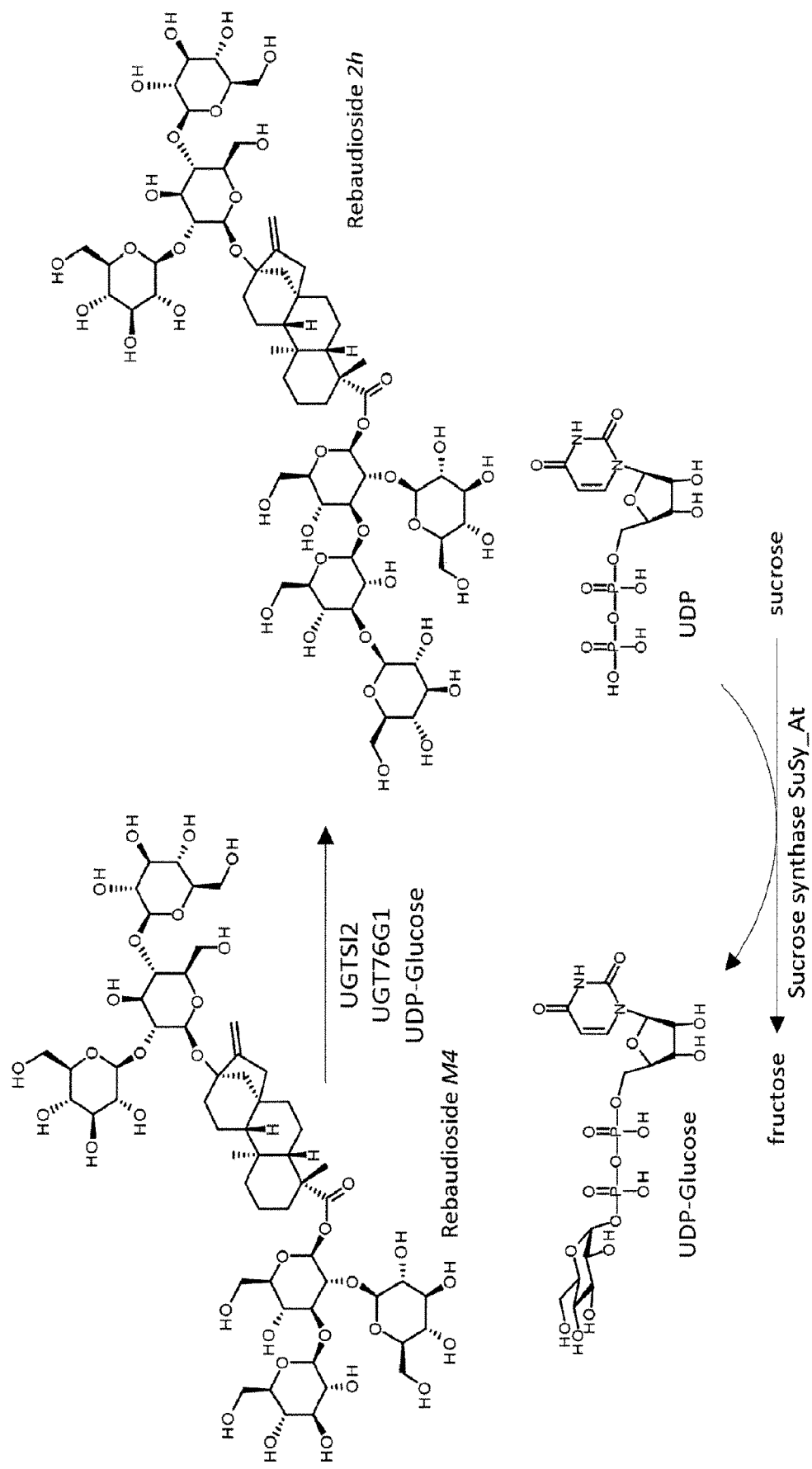
Figure 10I:
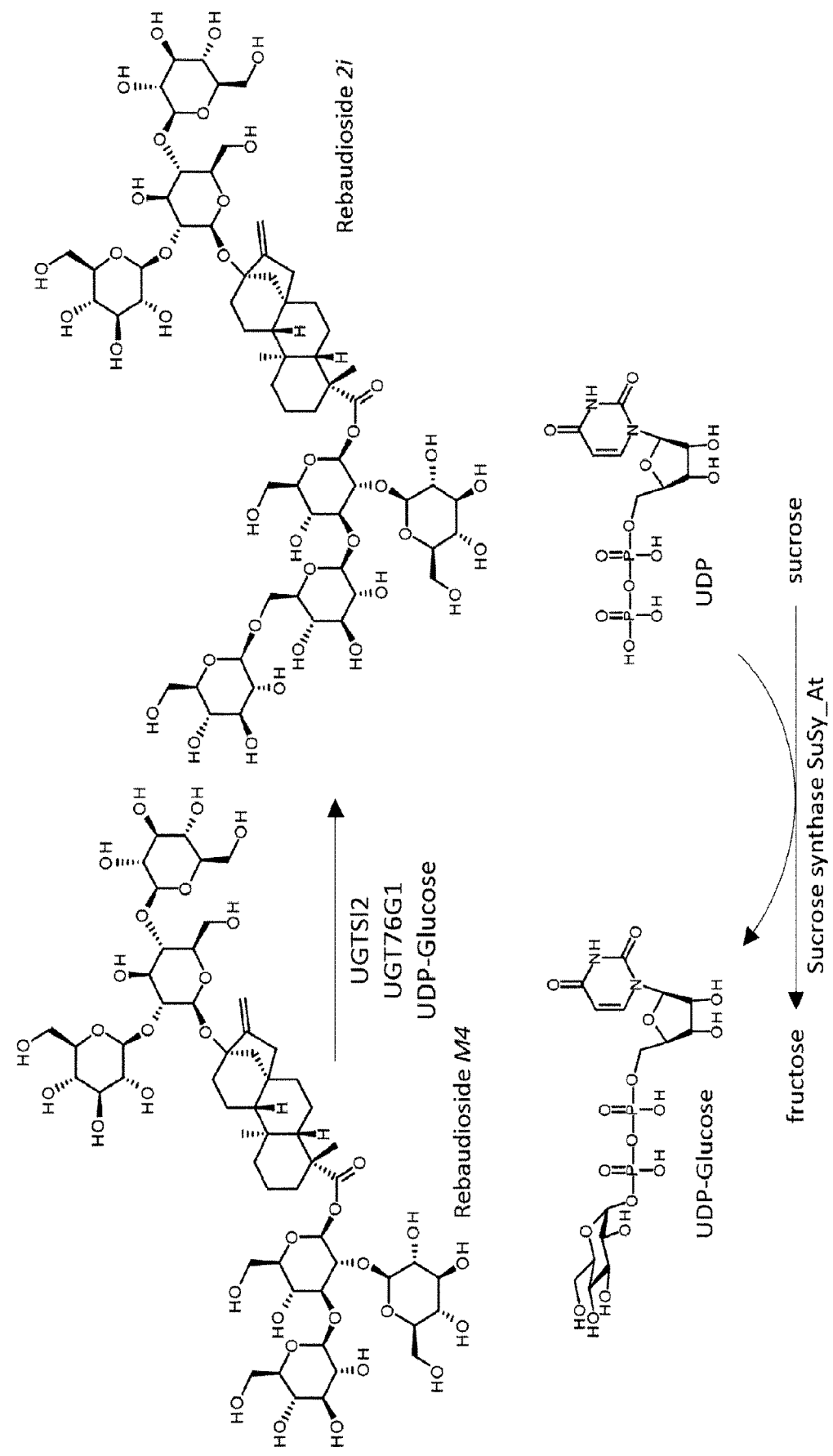
Figure 10J:
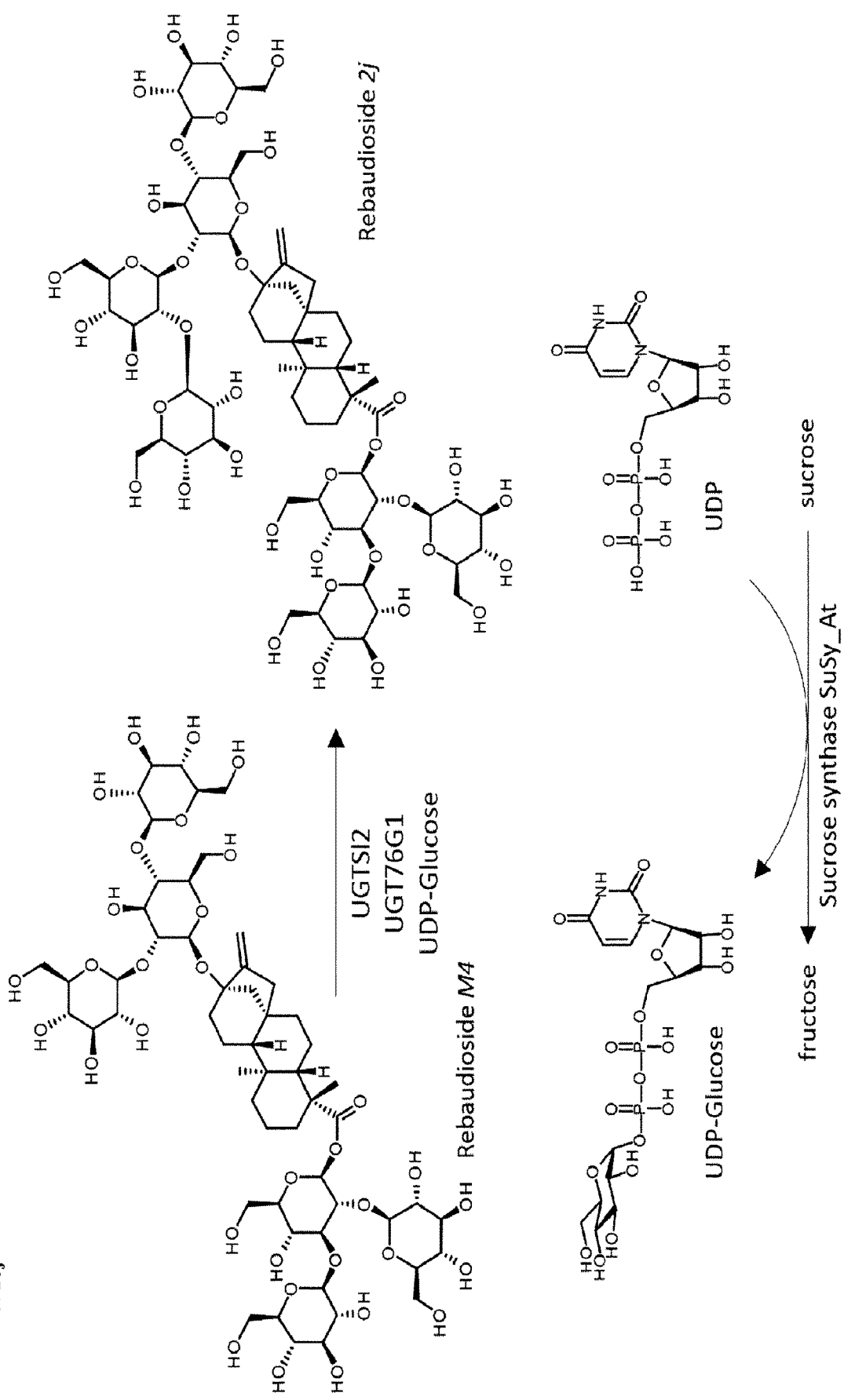
Figure 10K:
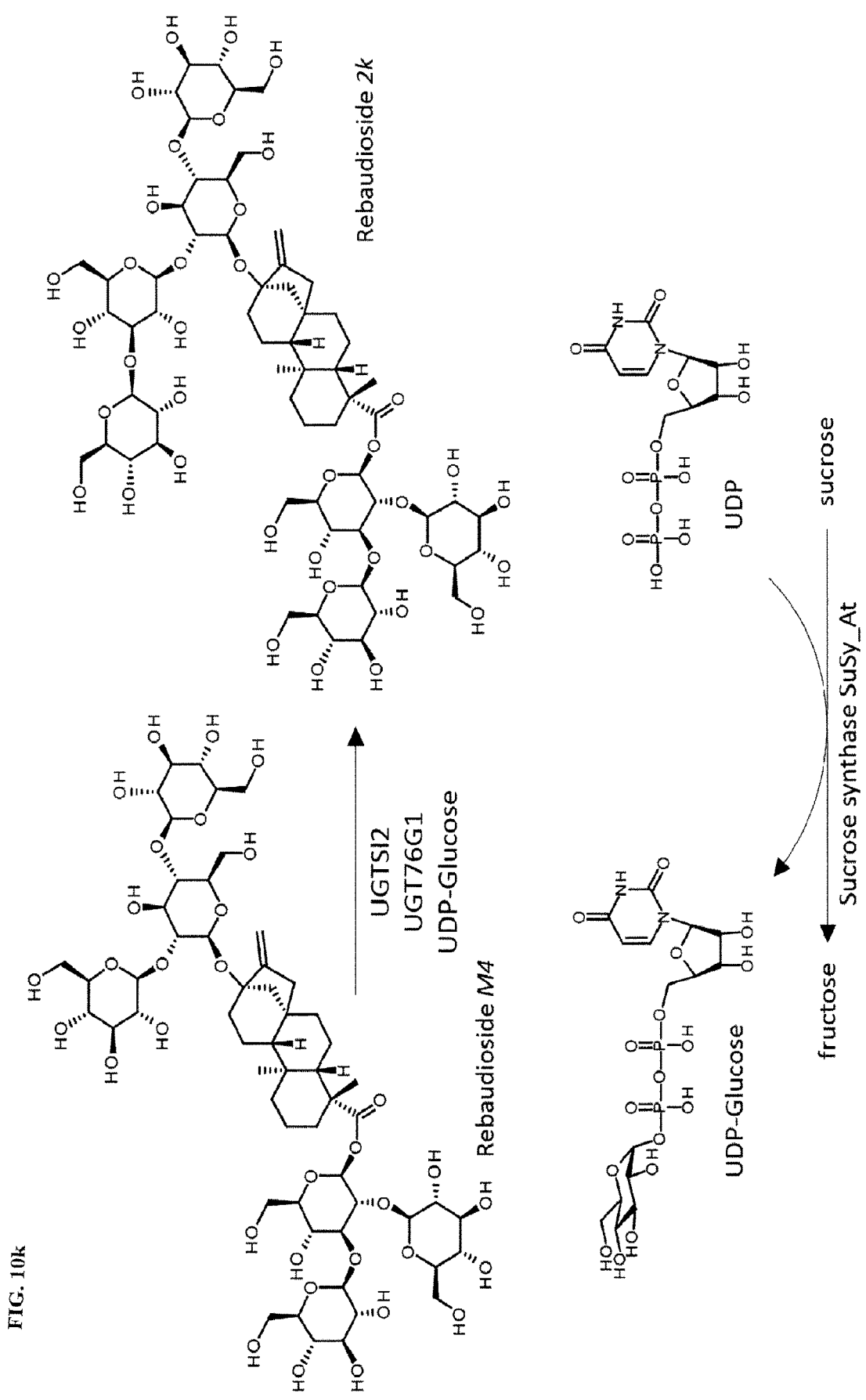
Figure 10I:
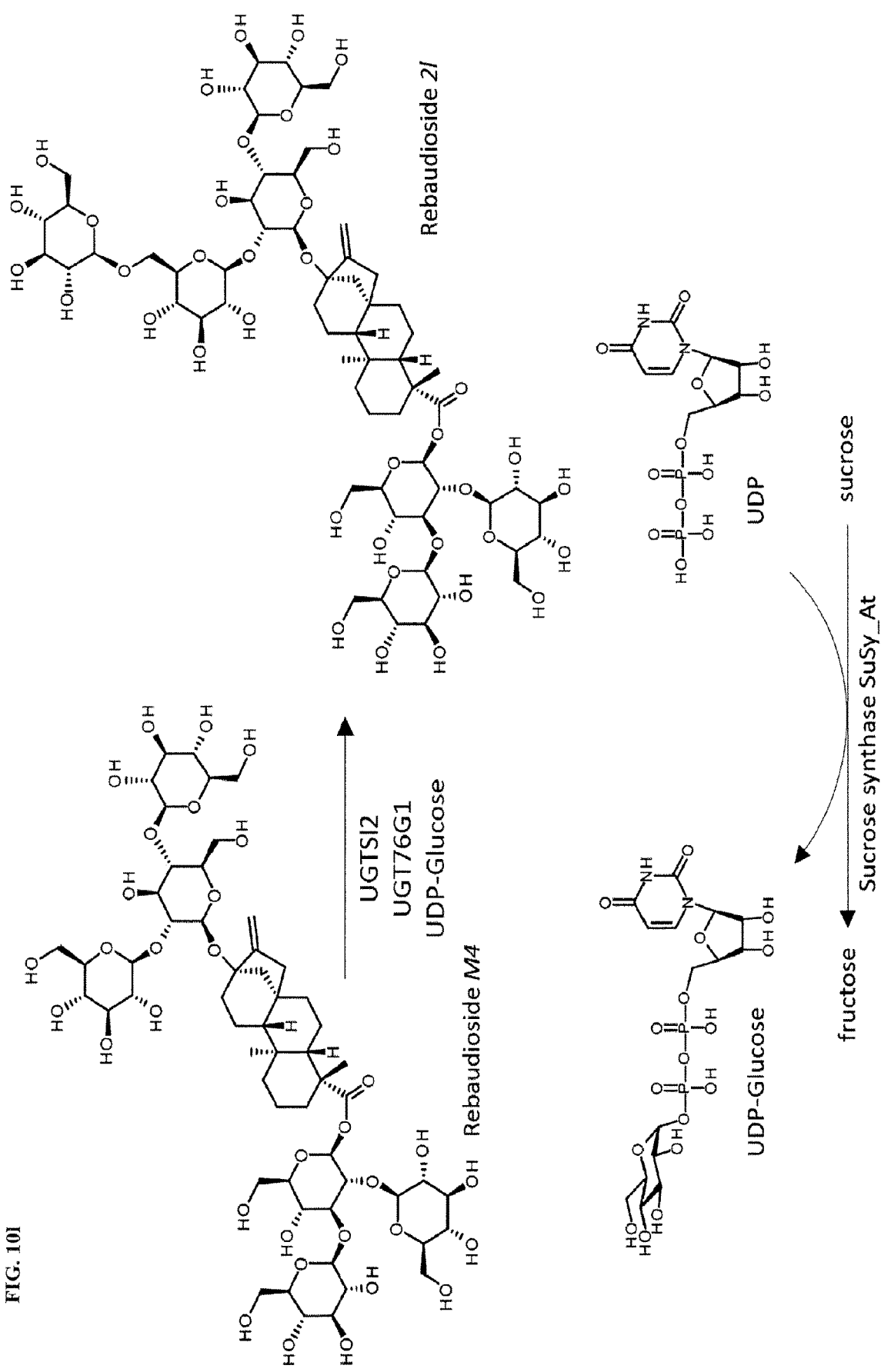
Figure 10M:
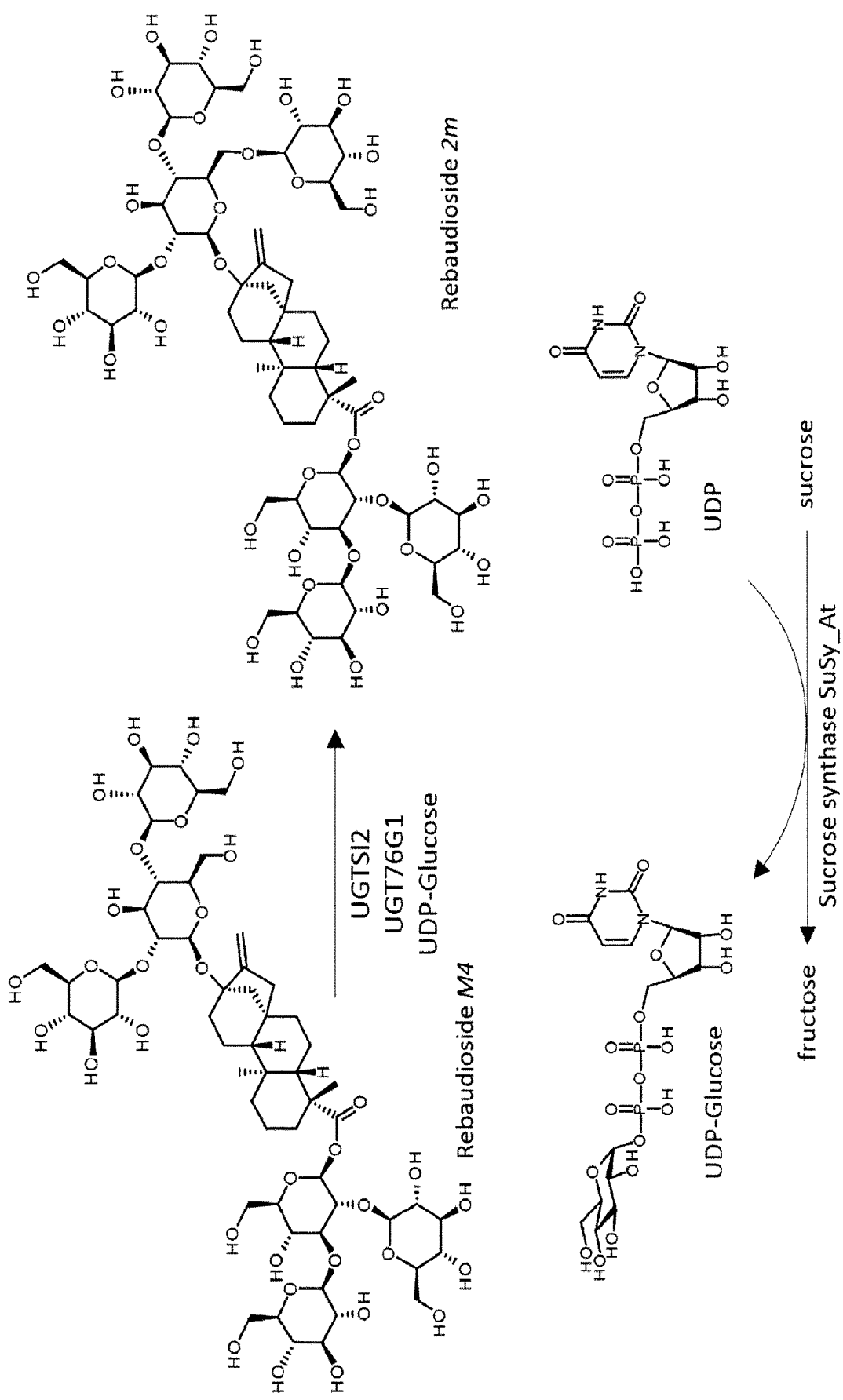
Figure 10N:
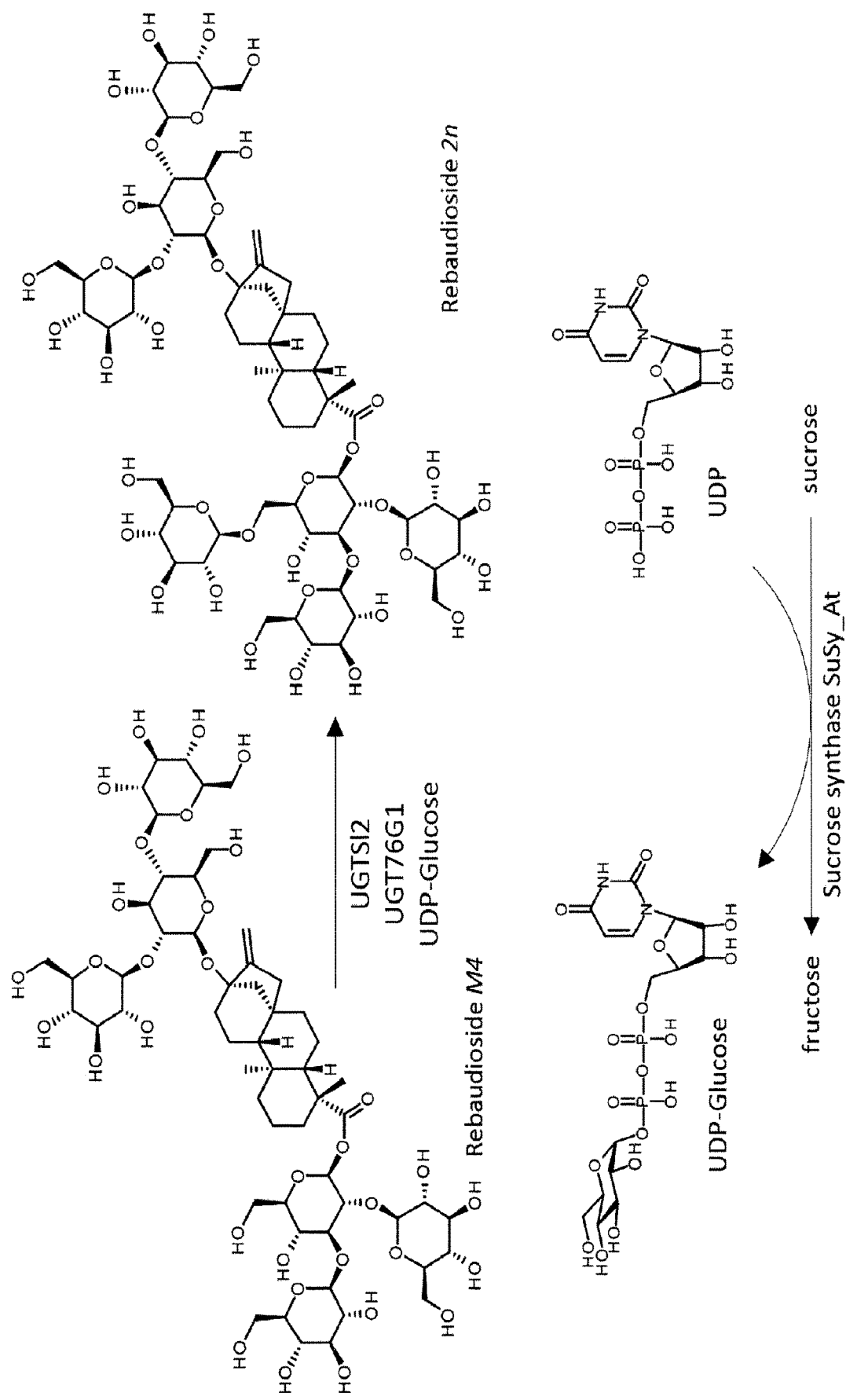
Figure 10O:
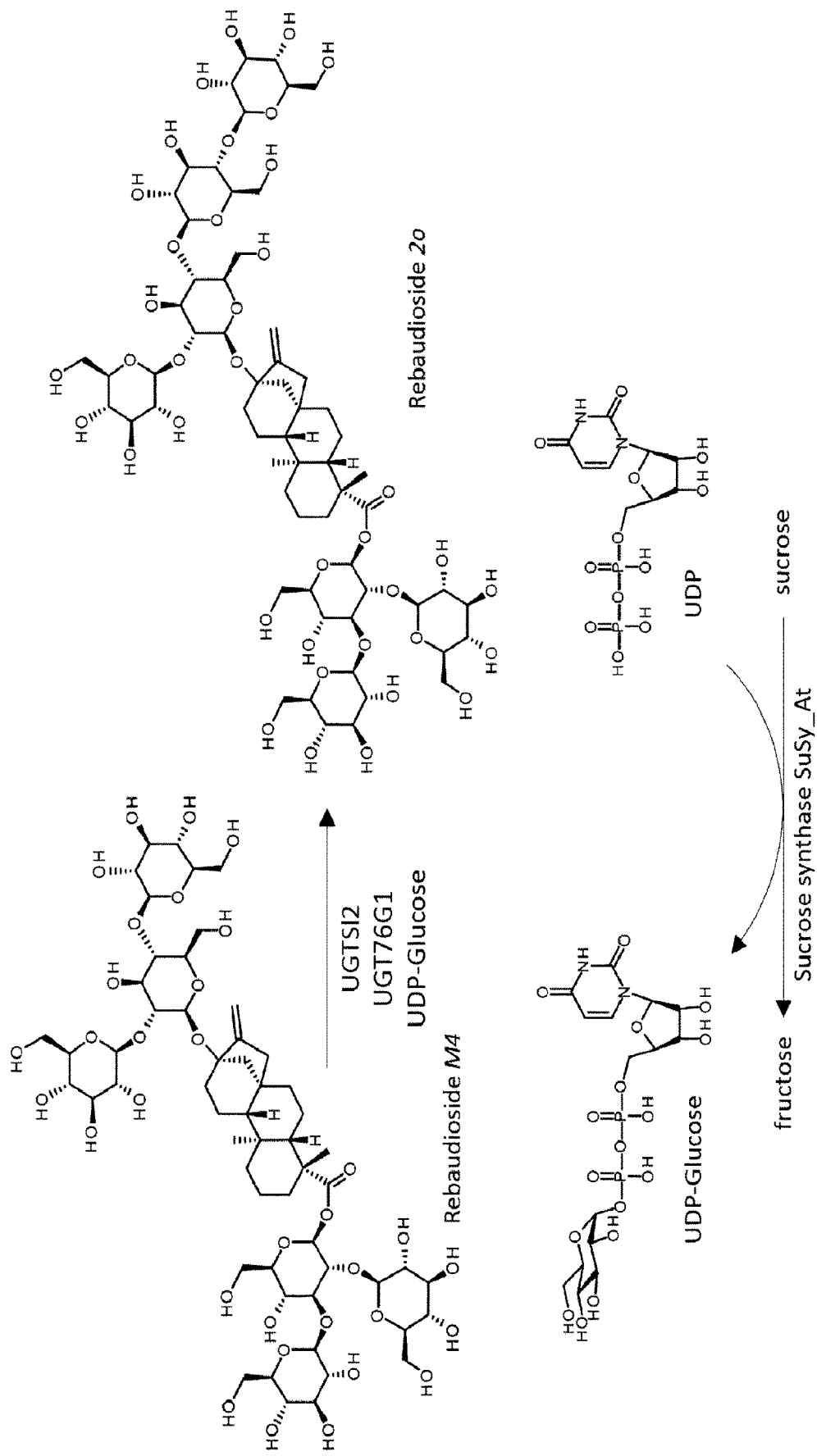
Figure 10P:
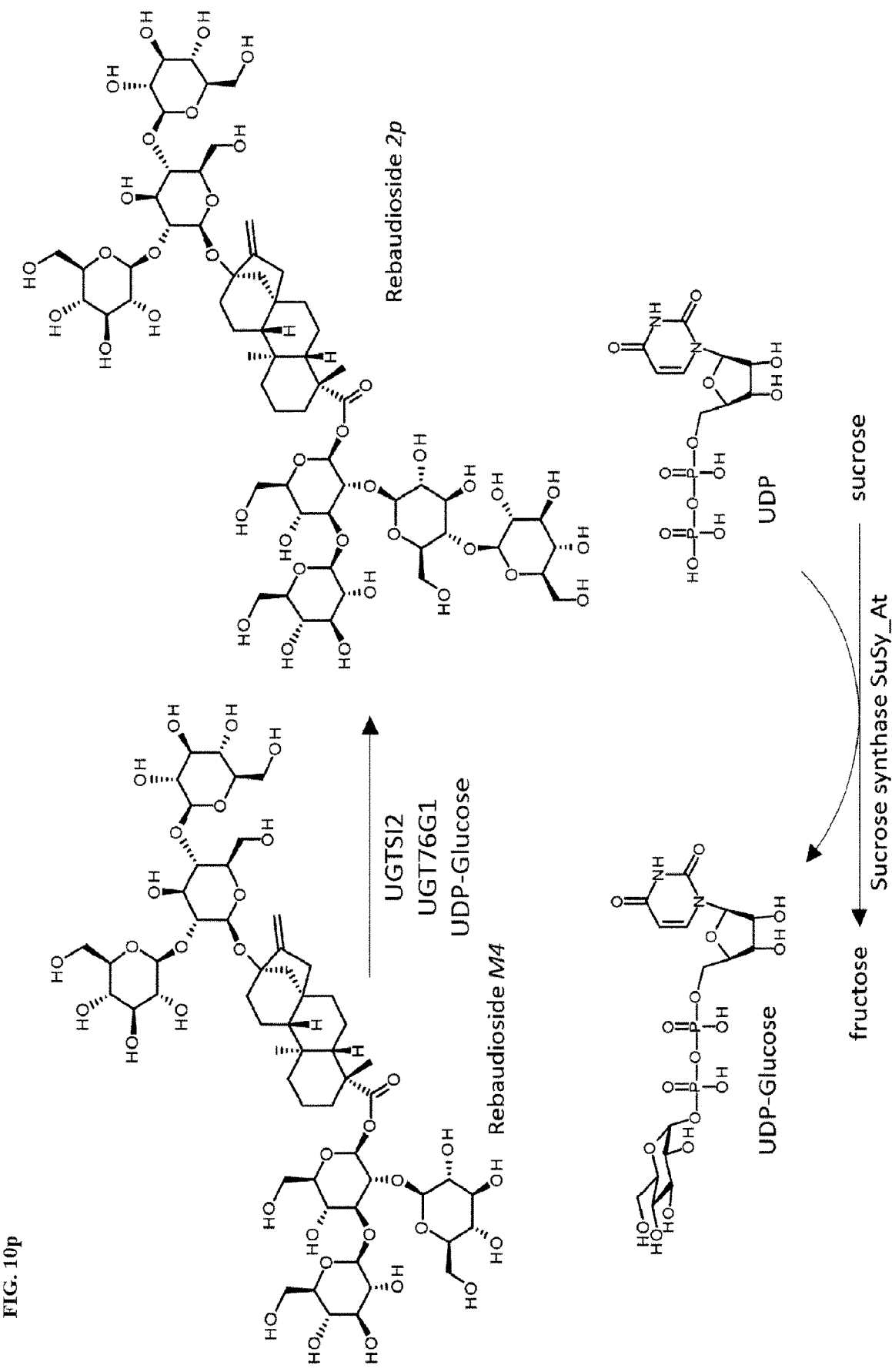
Figure 10Q:
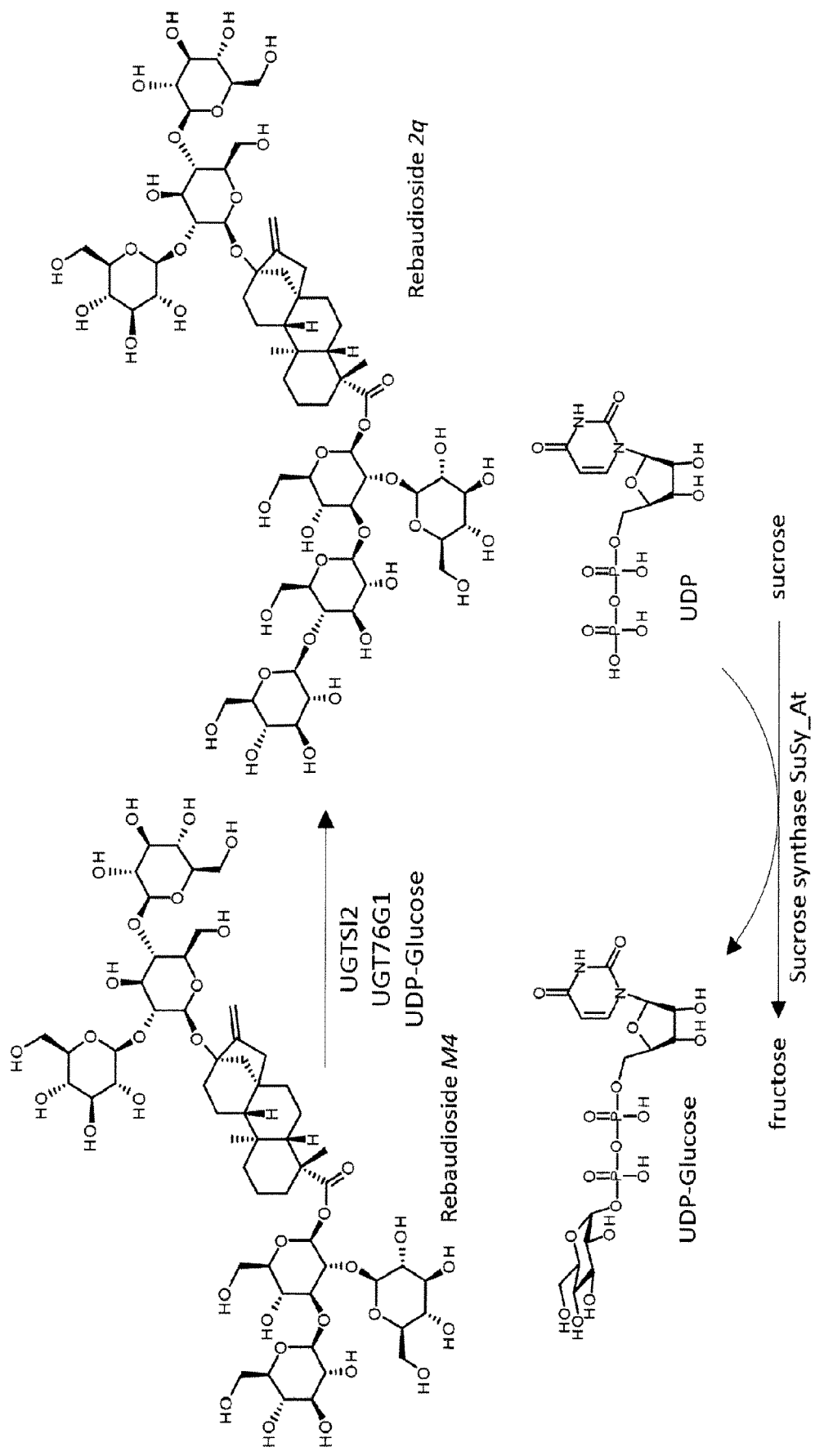
Figure 10R:
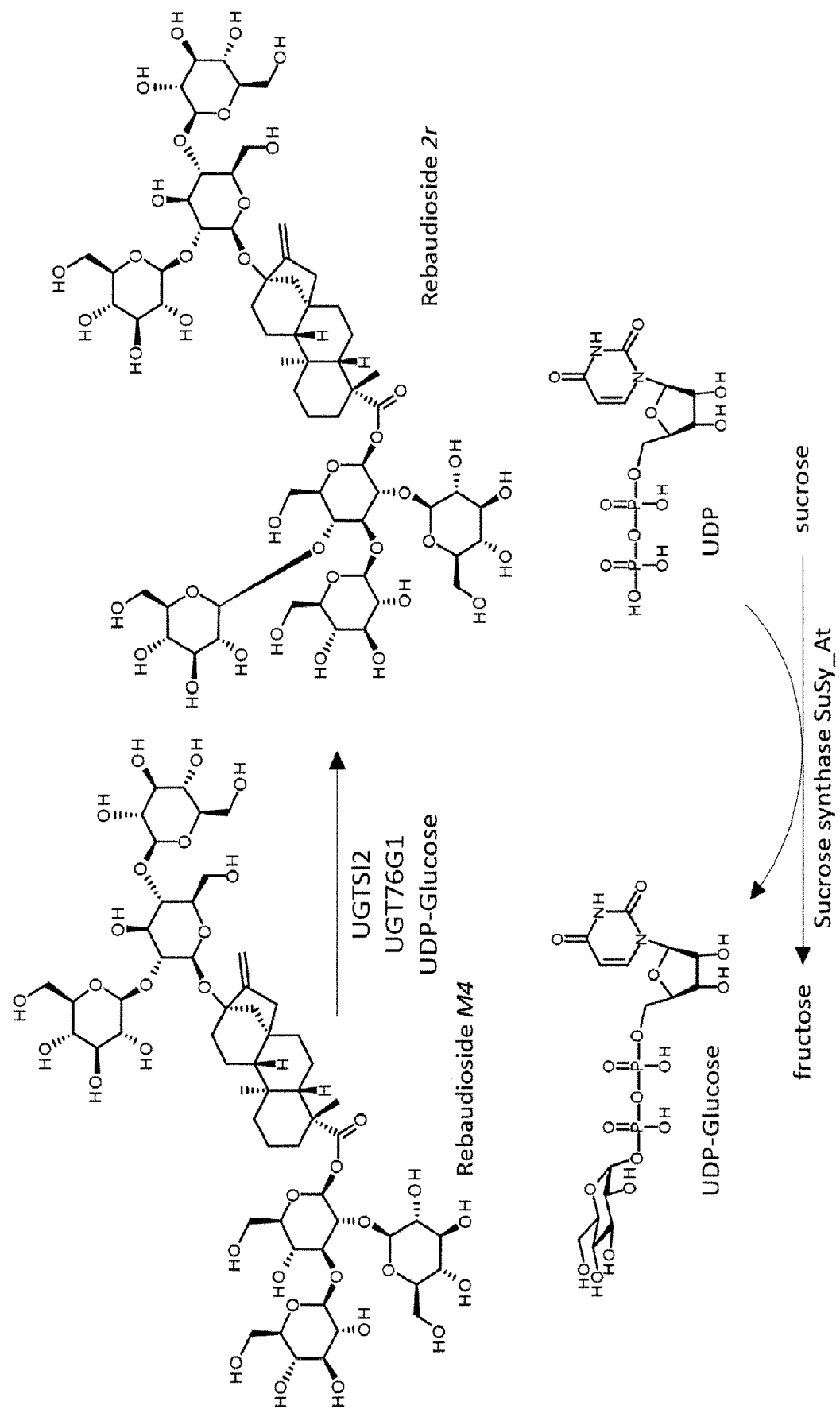
Figure 10S:
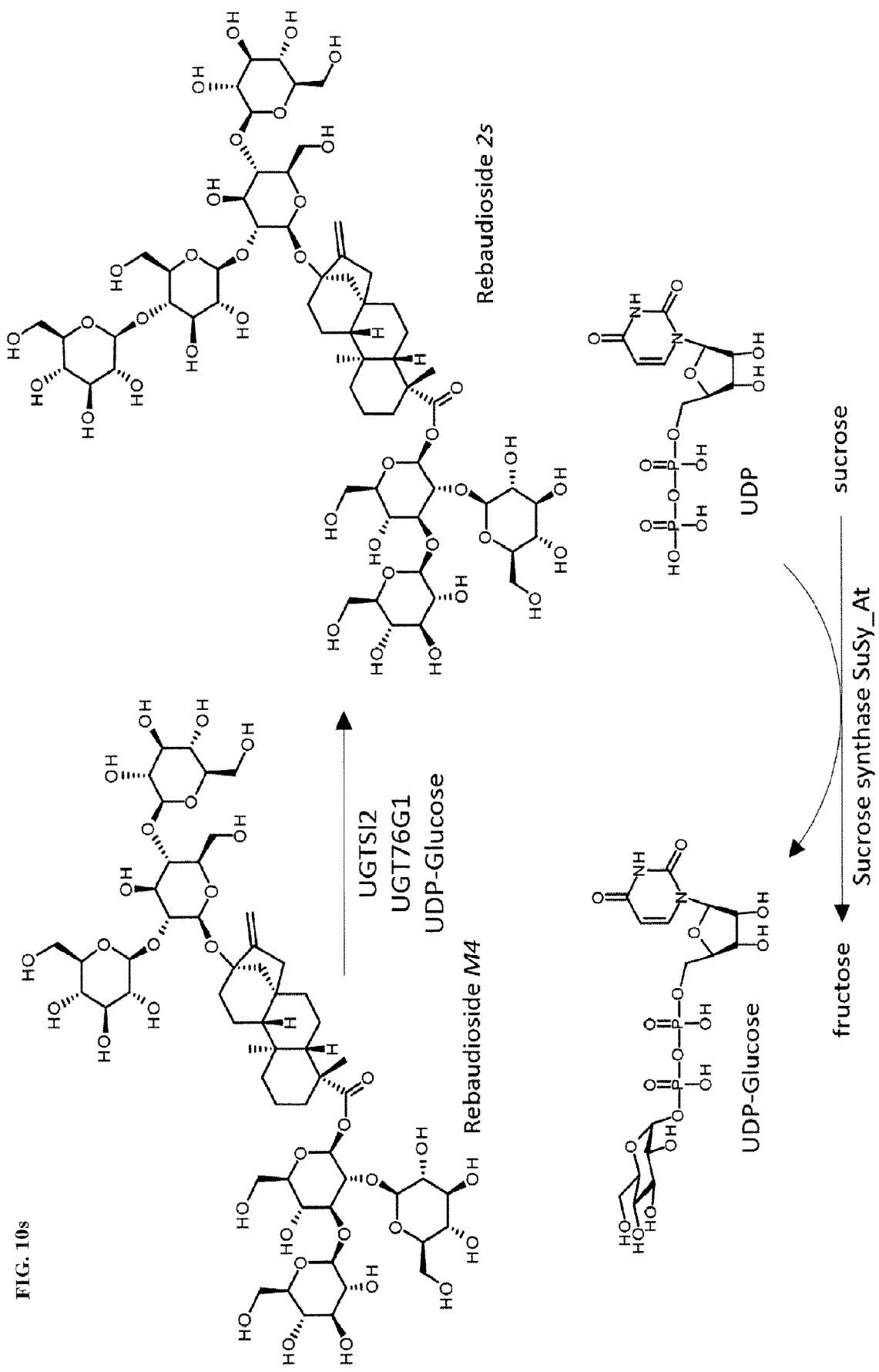
Figure 10T:
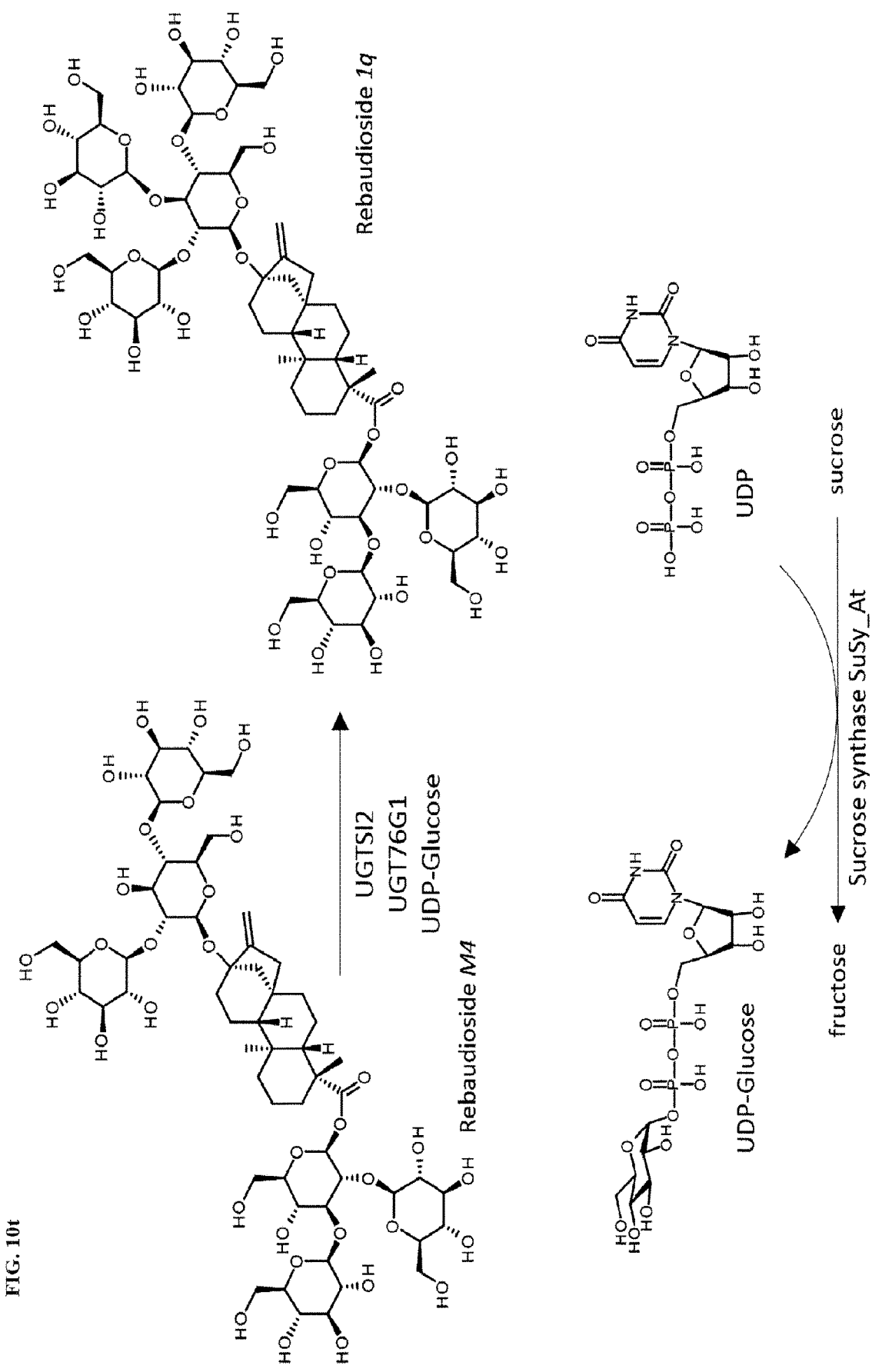
Figure 11A:
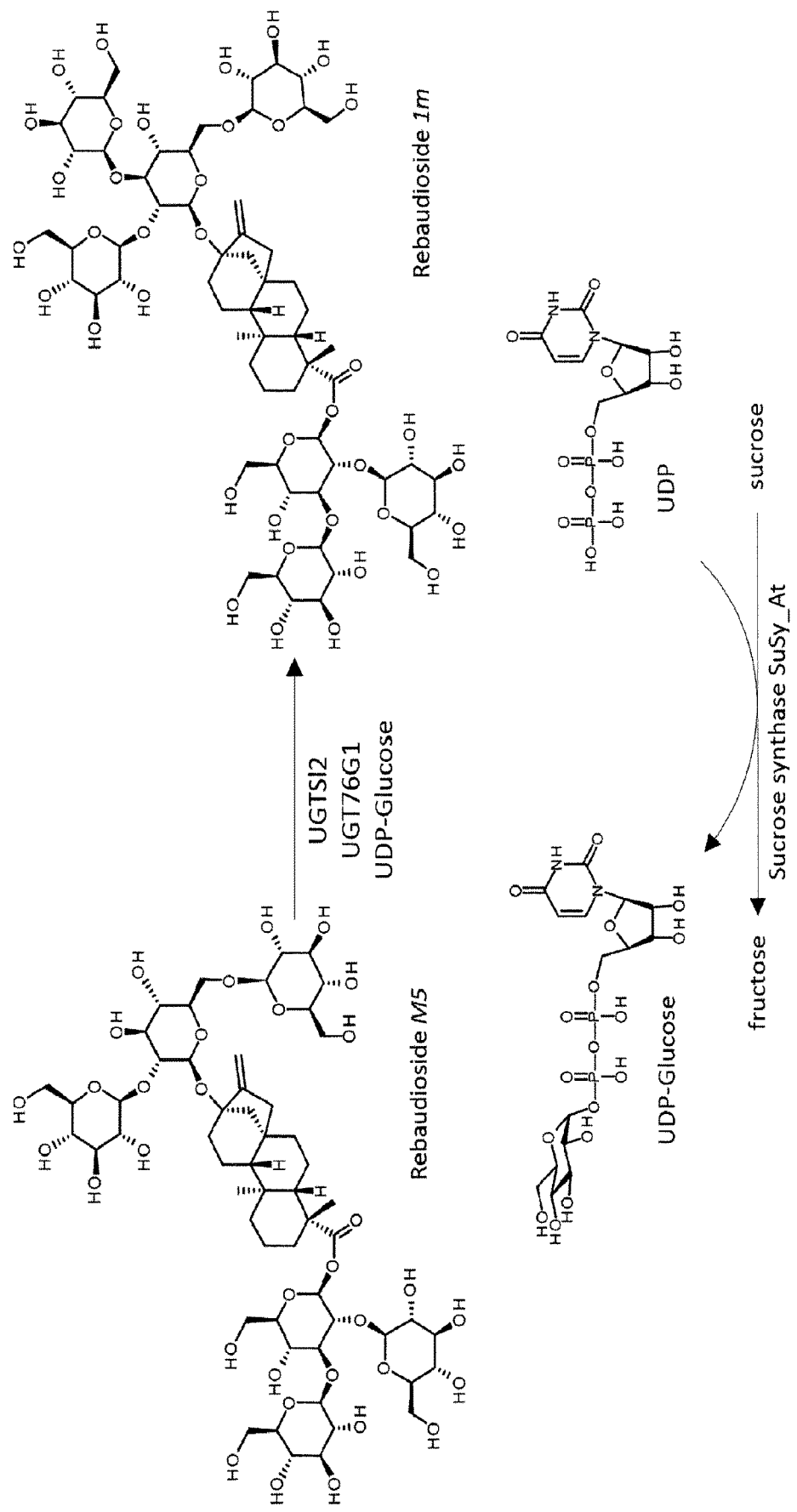
FIG. 11a through FIG. 11b show the biocatalytic production of rebaudioside 1m and rebaudioside 2m, respectively, from rebaudioside M5 using the enzymes UGTSl2 and UGT76G1 and concomitant recycling of UDP to UDP-glucose via sucrose synthase SuSy_At.
Figure 11B:
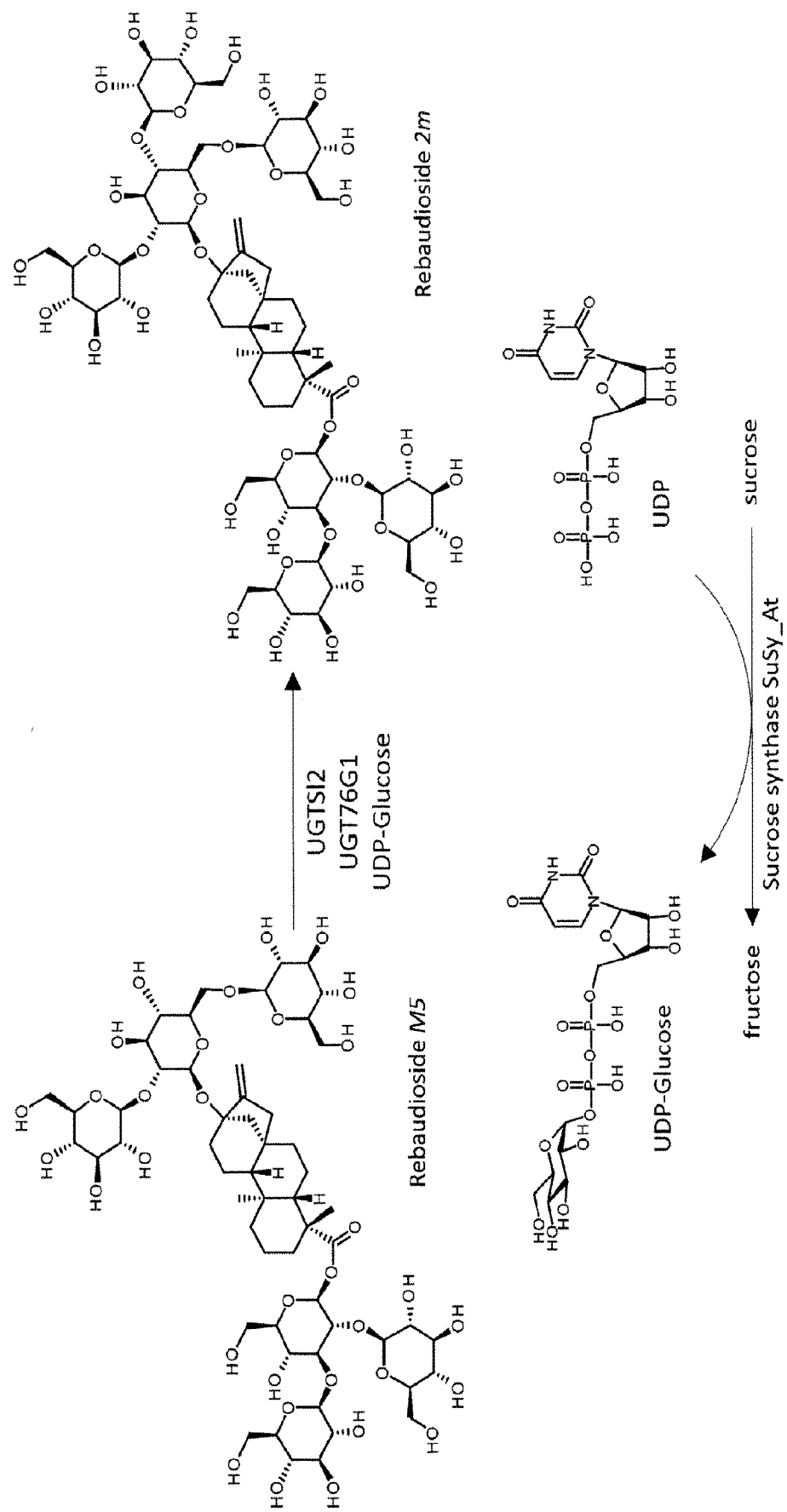

The present invention provides a process for preparing a composition comprising a target steviol glycoside by contacting a starting composition comprising an organic substrate with a microbial cell and/or enzyme preparation, thereby producing a composition comprising a target steviol glycoside.

One object of the invention is to provide an efficient biocatalytic method for preparing target steviol glycosides, particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s, and/or SvG7 or a synthetic steviol glycoside from various starting compositions.

Starting Composition

As used herein, "starting composition" refers to any composition (generally an aqueous solution) containing one or more organic compound comprising at least one carbon atom.

In one embodiment, the starting composition is selected from the group consisting of steviol, steviol glycosides, polyols and various carbohydrates.

The starting composition steviol glycoside is selected from the group consisting of steviol, steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4 and/or rebaudioside M5 or other glycoside of steviol occurring in *Stevia rebaudiana* plant, synthetic steviol glycosides, e.g. enzymatically glucosylated steviol glycosides and combinations thereof.

In one embodiment, the starting composition is steviol.

In another embodiment, the starting composition steviol glycoside is steviolmonoside.

In yet another embodiment, the starting composition steviol glycoside is steviolmonoside A.

In another embodiment, the starting composition steviol glycoside is steviolbioside.

In another embodiment, the starting composition steviol glycoside is steviolbioside D.

In another embodiment, the starting composition steviol glycoside is rubusoside.

In another embodiment, the starting composition steviol glycoside is steviolbioside A.

In another embodiment, the starting composition steviol glycoside is steviolbioside B.

In another embodiment, the starting composition steviol glycoside is rebaudioside B.

In another embodiment, the starting composition steviol glycoside is stevioside.

In another embodiment, the starting composition steviol glycoside is rebaudioside G.

In another embodiment, the starting composition steviol glycoside is stevioside A.

In another embodiment, the starting composition steviol glycoside is stevioside B.

In another embodiment, the starting composition steviol glycoside is stevioside C.

In another embodiment, the starting composition steviol glycoside is rebaudioside A.

In another embodiment, the starting composition steviol glycoside is rebaudioside E.

In another embodiment, the starting composition steviol glycoside is rebaudioside E2.

In another embodiment, the starting composition steviol glycoside is rebaudioside E4.

In another embodiment, the starting composition steviol glycoside is rebaudioside E6.

In another embodiment, the starting composition steviol glycoside is rebaudioside E3.

In another embodiment, the starting composition steviol glycoside is rebaudioside D.

In another embodiment, the starting composition steviol glycoside is rebaudioside I.

In another embodiment, the starting composition steviol glycoside is rebaudioside AM.

In another embodiment, the starting composition steviol glycoside is rebaudioside D7.

In another embodiment, the starting composition steviol glycoside is rebaudioside M.

In another embodiment, the starting composition steviol glycoside is rebaudioside M4.

In another embodiment, the starting composition steviol glycoside is rebaudioside M5.

The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced.

The term "carbohydrate" refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

The starting composition may be synthetic or purified (partially or entirely), commercially available or prepared.

In one embodiment, the starting composition is glycerol.

In another embodiment, the starting composition is glucose.

In another embodiment, the starting composition is rhamnose.

In still another embodiment, the starting composition is sucrose.

In yet another embodiment, the starting composition is starch.

In another embodiment, the starting composition is maltodextrin.

In yet another embodiment, the starting composition is cellulose.

In still another embodiment, the starting composition is amylose.

The organic compound(s) of starting composition serve as a substrate(s) for the production of the target steviol glycoside(s), as described herein.

Target Steviol Glycoside

The target steviol glycoside of the present method can be any steviol glycoside that can be prepared by the process disclosed herein. In one embodiment, the target steviol glycoside is selected from the group consisting of steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside 1, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s, SvG7 or other glycoside of steviol occurring in *Stevia rebaudiana* plant, synthetic steviol glycosides, e.g. enzymatically glucosylated steviol glycosides and combinations thereof.

In one embodiment, the target steviol glycoside is steviolmonoside.

In another embodiment, the target steviol glycoside is steviolmonoside A.

In another embodiment, the target steviol glycoside is steviolbioside.

In another embodiment, the target steviol glycoside is steviolbioside D.

In another embodiment, the target steviol glycoside is rubusoside.

In another embodiment, the target steviol glycoside is steviolbioside A.

In another embodiment, the target steviol glycoside is steviolbioside B.

In another embodiment, the target steviol glycoside is rebaudioside B.

In another embodiment, the target steviol glycoside is stevioside.

In another embodiment, the target steviol glycoside is rebaudioside G.

In another embodiment, the target steviol glycoside is stevioside A.

In another embodiment, the target steviol glycoside is stevioside B.

In another embodiment, the target steviol glycoside is stevioside C.

In another embodiment, the target steviol glycoside is rebaudioside A.

In another embodiment, the target steviol glycoside is rebaudioside E.

In another embodiment, the target steviol glycoside is rebaudioside E2.

In another embodiment, the target steviol glycoside is rebaudioside E4.

In another embodiment, the target steviol glycoside is rebaudioside E6.

In another embodiment, the target steviol glycoside is rebaudioside E3.

In another embodiment, the target steviol glycoside is rebaudioside D.

In another embodiment, the target steviol glycoside is rebaudioside I.

In another embodiment, the target steviol glycoside is rebaudioside AM.

In another embodiment, the target steviol glycoside is rebaudioside D7.

In another embodiment, the target steviol glycoside is rebaudioside M.

In another embodiment, the target steviol glycoside is rebaudioside M4.

In another embodiment, the target steviol glycoside is rebaudioside M5.

In another embodiment, the target steviol glycoside is rebaudioside 1a.

In another embodiment, the target steviol glycoside is rebaudioside 1b.

In another embodiment, the target steviol glycoside is rebaudioside 1c.

In another embodiment, the target steviol glycoside is rebaudioside 1d.

In another embodiment, the target steviol glycoside is rebaudioside 1e.

In another embodiment, the target steviol glycoside is rebaudioside 1f.

In another embodiment, the target steviol glycoside is rebaudioside 1g.

In another embodiment, the target steviol glycoside is rebaudioside 1h.

In another embodiment, the target steviol glycoside is rebaudioside 1i.

In another embodiment, the target steviol glycoside is rebaudioside 1j.

In another embodiment, the target steviol glycoside is rebaudioside 1k.

In another embodiment, the target steviol glycoside is rebaudioside 1l.

In another embodiment, the target steviol glycoside is rebaudioside 1m.

In another embodiment, the target steviol glycoside is rebaudioside 1n.

In another embodiment, the target steviol glycoside is rebaudioside 1o.

In another embodiment, the target steviol glycoside is rebaudioside 1p.

In another embodiment, the target steviol glycoside is rebaudioside 1q.

In another embodiment, the target steviol glycoside is rebaudioside 1r.

In another embodiment, the target steviol glycoside is rebaudioside 1s.

In another embodiment, the target steviol glycoside is rebaudioside 1t.

In another embodiment, the target steviol glycoside is rebaudioside 2a.

In another embodiment, the target steviol glycoside is rebaudioside 2b.

In another embodiment, the target steviol glycoside is rebaudioside 2c.

In another embodiment, the target steviol glycoside is rebaudioside 2d.

In another embodiment, the target steviol glycoside is rebaudioside 2e.

In another embodiment, the target steviol glycoside is rebaudioside 2f.

In another embodiment, the target steviol glycoside is rebaudioside 2g.

In another embodiment, the target steviol glycoside is rebaudioside 2h.

In another embodiment, the target steviol glycoside is rebaudioside 2i.

In another embodiment, the target steviol glycoside is rebaudioside 2j.

In another embodiment, the target steviol glycoside is rebaudioside 2k.

In another embodiment, the target steviol glycoside is rebaudioside 2l.

In another embodiment, the target steviol glycoside is rebaudioside 2m.

In another embodiment, the target steviol glycoside is rebaudioside 2n.

In another embodiment, the target steviol glycoside is rebaudioside 2o.

In another embodiment, the target steviol glycoside is rebaudioside 2p.

In another embodiment, the target steviol glycoside is rebaudioside 2q.

In another embodiment, the target steviol glycoside is rebaudioside 2r.

In another embodiment, the target steviol glycoside is rebaudioside 2s.

In another embodiment, the target steviol glycoside is SvG7.

The target steviol glycoside can be in any polymorphic or amorphous form, including hydrates, solvates, anhydrous or combinations thereof.

In one embodiment, the present invention is a biocatalytic process for the production of steviolmonoside.

In one embodiment, the present invention is a biocatalytic process for the production of steviolmonoside A.

In one embodiment, the present invention is a biocatalytic process for the production of steviolbioside.

In one embodiment, the present invention is a biocatalytic process for the production of steviolbioside D.

In one embodiment, the present invention is a biocatalytic process for the production of rubusoside.

In one embodiment, the present invention is a biocatalytic process for the production of steviolbioside A.

In one embodiment, the present invention is a biocatalytic process for the production of steviolbioside B.

In one embodiment, the present invention is a biocatalytic process for the production of rebaudioside B.

In one embodiment, the present invention is a biocatalytic process for the production of stevioside.

In one embodiment, the present invention is a biocatalytic process for the production of rebaudioside G.

In one embodiment, the present invention is a biocatalytic process for the production of stevioside A.

In one embodiment, the present invention is a biocatalytic process for the production of stevioside B.

In one embodiment, the present invention is a biocatalytic process for the production of stevioside C.

In one embodiment, the present invention is a biocatalytic process for the production of rebaudioside A.

In one embodiment, the present invention is a biocatalytic process for the production of rebaudioside E.

In one embodiment, the present invention is a biocatalytic process for the production of rebaudioside E2.

In one embodiment, the present invention is a biocatalytic process for the production of rebaudioside E4.

In one embodiment, the present invention is a biocatalytic process for the production of rebaudioside E6.

In one embodiment, the present invention is a biocatalytic process for the production of rebaudioside E3.

In one embodiment, the present invention is a biocatalytic process for the production of rebaudioside D.

In one embodiment, the present invention is a biocatalytic process for the production of rebaudioside I.

In one embodiment, the present invention is a biocatalytic process for the production of rebaudioside AM.

In one embodiment, the present invention is a biocatalytic process for the production of rebaudioside D7.

In one embodiment, the present invention is a biocatalytic process for the production of rebaudioside E3.

In one embodiment, the present invention is a biocatalytic process for the production of rebaudioside M.

In one embodiment, the present invention is a biocatalytic process for the production of rebaudioside M4.

In one embodiment, the present invention is a biocatalytic process for the production of rebaudioside M5.

In one embodiment, the present invention is a biocatalytic process for the production of rebaudioside 1a.

In one embodiment, the present invention is a biocatalytic process for the production of rebaudioside 1b.

In one embodiment, the present invention is a biocatalytic process for the production of rebaudioside 1c.

In one embodiment, the present invention is a biocatalytic process for the production of rebaudioside 1d.

In one embodiment, the present invention is a biocatalytic process for the production of rebaudioside 1e.

In one embodiment, the present invention is a biocatalytic process for the production of rebaudioside 1f.

In one embodiment, the present invention is a biocatalytic process for the production of rebaudioside 1g.

In one embodiment, the present invention is a biocatalytic process for the production of rebaudioside 1h.

In one embodiment, the present invention is a biocatalytic process for the production of rebaudioside 1i.

In one embodiment, the present invention is a biocatalytic process for the production of rebaudioside 1j.

In one embodiment, the present invention is a biocatalytic process for the production of rebaudioside 1k.

In one embodiment, the present invention is a biocatalytic process for the production of rebaudioside 1l.

In one embodiment, the present invention is a biocatalytic process for the production of rebaudioside 1m.

In one embodiment, the present invention is a biocatalytic process for the production of rebaudioside 1n.

In one embodiment, the present invention is a biocatalytic process for the production of rebaudioside 1o.

In one embodiment, the present invention is a biocatalytic process for the production of rebaudioside 1p.

In one embodiment, the present invention is a biocatalytic process for the production of rebaudioside 1q.

In one embodiment, the present invention is a biocatalytic process for the production of rebaudioside 1r.

In one embodiment, the present invention is a biocatalytic process for the production of rebaudioside 1s.

In one embodiment, the present invention is a biocatalytic process for the production of rebaudioside 1t.

In one embodiment, the present invention is a biocatalytic process for the production of rebaudioside 2a.

In one embodiment, the present invention is a biocatalytic process for the production of rebaudioside 2b.

In one embodiment, the present invention is a biocatalytic process for the production of rebaudioside 2c.

In one embodiment, the present invention is a biocatalytic process for the production of rebaudioside 2d.

In one embodiment, the present invention is a biocatalytic process for the production of rebaudioside 2e.

In one embodiment, the present invention is a biocatalytic process for the production of rebaudioside 2f.

In one embodiment, the present invention is a biocatalytic process for the production of rebaudioside 2g.

In one embodiment, the present invention is a biocatalytic process for the production of rebaudioside 2h.

In one embodiment, the present invention is a biocatalytic process for the production of rebaudioside 2i.

In one embodiment, the present invention is a biocatalytic process for the production of rebaudioside 2j.

In one embodiment, the present invention is a biocatalytic process for the production of rebaudioside 2k.

In one embodiment, the present invention is a biocatalytic process for the production of rebaudioside 2l.

In one embodiment, the present invention is a biocatalytic process for the production of rebaudioside 2m.

In one embodiment, the present invention is a biocatalytic process for the production of rebaudioside 2n.

In one embodiment, the present invention is a biocatalytic process for the production of rebaudioside 2o.

In one embodiment, the present invention is a biocatalytic process for the production of rebaudioside 2p.

In one embodiment, the present invention is a biocatalytic process for the production of rebaudioside 2q.

In one embodiment, the present invention is a biocatalytic process for the production of rebaudioside 2r.

In one embodiment, the present invention is a biocatalytic process for the production of rebaudioside 2s.

In one embodiment, the present invention is a biocatalytic process for the production of SvG7.

In a particular embodiment, the present invention provides for the biocatalytic process for the production of rebaudioside 1a from a starting composition comprising rebaudioside A and UDP-glucose.

In a particular embodiment, the present invention provides for the biocatalytic process for the production of rebaudioside 1b from a starting composition comprising rebaudioside A and UDP-glucose.

In a particular embodiment, the present invention provides for the biocatalytic process for the production of rebaudioside 1c from a starting composition comprising rebaudioside A and UDP-glucose.

In a particular embodiment, the present invention provides for the biocatalytic process for the production of rebaudioside 1d from a starting composition comprising rebaudioside A and UDP-glucose.

In a particular embodiment, the present invention provides for the biocatalytic process for the production of rebaudioside 1e from a starting composition comprising rebaudioside A and UDP-glucose.

In a particular embodiment, the present invention provides for the biocatalytic process for the production of rebaudioside 1f from a starting composition comprising rebaudioside A and UDP-glucose.

In a particular embodiment, the present invention provides for the biocatalytic process for the production of rebaudioside 1g from a starting composition comprising rebaudioside A and UDP-glucose.

In a particular embodiment, the present invention provides for the biocatalytic process for the production of rebaudioside 1h from a starting composition comprising rebaudioside A and UDP-glucose.

In a particular embodiment, the present invention provides for the biocatalytic process for the production of rebaudioside 1i from a starting composition comprising rebaudioside A and UDP-glucose.

In a particular embodiment, the present invention provides for the biocatalytic process for the production of rebaudioside 1j from a starting composition comprising rebaudioside A and UDP-glucose.

In a particular embodiment, the present invention provides for the biocatalytic process for the production of rebaudioside 1k from a starting composition comprising rebaudioside A and UDP-glucose.

In a particular embodiment, the present invention provides for the biocatalytic process for the production of rebaudioside 1l from a starting composition comprising rebaudioside A and UDP-glucose.

In a particular embodiment, the present invention provides for the biocatalytic process for the production of rebaudioside 1m from a starting composition comprising rebaudioside A and UDP-glucose.

In a particular embodiment, the present invention provides for the biocatalytic process for the production of rebaudioside 1n from a starting composition comprising rebaudioside A and UDP-glucose.

In a particular embodiment, the present invention provides for the biocatalytic process for the production of rebaudioside 1o from a starting composition comprising rebaudioside A and UDP-glucose.

In a particular embodiment, the present invention provides for the biocatalytic process for the production of rebaudioside 1p from a starting composition comprising rebaudioside A and UDP-glucose.

In a particular embodiment, the present invention provides for the biocatalytic process for the production of rebaudioside 1q from a starting composition comprising rebaudioside A and UDP-glucose.

In a particular embodiment, the present invention provides for the biocatalytic process for the production of rebaudioside 1r from a starting composition comprising rebaudioside A and UDP-glucose.

In a particular embodiment, the present invention provides for the biocatalytic process for the production of rebaudioside 1s from a starting composition comprising rebaudioside A and UDP-glucose.

In a particular embodiment, the present invention provides for the biocatalytic process for the production of rebaudioside 1t from a starting composition comprising rebaudioside A and UDP-glucose.

In a particular embodiment, the present invention provides for the biocatalytic process for the production of rebaudioside 2a from a starting composition comprising stevioside and UDP-glucose.

In a particular embodiment, the present invention provides for the biocatalytic process for the production of rebaudioside 2b from a starting composition comprising stevioside and UDP-glucose.

In a particular embodiment, the present invention provides for the biocatalytic process for the production of rebaudioside 2c from a starting composition comprising stevioside and UDP-glucose.

In a particular embodiment, the present invention provides for the biocatalytic process for the production of rebaudioside 2d from a starting composition comprising stevioside and UDP-glucose.

In a particular embodiment, the present invention provides for the biocatalytic process for the production of rebaudioside 2e from a starting composition comprising stevioside and UDP-glucose.

In a particular embodiment, the present invention provides for the biocatalytic process for the production of rebaudioside 2f from a starting composition comprising stevioside and UDP-glucose.

In a particular embodiment, the present invention provides for the biocatalytic process for the production of rebaudioside 2g from a starting composition comprising stevioside and UDP-glucose.

In a particular embodiment, the present invention provides for the biocatalytic process for the production of rebaudioside 2h from a starting composition comprising stevioside and UDP-glucose.

In a particular embodiment, the present invention provides for the biocatalytic process for the production of rebaudioside 2i from a starting composition comprising stevioside and UDP-glucose.

In a particular embodiment, the present invention provides for the biocatalytic process for the production of rebaudioside 2j from a starting composition comprising stevioside and UDP-glucose.

In a particular embodiment, the present invention provides for the biocatalytic process for the production of rebaudioside 2k from a starting composition comprising stevioside and UDP-glucose.

In a particular embodiment, the present invention provides for the biocatalytic process for the production of rebaudioside 2l from a starting composition comprising stevioside and UDP-glucose.

In a particular embodiment, the present invention provides for the biocatalytic process for the production of rebaudioside 2m from a starting composition comprising stevioside and UDP-glucose.

In a particular embodiment, the present invention provides for the biocatalytic process for the production of rebaudioside 2n from a starting composition comprising stevioside and UDP-glucose.

In a particular embodiment, the present invention provides for the biocatalytic process for the production of rebaudioside 2o from a starting composition comprising stevioside and UDP-glucose.

In a particular embodiment, the present invention provides for the biocatalytic process for the production of rebaudioside 2p from a starting composition comprising stevioside and UDP-glucose.

In a particular embodiment, the present invention provides for the biocatalytic process for the production of rebaudioside 2q from a starting composition comprising stevioside and UDP-glucose.

In a particular embodiment, the present invention provides for the biocatalytic process for the production of rebaudioside 2r from a starting composition comprising stevioside and UDP-glucose.

In a particular embodiment, the present invention provides for the biocatalytic process for the production of rebaudioside 2s from a starting composition comprising stevioside and UDP-glucose.

In a particular embodiment, the present invention provides for the biocatalytic process for the production of rebaudioside 1q from a starting composition comprising stevioside and UDP-glucose.

In a particular embodiment, the present invention provides for the biocatalytic process for the production of rebaudioside M4 from a starting composition comprising stevioside and UDP-glucose.

In a particular embodiment, the present invention provides for the biocatalytic process for the production of rebaudioside M5 from a starting composition comprising stevioside and UDP-glucose.

In a particular embodiment, the present invention provides for the biocatalytic process for the production of rebaudioside 2a from a starting composition comprising rebaudioside AM and UDP-glucose.

In a particular embodiment, the present invention provides for the biocatalytic process for the production of rebaudioside 2b from a starting composition comprising rebaudioside AM and UDP-glucose.

In a particular embodiment, the present invention provides for the biocatalytic process for the production of rebaudioside 2c from a starting composition comprising rebaudioside AM and UDP-glucose.

In a particular embodiment, the present invention provides for the biocatalytic process for the production of rebaudioside 2d from a starting composition comprising rebaudioside AM and UDP-glucose.

In a particular embodiment, the present invention provides for the biocatalytic process for the production of rebaudioside 2e from a starting composition comprising rebaudioside AM and UDP-glucose.

In a particular embodiment, the present invention provides for the biocatalytic process for the production of rebaudioside 2f from a starting composition comprising rebaudioside AM and UDP-glucose.

In a particular embodiment, the present invention provides for the biocatalytic process for the production of rebaudioside 2g from a starting composition comprising rebaudioside AM and UDP-glucose.

In a particular embodiment, the present invention provides for the biocatalytic process for the production of rebaudioside 2h from a starting composition comprising rebaudioside AM and UDP-glucose.

In a particular embodiment, the present invention provides for the biocatalytic process for the production of rebaudioside 2i from a starting composition comprising rebaudioside AM and UDP-glucose.

In a particular embodiment, the present invention provides for the biocatalytic process for the production of rebaudioside 2j from a starting composition comprising rebaudioside AM and UDP-glucose.

In a particular embodiment, the present invention provides for the biocatalytic process for the production of rebaudioside 2k from a starting composition comprising rebaudioside AM and UDP-glucose.

In a particular embodiment, the present invention provides for the biocatalytic process for the production of rebaudioside 2l from a starting composition comprising rebaudioside AM and UDP-glucose.

In a particular embodiment, the present invention provides for the biocatalytic process for the production of rebaudioside 2m from a starting composition comprising rebaudioside AM and UDP-glucose.

In a particular embodiment, the present invention provides for the biocatalytic process for the production of rebaudioside 2n from a starting composition comprising rebaudioside AM and UDP-glucose.

In a particular embodiment, the present invention provides for the biocatalytic process for the production of rebaudioside 2o from a starting composition comprising rebaudioside AM and UDP-glucose.

In a particular embodiment, the present invention provides for the biocatalytic process for the production of rebaudioside 2p from a starting composition comprising rebaudioside AM and UDP-glucose.

In a particular embodiment, the present invention provides for the biocatalytic process for the production of rebaudioside 2q from a starting composition comprising rebaudioside AM and UDP-glucose.

In a particular embodiment, the present invention provides for the biocatalytic process for the production of rebaudioside 2r from a starting composition comprising rebaudioside AM and UDP-glucose.

In a particular embodiment, the present invention provides for the biocatalytic process for the production of rebaudioside 2s from a starting composition comprising rebaudioside AM and UDP-glucose.

In a particular embodiment, the present invention provides for the biocatalytic process for the production of rebaudioside 1q from a starting composition comprising rebaudioside AM and UDP-glucose.

In a particular embodiment, the present invention provides for the biocatalytic process for the production of rebaudioside M4 from a starting composition comprising rebaudioside AM and UDP-glucose.

In a particular embodiment, the present invention provides for the biocatalytic process for the production of rebaudioside M5 from a starting composition comprising rebaudioside AM and UDP-glucose.

In a particular embodiment, the present invention provides for the biocatalytic process for the production of rebaudioside 2a from a starting composition comprising rebaudioside M4 and UDP-glucose.

In a particular embodiment, the present invention provides for the biocatalytic process for the production of rebaudioside 2b from a starting composition comprising rebaudioside M4 and UDP-glucose.

In a particular embodiment, the present invention provides for the biocatalytic process for the production of rebaudioside 2c from a starting composition comprising rebaudioside M4 and UDP-glucose.

In a particular embodiment, the present invention provides for the biocatalytic process for the production of rebaudioside 2d from a starting composition comprising rebaudioside M4 and UDP-glucose.

In a particular embodiment, the present invention provides for the biocatalytic process for the production of rebaudioside 2e from a starting composition comprising rebaudioside M4 and UDP-glucose.

In a particular embodiment, the present invention provides for the biocatalytic process for the production of rebaudioside 2f from a starting composition comprising rebaudioside M4 and UDP-glucose.

In a particular embodiment, the present invention provides for the biocatalytic process for the production of rebaudioside 2g from a starting composition comprising rebaudioside M4 and UDP-glucose.

In a particular embodiment, the present invention provides for the biocatalytic process for the production of rebaudioside 2h from a starting composition comprising rebaudioside M4 and UDP-glucose.

In a particular embodiment, the present invention provides for the biocatalytic process for the production of rebaudioside 2i from a starting composition comprising rebaudioside M4 and UDP-glucose.

In a particular embodiment, the present invention provides for the biocatalytic process for the production of rebaudioside 2j from a starting composition comprising rebaudioside M4 and UDP-glucose.

In a particular embodiment, the present invention provides for the biocatalytic process for the production of rebaudioside 2k from a starting composition comprising rebaudioside M4 and UDP-glucose.

In a particular embodiment, the present invention provides for the biocatalytic process for the production of rebaudioside 2l from a starting composition comprising rebaudioside M4 and UDP-glucose.

In a particular embodiment, the present invention provides for the biocatalytic process for the production of rebaudioside 2m from a starting composition comprising rebaudioside M4 and UDP-glucose.

In a particular embodiment, the present invention provides for the biocatalytic process for the production of rebaudioside 2n from a starting composition comprising rebaudioside M4 and UDP-glucose.

In a particular embodiment, the present invention provides for the biocatalytic process for the production of rebaudioside 2o from a starting composition comprising rebaudioside M4 and UDP-glucose.

In a particular embodiment, the present invention provides for the biocatalytic process for the production of rebaudioside 2p from a starting composition comprising rebaudioside M4 and UDP-glucose.

In a particular embodiment, the present invention provides for the biocatalytic process for the production of rebaudioside 2q from a starting composition comprising rebaudioside M4 and UDP-glucose.

In a particular embodiment, the present invention provides for the biocatalytic process for the production of rebaudioside 2r from a starting composition comprising rebaudioside M4 and UDP-glucose.

In a particular embodiment, the present invention provides for the biocatalytic process for the production of rebaudioside 2s from a starting composition comprising rebaudioside M4 and UDP-glucose.

In a particular embodiment, the present invention provides for the biocatalytic process for the production of rebaudioside 1q from a starting composition comprising rebaudioside M4 and UDP-glucose.

In a particular embodiment, the present invention provides for the biocatalytic process for the production of rebaudioside 1m from a starting composition comprising rebaudioside M5 and UDP-glucose.

In a particular embodiment, the present invention provides for the biocatalytic process for the production of rebaudioside 2m from a starting composition comprising rebaudioside M5 and UDP-glucose.

In a particular embodiment, the present invention provides for the biocatalytic process for the production of rebaudioside 1a from a starting composition comprising rebaudioside M and UDP-glucose.

In a particular embodiment, the present invention provides for the biocatalytic process for the production of rebaudioside 1b from a starting composition comprising rebaudioside M and UDP-glucose.

In a particular embodiment, the present invention provides for the biocatalytic process for the production of rebaudioside 1c from a starting composition comprising rebaudioside M and UDP-glucose.

In a particular embodiment, the present invention provides for the biocatalytic process for the production of rebaudioside 1d from a starting composition comprising rebaudioside M and UDP-glucose.

In a particular embodiment, the present invention provides for the biocatalytic process for the production of rebaudioside 1e from a starting composition comprising rebaudioside M and UDP-glucose.

In a particular embodiment, the present invention provides for the biocatalytic process for the production of rebaudioside 1f from a starting composition comprising rebaudioside M and UDP-glucose.

In a particular embodiment, the present invention provides for the biocatalytic process for the production of rebaudioside 1g from a starting composition comprising rebaudioside M and UDP-glucose.

In a particular embodiment, the present invention provides for the biocatalytic process for the production of rebaudioside 1h from a starting composition comprising rebaudioside M and UDP-glucose.

In a particular embodiment, the present invention provides for the biocatalytic process for the production of rebaudioside 1i from a starting composition comprising rebaudioside M and UDP-glucose.

In a particular embodiment, the present invention provides for the biocatalytic process for the production of rebaudioside 1j from a starting composition comprising rebaudioside M and UDP-glucose.

In a particular embodiment, the present invention provides for the biocatalytic process for the production of rebaudioside 1k from a starting composition comprising rebaudioside M and UDP-glucose.

In a particular embodiment, the present invention provides for the biocatalytic process for the production of rebaudioside 1l from a starting composition comprising rebaudioside M and UDP-glucose.

In a particular embodiment, the present invention provides for the biocatalytic process for the production of rebaudioside 1m from a starting composition comprising rebaudioside M and UDP-glucose.

In a particular embodiment, the present invention provides for the biocatalytic process for the production of rebaudioside 1n from a starting composition comprising rebaudioside M and UDP-glucose.

In a particular embodiment, the present invention provides for the biocatalytic process for the production of rebaudioside 1o from a starting composition comprising rebaudioside M and UDP-glucose.

In a particular embodiment, the present invention provides for the biocatalytic process for the production of rebaudioside 1p from a starting composition comprising rebaudioside M and UDP-glucose.

In a particular embodiment, the present invention provides for the biocatalytic process for the production of rebaudioside 1q from a starting composition comprising rebaudioside M and UDP-glucose.

In a particular embodiment, the present invention provides for the biocatalytic process for the production of rebaudioside 1r from a starting composition comprising rebaudioside M and UDP-glucose.

In a particular embodiment, the present invention provides for the biocatalytic process for the production of rebaudioside 1s from a starting composition comprising rebaudioside M and UDP-glucose.

In a particular embodiment, the present invention provides for the biocatalytic process for the production of rebaudioside 1t from a starting composition comprising rebaudioside M and UDP-glucose.

In a particular embodiment, the present invention provides for the biocatalytic process for the production of SvG7 from a starting composition comprising stevioside and UDP-glucose.

In a particular embodiment, the present invention provides for the biocatalytic process for the production of SvG7 from a starting composition comprising rebaudioside A and UDP-glucose.

In a particular embodiment, the present invention provides for the biocatalytic process for the production of SvG7 from a starting composition comprising stevioside, rebaudioside A and UDP-glucose.

In a particular embodiment, the present invention provides for the biocatalytic process for the production of SvG7 from a starting composition comprising rebaudioside AM and UDP-glucose.

In a particular embodiment, the present invention provides for the biocatalytic process for the production of SvG7 from a starting composition comprising rebaudioside M and UDP-glucose.

In a particular embodiment, the present invention provides for the biocatalytic process for the production of SvG7 from a starting composition comprising rebaudioside M4 and UDP-glucose.

In a particular embodiment, the present invention provides for the biocatalytic process for the production of SvG7 from a starting composition comprising rebaudioside M5 and UDP-glucose.

Optionally, the method of the present invention further comprises separating the target steviol glycoside from the medium to provide a highly purified target steviol glycoside composition. The target steviol glycoside can be separated by any suitable method, such as, for example, crystallization, separation by membranes, centrifugation, extraction, chromatographic separation or a combination of such methods.

In particular embodiments, the process described herein results in a highly purified target steviol glycoside composition. The term "highly purified", as used herein, refers to a composition having greater than about 80% by weight of the target steviol glycoside on an anhydrous (dried) basis. In one embodiment, the highly purified target steviol glycoside composition contains greater than about 90% by weight of the target steviol glycoside on an anhydrous (dried) basis, such as, for example, greater than about 91%, greater than about 92%, greater than about 93%, greater than about 94%, greater than about 95%, greater than about 96%, greater than about 97%, greater than about 98% or greater than about 99% target steviol glycoside content on a dried basis.

In one embodiment, when the target steviol glycoside is rebaudioside M4, the process described herein provides a composition having greater than about 90% rebaudioside M4 content by weight on a dried basis. In another particular embodiment, when the target steviol glycoside is rebaudioside M4, the process described herein provides a composition comprising greater than about 95% content by weight on a dried basis.

In one embodiment, when the target steviol glycoside is rebaudioside M5, the process described herein provides a composition having greater than about 90% rebaudioside M5 content by weight on a dried basis. In another particular embodiment, when the target steviol glycoside is rebaudioside M5, the process described herein provides a composition comprising greater than about 95% content by weight on a dried basis.

In one embodiment, when the target steviol glycoside is rebaudioside 1a, the process described herein provides a composition having greater than about 90% rebaudioside 1a content by weight on a dried basis. In another particular embodiment, when the target steviol glycoside is rebaudioside 1a, the process described herein provides a composition comprising greater than about 95% content by weight on a dried basis.

In one embodiment, when the target steviol glycoside is rebaudioside 1b, the process described herein provides a composition having greater than about 90% rebaudioside 1b content by weight on a dried basis. In another particular embodiment, when the target steviol glycoside is rebaudioside 1b, the process described herein provides a composition comprising greater than about 95% content by weight on a dried basis.

In one embodiment, when the target steviol glycoside is rebaudioside 1c, the process described herein provides a composition having greater than about 90% rebaudioside 1c content by weight on a dried basis. In another particular embodiment, when the target steviol glycoside is rebaudioside 1c, the process described herein provides a composition comprising greater than about 95% content by weight on a dried basis.

In one embodiment, when the target steviol glycoside is rebaudioside 1d, the process described herein provides a composition having greater than about 90% rebaudioside 1d content by weight on a dried basis. In another particular embodiment, when the target steviol glycoside is rebaudioside 1d, the process described herein provides a composition comprising greater than about 95% content by weight on a dried basis.

In one embodiment, when the target steviol glycoside is rebaudioside 1e, the process described herein provides a composition having greater than about 90% rebaudioside 1e content by weight on a dried basis. In another particular embodiment, when the target steviol glycoside is rebaudioside 1e, the process described herein provides a composition comprising greater than about 95% content by weight on a dried basis.

In one embodiment, when the target steviol glycoside is rebaudioside 1f the process described herein provides a composition having greater than about 90% rebaudioside 1f content by weight on a dried basis. In another particular embodiment, when the target steviol glycoside is rebaudioside 1f the process described herein provides a composition comprising greater than about 95% content by weight on a dried basis.

In one embodiment, when the target steviol glycoside is rebaudioside 1g, the process described herein provides a composition having greater than about 90% rebaudioside 1g content by weight on a dried basis. In another particular embodiment, when the target steviol glycoside is rebaudioside 1g, the process described herein provides a composition comprising greater than about 95% content by weight on a dried basis.

In one embodiment, when the target steviol glycoside is rebaudioside 1h, the process described herein provides a composition having greater than about 90% rebaudioside 1h content by weight on a dried basis. In another particular embodiment, when the target steviol glycoside is rebaudioside 1h, the process described herein provides a composition comprising greater than about 95% content by weight on a dried basis.

In one embodiment, when the target steviol glycoside is rebaudioside 1i, the process described herein provides a composition having greater than about 90% rebaudioside 1i content by weight on a dried basis. In another particular embodiment, when the target steviol glycoside is rebaudioside 1i, the process described herein provides a composition comprising greater than about 95% content by weight on a dried basis.

In one embodiment, when the target steviol glycoside is rebaudioside 1j, the process described herein provides a composition having greater than about 90% rebaudioside 1j content by weight on a dried basis. In another particular embodiment, when the target steviol glycoside is rebaudioside 1j, the process described herein provides a composition comprising greater than about 95% content by weight on a dried basis.

In one embodiment, when the target steviol glycoside is rebaudioside 1k, the process described herein provides a composition having greater than about 90% rebaudioside 1k content by weight on a dried basis. In another particular embodiment, when the target steviol glycoside is rebaudioside 1k, the process described herein provides a composition comprising greater than about 95% content by weight on a dried basis.

In one embodiment, when the target steviol glycoside is rebaudioside 1l, the process described herein provides a composition having greater than about 90% rebaudioside 1l content by weight on a dried basis. In another particular embodiment, when the target steviol glycoside is rebaudioside 1l, the process described herein provides a composition comprising greater than about 95% content by weight on a dried basis.

In one embodiment, when the target steviol glycoside is rebaudioside 1m, the process described herein provides a composition having greater than about 90% rebaudioside 1m content by weight on a dried basis. In another particular embodiment, when the target steviol glycoside is rebaudioside 1m, the process described herein provides a composition comprising greater than about 95% content by weight on a dried basis.

In one embodiment, when the target steviol glycoside is rebaudioside 1n, the process described herein provides a composition having greater than about 90% rebaudioside 1n content by weight on a dried basis. In another particular embodiment, when the target steviol glycoside is rebaudioside 1n, the process described herein provides a composition comprising greater than about 95% content by weight on a dried basis.

In one embodiment, when the target steviol glycoside is rebaudioside 1o, the process described herein provides a composition having greater than about 90% rebaudioside 1o content by weight on a dried basis. In another particular embodiment, when the target steviol glycoside is rebaudioside 1o, the process described herein provides a composition comprising greater than about 95% content by weight on a dried basis.

In one embodiment, when the target steviol glycoside is rebaudioside 1p, the process described herein provides a composition having greater than about 90% rebaudioside 1p content by weight on a dried basis. In another particular embodiment, when the target steviol glycoside is rebaudioside 1p, the process described herein provides a composition comprising greater than about 95% content by weight on a dried basis.

In one embodiment, when the target steviol glycoside is rebaudioside 1q, the process described herein provides a composition having greater than about 90% rebaudioside 1q content by weight on a dried basis. In another particular embodiment, when the target steviol glycoside is rebaudioside 1q, the process described herein provides a composition comprising greater than about 95% content by weight on a dried basis.

In one embodiment, when the target steviol glycoside is rebaudioside 1r, the process described herein provides a composition having greater than about 90% rebaudioside 1r content by weight on a dried basis. In another particular embodiment, when the target steviol glycoside is rebaudioside 1r, the process described herein provides a composition comprising greater than about 95% content by weight on a dried basis.

In one embodiment, when the target steviol glycoside is rebaudioside 1s, the process described herein provides a composition having greater than about 90% rebaudioside 1s content by weight on a dried basis. In another particular embodiment, when the target steviol glycoside is rebaudioside 1s, the process described herein provides a composition comprising greater than about 95% content by weight on a dried basis.

In one embodiment, when the target steviol glycoside is rebaudioside 1t, the process described herein provides a composition having greater than about 90% rebaudioside 1t content by weight on a dried basis. In another particular embodiment, when the target steviol glycoside is rebaudioside 1t, the process described herein provides a composition comprising greater than about 95% content by weight on a dried basis.

In one embodiment, when the target steviol glycoside is rebaudioside 2a, the process described herein provides a composition having greater than about 90% rebaudioside 2a content by weight on a dried basis. In another particular embodiment, when the target steviol glycoside is rebaudioside 2a, the process described herein provides a composition comprising greater than about 95% content by weight on a dried basis.

In one embodiment, when the target steviol glycoside is rebaudioside 2b, the process described herein provides a composition having greater than about 90% rebaudioside 2b content by weight on a dried basis. In another particular embodiment, when the target steviol glycoside is rebaudioside 2b, the process described herein provides a composition comprising greater than about 95% content by weight on a dried basis.

In one embodiment, when the target steviol glycoside is rebaudioside 2c, the process described herein provides a composition having greater than about 90% rebaudioside 2c content by weight on a dried basis. In another particular embodiment, when the target steviol glycoside is rebaudioside 2c, the process described herein provides a composition comprising greater than about 95% content by weight on a dried basis.

In one embodiment, when the target steviol glycoside is rebaudioside 2d, the process described herein provides a composition having greater than about 90% rebaudioside 2d content by weight on a dried basis. In another particular embodiment, when the target steviol glycoside is rebaudioside 2d, the process described herein provides a composition comprising greater than about 95% content by weight on a dried basis.

In one embodiment, when the target steviol glycoside is rebaudioside 2e, the process described herein provides a composition having greater than about 90% rebaudioside 2e content by weight on a dried basis. In another particular embodiment, when the target steviol glycoside is rebaudioside 2e, the process described herein provides a composition comprising greater than about 95% content by weight on a dried basis.

In one embodiment, when the target steviol glycoside is rebaudioside 2f the process described herein provides a composition having greater than about 90% rebaudioside 2f content by weight on a dried basis. In another particular embodiment, when the target steviol glycoside is rebaudioside 2f the process described herein provides a composition comprising greater than about 95% content by weight on a dried basis.

In one embodiment, when the target steviol glycoside is rebaudioside 2g, the process described herein provides a composition having greater than about 90% rebaudioside 2g content by weight on a dried basis. In another particular embodiment, when the target steviol glycoside is rebaudioside 2g, the process described herein provides a composition comprising greater than about 95% content by weight on a dried basis.

In one embodiment, when the target steviol glycoside is rebaudioside 2h, the process described herein provides a composition having greater than about 90% rebaudioside 2h content by weight on a dried basis. In another particular embodiment, when the target steviol glycoside is rebaudioside 2h, the process described herein provides a composition comprising greater than about 95% content by weight on a dried basis.

In one embodiment, when the target steviol glycoside is rebaudioside 2i, the process described herein provides a composition having greater than about 90% rebaudioside 2i content by weight on a dried basis. In another particular embodiment, when the target steviol glycoside is rebaudioside 2i, the process described herein provides a composition comprising greater than about 95% content by weight on a dried basis.

In one embodiment, when the target steviol glycoside is rebaudioside 2j, the process described herein provides a composition having greater than about 90% rebaudioside 2j content by weight on a dried basis. In another particular embodiment, when the target steviol glycoside is rebaudioside 2j, the process described herein provides a composition comprising greater than about 95% content by weight on a dried basis.

In one embodiment, when the target steviol glycoside is rebaudioside 2k, the process described herein provides a composition having greater than about 90% rebaudioside 2k content by weight on a dried basis. In another particular embodiment, when the target steviol glycoside is rebaudioside 2k, the process described herein provides a composition comprising greater than about 95% content by weight on a dried basis.

In one embodiment, when the target steviol glycoside is rebaudioside 2l, the process described herein provides a composition having greater than about 90% rebaudioside 2l content by weight on a dried basis. In another particular embodiment, when the target steviol glycoside is rebaudioside 2l, the process described herein provides a composition comprising greater than about 95% content by weight on a dried basis.

In one embodiment, when the target steviol glycoside is rebaudioside 2m, the process described herein provides a composition having greater than about 90% rebaudioside 2m content by weight on a dried basis. In another particular embodiment, when the target steviol glycoside is rebaudioside 2m, the process described herein provides a composition comprising greater than about 95% content by weight on a dried basis.

In one embodiment, when the target steviol glycoside is rebaudioside 2n, the process described herein provides a composition having greater than about 90% rebaudioside 2n content by weight on a dried basis. In another particular embodiment, when the target steviol glycoside is rebaudioside 2n, the process described herein provides a composition comprising greater than about 95% content by weight on a dried basis.

In one embodiment, when the target steviol glycoside is rebaudioside 2o, the process described herein provides a composition having greater than about 90% rebaudioside 2o content by weight on a dried basis. In another particular embodiment, when the target steviol glycoside is rebaudioside 2o, the process described herein provides a composition comprising greater than about 95% content by weight on a dried basis.

In one embodiment, when the target steviol glycoside is rebaudioside 2p, the process described herein provides a composition having greater than about 90% rebaudioside 2p content by weight on a dried basis. In another particular embodiment, when the target steviol glycoside is rebaudioside 2p, the process described herein provides a composition comprising greater than about 95% content by weight on a dried basis.

In one embodiment, when the target steviol glycoside is rebaudioside 2q, the process described herein provides a composition having greater than about 90% rebaudioside 2q content by weight on a dried basis. In another particular embodiment, when the target steviol glycoside is rebaudioside 2q, the process described herein provides a composition comprising greater than about 95% content by weight on a dried basis.

In one embodiment, when the target steviol glycoside is rebaudioside 2r, the process described herein provides a composition having greater than about 90% rebaudioside 2r content by weight on a dried basis. In another particular embodiment, when the target steviol glycoside is rebaudioside 2r, the process described herein provides a composition comprising greater than about 95% content by weight on a dried basis.

In one embodiment, when the target steviol glycoside is rebaudioside 2s, the process described herein provides a composition having greater than about 90% rebaudioside 2s content by weight on a dried basis. In another particular embodiment, when the target steviol glycoside is rebaudioside 2s, the process described herein provides a composition comprising greater than about 95% content by weight on a dried basis.

In one embodiment, when the target steviol glycoside is SvG7, the process described herein provides a composition having greater than about 90% SvG7 content by weight on a dried basis. In another particular embodiment, when the target steviol glycoside is SvG7, the process described herein provides a composition comprising greater than about 95% SvG7 content by weight on a dried basis.

Microorganisms and Enzyme Preparations

In one embodiment of present invention, a microorganism (microbial cell) and/or enzyme preparation is contacted with a medium containing the starting composition to produce target steviol glycosides.

The enzyme can be provided in the form of a whole cell suspension, a crude lysate, a purified enzyme or a combination thereof. In one embodiment, the biocatalyst is a purified enzyme capable of converting the starting composition to the target steviol glycoside. In another embodiment, the biocatalyst is a crude lysate comprising at least one enzyme capable of converting the starting composition to the target steviol glycoside. In still another embodiment, the biocatalyst is a whole cell suspension comprising at least one enzyme capable of converting the starting composition to the target steviol glycoside.

In another embodiment, the biocatalyst is one or more microbial cells comprising enzyme(s) capable of converting the starting composition to the target steviol glycoside. The enzyme can be located on the surface of the cell, inside the cell or located both on the surface of the cell and inside the cell.

Suitable enzymes for converting the starting composition to target steviol glycosides include, but are not limited to, the steviol biosynthesis enzymes, NDP-glucosyltransferases (NGTs), ADP-glucosyltransferases (AGTs), CDP-glucosyltransferases (CGTs), GDP-glucosyltransferases (GGTs), TDP-glucosyltransferases (TDPs), UDP-glucosyltransferases (UGTs). Optionally it may include NDP-recycling enzyme(s), ADP-recycling enzyme(s), CDP-recycling enzyme(s), GDP-recycling enzyme(s), TDP-recycling enzyme(s), and/or UDP-recycling enzyme(s).

In one embodiment, the steviol biosynthesis enzymes include mevalonate (MVA) pathway enzymes.

In another embodiment, the steviol biosynthesis enzymes include non-mevalonate 2-C-methyl-D-erythritol-4-phosphate pathway (MEP/DOXP) enzymes.

In one embodiment the steviol biosynthesis enzymes are selected from the group including geranylgeranyl diphosphate synthase, copalyl diphosphate synthase, kaurene synthase, kaurene oxidase, kaurenoic acid 13-hydroxylase (KAH), steviol synthetase, deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS), 1-hydroxy-2-methyl-2(E)-butenyl 4-diphosphate reductase (HDR), acetoacetyl-CoA thiolase, truncated HMG-CoA reductase, mevalonate kinase, phosphomevalonate kinase, mevalonate pyrophosphate decarboxylase, cytochrome P450 reductase etc.

The UDP-glucosyltransferase can be any UDP-glucosyltransferase capable of adding at least one glucose unit to steviol and/or a steviol glycoside substrate to provide the target steviol glycoside.

In one embodiment, steviol biosynthesis enzymes and UDP-glucosyltransferases are produced in a microbial cell. The microbial cell may be, for example, *E. coli, Saccharomyces* sp., *Aspergillus* sp., *Pichia* sp., *Bacillus* sp., *Yarrowia* sp. etc. In another embodiment, the UDP-glucosyltransferases are synthesized.

In one embodiment, the UDP-glucosyltransferase is selected from group including UGT74G1, UGT85C2, UGT76G1, UGT91D2, UGTSl2, EUGT11 and UGTs having substantial (>85%, >86%, >87%, >88%, >89%, >90%, >91%, >92%, >93%, >94%, >95%, >96%, >97%, >98%, >99%) amino-acid sequence identity to these polypeptides as well as isolated nucleic acid molecules that code for these UGTs.

In one embodiment, steviol biosynthesis enzymes, UGTs and UDP-glucose recycling system are present in one microorganism (microbial cell). The microorganism may be for example, *E. coli, Saccharomyces* sp., *Aspergillus* sp., *Pichia* sp., *Bacillus* sp., *Yarrowia* sp.

In one embodiment, the UDP-glucosyltransferase is any UDP-glucosyltransferase capable of adding at least one glucose unit to steviol or any starting steviol glycoside bearing an —OH functional group at C13 to give a target steviol glycoside having an —O-glucose beta glucopyranoside glycosidic linkage at C13. In a particular embodiment, the UDP-glucosyltransferase is UGT85C2, or a UGT having >85% amino-acid sequence identity with UGT85C2.

In another embodiment, the UDP-glucosyltransferase is any UDP-glucosyltransferase capable of adding at least one glucose unit to steviol or any starting steviol glycoside bearing a —COOH functional group at C19 to give a target steviol glycoside having a —COO-glucose beta-glucopyranoside glycosidic linkage at C19. In a particular embodiment, the UDP-glucosyltransferase is UGT74G1, or a UGT having >85% amino-acid sequence identity with UGT74G1.

In another embodiment, the UDP-glucosyltransferase is any UDP-glucosyltransferase capable of adding at least one glucose unit to any existing glucose on the C19 side of any starting steviol glycoside to give a target steviol glycoside with at least one additional glucose bearing at least one beta 1→2 glucopyranoside glycosidic linkage(s) at the newly formed glycosidic bond(s). In a particular embodiment, the UDP-glucosyltransferase is UGTSl2, or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to any existing glucose on the C19 side of any starting steviol glycoside to give a target steviol glycoside with at least one additional glucose bearing at least one beta 1→3 glucopyranoside glycosidic linkage(s) at the newly formed bond glycosidic bond(s). In a particular embodiment, the UDP-glucosyltransferase is UGT76G1, or a UGT having >85% amino-acid sequence identity with UGT76G1.

In another embodiment, the UDP-glucosyltransferase is any UDP-glucosyltransferase capable of adding at least one glucose unit to any existing glucose on the C19 side of any starting steviol glycoside to give a target steviol glycoside with at least one additional glucose bearing at least one beta 1→4 glucopyranoside glycosidic linkage(s) at the newly formed glycosidic bond(s). In a particular embodiment, the UDP-glucosyltransferase is UGTSl2, or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In another particular embodiment, the UDP-glucosyltransferase is UGT76G1, or a UGT having >85% amino-acid sequence identity with UGT76G1.

In another embodiment, the UDP-glucosyltransferase is any UDP-glucosyltransferase capable of adding at least one glucose unit to any existing glucose on the C19 side of any starting steviol glycoside to give a target steviol glycoside with at least one additional glucose bearing at least one beta 1→6 glucopyranoside glycosidic linkage(s) at the newly formed glycosidic bond(s). In a particular embodiment, the UDP-glucosyltransferase is UGTSl2, or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to any existing glucose on the C13 side of any starting steviol glycoside to give a target steviol glycoside with at least one additional glucose bearing at least one beta 1→2 glucopyranoside glycosidic linkage(s) at the newly formed glycosidic bond(s). In a particular embodiment, the UDP-glucosyltransferase is UGTSl2, or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to any existing glucose on the C13 side of any starting steviol glycoside to give a target steviol glycoside with at least one additional glucose bearing at least one beta 1→3 glucopyranoside glycosidic linkage(s) at the newly formed bond glycosidic bond(s). In a particular embodiment, the UDP-glucosyltransferase is UGT76G1, or a UGT having >85% amino-acid sequence identity with UGT76G1.

In another embodiment, the UDP-glucosyltransferase is any UDP-glucosyltransferase capable of adding at least one glucose unit to any existing glucose on the C13 side of any starting steviol glycoside to give a target steviol glycoside with at least one additional glucose bearing at least one beta 1→4 glucopyranoside glycosidic linkage(s) at the newly formed glycosidic bond(s). In a particular embodiment, the UDP-glucosyltransferase is UGTSl2, or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In another particular embodiment, the UDP-glucosyltransferase is UGT76G1, or a UGT having >85% amino-acid sequence identity with UGT76G1.

In another embodiment, the UDP-glucosyltransferase is any UDP-glucosyltransferase capable of adding at least one glucose unit to any existing glucose on the C13 side of any starting steviol glycoside to give a target steviol glycoside with at least one additional glucose bearing at least one beta 1→6 glucopyranoside glycosidic linkage(s) at the newly formed glycosidic bond(s). In a particular embodiment, the UDP-glucosyltransferase is UGTSl2, or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In one embodiment, the UDP-glucosyltransferase is any UDP-glucosyltransferase capable of adding at least one glucose unit to steviol to form steviolmonoside. In a particular embodiment, the UDP-glucosyltransferase is UGT85C2 or a UGT having >85% amino-acid sequence identity with UGT85C2 or a UGT having >85% amino-acid sequence identity with UGT85C2.

In another embodiment, the UDP-glucosyltransferase is any UDP-glucosyltransferase capable of adding at least one glucose unit to steviol to form steviolmonoside A. In a particular embodiment, the UDP-glucosyltransferase is UGT74G1 or a UGT having >85% amino-acid sequence identity with UGT74G1.

In another embodiment, the UDP-glucosyltransferase is any UDP-glucosyltransferase capable of adding at least one glucose unit to steviolmonoside to form steviolbioside. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to steviolmonoside to form steviolbioside D. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to steviolmonoside to form rubusoside. In a particular embodiment, the UDP-glucosyltransferase is UGT74G1 or a UGT having >85% amino-acid sequence identity with UGT74G1.

In one embodiment, the UDP-glucosyltransferase is any UDP-glucosyltransferase capable of adding at least one glucose unit to steviolmonoside A to form rubusoside. In a particular embodiment, the UDP-glucosyltransferase is UGT85C2 or a UGT having >85% amino-acid sequence identity with UGT85C2 or a UGT having >85% amino-acid sequence identity with UGT85C2.

In another embodiment, the UDP-glucosyltransferase is any UDP-glucosyltransferase capable of adding at least one glucose unit to steviolmonoside A to form steviolbioside A. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to steviolmonoside A to form steviolbioside B. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to steviolbioside to form rebaudioside B. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to steviolbioside to form stevioside. In a particular embodiment, the UDP-glucosyltransferase is UGT74G1 or a UGT having >85% amino-acid sequence identity with UGT74G1.

In another embodiment, the UDP-glucosyltransferase is any UDP-glucosyltransferase capable of adding at least one glucose unit to steviolbioside D to form rebaudioside B. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to steviolbioside D to form rebaudioside G. In a particular embodiment, the UDP-glucosyltransferase is UGT74G1 or a UGT having >85% amino-acid sequence identity with UGT74G1.

In another embodiment, the UDP-glucosyltransferase is any UDP-glucosyltransferase capable of adding at least one glucose unit to rubusoside to form stevioside. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rubusoside to form rebaudioside G. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rubusoside to form stevioside A. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rubusoside to form stevioside B. In a particular embodiment, the UDP-glucosyltransferase is UGT76G1 or a UGT having >85% amino-acid sequence identity with UGT76G1.

In one embodiment, the UDP-glucosyltransferase is any UDP-glucosyltransferase capable of adding at least one glucose unit to steviolbioside A to form stevioside A. In a particular embodiment, the UDP-glucosyltransferase is UGT85C2 or a UGT having >85% amino-acid sequence identity with UGT85C2 or a UGT having >85% amino-acid sequence identity with UGT85C2.

In another embodiment, the UDP-glucosyltransferase is any UDP-glucosyltransferase capable of adding at least one glucose unit to steviolbioside A to form stevioside C. In a particular embodiment, the UDP-glucosyltransferase is UGT76G1 or a UGT having >85% amino-acid sequence identity with UGT76G1.

In one embodiment, the UDP-glucosyltransferase is any UDP-glucosyltransferase capable of adding at least one glucose unit to steviolbioside B to form stevioside B. In a particular embodiment, the UDP-glucosyltransferase is UGT85C2 or a UGT having >85% amino-acid sequence identity with UGT85C2 or a UGT having >85% amino-acid sequence identity with UGT85C2.

In another embodiment, the UDP-glucosyltransferase is any UDP-glucosyltransferase capable of adding at least one glucose unit to steviolbioside B to form stevioside C. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside B to form rebaudioside A. In a particular embodiment, the UDP-glucosyltransferase is UGT74G1 or a UGT having >85% amino-acid sequence identity with UGT74G1.

In another embodiment, the UDP-glucosyltransferase is any UDP-glucosyltransferase capable of adding at least one glucose unit to stevioside to form rebaudioside A. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to stevioside to form rebaudioside E. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to stevioside to form rebaudioside E2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside G to form rebaudioside A. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside G to form rebaudioside E4. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside G to form rebaudioside E6. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to stevioside A to form rebaudioside E. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to stevioside A to form rebaudioside E4. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to stevioside A to form rebaudioside E3. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to stevioside B to form rebaudioside E2. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to stevioside B to form rebaudioside E6. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to stevioside B to form rebaudioside E3. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In one embodiment, the UDP-glucosyltransferase is any UDP-glucosyltransferase capable of adding at least one glucose unit to steviolbioside C to form rebaudioside E3. In a particular embodiment, the UDP-glucosyltransferase is UGT85C2 or a UGT having >85% amino-acid sequence identity with UGT85C2 or a UGT having >85% amino-acid sequence identity with UGT85C2.

In another embodiment, the UDP-glucosyltransferase is any UDP-glucosyltransferase capable of adding at least one glucose unit to rebaudioside A to form rebaudioside D. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside A to form rebaudioside I. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside E to form rebaudioside D. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside E to form rebaudioside AM. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside E2 to form rebaudioside 1. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside E2 to form rebaudioside AM. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside E4 to form rebaudioside D. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside E4 to form rebaudioside D7. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside E6 to form rebaudioside 1. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside E6 to form rebaudioside D7. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside E3 to form rebaudioside AM In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside E3 to form rebaudioside D7. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside D to form rebaudioside M. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside 1 to form rebaudioside M. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside AM to form rebaudioside M. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside AM to form rebaudioside M4. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside AM to form rebaudioside M5. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside D7 to form rebaudioside M. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1a. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1b. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1c. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransfer-ase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1d. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1e. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1f. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1g. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1h. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1i. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1j. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1k. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1l. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1m. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1n. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M to form rebaudioside 1o. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1p. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1q. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1r. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1s. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M to form rebaudioside 1t. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2a. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2b. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2c. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2d. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2e. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2f. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2g. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2h. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2i. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2j. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2k. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2l. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2m. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2n. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2.

In another embodiment, the UDP-glucosyltransferase is any UDP-glucosyltransferase capable of adding at least one glucose unit to rebaudioside M4 to form rebaudioside 2o. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2p. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2q. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2r. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 2s. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M4 to form rebaudioside 1q. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M5 to form rebaudioside 1m. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

In another embodiment, the UDP-glucosyltransferase is any UDP-glucosyltransferase capable of adding at least one glucose unit to rebaudioside M5 to form rebaudioside 2m. In a particular embodiment, the UDP-glucosyltransferase is UGTSl2 or a UGT having >85% amino-acid sequence identity with UGTSl2. In another particular embodiment, the UDP-glucosyltransferase is EUGT11, or a UGT having >85% amino-acid sequence identity with EUGT11. In yet another particular embodiment, the UDP-glucosyltransferase is UGT91D2, or a UGT having >85% amino-acid sequence identity with UGT91D2. In a particular embodiment, the UDP-glucosyltransferase is UGT76G1 or a UGT having >85% amino-acid sequence identity with UGT76G1.

Optionally, the method of the present invention further comprises recycling UDP to provide UDP-glucose. In one embodiment, the method comprises recycling UDP by providing a recycling catalyst and a recycling substrate, such that the biotransformation of steviol and/or the steviol glycoside substrate to the target steviol glycoside is carried out using catalytic amounts of UDP-glucosyltransferase and UDP-glucose.

In one embodiment, the recycling catalyst is sucrose synthase SuSy_At or a sucrose synthase having >85% amino-acid sequence identity with SuSy_At.

In one embodiment, the recycling substrate for UDP-glucose recycling catalyst is sucrose.

Optionally, the method of the present invention further comprises the use of transglycosidases that use oligo- or poly-saccharides as the sugar donor to modify recipient target steviol glycoside molecules. Non-limiting examples include cyclodextrin glycosyltransferase (CGTase), fructofuranosidase, amylase, saccharase, glucosucrase, beta-h-fructosidase, beta-fructosidase, sucrase, fructosylinvertase, alkaline invertase, acid invertase, fructofuranosidase. In some embodiments, glucose and sugar(s) other than glucose, including but not limited to fructose, xylose, rhamnose, arabinose, deoxyglucose, galactose are transferred to the recipient target steviol glycosides. In one embodiment, the recipient steviol glycoside is rebaudioside 1a, rebaudioside 1b, rebaudioside 1c, rebaudioside 1d rebaudioside 1e, rebaudioside t; rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f; rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, and/or rebaudioside 2s. In another embodiment, the recipient steviol glycoside is rebaudioside M4. In another embodiment, the recipient steviol glycoside is rebaudioside M5. In another embodiment, the recipient steviol glycoside is SvG7.

In another embodiment, the UDP-glucosyltransferase capable of adding at least one glucose unit to starting composition steviol glycoside has >85% amino-acid sequence identity with UGTs selected from the following listing of GenInfo identifier numbers, preferably from the group presented in Table 1, and Table 2.

| | | | | | |
|---|---|---|---|---|---|
| 397567 | 30680413 | 115480946 | 147798902 | 218193594 | 225443294 |
| 454245 | 32816174 | 116310259 | 147811764 | 218193942 | 225444853 |
| 1359905 | 32816178 | 116310985 | 147827151 | 219885307 | 225449296 |
| 1685003 | 34393978 | 116788066 | 147836230 | 222615927 | 225449700 |
| 1685005 | 37993665 | 116788606 | 147839909 | 222619587 | 225454338 |
| 2191136 | 37993671 | 116789315 | 147846163 | 222623142 | 225454340 |
| 2501497 | 37993675 | 119394507 | 147855977 | 222625633 | 225454342 |
| 2911049 | 39104603 | 119640480 | 148905778 | 222625635 | 225454473 |
| 4218003 | 41469414 | 122209731 | 148905999 | 222636620 | 225454475 |
| 4314356 | 41469452 | 125526997 | 148906835 | 222636621 | 225458362 |
| 13492674 | 42566366 | 125534279 | 148907340 | 222636628 | 225461551 |
| 13492676 | 42570280 | 125534461 | 148908935 | 222636629 | 225461556 |
| 15217773 | 42572855 | 125540090 | 148909182 | 224053242 | 225461558 |
| 15217796 | 44890129 | 125541516 | 148909920 | 224053386 | 225469538 |
| 15223396 | 46806235 | 125545408 | 148910082 | 224055535 | 225469540 |
| 15223589 | 50284482 | 125547340 | 148910154 | 224056138 | 226316457 |
| 15227766 | 51090402 | 125547520 | 148910612 | 224056160 | 226492603 |
| 15230017 | 51090594 | 125554547 | 148910769 | 224067918 | 226494221 |
| 15231757 | 52839682 | 125557592 | 156138791 | 224072747 | 226495389 |
| 15234056 | 56550539 | 125557593 | 156138797 | 224080189 | 226495945 |
| 15234195 | 62734263 | 125557608 | 156138799 | 224091845 | 226502400 |
| 15234196 | 62857204 | 125559566 | 156138803 | 224094703 | 226507980 |
| 15238503 | 62857206 | 125563266 | 165972256 | 224100653 | 226531147 |
| 15239523 | 62857210 | 125571055 | 168016721 | 224100657 | 226532094 |
| 15239525 | 62857212 | 125579728 | 171674071 | 224101569 | 238477377 |
| 15239543 | 75265643 | 125588307 | 171906258 | 224103105 | 240254512 |
| 15239937 | 75285934 | 125589492 | 183013901 | 224103633 | 242032615 |
| 15240305 | 75288884 | 125599469 | 183013903 | 224103637 | 242032621 |
| 15240534 | 77550661 | 125601477 | 186478321 | 224109218 | 242038423 |
| 15982889 | 77556148 | 126635837 | 187373030 | 224114583 | 242043290 |
| 18086351 | 82791223 | 126635845 | 187373042 | 224116284 | 242044836 |
| 18418378 | 83778990 | 126635847 | 190692175 | 224120552 | 242051252 |
| 18418380 | 89953335 | 126635863 | 194701936 | 224121288 | 242056217 |
| 18418382 | 110741436 | 126635867 | 195620060 | 224121296 | 242056219 |
| 19743740 | 110743955 | 126635883 | 209954691 | 224121300 | 242056663 |
| 19911201 | 115438196 | 126635887 | 209954719 | 224130358 | 242059339 |
| 20149064 | 115438785 | 133874210 | 209954725 | 224140703 | 242059341 |
| 20260654 | 115441237 | 133874212 | 209954733 | 224143404 | 242060922 |
| 21435782 | 115454819 | 145358033 | 210063105 | 224143406 | 242067411 |
| 21553613 | 115456047 | 147772508 | 210063107 | 224144306 | 242067413 |
| 21593514 | 115457492 | 147776893 | 212275846 | 224285244 | 242076258 |
| 22759895 | 115459312 | 147776894 | 216296854 | 225431707 | 242076396 |
| 23955910 | 115464719 | 147776895 | 217074506 | 225435532 | 242084750 |
| 26452040 | 115471069 | 147786916 | 218185693 | 225436321 | 242091005 |
| 28393204 | 115471071 | 147798900 | 218187075 | 225440041 | 242095206 |
| 30679796 | 115474009 | 147798901 | 218189427 | 225441116 | 242345159 |
| 242345161 | 297724601 | 326492035 | 356523945 | 357140904 | 359486938 |
| 255536859 | 297725463 | 326493430 | 356523957 | 357165849 | 359487055 |
| 255538228 | 297728331 | 326500410 | 356523959 | 357165852 | 359488135 |
| 255541676 | 297738632 | 326506816 | 356523961 | 357168415 | 359488708 |
| 255547075 | 297745347 | 326507826 | 356523963 | 357437837 | 359493630 |
| 255552620 | 297745348 | 326508394 | 356524387 | 357442755 | 359493632 |
| 255552622 | 297795735 | 326509445 | 356524403 | 357442757 | 359493634 |
| 255555343 | 297796253 | 326511261 | 356527181 | 357445729 | 359493636 |
| 255555361 | 297796257 | 326511866 | 356533209 | 357445731 | 359493815 |
| 255555363 | 297796261 | 326512412 | 356533852 | 357445733 | 359495856 |
| 255555365 | 297797587 | 326517673 | 356534718 | 357446799 | 359495858 |
| 255555369 | 297798502 | 326518800 | 356535480 | 357446805 | 359495869 |
| 255555373 | 297799226 | 326521124 | 356542996 | 357452779 | 359495871 |
| 255555377 | 297805988 | 326525567 | 356543136 | 357452781 | 359497638 |
| 255556812 | 297807499 | 326525957 | 356543932 | 357452783 | 359807261 |
| 255556818 | 297809125 | 326526607 | 356549841 | 357452787 | 374256637 |
| 255563008 | 297809127 | 326527141 | 356549843 | 357452789 | 377655465 |
| 255564074 | 297811403 | 326530093 | 356554358 | 357452791 | 378405177 |
| 255564531 | 297820040 | 326534036 | 356554360 | 357452797 | 378829085 |
| 255572878 | 297821483 | 326534123 | 356558606 | 357452799 | 387135070 |
| 255577901 | 297825217 | 332071132 | 356560333 | 357470367 | 387135072 |
| 255583249 | 297832276 | 339715876 | 356560599 | 357472193 | 387135078 |
| 255583253 | 297832280 | 342306012 | 356560749 | 357472195 | 387135092 |
| 255583255 | 297832518 | 342306016 | 356566018 | 357474295 | 387135094 |
| 255585664 | 297832520 | 343457675 | 356566169 | 357474493 | 387135098 |
| 255585666 | 297840825 | 343457677 | 356566173 | 357474497 | 387135100 |
| 255634688 | 297840827 | 350534960 | 356567761 | 357474499 | 387135134 |
| 255644801 | 297847402 | 356498085 | 356574704 | 357490035 | 387135136 |
| 255645821 | 297849372 | 356499771 | 356576401 | 357493567 | 387135174 |

-continued

| | | | | | |
|---|---|---|---|---|---|
| 255647456 | 300078590 | 356499777 | 356577660 | 357497139 | 387135176 |
| 255648275 | 300669727 | 356499779 | 357114993 | 357497581 | 387135184 |
| 260279126 | 302142947 | 356501328 | 357115447 | 357497671 | 387135186 |
| 260279128 | 302142948 | 356502523 | 357115451 | 357500579 | 387135188 |
| 261343326 | 302142950 | 356503180 | 357115453 | 357504663 | 387135190 |
| 283132367 | 302142951 | 356503184 | 357116080 | 357504691 | 387135192 |
| 283362112 | 302765302 | 356503295 | 357116928 | 357504699 | 387135194 |
| 289188052 | 302796334 | 356504436 | 357117461 | 357504707 | 387135282 |
| 295841350 | 302811470 | 356504523 | 357117463 | 357505859 | 387135284 |
| 296088529 | 302821107 | 356504765 | 357117829 | 357510851 | 387135294 |
| 296090415 | 302821679 | 356511113 | 357117839 | 357516975 | 387135298 |
| 296090524 | 319759260 | 356515120 | 357125059 | 359477003 | 387135300 |
| 296090526 | 319759266 | 356517088 | 357126015 | 359477998 | 387135302 |
| 297599503 | 320148814 | 356520732 | 357134488 | 359478043 | 387135304 |
| 297601531 | 326489963 | 356522586 | 357135657 | 359478286 | 387135312 |
| 297611791 | 326490273 | 356522588 | 357138503 | 359484299 | 387135314 |
| 297722841 | 326491131 | 356522592 | 357139683 | 359486936 | 387135316 |
| 387135318 | 449440433 | 460376293 | 460413408 | 462423864 | 475546199 |
| 387135320 | 449445896 | 460378310 | 460416351 | 470101924 | 475556485 |
| 387135322 | 449446454 | 460380744 | 462394387 | 470102280 | 475559699 |
| 387135324 | 449447657 | 460381726 | 462394433 | 470102858 | 475578293 |
| 387135326 | 449449002 | 460382093 | 462394557 | 470104211 | 475591753 |
| 387135328 | 449449004 | 460382095 | 462395646 | 470104264 | 475593742 |
| 388493506 | 449449006 | 460382754 | 462395678 | 470104266 | 475612072 |
| 388495496 | 449451379 | 460384935 | 462396388 | 470106317 | 475622476 |
| 388498446 | 449451589 | 460384937 | 462396389 | 470106357 | 475622507 |
| 388499220 | 449451591 | 460385076 | 462396419 | 470115448 | 475623787 |
| 388502176 | 449451593 | 460385872 | 462396542 | 470130404 | 482550481 |
| 388517521 | 449453712 | 460386018 | 462397507 | 470131550 | 482550499 |
| 388519407 | 449453714 | 460389217 | 462399998 | 470136482 | 482550740 |
| 388521413 | 449453716 | 460394872 | 462400798 | 470136484 | 482550999 |
| 388827901 | 449453732 | 460396139 | 462401217 | 470136488 | 482552352 |
| 388827903 | 449457075 | 460397862 | 462402118 | 470136492 | 482554970 |
| 388827907 | 449467555 | 460397864 | 462402237 | 470137933 | 482555336 |
| 388827909 | 449468742 | 460398541 | 462402284 | 470137937 | 482555478 |
| 388827913 | 449495638 | 460403139 | 462402416 | 470140422 | 482556454 |
| 393887637 | 449495736 | 460403141 | 462404228 | 470140426 | 482557289 |
| 393887646 | 449499880 | 460403143 | 462406358 | 470140908 | 482558462 |
| 393887649 | 449502786 | 460403145 | 462408262 | 470141232 | 482558508 |
| 393990627 | 449503471 | 460405998 | 462409325 | 470142008 | 482558547 |
| 397746860 | 449503473 | 460407578 | 462409359 | 470142010 | 482561055 |
| 397789318 | 449515807 | 460407900 | 462409777 | 470142012 | 482561555 |
| 413924864 | 449518643 | 460409128 | 462411467 | 470143607 | 482562795 |
| 414590349 | 449519559 | 460409134 | 462414311 | 470143939 | 482562850 |
| 414590661 | 449522783 | 460409136 | 462414416 | 470145404 | 482565074 |
| 414591157 | 449524530 | 460409459 | 462414476 | 473923244 | 482566269 |
| 414879558 | 449524591 | 460409461 | 462415526 | 474114354 | 482566296 |
| 414879559 | 449528823 | 460409463 | 462415603 | 474143634 | 482566307 |
| 414879560 | 449528825 | 460409465 | 462415731 | 474202268 | 482568689 |
| 414888074 | 449534021 | 460409467 | 462416307 | 474299266 | 482570049 |
| 431812559 | 460365546 | 460410124 | 462416920 | 474363119 | 482570572 |
| 449432064 | 460366882 | 460410126 | 462416922 | 474366157 | 482575121 |
| 449432066 | 460369823 | 460410128 | 462416923 | 474429346 | |
| 449433069 | 460369829 | 460410130 | 462416924 | 475432777 | |
| 449436944 | 460369831 | 460410132 | 462417401 | 475473002 | |
| 449438665 | 460369833 | 460410134 | 462419769 | 475489790 | |
| 449438667 | 460370755 | 460410213 | 462420317 | 475511330 | |
| 449440431 | 460374714 | 460411200 | 462423366 | 475516200 | |

TABLE 1

| GI number | Accession | Origin |
|---|---|---|
| 190692175 | ACE87855.1 | *Stevia rebaudiana* |
| 41469452 | AAS07253.1 | *Oryza sativa* |
| 62857204 | BAD95881.1 | *Ipomoea nil* |
| 62857206 | BAD95882.1 | *Ipomoea purperea* |
| 56550539 | BAD77944.1 | *Bellis perennis* |
| 115454819 | NP_001051010.1 | *Oryza saliva Japonica* Group |
| 115459312 | NP_001053256.1 | *Oryza saliva Japonica* Group |
| 115471069 | NP_001059133.1 | *Oryza saliva Japonica* Group |
| 115471071 | NP_001059134.1 | *Oryza saliva Japonica* Group |
| 116310985 | CAH67920.1 | *Oryza saliva Indica* Group |
| 116788066 | ABK24743.1 | *Picea sitchensis* |
| 122209731 | Q2V6J9.1 | *Fragaria × ananassa* |
| 125534461 | EAY81009.1 | *Oryza saliva Indica* Group |
| 125559566 | EAZ05102.1 | *Oryza saliva Indica* Group |

TABLE 1-continued

| GI number | Accession | Origin |
|---|---|---|
| 125588307 | EAZ28971.1 | *Oryza saliva Japonica* Group |
| 148907340 | ABR16806.1 | *Picea sitchensis* |
| 148910082 | ABR18123.1 | *Picea sitchensis* |
| 148910612 | ABR18376.1 | *Picea sitchensis* |
| 15234195 | NP_194486.1 | *Arabidopsis thaliana* |
| 15239523 | NP_200210.1 | *Arabidopsis thaliana* |
| 15239937 | NP_196793.1 | *Arabidopsis thaliana* |
| 1685005 | AAB36653.1 | *Nicotiana tabacum* |
| 183013903 | ACC38471.1 | *Medicago truncatula* |
| 186478321 | NP_172511.3 | *Arabidopsis thaliana* |
| 187373030 | ACD03249.1 | *Avena strigosa* |
| 194701936 | ACF85052.1 | *Zea mays* |
| 19743740 | AAL92461.1 | *Solanum lycopersicum* |
| 212275846 | NP 001131009.1 | *Zea mays* |
| 222619587 | EEE55719.1 | *Oryza saliva Japonica* Group |
| 224055535 | XP_002298527.1 | *Populus trichocarpa* |
| 224101569 | XP_002334266.1 | *Populus trichocarpa* |
| 224120552 | XP_002318358.1 | *Populus trichocarpa* |
| 224121288 | XP_002330790.1 | *Populus trichocarpa* |
| 225444853 | XP_002281094 | *Vitis vinifera* |
| 225454342 | XP_002275850.1 | *Vitis vinifera* |
| 225454475 | XP_002280923.1 | *Vitis vinifera* |
| 225461556 | XP_002285222 | *Vitis vinifera* |
| 225469540 | XP_002270294.1 | *Vitis vinifera* |
| 226495389 | NP_001148083.1 | *Zea mays* |
| 226502400 | NP_001147674.1 | *Zea mays* |
| 238477377 | ACR43489.1 | *Triticum aestivum* |
| 240254512 | NP 565540.4 | *Arabidopsis thaliana* |
| 2501497 | Q43716.1 | *Petunia × hybrida* |
| 255555369 | XP_002518721.1 | *Ricinus communis* |
| 26452040 | BAC43110.1 | *Arabidopsis thaliana* |
| 296088529 | CBI37520.3 | *Vitis vinifera* |
| 297611791 | NP_001067852.2 | *Oryza saliva Japonica* Group |
| 297795735 | XP_002865752.1 | *Arabidopsis lyrata* subsp. *lyrata* |
| 297798502 | XP_002867135.1 | *Arabidopsis lyrata* subsp. *lyrata* |
| 297820040 | XP_002877903.1 | *Arabidopsis lyrata* subsp. *lyrata* |
| 297832276 | XP_002884020.1 | *Arabidopsis lyrata* subsp. *lyrata* |
| 302821107 | XP_002992218.1 | *Selaginella moellendorffti* |
| 30680413 | NP_179446.2 | *Arabidopsis thaliana* |
| 319759266 | ADV71369.1 | *Pueraria montana* var. *lobata* |
| 326507826 | BAJ86656.1 | *Hordeum vulgare* subsp. *Vulgare* |
| 343457675 | AEM37036.1 | *Brassica rapa* subsp. *oleifera* |
| 350534960 | NP_001234680.1 | *Solanum lycopersicum* |
| 356501328 | XP_003519477.1 | *Glycine max* |
| 356522586 | XP_003529927.1 | *Glycine max* |
| 356535480 | XP_003536273.1 | *Glycine max* |
| 357445733 | XP_003593144.1 | *Medicago truncatula* |
| 357452783 | XP_003596668.1 | *Medicago truncatula* |
| 357474493 | XP_003607531.1 | *Medicago truncatula* |
| 357500579 | XP_003620578.1 | *Medicago truncatula* |
| 357504691 | XP_003622634.1 | *Medicago truncatula* |
| 359477998 | XP_003632051.1 | *Vitis vinifera* |
| 359487055 | XP_002271587 | *Vitis vinifera* |
| 359495869 | XP_003635104.1 | *Vitis vinifera* |
| 387135134 | AFJ52948.1 | *Linum usitatissimum* |
| 387135176 | AFJ52969.1 | *Linum usitatissimum* |
| 387135192 | AFJ52977.1 | *Linum usitatissimum* |
| 387135282 | AFJ53022.1 | *Linum usitatissimum* |
| 387135302 | AFJ53032.1 | *Linum usitatissimum* |
| 387135312 | AFJ53037.1 | *Linum usitatissimum* |
| 388519407 | AFK47765.1 | *Medicago truncatula* |
| 393887646 | AFN26668.1 | *Barbarea vulgaris* subsp. *arcuata* |
| 414888074 | DAA64088.1 | *Zea mays* |
| 42572855 | NP_974524.1 | *Arabidopsis thaliana* |
| 449440433 | XP_004137989.1 | *Cucumis sativus* |
| 449446454 | XP_004140986.1 | *Cucumis sativus* |
| 449449004 | XP_004142255.1 | *Cucumis sativus* |
| 449451593 | XP_004143546.1 | *Cucumis sativus* |
| 449515857 | XP_004164964.1 | *Cucumis sativus* |
| 460382095 | XP_004236775.1 | *Solanum lycopersicum* |
| 460409128 | XP_004249992.1 | *Solanum lycopersicum* |
| 460409461 | XP_004250157.1 | *Solanum lycopersicum* |
| 460409465 | XP_004250159.1 | *Solanum lycopersicum* |
| 462396388 | EMJ02187.1 | *Prunus persica* |
| 462402118 | EMJ07675.1 | *Prunus persica* |
| 462409359 | EMJ14693.1 | *Prunus persica* |
| 462416923 | EMJ21660.1 | *Prunus persica* |
| 46806235 | BAD17459.1 | *Oryza sativa Japonica* Group |
| 470104266 | XP_004288529.1 | *Fragaria vesca* subsp. *vesca* |
| 470142008 | XP_004306714.1 | *Fragaria vesca* subsp. *vesca* |
| 475432777 | EMT01232.1 | *Aegilops tauschii* |
| 51090402 | BAD35324.1 | *Oryza sativa Japonica* Group |

TABLE 2

| GI number | Accession | Origin | Internal reference |
|---|---|---|---|
| 460409128 | XP.004249992.1 | *Solatium lycopersicum* | UGTS1 |
| 460386018 | XP.004238697.1 | *Solanum lycopersicum* | — |
| 460409134 | XP.004249995.1 | *Solanum lycopersicum* | — |
| 460410132 | XP.004250485.1 | *Solanum lycopersicum* | UGTS12 |
| 460410130 | XP.004250484.1 | *Solanum lycopersicum* | — |
| 460410128 | XP.004250483.1 | *Solanum lycopersicum* | — |
| 460378310 | XP.004234916.1 | *Solanum lycopersicum* | — |
| 209954733 | BAG80557.1 | *Lycium barbarum* | UGTLB |
| 209954725 | BAG80553.1 | *Lycium barbarum* | — |

One embodiment of the present invention is a microbial cell comprising an enzyme, i.e. an enzyme capable of converting the starting composition to the target steviol glycoside. Accordingly, some embodiments of the present method include contacting a microorganism with a medium containing the starting composition to provide a medium comprising at least one target steviol glycoside.

The microorganism can be any microorganism possessing the necessary enzyme(s) for converting the starting composition to target steviol glycoside(s). These enzymes are encoded within the microorganism's genome.

Suitable microorganisms include, but are not limited to, *E. coli*, *Saccharomyces* sp., *Aspergillus* sp., *Pichia* sp., *Bacillus* sp., *Yarrowia* sp. etc.

In one embodiment, the microorganism is free when contacted with the starting composition.

In another embodiment, the microorganism is immobilized when contacted with the starting composition. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

In still another embodiment, the enzyme capable of converting the starting composition to the target steviol glycoside is secreted out of the microorganism and into the reaction medium.

The target steviol glycoside is optionally purified. Purification of the target steviol glycoside from the reaction medium can be achieved by at least one suitable method to provide a highly purified target steviol glycoside composition. Suitable methods include crystallization, separation by membranes, centrifugation, extraction (liquid or solid phase), chromatographic separation, HPLC (preparative or analytical) or a combination of such methods.

Uses

Highly purified target glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 obtained according to this invention can be used "as-is" or in combination with other sweeteners, flavors, food ingredients and combinations thereof. Non-limiting examples of flavors include, but are not limited to, lime, lemon, orange, fruit, banana, grape, pear, pineapple, mango, berry, bitter almond, cola, cinnamon, sugar, cotton candy, vanilla and combinations thereof.

Non-limiting examples of other food ingredients include, but are not limited to, acidulants, organic and amino acids, coloring agents, bulking agents, modified starches, gums, texturizers, preservatives, caffeine, antioxidants, emulsifiers, stabilizers, thickeners, gelling agents and combinations thereof.

Highly purified target glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 obtained according to this invention can be prepared in various polymorphic forms, including but not limited to hydrates, solvates, anhydrous, amorphous forms and combinations thereof.

Highly purified target glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 obtained according to this invention may be incorporated as a high intensity natural sweetener in foodstuffs, beverages, pharmaceutical compositions, cosmetics, chewing gums, table top products, cereals, dairy products, toothpastes and other oral cavity compositions, etc.

In some embodiments, the highly purified target glycoside(s) of present invention are present in foodstuffs, beverages, pharmaceutical compositions, cosmetics, chewing gums, table top products, cereals, dairy products, toothpastes and other oral cavity compositions, etc in an amount from about 0.0001% to about 12% by weight, such as, for example, about 0.0001% by weight, about 0.0005% by weight, about 0.001% by weight, about 0.005% by weight, about 0.01% by weight, about 0.05% by weight, about 0.1% by weight, about 0.5% by weight, about 1.0% by weight, about 1.5% by weight, about 2.0% by weight, about 2.5% by weight, about 3.0% by weight, about 3.5% by weight, about 4.0% by weight, about 4.5% by weight, about 5.0% by weight, about 5.5% by weight, about 6.0% by weight, about 6.5% by weight, about 7.0% by weight, about 7.5% by weight, about 8.0% by weight, about 8.5% by weight, about 9.0% by weight, about 9.5% by weight, about 10.0% by weight, about 10.5% by weight, about 11.0% by weight, about 11.5% by weight or about 12.0% by weight.

In a particular embodiment, the sweetener is present in the beverage in an amount from about 0.0001% by weight to about 8% by weight, such as for example, from about 0.0001% by weight to about 0.0005% by weight, from about 0.0005% by weight to about 0.001% by weight, from about 0.001% by weight to about 0.005% by weight, from about 0.005% by weight to about 0.01% by weight, from about 0.01% by weight to about 0.05% by weight, from about 0.05% by weight to about 0.1% by weight, from about 0.1% by weight to about 0.5% by weight, from about 0.5% by weight to about 1% by weight, from about 1% by weight to about 2% by weight, from about 2% by weight to about 3% by weight, from about 3% by weight to about 4% by weight, from about 4% by weight to about 5% by weight, from about 5% by weight to about 6% by weight, from about 6% by weight to about 7% by weight, and from about 7% by weight to about 8% by weight.

Highly purified target glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s SvG7 and/or combinations thereof, obtained according to this invention, may be employed as a sweetening compound, or it may be used together with at least one naturally occurring high intensity sweeteners such as dulcoside A, dulcoside B, dulcoside C, dulcoside D, rebaudioside A2, rebaudioside A3, rebaudioside A4, rebaudioside B2, rebaudioside C, rebaudioside C2, rebaudioside C3, rebaudioside C4, rebaudioside C5, rebaudioside C6, rebaudioside D2, rebaudioside D3, rebaudioside D4, rebaudioside D5, rebaudioside D6, rebaudioside D8, rebaudioside E5, rebaudioside E7, rebaudioside F, rebaudioside F2, rebaudioside F3, rebaudioside H, rebaudioside H2, rebaudioside H3, rebaudioside H4, rebaudioside H5, rebaudioside H6, rebaudioside I2, rebaudioside I3, rebaudioside J, rebaudioside K, rebaudioside K2, rebaudioside KA, rebaudioside L, rebaudioside M2, rebaudioside M3, rebaudioside N, rebaudioside N2, rebaudioside N3, rebaudioside N4, rebaudioside N5, rebaudioside O, rebaudioside O2, rebaudioside O3, rebaudioside O4, rebaudioside Q, rebaudioside Q2, rebaudioside Q3, rebaudioside R, rebaudioside S, rebaudioside T, rebaudioside TI, rebaudioside U, rebaudioside U2, rebaudioside V, rebaudioside V2, rebaudioside V3, rebaudioside W, rebaudioside W2, rebaudioside W3, rebaudioside Y, rebaudioside Z1, rebaudioside Z2, steviolbioside C, steviolbioside E, stevioside D, stevioside E, stevioside E2, stevioside F, stevioside G, stevioside H, mogrosides, brazzein, neohesperidin dihydrochalcone, glycyrrhizic acid and its salts, thaumatin, perillartine, pernandulcin, mukuroziosides, baiyunoside, phlomisoside-I, dimethyl-hexahydro-fluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin, monatin salts, other indole derivative sweeteners, selligueain A, hematoxylin, monellin, osladin, pterocaryoside A, pterocaryoside B, mabinlin, pentadin, miraculin, curculin, neoculin, chlorogenic acid, cynarin, Luo Han Guo sweetener, mogroside V, siamenoside, siratose and combinations thereof.

In a particular embodiment, steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside 1, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 can be used in a sweetener composition comprising a compound selected from the group consisting of dulcoside A, dulcoside B, dulcoside C, dulcoside D, rebaudioside A2, rebaudioside A3, rebaudioside A4, rebaudioside B2, rebaudioside C, rebaudioside C2, rebaudioside C3, rebaudioside C4, rebaudioside C5, rebaudioside C6, rebaudioside D2, rebaudioside D3, rebaudioside D4, rebaudioside D5, rebaudioside D6, rebaudioside D8, rebaudioside E5, rebaudioside E7, rebaudioside F, rebaudioside F2, rebaudioside F3, rebaudioside H, rebaudioside H2, rebaudioside H3, rebaudioside H4, rebaudioside H5, rebaudioside H6, rebaudioside 12, rebaudioside 13, rebaudioside J, rebaudioside K, rebaudioside K2, rebaudioside KA, rebaudioside L, rebaudioside M2, rebaudioside M3, rebaudioside N, rebaudioside N2, rebaudioside N3, rebaudioside N4, rebaudioside N5, rebaudioside O, rebaudioside O2, rebaudioside O3, rebaudioside O4, rebaudioside Q, rebaudioside Q2, rebaudioside Q3, rebaudioside R, rebaudioside S, rebaudioside T, rebaudioside TI, rebaudioside U, rebaudioside U2, rebaudioside V, rebaudioside V2, rebaudioside V3, rebaudioside W, rebaudioside W2, rebaudioside W3, rebaudioside Y, rebaudioside Z1, rebaudioside Z2, steviolbioside C, steviolbioside E, stevioside D, stevioside E, stevioside E2, stevioside F, stevioside G, stevioside H, NSF-02, Mogroside V, siratose, Luo Han Guo, allulose, allose, D-tagatose, erythritol and combinations thereof.

Highly purified target glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 may also be used in combination with synthetic high intensity sweeteners such as sucralose, potassium acesulfame, aspartame, alitame, saccharin, neohesperidin dihydrochalcone, cyclamate, neotame, dulcin, suosan advantame, salts thereof, and combinations thereof.

Moreover, highly purified target steviol glycoside(s) particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 can be used in combination with natural sweetener suppressors such as gymnemic acid, hodulcin, ziziphin, lactisole, and others. Steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 may also be combined with various umami taste enhancers. Steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 can be mixed with umami tasting and sweet amino acids such as glutamate, aspartic acid, glycine, alanine, threonine, proline, serine, glutamate, lysine, tryptophan and combinations thereof.

Highly purified target steviol glycoside(s) particularly, steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 can be used in combination with one or more additive selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

Highly purified target steviol glycoside(s) particularly, steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 may be combined with polyols or sugar alcohols. The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced which do not adversely affect the taste of the sweetener composition.

Highly purified target steviol glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 may be combined with reduced calorie sweeteners such as, for example, D-tagatose, L-sugars, L-sorbose, L-arabinose and combinations thereof.

Highly purified target steviol glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 may also be combined with various carbohydrates. The term "carbohydrate" generally refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, psicose, turanose, allose, tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

Highly purified target steviol glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 obtained according to this invention can be used in combination with various physiologically active substances or functional ingredients. Functional ingredients generally are classified into categories such as carotenoids, dietary fiber, fatty acids, saponins, antioxidants, nutraceuticals, flavonoids, isothiocyanates, phenols, plant sterols and stanols (phytosterols and phytostanols); polyols; prebiotics, probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory. Exemplary functional ingredients are provided in WO2013/096420, the contents of which is hereby incorporated by reference.

Highly purified target steviol glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 obtained according to this invention may be applied as a high intensity sweetener to produce zero calorie, reduced calorie or diabetic beverages and food products with improved taste characteristics. It may also be used in drinks, foodstuffs, pharmaceuticals, and other products in which sugar cannot be used. In addition, highly purified target steviol glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 can be used as a sweetener not only for drinks, foodstuffs, and other products dedicated for human consumption, but also in animal feed and fodder with improved characteristics.

Highly purified target steviol glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 obtained according to this invention may be applied as a foaming suppressor to produce zero calorie, reduced calorie or diabetic beverages and food products.

Examples of consumable products in which highly purified target steviol glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside 1, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 may be used as a sweetening compound include, but are not limited to, alcoholic beverages such as vodka, wine, beer, liquor, and sake, etc.; natural juices; refreshing drinks; carbonated soft drinks; diet drinks; zero calorie drinks; reduced calorie drinks and foods; yogurt drinks; instant juices; instant coffee; powdered types of instant beverages; canned products; syrups; fermented soybean paste; soy sauce; vinegar; dressings; mayonnaise; ketchups; curry; soup; instant bouillon; powdered soy sauce; powdered vinegar; types of biscuits; rice biscuit; crackers; bread; chocolates; caramel; candy; chewing gum; jelly; pudding; preserved fruits and vegetables; fresh cream; jam; marmalade; flower paste; powdered milk; ice cream; sorbet; vegetables and fruits packed in bottles; canned and boiled beans; meat and foods boiled in sweetened sauce; agricultural vegetable food products; seafood; ham; sausage; fish ham; fish sausage; fish paste; deep fried fish products; dried seafood products; frozen food products; preserved seaweed; preserved meat; tobacco; medicinal products; and many others. In principle it can have unlimited applications.

Examples of consumable products in which highly purified target steviol glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside 1, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 may be used as a flavor modifier or flavor with modifying properties include, but are not limited to, alcoholic beverages such as vodka, wine, beer, liquor, and sake, etc.; natural juices; refreshing drinks; carbonated soft drinks; diet drinks; zero calorie drinks; reduced calorie drinks and foods; yogurt drinks; instant juices; instant coffee; powdered types of instant beverages; canned products; syrups; fermented soybean paste; soy sauce; vinegar; dressings; mayonnaise; ketchups; curry; soup; instant bouillon; powdered soy sauce; powdered vinegar; types of biscuits; rice biscuit; crackers; bread; chocolates; caramel; candy; chewing gum; jelly; pudding; preserved fruits and vegetables; fresh cream; jam; marmalade; flower paste; powdered milk; ice cream; sorbet; vegetables and fruits packed in bottles; canned and boiled beans; meat and foods boiled in sweetened sauce; agricultural vegetable food products; seafood; ham; sausage; fish ham; fish sausage; fish paste; deep fried fish products; dried seafood products; frozen food products; preserved seaweed; preserved meat; tobacco; medicinal products; and many others. In principle it can have unlimited applications.

During the manufacturing of products such as foodstuffs, drinks, pharmaceuticals, cosmetics, table top products, and chewing gum, the conventional methods such as mixing, kneading, dissolution, pickling, permeation, percolation, sprinkling, atomizing, infusing and other methods may be used.

Moreover, the highly purified target steviol glycoside(s) steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 obtained in this invention may be used in dry or liquid forms.

The highly purified target steviol glycoside can be added before or after heat treatment of food products. The amount of the highly purified target steviol glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 depends on the purpose of usage. As discussed above, it can be added alone or in combination with other compounds.

The present invention is also directed to sweetness enhancement in beverages using steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 as a sweetness enhancer, wherein steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 is present in a concentration at or below their respective sweetness recognition thresholds.

As used herein, the term "sweetness enhancer" refers to a compound capable of enhancing or intensifying the perception of sweet taste in a composition, such as a beverage. The term "sweetness enhancer" is synonymous with the terms "sweet taste potentiator," "sweetness potentiator," "sweetness amplifier," and "sweetness intensifier."

The term "sweetness recognition threshold concentration," as generally used herein, is the lowest known concentration of a sweet compound that is perceivable by the human sense of taste, typically around 1.0% sucrose equivalence (1.0% SE). Generally, the sweetness enhancers may enhance or potentiate the sweet taste of sweeteners without providing any noticeable sweet taste by themselves when present at or below the sweetness recognition threshold concentration of a given sweetness enhancer; however, the sweetness enhancers may themselves provide sweet taste at concentrations above their sweetness recognition threshold concentration. The sweetness recognition threshold concentration is specific for a particular enhancer and can vary based on the beverage matrix. The sweetness recognition threshold concentration can be easily determined by taste testing increasing concentrations of a given enhancer until greater than 1.0% sucrose equivalence in a given beverage matrix is detected. The concentration that provides about 1.0% sucrose equivalence is considered the sweetness recognition threshold.

In some embodiments, sweetener is present in the beverage in an amount from about 0.0001% to about 12% by weight, such as, for example, about 0.0001% by weight, about 0.0005% by weight, about 0.001% by weight, about 0.005% by weight, about 0.01% by weight, about 0.05% by weight, about 0.1% by weight, about 0.5% by weight, about 1.0% by weight, about 1.5% by weight, about 2.0% by weight, about 2.5% by weight, about 3.0% by weight, about 3.5% by weight, about 4.0% by weight, about 4.5% by weight, about 5.0% by weight, about 5.5% by weight, about 6.0% by weight, about 6.5% by weight, about 7.0% by weight, about 7.5% by weight, about 8.0% by weight, about 8.5% by weight, about 9.0% by weight, about 9.5% by weight, about 10.0% by weight, about 10.5% by weight, about 11.0% by weight, about 11.5% by weight or about 12.0% by weight.

In a particular embodiment, the sweetener is present in the beverage in an amount from about 0.0001% by weight to about 10% by weight, such as for example, from about 0.0001% by weight to about 0.0005% by weight, from about 0.0005% by weight to about 0.001% by weight, from about 0.001% by weight to about 0.005% by weight, from about 0.005% by weight to about 0.01% by weight, from about 0.01% by weight to about 0.05% by weight, from about 0.05% by weight to about 0.1% by weight, from about 0.1% by weight to about 0.5% by weight, from about 0.5% by weight to about 1% by weight, from about 1% by weight to about 2% by weight, from about 2% by weight to about 3% by weight, from about 3% by weight to about 4% by weight, from about 4% by weight to about 5% by weight, from about 5% by weight to about 6% by weight, from about 6% by weight to about 7% by weight, from about 7% by weight to about 8% by weight, from about 8% by weight to about 9% by weight, or from about 9% by weight to about 10% by weight. In a particular embodiment, the sweetener is present in the beverage in an amount from about 0.5% by weight to about 10% by weight. In another particular embodiment, the sweetener is present in the beverage in an amount from about 2% by weight to about 8% by weight.

In one embodiment, the sweetener is a traditional caloric sweetener. Suitable sweeteners include, but are not limited to, sucrose, fructose, glucose, high fructose corn syrup and high fructose starch syrup.

In another embodiment, the sweetener is erythritol.

In still another embodiment, the sweetener is a rare sugar. Suitable rare sugars include, but are not limited to, D-allose, D-psicose, D-ribose, D-tagatose, L-glucose, L-fucose, L-arabinose, D-turanose, D-leucrose and combinations thereof.

It is contemplated that a sweetener can be used alone, or in combination with other sweeteners.

In one embodiment, the rare sugar is D-allose. In a more particular embodiment, D-allose is present in the beverage in an amount of about 0.5% to about 10% by weight, such as, for example, from about 2% to about 8%.

In another embodiment, the rare sugar is D-psicose. In a more particular embodiment, D-psicose is present in the beverage in an amount of about 0.5% to about 10% by weight, such as, for example, from about 2% to about 8%.

In still another embodiment, the rare sugar is D-ribose. In a more particular embodiment, D-ribose is present in the beverage in an amount of about 0.5% to about 10% by weight, such as, for example, from about 2% to about 8%.

In yet another embodiment, the rare sugar is D-tagatose. In a more particular embodiment, D-tagatose is present in the beverage in an amount of about 0.5% to about 10% by weight, such as, for example, from about 2% to about 8%.

In a further embodiment, the rare sugar is L-glucose. In a more particular embodiment, L-glucose is present in the beverage in an amount of about 0.5% to about 10% by weight, such as, for example, from about 2% to about 8%.

In one embodiment, the rare sugar is L-fucose. In a more particular embodiment, L-fucose is present in the beverage in an amount of about 0.5% to about 10% by weight, such as, for example, from about 2% to about 8%.

In another embodiment, the rare sugar is L-arabinose. In a more particular embodiment, L-arabinose is present in the beverage in an amount of about 0.5% to about 10% by weight, such as, for example, from about 2% to about 8%.

In yet another embodiment, the rare sugar is D-turanose. In a more particular embodiment, D-turanose is present in the beverage in an amount of about 0.5% to about 10% by weight, such as, for example, from about 2% to about 8%.

In yet another embodiment, the rare sugar is D-leucrose. In a more particular embodiment, D-leucrose is present in the beverage in an amount of about 0.5% to about 10% by weight, such as, for example, from about 2% to about 8%.

The addition of the sweetness enhancer at a concentration at or below its sweetness recognition threshold increases the detected sucrose equivalence of the beverage comprising the sweetener and the sweetness enhancer compared to a corresponding beverage in the absence of the sweetness enhancer. Moreover, sweetness can be increased by an amount more than the detectable sweetness of a solution containing the same concentration of the at least one sweetness enhancer in the absence of any sweetener.

Accordingly, the present invention also provides a method for enhancing the sweetness of a beverage comprising a sweetener comprising providing a beverage comprising a sweetener and adding a sweetness enhancer selected from steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f, rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 or a combination thereof, wherein steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 are present in a concentration at or below their sweetness recognition thresholds.

Addition of steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7 in a concentration at or below the sweetness recognition threshold to a beverage containing a sweetener may increase the detected sucrose equivalence from about 1.0% to about 5.0%, such as, for example, about 1.0%, about 1.5%, about 2.0%, about 2.5%, about 3.0%, about 3.5%, about 4.0%, about 4.5% or about 5.0%.

The following examples illustrate preferred embodiments of the invention for the preparation of highly purified target steviol glycoside(s), particularly steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, rebaudioside 1a, rebaudioside 1b, rebaudioside 1c, rebaudioside 1d, rebaudioside 1e, rebaudioside 1f rebaudioside 1g, rebaudioside 1h, rebaudioside 1i, rebaudioside 1j, rebaudioside 1k, rebaudioside 1l, rebaudioside 1m, rebaudioside 1n, rebaudioside 1o, rebaudioside 1p, rebaudioside 1q, rebaudioside 1r, rebaudioside 1s, rebaudioside 1t, rebaudioside 2a, rebaudioside 2b, rebaudioside 2c, rebaudioside 2d, rebaudioside 2e, rebaudioside 2f rebaudioside 2g, rebaudioside 2h, rebaudioside 2i, rebaudioside 2j, rebaudioside 2k, rebaudioside 2l, rebaudioside 2m, rebaudioside 2n, rebaudioside 2o, rebaudioside 2p, rebaudioside 2q, rebaudioside 2r, rebaudioside 2s and/or SvG7. It will be understood that the invention is not limited to the materials, proportions, conditions and procedures set forth in the examples, which are only illustrative.

EXAMPLES

Example 1

Protein sequences of engineered enzymes used in the biocatalytic process

```
SEQ ID 1:
>SuSy_At, variant PM1-54-2-E05 (engineered sucrose
synthase; source of WT gene Arabidopsis thaliana)
MANAERMITRVHSQRERLNETLVSERNEVLALLSRVEAKGKGILQQNQII

AEFEALPEQTRKKLEGGPFFDLLKSTQEAIVLPPWVALAVRPRPGVWEYL

RVNLHALVVEELQPAEFLHFKEELVDGVKNGNFTLELDFEPFNASIPRPT

LHKYIGNGVDFLNRHLSAKLFHDKESLLPLLDFLRLHSHQGKNLMLSEKI

QNLNTLQHTLRKAEEYLAELKSETLYEEFEAKFEEIGLERGWGDNAERVL

DMIRLLLDLLEAPDPSTLETFLGRVPMVFNVVILSPHGYFAQDNVLGYPD

TGGQVVYILDQVRALEIEMLQRIKQQGLNIKPRILILTRLLPDAVGTTCG

ERLERVYDSEYCDILRVPFRTEKGIVRKWISRFEVWPYLETYTEDAAVEL

SKELNGKPDLIIGNYSDGNLVASLLAHKLGVTQCTIAHALEKTKYPDSDI

YWKKLDDKYHFSCQFTADIFAMNHTDFIITSTFQEIAGSKETVGQYESHT

AFTLPGLYRVVHGIDVFDPKFNIVSPGADMSIYFPYTEEKRRLTKFHSEI

EELLYSDVENDEHLCVLKDKKKPILFTMARLDRVKNLSGLVEWYGKNTRL

RELVNLVVVGGDRRKESKDNEEKAEMKKMYDLIEEYKLNGQFRWISSQMD

RVRNGELYRYICDTKGAFVQPALYEAFGLTVVEAMTCGLPTFATCKGGPA

EIIVHGKSGFHIDPYHGDQAADLLADFFTKCKEDPSHWDEISKGGLQRIE

EKYTWQIYSQRLLTLTGVYGFWKHVSNLDRLEHRRYLEMFYALKYRPLAQ

AVPLAQDD

SEQ ID 2:
>UGTS12 variant 0234 (engineered
glucosyltransferase; source of WT gene: Solarium
lycopersicum)
MATNLRVLMFPWLAYGHISPFLNIAKQLADRGFLIYLCSTRINLESIIKK

IPEKYADSIHLIELQLPELPELPPHYHTTNGLPPHLNPTLHKALKMSKPN

FSRILQNLKPDLLIYDVLQPWAEHVANEQGIPAGKLLVSCAAVFSYFFSF

RKNPGVEFPFPAIHLPEVEKVKIREILAKEPEEGGRLDEGNKQMMLMCTS

RTIEAKYIDYCTELCNWKVVPVGPPFQDLITNDADNKELIDWLGTKPENS

TVFVSFGSEYFLSKEDMEEIAFALEASNVNFIWVVRFPKGEERNLEDALP

EGFLERIGERGRVLDKFAPQPRILNHPSTGGFISHCGWNSVMESIDFGVP

IIAMPIHNDQPINAKLMVELGVAVEIVRDDDGKIHRGEIAEALKSVVTGE

TGEILRAKVREISKNLKSIRDEEMDAVAEELIQLCRNSNKSK

SEQ ID 3:
>UGT76G1 variant 0042 (engineered
glucosyltransferase; source of WT gene: Stevia
rebaudiana)
MENKTETTVRRRRRIILFPVPFQGHINPILQLANVLYSKGFAITILHTNF

NKPKTSNYPHFTFRFILDNDPQDERISNLPTHGPLAGMRIPIINEHGADE

LRRELELLMLASEEDEEVSCLITDALWYFAQDVADSLNLRRLVLMTSSLF

NFHAHVSLPQFDELGYLDPDDKTRLEEQASGFPMLKVKDIKSAYSNWQIG

KEILGKMIKQTKASSGVIWNSFKELEESELETVIREIPAPSFLIPLPKHL

TASSSSLLDHDRTVFEWLDQQAPSSVLYVSFGSTSEVDEKDFLEIARGLV

DSGQSFLWVVRPGFVKGSTWVEPLPDGFLGERGKIVKWVPQQEVLAHPAI

GAFWTHSGWNSTLESVCEGVPMIFSSFGGDQPLNARYMSDVLRVGVYLEN

GWERGEVVNAIRRVMVDEEGEYIRQNARVLKQKADVSLMKGGSSYESLES

LVSYISSL
```

Example 2

Expression and formulation of SuSy_At variant of SEQ ID 1 The gene coding for the SuSy_At variant of SEQ ID 1 (EXAMPLE 1) was cloned into the expression vector pLE1A17 (derivative of pRSF-1b, Novagen). The resulting plasmid was used for transformation of E. coli BL21(DE3) cells.

Cells were cultivated in ZYM505 medium (F. William Studier, Protein Expression and Purification 41 (2005) 207-234) supplemented with kanamycin (50 mg/l) at 37° C. Expression of the genes was induced at logarithmic phase by IPTG (0.2 mM) and carried out at 30° C. and 200 rpm for 16-18 hours.

Cells were harvested by centrifugation (3220×g, 20 min, 4° C.) and re-suspended to an optical density of 200 (measured at 600 nm ($OD_{600}$)) with cell lysis buffer (100 mM Tris-HCl pH 7.0; 2 mM $MgCl_2$, DNA nuclease 20 U/mL, lysozyme 0.5 mg/mL). Cells were then disrupted by sonication and crude extracts were separated from cell debris by centrifugation (18000×g 40 min, 4° C.). The supernatant was sterilized by filtration through a 0.2 μm filter and diluted 50:50 with distilled water, resulting in an enzymatic active preparation.

For enzymatic active preparations of SuSy_At, activity in Units is defined as follows: 1 mU of SuSy_At turns over 1 nmol of sucrose into fructose in 1 minute. Reaction conditions for the assay are 30° C., 50 mM potassium phosphate buffer pH 7.0, 400 mM sucrose at to, 3 mM MgCl$_2$, and 15 mM uridine diphosphate (UDP).

Example 3

Expression and formulation of UGTSl2 variant of SEQ ID 2 The gene coding for the UGTSl2 variant of SEQ ID 2 (EXAMPLE 1) was cloned into the expression vector pLE1A17 (derivative of pRSF-1b, Novagen). The resulting plasmid was used for transformation of *E. coli* BL21(DE3) cells.

Cells were cultivated in ZYM505 medium (F. William Studier, Protein Expression and Purification 41 (2005) 207-234) supplemented with kanamycin (50 mg/l) at 37° C. Expression of the genes was induced at logarithmic phase by IPTG (0.1 mM) and carried out at 30° C. and 200 rpm for 16-18 hours.

Cells were harvested by centrifugation (3220×g, 20 min, 4° C.) and re-suspended to an optical density of 200 (measured at 600 nm (OD$_{600}$)) with cell lysis buffer (100 mM Tris-HCl pH 7.0; 2 mM MgCl$_2$, DNA nuclease 20 U/mL, lysozyme 0.5 mg/mL). Cells were then disrupted by sonication and crude extracts were separated from cell debris by centrifugation (18000×g 40 min, 4° C.). The supernatant was sterilized by filtration through a 0.2 μm filter and diluted 50:50 with 1 M sucrose solution, resulting in an enzymatic active preparation.

For enzymatic active preparations of UGTSl2, activity in Units is defined as follows: 1 mU of UGTSl2 turns over 1 nmol of rebaudioside A (Reb A) into rebaudioside D (Reb D) in 1 minute. Reaction conditions for the assay are 30° C., 50 mM potassium phosphate buffer pH 7.0, 10 mM Reb A at to, 500 mM sucrose, 3 mM MgCl$_2$, 0.25 mM uridine diphosphate (UDP) and 3 U/mL of SuSy_At.

Example 4

Expression and Formulation of UGT76G1 Variant of SEQ ID 3

The gene coding for the UGT76G1 variant of SEQ ID 3 (EXAMPLE 1) was cloned into the expression vector pLE1A17 (derivative of pRSF-1b, Novagen). The resulting plasmid was used for transformation of *E. coli* BL21(DE3) cells.

Cells were cultivated in ZYM505 medium (F. William Studier, Protein Expression and Purification 41 (2005) 207-234) supplemented with kanamycin (50 mg/l) at 37° C. Expression of the genes was induced at logarithmic phase by IPTG (0.1 mM) and carried out at 30° C. and 200 rpm for 16-18 hours.

Cells were harvested by centrifugation (3220×g, 20 min, 4° C.) and re-suspended to an optical density of 200 (measured at 600 nm (OD$_{600}$)) with cell lysis buffer (100 mM Tris-HCl pH 7.0; 2 mM MgCl$_2$, DNA nuclease 20 U/mL, lysozyme 0.5 mg/mL). Cells were then disrupted by sonication and crude extracts were separated from cell debris by centrifugation (18000×g 40 min, 4° C.). The supernatant was sterilized by filtration through a 0.2 μm filter and diluted 50:50 with 1 M sucrose solution, resulting in an enzymatic active preparation.

For enzymatic active preparations of UGT76G1, activity in Units is defined as follows: 1 mU of UGT76G1 turns over 1 nmol of rebaudioside D (Reb D) into rebaudioside M (Reb M) in 1 minute. Reaction conditions for the assay are 30° C., 50 mM potassium phosphate buffer pH 7.0, 10 mM Reb D at to, 500 mM sucrose, 3 mM MgCl$_2$, 0.25 mM uridine diphosphate (UDP) and 3 U/mL of SuSy_At.

Example 5

Synthesis of SvG7 in a One-Pot Reaction, Adding UGTSl2, SuSy_At and UGT76G1 at the Same Time.

Various SvG7 molecules were synthesized directly from stevioside (see FIG. 12*a*) in a one-pot reaction, utilizing the three enzymes (see EXAMPLES 1, 2, 3 and 4): UGTSl2 (variant of SEQ ID 2), SuSy_At (variant of SEQ ID 1) and UGT76G1 (variant of SEQ ID 3).

The final reaction solution contained 348 U/L UGTSl2, 1341 U/L SuSy_At, 10 U/L UGT76G1, 47 mM stevioside, 0.32 mM uridine diphosphate (UDP), 0.99 M sucrose, 3.9 mM MgCl$_2$ and potassium phosphate buffer (pH 6.6). First, 206 mL of distilled water were mixed with 0.24 g MgCl$_2$.6H$_2$O, 102 g sucrose, 9.8 mL of 1.5 M potassium phosphate buffer (pH 6.6) and 15 g stevioside. The final volume of the reaction mixture was adjusted to 300 mL.

After dissolving the components, the temperature was adjusted to 45° C. and UGTSl2, SuSy_At, UGT76G1 and 39 mg UDP were added. The reaction mixture was incubated at 45° C. shaker for 24 hrs. Additional 39 mg UDP was added at 12 hours, 24 hours, and 36 hours. The content of reb M5, reb 2a, reb 2m and various SvG7 at the end of the reaction (48 hours) was analyzed by HPLC.

Example 6

HPLC Analysis

For analysis, biotransformation samples were inactivated by adjusting the reaction mixture to pH5.5 using 17% H$_3$PO$_4$ and then boiled for 10 minutes. Resulting samples were filtered, the filtrates were diluted 10 times and used as samples for HPLC analysis. HPLC assay was carried out on Agilent HP 1200 HPLC system, comprised of a pump, a column thermostat, an auto sampler, a UV detector capable of background correction and a data acquisition system. Analytes were separated using Agilent Poroshell 120 SB-C18, 4.6 mm×150 mm, 2.7 μm at 40° C. The mobile phase consisted of two premixes:

premix 1 containing 75% 10 mM phosphate buffer (pH2.6) and 25% acetonitrile, and premix 2 containing 68% 10 mM phosphate buffer (pH2.6) and 32% acetonitrile.

Elution gradient started with premix 1, changed to premix 2 to 50% at 12.5 minute, changed to premix 2 to 100% at 13 minutes. Total run time was 45 minutes. The column temperature was maintained at 40° C. The injection volume was 5 μL. Rebaudioside species were detected by UV at 210 nm.

Figure 12A:
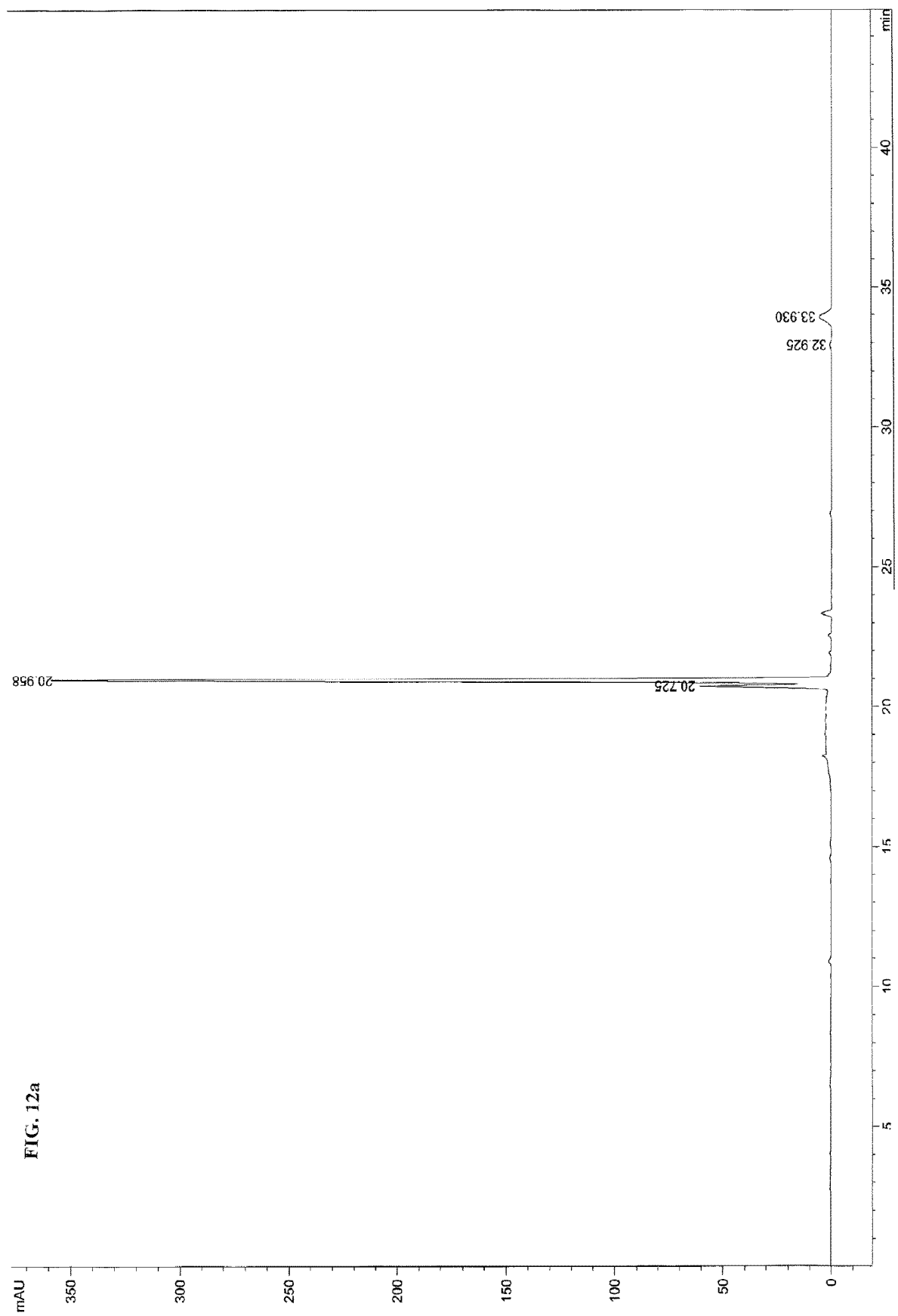
FIG. 12a shows the HPLC chromatogram of stevioside. The peak with retention time of 20.958 minutes corresponds to stevioside. The peak with retention time 20.725 minutes corresponds to rebaudioside A. The peak at 32.925 minutes corresponds to rebaudioside B. The peak at 33.930 minutes corresponds to steviolbioside.
Figure 12B:
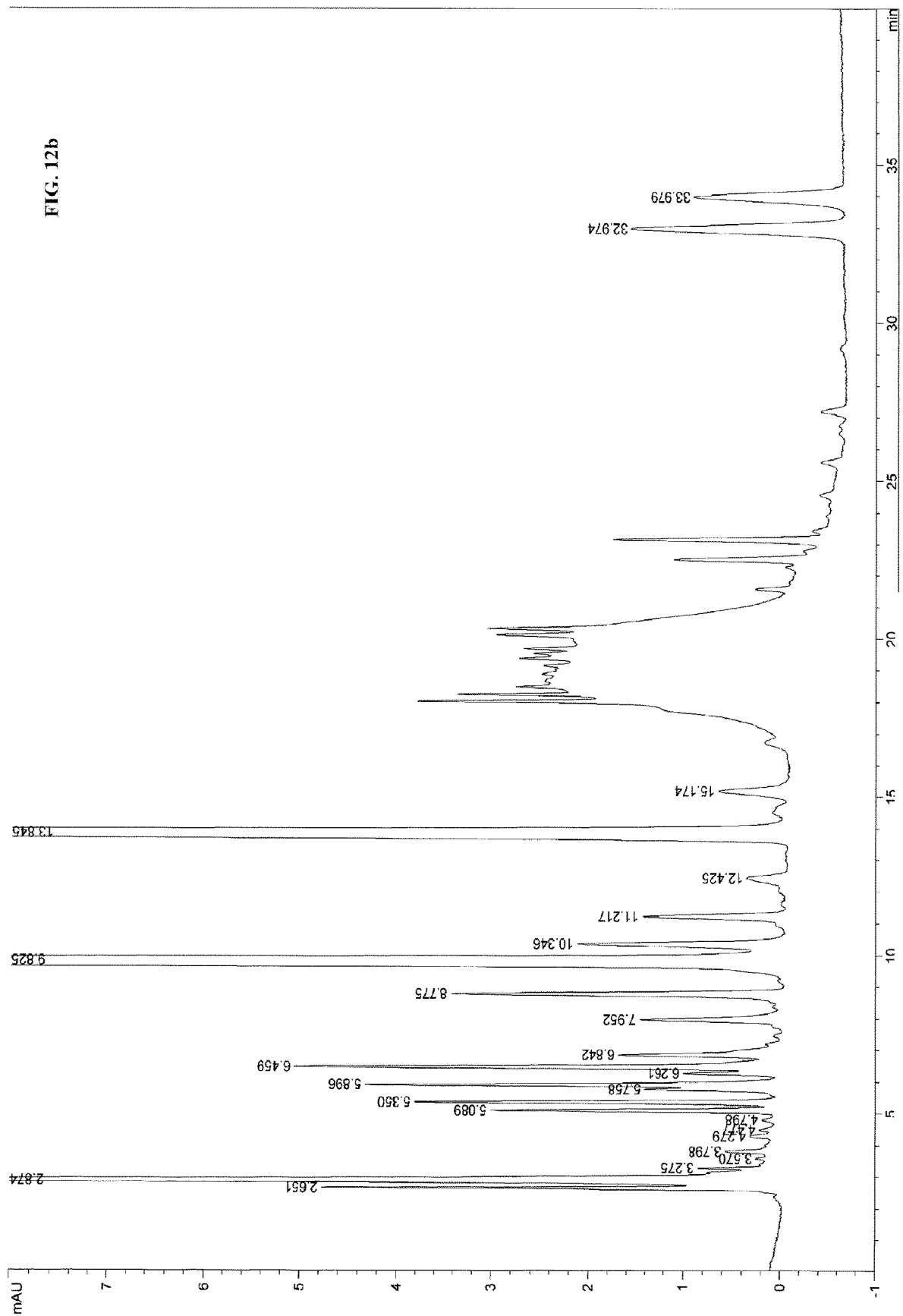
FIG. 12b shows the HPLC chromatogram of the product of the biocatalytic production of SvG7 molecules from stevioside. The peak at 5.089 minutes corresponds to rebaudioside 2m. The peak at 5.350 minutes corresponds to rebaudioside M5. The peak at 6.459 minutes corresponds to rebaudioside 2a. The peak at 9.825 minutes corresponds to rebaudioside AM. The peak at 13.845 minutes corresponds to rebaudioside M. The peak at 32.974 minutes corresponds to rebaudioside B. The peak at 33.979 minutes corresponds to steviolbioside.

Table 3 shows for each time point the conversion of stevioside into identified rebaudioside species (area percentage). The chromatograms of the starting material stevioside and the reaction mixture at 48 hours are shown in FIG. 12*a* and FIG. 12*b* respectively. Those with skill in the art will appreciate that retention times can occasionally vary with changes in solvent and/or equipment.

TABLE 3

Biotransformation of stevioside to reb M5 (rt 5.350), reb 2a (rt 6.459), reb 2m (rt 5.089) and various SvG7

| Peak | % conversion from stevioside | |
|---|---|---|
| | reaction time 0 hr | reaction time 48 hr |
| rt 2.651 | 0 | 0.83 |
| rt 2.874 | 0 | 6.79 |
| rt 3.275 | 0 | 0.15 |
| rt 3.570 | 0 | 0.05 |
| rt 3.798 | 0 | 0.18 |
| rt 4.279 | 0 | 0.08 |
| rt 4.477 | 0 | 0.05 |
| rt 4.798 | 0 | 0.04 |
| rt 5.089 | 0 | 0.68 |
| rt 5.350 | 0 | 0.86 |
| rt 5.758 | 0 | 0.28 |
| rt 5.896 | 0 | 1.06 |
| rt 6.261 | 0 | 0.22 |
| rt 6.459 | 0 | 1.37 |
| rt 6.842 | 0 | 0.57 |
| rt 7.952 | 0 | 0.5 |
| rt 8.775 | 0 | 1.07 |
| reb AM | 0 | 65.7 |
| rt 10.346 | 0 | 0.83 |
| rt 11.217 | 0 | 0.54 |
| rt 12.425 | 0 | 0.2 |
| reb M | 0 | 14.97 |
| rt 15.174 | 0 | 0.4 |
| reb A | 12.97 | 0 |
| stevioside | 82.83 | 0 |
| reb B | 0.38 | 1.47 |
| steviolbioside | 3.82 | 1.11 |

Example 7

Purification of Rebaudioside M5, 2a, 2m and Various SvG7

300 mL of the reaction mixture of EXAMPLE 5, (after 48 hrs), was inactivated by adjusting the pH to pH 5.5 with $H_3PO_4$ and then boiled for 10 minutes and filtered. The filtrate was loaded into a column containing 500 mL YWD03 (Cangzhou Yuanwei, China) resin pre-equilibrated with water. The resin was washed with 2.5 L water and the water effluent from this step was discarded.

The steviol glycosides were eluted from the YWD03 resin column by elution with 2.5 L 70% v/v ethanol/water. The effluent from this step was collected and dried under vacuum at 60° C. to yield 20g of dried solid product. This sample was dissolved in water and subjected to further fractionation and separation by HPLC, using the conditions listed in Table 4 below.

HPLC fractions that corresponded to individual compounds from multiple runs were combined according to retention time. The fractions were freeze-dried.

TABLE 4

| Conditions for HPLC | |
|---|---|
| Column | Agilent Prodigy 3u ODS(3) 100A, 4.6 mm × 250 mm, 3 micron |
| Temperature | 40° C. |
| Mobile Phase | Isocratic—Water 77% Acetonitrile 23% |
| Flow rate | 0.5 mL/min |
| Injection | 10 µL |
| Stop time | 45 mins |
| Autosampler temperature | Ambient |
| Detection | UV at 210 nm |

Figure 12C:
Figure 12E:
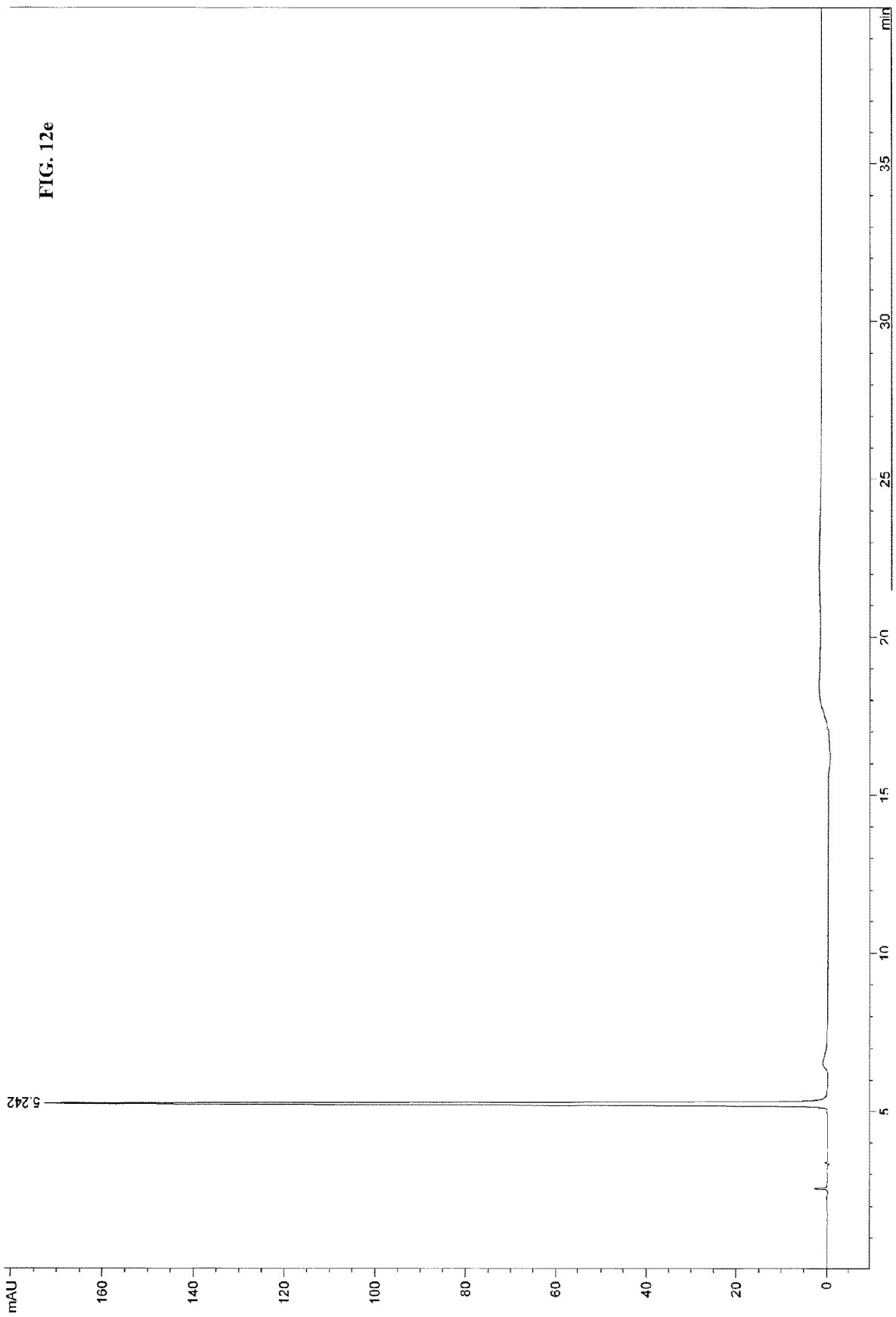
FIG. 12e shows the HPLC chromatogram of rebaudioside M5 after purification by HPLC. The peak with retention time of 5.242 minutes correspond to rebaudioside M5.

The purity of obtained fractions was evaluated by analytical HPLC method described in EXAMPLE 6. The chromatogram of purified rebaudioside 2a is shown in FIG. 12c. The chromatogram of purified rebaudioside 2m is shown in FIG. 12d. The chromatogram of purified rebaudioside M5 is shown in FIG. 12e.

Example 8

Structure Elucidation of Rebaudioside 2a

Figure 13A:
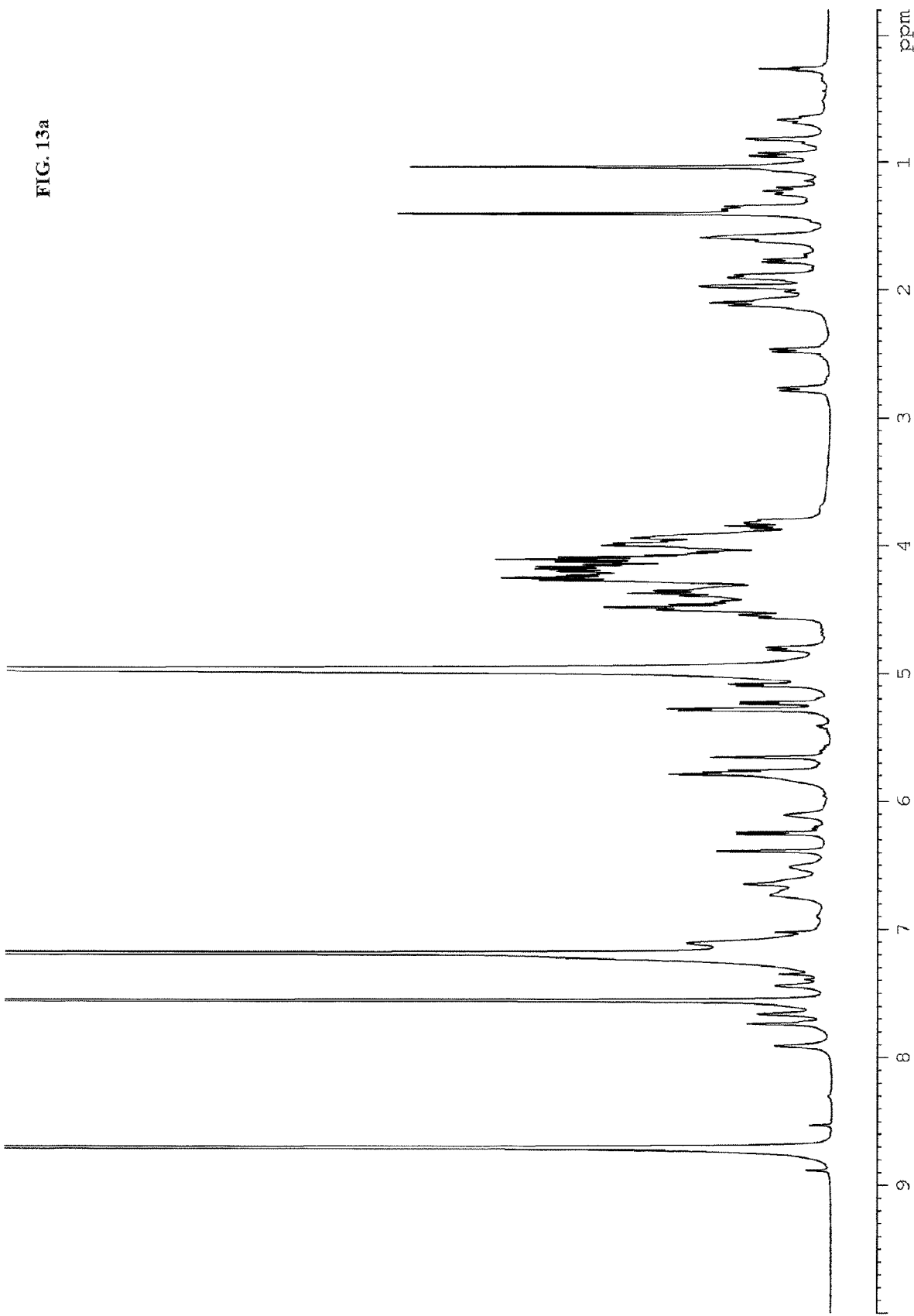
FIG. 13a shows the 1H NMR spectrum of rebaudioside 2a (500 MHz, pyridine-d5).
Figure 13B:
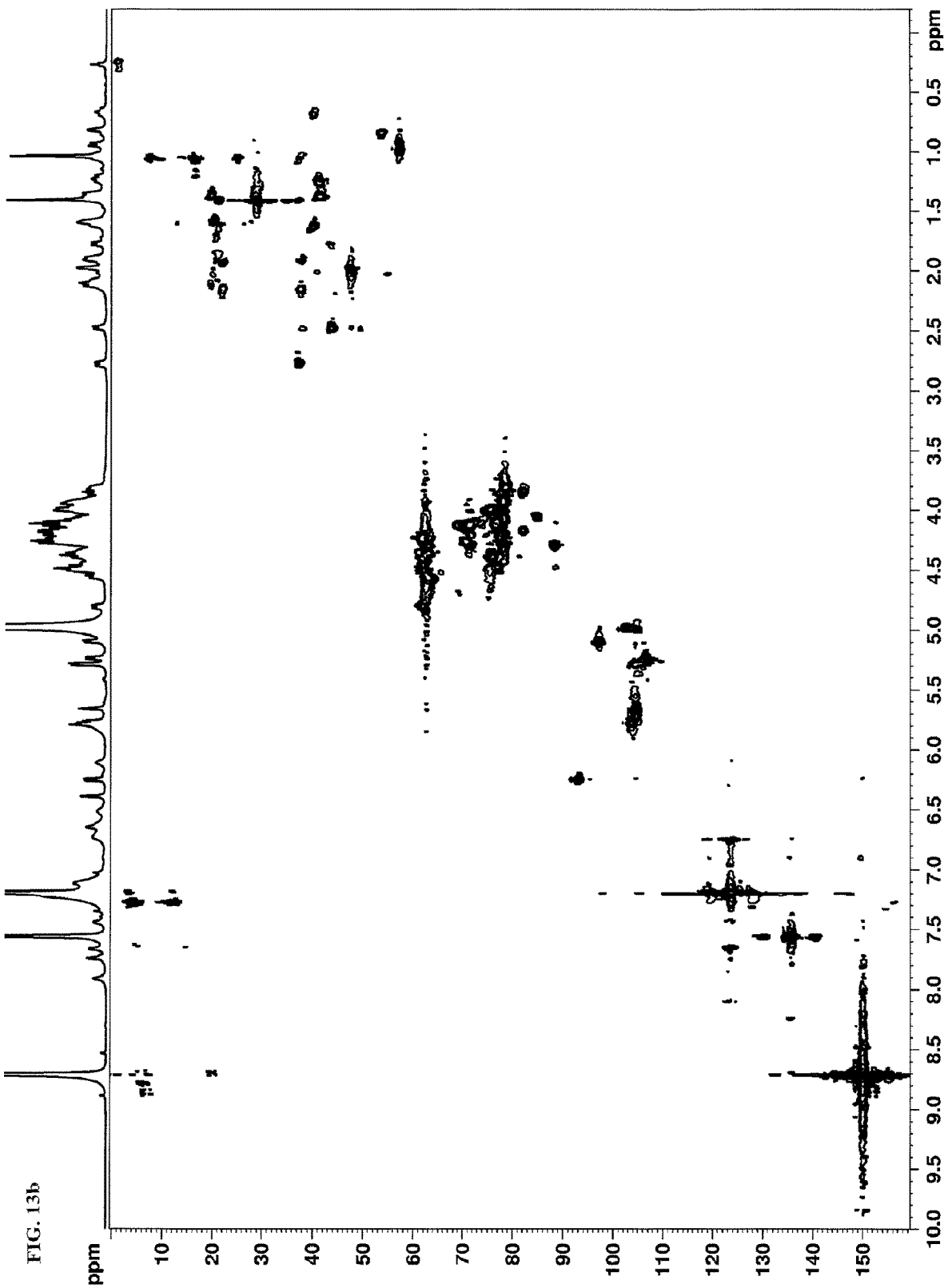
FIG. 13b shows the HSQC spectrum of rebaudioside 2a (500 MHz, pyridine-d5).
Figure 13C:
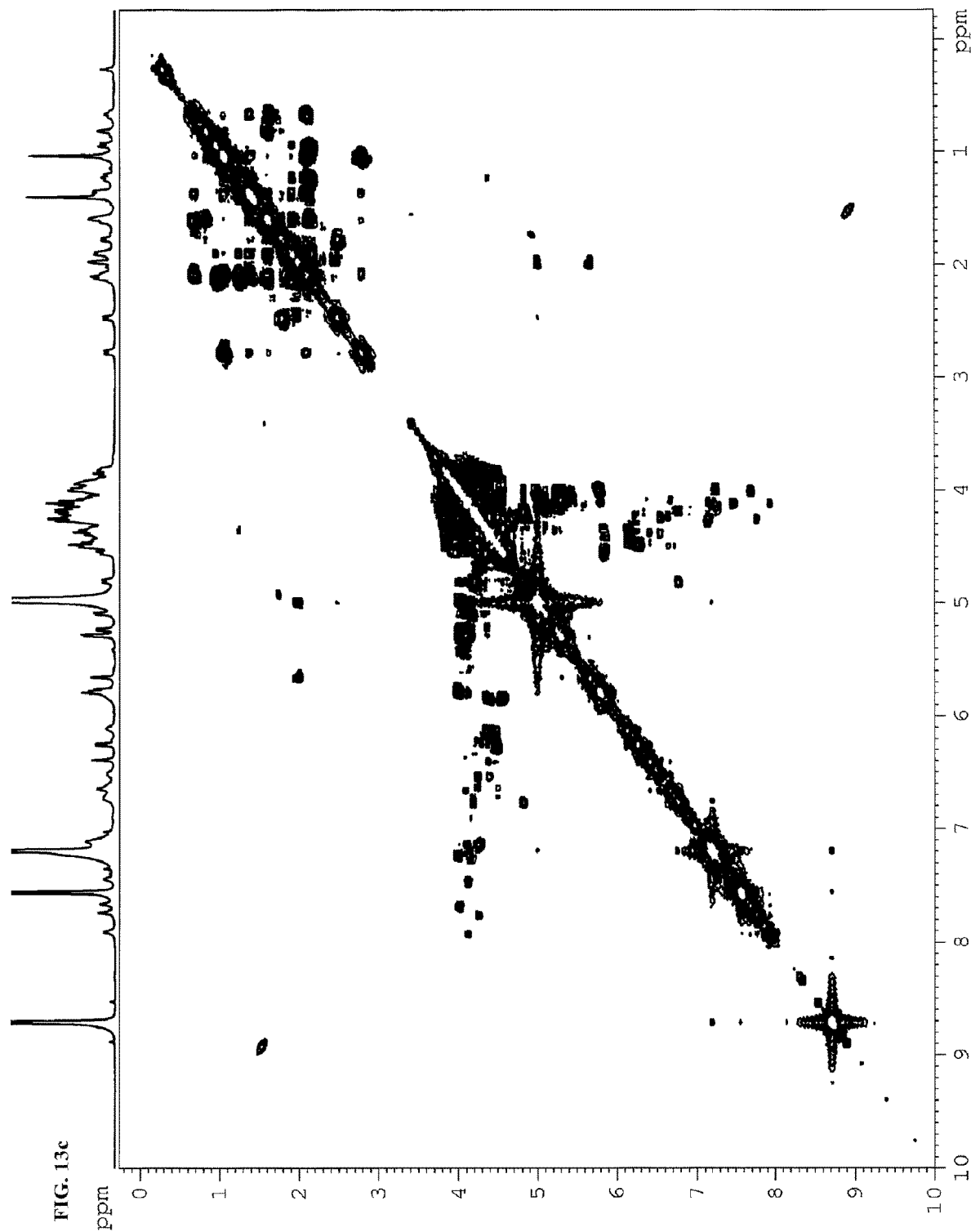
FIG. 13c shows the H,H COSY spectrum of rebaudioside 2a (500 MHz, pyridine-d5).
Figure 13D:
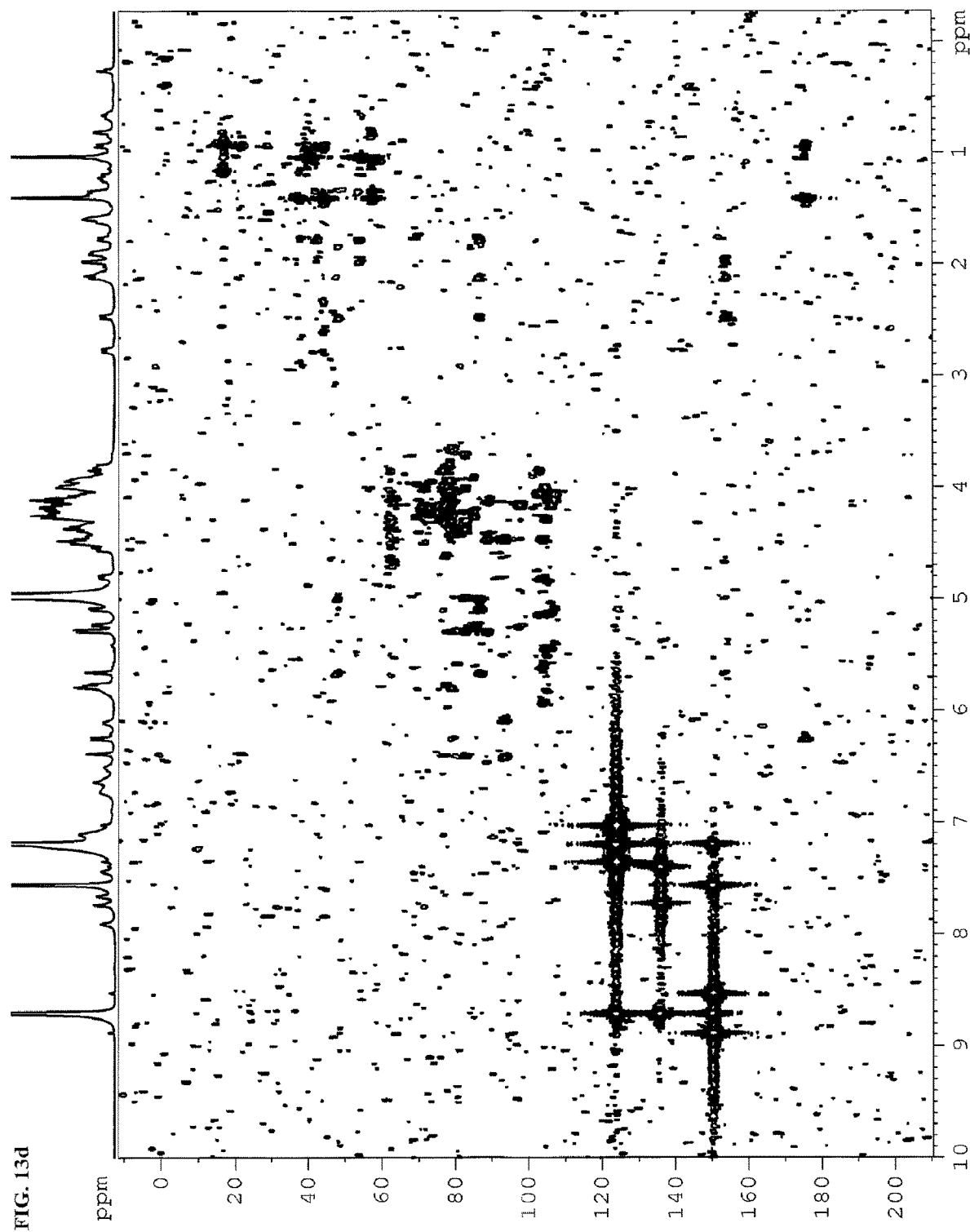
FIG. 13d shows the HMBC spectrum of rebaudioside 2a (500 MHz, pyridine-d5).

NMR experiments were performed on a Bruker 500 MHz spectrometer, with the sample dissolved in pyridine-d5. Along with signals from the sample, signals from pyridine-d5 at $\delta_C$ 123.5, 135.5, 149.9 ppm and $\delta_H$ 7.19, 7.55, 8.71 ppm were observed. $^1$H-NMR spectrum of rebaudioside 2a recorded in pyridine-$d_5$ confirmed the excellent quality of the sample (see FIG. 13a). HSQC (see FIG. 13b) shows the presence of an exo-methylene group in the sugar region with a long-range coupling to C-15, observable in the H,H-COSY (FIG. 13c). Other deep-fielded signals of the quaternary carbons (C-13, C-16 and C-19) are detected by the HMBC (FIG. 13d). Correlation of the signals in the HSQC, HMBC and H,H-COSY reveal the presence of steviol glycoside with the following aglycone structure:

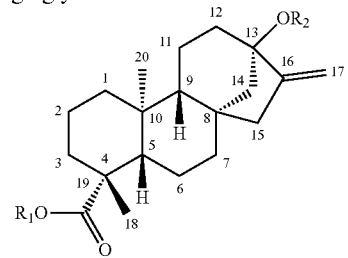

Correlation of HSQC and HMBC shows the presence seven anomeric signals, marked with 1i, 1ii, 1iii, 1iv, 1v, 1vi and 1vii. The coupling constant of the anomeric protons of about 8 Hz, the broad signals of their sugar linkage and the NOE-correlations of the anomeric protons allow the identification of these seven sugars as β-D-glucopyranosides.

Figure 13E:
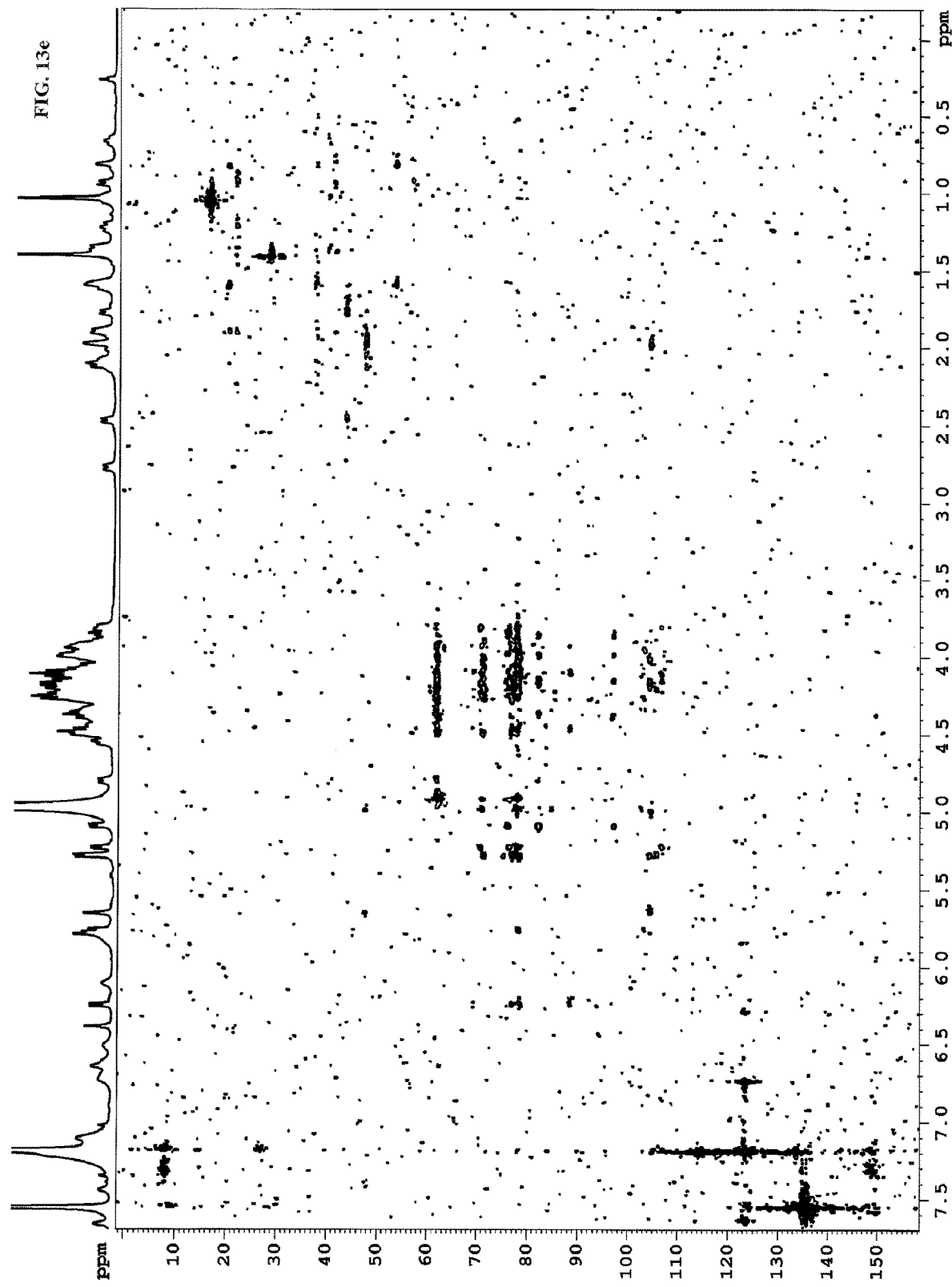
FIG. 13e shows the HSQC-TOCSY spectrum of rebaudioside 2a (500 MHz, pyridine-d5).
Figure 13F:
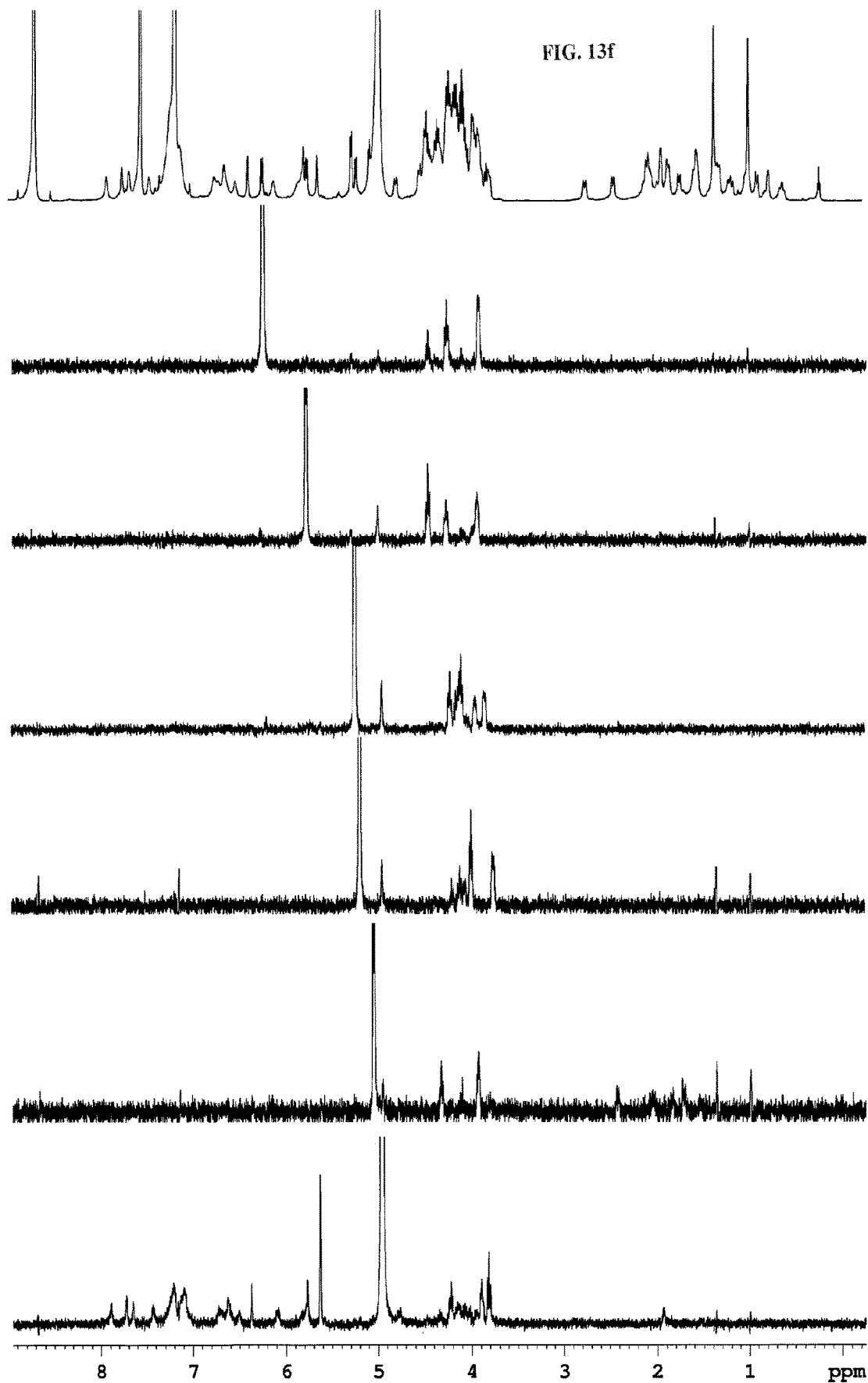
FIG. 13f shows the 1D-NOESY spectrum of rebaudioside 2a (500 MHz, pyridine-d5).

Combined data from HSQC and HMBC reveal the sugar-sugar linkages and sugar-aglycone linkages. The assignment of the sugar sequence was confirmed by using the combination of HSQC-TOCSY (FIG. 13e) and NOESY (FIG. 13f).

Altogether, results from NMR experiments above were used to assign the chemical shifts of the protons and carbons of the structure of rebaudioside 2a (see Table 5).

TABLE 5

Chemical shifts of rebaudioside 2a

| Position | $\delta_C$ [ppm] | | $\delta_H$ [ppm] | J [Hz]/(INT) | HMBC (H -> C) |
|---|---|---|---|---|---|
| Aglycone moiety | | | | | |
| 1 | 40.1 | t | 0.67 | m | |
| | | | 1.62 | m | |
| 2 | 19.5 | t | 1.36 | m | |
| | | | 2.10 | m | |
| 3 | 37.1 | t | 1.05 | m | |
| | | | 2.77 | m | |
| 4 | 44.5 | s | — | | |
| 5 | 57.1 | d | 0.94 | m | |
| 6 | 21.8 | t | 1.92 | m | |
| | | | 2.13 | m | |
| 7 | 40.9 | t | 1.22 | m | |
| | | | 1.36 | m | |
| 8 | 42.1 | s | — | | |

TABLE 5-continued

Chemical shifts of rebaudioside 2a

| Position | $\delta_C$ [ppm] | | $\delta_H$ [ppm] | | J [Hz]/(Int) | HMBC (H → C) | NOE (H → H) |
|---|---|---|---|---|---|---|---|
| 9 | 53.4 | d | 0.82 | m | | | |
| 10 | 39.1 | s | — | | | | |
| 11 | 20.4 | t | 1.57 | m | | | |
| | | | 1.60 | m | | | |
| 12 | 37.4 | t | 1.90 | m | | | |
| | | | 2.13 | m | | | |
| 13 | 86.5 | s | — | | | | |
| 14 | 43.4 | t | 1.77 | d | 11.1 | | |
| | | | 2.47 | d | 11.1 | | |
| 15 | 47.2 | t | 1.96 | d | 16.0 | 7, 8, 9, 14 | |
| | | | 1.99 | d | 16.0 | | |
| 16 | 153.7 | s | — | | | | |
| 17 | 104.4 | t | 4.99 | br s | | 13, 15, 16 | |
| | | | 5.67 | br s | | | |
| 18 | 28.5 | q | 1.40 | s | (3H) | 3, 4, 5, 19 | |
| 19 | 175.7 | s | — | | | | |
| 20 | 16.0 | q | 1.04 | s | (3H) | 1, 5, 9, 10 | |

| Position | $\delta_C$ [ppm] | | $\delta_H$ [ppm] | | J [Hz]/(Int) | HMBC (H → C) | NOE (H → H) |
|---|---|---|---|---|---|---|---|
| Sugar moiety | | | | | | | |
| Sugar I: β-D-Glucopyranoside | | | | | | | |
| $1^i$ | 97.0 | d | 5.09 | d | 7.7 | 13 | |
| $2^i$ | 81.9 | d | 4.16 | m | | | |
| $3^i$ | 75.8 | d | 4.37 | m | | | |
| $4^i$ | 81.9 | d | 3.85 | m | | | |
| $5^i$ | 75.6 | d | 3.97 | m | | | |
| $6^i$ | 61.8 | t | 4.20 | m | | | |
| | | | 4.80 | m | | | |
| Sugar II: β-D-Glucopyranoside | | | | | | | |
| $1^{ii}$ | 105.0 | d | 5.28 | d | 8.0 | $2^i$ | $2^i$ |
| $2^{ii}$ | 76.3 | d | 4.09 | m | | | |
| $3^{ii}$ | 78.0 | d | 4.29 | m | | | |
| $4^{ii}$ | 70.8 | d | 4.24 | m | | | |
| $5^{ii}$ | 78.1 | d | 3.91 | m | | | |
| $6^{ii}$ | 61.4 | t | 4.39 | m | | | |
| | | | 4.50 | m | | | |
| Sugar III: β-D-Glucopyranoside | | | | | | | |
| $1^{iii}$ | 102.4 | d | 4.98 | d | 8.1 | $4^i$ | $4^i$ |
| $2^{iii}$ | 84.8 | d | 4.05 | m | | | |
| $3^{iii}$ | 77.9 | d | 4.22 | m | | | |
| $4^{iii}$ | 70.9 | d | 4.12 | m | | | |
| $5^{iii}$ | 77.6 | d | 3.92 | m | | | |
| $6^{iii}$ | 62.5 | t | 4.31 | m | | | |
| | | | 4.53 | m | | | |
| Sugar IV: β-D-Glucopyranoside | | | | | | | |
| $1^{iv}$ | 106.4 | d | 5.22 | d | 7.8 | $2^{iii}$ | $2^{iii}$ |
| $2^{iv}$ | 76.1 | d | 4.12 | m | | | |
| $3^{iv}$ | 78.1 | d | 4.06 | m | | | |
| $4^{iv}$ | 70.4 | d | 4.25 | m | | | |
| $5^{iv}$ | 78.3 | d | 3.81 | m | | | |
| $6^{iv}$ | 61.6 | t | 4.24 | m | | | |
| | | | 4.50 | m | | | |
| Sugar V: β-D-Glucopyranoside | | | | | | | |
| $1^v$ | 93.0 | d | 6.25 | d | 8.1 | 19 | |
| $2^v$ | 76.8 | d | 4.47 | m | | | |
| $3^v$ | 88.2 | d | 4.28 | m | | | |
| $4^v$ | 69.1 | d | 4.12 | m | | | |
| $5^v$ | 78.2 | d | 3.92 | m | | | |
| $6^v$ | 61.5 | t | 4.16 | m | | | |
| | | | 4.33 | m | | | |
| Sugar VI: β-D-Glucopyranoside | | | | | | | |
| $1^{vi}$ | 103.5 | d | 5.77 | d | 7.8 | $2^v$ | $2^v$ |
| $2^{vi}$ | 75.4 | d | 4.00 | m | | | |
| $3^{vi}$ | 77.6 | d | 4.27 | m | | | |
| $4^{vi}$ | 71.1 | d | 4.27 | m | | | |
| $5^{vi}$ | 78.0 | d | 3.96 | m | | | |
| $6^{vi}$ | 62.7 | t | 4.42 | m | | | |
| | | | 4.58 | m | | | |
| Sugar VII: β-D-Glucopyranoside | | | | | | | |
| $1^{vii}$ | 104.4 | d | 5.28 | d | 8.0 | $3^v$ | $3^v$ |
| $2^{vii}$ | 75.0 | d | 4.01 | m | | | |
| $3^{vii}$ | 77.2 | d | 4.17 | m | | | |
| $4^{vii}$ | 71.5 | d | 4.10 | m | | | |
| $5^{vii}$ | 77.9 | d | 4.00 | m | | | |
| $6^{vii}$ | 61.8 | t | 4.42 | m | | | |
| | | | 4.52 | m | | | |

Correlation of all NMR results indicates rebaudioside 2a with seven β-D-glucoses attached to steviol aglycone, as depicted with the following chemical structure:

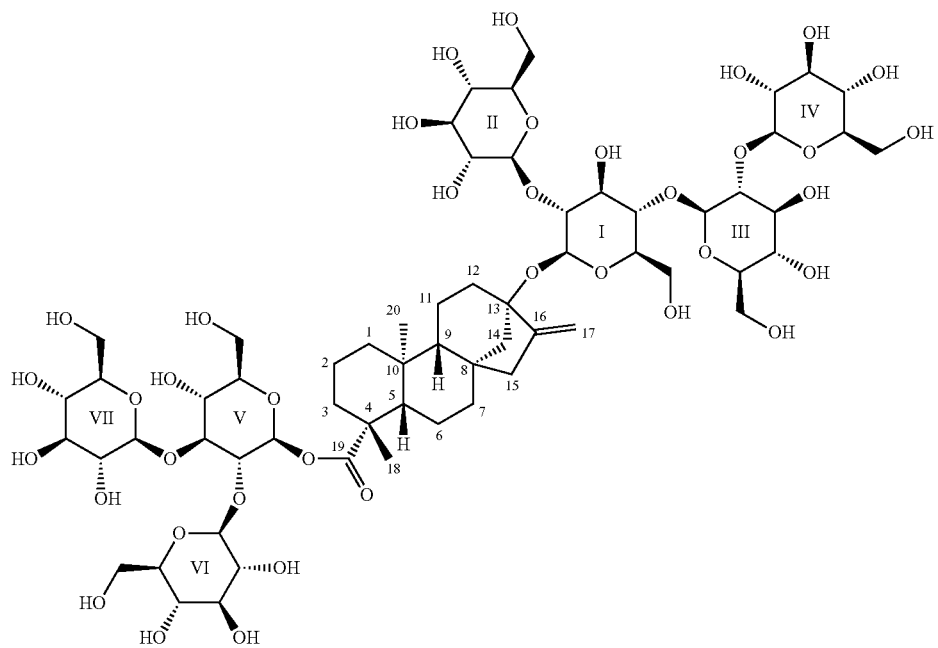

Figure 13G:
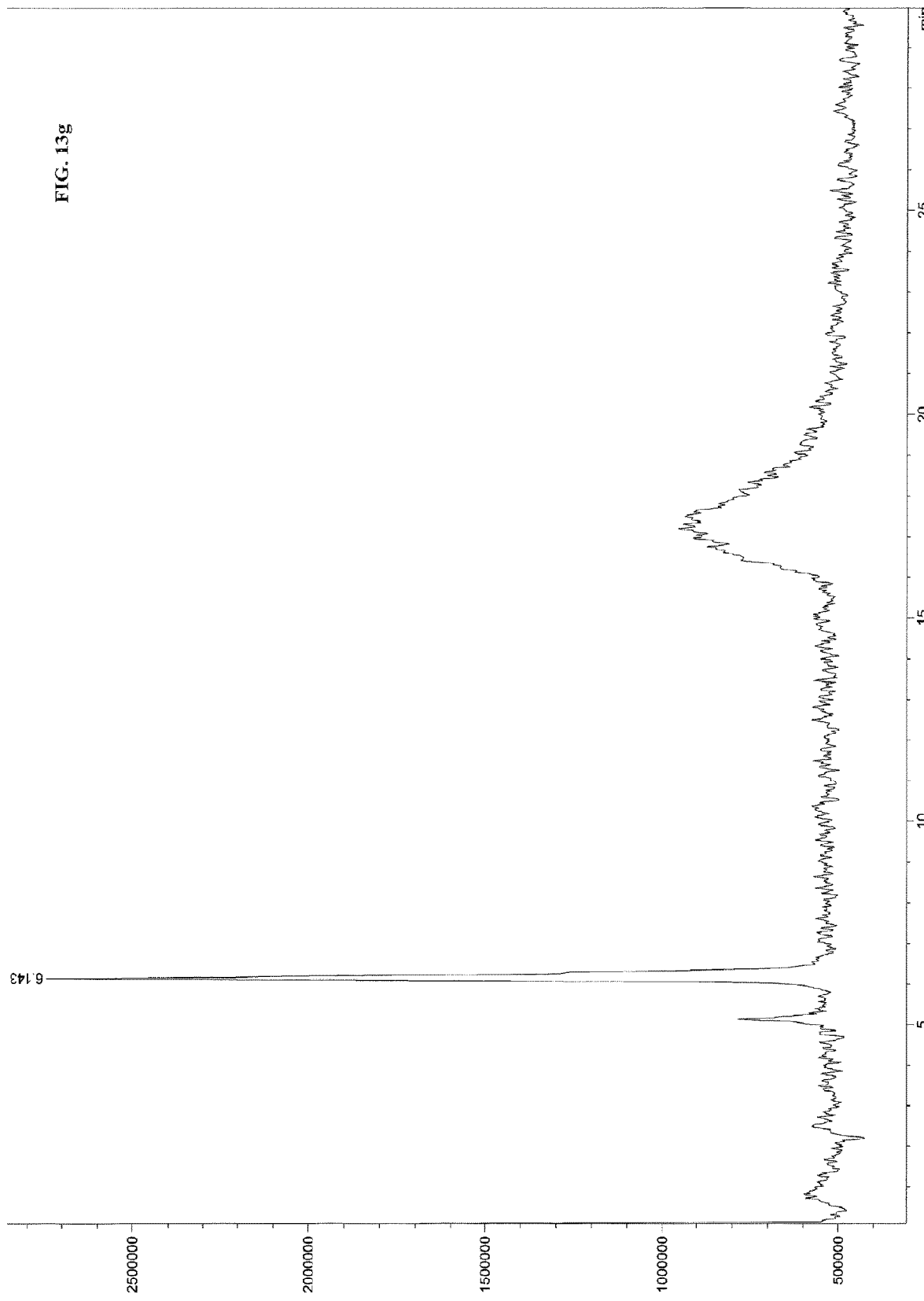
Figure 13H:
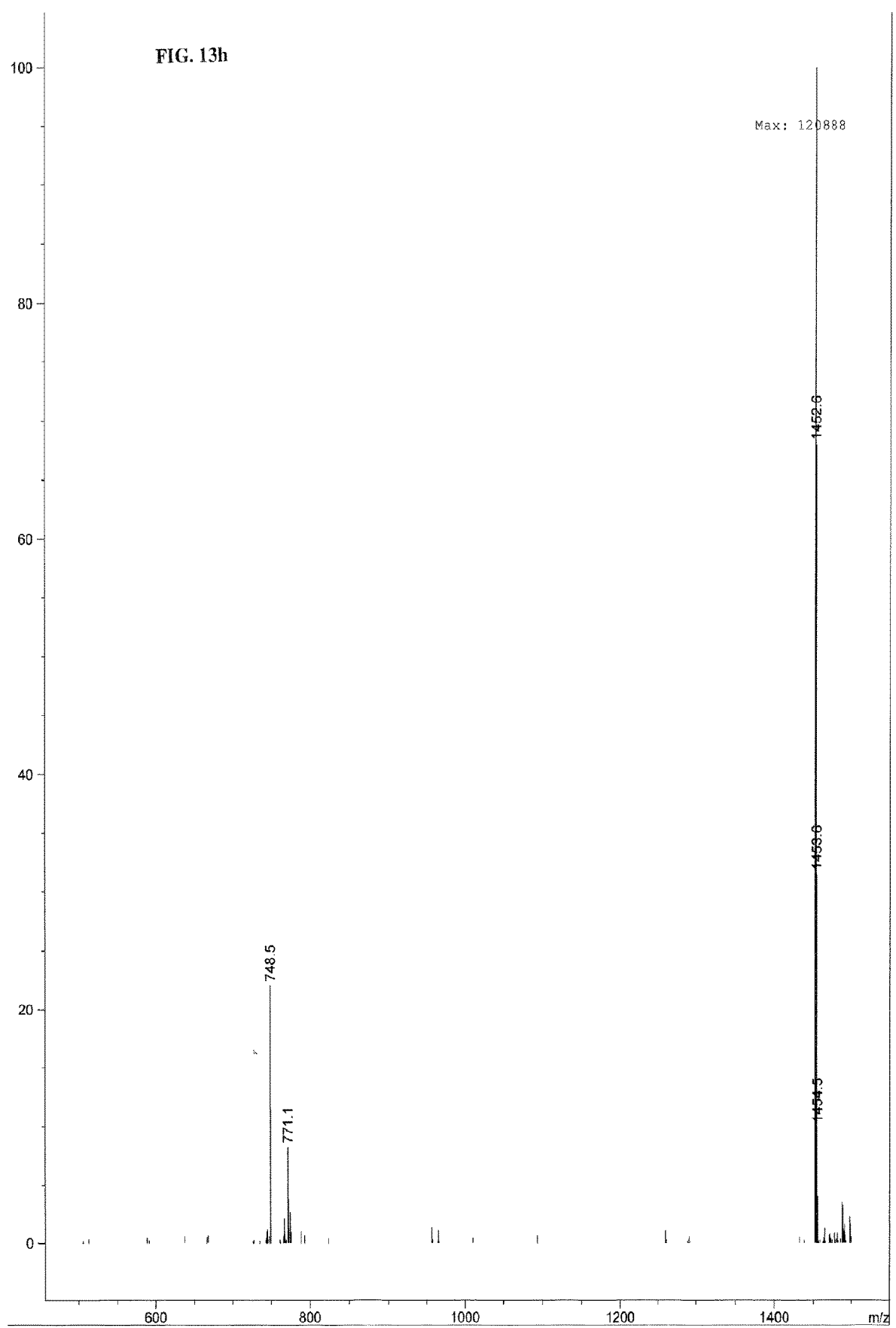

LCMS (FIG. 13g and FIG. 13h) analysis of rebaudioside 2a showed a [M-H]− ion at m/z 1451.6, in good agreement with the expected molecular formula of $C_{62}H_{100}O_{38}$ (calculated for $[C_{62}H_{99}O_{38}]^-$ monoisotopic ion: 1451.6). The M5 data confirms that rebaudioside 2a has a molecular formula of $C_{62}H_{100}O_{38}$. LCMS analysis was performed in the following conditions listed in Table 6.

TABLE 6

Conditions for LCMS analysis

| | |
|---|---|
| Column | Agilent Poroshell 120 SB-C18, 4.6 mm × 150 mm, 2.7 μm |
| Temperature | 40° C. |
| Mobile Phase | A: Mobile Phase Premix Solution 25% Acetonitrile: 75% Formic Acid (0.1% in Water) B: Mobile Phase Premix Solution 32% Acetonitrile: 68% Formic Acid (0.1% in Water) |
| Gradient | Time (min) A (%) B (%)<br>0 100 0<br>12.0 100 0<br>12.5 50 50<br>13.0 0 100<br>60.0 0 100 |
| Flow rate | 0.5 mL/min |
| Injection | 2 μL |
| Run time | 45 mins |
| Post time | 5 mins |
| Autosampler temperature | Ambient |
| Detection | MSD at Negative Scan mode |
| MSD Setting | Mode: ES-API, Negative Polarity Drying gas flow: 13.0 L/min Nebulizer Pressure: 30 psig Drying gas temperature: 270° C. Fragmentor: 50 V Scan ranges: 500 to 1500 of mass |
| Sample Preparation | 1 mg/ml (30% ACN in water) |

Example 9

Structure Elucidation of Rebaudioside 2m

Figure 14A:
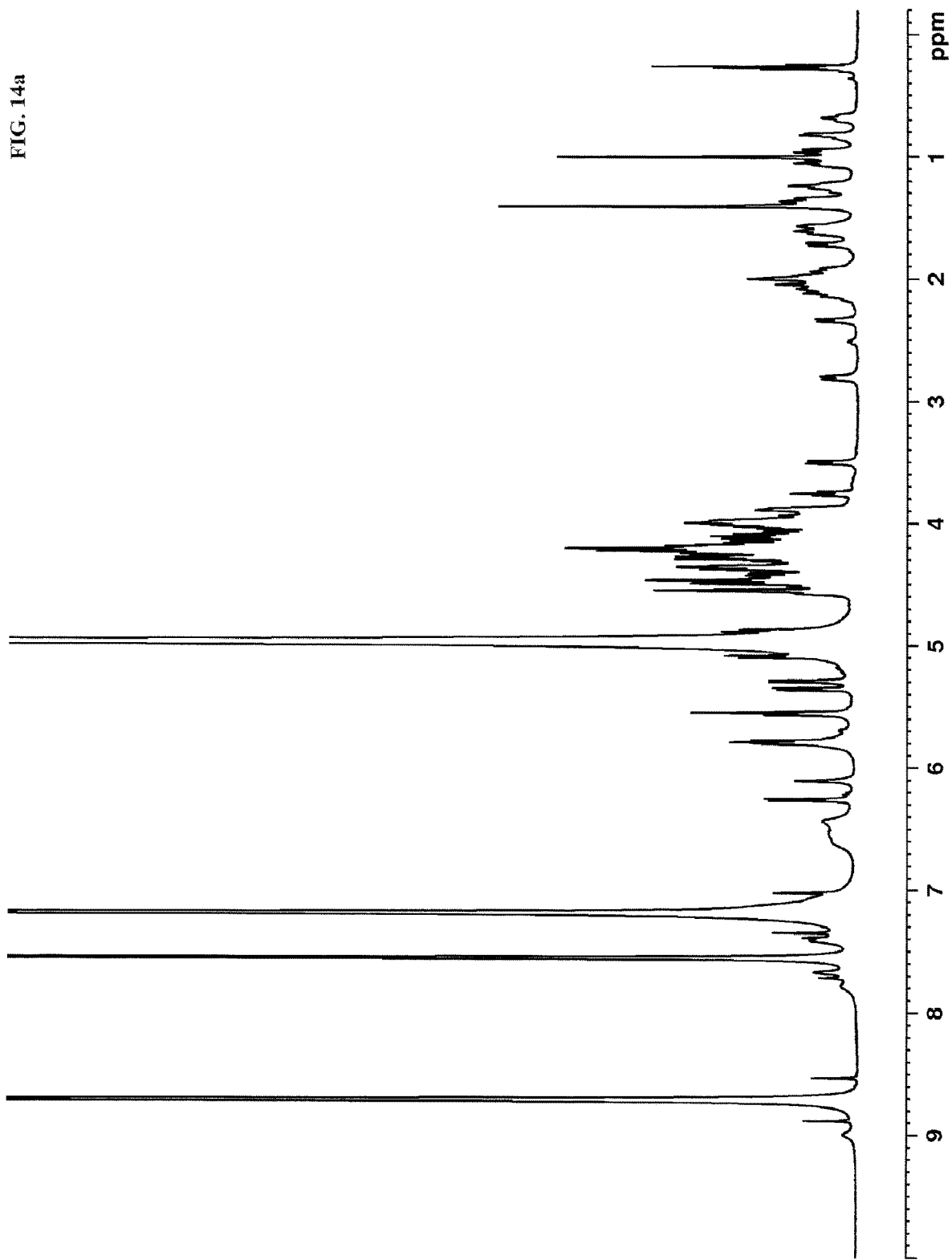
FIG. 14a shows the 1H NMR spectrum of rebaudioside 2m (500 MHz, pyridine-d5).
Figure 14B:
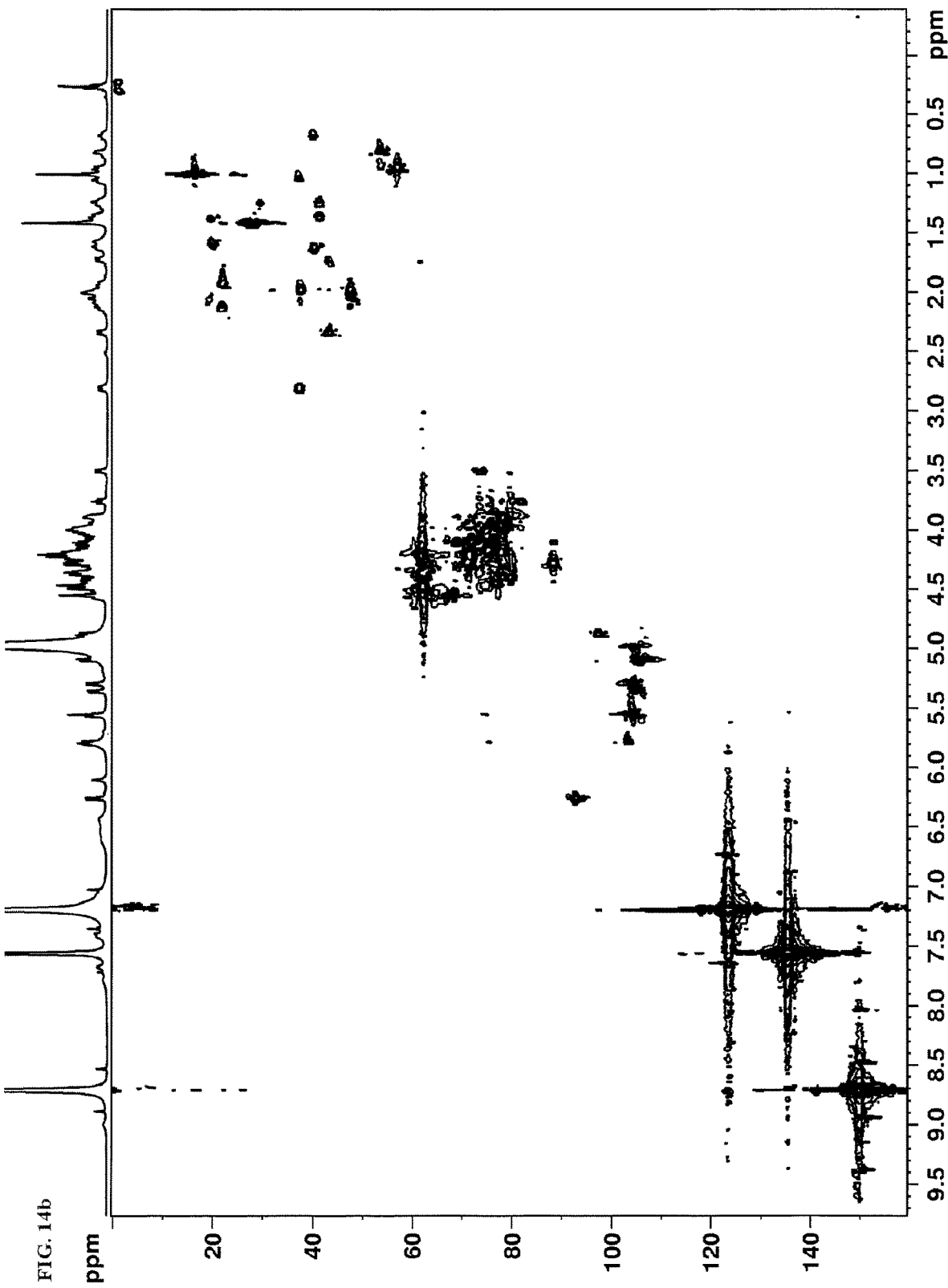
FIG. 14b shows the HSQC spectrum of rebaudioside 2m (500 MHz, pyridine-d5).
Figure 14C:
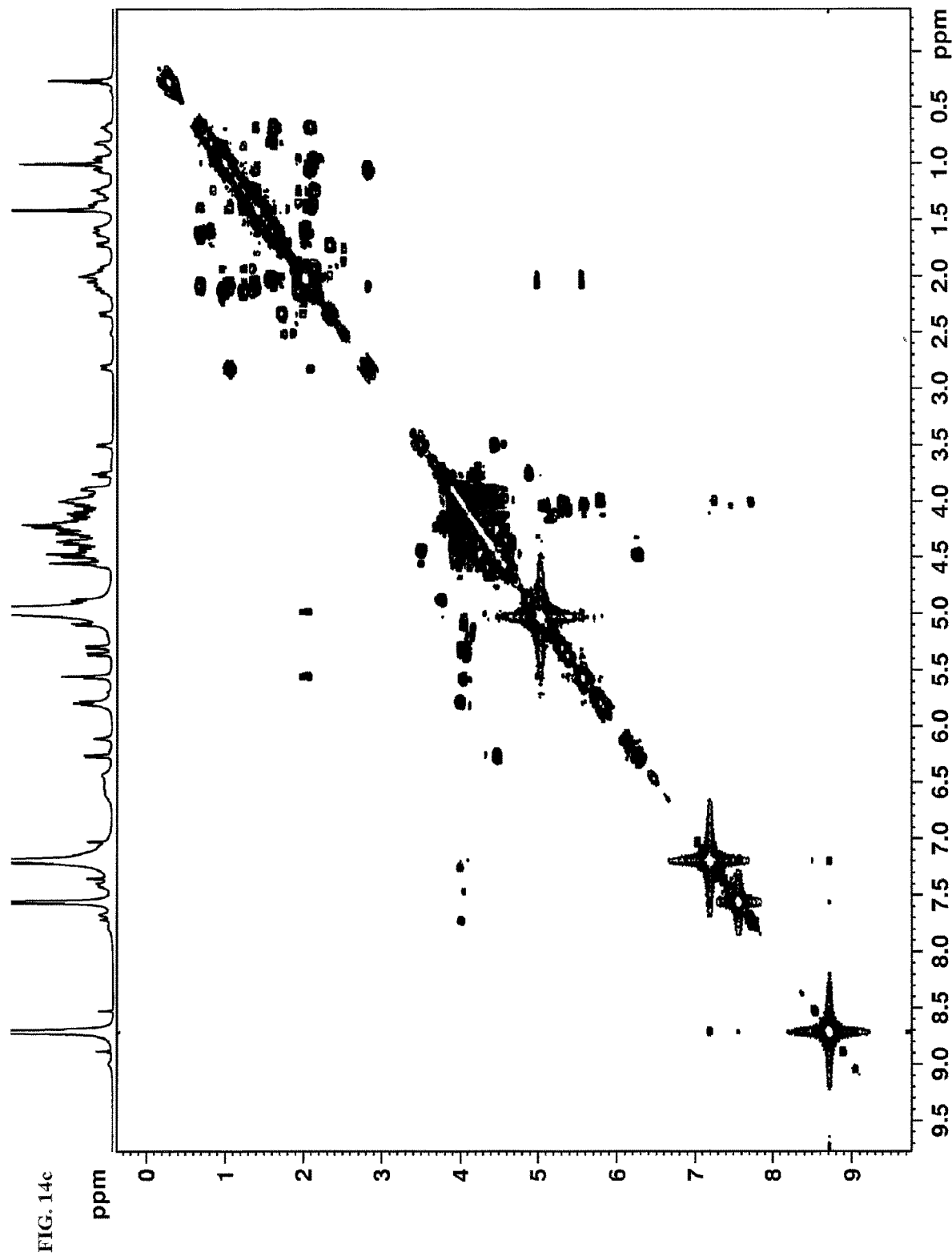
FIG. 14c shows the H,H COSY spectrum of rebaudioside 2m (500 MHz, pyridine-d5).
Figure 14D:
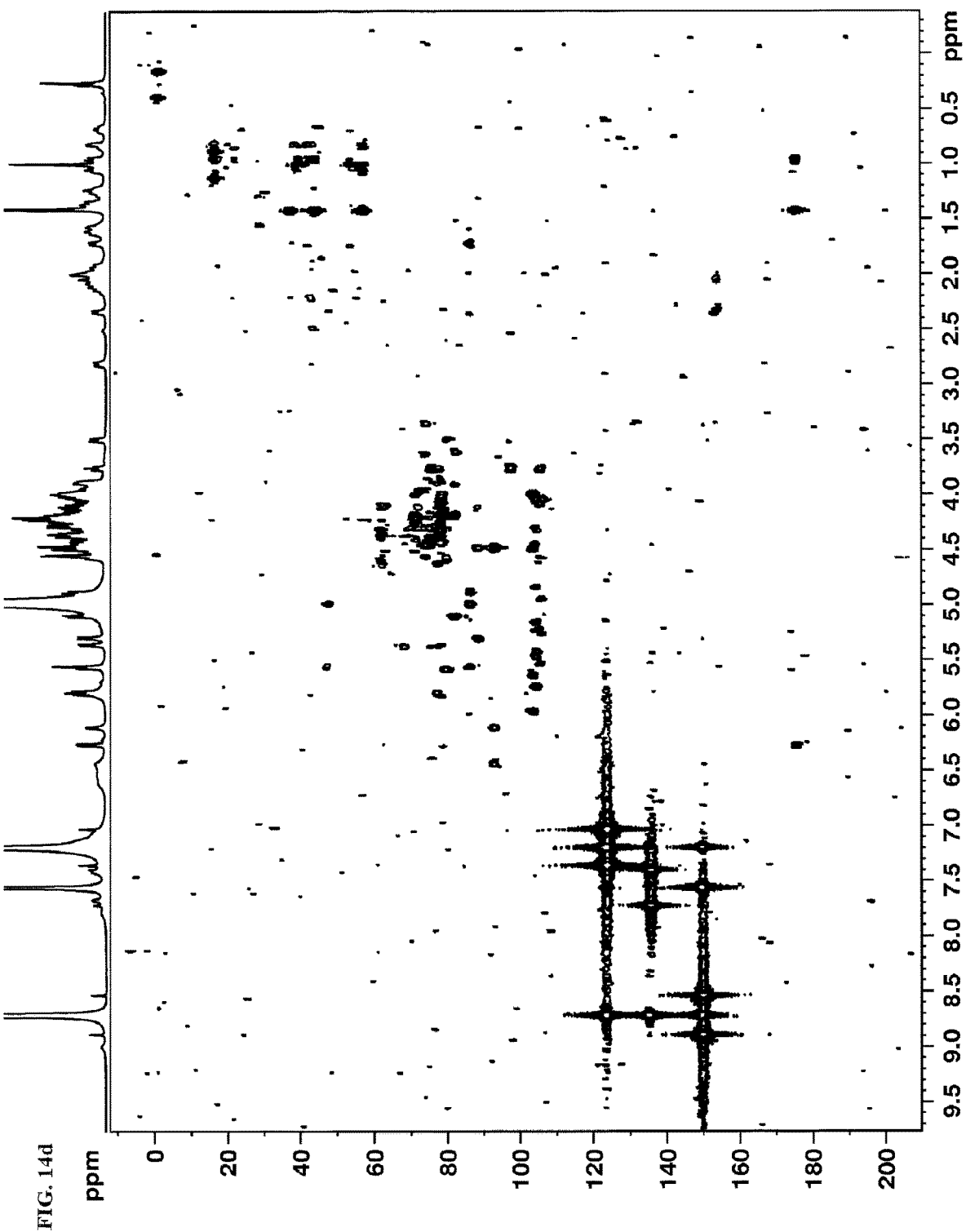
FIG. 14d shows the HMBC spectrum of rebaudioside 2m (500 MHz, pyridine-d5).

NMR experiments were performed on a Bruker 500 MHz spectrometer, with the sample dissolved in pyridine-d5. Along with signals from the sample, signals from pyridine-d5 at $\delta_C$ 123.5, 135.5, 149.9 ppm and $\delta_H$ 7.19, 7.55, 8.71 ppm were observed. $^1$H-NMR spectrum of rebaudioside 2m recorded in pyridine-d5 confirmed the excellent quality of the sample (see FIG. 14a). HSQC (see FIG. 14b) shows the presence of an exo-methylene group in the sugar region with a long-range coupling to C-15, observable in the H,H-COSY (FIG. 14c). Other deep-fielded signals of the quaternary carbons (C-13, C-16 and C-19) are detected by the HMBC (FIG. 14d). Correlation of the signals in the HSQC, HMBC and H,H-COSY reveal the presence of steviol glycoside with the following aglycone structure:

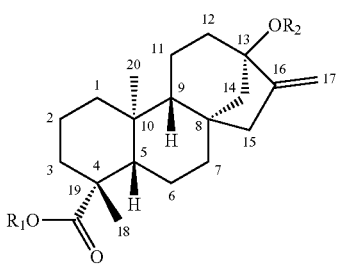

Correlation of HSQC and HMBC shows the presence seven anomeric signals, marked with 1i, 1ii, 1iii, 1iv, 1v, 1vi and 1vii. The coupling constant of the anomeric protons of about 8 Hz, the broad signals of their sugar linkage and the NOE-correlations of the anomeric protons allow the identification of these seven sugars as β-D-glucopyranosides.

Figure 14E:
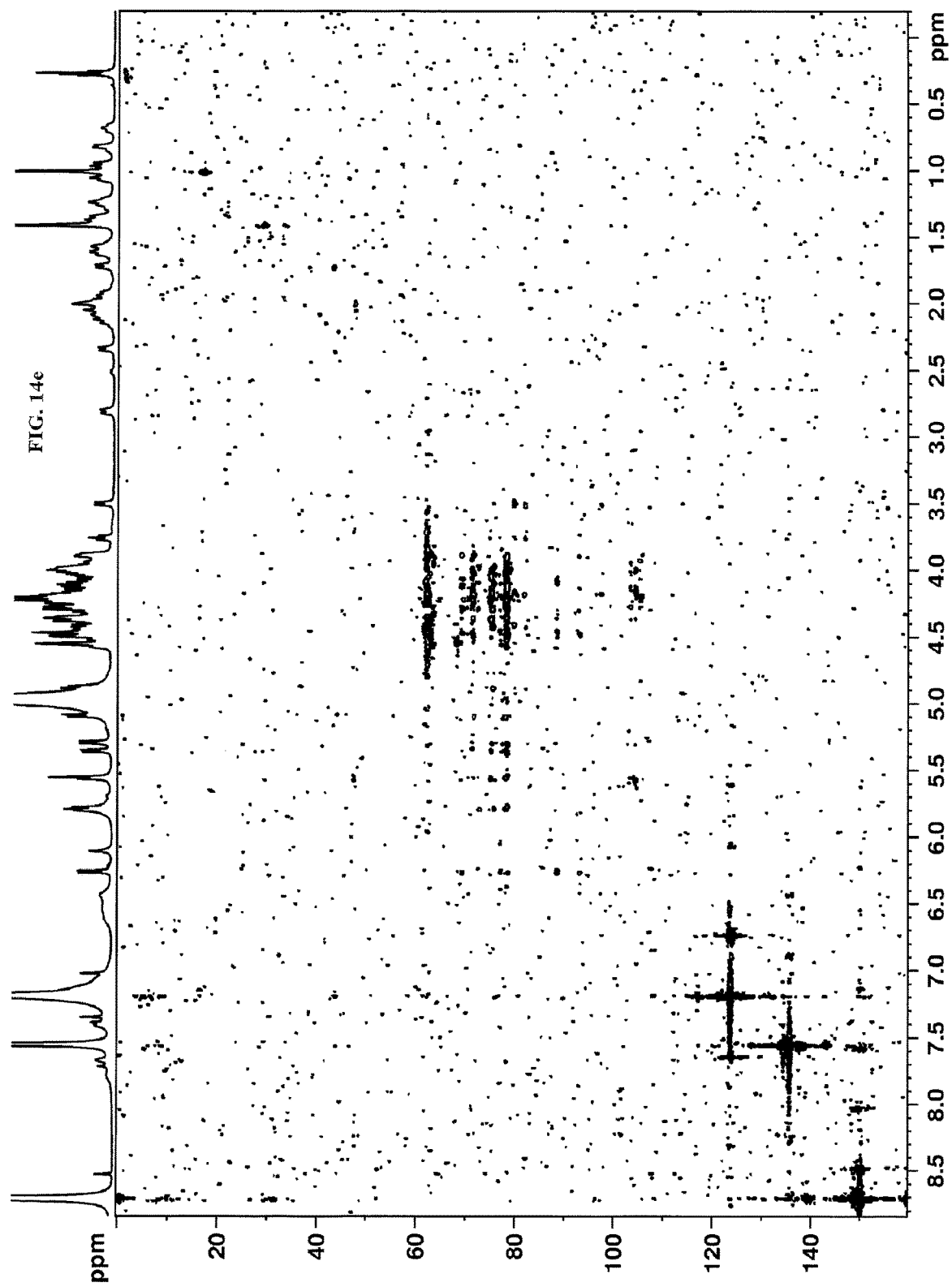
FIG. 14e shows the HSQC-TOCSY spectrum of rebaudioside 2m (500 MHz, pyridine-d5).
Figure 14F:
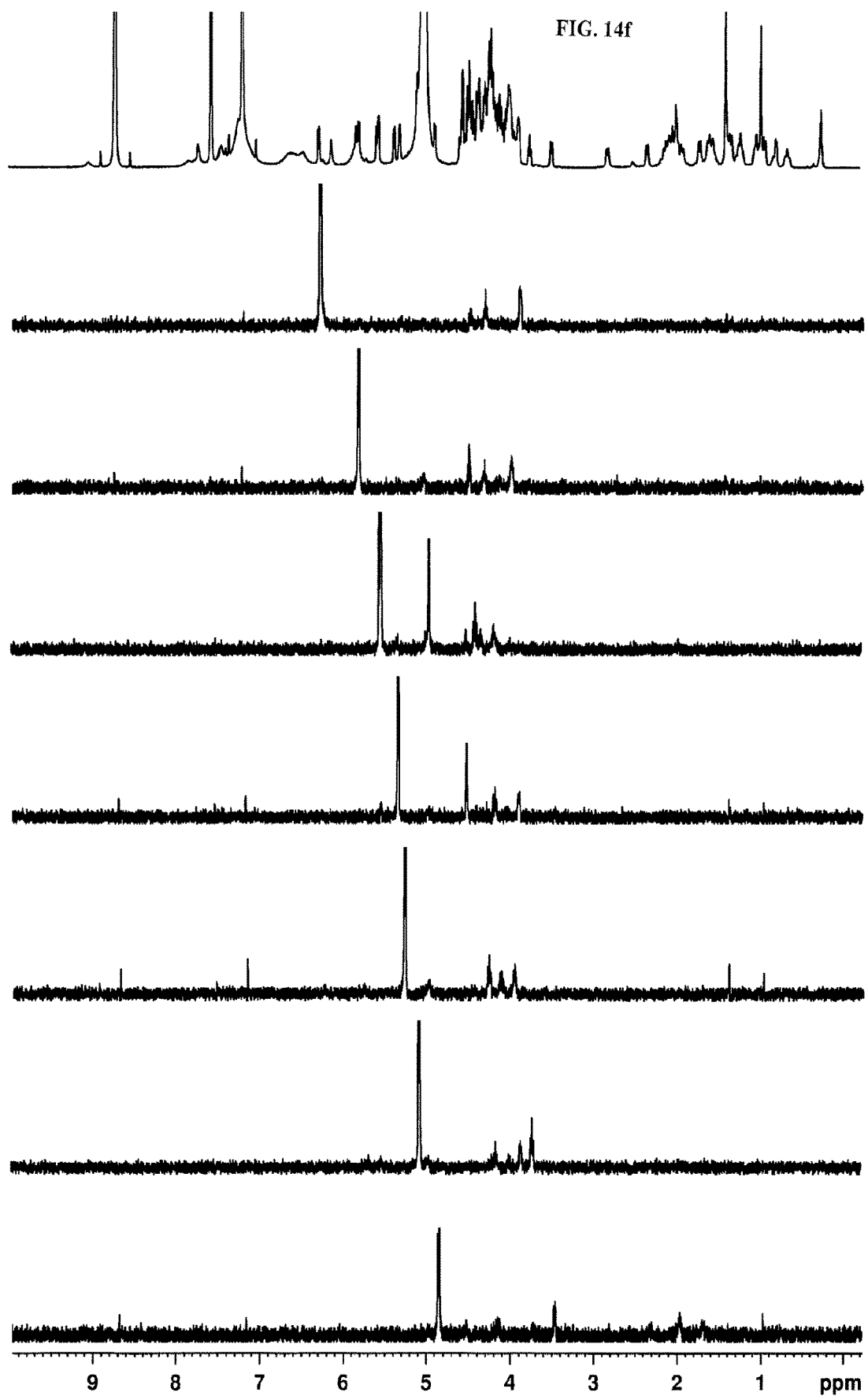
FIG. 14f shows the 1D-NOESY spectrum of rebaudioside 2m (500 MHz, pyridine-d5).

Combined data from HSQC and HMBC reveal the sugar-sugar linkages and sugar-aglycone linkages. The assignment of the sugar sequence was confirmed by using the combination of HSQC-TOCSY (FIG. 14e) and NOESY (FIG. 14f).

Altogether, results from NMR experiments above were used to assign the chemical shifts of the protons and carbons of the structure of rebaudioside 2m (see Table 7).

TABLE 7

Chemical shifts of rebaudioside 2m

| Position | $\delta_C$ [ppm] | | $\delta_H$ [ppm] | | J [Hz]/(INT) | HMBC (H -> C) |
|---|---|---|---|---|---|---|
| Aglycone moiety | | | | | | |
| 1 | 40.0 | t | 0.68 | m | | |
| | | | 1.63 | m | | |
| 2 | 19.3 | t | 1.38 | m | | |
| | | | 2.06 | m | | |
| 3 | 37.1 | t | 1.04 | m | | |
| | | | 2.81 | m | | |
| 4 | 44.0 | s | — | | | |
| 5 | 56.9 | d | 0.96 | m | | |
| 6 | 21.8 | t | 1.93 | m | | |
| | | | 2.13 | m | | |
| 7 | 41.1 | t | 1.25 | m | | |
| | | | 1.36 | m | | |
| 8 | 41.6 | s | — | | | |
| 9 | 53.6 | d | 0.82 | m | | |
| 10 | 40.4 | s | — | | | |
| 11 | 19.8 | t | 1.58 | m | | |
| | | | 1.61 | m | | |
| 12 | 37.5 | t | 1.96 | m | | |
| | | | 1.99 | m | | |
| 13 | 86.2 | s | — | | | |
| 14 | 43.1 | t | 1.73 | d | 10.9 | |
| | | | 2.34 | d | 10.9 | |
| 15 | 47.5 | t | 1.96 | d | 15.9 | 7, 8, 9, 14 |
| | | | 2.02 | d | 15.9 | |
| 16 | 153.4 | s | — | | | |
| 17 | 104.3 | t | 4.98 | br s | | 13, 15, 16 |
| | | | 5.55 | br s | | |
| 18 | 28.6 | q | 1.42 | s | (3H) | 3, 4, 5, 19 |
| 19 | 175.3 | s | — | | | |
| 20 | 16.3 | q | 1.01 | s | (3H) | 1, 5, 9, 10 |

| Position | $\delta_C$ [ppm] | | $\delta_H$ [ppm] | | J [Hz]/ (Int) | HMBC (H → C) | NOE (H → H) |
|---|---|---|---|---|---|---|---|
| Sugar moiety | | | | | | | |
| Sugar I: β-D-Glucopyranoside | | | | | | | |
| $1^i$ | 97.3 | d | 4.88 | d | 7.8 | 13 | $3^i$, $5^i$ |
| $2^i$ | 81.9 | d | 3.75 | m | | | |
| $3^i$ | 75.3 | d | 4.18 | d | | | |
| $4^i$ | 79.6 | d | 4.40 | m | | | |
| $5^i$ | 74.0 | d | 3.50 | m | | | |
| $6^i$ | 67.9 | t | 4.55 | m | (2H) | | $5^i$, $1^{iv}$ |
| Sugar II: β-D-Glucopyranoside | | | | | | | |
| $1^{ii}$ | 105.7 | d | 5.10 | d | 8.0 | $2^i$ | $2^i$, $3^{ii}$, $5^{ii}$ |
| $2^{ii}$ | 74.6 | d | 4.02 | m | | | |
| $3^{ii}$ | 77.9 | d | 4.18 | d | | | |
| $4^{ii}$ | 71.4 | d | 4.20 | m | | | |
| $5^{ii}$ | 78.1 | d | 3.87 | m | | | |
| $6^{ii}$ | 61.8 | t | 4.19 | m | | | |
| | | | 4.46 | m | | | |

TABLE 7-continued

Chemical shifts of rebaudioside 2m

Sugar III: β-D-Glucopyranoside

| | | | | | | | |
|---|---|---|---|---|---|---|---|
| $1^{iii}$ | 104.3 | d | 5.57 | d | 8.1 | $4^i$ | $4^i$, $3^{iii}$, $5^{iii}$ |
| $2^{iii}$ | 75.2 | d | 4.03 | m | | | |
| $3^{iii}$ | 77.1 | d | 4.35 | m | | | |
| $4^{iii}$ | 71.4 | d | 4.23 | m | | | |
| $5^{iii}$ | 76.8 | d | 4.19 | m | | | |
| $6^{iii}$ | 63.3 | t | 4.34 | m | | | |
| | | | 4.56 | m | | | |

Sugar IV: β-D-Glucopyranoside

| | | | | | | | |
|---|---|---|---|---|---|---|---|
| $1^{iv}$ | 104.9 | d | 5.37 | d | 8.0 | $6^i$ | $6^i$, $3^{iv}$, $5^{iv}$ |
| $2^{iv}$ | 75.0 | d | 4.06 | m | | | |
| $3^{iv}$ | 78.3 | d | 4.29 | m | | | |
| $4^{iv}$ | 71.1 | d | 4.27 | m | | | |
| $5^{iv}$ | 78.0 | d | 3.99 | m | | | |
| $6^{iv}$ | 62.1 | t | 4.22 | m | | | |
| | | | 4.36 | m | | | |

Sugar V: β-D-Glucopyranoside

| | | | | | | | |
|---|---|---|---|---|---|---|---|
| $1^v$ | 92.8 | d | 6.27 | d | 8.1 | 19 | $3^v$, $5^v$ |
| $2^v$ | 77.0 | d | 4.47 | m | | | |
| $3^v$ | 88.2 | d | 4.28 | m | | | |
| $4^v$ | 69.0 | d | 4.10 | m | | | |
| $5^v$ | 78.1 | d | 3.88 | m | | | |
| $6^v$ | 61.7 | t | 4.22 | m | | | |
| | | | 4.36 | m | | | |

Sugar VI: β-D-Glucopyranoside

| | | | | | | | |
|---|---|---|---|---|---|---|---|
| $1^{vi}$ | 103.2 | d | 5.78 | d | 7.8 | $2^v$ | $2^v$, $3^{vi}$, $5^{vi}$ |
| $2^{vi}$ | 75.6 | d | 3.99 | m | | | |
| $3^{vi}$ | 78.2 | d | 4.25 | m | | | |
| $4^{vi}$ | 72.7 | d | 4.10 | m | | | |
| $5^{vi}$ | 78.0 | d | 3.93 | m | | | |
| $6^{vi}$ | 62.6 | t | 4.29 | m | | | |
| | | | 4.40 | m | | | |

Sugar VII: β-D-Glucopyranoside

| | | | | | | | |
|---|---|---|---|---|---|---|---|
| $1^{vii}$ | 104.4 | d | 5.30 | d | 8.0 | $3^v$ | $3^v$, $3^{vii}$, $5^{vii}$ |
| $2^{vii}$ | 75.3 | d | 4.00 | m | | | |
| $3^{vii}$ | 78.1 | d | 4.12 | m | | | |
| $4^{vii}$ | 71.2 | d | 4.12 | m | | | |
| $5^{vii}$ | 78.1 | d | 3.97 | m | | | |
| $6^{vii}$ | 62.0 | t | 4.26 | m | | | |
| | | | 4.46 | m | | | |

Correlation of all NMR results indicates rebaudioside 2m with seven β-D-glucoses attached to steviol aglycone, as depicted with the following chemical structure:

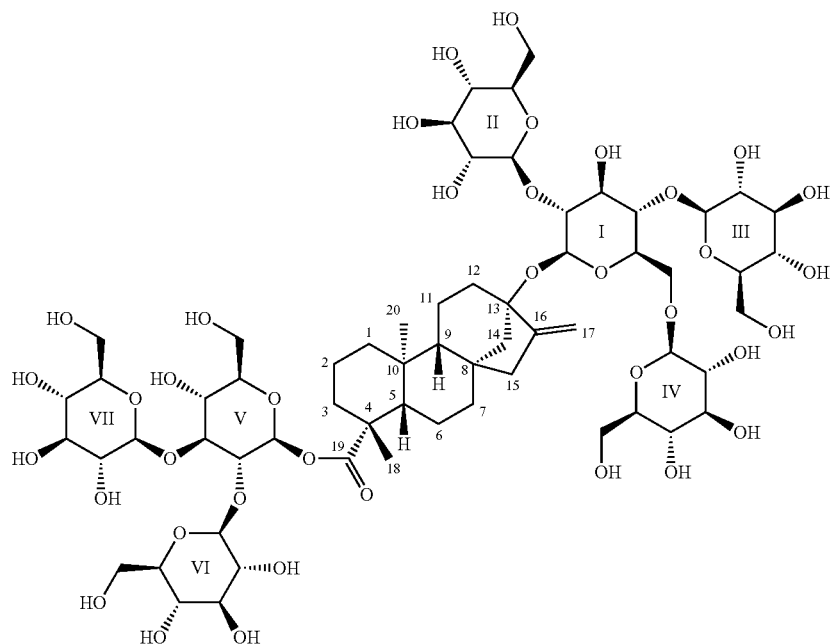

Figure 14G:
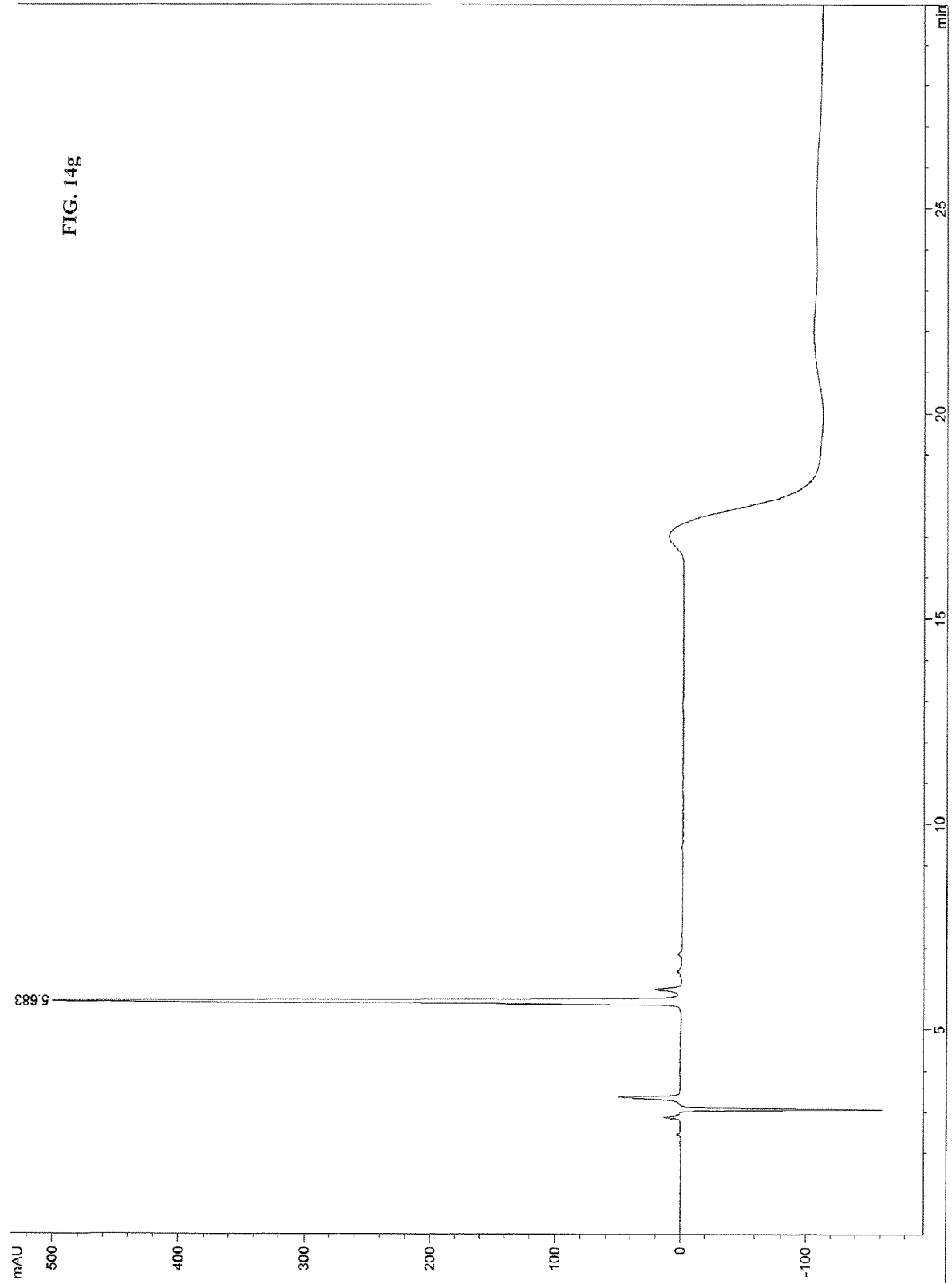
FIG. 14g shows the LC chromatogram of rebaudioside 2m.
Figure 14H:
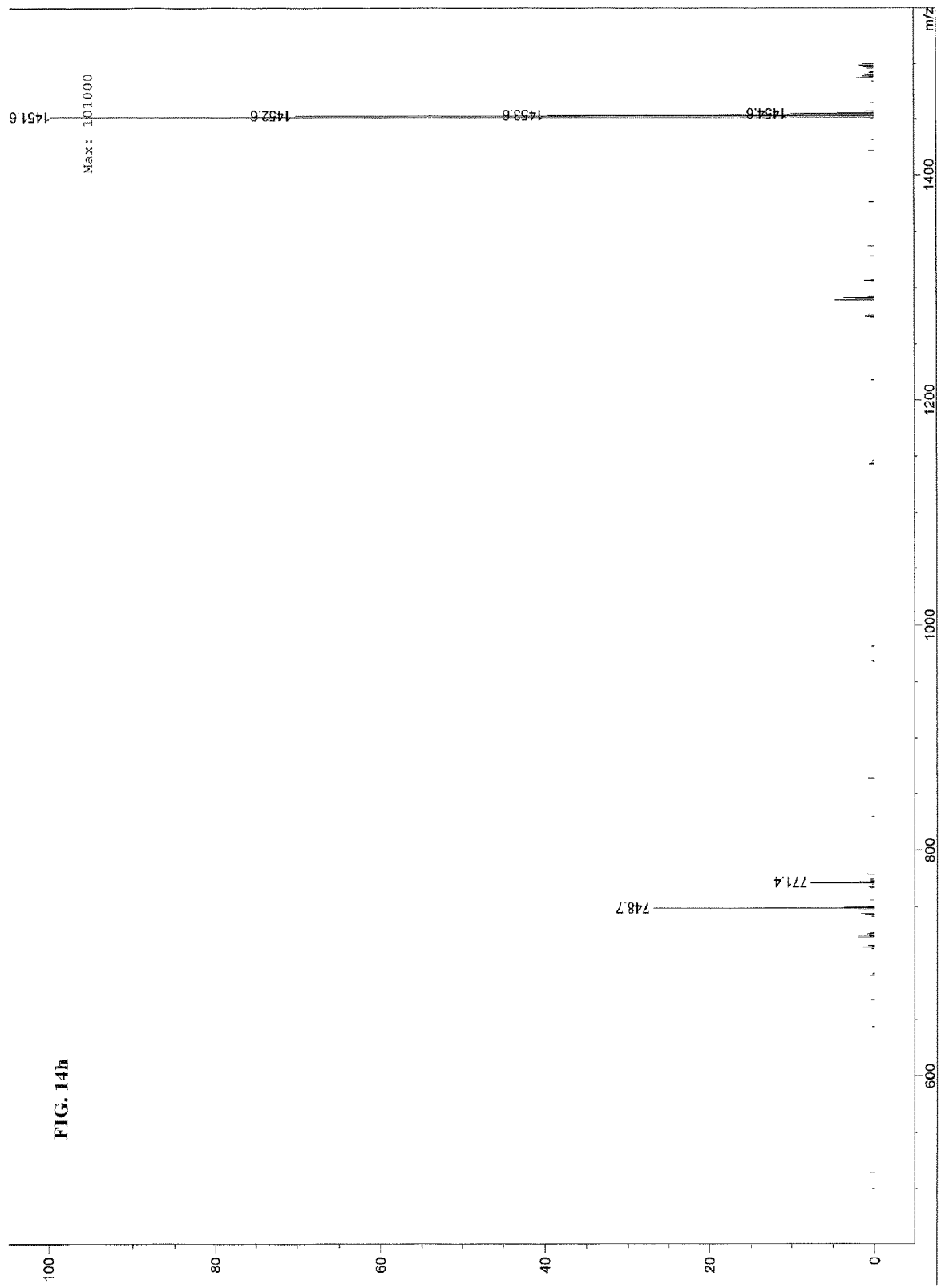
FIG. 14h shows the mass spectrum of rebaudioside 2m.

LCMS (FIG. 14g and FIG. 14h) analysis of rebaudioside 2m showed a [M-H]⁻ ion at m/z 1451.6, in good agreement with the expected molecular formula of $C_{62}H_{100}O_{38}$ (calculated for $[C_{62}H_{99}O_{38}]^-$ monoisotopic ion: 1451.6). The MS data confirms that rebaudioside 2m has a molecular formula of $C_{62}H_{100}O_{38}$. LCMS analysis was performed in the conditions listed in Table 6.

Example 10

Structure Elucidation of Rebaudioside M5

Figure 15A:
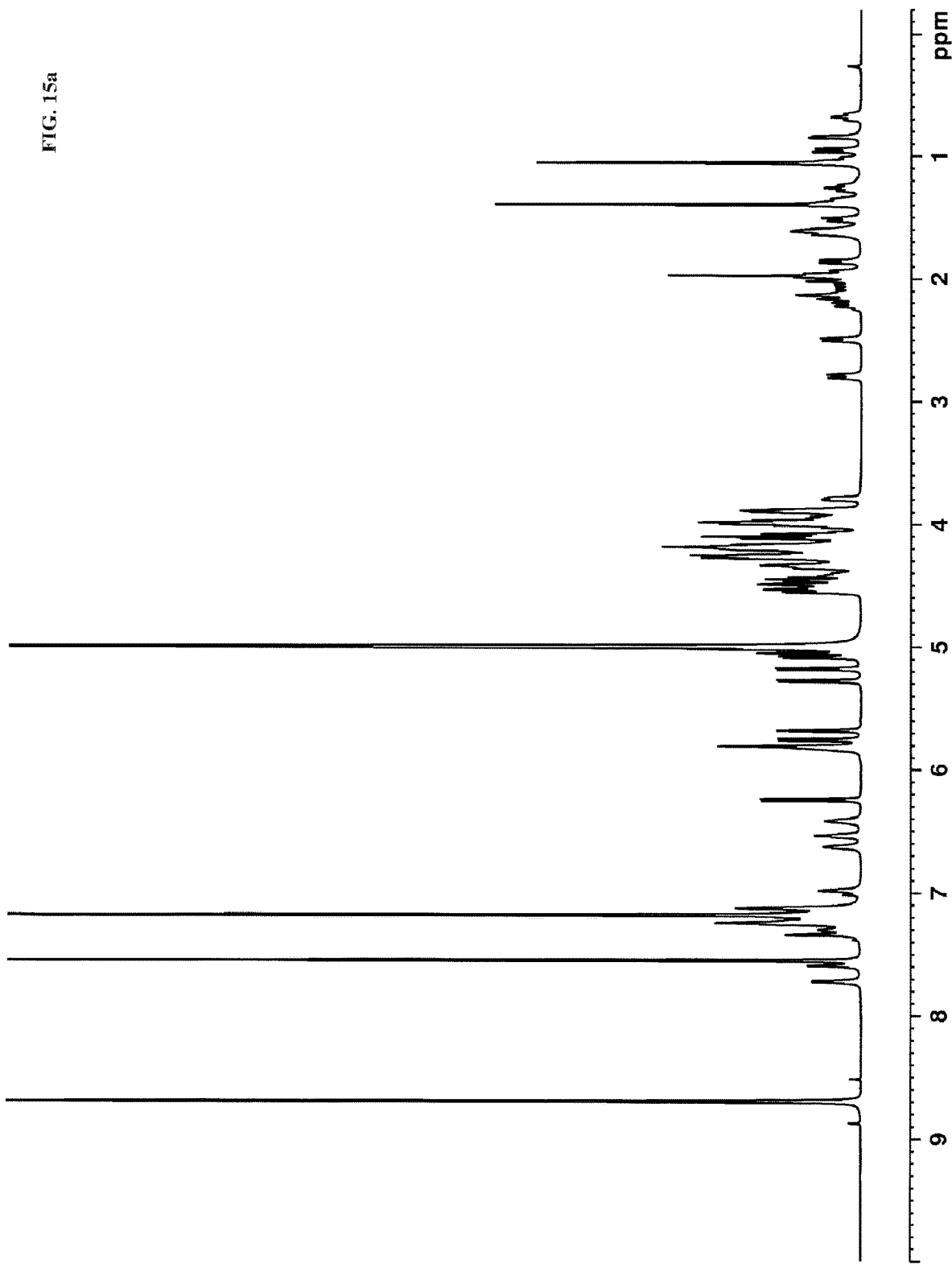
FIG. 15a shows the 1H NMR spectrum of rebaudioside M5 (500 MHz, pyridine-d5).
Figure 15B:
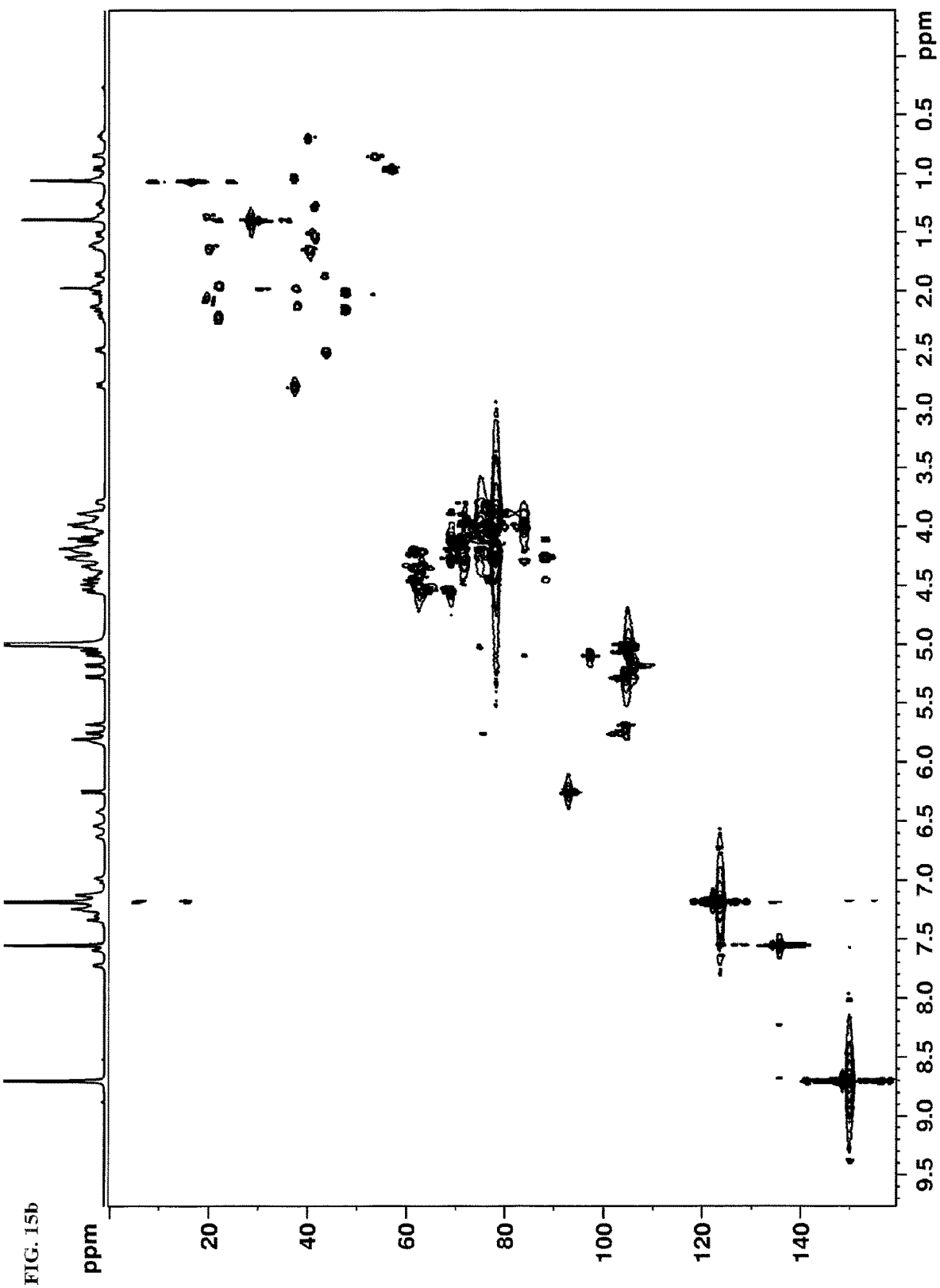
FIG. 15b shows the HSQC spectrum of rebaudioside M5 (500 MHz, pyridine-d5).
Figure 15C:
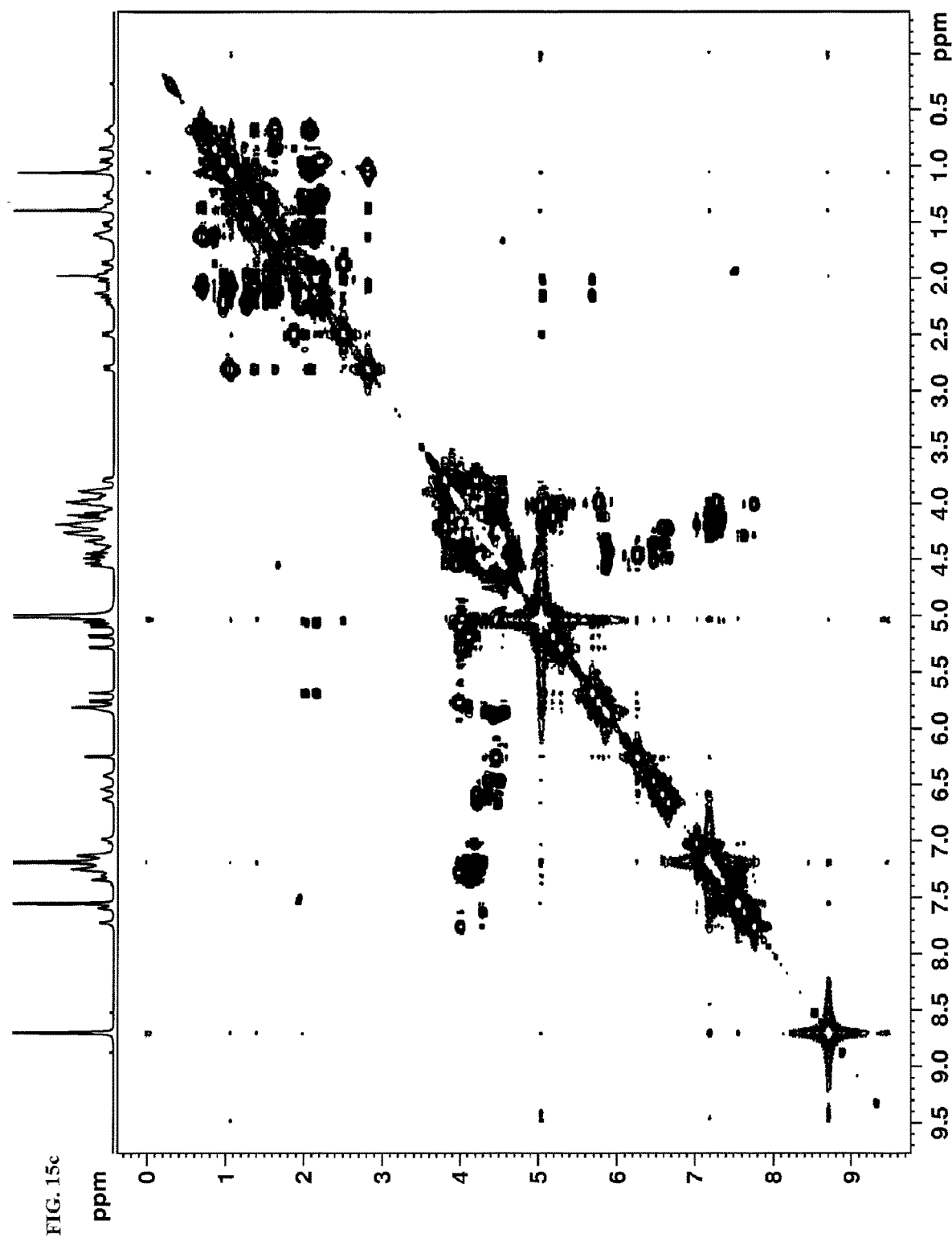
FIG. 15c shows the H,H COSY spectrum of rebaudioside M5 (500 MHz, pyridine-d5).
Figure 15D:
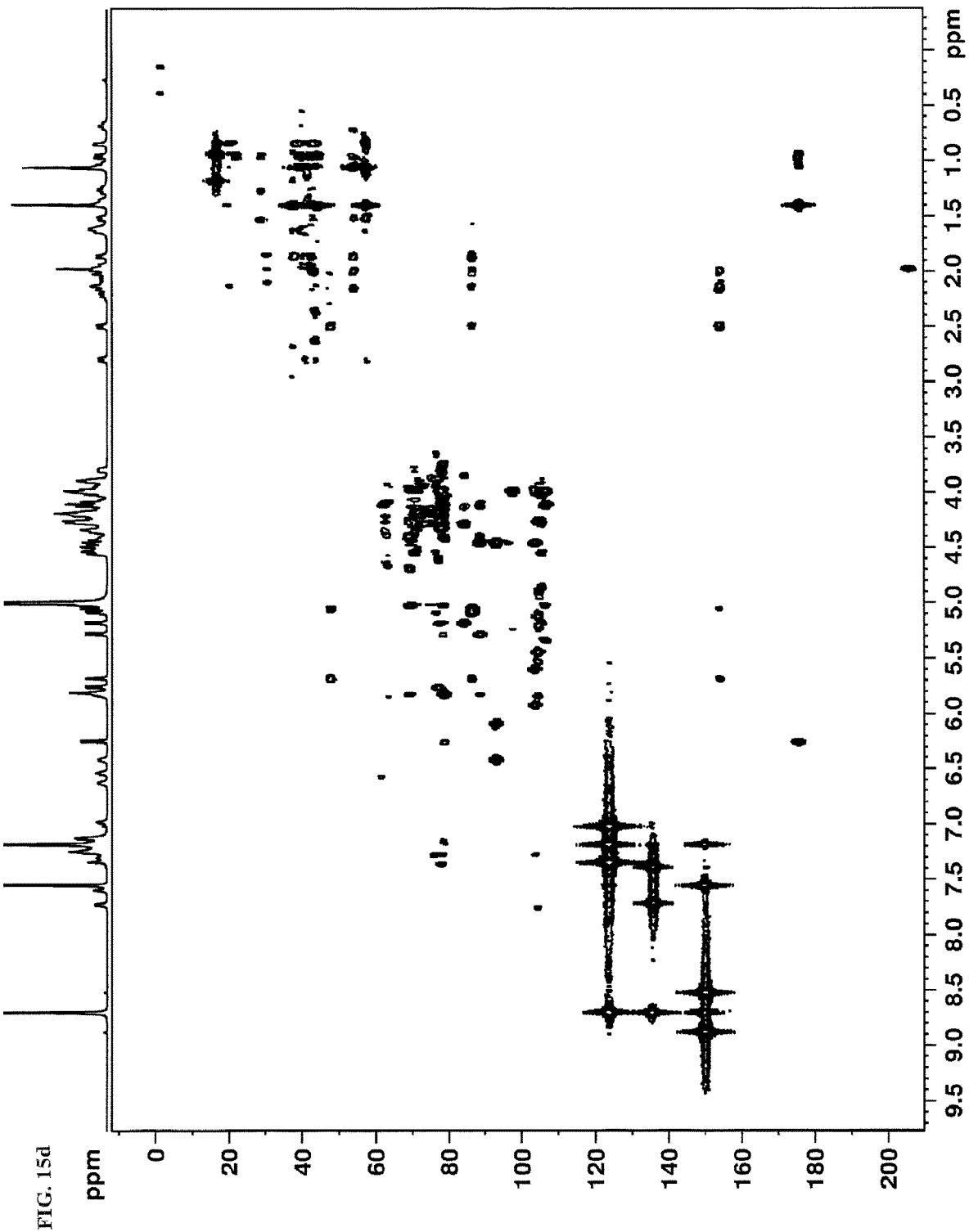
FIG. 15d shows the HMBC spectrum of rebaudioside M5 (500 MHz, pyridine-d5).

NMR experiments were performed on a Bruker 500 MHz spectrometer, with the sample dissolved in pyridine-d5. Along with signals from the sample, signals from pyridine-d5 at $\delta_C$ 123.5, 135.5, 149.9 ppm and $\delta_H$ 7.19, 7.55, 8.71 ppm were observed. ¹H-NMR spectrum of rebaudioside M5 recorded in pyridine-d₅ confirmed the excellent quality of the sample (see FIG. 15a). HSQC (see FIG. 15b) shows the presence of an exo-methylene group in the sugar region with a long-range coupling to C-15, observable in the H,H-COSY (FIG. 15c). Other deep-fielded signals of the quaternary carbons (C-13, C-16 and C-19) are detected by the HMBC (FIG. 15d). Correlation of the signals in the HSQC, HMBC and H,H-COSY reveal the presence of steviol glycoside with the following aglycone structure:

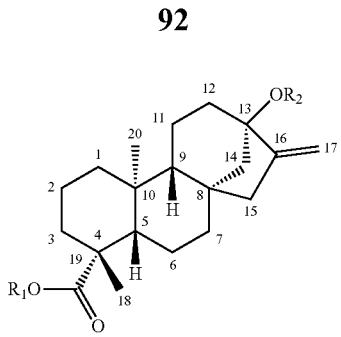

Correlation of HSQC and HMBC shows the presence six anomeric signals, marked with 1i, 1ii, 1iii, 1iv, 1v, and 1vi. The coupling constant of the anomeric protons of about 8 Hz, the broad signals of their sugar linkage and the NOE-correlations of the anomeric protons allow the identification of these six sugars as β-D-glucopyranosides.

Figure 15E:
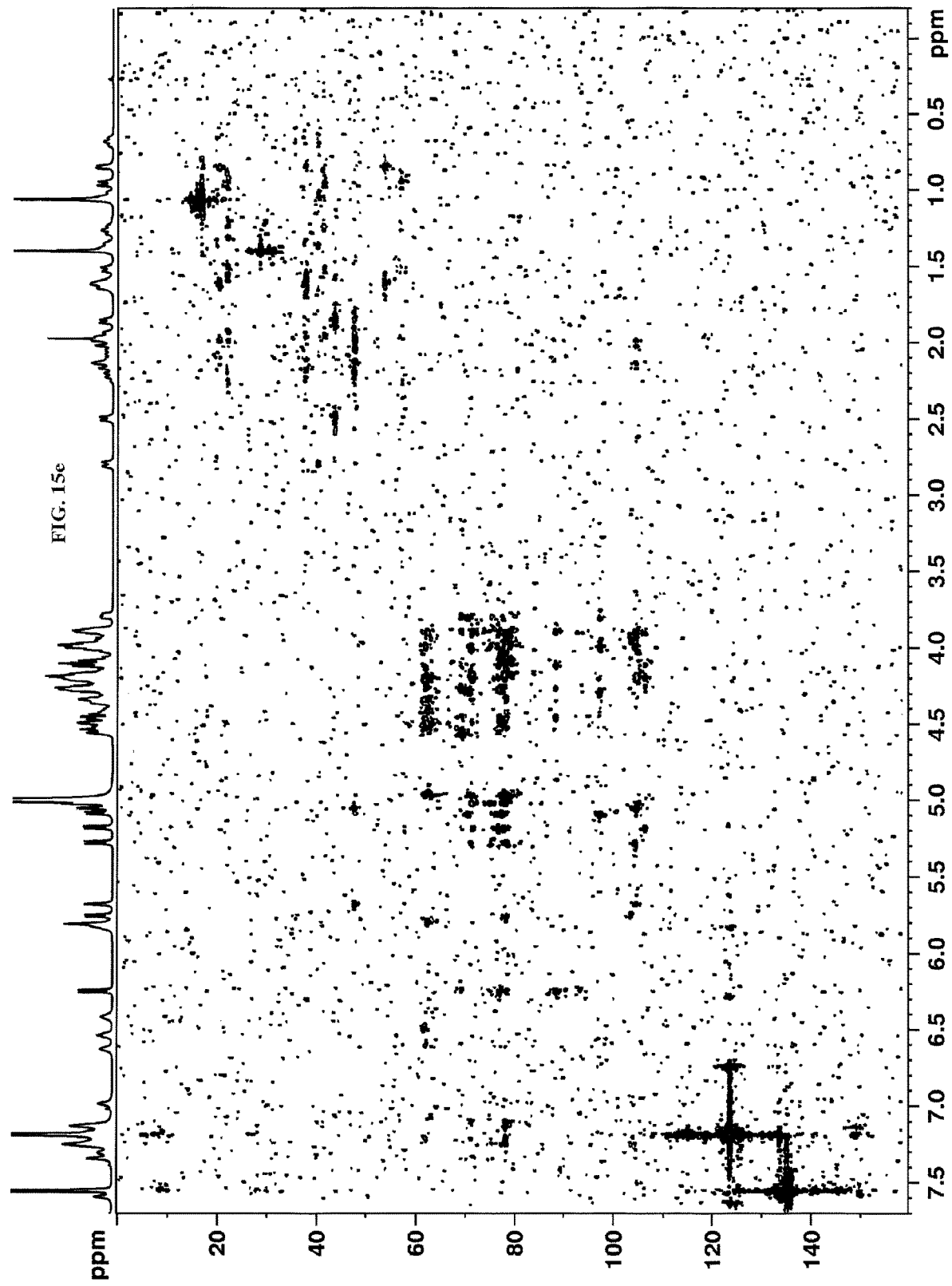
FIG. 15e shows the HSQC-TOCSY spectrum of rebaudioside M5 (500 MHz, pyridine-d5).
Figure 15F:
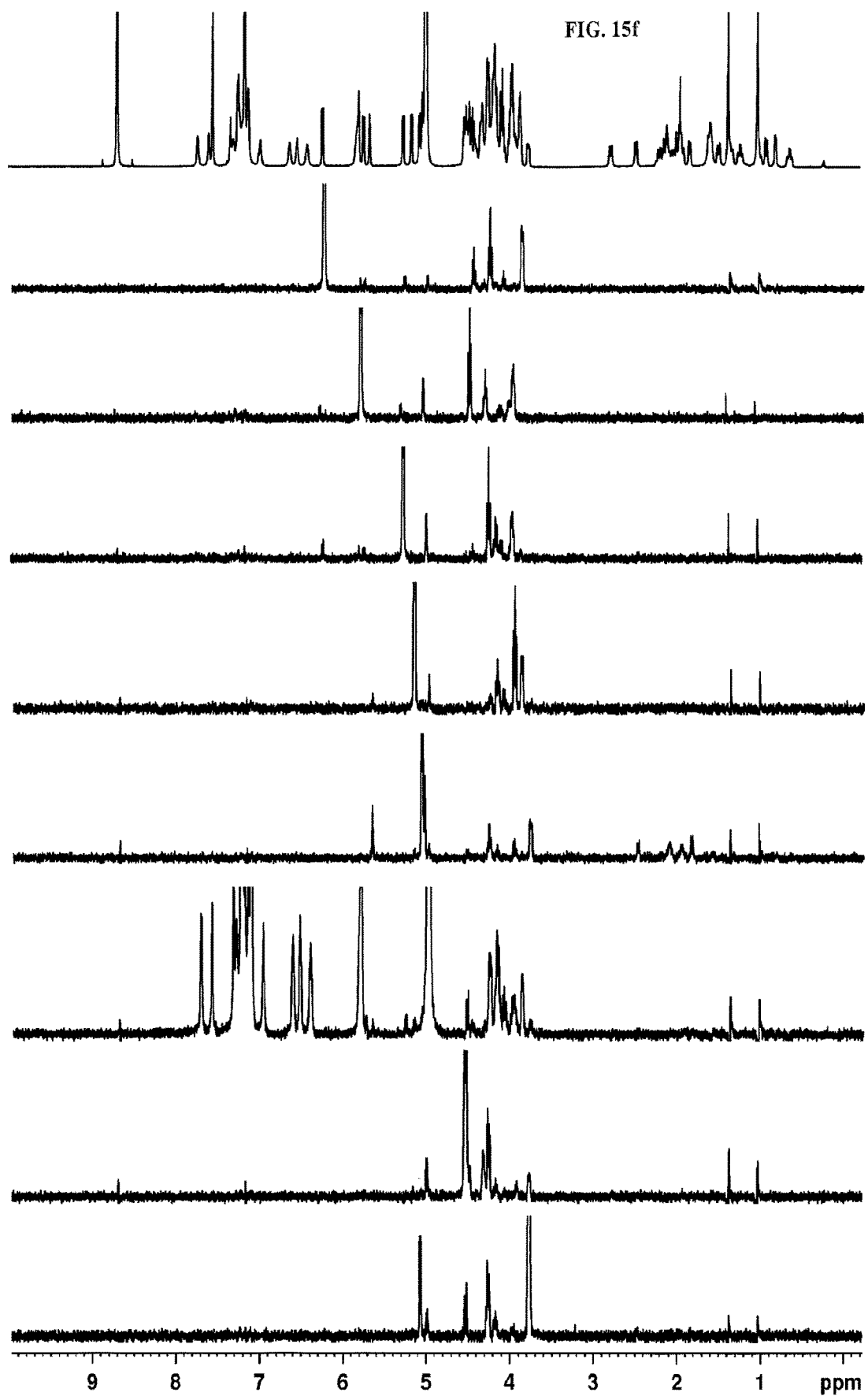
FIG. 15f shows the 1D-NOESY spectrum of rebaudioside M5 (500 MHz, pyridine-d5).

Combined data from HSQC and HMBC reveal the sugar-sugar linkages and sugar-aglycone linkages. The assignment of the sugar sequence was confirmed by using the combination of HSQC-TOCSY (FIG. 15e) and NOESY (FIG. 15f).

Altogether, results from NMR experiments above were used to assign the chemical shifts of the protons and carbons of the structure of rebaudioside M5 (see Table 8).

TABLE 8

Chemical shifts of rebaudioside M5

| Position | $\delta_C$ [ppm] | | $\delta_H$ [ppm] | J [Hz]/(INT) | HMBC (H -> C) |
|---|---|---|---|---|---|
| Aglycone moiety | | | | | |
| 1 | 39.9 | t | 0.68 m | | |
|  |  |  | 1.63 m | | |
| 2 | 19.4 | t | 1.36 m | | |
|  |  |  | 2.05 m | | |
| 3 | 37.2 | t | 1.03 m | | |
|  |  |  | 2.80 m | | |
| 4 | 44.2 | s | — | | |
| 5 | 57.1 | d | 0.95 m | | |
| 6 | 21.7 | t | 1.95 m | | |
|  |  |  | 2.21 m | | |
| 7 | 41.2 | t | 1.26 m | | |
|  |  |  | 1.51 m | | |
| 8 | 42.3 | s | — | | |
| 9 | 53.6 | d | 0.85 m | | |
| 10 | 40.3 | s | — | | |
| 11 | 19.8 | t | 1.61 m | | |
|  |  |  | 1.63 m | | |
| 12 | 37.6 | t | 1.97 m | | |
|  |  |  | 2.12 m | | |
| 13 | 85.9 | s | — | | |
| 14 | 43.4 | t | 1.86 d | 11.0 | |
|  |  |  | 2.50 d | 11.0 | |
| 15 | 47.6 | t | 2.00 d | 16.0 | 7, 8, 9, 14 |
|  |  |  | 2.15 d | 16.0 | |
| 16 | 153.8 | s | — | | |
| 17 | 104.5 | t | 5.05 br s | | 13, 15, 16 |
|  |  |  | 5.68 br s | | |
| 18 | 28.4 | q | 1.40 s | (3H) | 3, 4, 5, 19 |
| 19 | 175.4 | s | — | | |
| 20 | 16.2 | q | 1.06 s | (3H) | 1, 5, 9, 10 |

TABLE 8-continued

| | Chemical shifts of rebaudioside M5 | | | | | |
|---|---|---|---|---|---|---|
| Position | $\delta_C$ [ppm] | | $\delta_H$ [ppm] | J [Hz]/ (Int) | HMBC (H → C) | NOE (H → H) |

Sugar moiety

Sugar I: β-D-Glucopyranoside

| | | | | | | |
|---|---|---|---|---|---|---|
| $1^i$ | 97.2 | d | 5.09 | d | 7.7 | 13 | $3^i, 5^i$ |
| $2^i$ | 83.9 | d | 4.00 | m | | | |
| $3^i$ | 77.5 | d | 4.29 | m | | | |
| $4^i$ | 70.7 | d | 4.19 | m | | | |
| $5^i$ | 76.5 | d | 3.79 | m | | | $1^i, 3^i, 6^i$ |
| $6^i$ | 69.0 | t | 4.27 | m | | | $5^i, 1^{iii}$ |
| | | | 4.55 | m | | | |

Sugar II: β-D-Glucopyranoside

| | | | | | | |
|---|---|---|---|---|---|---|
| $1^{ii}$ | 105.9 | d | 5.18 | d | 7.8 | $2^i$ | $2^i, 3^{ii}, 5^{ii}$ |
| $2^{ii}$ | 76.1 | d | 4.11 | m | | | |
| $3^{ii}$ | 77.6 | d | 4.19 | m | | | |
| $4^{ii}$ | 71.4 | d | 4.27 | m | | | |
| $5^{ii}$ | 78.1 | d | 3.91 | m | | | |
| $6^{ii}$ | 62.8 | t | 4.34 | m | | | |
| | | | 4.55 | m | | | |

Sugar III: β-D-Glucopyranoside

| | | | | | | |
|---|---|---|---|---|---|---|
| $1^{iii}$ | 105.0 | d | 5.01 | d | 8.0 | $6^i$ | $6^i, 3^{iii}, 5^{iii}$ |
| $2^{iii}$ | 74.9 | d | 4.02 | m | | | |
| $3^{iii}$ | 78.0 | d | 4.20 | m | | | |
| $4^{iii}$ | 70.8 | d | 4.16 | m | | | |
| $5^{iii}$ | 78.3 | d | 3.92 | m | | | |
| $6^{iii}$ | 62.4 | t | 4.42 | m | | | |
| | | | 4.50 | m | | | |

Sugar IV: β-D-Ghicopyranoside

| | | | | | | |
|---|---|---|---|---|---|---|
| $1^{iv}$ | 92.8 | d | 6.25 | d | 7.8 | 19 | $3^{iv}, 5^{iv}$ |
| $2^{iv}$ | 77.0 | d | 4.44 | m | | | |
| $3^{iv}$ | 88.1 | d | 4.27 | m | | | |
| $4^{iv}$ | 69.0 | d | 4.11 | m | | | |
| $5^{iv}$ | 78.1 | d | 3.88 | m | | | |
| $6^{iv}$ | 61.7 | t | 4.21 | m | | | |
| | | | 4.34 | m | | | |

Sugar V: β-D-Ghicopyranoside

| | | | | | | |
|---|---|---|---|---|---|---|
| $1^v$ | 103.4 | d | 5.75 | d | 8.1 | 2 | $2^{iv}, 3^v, 5^v$ |
| $2^v$ | 75.5 | d | 3.98 | m | | | |
| $3^v$ | 78.1 | d | 4.27 | m | | | |
| $4^v$ | 71.2 | d | 4.12 | m | | | |
| $5^v$ | 77.9 | d | 3.95 | m | | | |
| $6^v$ | 62.1 | t | 4.34 | m | | | |
| | | | 4.50 | m | | | |

| Position | $\delta_C$ [ppm] | | $\delta_H$ [ppm] | J [Hz]/ (Int) | HMBC (H → C) | NOE (H → H) |
|---|---|---|---|---|---|---|

Sugar moiety

Sugar VI: β-D-Glucopyranoside

| | | | | | | |
|---|---|---|---|---|---|---|
| $1^{vi}$ | 104.4 | d | 5.28 | d | 7.8 | $3^{iv}$ | $3^{iv}, 3^{iv}, 5^{iv}$ |
| $2^{vi}$ | 75.1 | d | 4.00 | m | | | |
| $3^{vi}$ | 78.0 | d | 4.18 | m | | | |
| $4^{vi}$ | 71.2 | d | 4.20 | m | | | |
| $5^{vi}$ | 78.1 | d | 3.99 | m | | | |
| $6^{vi}$ | 61.8 | t | 4.34 | m | | | |
| | | | 4.50 | m | | | |

Correlation of all NMR results indicates rebaudioside M5 with six β-D-glucoses attached to steviol aglycone, as depicted with the following chemical structure:

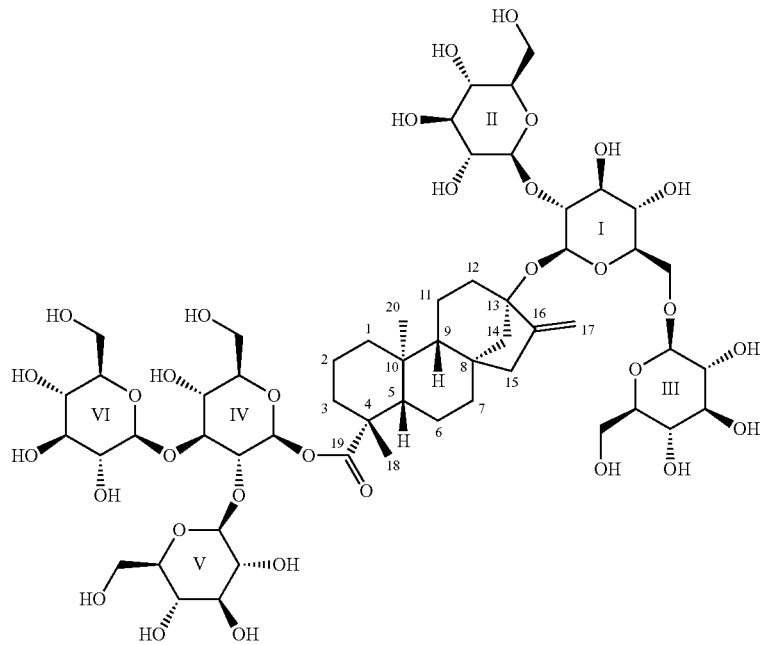

Figure 15G:
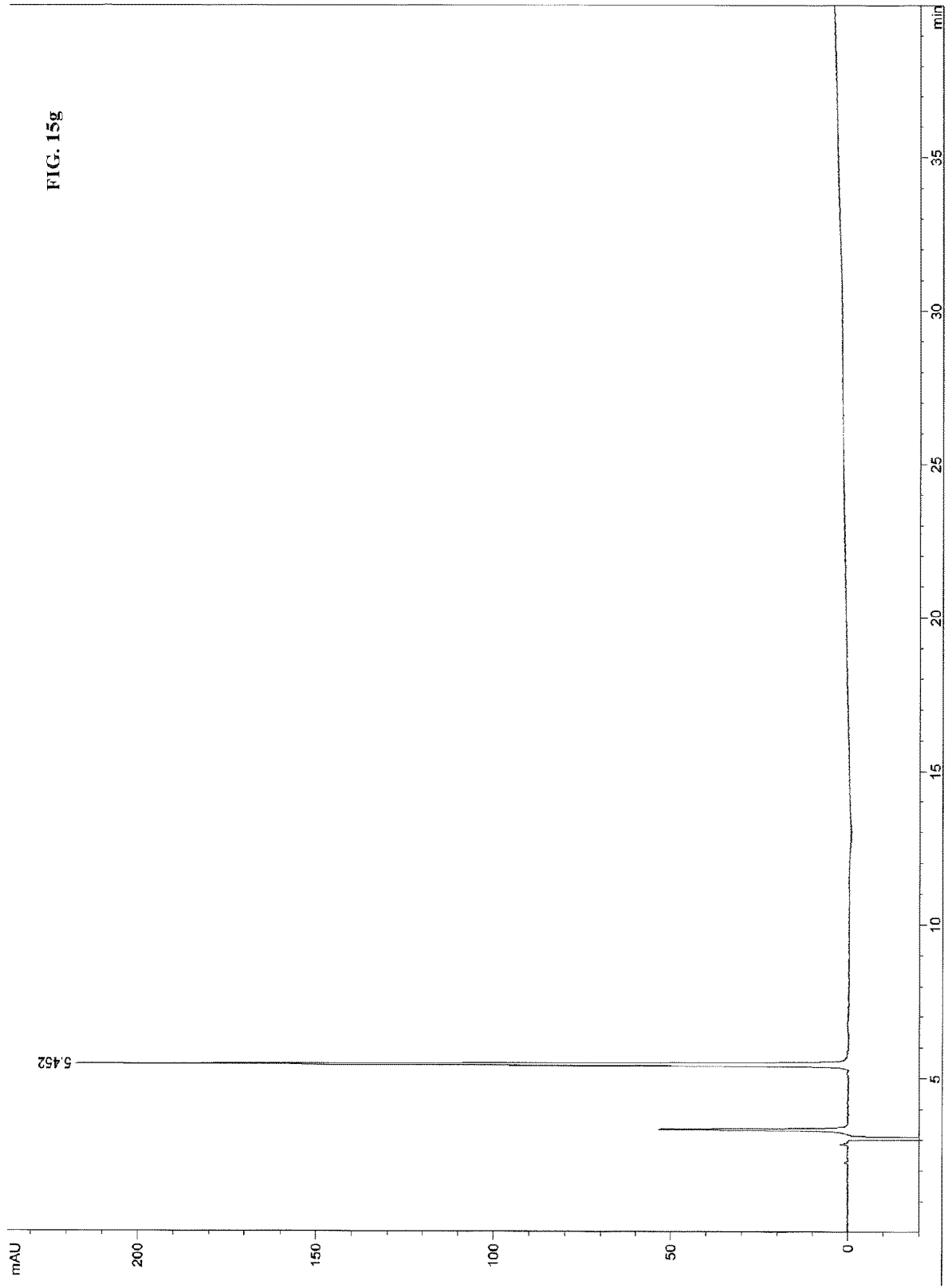
FIG. 15g shows the LC chromatogram of rebaudioside M5.
Figure 15H:
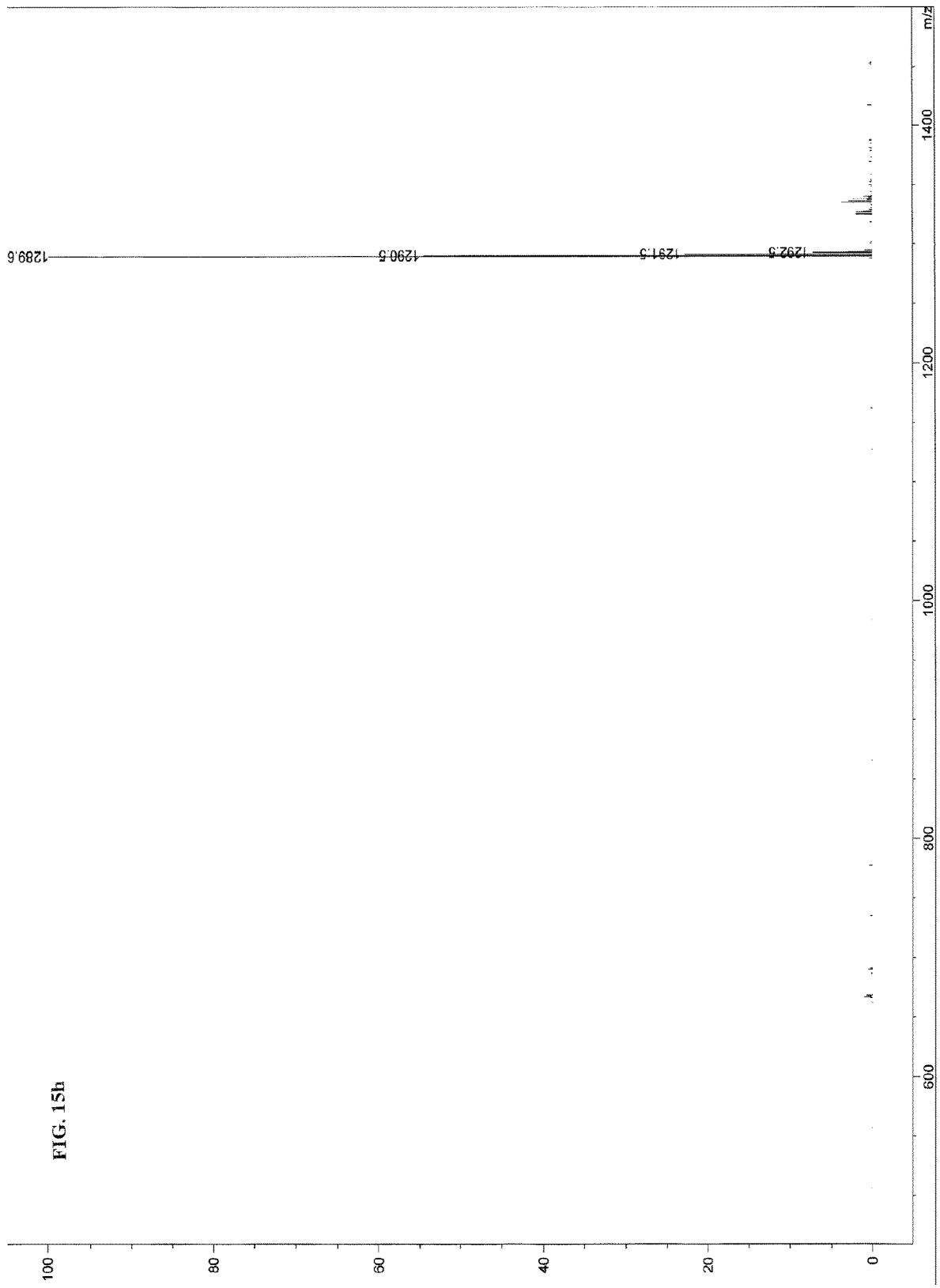
FIG. 15h shows the mass spectrum of rebaudioside M5.

LCMS (FIG. 15g and FIG. 15h) analysis of rebaudioside M5 showed a [M-H]⁻ ion at m/z1289.6, in good agreement with the expected molecular formula of $C_{56}H_{90}O_{33}$ (calculated for $[C_{56}H_{99}O_{33}]^-$ monoisotopic ion: 1289.5, error <0.05%). The MS data confirms that rebaudioside M5 has a molecular formula of $C_{56}H_{90}O_{33}$. LCMS analysis was performed in the conditions listed in Table 6.

Although the invention and its advantages have been described in detail, it should be understood that various changes, substitutions and alterations can be made herein without departing from the spirit and scope of the invention as defined by the appended claims. Moreover, the scope of the application is not intended to be limited to the particular embodiments of the invention described in the specification. As one of ordinary skill in the art will readily appreciate from the disclosure of the invention, the compositions, processes, methods, and steps, presently existing or later to be developed that perform substantially the same function or achieve substantially the same result as the corresponding embodiments described herein may be utilized according to the invention.

We claim:
1. Steviol glycosides XV-XX and XXII-XXXIX with the following formulae:
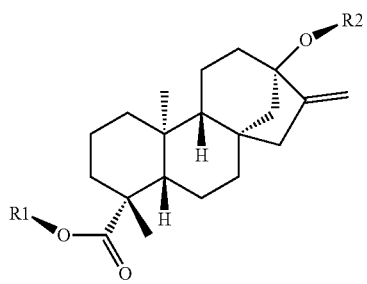
wherein R1 and R2 are sugar chains that are defined in the following table;
| No. | R1 |
|---|---|
| XV | 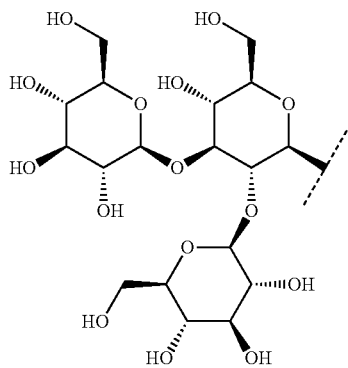 |
| XVI | 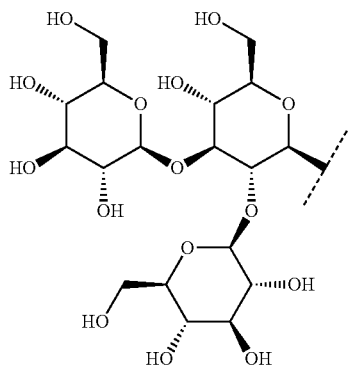 |
| XVII | 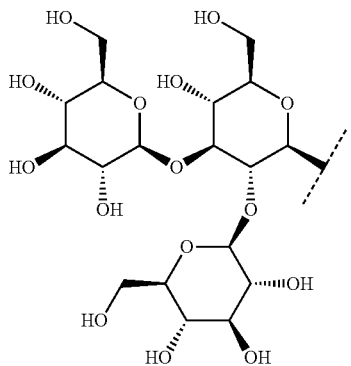 |
| XVIII | 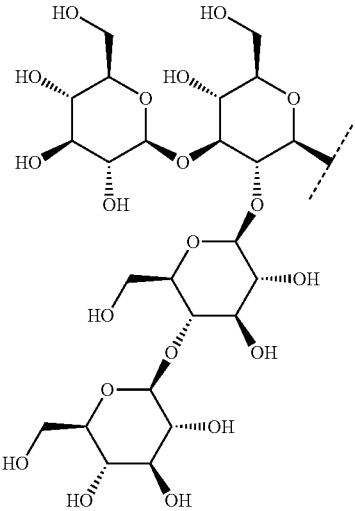 |
| XIX | 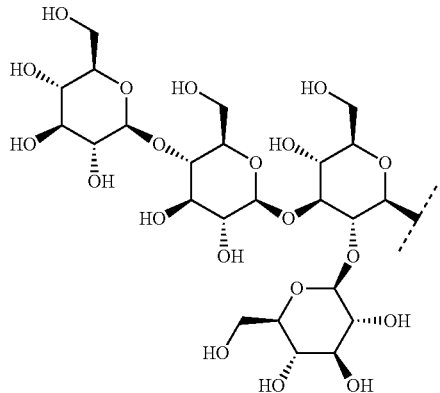 |

XX 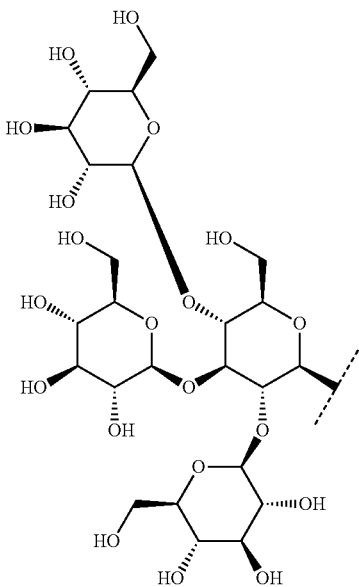
XXII 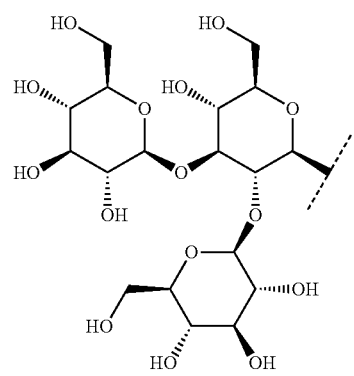
XXIII 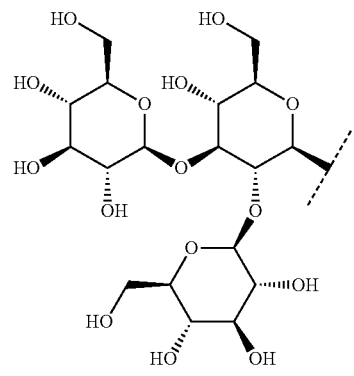
XXIV 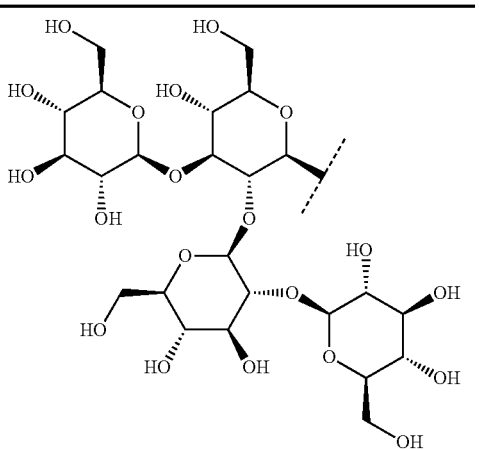
XXV 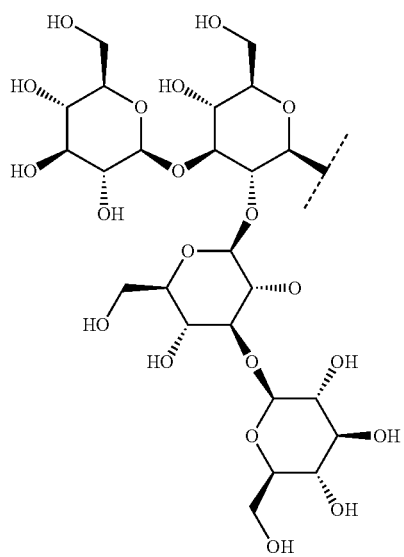
XXVI 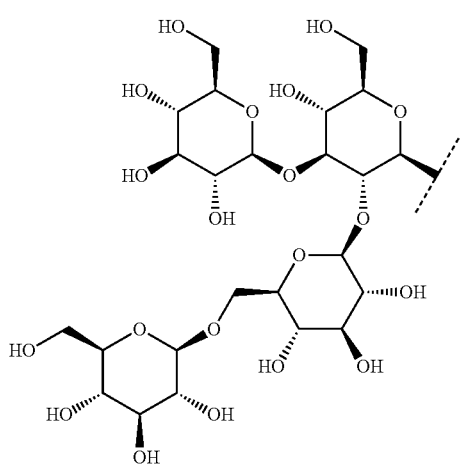

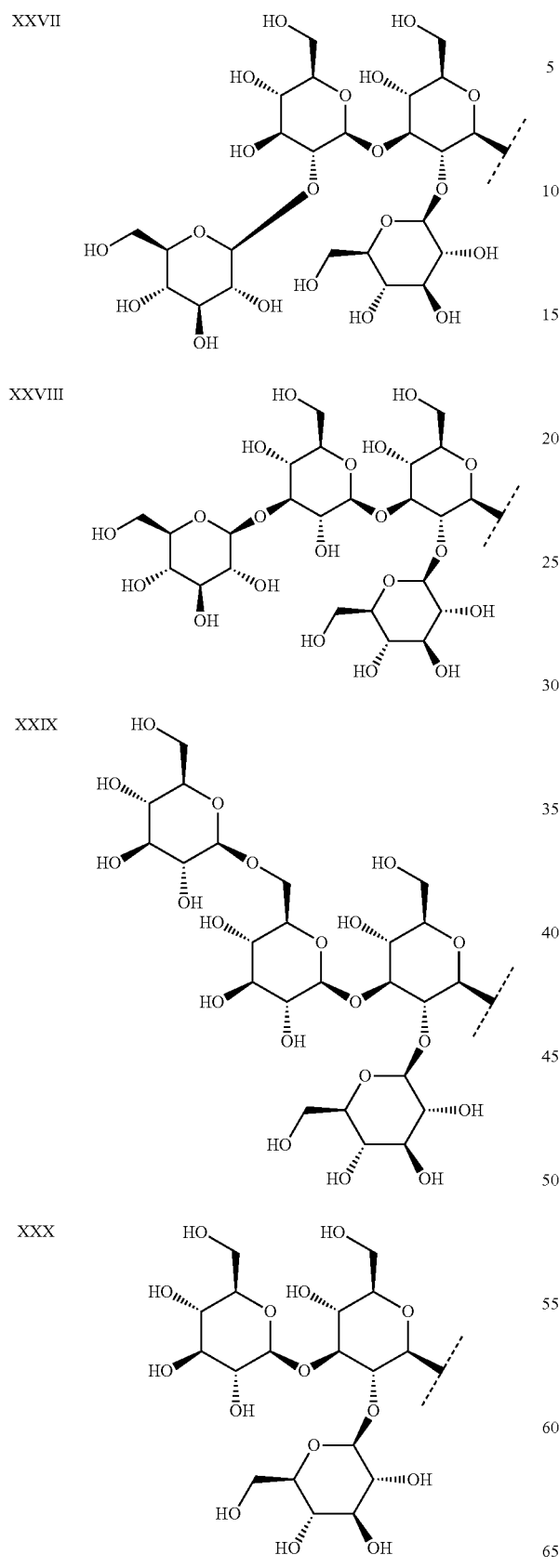
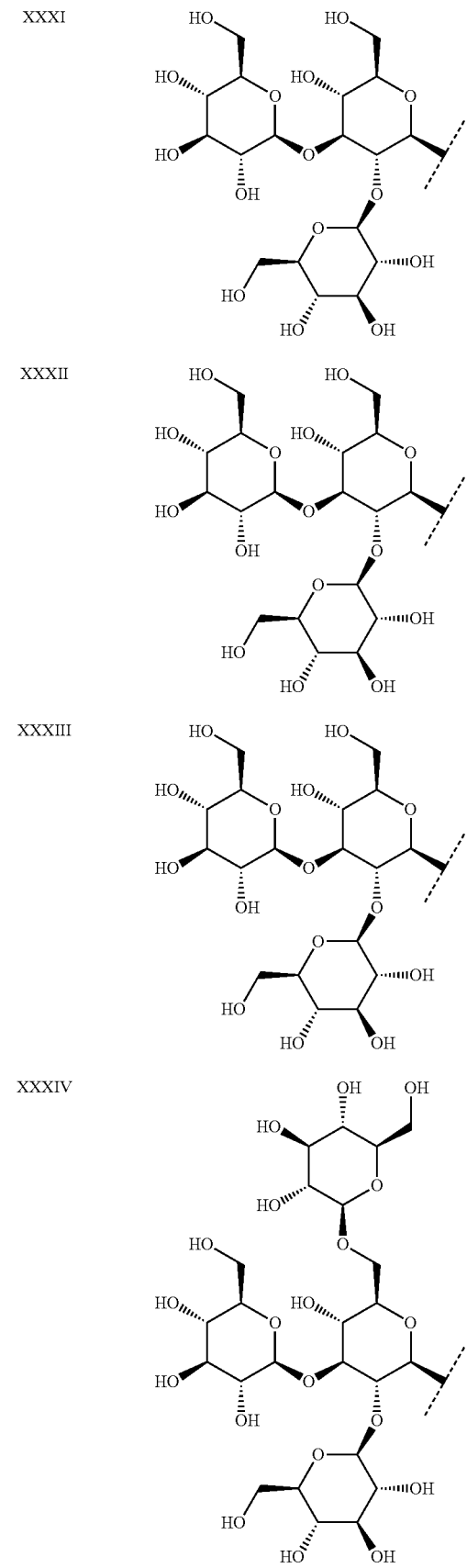

-continued
XXXV
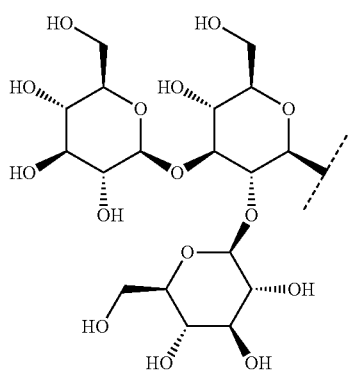
XXXVI
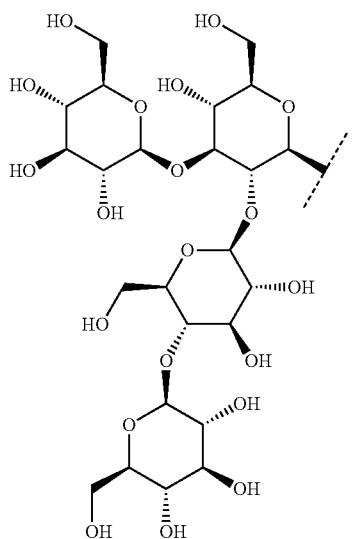
XXXVII
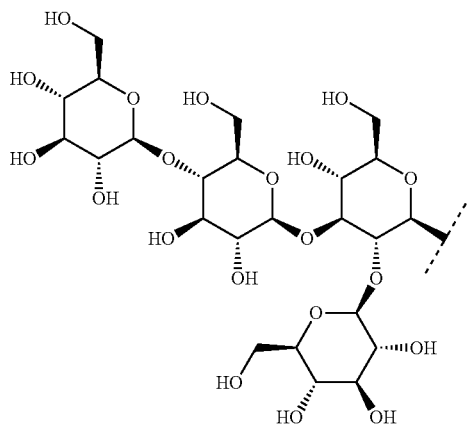
-continued
XXXVIII
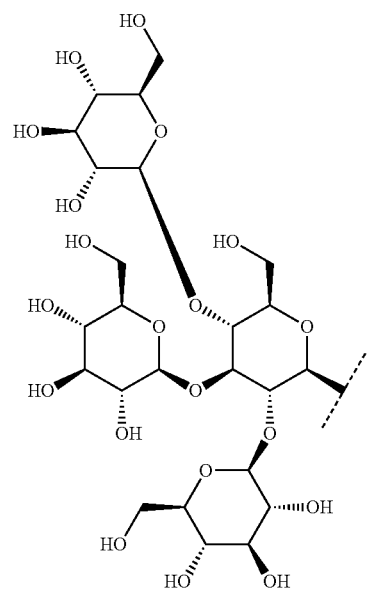
XXXIX
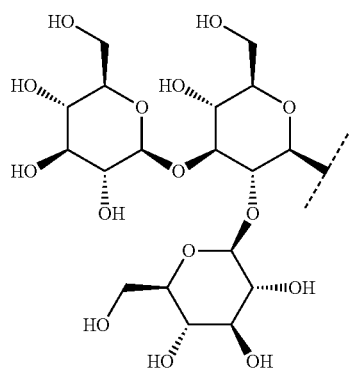
| No. | R2 |
|---|---|
| XV | |
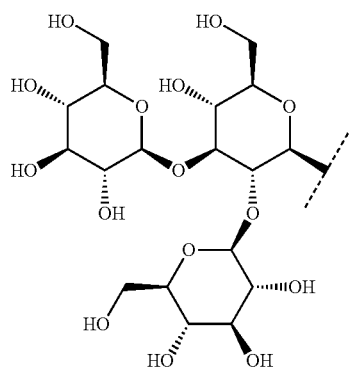

XVI
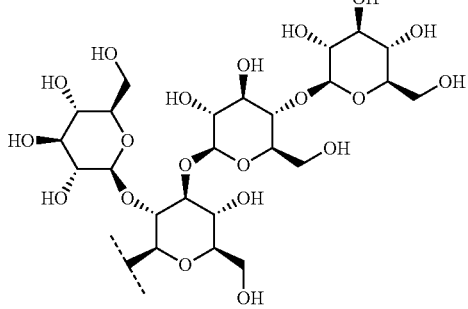
XVII
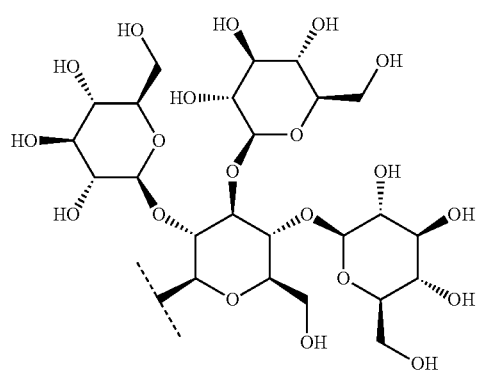
XVIII
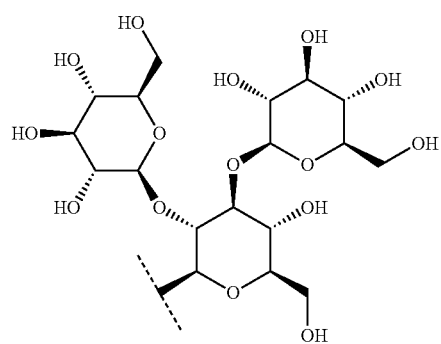
XIX
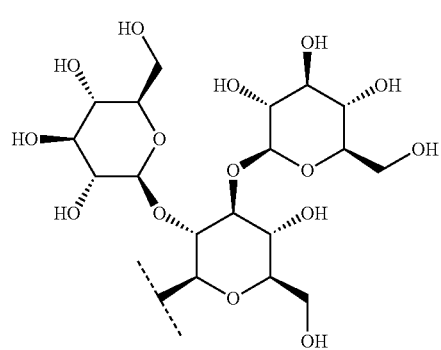
XX
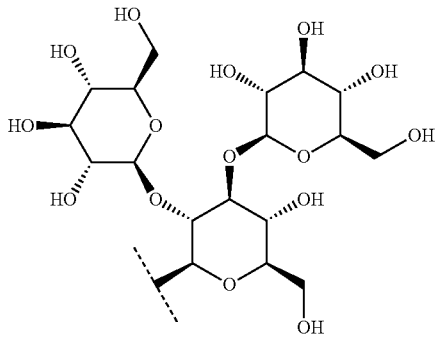
XXII
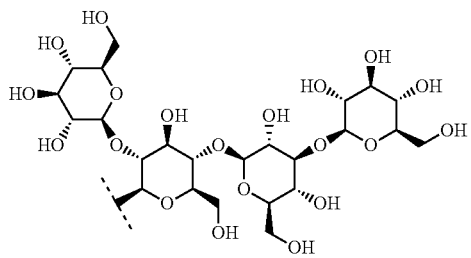
XXIII
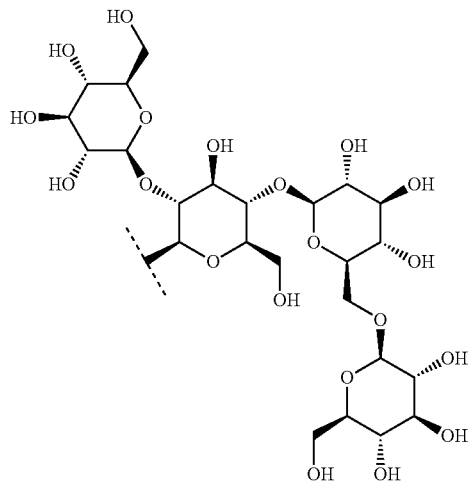
XXIV
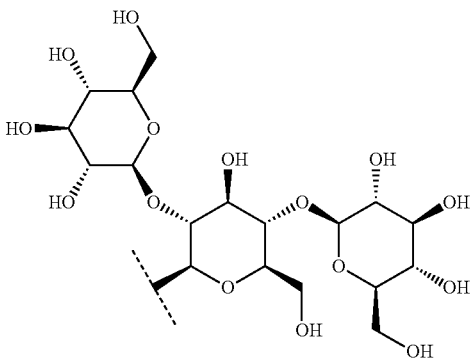

XXV 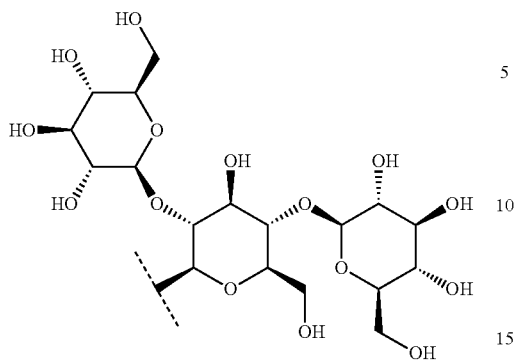
XXVI 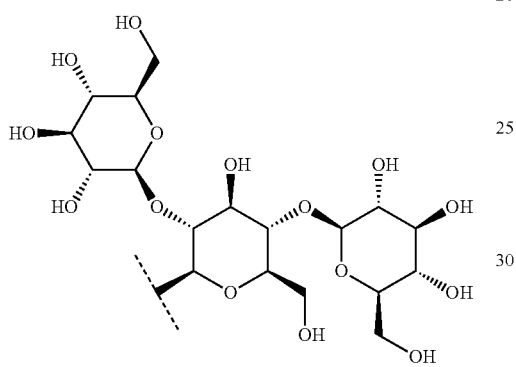
XXVII 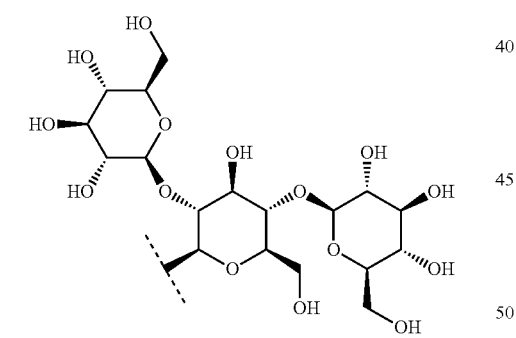
XXVIII 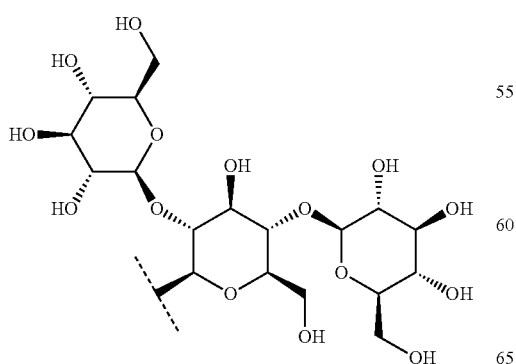
XXIX 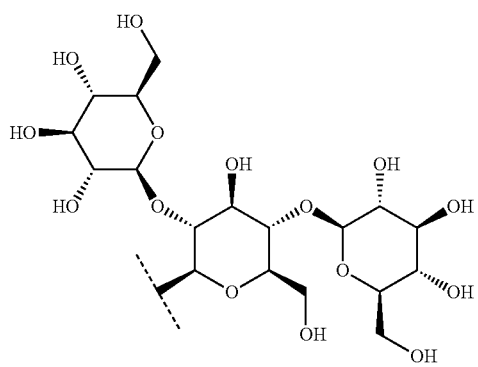
XXX 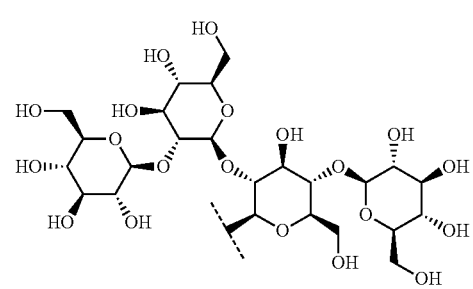
XXXI 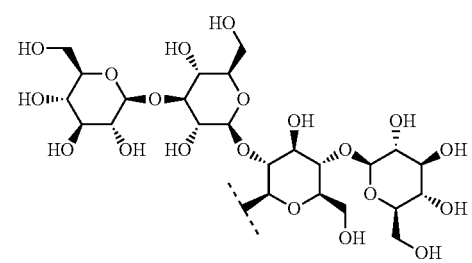
XXXII 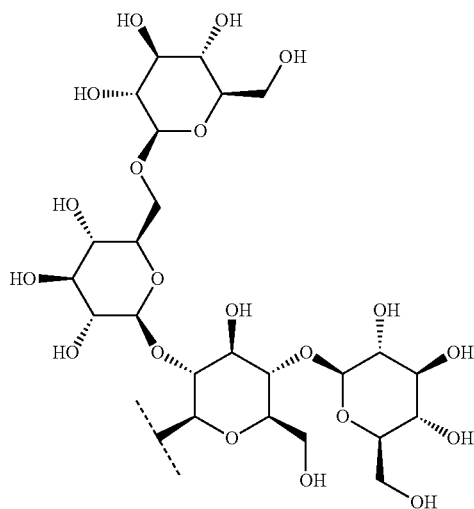

XXXIII

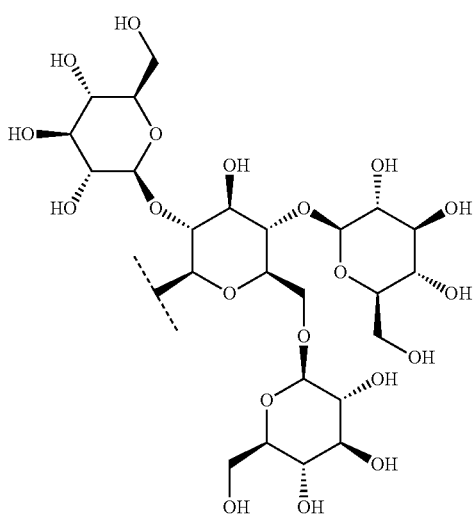

XXXIV

XXXV

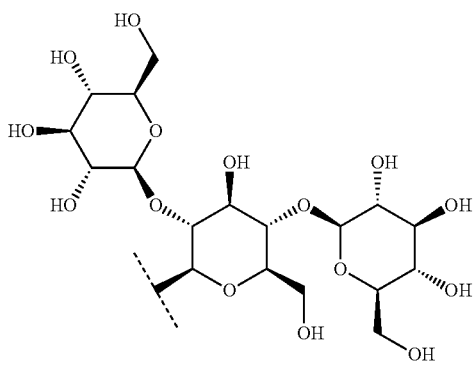

XXXVI

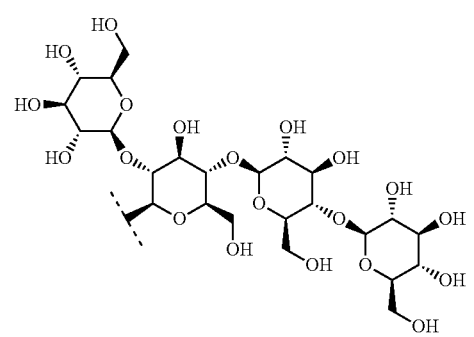

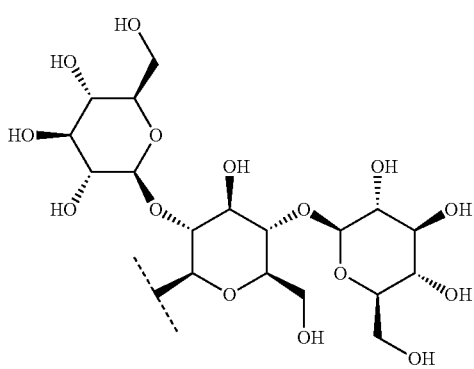

XXXVII

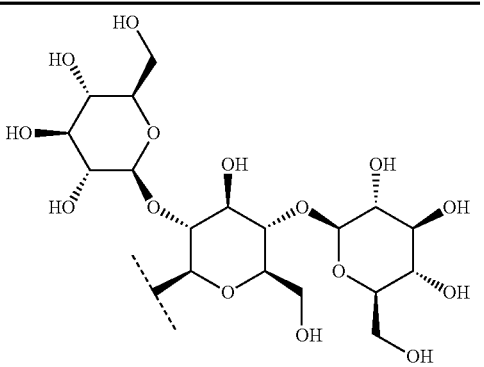

XXXVIII

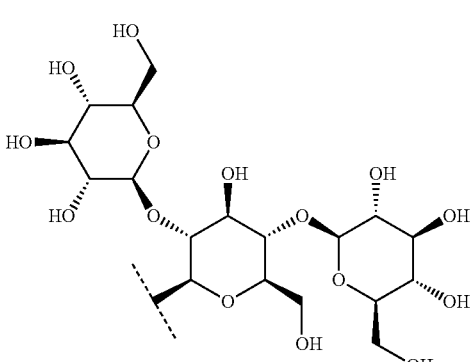

XXXIX

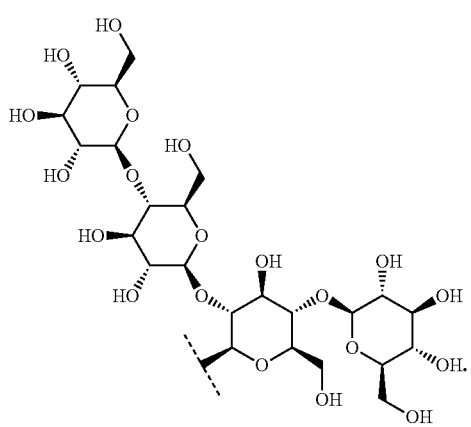

2. A consumable product comprising at least one of the steviol glycosides of claim 1, wherein the product is selected from the group consisting of a food, a beverage, a pharmaceutical composition, a tobacco product, a nutraceutical composition, an oral hygiene composition, and a cosmetic composition.

3. The consumable product of claim 2, wherein the product is selected from the group consisting of beverages; natural juices; refreshing drinks; carbonated soft drinks; diet drinks; zero calorie drinks; reduced calorie drinks; reduced calorie foods; yogurt drinks; instant juices; instant coffee; powdered instant beverages; canned products; syrups; fermented soybean paste; soy sauce; vinegar; dressings; mayonnaise; ketchups; curry; soup; instant bouillon; powdered soy sauce; powdered vinegar; biscuits; rice biscuit; crackers; bread; chocolates; caramel; candy; chewing gum; jelly; pudding; preserved fruits; preserved vegetables; fresh cream; jam; marmalade; flower paste; powdered milk; ice cream; sorbet; vegetables packed in bottles; fruits packed in bottles; canned boiled beans; meat boiled in sweetened sauce; foods boiled in sweetened sauce; agricultural vegetable food products; seafood; ham; sausage; fish ham; fish sausage; fish paste; deep fried fish products; dried seafood products; frozen food products; preserved seaweed; preserved meat; tobacco and medicinal products.

4. The consumable product of claim 2, further comprising at least one additive selected from the group consisting of carbohydrates, polyols, amino acids, amino acids salts, poly-amino acids, poly-amino acids salts, sugar acids, sugar acids salts, nucleotides, organic acids, inorganic acids, organic salts, inorganic salts, bitter compounds, caffeine, flavorants, flavoring ingredients, astringent compounds, proteins, protein hydrolysates, surfactants, emulsifiers, flavonoids, alcohols, polymers and combinations thereof.

5. The consumable product of claim 2, further comprising at least one functional ingredient selected from the group consisting of saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

6. The consumable product of claim 2, further comprising a compound selected from the group consisting of steviolmonoside, steviolmonoside A, steviolbioside, steviolbioside A, steviolbioside B, steviolbioside C, steviolbioside D, steviolbioside E, rubusoside, dulcoside A, dulcoside B, dulcoside C, dulcoside D, stevioside, stevioside A, stevioside B, stevioside C, stevioside D, stevioside E, stevioside E2, stevioside F, stevioside G, stevioside H, rebaudioside A, rebaudioside A2, rebaudioside A3, rebaudioside A4, rebaudioside B, rebaudioside B2, rebaudioside C, rebaudioside C2, rebaudioside C3, rebaudioside C4, rebaudioside C5, rebaudioside C6, rebaudioside D, rebaudioside D2, rebaudioside D3, rebaudioside D4, rebaudioside D5, rebaudioside D6, rebaudioside D7, rebaudioside D8, rebaudioside E, rebaudioside E2, rebaudioside E3, rebaudioside E4, rebaudioside E5, rebaudioside E6, rebaudioside E7, rebaudioside F, rebaudioside F2, rebaudioside F3, rebaudioside G, rebaudioside H, rebaudioside H2, rebaudioside H3, rebaudioside H4, rebaudioside H5, rebaudioside H6, rebaudioside I, rebaudioside I2, rebaudioside I3, rebaudioside J, rebaudioside K, rebaudioside K2, rebaudioside KA, rebaudioside L, rebaudioside M, rebaudioside M2, rebaudioside M3, rebaudioside N, rebaudioside N2, rebaudioside N3, rebaudioside N4, rebaudioside N5, rebaudioside O, rebaudioside O2, rebaudioside O3, rebaudioside O4, rebaudioside Q, rebaudioside Q2, rebaudioside Q3, rebaudioside R, rebaudioside S, rebaudioside T, rebaudioside TI, rebaudioside U, rebaudioside U2, rebaudioside V, rebaudioside V2, rebaudioside V3, rebaudioside W, rebaudioside W2, rebaudioside W3, rebaudioside Y, rebaudioside Z1, rebaudioside Z2, rebaudioside AM, SvG7, NSF-02, Mogroside V, siratose, Luo Han Guo, allulose, D-allose, D-tagatose, erythritol, brazzein, neohesperidin dihydrochalcone, glycyrrhizic acid and its salts, thaumatin, perillartine, pernandulcin, mukuroziosides, baiyunoside, phlomisoside-I, dimethyl-hexahydrofluorenedicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, siamenoside, sucralose, potassium acesulfame, aspartame, alitame, saccharin, cyclamate, neotame, dulcin, suosan advantame, gymnemic acid, hodulcin, ziziphin, lactisole, glutamate, aspartic acid, glycine, alanine, threonine, proline, serine, lysine, tryptophan, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols, sugar alcohols, L-sugars, L-sorbose, L-arabinose, trehalose, galactose, rhamnose, various cyclodextrins, cyclic oligosaccharides, maltodextrins, dextran, sucrose, glucose, ribulose, fructose, threose, xylose, lyxose, altrose, mannose, idose, lactose, maltose, invert sugar, isotrehalose, neotrehalose, isomaltulose, erythrose, deoxyribose, gulose, talose, erythrulose, xylulose, cellobiose, amylopectin, glucosamine, mannosamine, glucuronic acid, gluconic acid, glucono-lactone, abequose, galactosamine, beet oligosaccharides, isomaltooligosaccharides, xylo-oligosaccharides, xylo-terminated oligosaccharides, gentio-oligosaccharides, nigero-oligosaccharides, palatinose oligosaccharides, fructooligosaccharides, maltotetraol, maltotriol, malto-oligosaccharides, starch, inulin, inulo-oligosaccharides, lactulose, melibiose, raffinose, isomerized liquid sugars, high fructose corn syrups, coupling sugars, soybean oligosaccharides, D-psicose, D-ribose, L-glucose, L-fucose, D-turanose, and D-leucrose.

7. A method for enhancing sweetness of a beverage or food product comprising:
   a. providing a beverage or food product comprising a sweetener; and
   b. adding a sweetness enhancer comprising at least one of the steviol glycosides of claim 1 to the beverage or food product, wherein the at least one of the steviol glycosides of claim 1 is present in a concentration at or below the sweetness recognition threshold.

8. A method for modifying the flavor of a beverage or food product, comprising
   a. providing a beverage or food product, and
   b. adding a composition comprising at least one of the steviol glycosides of claim 1 to the beverage or food product.

9. A method for suppressing foaming of a beverage or food product, comprising
   a. providing a beverage or a food product, and
   b. adding a foam suppressor comprising at least one of the steviol glycosides of claim 1 to the beverage or food product.

10. A method for producing at least one steviol glycoside with the formulae:

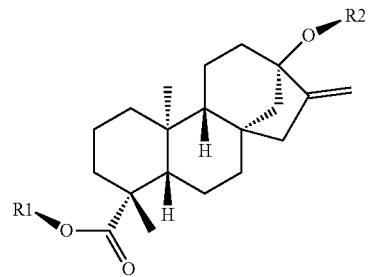

wherein R1 and R2 are sugar chains that are defined in the following table;

| 121 | 122 |
|---|---|
| R1 | R2 |
No.
XV
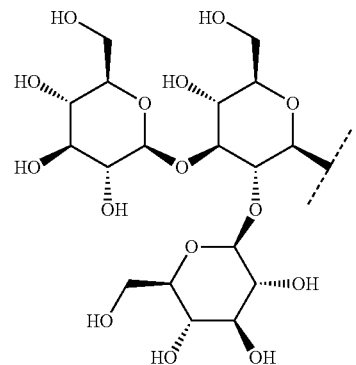 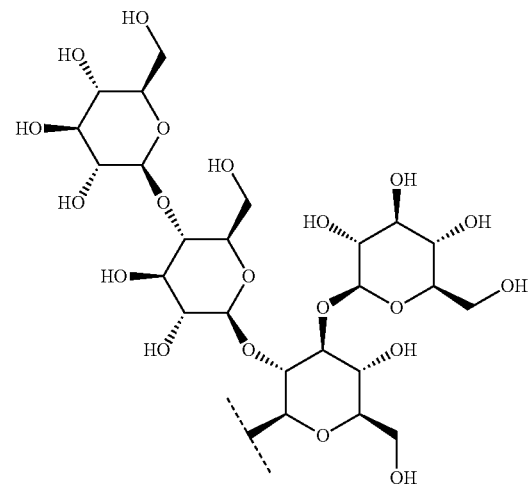
XVI
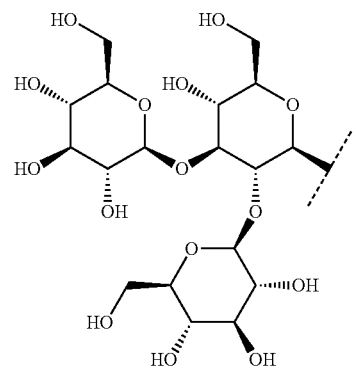 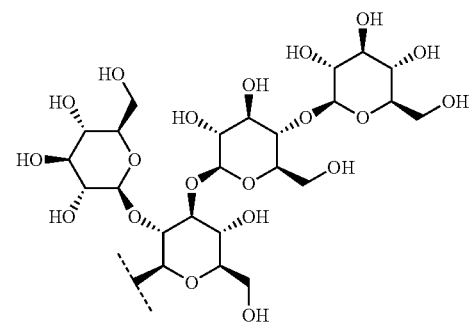
XVII
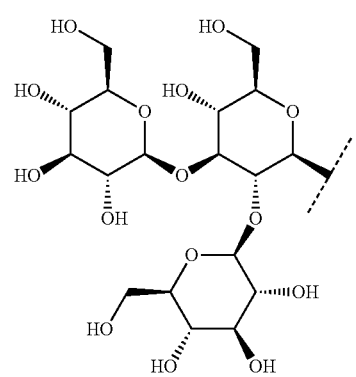 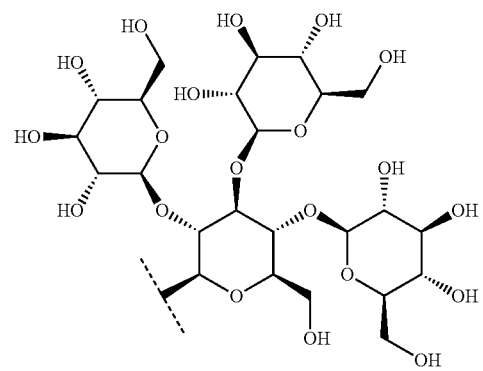

-continued
| No. | R1 | R2 |
|---|---|---|
| XVIII | | |
| XIX | | |
| XX | | |
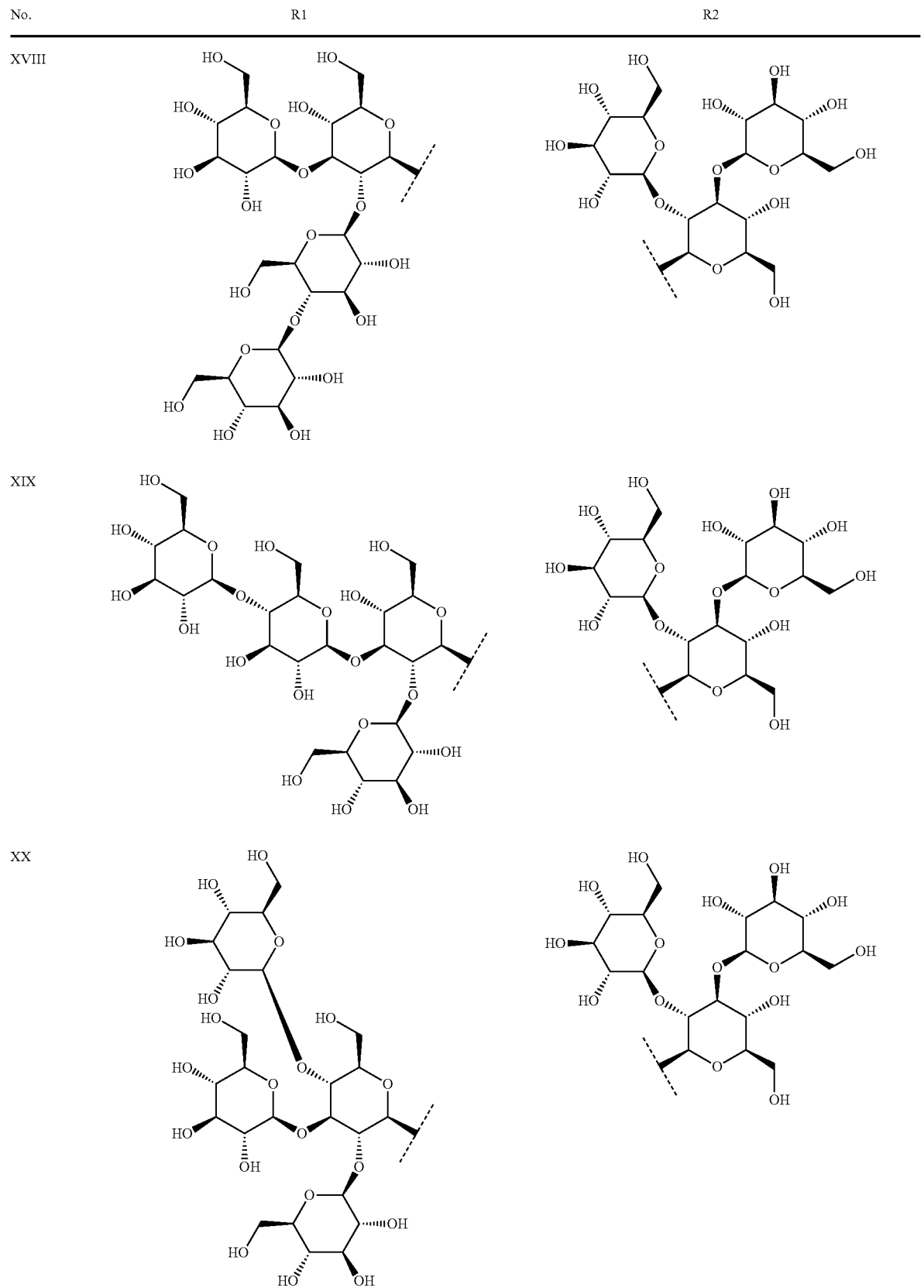

| No. | R1 | R2 |
|---|---|---|
| XXII | 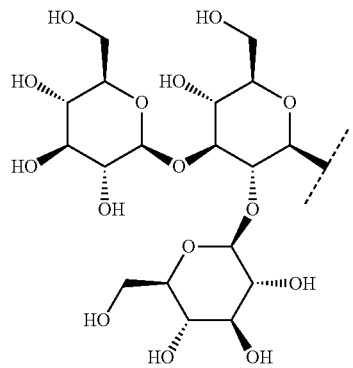 | 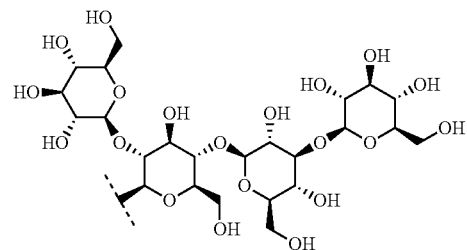 |
| XXIII | 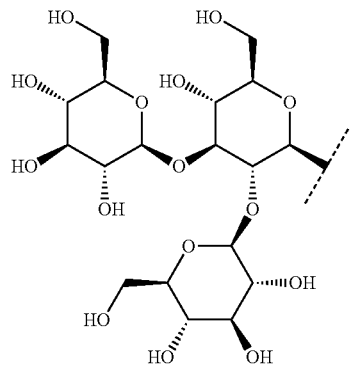 | 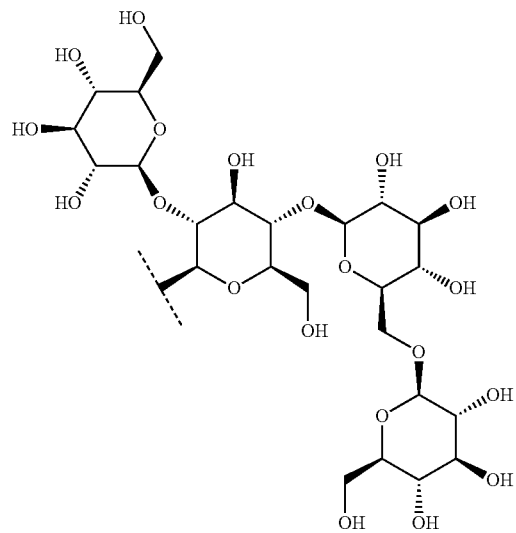 |
| XXIV | 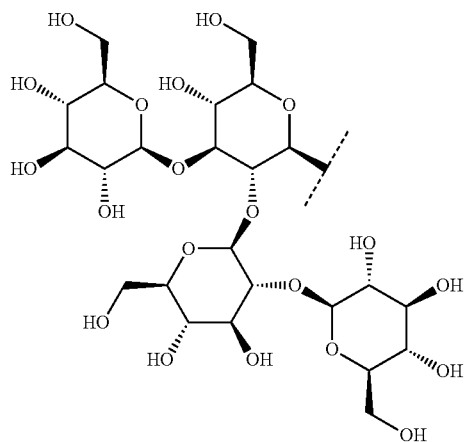 | 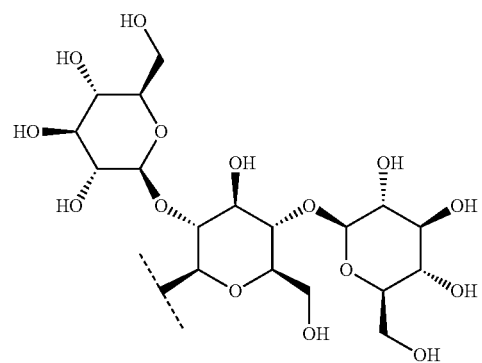 |

| No. | R1 | R2 |
|---|---|---|
| XXV | (structure) | (structure) |
| XXVI | (structure) | (structure) |
| XXVII | (structure) | (structure) |

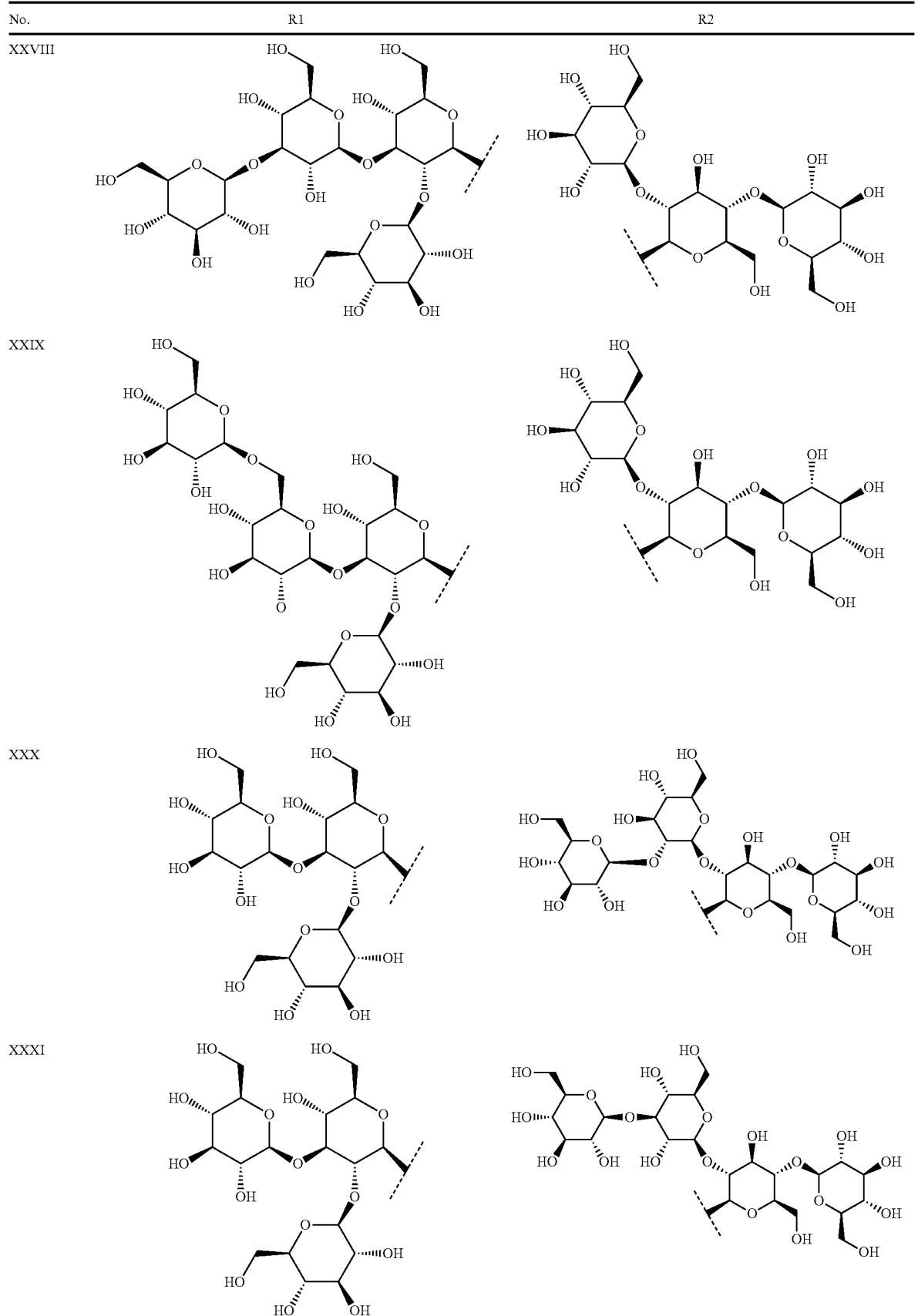

-continued
| No. | R1 | R2 |
|---|---|---|
| XXXII | 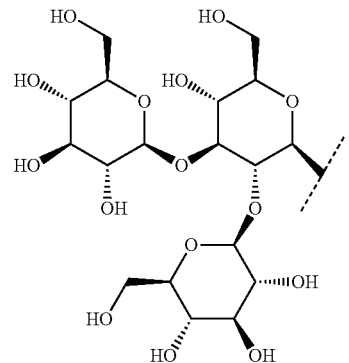 | 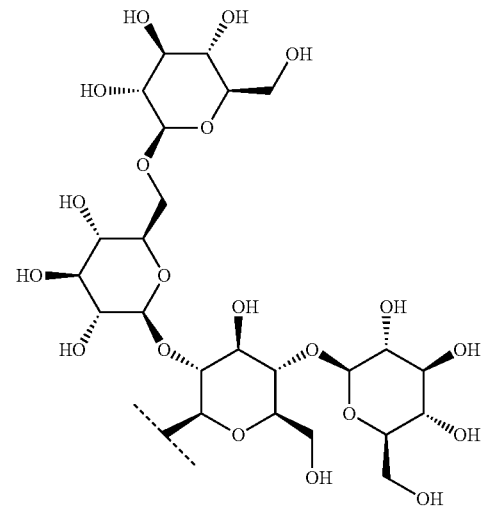 |
| XXXIII | 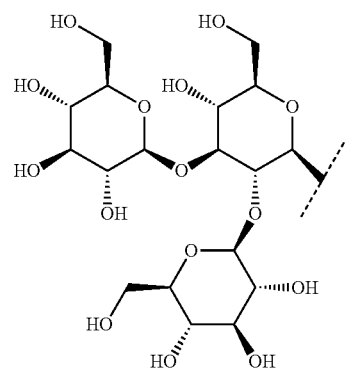 | 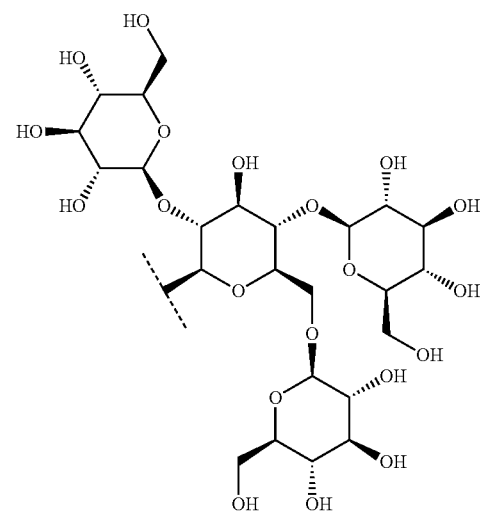 |
| XXXIV | 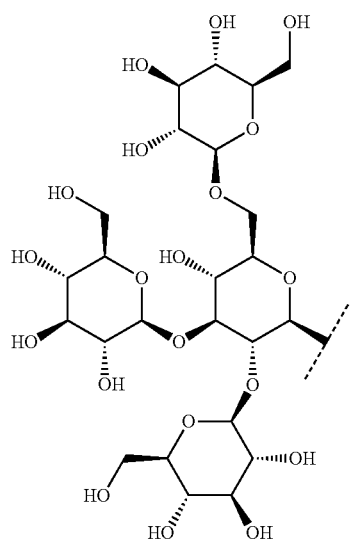 | 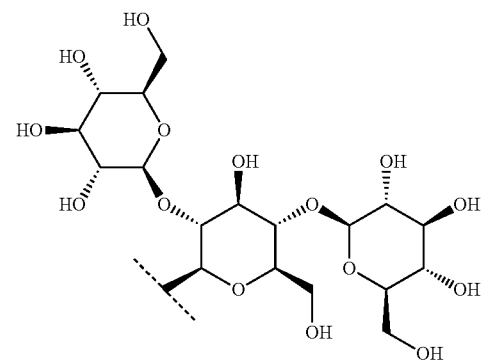 |

| No. | R1 | R2 |
|---|---|---|
| XXXV | 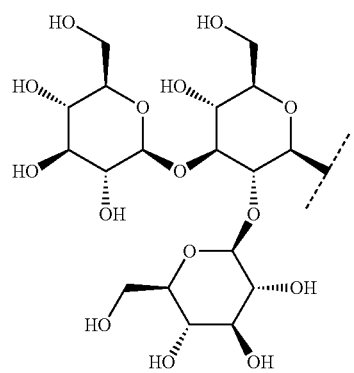 | 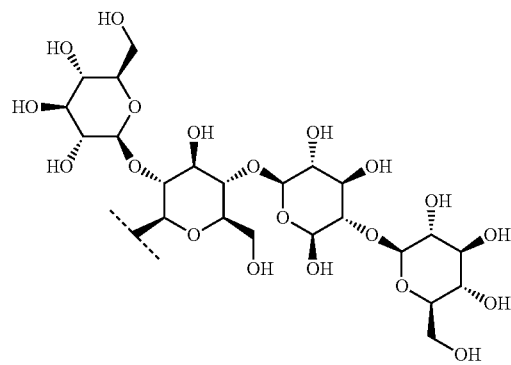 |
| XXXVI | 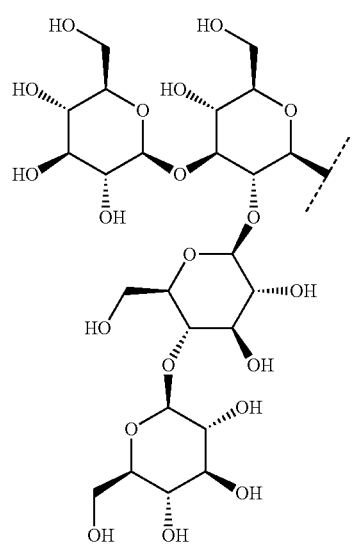 | 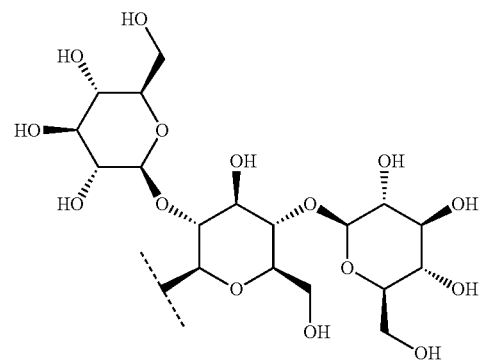 |
| XXXVII | 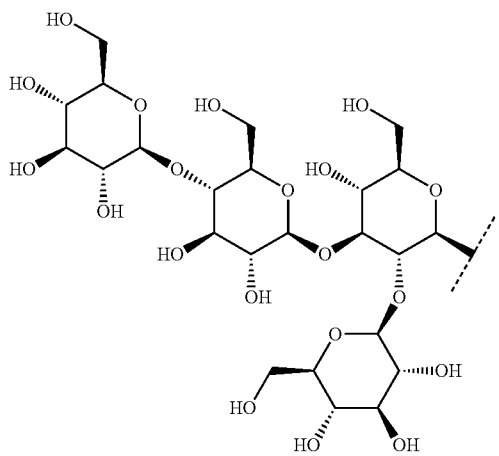 | 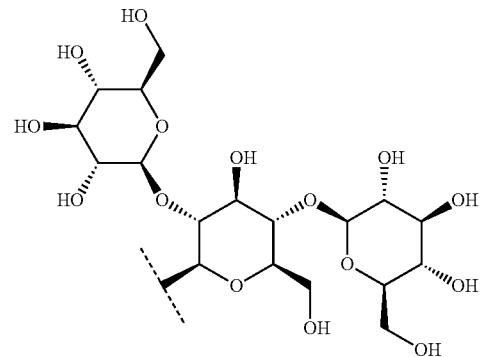 |

| No. | R1 | R2 |
|---|---|---|
| XXXVIII | | |
| XXXIX | | |

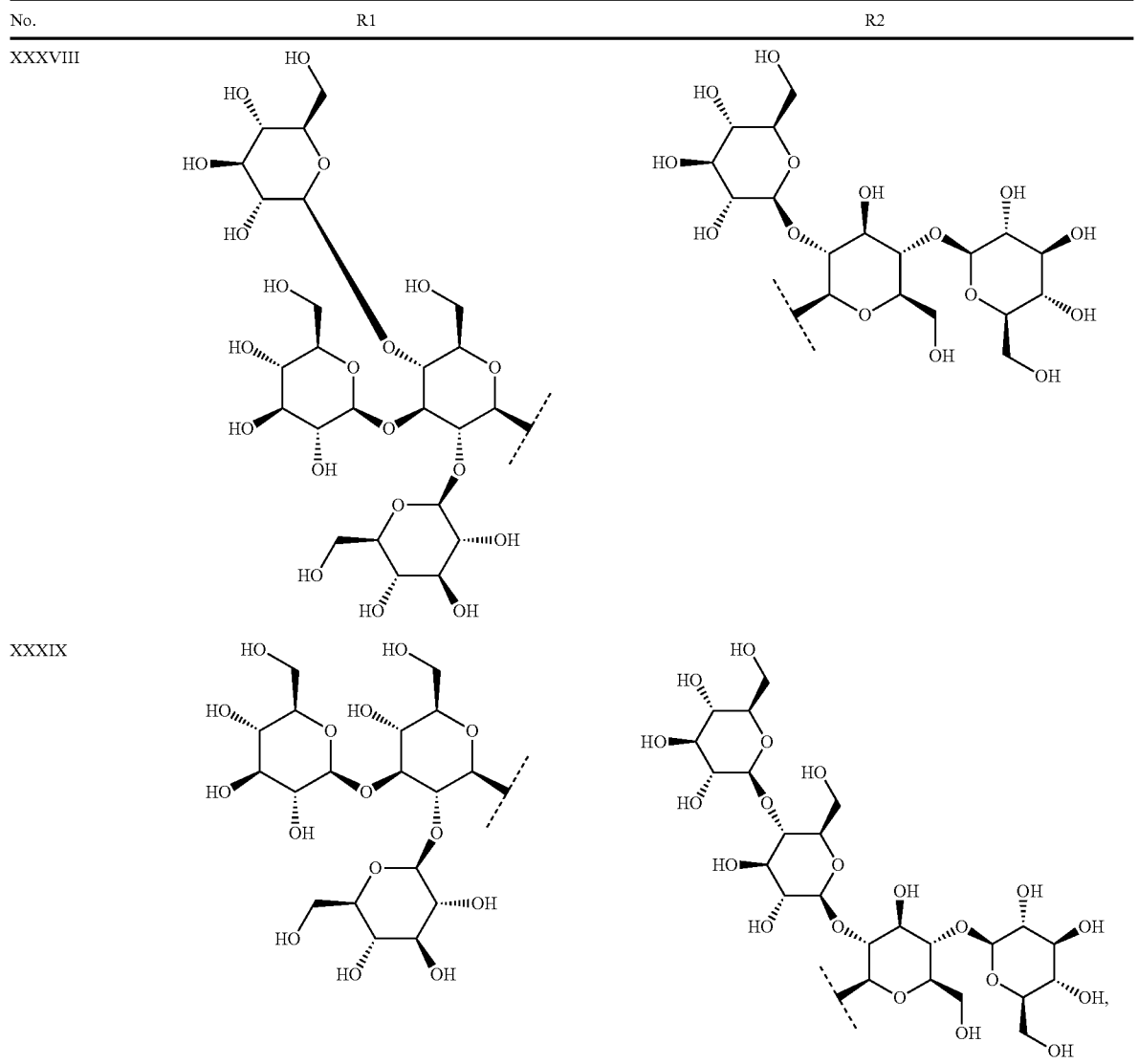

comprising the steps of:
  a) providing a starting composition comprising an organic compound with at least one carbon atom, wherein the starting composition is selected from the group consisting of steviol, steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, other steviol glycosides, polyols, carbohydrates, and combinations thereof;
  b) providing an enzyme preparation or a microorganism containing at least one enzyme selected from the group consisting of steviol biosynthesis enzymes, NDP-glucosyltransferases, and NDP-glucose recycling enzymes;
  c) contacting the enzyme preparation or microorganism with a medium containing the starting composition to produce a medium comprising the at least one steviol glycoside.

11. The method of claim 10 further comprising the step of:
  d) separating the at least one steviol glycoside from the medium comprising the at least one steviol glycoside to provide a highly purified composition of the at least one steviol glycoside.

12. The method of claim 11, wherein the content of the at least one steviol glycoside in the highly purified composition of the at least one steviol glycoside is greater than about 95% by weight on a dry basis.

13. The method of claim 10, wherein the microorganism is selected from the group consisting of *E. coli*, *Saccharomyces* sp., *Aspergillus* sp., *Pichia* sp., *Bacillus* sp., and *Yarrowia* sp.

14. The method of claim 10, wherein the enzyme is selected from the group consisting of a mevalonate (MVA) pathway enzyme, a 2-C-methyl-D-erythritol-4-phosphate pathway (MEP/DOXP) enzyme, geranylgeranyl diphosphate synthase, copalyl diphosphate synthase, kaurene synthase, kaurene oxidase, kaurenoic acid 13-hydroxylase (KAH), steviol synthetase, deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2 (E)-butenyl 4-diphosphate synthase (HDS), 1-hydroxy-2-methyl-2 (E)-butenyl 4-diphosphate reductase (HDR), acetoacetyl-CoA thiolase, truncated HMG-COA reductase, mevalonate kinase, phosphomevalonate kinase, mevalonate pyrophosphate decarboxylase, cytochrome P450 reductase, UGT74G1, UGT85C2, UGT91D2, EUGT11, UGTSl2, UGT76G1, UGlyT91C1 or mutant variant of the UGTSl2 or the UGT76G1 wherein the mutant variant has >95% amino-acid sequence identity, >96% amino-acid sequence identity, >97% amino-acid sequence identity, >98% amino-acid sequence identity, >99% amino-acid sequence identity of the UGTSl2 of SEQ ID NO: 2 or the UGT76G1 of SEQ ID NO: 3.

15. A method for producing at least one steviol glycoside with the formulae:

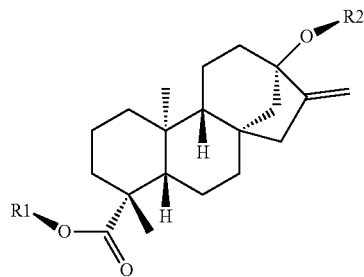

wherein R1 and R2 are sugar chains that are defined in the following table;

| No. | R1 | R2 |
|---|---|---|
| XV | 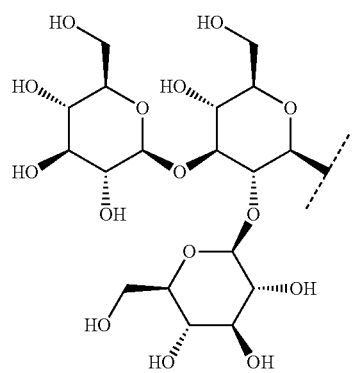 | 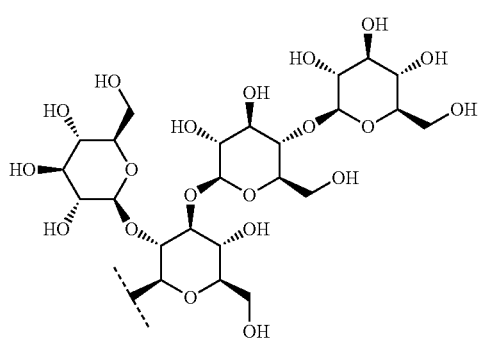 |
| XVI | 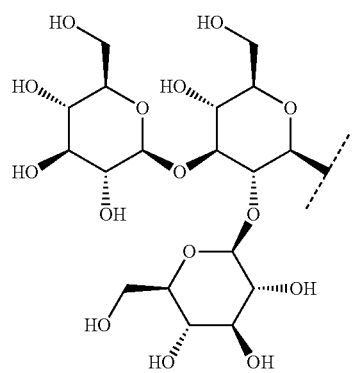 | 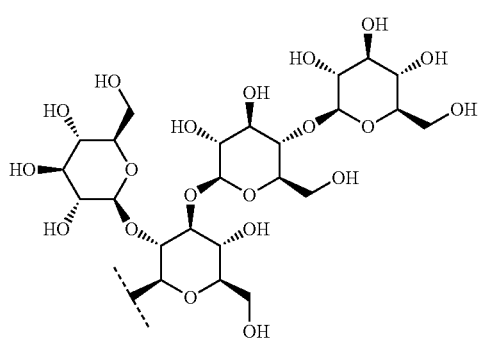 |

-continued
| No. | R1 | R2 |
|---|---|---|
| XVII | 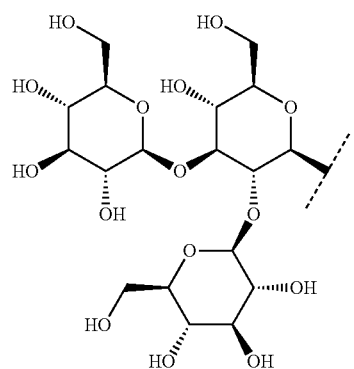 | 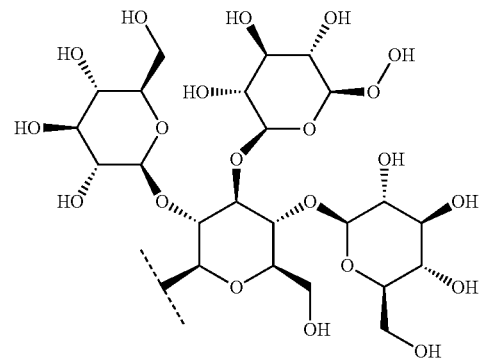 |
| XVIII | 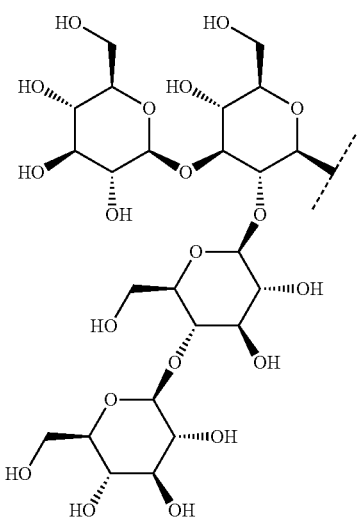 | 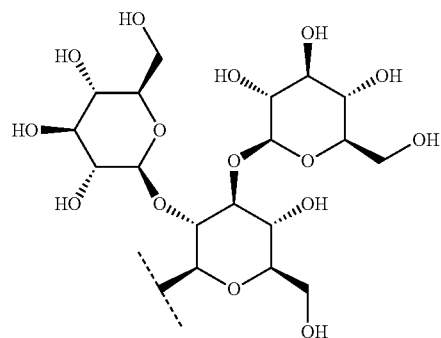 |
| XIX | 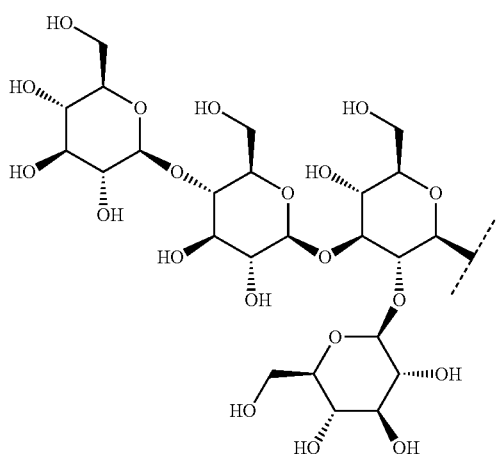 | 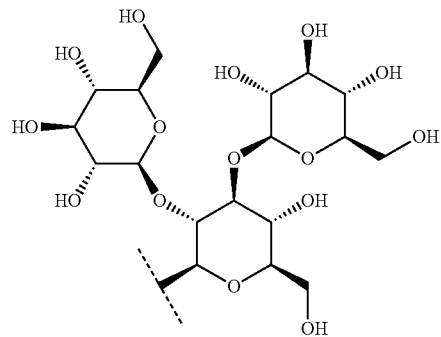 |

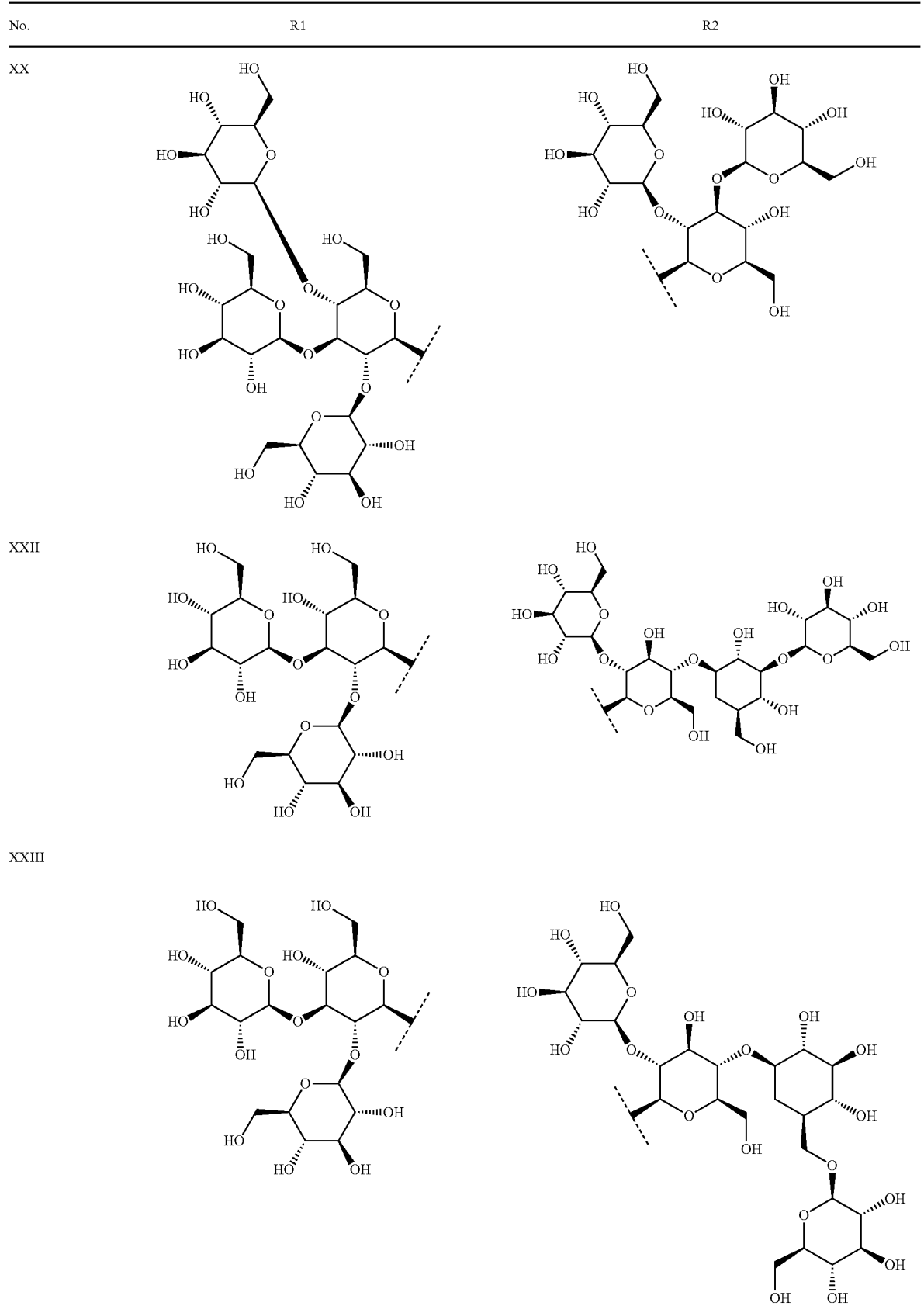

-continued
| No. | R1 | R2 |
|---|---|---|
| XXIV | 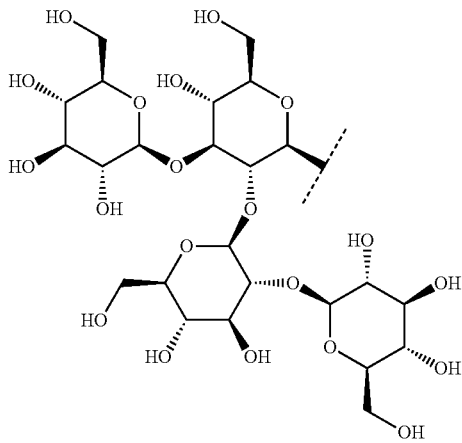 | 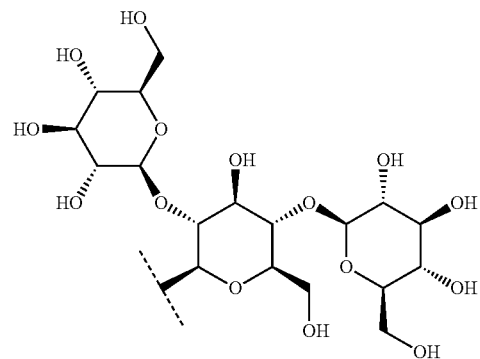 |
| XXV | 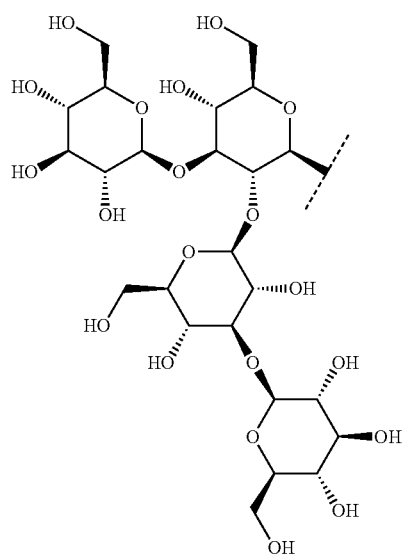 | 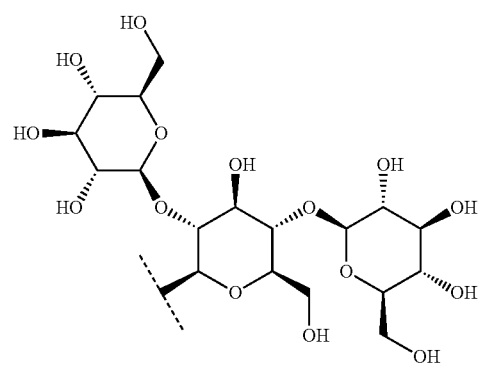 |
| XXVI | 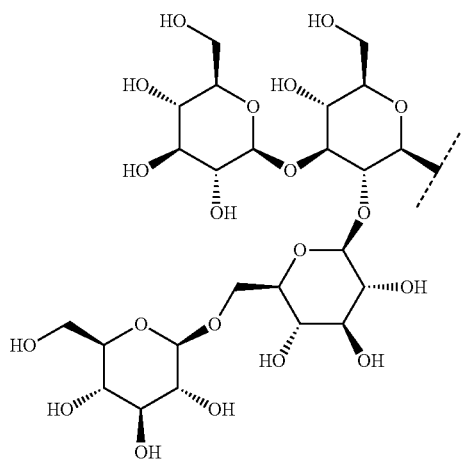 | 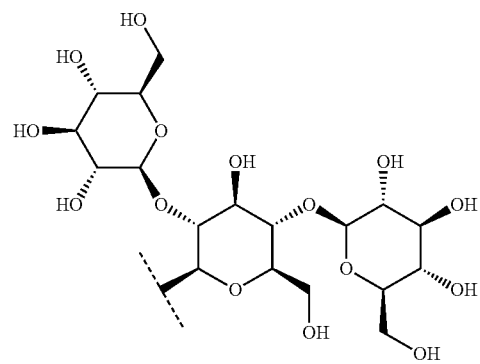 |

-continued
| No. | R1 | R2 |
|---|---|---|
| XXVII | 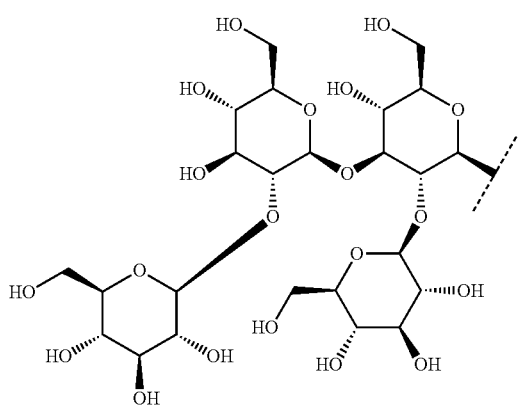 | 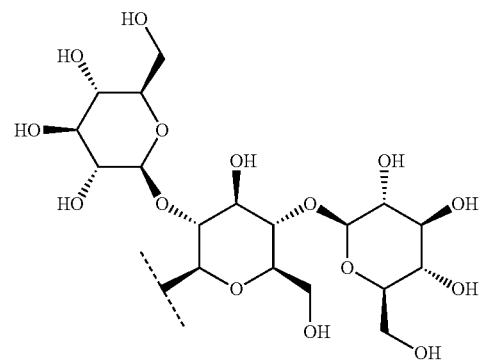 |
| XXVIII | 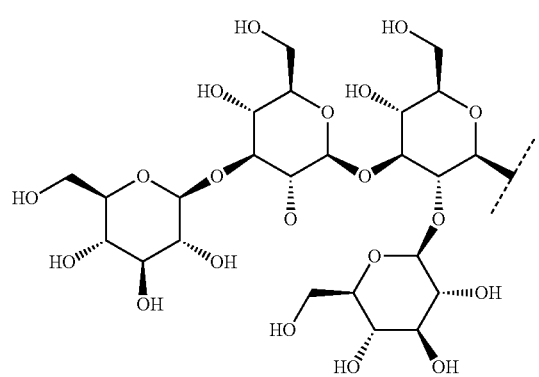 | 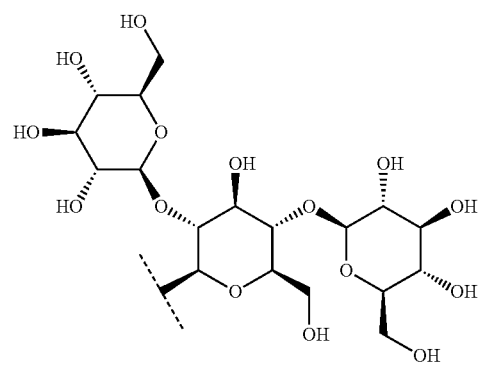 |
| XXIX | 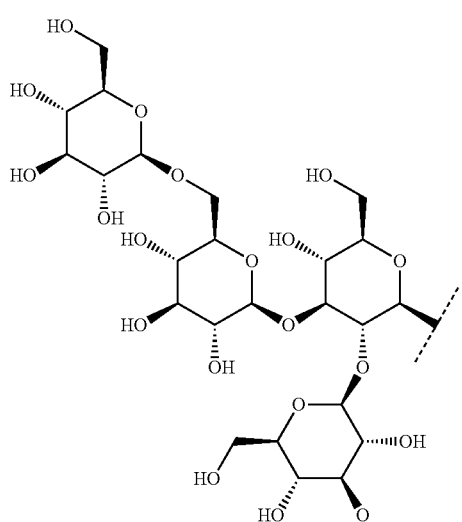 | 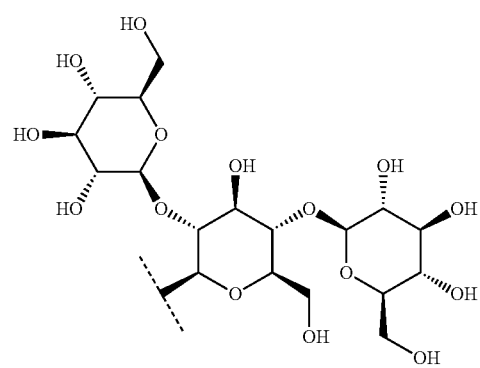 |

-continued
| No. | R1 | R2 |
|---|---|---|
| XXX | | |
| XXXI | | |
| XXXII | | |
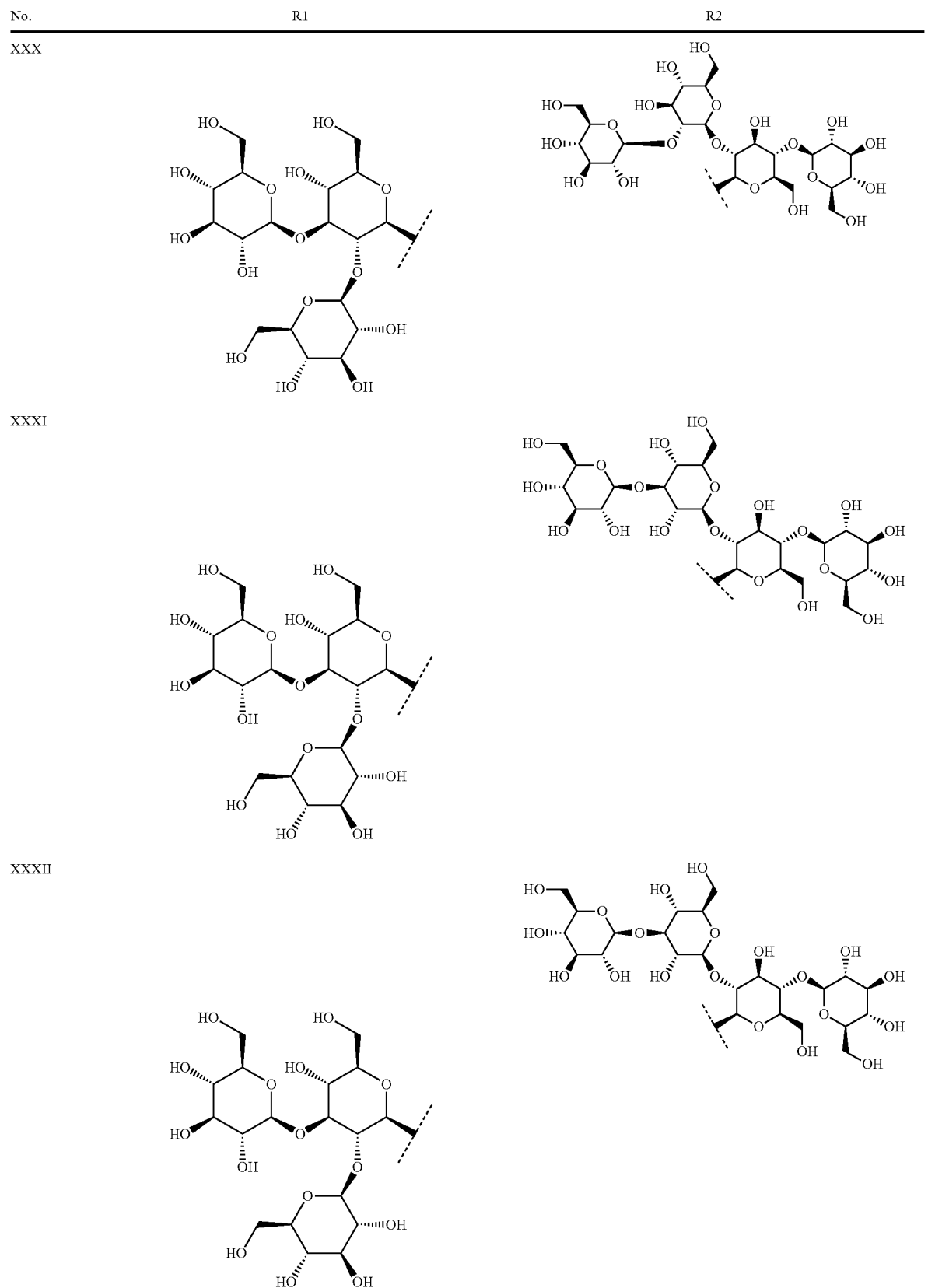

| No. | R1 | R2 |
|---|---|---|
| XXXIII | | |
| XXXIV | | |
| XXXV | | |
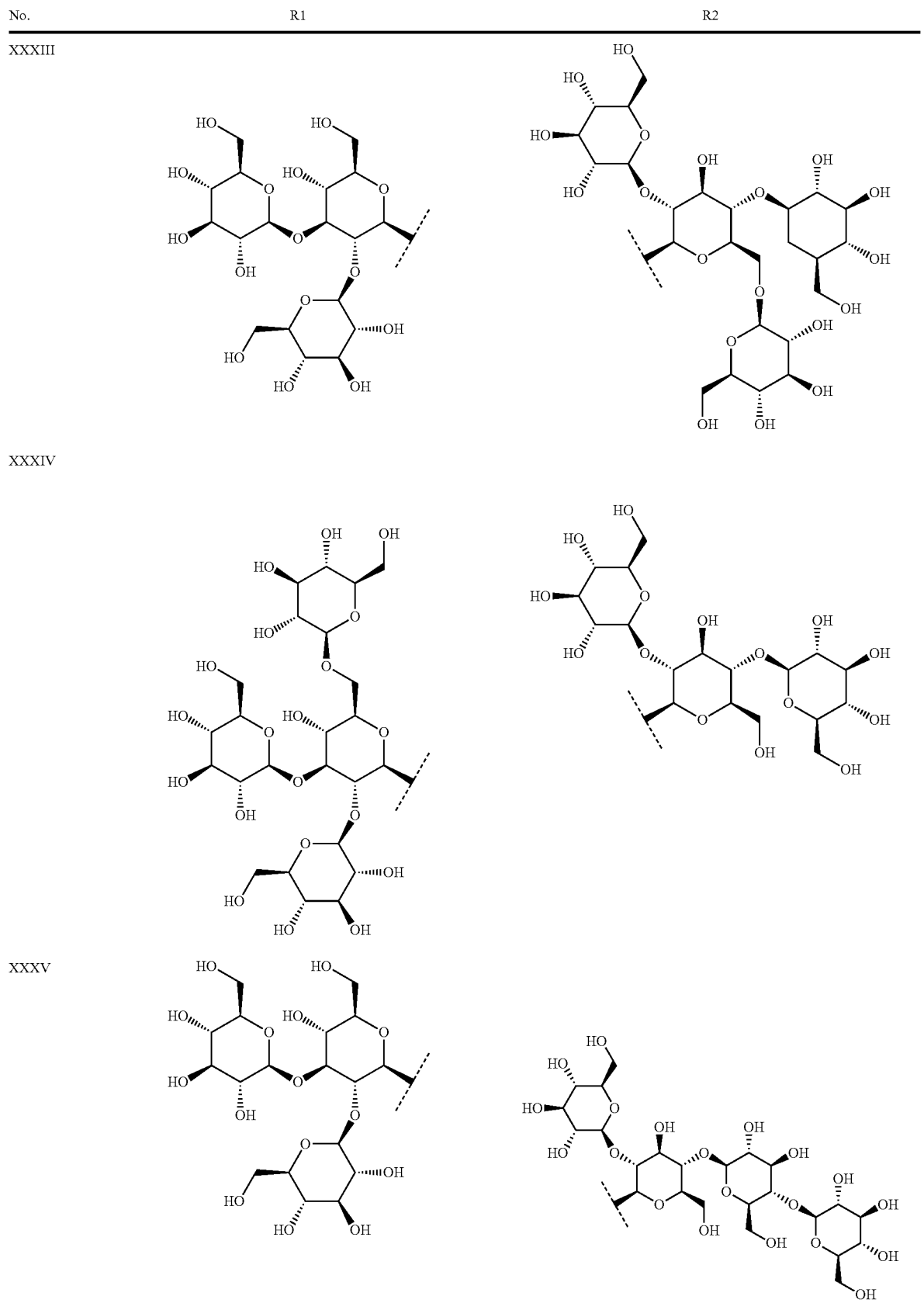

-continued
| No. | R1 | R2 |
|---|---|---|
| XXXVI | | |
| XXXVII | | |
| XXXVIII | | |
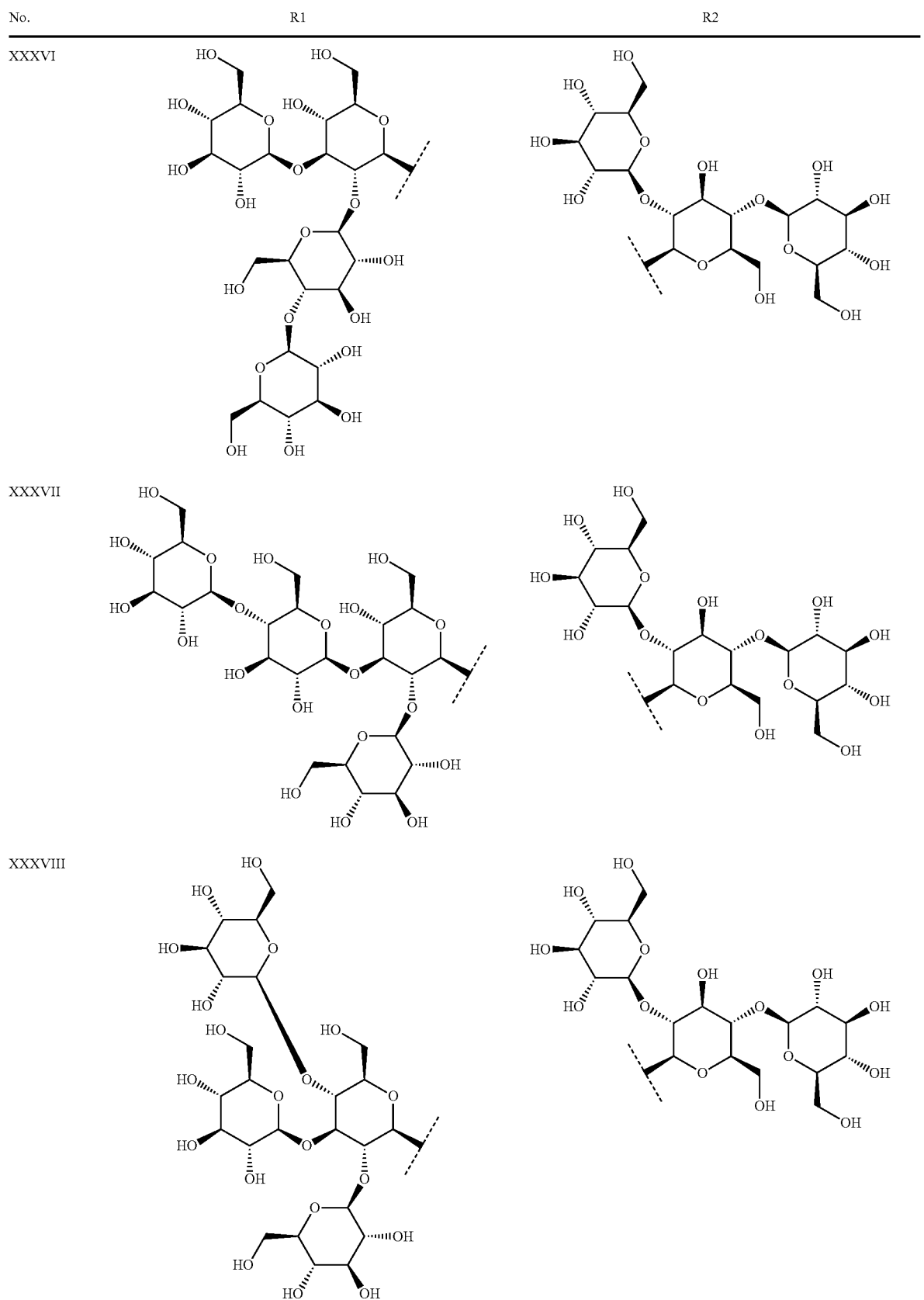

| No. | R1 | R2 |
|---|---|---|
| XXXIX | | 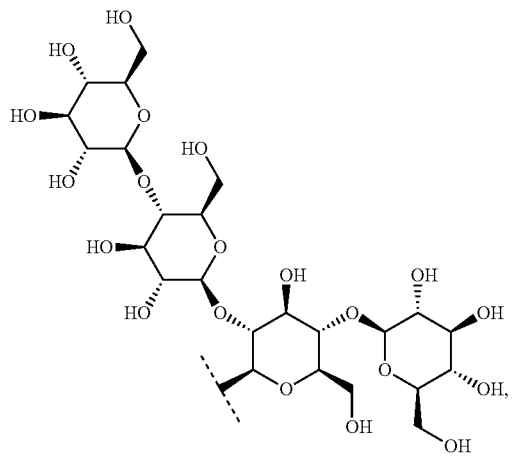 | comprising the steps of:
a) providing a starting composition comprising an organic compound with at least one carbon atom, wherein the starting composition is selected from the group consisting of steviol, steviolmonoside, steviolmonoside A, steviolbioside, steviolbioside D, rubusoside, steviolbioside A, steviolbioside B, rebaudioside B, stevioside, rebaudioside G, stevioside A, stevioside B, stevioside C, rebaudioside A, rebaudioside E, rebaudioside E2, rebaudioside E4, rebaudioside E6, rebaudioside E3, rebaudioside D, rebaudioside I, rebaudioside AM, rebaudioside D7, rebaudioside M, rebaudioside M4, rebaudioside M5, other steviol glycosides, polyols, carbohydrates, and combinations thereof;
b) providing a biocatalyst comprising at least one enzyme selected from the group consisting of steviol biosynthesis enzymes, NDP-glucosyltransferases, and NDP-glucose recycling enzymes;
c) contacting the biocatalyst with a medium containing the starting composition to produce a medium comprising the at least one steviol glycoside.

16. The method of claim 15, wherein the biocatalyst is an enzyme, or a cell comprising one or more enzymes, capable of converting the starting composition to the at least one steviol glycoside.

17. The method of claim 15 further comprising the step of:
d) separating the at least one steviol glycoside from the medium to provide a highly purified composition of the at least one steviol glycoside.

* * * * *

SEQUENCE LISTING

```
<160> NUMBER OF SEQ ID NOS: 3

<210> SEQ ID NO 1
<211> LENGTH: 808
<212> TYPE: PRT
<213> ORGANISM: Arabidopsis thaliana

<400> SEQUENCE: 1

Met Ala Asn Ala Glu Arg Met Ile Thr Arg Val His Ser Gln Arg Glu
1               5                   10                  15

Arg Leu Asn Glu Thr Leu Val Ser Glu Arg Asn Glu Val Leu Ala Leu
            20                  25                  30

Leu Ser Arg Val Glu Ala Lys Gly Lys Gly Ile Leu Gln Gln Asn Gln
        35                  40                  45

Ile Ile Ala Glu Phe Glu Ala Leu Pro Glu Gln Thr Arg Lys Lys Leu
    50                  55                  60

Glu Gly Gly Pro Phe Phe Asp Leu Leu Lys Ser Thr Gln Glu Ala Ile
65                  70                  75                  80

Val Leu Pro Pro Trp Val Ala Leu Ala Val Arg Pro Arg Pro Gly Val
```

```
                        85                  90                  95
Trp Glu Tyr Leu Arg Val Asn Leu His Ala Leu Val Val Glu Glu Leu
                100                 105                 110

Gln Pro Ala Glu Phe Leu His Phe Lys Glu Glu Leu Val Asp Gly Val
            115                 120                 125

Lys Asn Gly Asn Phe Thr Leu Glu Leu Asp Phe Glu Pro Phe Asn Ala
        130                 135                 140

Ser Ile Pro Arg Pro Thr Leu His Lys Tyr Ile Gly Asn Gly Val Asp
145                 150                 155                 160

Phe Leu Asn Arg His Leu Ser Ala Lys Leu Phe His Asp Lys Glu Ser
                165                 170                 175

Leu Leu Pro Leu Leu Asp Phe Leu Arg Leu His Ser His Gln Gly Lys
            180                 185                 190

Asn Leu Met Leu Ser Glu Lys Ile Gln Asn Leu Asn Thr Leu Gln His
        195                 200                 205

Thr Leu Arg Lys Ala Glu Glu Tyr Leu Ala Glu Leu Lys Ser Glu Thr
210                 215                 220

Leu Tyr Glu Glu Phe Glu Ala Lys Phe Glu Glu Ile Gly Leu Glu Arg
225                 230                 235                 240

Gly Trp Gly Asp Asn Ala Glu Arg Val Leu Asp Met Ile Arg Leu Leu
                245                 250                 255

Leu Asp Leu Leu Glu Ala Pro Asp Pro Ser Thr Leu Glu Thr Phe Leu
            260                 265                 270

Gly Arg Val Pro Met Val Phe Asn Val Ile Leu Ser Pro His Gly
        275                 280                 285

Tyr Phe Ala Gln Asp Asn Val Leu Gly Tyr Pro Asp Thr Gly Gly Gln
    290                 295                 300

Val Val Tyr Ile Leu Asp Gln Val Arg Ala Leu Glu Ile Glu Met Leu
305                 310                 315                 320

Gln Arg Ile Lys Gln Gln Gly Leu Asn Ile Lys Pro Arg Ile Leu Ile
                325                 330                 335

Leu Thr Arg Leu Leu Pro Asp Ala Val Gly Thr Thr Cys Gly Glu Arg
            340                 345                 350

Leu Glu Arg Val Tyr Asp Ser Glu Tyr Cys Asp Ile Leu Arg Val Pro
        355                 360                 365

Phe Arg Thr Glu Lys Gly Ile Val Arg Lys Trp Ile Ser Arg Phe Glu
    370                 375                 380

Val Trp Pro Tyr Leu Glu Thr Tyr Thr Glu Asp Ala Ala Val Glu Leu
385                 390                 395                 400

Ser Lys Glu Leu Asn Gly Lys Pro Asp Leu Ile Ile Gly Asn Tyr Ser
                405                 410                 415

Asp Gly Asn Leu Val Ala Ser Leu Leu Ala His Lys Leu Gly Val Thr
            420                 425                 430

Gln Cys Thr Ile Ala His Ala Leu Glu Lys Thr Lys Tyr Pro Asp Ser
        435                 440                 445

Asp Ile Tyr Trp Lys Lys Leu Asp Asp Lys Tyr His Phe Ser Cys Gln
    450                 455                 460

Phe Thr Ala Asp Ile Phe Ala Met Asn His Thr Asp Phe Ile Ile Thr
465                 470                 475                 480

Ser Thr Phe Gln Glu Ile Ala Gly Ser Lys Glu Thr Val Gly Gln Tyr
                485                 490                 495

Glu Ser His Thr Ala Phe Thr Leu Pro Gly Leu Tyr Arg Val Val His
            500                 505                 510
```

-continued

```
Gly Ile Asp Val Phe Asp Pro Lys Phe Asn Ile Val Ser Pro Gly Ala
            515                 520                 525

Asp Met Ser Ile Tyr Phe Pro Tyr Thr Glu Glu Lys Arg Arg Leu Thr
        530                 535                 540

Lys Phe His Ser Glu Ile Glu Glu Leu Leu Tyr Ser Asp Val Glu Asn
545                 550                 555                 560

Asp Glu His Leu Cys Val Leu Lys Asp Lys Lys Pro Ile Leu Phe
                565                 570                 575

Thr Met Ala Arg Leu Asp Arg Val Lys Asn Leu Ser Gly Leu Val Glu
                580                 585                 590

Trp Tyr Gly Lys Asn Thr Arg Leu Arg Glu Leu Val Asn Leu Val Val
            595                 600                 605

Val Gly Gly Asp Arg Arg Lys Glu Ser Lys Asp Asn Glu Glu Lys Ala
        610                 615                 620

Glu Met Lys Lys Met Tyr Asp Leu Ile Glu Glu Tyr Lys Leu Asn Gly
625                 630                 635                 640

Gln Phe Arg Trp Ile Ser Ser Gln Met Asp Arg Val Arg Asn Gly Glu
                645                 650                 655

Leu Tyr Arg Tyr Ile Cys Asp Thr Lys Gly Ala Phe Val Gln Pro Ala
                660                 665                 670

Leu Tyr Glu Ala Phe Gly Leu Thr Val Val Glu Ala Met Thr Cys Gly
            675                 680                 685

Leu Pro Thr Phe Ala Thr Cys Lys Gly Gly Pro Ala Glu Ile Ile Val
        690                 695                 700

His Gly Lys Ser Gly Phe His Ile Asp Pro Tyr His Gly Asp Gln Ala
705                 710                 715                 720

Ala Asp Leu Leu Ala Asp Phe Phe Thr Lys Cys Lys Glu Asp Pro Ser
                725                 730                 735

His Trp Asp Glu Ile Ser Lys Gly Gly Leu Gln Arg Ile Glu Glu Lys
            740                 745                 750

Tyr Thr Trp Gln Ile Tyr Ser Gln Arg Leu Leu Thr Leu Thr Gly Val
        755                 760                 765

Tyr Gly Phe Trp Lys His Val Ser Asn Leu Asp Arg Leu Glu His Arg
    770                 775                 780

Arg Tyr Leu Glu Met Phe Tyr Ala Leu Lys Tyr Arg Pro Leu Ala Gln
785                 790                 795                 800

Ala Val Pro Leu Ala Gln Asp Asp
                805

<210> SEQ ID NO 2
<211> LENGTH: 442
<212> TYPE: PRT
<213> ORGANISM: Solanum lycopersicum

<400> SEQUENCE: 2

Met Ala Thr Asn Leu Arg Val Leu Met Phe Pro Trp Leu Ala Tyr Gly
1               5                   10                  15

His Ile Ser Pro Phe Leu Asn Ile Ala Lys Gln Leu Ala Asp Arg Gly
            20                  25                  30

Phe Leu Ile Tyr Leu Cys Ser Thr Arg Ile Asn Leu Glu Ser Ile Ile
        35                  40                  45

Lys Lys Ile Pro Glu Lys Tyr Ala Asp Ser Ile His Leu Ile Glu Leu
    50                  55                  60

Gln Leu Pro Glu Leu Pro Glu Leu Pro Pro His Tyr His Thr Thr Asn
```

```
             65                  70                  75                  80
Gly Leu Pro Pro His Leu Asn Pro Thr Leu His Lys Ala Leu Lys Met
                     85                  90                  95

Ser Lys Pro Asn Phe Ser Arg Ile Leu Gln Asn Leu Lys Pro Asp Leu
                100                 105                 110

Leu Ile Tyr Asp Val Leu Gln Pro Trp Ala Glu His Val Ala Asn Glu
                115                 120                 125

Gln Gly Ile Pro Ala Gly Lys Leu Leu Val Ser Cys Ala Ala Val Phe
130                 135                 140

Ser Tyr Phe Phe Ser Phe Arg Lys Asn Pro Gly Val Glu Phe Pro Phe
145                 150                 155                 160

Pro Ala Ile His Leu Pro Glu Val Glu Lys Val Lys Ile Arg Glu Ile
                165                 170                 175

Leu Ala Lys Glu Pro Glu Glu Gly Gly Arg Leu Asp Glu Gly Asn Lys
                180                 185                 190

Gln Met Met Leu Met Cys Thr Ser Arg Thr Ile Glu Ala Lys Tyr Ile
                195                 200                 205

Asp Tyr Cys Thr Glu Leu Cys Asn Trp Lys Val Val Pro Val Gly Pro
210                 215                 220

Pro Phe Gln Asp Leu Ile Thr Asn Asp Ala Asp Asn Lys Glu Leu Ile
225                 230                 235                 240

Asp Trp Leu Gly Thr Lys Pro Glu Asn Ser Thr Val Phe Val Ser Phe
                245                 250                 255

Gly Ser Glu Tyr Phe Leu Ser Lys Glu Asp Met Glu Glu Ile Ala Phe
                260                 265                 270

Ala Leu Glu Ala Ser Asn Val Asn Phe Ile Trp Val Arg Phe Pro
                275                 280                 285

Lys Gly Glu Glu Arg Asn Leu Glu Asp Ala Leu Pro Glu Gly Phe Leu
290                 295                 300

Glu Arg Ile Gly Glu Arg Gly Arg Val Leu Asp Lys Phe Ala Pro Gln
305                 310                 315                 320

Pro Arg Ile Leu Asn His Pro Ser Thr Gly Gly Phe Ile Ser His Cys
                325                 330                 335

Gly Trp Asn Ser Val Met Glu Ser Ile Asp Phe Gly Val Pro Ile Ile
                340                 345                 350

Ala Met Pro Ile His Asn Asp Gln Pro Ile Asn Ala Lys Leu Met Val
                355                 360                 365

Glu Leu Gly Val Ala Val Glu Ile Val Arg Asp Asp Asp Gly Lys Ile
370                 375                 380

His Arg Gly Glu Ile Ala Glu Ala Leu Lys Ser Val Val Thr Gly Glu
385                 390                 395                 400

Thr Gly Glu Ile Leu Arg Ala Lys Val Arg Glu Ile Ser Lys Asn Leu
                405                 410                 415

Lys Ser Ile Arg Asp Glu Glu Met Asp Ala Val Ala Glu Glu Leu Ile
                420                 425                 430

Gln Leu Cys Arg Asn Ser Asn Lys Ser Lys
                435                 440

<210> SEQ ID NO 3
<211> LENGTH: 458
<212> TYPE: PRT
<213> ORGANISM: Stevia rebaudiana

<400> SEQUENCE: 3
```

-continued

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ala Ile Thr Ile Leu His Thr
                35                  40                  45

Asn Phe Asn Lys Pro Lys Thr Ser Asn Tyr Pro His Phe Thr Phe Arg
            50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
            115                 120                 125

Phe Ala Gln Asp Val Ala Asp Ser Leu Asn Leu Arg Arg Leu Val Leu
            130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
                180                 185                 190

Ala Tyr Ser Asn Trp Gln Ile Gly Lys Glu Ile Leu Gly Lys Met Ile
                195                 200                 205

Lys Gln Thr Lys Ala Ser Ser Gly Val Ile Trp Asn Ser Phe Lys Glu
            210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Glu Trp Leu Asp Gln Gln Ala
                260                 265                 270

Pro Ser Ser Val Leu Tyr Val Ser Phe Gly Ser Thr Ser Glu Val Asp
            275                 280                 285

Glu Lys Asp Phe Leu Glu Ile Ala Arg Gly Leu Val Asp Ser Gly Gln
            290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Lys Ile Val
                325                 330                 335

Lys Trp Val Pro Gln Gln Glu Val Leu Ala His Pro Ala Ile Gly Ala
            340                 345                 350

Phe Trp Thr His Ser Gly Trp Asn Ser Thr Leu Glu Ser Val Cys Glu
            355                 360                 365

Gly Val Pro Met Ile Phe Ser Ser Phe Gly Gly Asp Gln Pro Leu Asn
            370                 375                 380

Ala Arg Tyr Met Ser Asp Val Leu Arg Val Gly Val Tyr Leu Glu Asn
385                 390                 395                 400

Gly Trp Glu Arg Gly Glu Val Val Asn Ala Ile Arg Arg Val Met Val
                405                 410                 415

Asp Glu Glu Gly Glu Tyr Ile Arg Gln Asn Ala Arg Val Leu Lys Gln
```

|   |   |   |   |   |   |   | 420 |   |   |   | 425 |   |   |   | 430 |   |   |
|---|---|---|---|---|---|---|---|---|---|---|---|---|---|---|---|---|---|---|
| Lys | Ala | Asp | Val | Ser | Leu | Met | Lys | Gly | Gly | Ser | Ser | Tyr | Glu | Ser | Leu |
|   |   |   | 435 |   |   |   |   |   | 440 |   |   |   |   |   | 445 |
| Glu | Ser | Leu | Val | Ser | Tyr | Ile | Ser | Ser | Leu |
|   |   |   | 450 |   |   |   | 455 |